(12) United States Patent
Ma et al.

(10) Patent No.: US 8,946,697 B1
(45) Date of Patent: Feb. 3, 2015

(54) IRIDIUM COMPLEXES WITH AZA-BENZO FUSED LIGANDS

(71) Applicant: Universal Display Corporation, Ewing, NJ (US)

(72) Inventors: Bin Ma, Plainsboro, NJ (US); Edward Barron, Hamilton, NJ (US); Alan DeAngelis, Pennington, NJ (US); Walter Yeager, Yardley, PA (US); Chuanjun Xia, Lawrenceville, NJ (US); Kwang-Ohk Cheon, Holland, PA (US); Scott Beers, Flemington, NJ (US); Michael S. Weaver, Princeton, NJ (US)

(73) Assignee: Universal Display Corporation, Ewing, NJ (US)

( * ) Notice: Subject to any disclaimer, the term of this patent is extended or adjusted under 35 U.S.C. 154(b) by 0 days.

(21) Appl. No.: 14/028,499

(22) Filed: Sep. 16, 2013

(51) Int. Cl.
*H01L 51/00* (2006.01)
*H01L 35/24* (2006.01)
*H01L 51/50* (2006.01)

(52) U.S. Cl.
CPC ........ *H01L 51/0085* (2013.01); *H01L 51/5024* (2013.01); *H01L 51/0072* (2013.01); *H01L 51/5012* (2013.01); *H01L 51/0071* (2013.01); *H01L 51/50* (2013.01)
USPC .............. 257/40; 257/E51.001; 257/E51.041; 546/4; 428/690; 313/504

(58) Field of Classification Search
CPC ............ H01L 51/0085; H01L 51/0072; H01L 51/0074; H01L 51/0067; H01L 51/5012; H01L 51/0059; H01L 51/50; H01L 51/0035; H01L 51/0052; C09K 2211/185; C09K 2211/1037; C09K 2211/1433; H05B 33/14; H05B 33/20
USPC .............................. 257/40, E51.001, E51.041
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Marcos D. Pizarro
*Assistant Examiner* — Nelson Garces
(74) *Attorney, Agent, or Firm* — Duane Morris LLP

(57) ABSTRACT

Novel iridium complexes containing phenylpyridine and pyridyl aza-benzo fused ligands are described. Iridium complexes containing aza-benzo fused ligands in which an aryl group is conjugated to the aza ring of the specific aza-dibenzofuran ring system results in the formation of yellow phosphorescent compounds with superior device stability and efficiency. These complexes are useful as light emitters when incorporated into OLEDs.

43 Claims, 3 Drawing Sheets

Formula I

Formula II

Formula III

(56) References Cited

U.S. PATENT DOCUMENTS

| | | |
|---|---|---|
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0151042 A1 | 8/2003 | Hueschen |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0196691 A1* | 8/2007 | Ikemizu et al. ............... 428/690 |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0261076 A1* | 10/2008 | Kwong et al. ............... 428/690 |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0244004 A1* | 9/2010 | Xia et al. .................. 257/40 |
| 2011/0227049 A1* | 9/2011 | Xia et al. .................. 257/40 |
| 2012/0061654 A1* | 3/2012 | Rayabarapu et al. ........ 257/40 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008044723 A1 | 4/2008 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2010/111175 | 9/2010 |
| WO | 2010/118029 | 10/2010 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

(56) References Cited

OTHER PUBLICATIONS

Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1)162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing $N^{\wedge}C^{\wedge}N$-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Rayabararu, Dinesh et al., "Metal complexes and light-emitting devices using them", XP002718489 retrieved from STN Database accession No. 2010:1282120.
European Search Report dated Jan. 27, 2014 for corresponding EP Application No. 13191819.5.

\* cited by examiner

Formula I

Formula II

Formula III

IRIDIUM COMPLEXES WITH AZA-BENZO FUSED LIGANDS

CROSS-REFERENCE TO RELATED APPLICATIONS

This application is related to U.S. patent application Ser. No. 13/928,456, filed Jun. 27, 2013 and U.S. patent application Ser. No. 13/673,338, filed Nov. 9, 2012.

JOINT RESEARCH AGREEMENT

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to iridium complexes containing aza-benzo fused ligands. In particular, iridium complexes containing both phenylpyridine ligands and aza-benzo fused ligands were found to be useful as phosphorescent emitters when used in OLED devices. Additionally, iridium complexes containing both phenylpyridine ligands and aza-benzo fused ligands where an alkyl group is bonded to the pyridine ring of the aza-dibenzofuran moiety of the ligand were also found to be useful as phosphorescent emitters.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

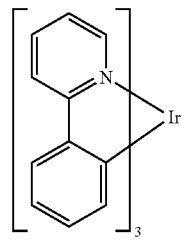

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A compound having the formula $Ir(L_A)_n(L_B)_{3-n}$, and having the structure according to Formula I below

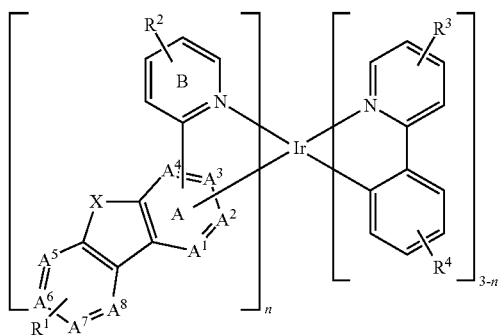

is provided. In the compound of Formula I, $A^1$, $A^2$, $A^3$, $A^4$, $A^5$, $A^6$, $A^7$, and $A^8$ comprise carbon or nitrogen, and at least one of $A^1$, $A^2$, $A^3$, $A^4$, $A^5$, $A^6$, $A^7$, and $A^8$ is nitrogen. Ring B is bonded to ring A through a C—C bond, the iridium is bonded to ring A through a Ir—C bond. X is O, S, or Se. $R^1$, $R^2$, $R^3$, and $R^4$ independently represent mono-, di-, tri-, tetra-substitution, or no substitution, and any adjacent substitutions in $R^1$, $R^3$, and $R^4$ are optionally linked together to form a ring. $R^1$, $R^3$, and $R^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R^2$ is selected from the group consisting of aryl, substituted aryl, heteroaryl, and substituted heteroaryl. n is an integer from 1 to 3. In one aspect, the compound has the structure according to Formula I, where n is 1.

In one aspect, the compound has the structure according to Formula II below where all variables are as defined above in connection with Formula I:

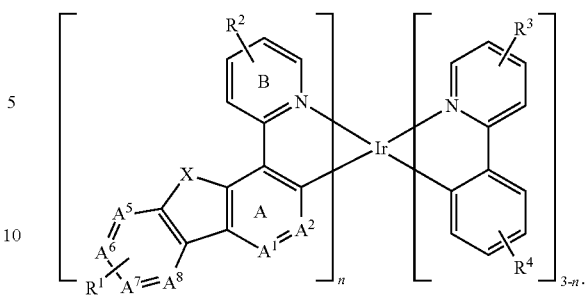

In one aspect, the compound has the structure according to Formula II where n is 1.

In one aspect of the compound according to Formula I, only one of $A^1$ to $A^8$ is nitrogen. In one aspect, only one of $A^5$ to $A^8$ is nitrogen. In one aspect, X is O.

In one aspect, $R^1$, $R^3$, and $R^4$ are independently selected from the group consisting of hydrogen, deuterium, alkyl, and combinations thereof. In one aspect, $R^3$ is alkyl. In one aspect, the alkyl is deuterated or partially deuterated.

According to another aspect of the present disclosure, in the compound of Formula I, $A^1$-$A^4$ and $A^6$-$A^8$ are C, and $A^5$ is N, resulting in a compound having the structure according to Formula III

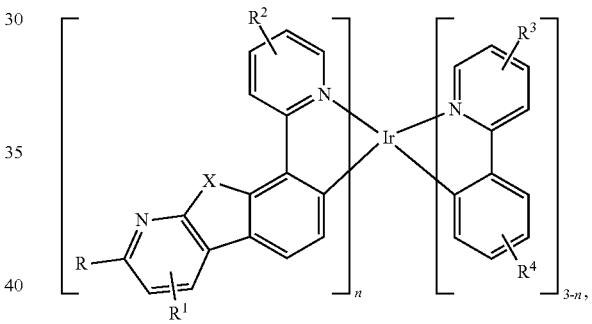

wherein R is selected from the group consisting of alkyl, cycloalkyl, and combinations thereof.

In one aspect, $R^1$ in Formula III represents mono-, di-substitution, or no substitution; $R^2$, $R^3$, and $R^4$ independently represent mono-, di-, tri-, tetra-substitution, or no substitution; any adjacent substitutions in $R^1$, $R^3$, and $R^4$ are optionally linked together to form a ring; $R^1$, $R^3$, and $R^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; R2 is selected from the group consisting of aryl, substituted aryl, heteroaryl, and substituted heteroaryl; and n is an integer from 1 to 3.

In one embodiment, a first device comprising a first organic light emitting device is provided. The first device further comprises an anode, a cathode, and an organic layer, disposed between the anode and the cathode. The organic layer comprises a compound having the formula $Ir(L_A)_n(L_B)_{3-n}$, and having the structure according to Formula I.

According to an embodiment, the organic layer comprises a compound having the formula $Ir(L_A)_n(L_B)_{3-n}$, and having the structure according to Formula III.

The inventors have discovered that addition of an aryl group to the aza ring of the specific aza-dibenzofuran ring system in the iridium complexes containing aza-benzo fused ligands results in the formation of yellow phosphorescent compounds with superior device efficiency. The inventors have discovered that conjugating the pyridine ring in the $L_A$ ligand with aryl rings result in a new class of novel efficient yellow phosphorescent emitters for PHOLEDs.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
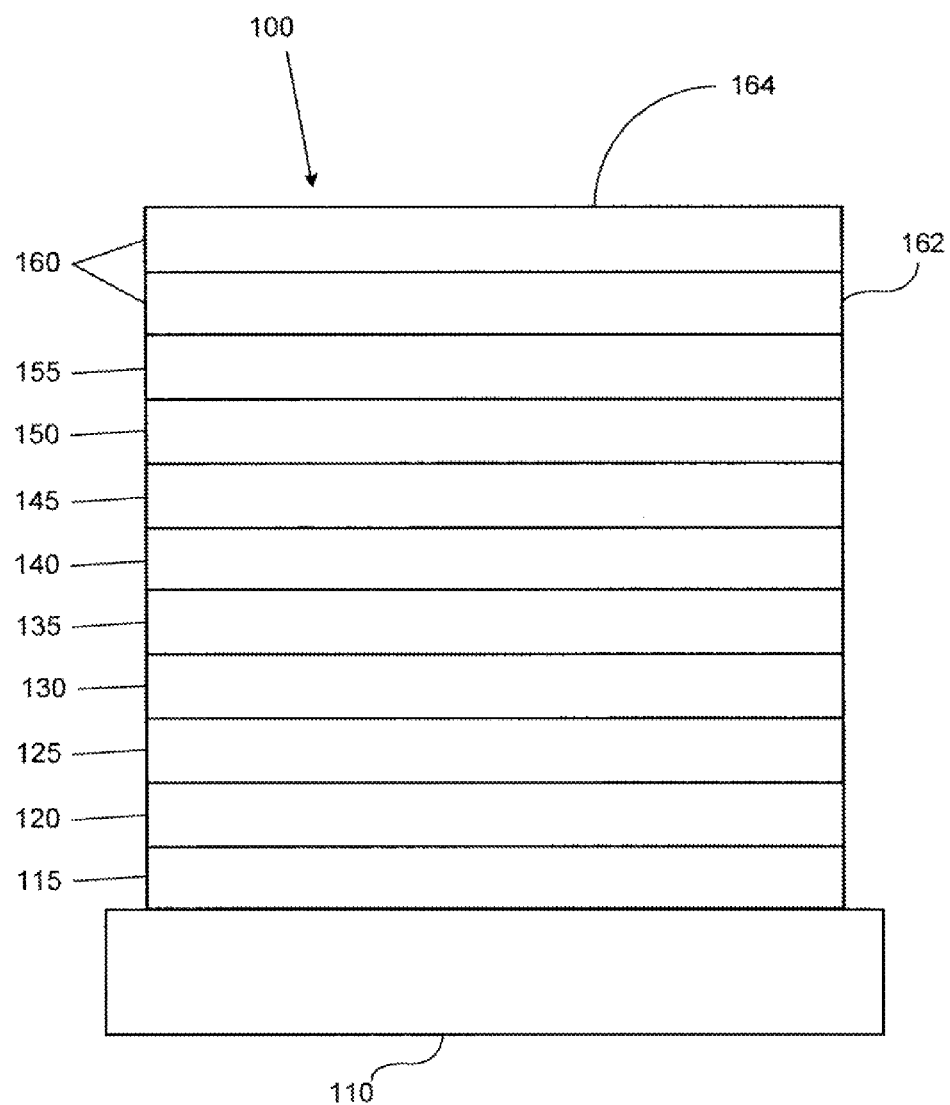
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
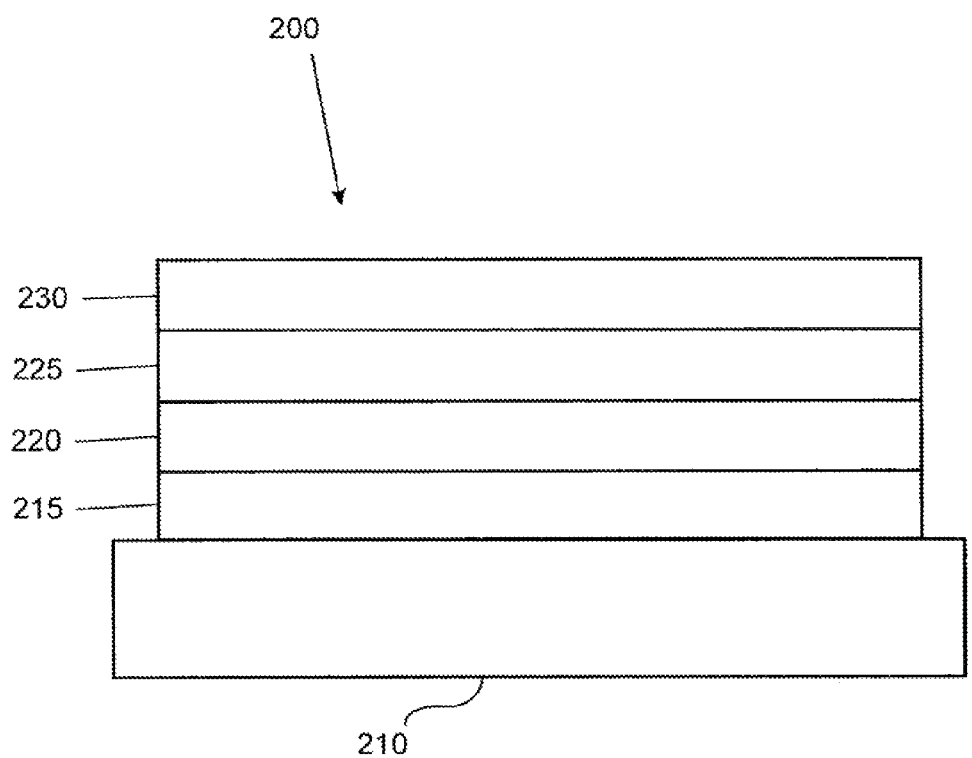
FIG. 2 shows an inverted organic light emitting device that does not have a separate electron transport layer.
Figure 3:
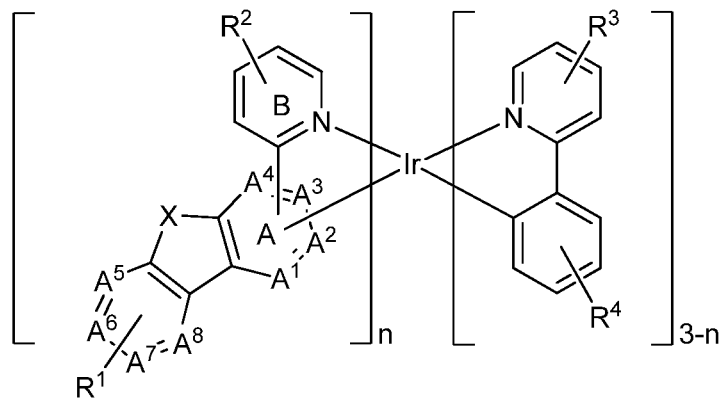
FIG. 3 shows structural Formula I, Formula II, and Formula III.
Figure 3:
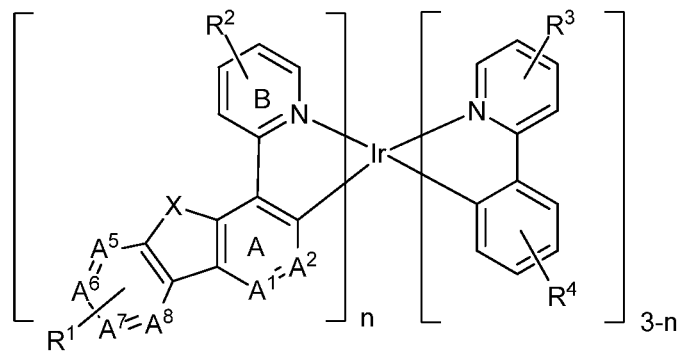
Figure 3:
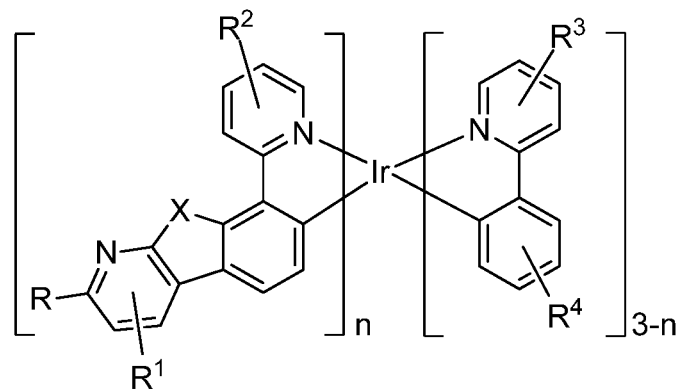

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

A compound having the formula $Ir(L_A)_n(L_B)_{3-n}$, and having the structure according to Formula I below

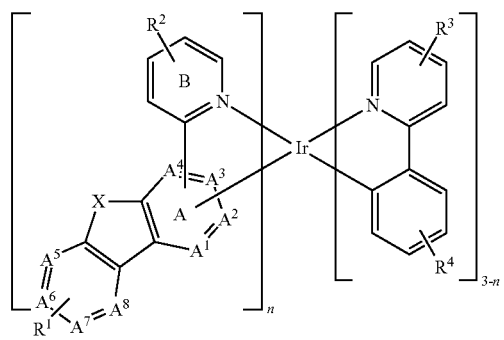

is provided. In the compound of Formula I, $A^1$, $A^2$, $A^3$, $A^4$, $A^5$, $A^6$, $A^7$, and $A^8$ comprise carbon or nitrogen, and at least one of $A^1$, $A^2$, $A^3$, $A^4$, $A^5$, $A^6$, $A^7$, and $A^8$ is nitrogen. Ring B is bonded to ring A through a C—C bond, the iridium is bonded to ring A through a Ir—C bond. X is O, S, or Se. $R^1$, $R^2$, $R^3$, and $R^4$ independently represent mono-, di-, tri-, tetra-substitution, or no substitution, and any adjacent substitutions in $R^1$, $R^3$, and $R^4$ are optionally linked together to form a ring. $R^1$, $R^3$, and $R^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R^2$ is selected from the group consisting of aryl, substituted aryl, heteroaryl, and substituted heteroaryl. n is an integer from 1 to 3. In one aspect, the compound has the structure according to Formula I, where n is 1.

In an embodiment of the compound having the structure of Formula I, $R^2$ is phenyl or substituted phenyl. In one embodiment, $R^2$ is pyridine or substituted pyridine. In one embodiment, $R^2$ represents mono-substitution.

In one aspect, the compound has the structure according to Formula II below where all variables are as defined above in connection with Formula I:

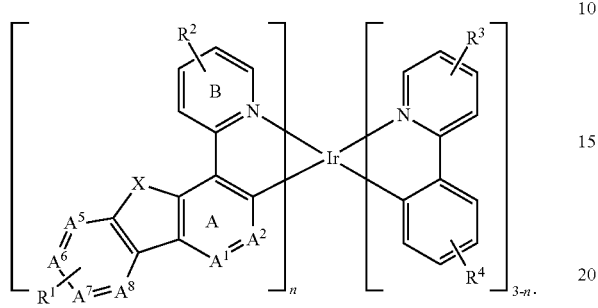

In one aspect, the compound has the structure according to Formula II where n is 1.

In one aspect of the compound according to Formula I, only one of $A^1$ to $A^8$ is nitrogen. In one aspect, only one of $A^5$ to $A^8$ is nitrogen. In one aspect, X is O.

In one aspect, $R^1$, $R^3$, and $R^4$ are independently selected from the group consisting of hydrogen, deuterium, alkyl, and combinations thereof. In one aspect, $R^3$ is alkyl. In one aspect, the alkyl is deuterated or partially deuterated.

In one aspect, in the compound of Formula I, $L_A$ is selected from the group consisting of:

$L_{A318}$

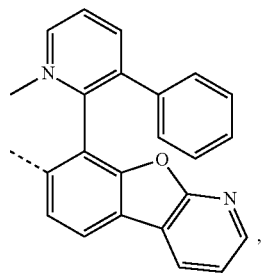

$L_{A319}$

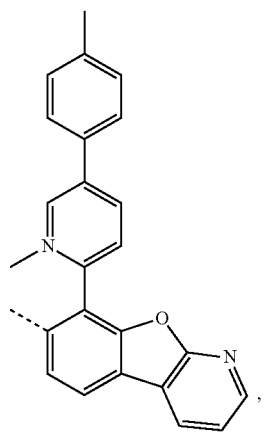

$L_{A320}$

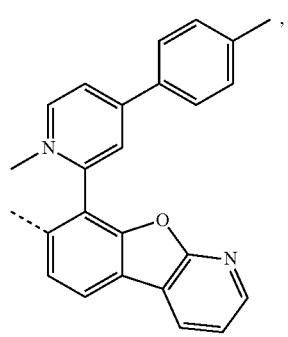

$L_{A321}$

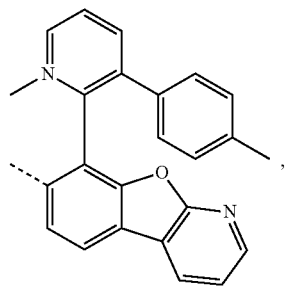

$L_{A322}$ $L_{A323}$

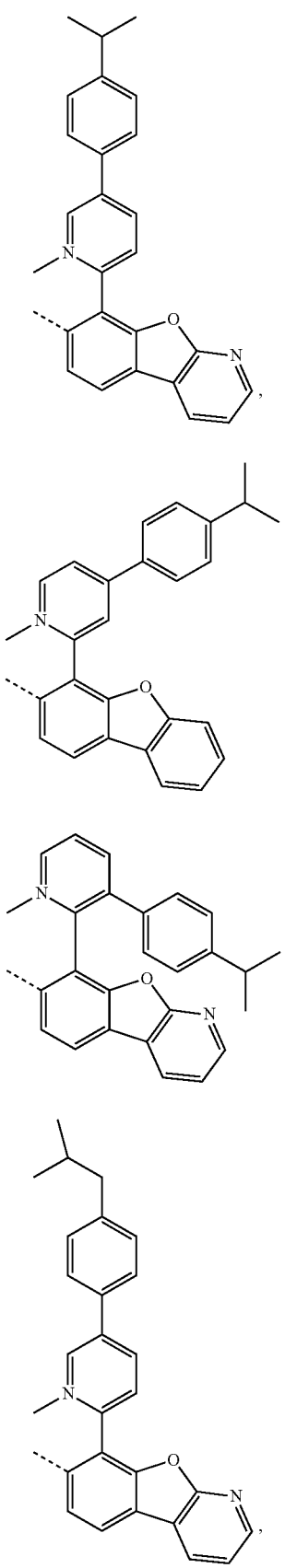
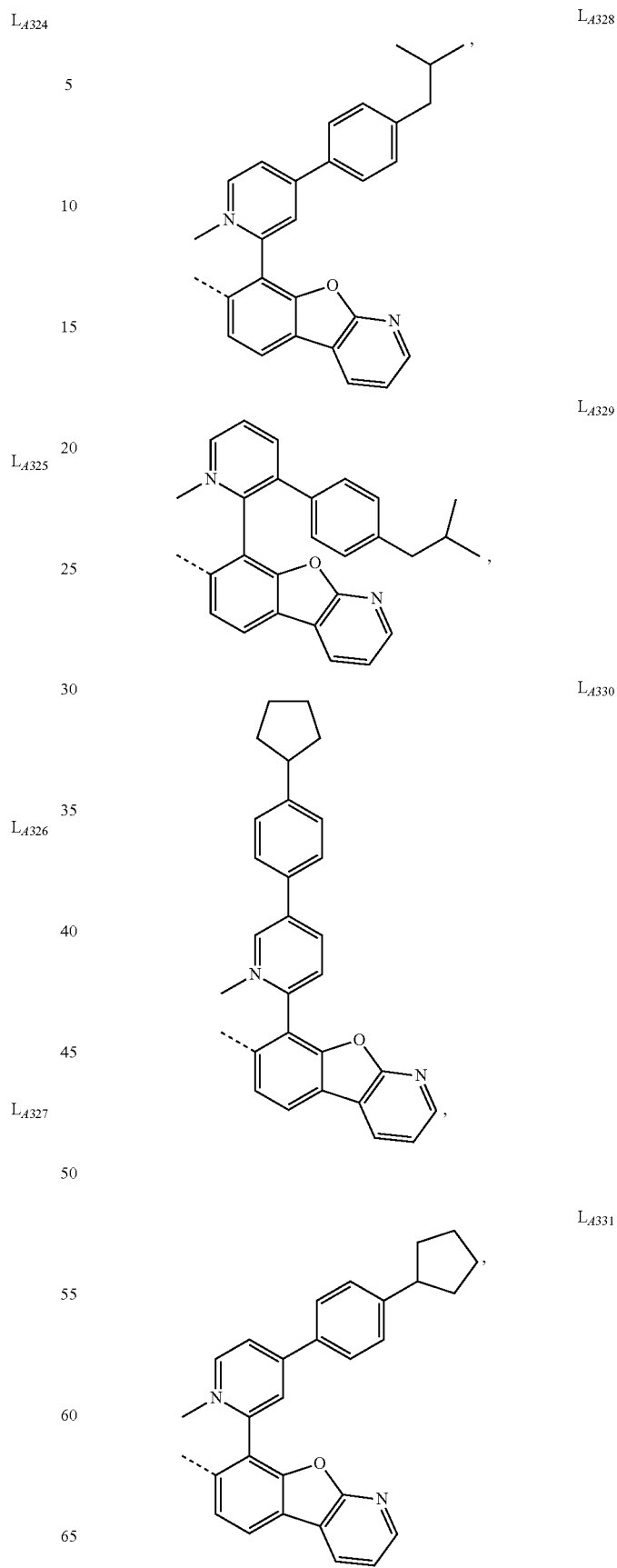

L<sub>A332</sub>
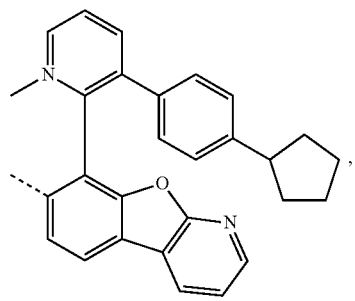
L<sub>A333</sub>
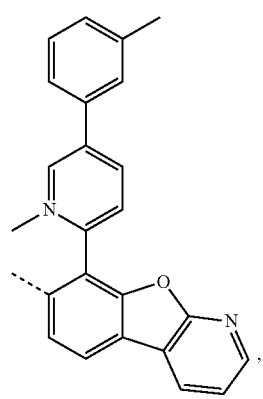
L<sub>A334</sub>
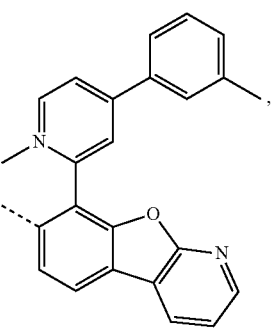
L<sub>A335</sub>
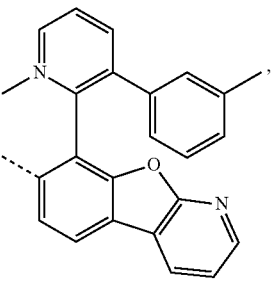
L<sub>A336</sub>
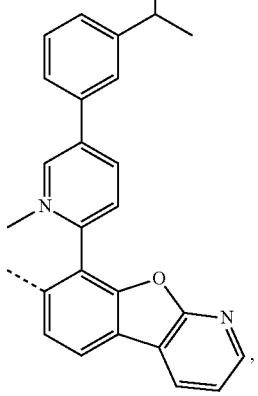
L<sub>A337</sub>
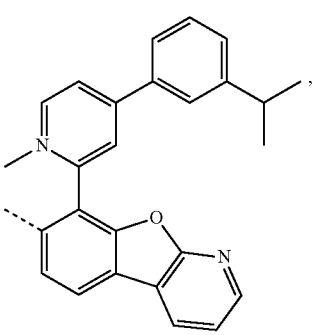
L<sub>A338</sub>
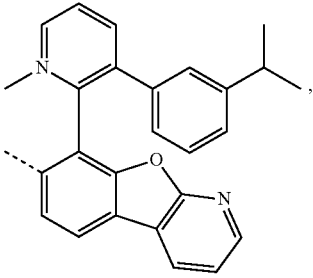
L<sub>A339</sub>
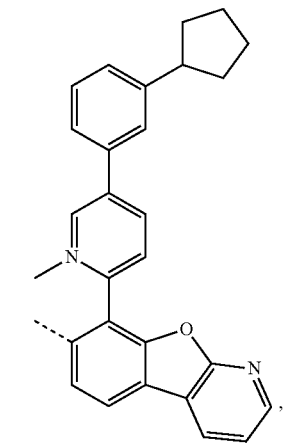

L_{A340}
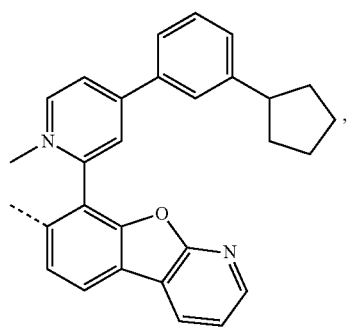
L_{A341}
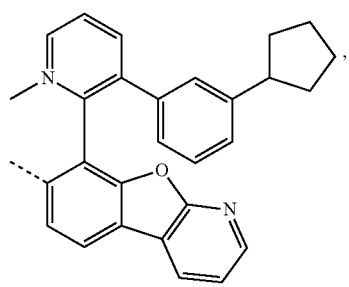
L_{A342}
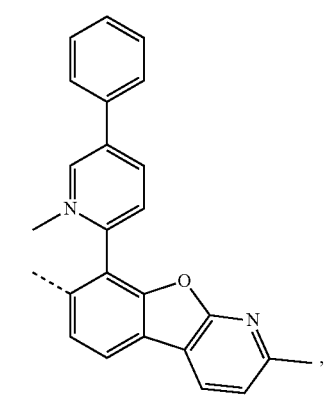
L_{A343}
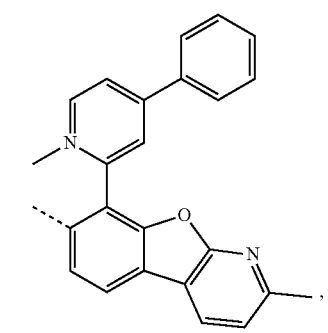
L_{A344}
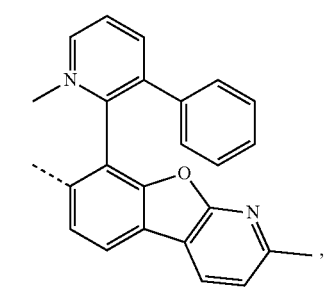
L_{A345}
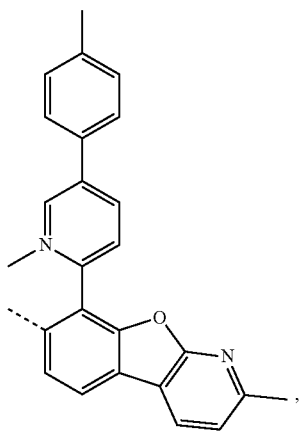
L_{A346}
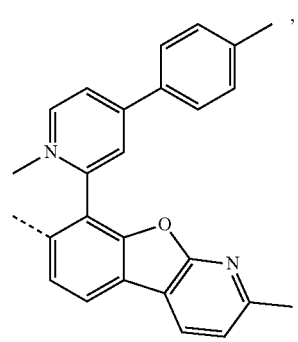
L_{A347}
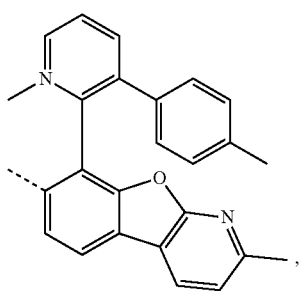
L_{A348}
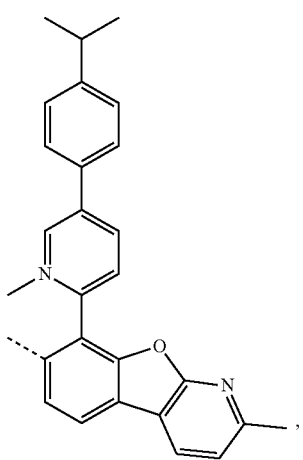

L$_{A349}$
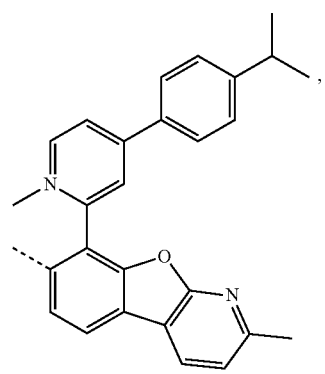
L$_{A350}$
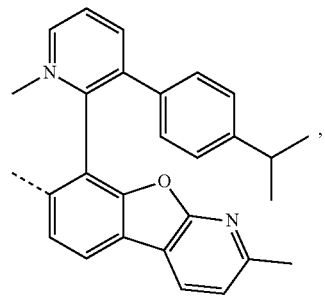
L$_{A351}$
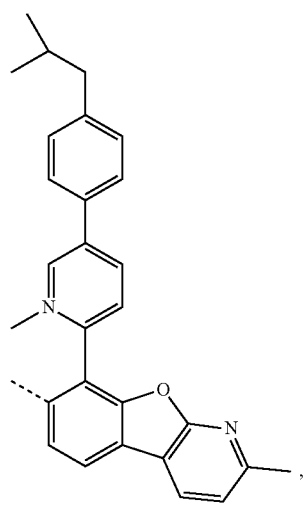
L$_{A352}$
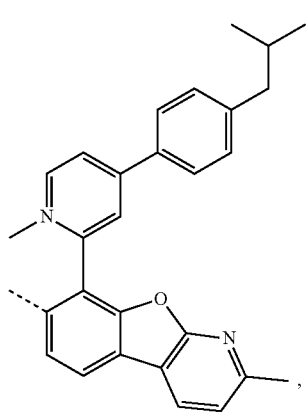
L$_{A353}$
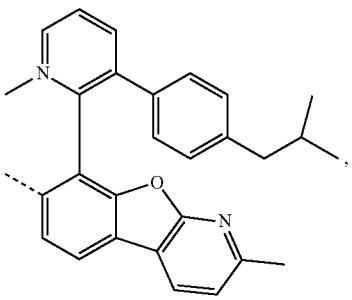
L$_{A354}$
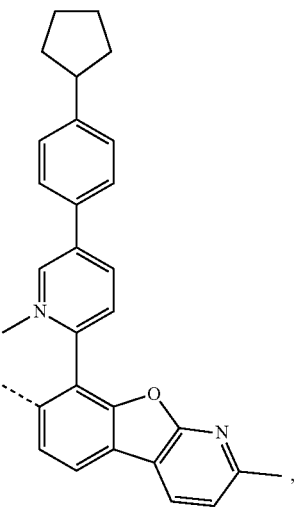
L$_{A355}$
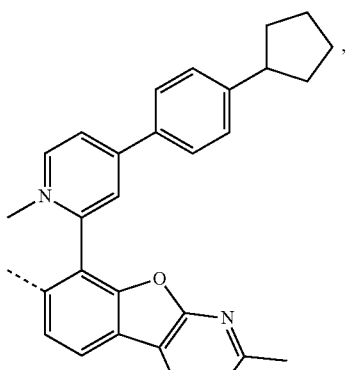
L$_{A356}$
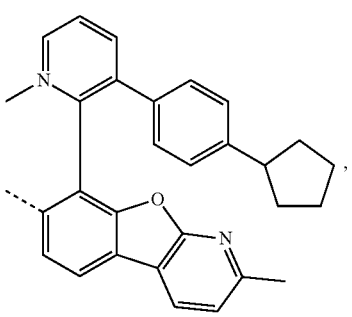

L<sub>A357</sub> 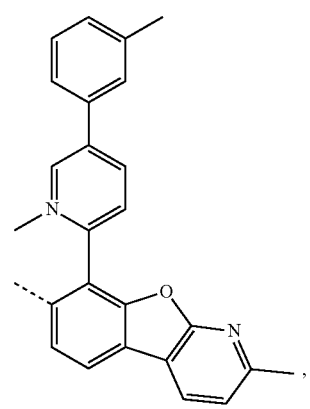
L<sub>A358</sub> 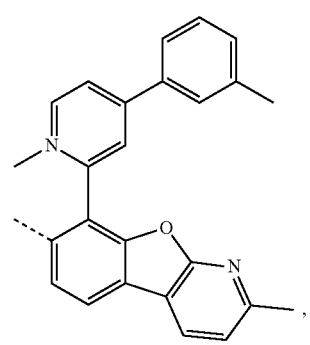
L<sub>A359</sub> 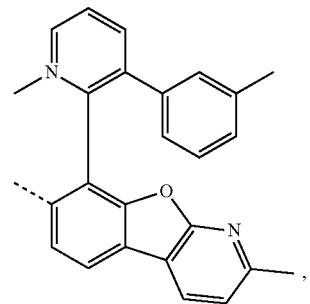
L<sub>A360</sub> 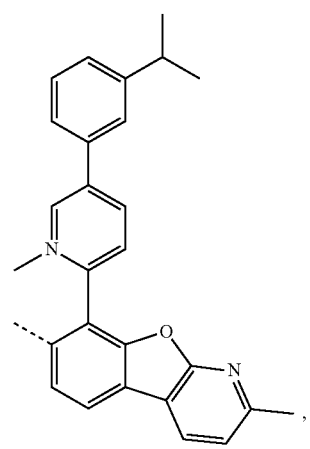
L<sub>A361</sub> 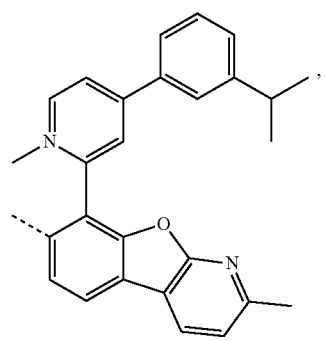
L<sub>A362</sub> 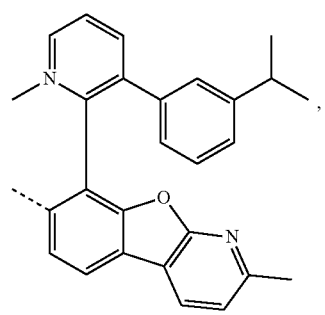
L<sub>A363</sub> 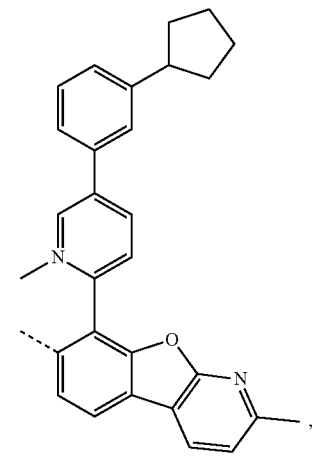
L<sub>A364</sub> 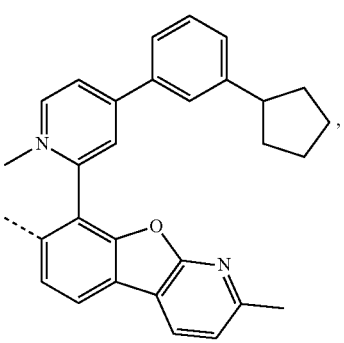

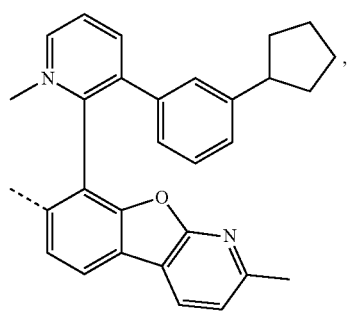
L<sub>A365</sub>
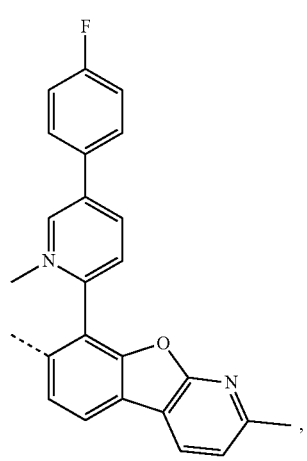
L<sub>A366</sub>
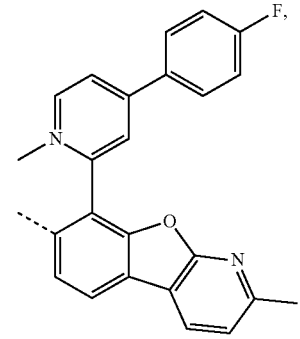
L<sub>A367</sub>
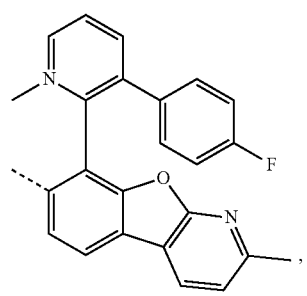
L<sub>A368</sub>
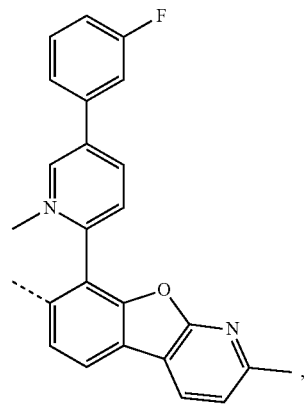
L<sub>A369</sub>
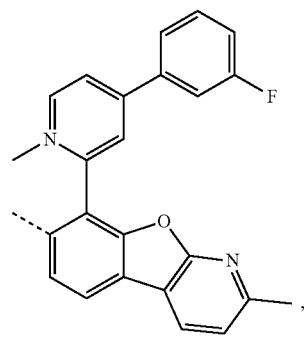
L<sub>A370</sub>
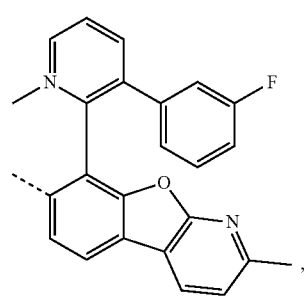
L<sub>A371</sub>
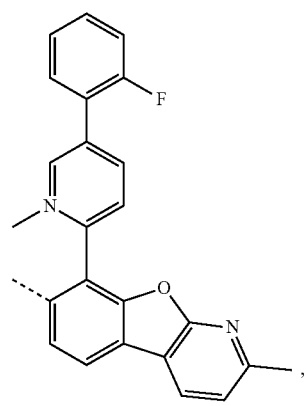
L<sub>A372</sub>

L<sub>A373</sub>
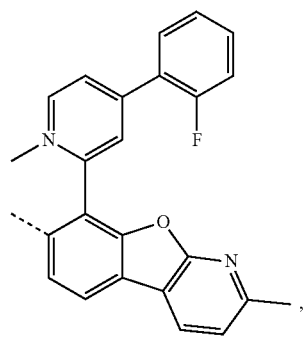
L<sub>A374</sub>
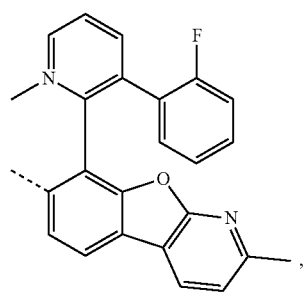
L<sub>A375</sub>
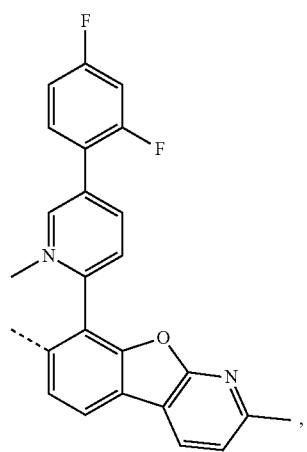
L<sub>A376</sub>
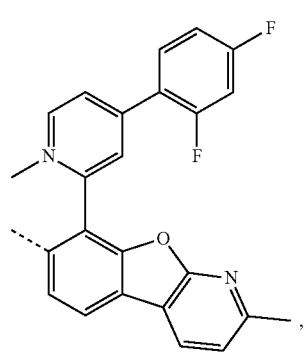
L<sub>A377</sub>
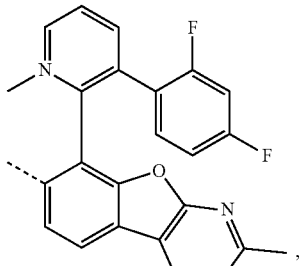
L<sub>A378</sub>
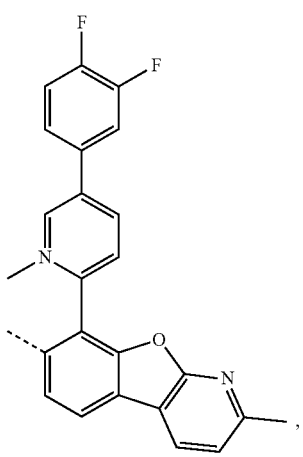
L<sub>A379</sub>
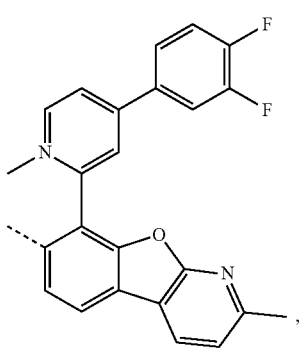
L<sub>A380</sub>
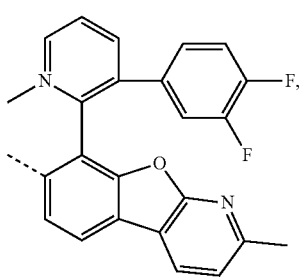

L<sub>A381</sub> 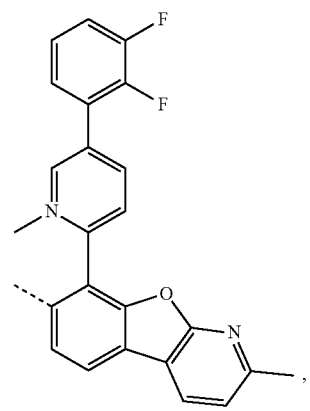
L<sub>A382</sub> 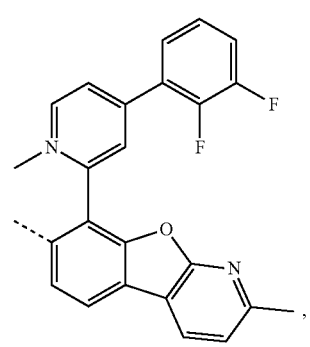
L<sub>A383</sub> 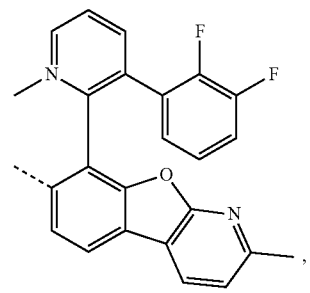
L<sub>A384</sub> 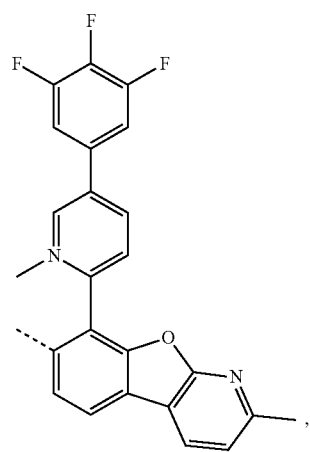
L<sub>A385</sub> 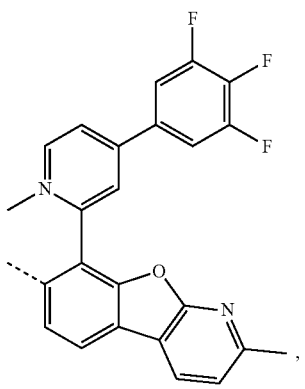
L<sub>A386</sub> 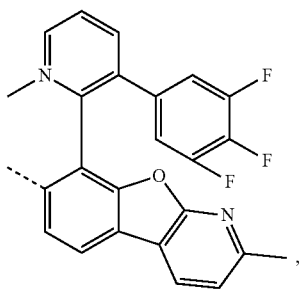
L<sub>A387</sub> 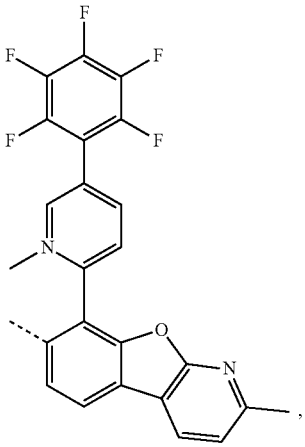
L<sub>A388</sub> 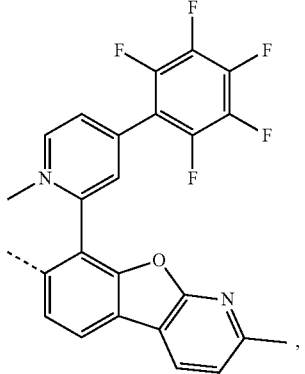

L<sub>A389</sub>
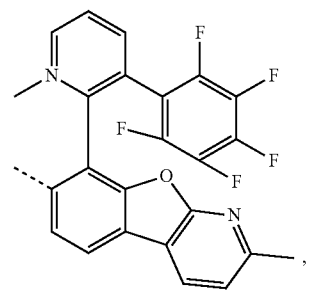
L<sub>A390</sub>
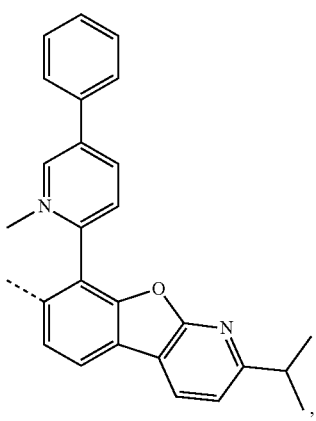
L<sub>A391</sub>
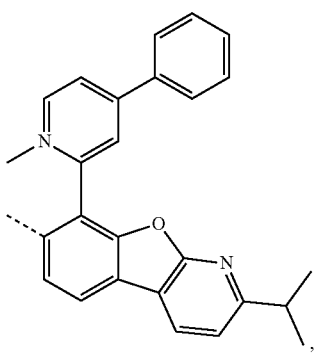
L<sub>A392</sub>
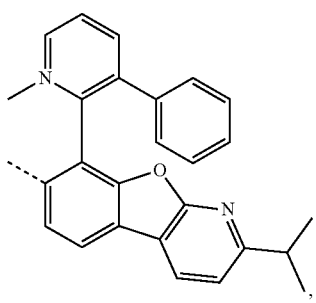
L<sub>A393</sub>
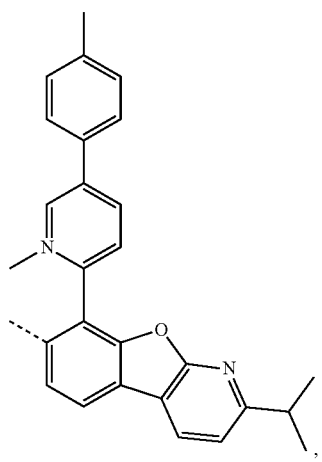
L<sub>A394</sub>
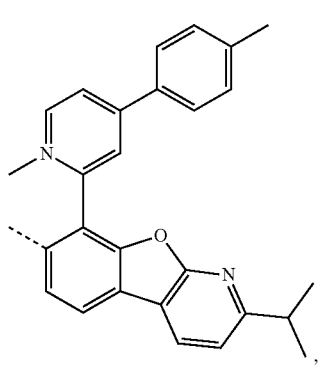
L<sub>A395</sub>
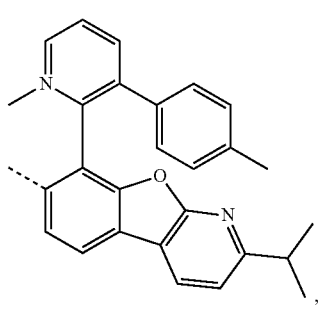
L<sub>A396</sub>
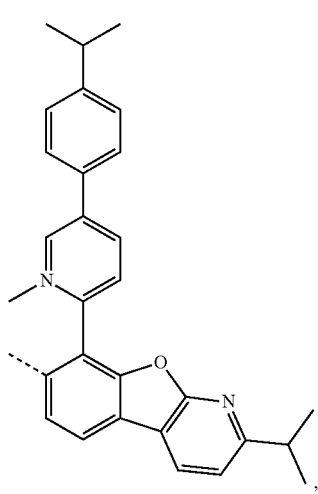

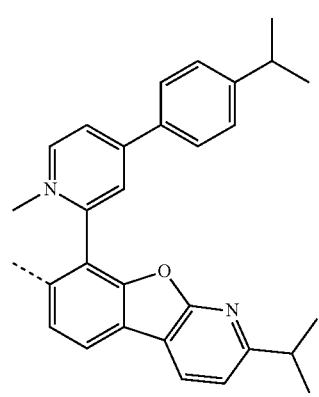
$L_{A397}$
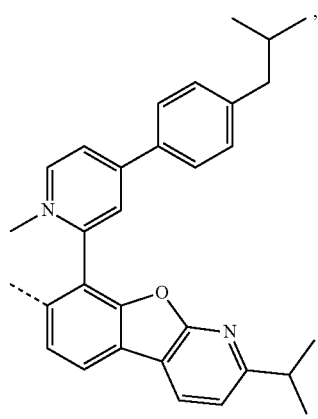
$L_{A400}$
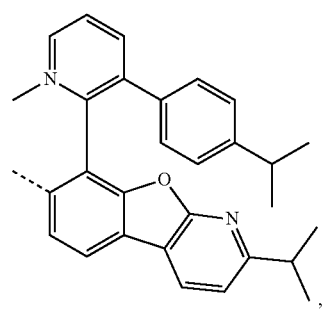
$L_{A398}$
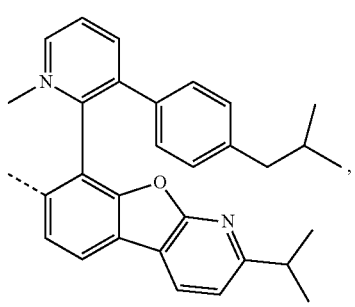
$L_{A401}$
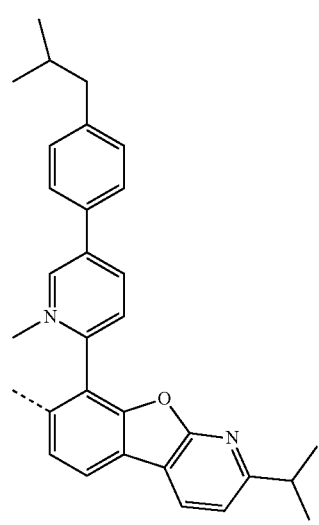
$L_{A399}$
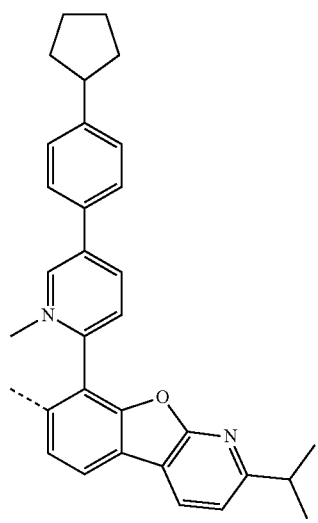
$L_{A402}$ L_{A403}
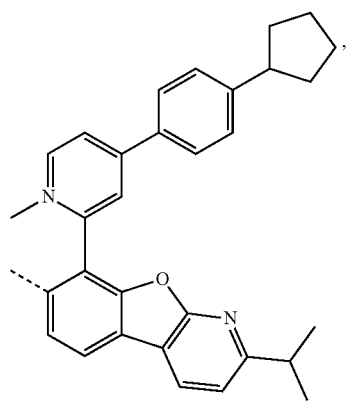
L_{A404}
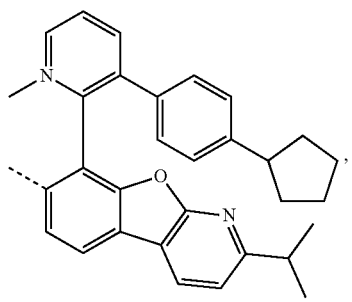
L_{A405}
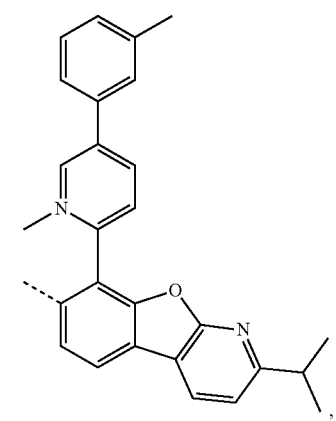
L_{A406}
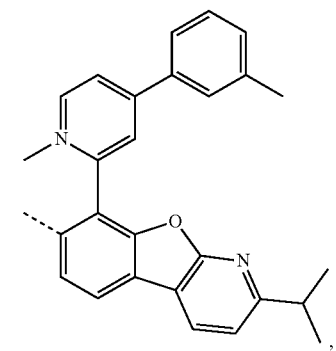
L_{A407}
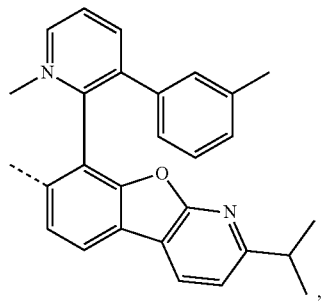
L_{A408}
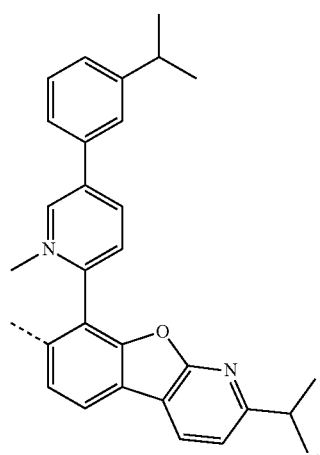
L_{A409}
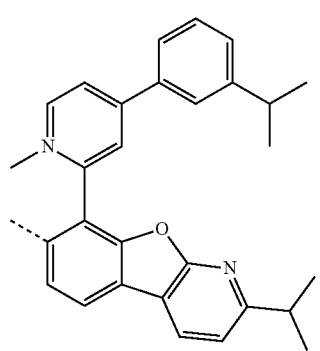
L_{A410}
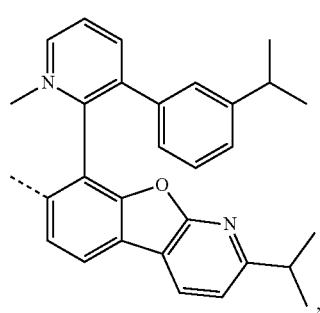

33
-continued
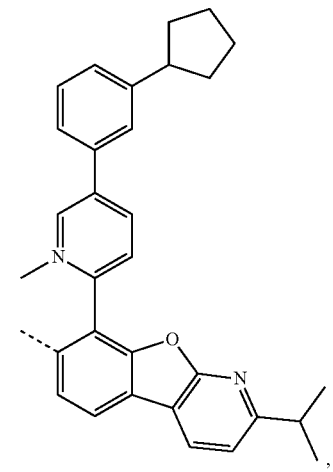
L_{A411}
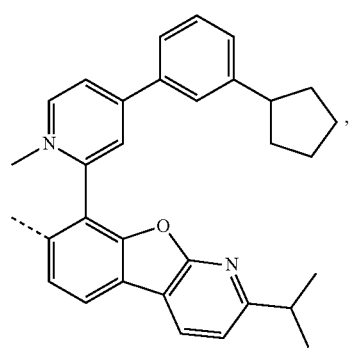
L_{A412}
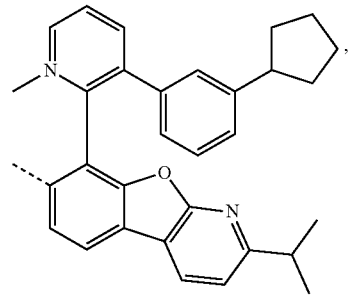
L_{A413}
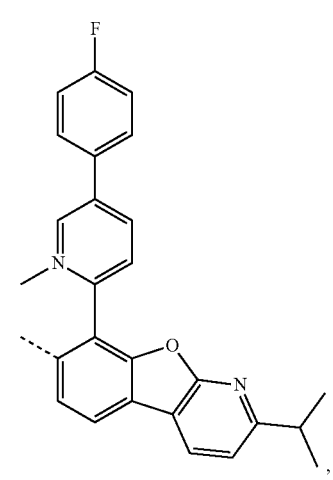
L_{A414}
34
-continued
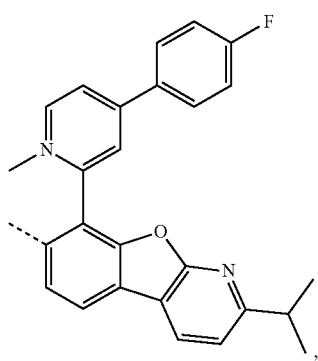
L_{A415}
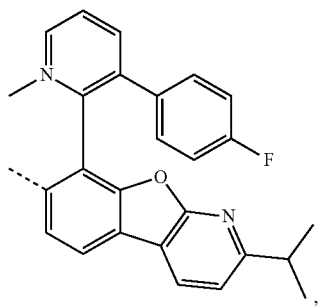
L_{A416}
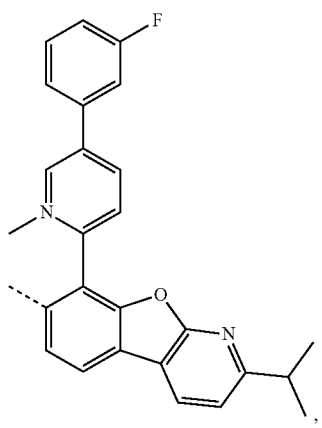
L_{A417}
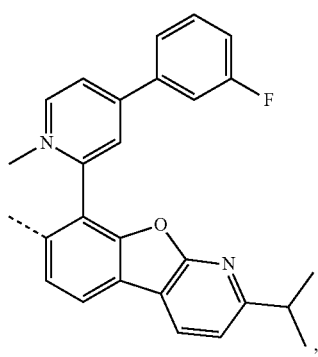
L_{A418}

L_{A419}
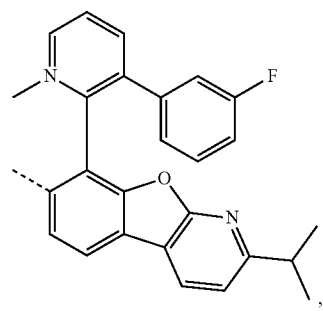
L_{A420}
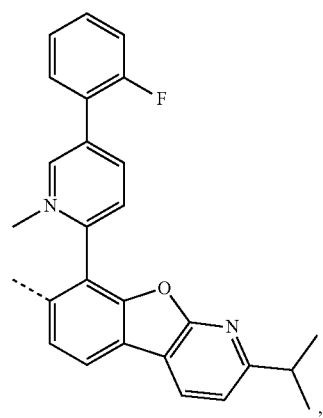
L_{A421}
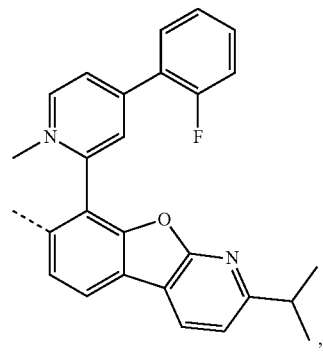
L_{A422}
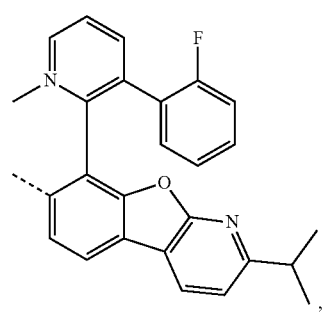
L_{A423}
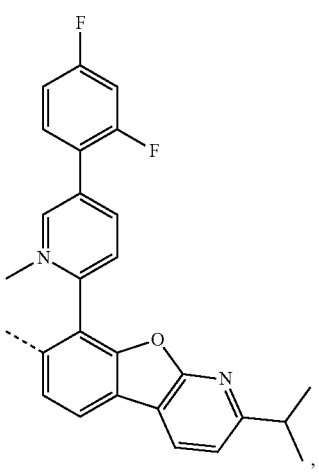
L_{A424}
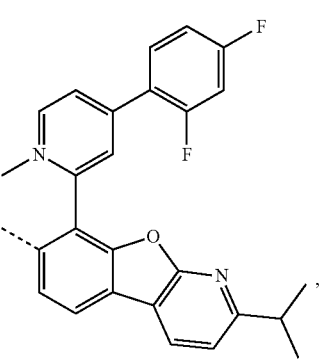
L_{A425}
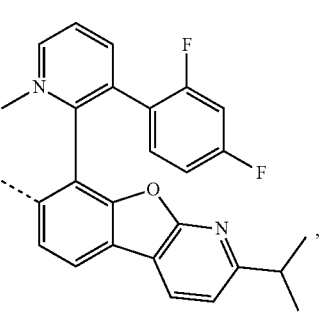
L_{A426}
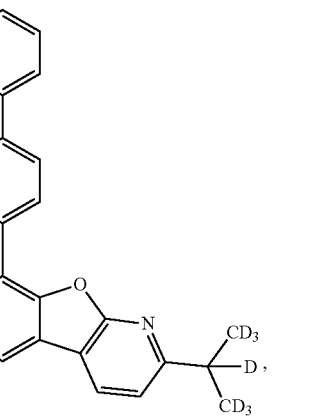

L<sub>A427</sub>
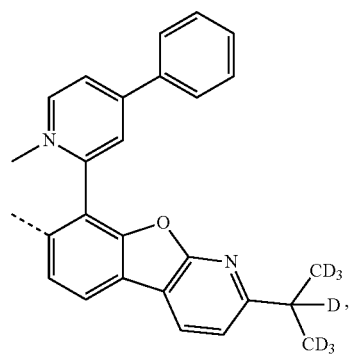
L<sub>A428</sub>
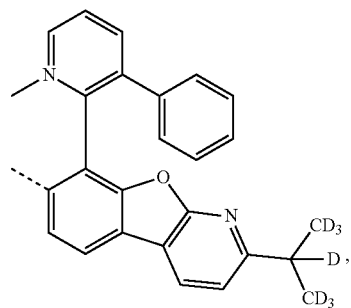
L<sub>A429</sub>
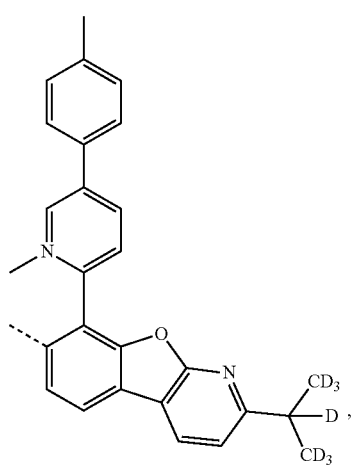
L<sub>A430</sub>
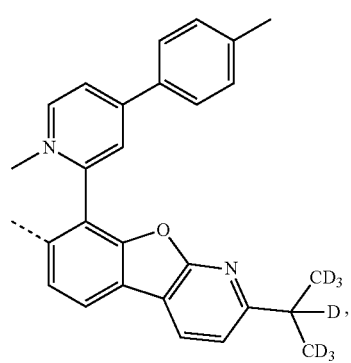
L<sub>A431</sub>
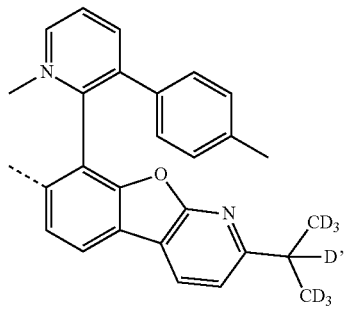
L<sub>A432</sub>
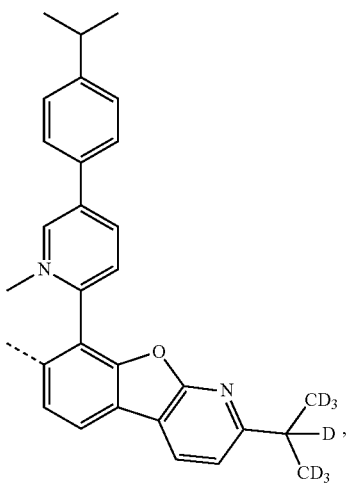
L<sub>A433</sub>
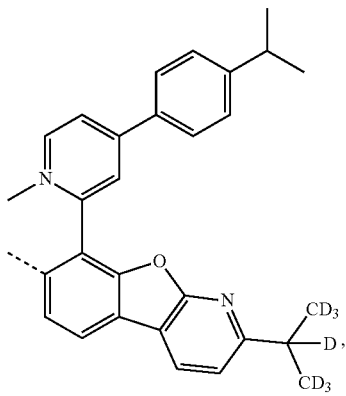
L<sub>A434</sub>
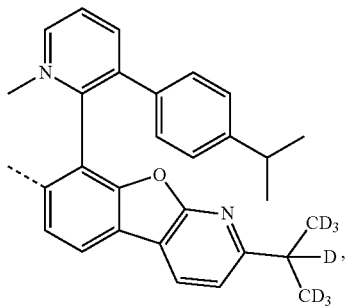

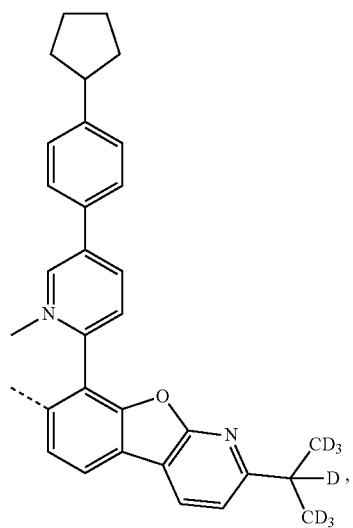
L<sub>A435</sub>
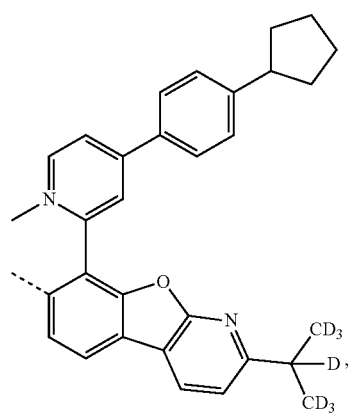
L<sub>A436</sub>
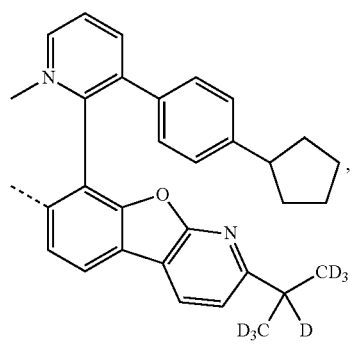
L<sub>A437</sub>
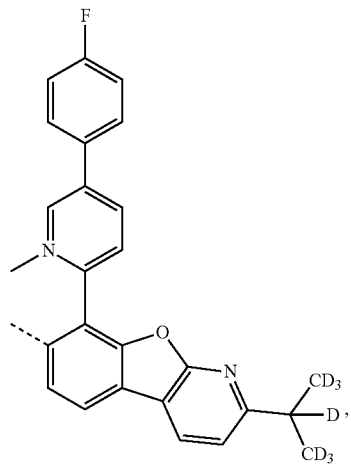
L<sub>A438</sub>
L<sub>A439</sub>
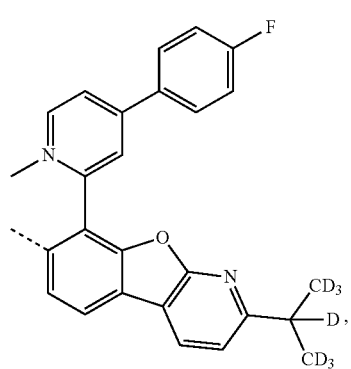
L<sub>A440</sub>
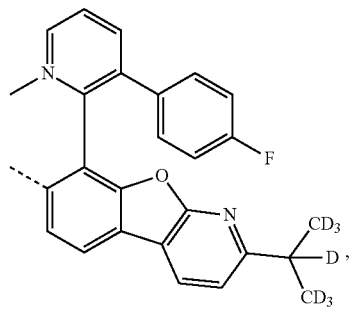
L<sub>A441</sub>

41
-continued
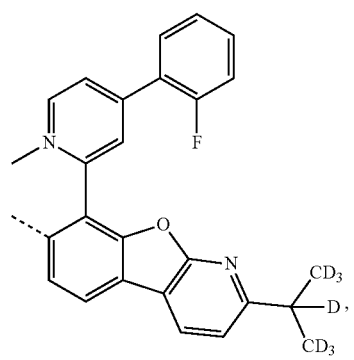
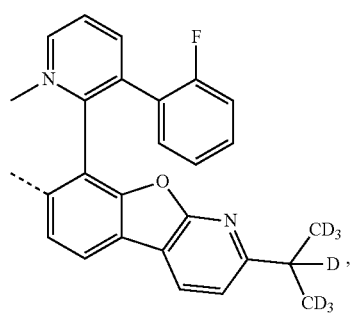 L$_{A443}$
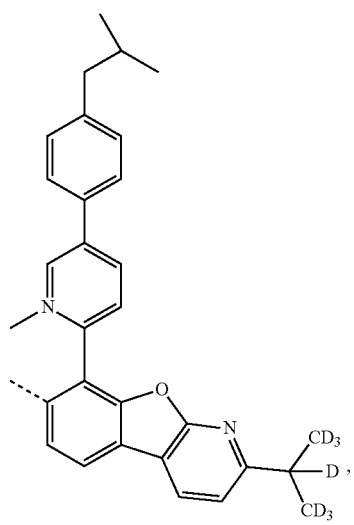 L$_{A444}$
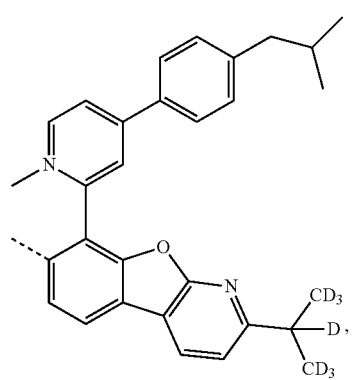 L$_{A445}$
42
-continued
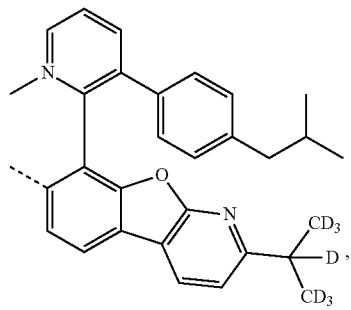 L$_{A442}$
L$_{A446}$
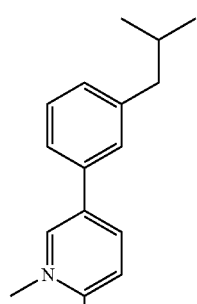 L$_{A447}$
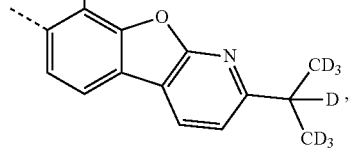
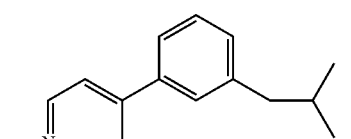 L$_{A448}$
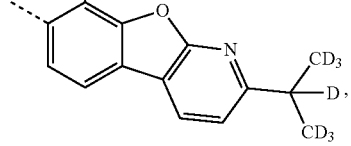
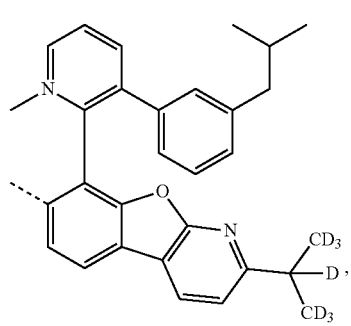 L$_{A449}$

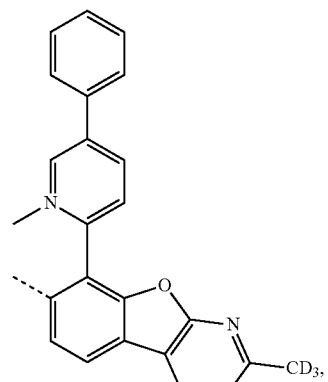
L_{A450}
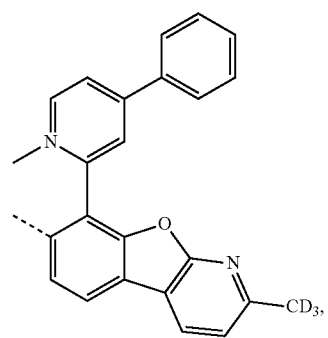
L_{A451}
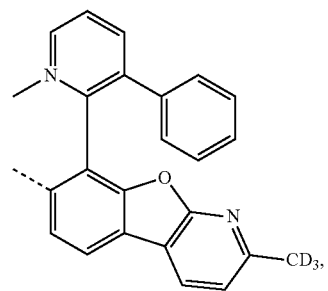
L_{A452}
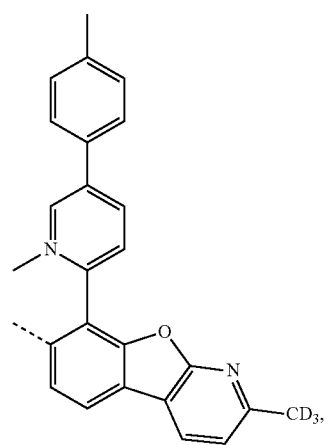
L_{A453}
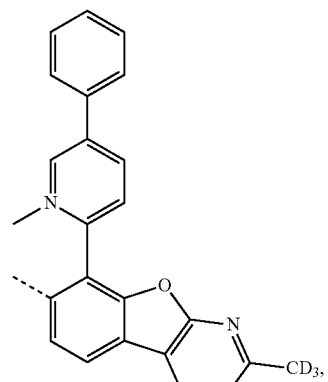
L_{A454}
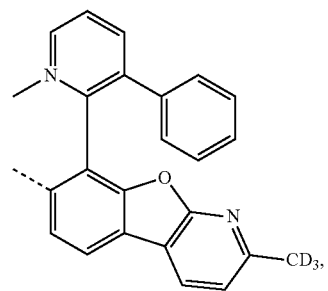
L_{A455}
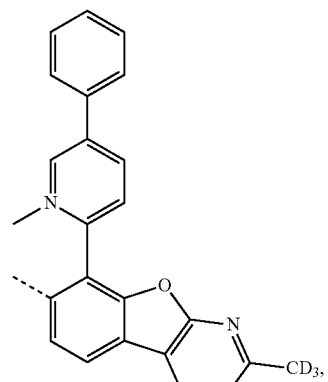
L_{A456}
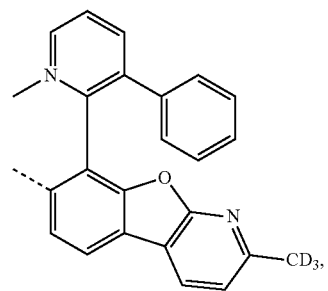
L_{A457}

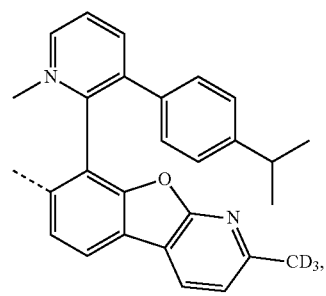
$L_{A458}$
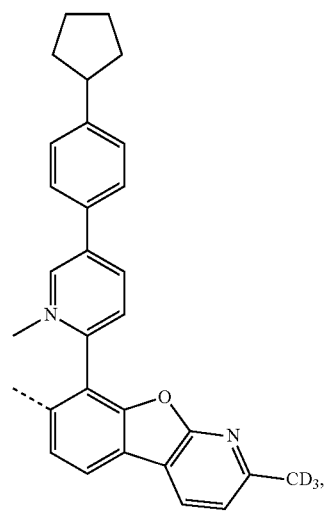
$L_{A459}$
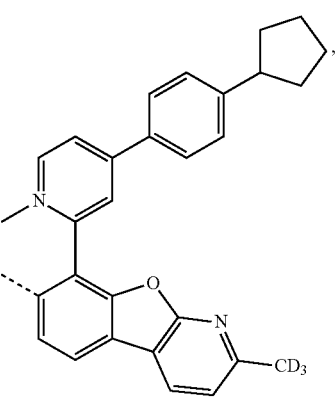
$L_{A460}$
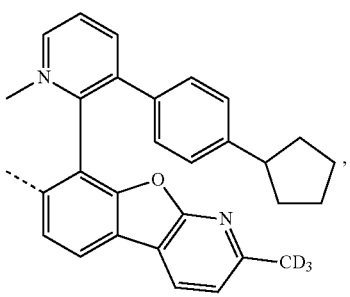
$L_{A461}$
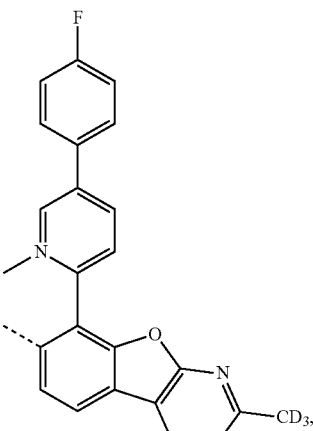
$L_{A462}$
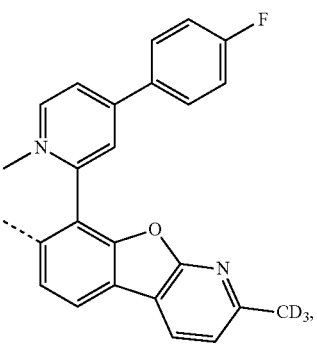
$L_{A463}$
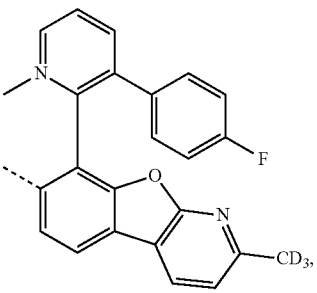
$L_{A464}$
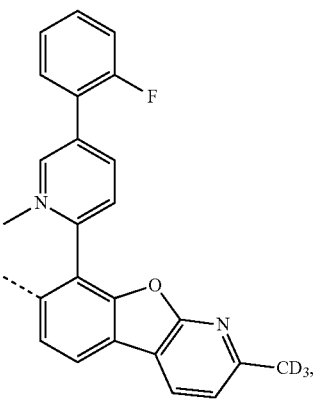
$L_{A465}$ L_A466 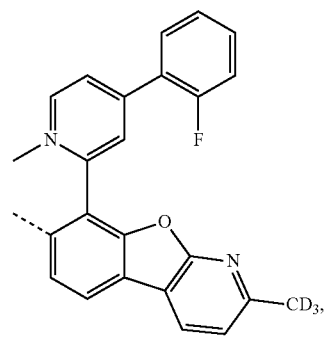
L_A467 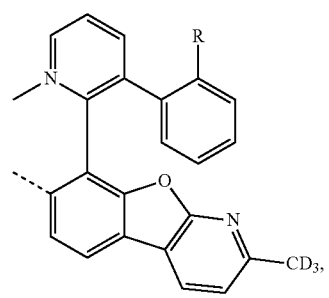
L_A468 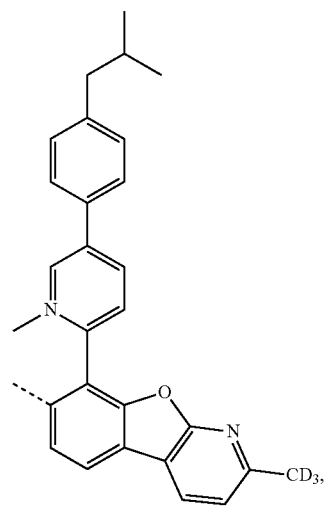
L_A469 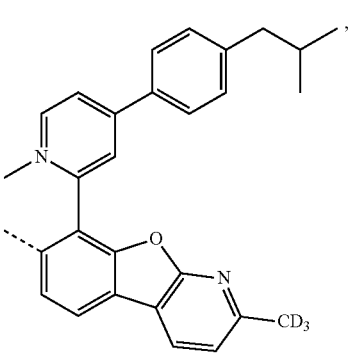
L_A470 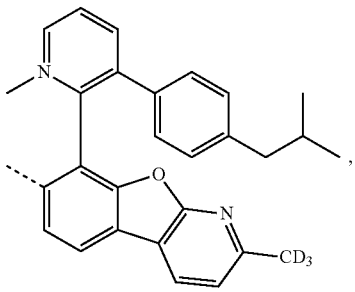
L_A471 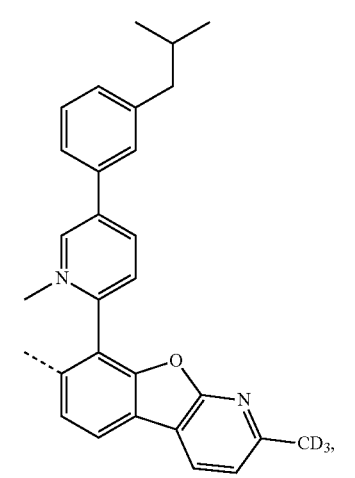
L_A472 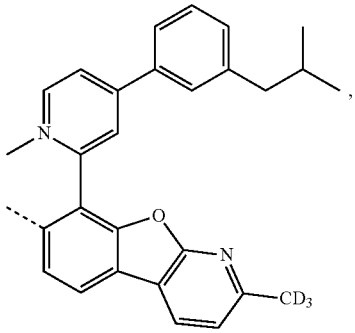
L_A473 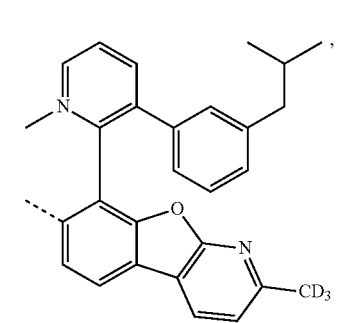

| | |
|---|---|
| L_{A474} 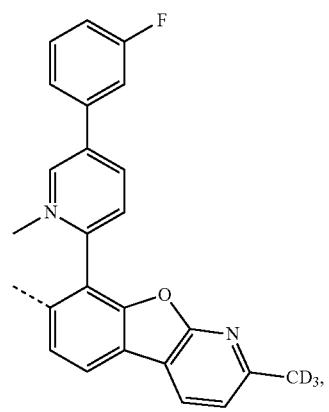 | L_{A478} 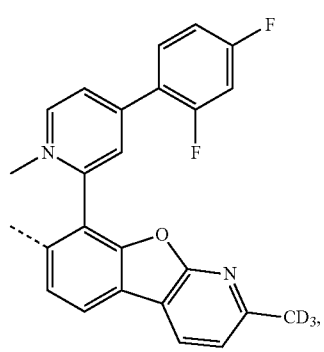 |
| L_{A475} 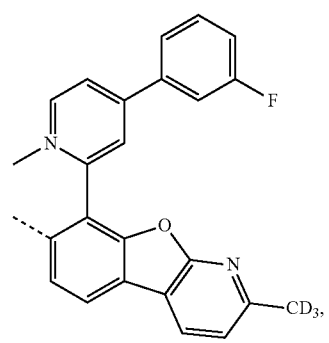 | L_{A479} 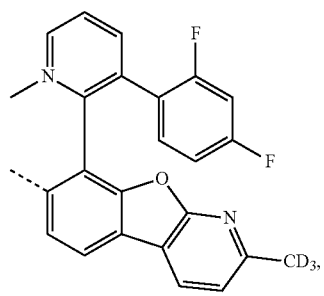 |
| L_{A476} 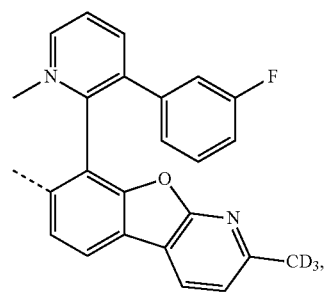 | L_{A480} 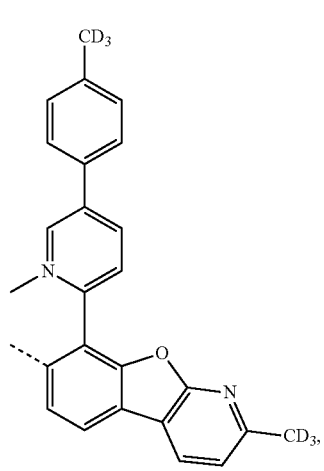 |
| L_{A477} 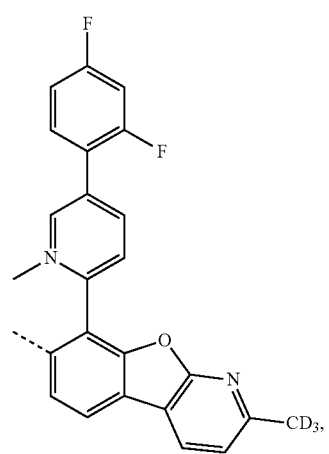 | L_{A481} 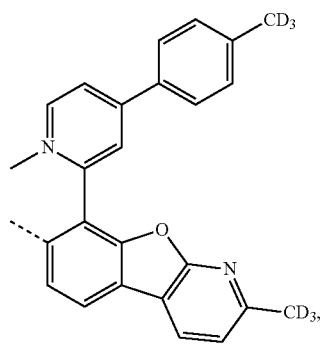 |

L<sub>A482</sub>
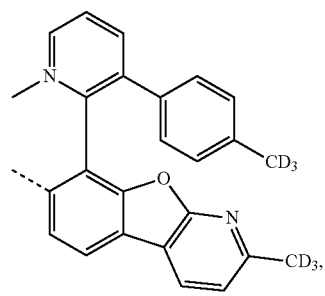
L<sub>A483</sub>
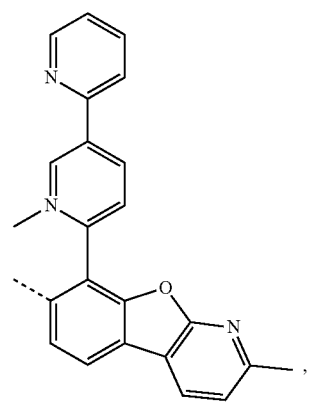
L<sub>A484</sub>
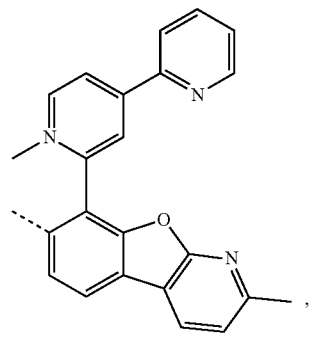
L<sub>A485</sub>
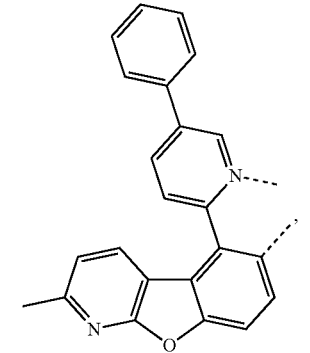
L<sub>A486</sub>
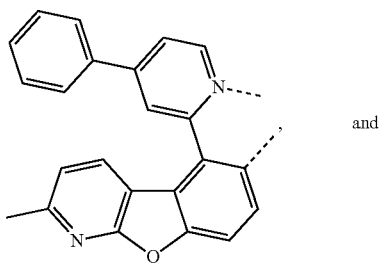
and
L<sub>A487</sub>
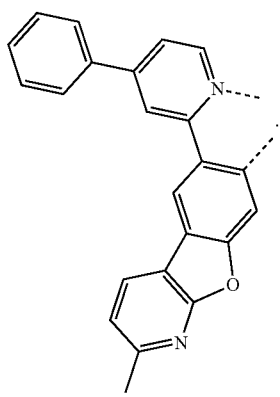
In another aspect, in the compound of Formula I, L<sub>A</sub> is selected from the group consisting of
L<sub>B1</sub>
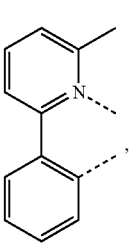
L<sub>B2</sub>
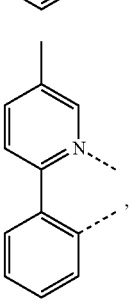
L<sub>B3</sub>

-continued

L_{B4}

L_{B5}

L_{B6}

L_{B7}

L_{B8}

L_{B9}

-continued

L_{B10}

L_{B11}

L_{B12}

L_{B13}

L_{B14}

L_{B15}

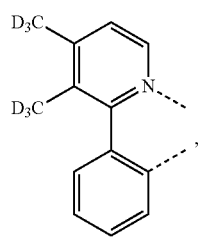     L_{B16}
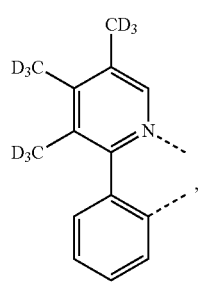     L_{B17}
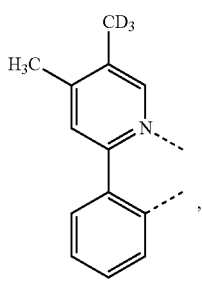     L_{B18}
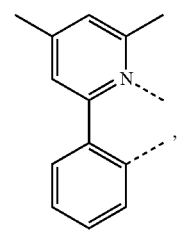     L_{B19}
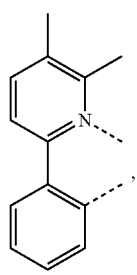     L_{B20}
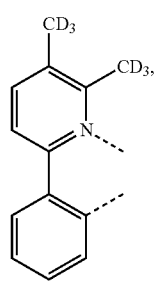     L_{B21}
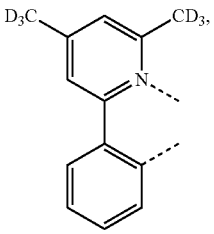     L_{B22}
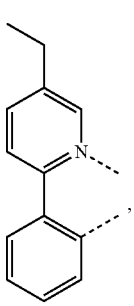     L_{B23}
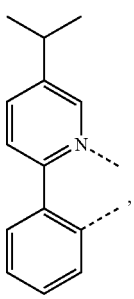     L_{B24}
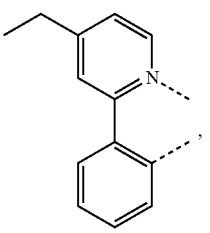    L_{B25}
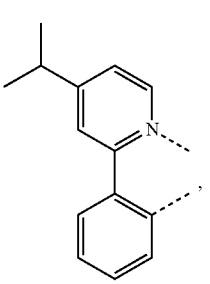    L_{B26}

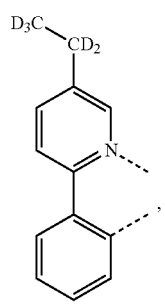 L_{B27}
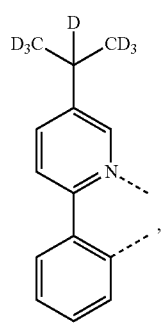 L_{B28}
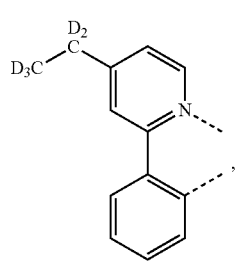 L_{B29}
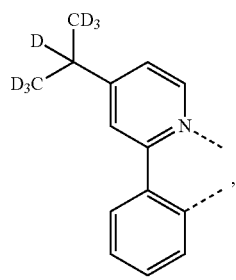 L_{B30}
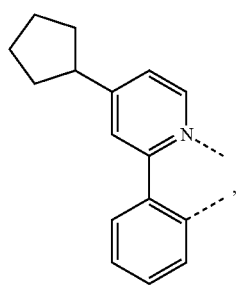 L_{B31}
 L_{B32}
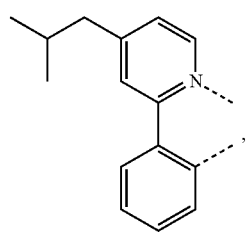 L_{B33}
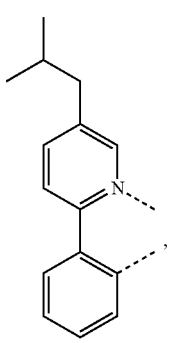 L_{B34}
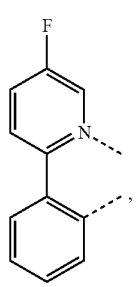 L_{B35}
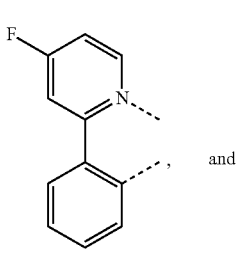 L_{B36}
and

L_{B37}

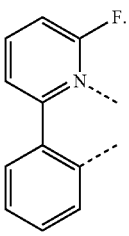

According to another aspect of the present disclosure, in the compound of Formula I, $A^1$-$A^4$ and $A^6$-$A^8$ are C, and $A^5$ is N, resulting in a compound having the structure according to Formula III

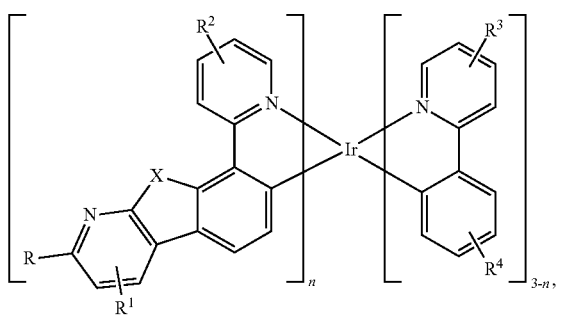

wherein R is selected from the group consisting of alkyl, cycloalkyl, and combinations thereof.

In one aspect, $R^1$ in Formula III represents mono-, di-substitution, or no substitution; $R^2$, $R^3$, and $R^4$ independently represent mono-, di-, tri-, tetra-substitution, or no substitution; any adjacent substitutions in $R^1$, $R^3$, and $R^4$ are optionally linked together to form a ring; $R^1$, $R^3$, and $R^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; $R^2$ is selected from the group consisting of aryl, substituted aryl, heteroaryl, and substituted heteroaryl; and n is an integer from 1 to 3.

In one embodiment, the compound of formula $Ir(L_A)(L_B)_2$ has one of the the formulas listed in Table 1 below:

| Compound Number | $L_A$ | $L_B$ |
|---|---|---|
| III-1 | $L_{A318}$ | $L_{B1}$ |
| III-2 | $L_{A319}$ | $L_{B1}$ |
| III-3 | $L_{A320}$ | $L_{B1}$ |
| III-4 | $L_{A321}$ | $L_{B1}$ |
| III-5 | $L_{A322}$ | $L_{B1}$ |
| III-6 | $L_{A323}$ | $L_{B1}$ |
| III-7 | $L_{A324}$ | $L_{B1}$ |
| III-8 | $L_{A325}$ | $L_{B1}$ |
| III-9 | $L_{A326}$ | $L_{B1}$ |
| III-10 | $L_{A327}$ | $L_{B1}$ |
| III-11 | $L_{A328}$ | $L_{B1}$ |
| III-12 | $L_{A329}$ | $L_{B1}$ |
| III-13 | $L_{A330}$ | $L_{B1}$ |
| III-14 | $L_{A331}$ | $L_{B1}$ |
| III-15 | $L_{A332}$ | $L_{B1}$ |
| III-16 | $L_{A333}$ | $L_{B1}$ |
| III-17 | $L_{A334}$ | $L_{B1}$ |
| III-18 | $L_{A335}$ | $L_{B1}$ |
| III-19 | $L_{A336}$ | $L_{B1}$ |
| III-20 | $L_{A337}$ | $L_{B1}$ |
| III-21 | $L_{A338}$ | $L_{B1}$ |
| III-22 | $L_{A339}$ | $L_{B1}$ |
| III-23 | $L_{A340}$ | $L_{B1}$ |
| III-24 | $L_{A341}$ | $L_{B1}$ |
| III-25 | $L_{A342}$ | $L_{B1}$ |
| III-26 | $L_{A343}$ | $L_{B1}$ |
| III-27 | $L_{A344}$ | $L_{B1}$ |
| III-28 | $L_{A345}$ | $L_{B1}$ |
| III-29 | $L_{A346}$ | $L_{B1}$ |
| III-30 | $L_{A347}$ | $L_{B1}$ |
| III-31 | $L_{A348}$ | $L_{B1}$ |
| III-32 | $L_{A349}$ | $L_{B1}$ |
| III-33 | $L_{A350}$ | $L_{B1}$ |
| III-34 | $L_{A351}$ | $L_{B1}$ |
| III-35 | $L_{A352}$ | $L_{B1}$ |
| III-36 | $L_{A353}$ | $L_{B1}$ |
| III-37 | $L_{A354}$ | $L_{B1}$ |
| III-38 | $L_{A355}$ | $L_{B1}$ |
| III-39 | $L_{A356}$ | $L_{B1}$ |
| III-40 | $L_{A357}$ | $L_{B1}$ |
| III-41 | $L_{A358}$ | $L_{B1}$ |
| III-42 | $L_{A359}$ | $L_{B1}$ |
| III-43 | $L_{A360}$ | $L_{B1}$ |
| III-44 | $L_{A361}$ | $L_{B1}$ |
| III-45 | $L_{A362}$ | $L_{B1}$ |
| III-46 | $L_{A363}$ | $L_{B1}$ |
| III-47 | $L_{A364}$ | $L_{B1}$ |
| III-48 | $L_{A365}$ | $L_{B1}$ |
| III-49 | $L_{A366}$ | $L_{B1}$ |
| III-50 | $L_{A367}$ | $L_{B1}$ |
| III-51 | $L_{A368}$ | $L_{B1}$ |
| III-52 | $L_{A369}$ | $L_{B1}$ |
| III-53 | $L_{A370}$ | $L_{B1}$ |
| III-54 | $L_{A371}$ | $L_{B1}$ |
| III-55 | $L_{A372}$ | $L_{B1}$ |
| III-56 | $L_{A373}$ | $L_{B1}$ |
| III-57 | $L_{A374}$ | $L_{B1}$ |
| III-58 | $L_{A375}$ | $L_{B1}$ |
| III-59 | $L_{A376}$ | $L_{B1}$ |
| III-60 | $L_{A377}$ | $L_{B1}$ |
| III-61 | $L_{A378}$ | $L_{B1}$ |
| III-62 | $L_{A379}$ | $L_{B1}$ |
| III-63 | $L_{A380}$ | $L_{B1}$ |
| III-64 | $L_{A381}$ | $L_{B1}$ |
| III-65 | $L_{A382}$ | $L_{B1}$ |
| III-66 | $L_{A383}$ | $L_{B1}$ |
| III-67 | $L_{A384}$ | $L_{B1}$ |
| III-68 | $L_{A385}$ | $L_{B1}$ |
| III-69 | $L_{A386}$ | $L_{B1}$ |
| III-70 | $L_{A387}$ | $L_{B1}$ |
| III-71 | $L_{A388}$ | $L_{B1}$ |
| III-72 | $L_{A389}$ | $L_{B1}$ |
| III-73 | $L_{A390}$ | $L_{B1}$ |
| III-74 | $L_{A391}$ | $L_{B1}$ |
| III-75 | $L_{A392}$ | $L_{B1}$ |
| III-76 | $L_{A393}$ | $L_{B1}$ |
| III-77 | $L_{A394}$ | $L_{B1}$ |
| III-78 | $L_{A395}$ | $L_{B1}$ |
| III-79 | $L_{A396}$ | $L_{B1}$ |
| III-80 | $L_{A397}$ | $L_{B1}$ |
| III-81 | $L_{A398}$ | $L_{B1}$ |
| III-82 | $L_{A399}$ | $L_{B1}$ |
| III-83 | $L_{A400}$ | $L_{B1}$ |
| III-84 | $L_{A401}$ | $L_{B1}$ |
| III-85 | $L_{A402}$ | $L_{B1}$ |
| III-86 | $L_{A403}$ | $L_{B1}$ |
| III-87 | $L_{A404}$ | $L_{B1}$ |
| III-88 | $L_{A405}$ | $L_{B1}$ |
| III-89 | $L_{A406}$ | $L_{B1}$ |
| III-90 | $L_{A407}$ | $L_{B1}$ |
| III-91 | $L_{A408}$ | $L_{B1}$ |
| III-92 | $L_{A409}$ | $L_{B1}$ |
| III-93 | $L_{A410}$ | $L_{B1}$ |

| Compound Number | $L_A$ | $L_B$ |
|---|---|---|
| III-94 | $L_{A411}$ | $L_{B1}$ |
| III-95 | $L_{A412}$ | $L_{B1}$ |
| III-96 | $L_{A413}$ | $L_{B1}$ |
| III-97 | $L_{A414}$ | $L_{B1}$ |
| III-98 | $L_{A415}$ | $L_{B1}$ |
| III-99 | $L_{A416}$ | $L_{B1}$ |
| III-100 | $L_{A417}$ | $L_{B1}$ |
| III-101 | $L_{A418}$ | $L_{B1}$ |
| III-102 | $L_{A419}$ | $L_{B1}$ |
| III-103 | $L_{A420}$ | $L_{B1}$ |
| III-104 | $L_{A421}$ | $L_{B1}$ |
| III-105 | $L_{A422}$ | $L_{B1}$ |
| III-106 | $L_{A423}$ | $L_{B1}$ |
| III-107 | $L_{A424}$ | $L_{B1}$ |
| III-108 | $L_{A425}$ | $L_{B1}$ |
| III-109 | $L_{A426}$ | $L_{B1}$ |
| III-110 | $L_{A427}$ | $L_{B1}$ |
| III-111 | $L_{A428}$ | $L_{B1}$ |
| III-112 | $L_{A429}$ | $L_{B1}$ |
| III-113 | $L_{A430}$ | $L_{B1}$ |
| III-114 | $L_{A431}$ | $L_{B1}$ |
| III-115 | $L_{A432}$ | $L_{B1}$ |
| III-116 | $L_{A433}$ | $L_{B1}$ |
| III-117 | $L_{A434}$ | $L_{B1}$ |
| III-118 | $L_{A435}$ | $L_{B1}$ |
| III-119 | $L_{A436}$ | $L_{B1}$ |
| III-120 | $L_{A437}$ | $L_{B1}$ |
| III-121 | $L_{A438}$ | $L_{B1}$ |
| III-122 | $L_{A439}$ | $L_{B1}$ |
| III-123 | $L_{A440}$ | $L_{B1}$ |
| III-124 | $L_{A441}$ | $L_{B1}$ |
| III-125 | $L_{A442}$ | $L_{B1}$ |
| III-126 | $L_{A443}$ | $L_{B1}$ |
| III-127 | $L_{A444}$ | $L_{B1}$ |
| III-128 | $L_{A445}$ | $L_{B1}$ |
| III-129 | $L_{A446}$ | $L_{B1}$ |
| III-130 | $L_{A447}$ | $L_{B1}$ |
| III-131 | $L_{A448}$ | $L_{B1}$ |
| III-132 | $L_{A449}$ | $L_{B1}$ |
| III-133 | $L_{A450}$ | $L_{B1}$ |
| III-134 | $L_{A451}$ | $L_{B1}$ |
| III-135 | $L_{A452}$ | $L_{B1}$ |
| III-136 | $L_{A453}$ | $L_{B1}$ |
| III-137 | $L_{A454}$ | $L_{B1}$ |
| III-138 | $L_{A455}$ | $L_{B1}$ |
| III-139 | $L_{A456}$ | $L_{B1}$ |
| III-140 | $L_{A457}$ | $L_{B1}$ |
| III-141 | $L_{A458}$ | $L_{B1}$ |
| III-142 | $L_{A459}$ | $L_{B1}$ |
| III-143 | $L_{A460}$ | $L_{B1}$ |
| III-144 | $L_{A461}$ | $L_{B1}$ |
| III-145 | $L_{A462}$ | $L_{B1}$ |
| III-146 | $L_{A463}$ | $L_{B1}$ |
| III-147 | $L_{A464}$ | $L_{B1}$ |
| III-148 | $L_{A465}$ | $L_{B1}$ |
| III-149 | $L_{A466}$ | $L_{B1}$ |
| III-150 | $L_{A467}$ | $L_{B1}$ |
| III-151 | $L_{A468}$ | $L_{B1}$ |
| III-152 | $L_{A469}$ | $L_{B1}$ |
| III-153 | $L_{A470}$ | $L_{B1}$ |
| III-154 | $L_{A471}$ | $L_{B1}$ |
| III-155 | $L_{A472}$ | $L_{B1}$ |
| III-156 | $L_{A473}$ | $L_{B1}$ |
| III-157 | $L_{A474}$ | $L_{B1}$ |
| III-158 | $L_{A475}$ | $L_{B1}$ |
| III-159 | $L_{A476}$ | $L_{B1}$ |
| III-160 | $L_{A477}$ | $L_{B1}$ |
| III-161 | $L_{A478}$ | $L_{B1}$ |
| III-162 | $L_{A479}$ | $L_{B1}$ |
| III-163 | $L_{A480}$ | $L_{B1}$ |
| III-164 | $L_{A481}$ | $L_{B1}$ |
| III-165 | $L_{A482}$ | $L_{B1}$ |
| III-166 | $L_{A483}$ | $L_{B1}$ |
| III-167 | $L_{A484}$ | $L_{B1}$ |
| III-168 | $L_{A485}$ | $L_{B1}$ |
| III-169 | $L_{A486}$ | $L_{B1}$ |
| III-170 | $L_{A487}$ | $L_{B1}$ |
| III-171 | $L_{A318}$ | $L_{B2}$ |
| III-172 | $L_{A319}$ | $L_{B2}$ |
| III-173 | $L_{A320}$ | $L_{B2}$ |
| III-174 | $L_{A321}$ | $L_{B2}$ |
| III-175 | $L_{A322}$ | $L_{B2}$ |
| III-176 | $L_{A323}$ | $L_{B2}$ |
| III-177 | $L_{A324}$ | $L_{B2}$ |
| III-178 | $L_{A325}$ | $L_{B2}$ |
| III-179 | $L_{A326}$ | $L_{B2}$ |
| III-180 | $L_{A327}$ | $L_{B2}$ |
| III-181 | $L_{A328}$ | $L_{B2}$ |
| III-182 | $L_{A329}$ | $L_{B2}$ |
| III-183 | $L_{A330}$ | $L_{B2}$ |
| III-184 | $L_{A331}$ | $L_{B2}$ |
| III-185 | $L_{A332}$ | $L_{B2}$ |
| III-186 | $L_{A333}$ | $L_{B2}$ |
| III-187 | $L_{A334}$ | $L_{B2}$ |
| III-188 | $L_{A335}$ | $L_{B2}$ |
| III-189 | $L_{A336}$ | $L_{B2}$ |
| III-190 | $L_{A337}$ | $L_{B2}$ |
| III-191 | $L_{A338}$ | $L_{B2}$ |
| III-192 | $L_{A339}$ | $L_{B2}$ |
| III-193 | $L_{A340}$ | $L_{B2}$ |
| III-194 | $L_{A341}$ | $L_{B2}$ |
| III-195 | $L_{A342}$ | $L_{B2}$ |
| III-196 | $L_{A343}$ | $L_{B2}$ |
| III-197 | $L_{A344}$ | $L_{B2}$ |
| III-198 | $L_{A345}$ | $L_{B2}$ |
| III-199 | $L_{A346}$ | $L_{B2}$ |
| III-200 | $L_{A347}$ | $L_{B2}$ |
| III-201 | $L_{A348}$ | $L_{B2}$ |
| III-202 | $L_{A349}$ | $L_{B2}$ |
| III-203 | $L_{A350}$ | $L_{B2}$ |
| III-204 | $L_{A351}$ | $L_{B2}$ |
| III-205 | $L_{A352}$ | $L_{B2}$ |
| III-206 | $L_{A353}$ | $L_{B2}$ |
| III-207 | $L_{A354}$ | $L_{B2}$ |
| III-208 | $L_{A355}$ | $L_{B2}$ |
| III-209 | $L_{A356}$ | $L_{B2}$ |
| III-210 | $L_{A357}$ | $L_{B2}$ |
| III-211 | $L_{A358}$ | $L_{B2}$ |
| III-212 | $L_{A359}$ | $L_{B2}$ |
| III-213 | $L_{A360}$ | $L_{B2}$ |
| III-214 | $L_{A361}$ | $L_{B2}$ |
| III-215 | $L_{A362}$ | $L_{B2}$ |
| III-216 | $L_{A363}$ | $L_{B2}$ |
| III-217 | $L_{A364}$ | $L_{B2}$ |
| III-218 | $L_{A365}$ | $L_{B2}$ |
| III-219 | $L_{A366}$ | $L_{B2}$ |
| III-220 | $L_{A367}$ | $L_{B2}$ |
| III-221 | $L_{A368}$ | $L_{B2}$ |
| III-222 | $L_{A369}$ | $L_{B2}$ |
| III-223 | $L_{A370}$ | $L_{B2}$ |
| III-224 | $L_{A371}$ | $L_{B2}$ |
| III-225 | $L_{A372}$ | $L_{B2}$ |
| III-226 | $L_{A373}$ | $L_{B2}$ |
| III-227 | $L_{A374}$ | $L_{B2}$ |
| III-228 | $L_{A375}$ | $L_{B2}$ |
| III-229 | $L_{A376}$ | $L_{B2}$ |
| III-230 | $L_{A377}$ | $L_{B2}$ |
| III-231 | $L_{A378}$ | $L_{B2}$ |
| III-232 | $L_{A379}$ | $L_{B2}$ |
| III-233 | $L_{A380}$ | $L_{B2}$ |
| III-234 | $L_{A381}$ | $L_{B2}$ |
| III-235 | $L_{A382}$ | $L_{B2}$ |
| III-236 | $L_{A383}$ | $L_{B2}$ |
| III-237 | $L_{A384}$ | $L_{B2}$ |
| III-238 | $L_{A385}$ | $L_{B2}$ |
| III-239 | $L_{A386}$ | $L_{B2}$ |
| III-240 | $L_{A387}$ | $L_{B2}$ |
| III-241 | $L_{A388}$ | $L_{B2}$ |
| III-242 | $L_{A389}$ | $L_{B2}$ |
| III-243 | $L_{A390}$ | $L_{B2}$ |
| III-244 | $L_{A391}$ | $L_{B2}$ |
| III-245 | $L_{A392}$ | $L_{B2}$ |

| Compound Number | $L_A$ | $L_B$ |
|---|---|---|
| III-246 | $L_{A393}$ | $L_{B2}$ |
| III-247 | $L_{A394}$ | $L_{B2}$ |
| III-248 | $L_{A395}$ | $L_{B2}$ |
| III-249 | $L_{A396}$ | $L_{B2}$ |
| III-250 | $L_{A397}$ | $L_{B2}$ |
| III-251 | $L_{A398}$ | $L_{B2}$ |
| III-252 | $L_{A399}$ | $L_{B2}$ |
| III-253 | $L_{A400}$ | $L_{B2}$ |
| III-254 | $L_{A401}$ | $L_{B2}$ |
| III-255 | $L_{A402}$ | $L_{B2}$ |
| III-256 | $L_{A403}$ | $L_{B2}$ |
| III-257 | $L_{A404}$ | $L_{B2}$ |
| III-258 | $L_{A405}$ | $L_{B2}$ |
| III-259 | $L_{A406}$ | $L_{B2}$ |
| III-260 | $L_{A407}$ | $L_{B2}$ |
| III-261 | $L_{A408}$ | $L_{B2}$ |
| III-262 | $L_{A409}$ | $L_{B2}$ |
| III-263 | $L_{A410}$ | $L_{B2}$ |
| III-264 | $L_{A411}$ | $L_{B2}$ |
| III-265 | $L_{A412}$ | $L_{B2}$ |
| III-266 | $L_{A413}$ | $L_{B2}$ |
| III-267 | $L_{A414}$ | $L_{B2}$ |
| III-268 | $L_{A415}$ | $L_{B2}$ |
| III-269 | $L_{A416}$ | $L_{B2}$ |
| III-270 | $L_{A417}$ | $L_{B2}$ |
| III-271 | $L_{A418}$ | $L_{B2}$ |
| III-272 | $L_{A419}$ | $L_{B2}$ |
| III-273 | $L_{A420}$ | $L_{B2}$ |
| III-274 | $L_{A421}$ | $L_{B2}$ |
| III-275 | $L_{A422}$ | $L_{B2}$ |
| III-276 | $L_{A423}$ | $L_{B2}$ |
| III-277 | $L_{A424}$ | $L_{B2}$ |
| III-278 | $L_{A425}$ | $L_{B2}$ |
| III-279 | $L_{A426}$ | $L_{B2}$ |
| III-280 | $L_{A427}$ | $L_{B2}$ |
| III-281 | $L_{A428}$ | $L_{B2}$ |
| III-282 | $L_{A429}$ | $L_{B2}$ |
| III-283 | $L_{A430}$ | $L_{B2}$ |
| III-284 | $L_{A431}$ | $L_{B2}$ |
| III-285 | $L_{A432}$ | $L_{B2}$ |
| III-286 | $L_{A433}$ | $L_{B2}$ |
| III-287 | $L_{A434}$ | $L_{B2}$ |
| III-288 | $L_{A435}$ | $L_{B2}$ |
| III-289 | $L_{A436}$ | $L_{B2}$ |
| III-290 | $L_{A437}$ | $L_{B2}$ |
| III-291 | $L_{A438}$ | $L_{B2}$ |
| III-292 | $L_{A439}$ | $L_{B2}$ |
| III-293 | $L_{A440}$ | $L_{B2}$ |
| III-294 | $L_{A441}$ | $L_{B2}$ |
| III-295 | $L_{A442}$ | $L_{B2}$ |
| III-296 | $L_{A443}$ | $L_{B2}$ |
| III-297 | $L_{A444}$ | $L_{B2}$ |
| III-298 | $L_{A445}$ | $L_{B2}$ |
| III-299 | $L_{A446}$ | $L_{B2}$ |
| III-300 | $L_{A447}$ | $L_{B2}$ |
| III-301 | $L_{A448}$ | $L_{B2}$ |
| III-302 | $L_{A449}$ | $L_{B2}$ |
| III-303 | $L_{A450}$ | $L_{B2}$ |
| III-304 | $L_{A451}$ | $L_{B2}$ |
| III-305 | $L_{A452}$ | $L_{B2}$ |
| III-306 | $L_{A453}$ | $L_{B2}$ |
| III-307 | $L_{A454}$ | $L_{B2}$ |
| III-308 | $L_{A455}$ | $L_{B2}$ |
| III-309 | $L_{A456}$ | $L_{B2}$ |
| III-310 | $L_{A457}$ | $L_{B2}$ |
| III-311 | $L_{A458}$ | $L_{B2}$ |
| III-312 | $L_{A459}$ | $L_{B2}$ |
| III-313 | $L_{A460}$ | $L_{B2}$ |
| III-314 | $L_{A461}$ | $L_{B2}$ |
| III-315 | $L_{A462}$ | $L_{B2}$ |
| III-316 | $L_{A463}$ | $L_{B2}$ |
| III-317 | $L_{A464}$ | $L_{B2}$ |
| III-318 | $L_{A465}$ | $L_{B2}$ |
| III-319 | $L_{A466}$ | $L_{B2}$ |
| III-320 | $L_{A467}$ | $L_{B2}$ |
| III-321 | $L_{A468}$ | $L_{B2}$ |
| III-322 | $L_{A469}$ | $L_{B2}$ |
| III-323 | $L_{A470}$ | $L_{B2}$ |
| III-324 | $L_{A471}$ | $L_{B2}$ |
| III-325 | $L_{A472}$ | $L_{B2}$ |
| III-326 | $L_{A473}$ | $L_{B2}$ |
| III-327 | $L_{A474}$ | $L_{B2}$ |
| III-328 | $L_{A475}$ | $L_{B2}$ |
| III-329 | $L_{A476}$ | $L_{B2}$ |
| III-330 | $L_{A477}$ | $L_{B2}$ |
| III-331 | $L_{A478}$ | $L_{B2}$ |
| III-332 | $L_{A479}$ | $L_{B2}$ |
| III-333 | $L_{A480}$ | $L_{B2}$ |
| III-334 | $L_{A481}$ | $L_{B2}$ |
| III-335 | $L_{A482}$ | $L_{B2}$ |
| III-336 | $L_{A483}$ | $L_{B2}$ |
| III-337 | $L_{A484}$ | $L_{B2}$ |
| III-338 | $L_{A485}$ | $L_{B2}$ |
| III-339 | $L_{A486}$ | $L_{B2}$ |
| III-340 | $L_{A487}$ | $L_{B2}$ |
| III-341 | $L_{A318}$ | $L_{B3}$ |
| III-342 | $L_{A319}$ | $L_{B3}$ |
| III-343 | $L_{A320}$ | $L_{B3}$ |
| III-344 | $L_{A321}$ | $L_{B3}$ |
| III-345 | $L_{A322}$ | $L_{B3}$ |
| III-346 | $L_{A323}$ | $L_{B3}$ |
| III-347 | $L_{A324}$ | $L_{B3}$ |
| III-348 | $L_{A325}$ | $L_{B3}$ |
| III-349 | $L_{A326}$ | $L_{B3}$ |
| III-350 | $L_{A327}$ | $L_{B3}$ |
| III-351 | $L_{A328}$ | $L_{B3}$ |
| III-352 | $L_{A329}$ | $L_{B3}$ |
| III-353 | $L_{A330}$ | $L_{B3}$ |
| III-354 | $L_{A331}$ | $L_{B3}$ |
| III-355 | $L_{A332}$ | $L_{B3}$ |
| III-356 | $L_{A333}$ | $L_{B3}$ |
| III-357 | $L_{A334}$ | $L_{B3}$ |
| III-358 | $L_{A335}$ | $L_{B3}$ |
| III-359 | $L_{A336}$ | $L_{B3}$ |
| III-360 | $L_{A337}$ | $L_{B3}$ |
| III-361 | $L_{A338}$ | $L_{B3}$ |
| III-362 | $L_{A339}$ | $L_{B3}$ |
| III-363 | $L_{A340}$ | $L_{B3}$ |
| III-364 | $L_{A341}$ | $L_{B3}$ |
| III-365 | $L_{A342}$ | $L_{B3}$ |
| III-366 | $L_{A343}$ | $L_{B3}$ |
| III-367 | $L_{A344}$ | $L_{B3}$ |
| III-368 | $L_{A345}$ | $L_{B3}$ |
| III-369 | $L_{A346}$ | $L_{B3}$ |
| III-370 | $L_{A347}$ | $L_{B3}$ |
| III-371 | $L_{A348}$ | $L_{B3}$ |
| III-372 | $L_{A349}$ | $L_{B3}$ |
| III-373 | $L_{A350}$ | $L_{B3}$ |
| III-374 | $L_{A351}$ | $L_{B3}$ |
| III-375 | $L_{A352}$ | $L_{B3}$ |
| III-376 | $L_{A353}$ | $L_{B3}$ |
| III-377 | $L_{A354}$ | $L_{B3}$ |
| III-378 | $L_{A355}$ | $L_{B3}$ |
| III-379 | $L_{A356}$ | $L_{B3}$ |
| III-380 | $L_{A357}$ | $L_{B3}$ |
| III-381 | $L_{A358}$ | $L_{B3}$ |
| III-382 | $L_{A359}$ | $L_{B3}$ |
| III-383 | $L_{A360}$ | $L_{B3}$ |
| III-384 | $L_{A361}$ | $L_{B3}$ |
| III-385 | $L_{A362}$ | $L_{B3}$ |
| III-386 | $L_{A363}$ | $L_{B3}$ |
| III-387 | $L_{A364}$ | $L_{B3}$ |
| III-388 | $L_{A365}$ | $L_{B3}$ |
| III-389 | $L_{A366}$ | $L_{B3}$ |
| III-390 | $L_{A367}$ | $L_{B3}$ |
| III-391 | $L_{A368}$ | $L_{B3}$ |
| III-392 | $L_{A369}$ | $L_{B3}$ |
| III-393 | $L_{A370}$ | $L_{B3}$ |
| III-394 | $L_{A371}$ | $L_{B3}$ |
| III-395 | $L_{A372}$ | $L_{B3}$ |
| III-396 | $L_{A373}$ | $L_{B3}$ |
| III-397 | $L_{A374}$ | $L_{B3}$ |

| Compound Number | $L_A$ | $L_B$ |
|---|---|---|
| III-398 | $L_{A375}$ | $L_{B3}$ |
| III-399 | $L_{A376}$ | $L_{B3}$ |
| III-400 | $L_{A377}$ | $L_{B3}$ |
| III-401 | $L_{A378}$ | $L_{B3}$ |
| III-402 | $L_{A379}$ | $L_{B3}$ |
| III-403 | $L_{A380}$ | $L_{B3}$ |
| III-404 | $L_{A381}$ | $L_{B3}$ |
| III-405 | $L_{A382}$ | $L_{B3}$ |
| III-406 | $L_{A383}$ | $L_{B3}$ |
| III-407 | $L_{A384}$ | $L_{B3}$ |
| III-408 | $L_{A385}$ | $L_{B3}$ |
| III-409 | $L_{A386}$ | $L_{B3}$ |
| III-410 | $L_{A387}$ | $L_{B3}$ |
| III-411 | $L_{A388}$ | $L_{B3}$ |
| III-412 | $L_{A389}$ | $L_{B3}$ |
| III-413 | $L_{A390}$ | $L_{B3}$ |
| III-414 | $L_{A391}$ | $L_{B3}$ |
| III-415 | $L_{A392}$ | $L_{B3}$ |
| III-416 | $L_{A393}$ | $L_{B3}$ |
| III-417 | $L_{A394}$ | $L_{B3}$ |
| III-418 | $L_{A395}$ | $L_{B3}$ |
| III-419 | $L_{A396}$ | $L_{B3}$ |
| III-420 | $L_{A397}$ | $L_{B3}$ |
| III-421 | $L_{A398}$ | $L_{B3}$ |
| III-422 | $L_{A399}$ | $L_{B3}$ |
| III-423 | $L_{A400}$ | $L_{B3}$ |
| III-424 | $L_{A401}$ | $L_{B3}$ |
| III-425 | $L_{A402}$ | $L_{B3}$ |
| III-426 | $L_{A403}$ | $L_{B3}$ |
| III-427 | $L_{A404}$ | $L_{B3}$ |
| III-428 | $L_{A405}$ | $L_{B3}$ |
| III-429 | $L_{A406}$ | $L_{B3}$ |
| III-430 | $L_{A407}$ | $L_{B3}$ |
| III-431 | $L_{A408}$ | $L_{B3}$ |
| III-432 | $L_{A409}$ | $L_{B3}$ |
| III-433 | $L_{A410}$ | $L_{B3}$ |
| III-434 | $L_{A411}$ | $L_{B3}$ |
| III-435 | $L_{A412}$ | $L_{B3}$ |
| III-436 | $L_{A413}$ | $L_{B3}$ |
| III-437 | $L_{A414}$ | $L_{B3}$ |
| III-438 | $L_{A415}$ | $L_{B3}$ |
| III-439 | $L_{A416}$ | $L_{B3}$ |
| III-440 | $L_{A417}$ | $L_{B3}$ |
| III-441 | $L_{A418}$ | $L_{B3}$ |
| III-442 | $L_{A419}$ | $L_{B3}$ |
| III-443 | $L_{A420}$ | $L_{B3}$ |
| III-444 | $L_{A421}$ | $L_{B3}$ |
| III-445 | $L_{A422}$ | $L_{B3}$ |
| III-446 | $L_{A423}$ | $L_{B3}$ |
| III-447 | $L_{A424}$ | $L_{B3}$ |
| III-448 | $L_{A425}$ | $L_{B3}$ |
| III-449 | $L_{A426}$ | $L_{B3}$ |
| III-450 | $L_{A427}$ | $L_{B3}$ |
| III-451 | $L_{A428}$ | $L_{B3}$ |
| III-452 | $L_{A429}$ | $L_{B3}$ |
| III-453 | $L_{A430}$ | $L_{B3}$ |
| III-454 | $L_{A431}$ | $L_{B3}$ |
| III-455 | $L_{A432}$ | $L_{B3}$ |
| III-456 | $L_{A433}$ | $L_{B3}$ |
| III-457 | $L_{A434}$ | $L_{B3}$ |
| III-458 | $L_{A435}$ | $L_{B3}$ |
| III-459 | $L_{A436}$ | $L_{B3}$ |
| III-460 | $L_{A437}$ | $L_{B3}$ |
| III-461 | $L_{A438}$ | $L_{B3}$ |
| III-462 | $L_{A439}$ | $L_{B3}$ |
| III-463 | $L_{A440}$ | $L_{B3}$ |
| III-464 | $L_{A441}$ | $L_{B3}$ |
| III-465 | $L_{A442}$ | $L_{B3}$ |
| III-466 | $L_{A443}$ | $L_{B3}$ |
| III-467 | $L_{A444}$ | $L_{B3}$ |
| III-468 | $L_{A445}$ | $L_{B3}$ |
| III-469 | $L_{A446}$ | $L_{B3}$ |
| III-470 | $L_{A447}$ | $L_{B3}$ |
| III-471 | $L_{A448}$ | $L_{B3}$ |
| III-472 | $L_{A449}$ | $L_{B3}$ |
| III-473 | $L_{A450}$ | $L_{B3}$ |
| III-474 | $L_{A451}$ | $L_{B3}$ |
| III-475 | $L_{A452}$ | $L_{B3}$ |
| III-476 | $L_{A453}$ | $L_{B3}$ |
| III-477 | $L_{A454}$ | $L_{B3}$ |
| III-478 | $L_{A455}$ | $L_{B3}$ |
| III-479 | $L_{A456}$ | $L_{B3}$ |
| III-480 | $L_{A457}$ | $L_{B3}$ |
| III-481 | $L_{A458}$ | $L_{B3}$ |
| III-482 | $L_{A459}$ | $L_{B3}$ |
| III-483 | $L_{A460}$ | $L_{B3}$ |
| III-484 | $L_{A461}$ | $L_{B3}$ |
| III-485 | $L_{A462}$ | $L_{B3}$ |
| III-486 | $L_{A463}$ | $L_{B3}$ |
| III-487 | $L_{A464}$ | $L_{B3}$ |
| III-488 | $L_{A465}$ | $L_{B3}$ |
| III-489 | $L_{A466}$ | $L_{B3}$ |
| III-490 | $L_{A467}$ | $L_{B3}$ |
| III-491 | $L_{A468}$ | $L_{B3}$ |
| III-492 | $L_{A469}$ | $L_{B3}$ |
| III-493 | $L_{A470}$ | $L_{B3}$ |
| III-494 | $L_{A471}$ | $L_{B3}$ |
| III-495 | $L_{A472}$ | $L_{B3}$ |
| III-496 | $L_{A473}$ | $L_{B3}$ |
| III-497 | $L_{A474}$ | $L_{B3}$ |
| III-498 | $L_{A475}$ | $L_{B3}$ |
| III-499 | $L_{A476}$ | $L_{B3}$ |
| III-500 | $L_{A477}$ | $L_{B3}$ |
| III-501 | $L_{A478}$ | $L_{B3}$ |
| III-502 | $L_{A479}$ | $L_{B3}$ |
| III-503 | $L_{A480}$ | $L_{B3}$ |
| III-504 | $L_{A481}$ | $L_{B3}$ |
| III-505 | $L_{A482}$ | $L_{B3}$ |
| III-506 | $L_{A483}$ | $L_{B3}$ |
| III-507 | $L_{A484}$ | $L_{B3}$ |
| III-508 | $L_{A485}$ | $L_{B3}$ |
| III-509 | $L_{A486}$ | $L_{B3}$ |
| III-510 | $L_{A487}$ | $L_{B3}$ |
| III-511 | $L_{A318}$ | $L_{B4}$ |
| III-512 | $L_{A319}$ | $L_{B4}$ |
| III-513 | $L_{A320}$ | $L_{B4}$ |
| III-514 | $L_{A321}$ | $L_{B4}$ |
| III-515 | $L_{A322}$ | $L_{B4}$ |
| III-516 | $L_{A323}$ | $L_{B4}$ |
| III-517 | $L_{A324}$ | $L_{B4}$ |
| III-518 | $L_{A325}$ | $L_{B4}$ |
| III-519 | $L_{A326}$ | $L_{B4}$ |
| III-520 | $L_{A327}$ | $L_{B4}$ |
| III-521 | $L_{A328}$ | $L_{B4}$ |
| III-522 | $L_{A329}$ | $L_{B4}$ |
| III-523 | $L_{A330}$ | $L_{B4}$ |
| III-524 | $L_{A331}$ | $L_{B4}$ |
| III-525 | $L_{A332}$ | $L_{B4}$ |
| III-526 | $L_{A333}$ | $L_{B4}$ |
| III-527 | $L_{A334}$ | $L_{B4}$ |
| III-528 | $L_{A335}$ | $L_{B4}$ |
| III-529 | $L_{A336}$ | $L_{B4}$ |
| III-530 | $L_{A337}$ | $L_{B4}$ |
| III-531 | $L_{A338}$ | $L_{B4}$ |
| III-532 | $L_{A339}$ | $L_{B4}$ |
| III-533 | $L_{A340}$ | $L_{B4}$ |
| III-534 | $L_{A341}$ | $L_{B4}$ |
| III-535 | $L_{A342}$ | $L_{B4}$ |
| III-536 | $L_{A343}$ | $L_{B4}$ |
| III-537 | $L_{A344}$ | $L_{B4}$ |
| III-538 | $L_{A345}$ | $L_{B4}$ |
| III-539 | $L_{A346}$ | $L_{B4}$ |
| III-540 | $L_{A347}$ | $L_{B4}$ |
| III-541 | $L_{A348}$ | $L_{B4}$ |
| III-542 | $L_{A349}$ | $L_{B4}$ |
| III-543 | $L_{A350}$ | $L_{B4}$ |
| III-544 | $L_{A351}$ | $L_{B4}$ |
| III-545 | $L_{A352}$ | $L_{B4}$ |
| III-546 | $L_{A353}$ | $L_{B4}$ |
| III-547 | $L_{A354}$ | $L_{B4}$ |
| III-548 | $L_{A355}$ | $L_{B4}$ |
| III-549 | $L_{A356}$ | $L_{B4}$ |

| Compound Number | $L_A$ | $L_B$ |
|---|---|---|
| III-550 | $L_{A357}$ | $L_{B4}$ |
| III-551 | $L_{A358}$ | $L_{B4}$ |
| III-552 | $L_{A359}$ | $L_{B4}$ |
| III-553 | $L_{A360}$ | $L_{B4}$ |
| III-554 | $L_{A361}$ | $L_{B4}$ |
| III-555 | $L_{A362}$ | $L_{B4}$ |
| III-556 | $L_{A363}$ | $L_{B4}$ |
| III-557 | $L_{A364}$ | $L_{B4}$ |
| III-558 | $L_{A365}$ | $L_{B4}$ |
| III-559 | $L_{A366}$ | $L_{B4}$ |
| III-560 | $L_{A367}$ | $L_{B4}$ |
| III-561 | $L_{A368}$ | $L_{B4}$ |
| III-562 | $L_{A369}$ | $L_{B4}$ |
| III-563 | $L_{A370}$ | $L_{B4}$ |
| III-564 | $L_{A371}$ | $L_{B4}$ |
| III-565 | $L_{A372}$ | $L_{B4}$ |
| III-566 | $L_{A373}$ | $L_{B4}$ |
| III-567 | $L_{A374}$ | $L_{B4}$ |
| III-568 | $L_{A375}$ | $L_{B4}$ |
| III-569 | $L_{A376}$ | $L_{B4}$ |
| III-570 | $L_{A377}$ | $L_{B4}$ |
| III-571 | $L_{A378}$ | $L_{B4}$ |
| III-572 | $L_{A379}$ | $L_{B4}$ |
| III-573 | $L_{A380}$ | $L_{B4}$ |
| III-574 | $L_{A381}$ | $L_{B4}$ |
| III-575 | $L_{A382}$ | $L_{B4}$ |
| III-576 | $L_{A383}$ | $L_{B4}$ |
| III-577 | $L_{A384}$ | $L_{B4}$ |
| III-578 | $L_{A385}$ | $L_{B4}$ |
| III-579 | $L_{A386}$ | $L_{B4}$ |
| III-580 | $L_{A387}$ | $L_{B4}$ |
| III-581 | $L_{A388}$ | $L_{B4}$ |
| III-582 | $L_{A389}$ | $L_{B4}$ |
| III-583 | $L_{A390}$ | $L_{B4}$ |
| III-584 | $L_{A391}$ | $L_{B4}$ |
| III-585 | $L_{A392}$ | $L_{B4}$ |
| III-586 | $L_{A393}$ | $L_{B4}$ |
| III-587 | $L_{A394}$ | $L_{B4}$ |
| III-588 | $L_{A395}$ | $L_{B4}$ |
| III-589 | $L_{A396}$ | $L_{B4}$ |
| III-590 | $L_{A397}$ | $L_{B4}$ |
| III-591 | $L_{A398}$ | $L_{B4}$ |
| III-592 | $L_{A399}$ | $L_{B4}$ |
| III-593 | $L_{A400}$ | $L_{B4}$ |
| III-594 | $L_{A401}$ | $L_{B4}$ |
| III-595 | $L_{A402}$ | $L_{B4}$ |
| III-596 | $L_{A403}$ | $L_{B4}$ |
| III-597 | $L_{A404}$ | $L_{B4}$ |
| III-598 | $L_{A405}$ | $L_{B4}$ |
| III-599 | $L_{A406}$ | $L_{B4}$ |
| III-600 | $L_{A407}$ | $L_{B4}$ |
| III-601 | $L_{A408}$ | $L_{B4}$ |
| III-602 | $L_{A409}$ | $L_{B4}$ |
| III-603 | $L_{A410}$ | $L_{B4}$ |
| III-604 | $L_{A411}$ | $L_{B4}$ |
| III-605 | $L_{A412}$ | $L_{B4}$ |
| III-606 | $L_{A413}$ | $L_{B4}$ |
| III-607 | $L_{A414}$ | $L_{B4}$ |
| III-608 | $L_{A415}$ | $L_{B4}$ |
| III-609 | $L_{A416}$ | $L_{B4}$ |
| III-610 | $L_{A417}$ | $L_{B4}$ |
| III-611 | $L_{A418}$ | $L_{B4}$ |
| III-612 | $L_{A419}$ | $L_{B4}$ |
| III-613 | $L_{A420}$ | $L_{B4}$ |
| III-614 | $L_{A421}$ | $L_{B4}$ |
| III-615 | $L_{A422}$ | $L_{B4}$ |
| III-616 | $L_{A423}$ | $L_{B4}$ |
| III-617 | $L_{A424}$ | $L_{B4}$ |
| III-618 | $L_{A425}$ | $L_{B4}$ |
| III-619 | $L_{A426}$ | $L_{B4}$ |
| III-620 | $L_{A427}$ | $L_{B4}$ |
| III-621 | $L_{A428}$ | $L_{B4}$ |
| III-622 | $L_{A429}$ | $L_{B4}$ |
| III-623 | $L_{A430}$ | $L_{B4}$ |
| III-624 | $L_{A431}$ | $L_{B4}$ |
| III-625 | $L_{A432}$ | $L_{B4}$ |
| III-626 | $L_{A433}$ | $L_{B4}$ |
| III-627 | $L_{A434}$ | $L_{B4}$ |
| III-628 | $L_{A435}$ | $L_{B4}$ |
| III-629 | $L_{A436}$ | $L_{B4}$ |
| III-630 | $L_{A437}$ | $L_{B4}$ |
| III-631 | $L_{A438}$ | $L_{B4}$ |
| III-632 | $L_{A439}$ | $L_{B4}$ |
| III-633 | $L_{A440}$ | $L_{B4}$ |
| III-634 | $L_{A441}$ | $L_{B4}$ |
| III-635 | $L_{A442}$ | $L_{B4}$ |
| III-636 | $L_{A443}$ | $L_{B4}$ |
| III-637 | $L_{A444}$ | $L_{B4}$ |
| III-638 | $L_{A445}$ | $L_{B4}$ |
| III-639 | $L_{A446}$ | $L_{B4}$ |
| III-640 | $L_{A447}$ | $L_{B4}$ |
| III-641 | $L_{A448}$ | $L_{B4}$ |
| III-642 | $L_{A449}$ | $L_{B4}$ |
| III-643 | $L_{A450}$ | $L_{B4}$ |
| III-644 | $L_{A451}$ | $L_{B4}$ |
| III-645 | $L_{A452}$ | $L_{B4}$ |
| III-646 | $L_{A453}$ | $L_{B4}$ |
| III-647 | $L_{A454}$ | $L_{B4}$ |
| III-648 | $L_{A455}$ | $L_{B4}$ |
| III-649 | $L_{A456}$ | $L_{B4}$ |
| III-650 | $L_{A457}$ | $L_{B4}$ |
| III-651 | $L_{A458}$ | $L_{B4}$ |
| III-652 | $L_{A459}$ | $L_{B4}$ |
| III-653 | $L_{A460}$ | $L_{B4}$ |
| III-654 | $L_{A461}$ | $L_{B4}$ |
| III-655 | $L_{A462}$ | $L_{B4}$ |
| III-656 | $L_{A463}$ | $L_{B4}$ |
| III-657 | $L_{A464}$ | $L_{B4}$ |
| III-658 | $L_{A465}$ | $L_{B4}$ |
| III-659 | $L_{A466}$ | $L_{B4}$ |
| III-660 | $L_{A467}$ | $L_{B4}$ |
| III-661 | $L_{A468}$ | $L_{B4}$ |
| III-662 | $L_{A469}$ | $L_{B4}$ |
| III-663 | $L_{A470}$ | $L_{B4}$ |
| III-664 | $L_{A471}$ | $L_{B4}$ |
| III-665 | $L_{A472}$ | $L_{B4}$ |
| III-666 | $L_{A473}$ | $L_{B4}$ |
| III-667 | $L_{A474}$ | $L_{B4}$ |
| III-668 | $L_{A475}$ | $L_{B4}$ |
| III-669 | $L_{A476}$ | $L_{B4}$ |
| III-670 | $L_{A477}$ | $L_{B4}$ |
| III-671 | $L_{A478}$ | $L_{B4}$ |
| III-672 | $L_{A479}$ | $L_{B4}$ |
| III-673 | $L_{A480}$ | $L_{B4}$ |
| III-674 | $L_{A481}$ | $L_{B4}$ |
| III-675 | $L_{A482}$ | $L_{B4}$ |
| III-676 | $L_{A483}$ | $L_{B4}$ |
| III-677 | $L_{A484}$ | $L_{B4}$ |
| III-678 | $L_{A485}$ | $L_{B4}$ |
| III-679 | $L_{A486}$ | $L_{B4}$ |
| III-680 | $L_{A487}$ | $L_{B4}$ |
| III-681 | $L_{A318}$ | $L_{B5}$ |
| III-682 | $L_{A319}$ | $L_{B5}$ |
| III-683 | $L_{A320}$ | $L_{B5}$ |
| III-684 | $L_{A321}$ | $L_{B5}$ |
| III-685 | $L_{A322}$ | $L_{B5}$ |
| III-686 | $L_{A323}$ | $L_{B5}$ |
| III-687 | $L_{A324}$ | $L_{B5}$ |
| III-688 | $L_{A325}$ | $L_{B5}$ |
| III-689 | $L_{A326}$ | $L_{B5}$ |
| III-690 | $L_{A327}$ | $L_{H}$ |
| III-691 | $L_{A328}$ | $L_{H}$ |
| III-692 | $L_{A329}$ | $L_{H}$ |
| III-693 | $L_{A330}$ | $L_{H}$ |
| III-694 | $L_{A331}$ | $L_{B5}$ |
| III-695 | $L_{A332}$ | $L_{B5}$ |
| III-696 | $L_{A333}$ | $L_{B5}$ |
| III-697 | $L_{A334}$ | $L_{B5}$ |
| III-698 | $L_{A335}$ | $L_{B5}$ |
| III-699 | $L_{A336}$ | $L_{B5}$ |
| III-700 | $L_{A337}$ | $L_{B5}$ |
| III-701 | $L_{A338}$ | $L_{B5}$ |

| Compound Number | $L_A$ | $L_B$ |
| --- | --- | --- |
| III-702 | $L_{A339}$ | $L_{B5}$ |
| III-703 | $L_{A340}$ | $L_{B5}$ |
| III-704 | $L_{A341}$ | $L_{B5}$ |
| III-705 | $L_{A342}$ | $L_{B5}$ |
| III-706 | $L_{A343}$ | $L_{B5}$ |
| III-707 | $L_{A344}$ | $L_{B5}$ |
| III-708 | $L_{A345}$ | $L_H$ |
| III-709 | $L_{A346}$ | $L_H$ |
| III-710 | $L_{A347}$ | $L_H$ |
| III-711 | $L_{A348}$ | $L_H$ |
| III-712 | $L_{A349}$ | $L_H$ |
| III-713 | $L_{A350}$ | $L_{B5}$ |
| III-714 | $L_{A351}$ | $L_{B5}$ |
| III-715 | $L_{A352}$ | $L_{B5}$ |
| III-716 | $L_{A353}$ | $L_{B5}$ |
| III-717 | $L_{A354}$ | $L_{B5}$ |
| III-718 | $L_{A355}$ | $L_{B5}$ |
| III-719 | $L_{A356}$ | $L_{B5}$ |
| III-720 | $L_{A357}$ | $L_{B5}$ |
| III-721 | $L_{A358}$ | $L_H$ |
| III-722 | $L_{A359}$ | $L_H$ |
| III-723 | $L_{A360}$ | $L_H$ |
| III-724 | $L_{A361}$ | $L_H$ |
| III-725 | $L_{A362}$ | $L_H$ |
| III-726 | $L_{A363}$ | $L_{B5}$ |
| III-727 | $L_{A364}$ | $L_{B5}$ |
| III-728 | $L_{A365}$ | $L_{B5}$ |
| III-729 | $L_{A366}$ | $L_{B5}$ |
| III-730 | $L_{A367}$ | $L_{B5}$ |
| III-731 | $L_{A368}$ | $L_{B5}$ |
| III-732 | $L_{A369}$ | $L_{B5}$ |
| III-733 | $L_{A370}$ | $L_{B5}$ |
| III-734 | $L_{A371}$ | $L_{B5}$ |
| III-735 | $L_{A372}$ | $L_{B5}$ |
| III-736 | $L_{A373}$ | $L_{B5}$ |
| III-737 | $L_{A374}$ | $L_{B5}$ |
| III-738 | $L_{A375}$ | $L_{B5}$ |
| III-739 | $L_{A376}$ | $L_{B5}$ |
| III-740 | $L_{A377}$ | $L_H$ |
| III-741 | $L_{A378}$ | $L_H$ |
| III-742 | $L_{A379}$ | $L_H$ |
| III-743 | $L_{A380}$ | $L_H$ |
| III-744 | $L_{A381}$ | $L_{B5}$ |
| III-745 | $L_{A382}$ | $L_{B5}$ |
| III-746 | $L_{A383}$ | $L_{B5}$ |
| III-747 | $L_{A384}$ | $L_{B5}$ |
| III-748 | $L_{A385}$ | $L_{B5}$ |
| III-749 | $L_{A386}$ | $L_{B5}$ |
| III-750 | $L_{A387}$ | $L_{B5}$ |
| III-751 | $L_{A388}$ | $L_{B5}$ |
| III-752 | $L_{A389}$ | $L_{B5}$ |
| III-753 | $L_{A390}$ | $L_{B5}$ |
| III-754 | $L_{A391}$ | $L_{B5}$ |
| III-755 | $L_{A392}$ | $L_{B5}$ |
| III-756 | $L_{A393}$ | $L_{B5}$ |
| III-757 | $L_{A394}$ | $L_{B5}$ |
| III-758 | $L_{A395}$ | $L_H$ |
| III-759 | $L_{A396}$ | $L_H$ |
| III-760 | $L_{A397}$ | $L_H$ |
| III-761 | $L_{A398}$ | $L_H$ |
| III-762 | $L_{A399}$ | $L_H$ |
| III-763 | $L_{A400}$ | $L_{B5}$ |
| III-764 | $L_{A401}$ | $L_{B5}$ |
| III-765 | $L_{A402}$ | $L_{B5}$ |
| III-766 | $L_{A403}$ | $L_{B5}$ |
| III-767 | $L_{A404}$ | $L_{B5}$ |
| III-768 | $L_{A405}$ | $L_{B5}$ |
| III-769 | $L_{A406}$ | $L_{B5}$ |
| III-770 | $L_{A407}$ | $L_{B5}$ |
| III-771 | $L_{A408}$ | $L_{B5}$ |
| III-772 | $L_{A409}$ | $L_{B5}$ |
| III-773 | $L_{A410}$ | $L_{B5}$ |
| III-774 | $L_{A411}$ | $L_{B5}$ |
| III-775 | $L_{A412}$ | $L_{B5}$ |
| III-776 | $L_{A413}$ | $L_{B5}$ |
| III-777 | $L_{A414}$ | $L_{B5}$ |
| III-778 | $L_{A415}$ | $L_{B5}$ |
| III-779 | $L_{A416}$ | $L_{B5}$ |
| III-780 | $L_{A417}$ | $L_{B5}$ |
| III-781 | $L_{A418}$ | $L_{B5}$ |
| III-782 | $L_{A419}$ | $L_{B5}$ |
| III-783 | $L_{A420}$ | $L_{B5}$ |
| III-784 | $L_{A421}$ | $L_{B5}$ |
| III-785 | $L_{A422}$ | $L_{B5}$ |
| III-786 | $L_{A423}$ | $L_{B5}$ |
| III-787 | $L_{A424}$ | $L_{B5}$ |
| III-788 | $L_{A425}$ | $L_{B5}$ |
| III-789 | $L_{A426}$ | $L_{B5}$ |
| III-790 | $L_{A427}$ | $L_{B5}$ |
| III-791 | $L_{A428}$ | $L_{B5}$ |
| III-792 | $L_{A429}$ | $L_{B5}$ |
| III-793 | $L_{A430}$ | $L_{B5}$ |
| III-794 | $L_{A431}$ | $L_{B5}$ |
| III-795 | $L_{A432}$ | $L_{B5}$ |
| III-796 | $L_{A433}$ | $L_{B5}$ |
| III-797 | $L_{A434}$ | $L_{B5}$ |
| III-798 | $L_{A435}$ | $L_{B5}$ |
| III-799 | $L_{A436}$ | $L_{B5}$ |
| III-800 | $L_{A437}$ | $L_{B5}$ |
| III-801 | $L_{A438}$ | $L_{B5}$ |
| III-802 | $L_{A439}$ | $L_{B5}$ |
| III-803 | $L_{A440}$ | $L_{B5}$ |
| III-804 | $L_{A441}$ | $L_{B5}$ |
| III-805 | $L_{A442}$ | $L_{B5}$ |
| III-806 | $L_{A443}$ | $L_{B5}$ |
| III-807 | $L_{A444}$ | $L_{B5}$ |
| III-808 | $L_{A445}$ | $L_{B5}$ |
| III-809 | $L_{A446}$ | $L_{B5}$ |
| III-810 | $L_{A447}$ | $L_{B5}$ |
| III-811 | $L_{A448}$ | $L_{B5}$ |
| III-812 | $L_{A449}$ | $L_{B5}$ |
| III-813 | $L_{A450}$ | $L_{B5}$ |
| III-814 | $L_{A451}$ | $L_{B5}$ |
| III-815 | $L_{A452}$ | $L_{B5}$ |
| III-816 | $L_{A453}$ | $L_{B5}$ |
| III-817 | $L_{A454}$ | $L_{B5}$ |
| III-818 | $L_{A455}$ | $L_{B5}$ |
| III-819 | $L_{A456}$ | $L_{B5}$ |
| III-820 | $L_{A457}$ | $L_{B5}$ |
| III-821 | $L_{A458}$ | $L_{B5}$ |
| III-822 | $L_{A459}$ | $L_{B5}$ |
| III-823 | $L_{A460}$ | $L_{B5}$ |
| III-824 | $L_{A461}$ | $L_{B5}$ |
| III-825 | $L_{A462}$ | $L_{B5}$ |
| III-826 | $L_{A463}$ | $L_{B5}$ |
| III-827 | $L_{A464}$ | $L_{B5}$ |
| III-828 | $L_{A465}$ | $L_{B5}$ |
| III-829 | $L_{A466}$ | $L_{B5}$ |
| III-830 | $L_{A467}$ | $L_{B5}$ |
| III-831 | $L_{A468}$ | $L_{B5}$ |
| III-832 | $L_{A469}$ | $L_{B5}$ |
| III-833 | $L_{A470}$ | $L_{B5}$ |
| III-834 | $L_{A471}$ | $L_{B5}$ |
| III-835 | $L_{A472}$ | $L_{B5}$ |
| III-836 | $L_{A473}$ | $L_{B5}$ |
| III-837 | $L_{A474}$ | $L_{B5}$ |
| III-838 | $L_{A475}$ | $L_{B5}$ |
| III-839 | $L_{A476}$ | $L_{B5}$ |
| III-840 | $L_{A477}$ | $L_{B5}$ |
| III-841 | $L_{A478}$ | $L_{B5}$ |
| III-842 | $L_{A479}$ | $L_{B5}$ |
| III-843 | $L_{A480}$ | $L_{B5}$ |
| III-844 | $L_{A481}$ | $L_{B5}$ |
| III-845 | $L_{A482}$ | $L_{B5}$ |
| III-846 | $L_{A483}$ | $L_{B5}$ |
| III-847 | $L_{A484}$ | $L_{B5}$ |
| III-848 | $L_{A485}$ | $L_{B5}$ |
| III-849 | $L_{A486}$ | $L_{B5}$ |
| III-850 | $L_{A487}$ | $L_{B5}$ |
| III-851 | $L_{A318}$ | $L_{B6}$ |
| III-852 | $L_{A319}$ | $L_{B6}$ |
| III-853 | $L_{A320}$ | $L_{B6}$ |

| Compound Number | $L_A$ | $L_B$ |
|---|---|---|
| III-854 | $L_{A321}$ | $L_{B6}$ |
| III-855 | $L_{A322}$ | $L_{B6}$ |
| III-856 | $L_{A323}$ | $L_{B6}$ |
| III-857 | $L_{A324}$ | $L_{B6}$ |
| III-858 | $L_{A325}$ | $L_{B6}$ |
| III-859 | $L_{A326}$ | $L_{B6}$ |
| III-860 | $L_{A327}$ | $L_{B6}$ |
| III-861 | $L_{A328}$ | $L_{B6}$ |
| III-862 | $L_{A329}$ | $L_{B6}$ |
| III-863 | $L_{A330}$ | $L_{B6}$ |
| III-864 | $L_{A331}$ | $L_{B6}$ |
| III-865 | $L_{A332}$ | $L_{B6}$ |
| III-866 | $L_{A333}$ | $L_{B6}$ |
| III-867 | $L_{A334}$ | $L_{B6}$ |
| III-868 | $L_{A335}$ | $L_{B6}$ |
| III-869 | $L_{A336}$ | $L_{B6}$ |
| III-870 | $L_{A337}$ | $L_{B6}$ |
| III-871 | $L_{A338}$ | $L_{B6}$ |
| III-872 | $L_{A339}$ | $L_{B6}$ |
| III-873 | $L_{A340}$ | $L_{B6}$ |
| III-874 | $L_{A341}$ | $L_{B6}$ |
| III-875 | $L_{A342}$ | $L_{B6}$ |
| III-876 | $L_{A343}$ | $L_{B6}$ |
| III-877 | $L_{A344}$ | $L_{B6}$ |
| III-878 | $L_{A345}$ | $L_{B6}$ |
| III-879 | $L_{A346}$ | $L_{B6}$ |
| III-880 | $L_{A347}$ | $L_{B6}$ |
| III-881 | $L_{A348}$ | $L_{B6}$ |
| III-882 | $L_{A349}$ | $L_{B6}$ |
| III-883 | $L_{A350}$ | $L_{B6}$ |
| III-884 | $L_{A351}$ | $L_{B6}$ |
| III-885 | $L_{A352}$ | $L_{B6}$ |
| III-886 | $L_{A353}$ | $L_{B6}$ |
| III-887 | $L_{A354}$ | $L_{B6}$ |
| III-888 | $L_{A355}$ | $L_{B6}$ |
| III-889 | $L_{A356}$ | $L_{B6}$ |
| III-890 | $L_{A357}$ | $L_{B6}$ |
| III-891 | $L_{A358}$ | $L_{B6}$ |
| III-892 | $L_{A359}$ | $L_{B6}$ |
| III-893 | $L_{A360}$ | $L_{B6}$ |
| III-894 | $L_{A361}$ | $L_{B6}$ |
| III-895 | $L_{A362}$ | $L_{B6}$ |
| III-896 | $L_{A363}$ | $L_{B6}$ |
| III-897 | $L_{A364}$ | $L_{B6}$ |
| III-898 | $L_{A365}$ | $L_{B6}$ |
| III-899 | $L_{A366}$ | $L_{B6}$ |
| III-900 | $L_{A367}$ | $L_{B6}$ |
| III-901 | $L_{A368}$ | $L_{B6}$ |
| III-902 | $L_{A369}$ | $L_{B6}$ |
| III-903 | $L_{A370}$ | $L_{B6}$ |
| III-904 | $L_{A371}$ | $L_{B6}$ |
| III-905 | $L_{A372}$ | $L_{B6}$ |
| III-906 | $L_{A373}$ | $L_{B6}$ |
| III-907 | $L_{A374}$ | $L_{B6}$ |
| III-908 | $L_{A375}$ | $L_{B6}$ |
| III-909 | $L_{A376}$ | $L_{B6}$ |
| III-910 | $L_{A377}$ | $L_{B6}$ |
| III-911 | $L_{A378}$ | $L_{B6}$ |
| III-912 | $L_{A379}$ | $L_{B6}$ |
| III-913 | $L_{A380}$ | $L_{B6}$ |
| III-914 | $L_{A381}$ | $L_{B6}$ |
| III-915 | $L_{A382}$ | $L_{B6}$ |
| III-916 | $L_{A383}$ | $L_{B6}$ |
| III-917 | $L_{A384}$ | $L_{B6}$ |
| III-918 | $L_{A385}$ | $L_{B6}$ |
| III-919 | $L_{A386}$ | $L_{B6}$ |
| III-920 | $L_{A387}$ | $L_{B6}$ |
| III-921 | $L_{A388}$ | $L_{B6}$ |
| III-922 | $L_{A389}$ | $L_{B6}$ |
| III-923 | $L_{A390}$ | $L_{B6}$ |
| III-924 | $L_{A391}$ | $L_{B6}$ |
| III-925 | $L_{A392}$ | $L_{B6}$ |
| III-926 | $L_{A393}$ | $L_{B6}$ |
| III-927 | $L_{A394}$ | $L_{B6}$ |
| III-928 | $L_{A395}$ | $L_{B6}$ |
| III-929 | $L_{A396}$ | $L_{B6}$ |
| III-930 | $L_{A397}$ | $L_{B6}$ |
| III-931 | $L_{A398}$ | $L_{B6}$ |
| III-932 | $L_{A399}$ | $L_{B6}$ |
| III-933 | $L_{A400}$ | $L_{B6}$ |
| III-934 | $L_{A401}$ | $L_{B6}$ |
| III-935 | $L_{A402}$ | $L_{B6}$ |
| III-936 | $L_{A403}$ | $L_{B6}$ |
| III-937 | $L_{A404}$ | $L_{B6}$ |
| III-938 | $L_{A405}$ | $L_{B6}$ |
| III-939 | $L_{A406}$ | $L_{B6}$ |
| III-940 | $L_{A407}$ | $L_{B6}$ |
| III-941 | $L_{A408}$ | $L_{B6}$ |
| III-942 | $L_{A409}$ | $L_{B6}$ |
| III-943 | $L_{A410}$ | $L_{B6}$ |
| III-944 | $L_{A411}$ | $L_{B6}$ |
| III-945 | $L_{A412}$ | $L_{B6}$ |
| III-946 | $L_{A413}$ | $L_{B6}$ |
| III-947 | $L_{A414}$ | $L_{B6}$ |
| III-948 | $L_{A415}$ | $L_{B6}$ |
| III-949 | $L_{A416}$ | $L_{B6}$ |
| III-950 | $L_{A417}$ | $L_{B6}$ |
| III-951 | $L_{A418}$ | $L_{B6}$ |
| III-952 | $L_{A419}$ | $L_{B6}$ |
| III-953 | $L_{A420}$ | $L_{B6}$ |
| III-954 | $L_{A421}$ | $L_{B6}$ |
| III-955 | $L_{A422}$ | $L_{B6}$ |
| III-956 | $L_{A423}$ | $L_{B6}$ |
| III-957 | $L_{A424}$ | $L_{B6}$ |
| III-958 | $L_{A425}$ | $L_{B6}$ |
| III-959 | $L_{A426}$ | $L_{B6}$ |
| III-960 | $L_{A427}$ | $L_{B6}$ |
| III-961 | $L_{A428}$ | $L_{B6}$ |
| III-962 | $L_{A429}$ | $L_{B6}$ |
| III-963 | $L_{A430}$ | $L_{B6}$ |
| III-964 | $L_{A431}$ | $L_{B6}$ |
| III-965 | $L_{A432}$ | $L_{B6}$ |
| III-966 | $L_{A433}$ | $L_{B6}$ |
| III-967 | $L_{A434}$ | $L_{B6}$ |
| III-968 | $L_{A435}$ | $L_{B6}$ |
| III-969 | $L_{A436}$ | $L_{B6}$ |
| III-970 | $L_{A437}$ | $L_{B6}$ |
| III-971 | $L_{A438}$ | $L_{B6}$ |
| III-972 | $L_{A439}$ | $L_{B6}$ |
| III-973 | $L_{A440}$ | $L_{B6}$ |
| III-974 | $L_{A441}$ | $L_{B6}$ |
| III-975 | $L_{A442}$ | $L_{B6}$ |
| III-976 | $L_{A443}$ | $L_{B6}$ |
| III-977 | $L_{A444}$ | $L_{B6}$ |
| III-978 | $L_{A445}$ | $L_{B6}$ |
| III-979 | $L_{A446}$ | $L_{B6}$ |
| III-980 | $L_{A447}$ | $L_{B6}$ |
| III-981 | $L_{A448}$ | $L_{B6}$ |
| III-982 | $L_{A449}$ | $L_{B6}$ |
| III-983 | $L_{A450}$ | $L_{B6}$ |
| III-984 | $L_{A451}$ | $L_{B6}$ |
| III-985 | $L_{A452}$ | $L_{B6}$ |
| III-986 | $L_{A453}$ | $L_{B6}$ |
| III-987 | $L_{A454}$ | $L_{B6}$ |
| III-988 | $L_{A455}$ | $L_{B6}$ |
| III-989 | $L_{A456}$ | $L_{B6}$ |
| III-990 | $L_{A457}$ | $L_{B6}$ |
| III-991 | $L_{A458}$ | $L_{B6}$ |
| III-992 | $L_{A459}$ | $L_{B6}$ |
| III-993 | $L_{A460}$ | $L_{B6}$ |
| III-994 | $L_{A461}$ | $L_{B6}$ |
| III-995 | $L_{A462}$ | $L_{B6}$ |
| III-996 | $L_{A463}$ | $L_{B6}$ |
| III-997 | $L_{A464}$ | $L_{B6}$ |
| III-998 | $L_{A465}$ | $L_{B6}$ |
| III-999 | $L_{A466}$ | $L_{B6}$ |
| III-1000 | $L_{A467}$ | $L_{B6}$ |
| III-1001 | $L_{A468}$ | $L_{B6}$ |
| III-1002 | $L_{A469}$ | $L_{B6}$ |
| III-1003 | $L_{A470}$ | $L_{B6}$ |
| III-1004 | $L_{A471}$ | $L_{B6}$ |
| III-1005 | $L_{A472}$ | $L_{B6}$ |

| Compound Number | $L_A$ | $L_B$ |
|---|---|---|
| III-1006 | $L_{A473}$ | $L_{B6}$ |
| III-1007 | $L_{A474}$ | $L_{B6}$ |
| III-1008 | $L_{A475}$ | $L_{B6}$ |
| III-1009 | $L_{A476}$ | $L_{B6}$ |
| III-1010 | $L_{A477}$ | $L_{B6}$ |
| III-1011 | $L_{A478}$ | $L_{B6}$ |
| III-1012 | $L_{A479}$ | $L_{B6}$ |
| III-1013 | $L_{A480}$ | $L_{B6}$ |
| III-1014 | $L_{A481}$ | $L_{B6}$ |
| III-1015 | $L_{A482}$ | $L_{B6}$ |
| III-1016 | $L_{A483}$ | $L_{B6}$ |
| III-1017 | $L_{A484}$ | $L_{B6}$ |
| III-1018 | $L_{A485}$ | $L_{B6}$ |
| III-1019 | $L_{A486}$ | $L_{B6}$ |
| III-1020 | $L_{A487}$ | $L_{B6}$ |
| III-1021 | $L_{A318}$ | $L_{B7}$ |
| III-1022 | $L_{A319}$ | $L_{B7}$ |
| III-1023 | $L_{A320}$ | $L_{B7}$ |
| III-1024 | $L_{A321}$ | $L_{B7}$ |
| III-1025 | $L_{A322}$ | $L_{B7}$ |
| III-1026 | $L_{A323}$ | $L_{B7}$ |
| III-1027 | $L_{A324}$ | $L_{B7}$ |
| III-1028 | $L_{A325}$ | $L_{B7}$ |
| III-1029 | $L_{A326}$ | $L_{B7}$ |
| III-1030 | $L_{A327}$ | $L_{B7}$ |
| III-1031 | $L_{A328}$ | $L_{B7}$ |
| III-1032 | $L_{A329}$ | $L_{B7}$ |
| III-1033 | $L_{A330}$ | $L_{B7}$ |
| III-1034 | $L_{A331}$ | $L_{B7}$ |
| III-1035 | $L_{A332}$ | $L_{B7}$ |
| III-1036 | $L_{A333}$ | $L_{B7}$ |
| III-1037 | $L_{A334}$ | $L_{B7}$ |
| III-1038 | $L_{A335}$ | $L_{B7}$ |
| III-1039 | $L_{A336}$ | $L_{B7}$ |
| III-1040 | $L_{A337}$ | $L_{B7}$ |
| III-1041 | $L_{A338}$ | $L_{B7}$ |
| III-1042 | $L_{A339}$ | $L_{B7}$ |
| III-1043 | $L_{A340}$ | $L_{B7}$ |
| III-1044 | $L_{A341}$ | $L_{B7}$ |
| III-1045 | $L_{A342}$ | $L_{B7}$ |
| III-1046 | $L_{A343}$ | $L_{B7}$ |
| III-1047 | $L_{A344}$ | $L_{B7}$ |
| III-1048 | $L_{A345}$ | $L_{B7}$ |
| III-1049 | $L_{A346}$ | $L_{B7}$ |
| III-1050 | $L_{A347}$ | $L_{B7}$ |
| III-1051 | $L_{A348}$ | $L_{B7}$ |
| III-1052 | $L_{A349}$ | $L_{B7}$ |
| III-1053 | $L_{A350}$ | $L_{B7}$ |
| III-1054 | $L_{A351}$ | $L_{B7}$ |
| III-1055 | $L_{A352}$ | $L_{B7}$ |
| III-1056 | $L_{A353}$ | $L_{B7}$ |
| III-1057 | $L_{A354}$ | $L_{B7}$ |
| III-1058 | $L_{A355}$ | $L_{B7}$ |
| III-1059 | $L_{A356}$ | $L_{B7}$ |
| III-1060 | $L_{A357}$ | $L_{B7}$ |
| III-1061 | $L_{A358}$ | $L_{B7}$ |
| III-1062 | $L_{A359}$ | $L_{B7}$ |
| III-1063 | $L_{A360}$ | $L_{B7}$ |
| III-1064 | $L_{A361}$ | $L_{B7}$ |
| III-1065 | $L_{A362}$ | $L_{B7}$ |
| III-1066 | $L_{A363}$ | $L_{B7}$ |
| III-1067 | $L_{A364}$ | $L_{B7}$ |
| III-1068 | $L_{A365}$ | $L_{B7}$ |
| III-1069 | $L_{A366}$ | $L_{B7}$ |
| III-1070 | $L_{A367}$ | $L_{B7}$ |
| III-1071 | $L_{A368}$ | $L_{B7}$ |
| III-1072 | $L_{A369}$ | $L_{B7}$ |
| III-1073 | $L_{A370}$ | $L_{B7}$ |
| III-1074 | $L_{A371}$ | $L_{B7}$ |
| III-1075 | $L_{A372}$ | $L_{B7}$ |
| III-1076 | $L_{A373}$ | $L_{B7}$ |
| III-1077 | $L_{A374}$ | $L_{B7}$ |
| III-1078 | $L_{A375}$ | $L_{B7}$ |
| III-1079 | $L_{A376}$ | $L_{B7}$ |
| III-1080 | $L_{A377}$ | $L_{B7}$ |
| III-1081 | $L_{A378}$ | $L_{B7}$ |
| III-1082 | $L_{A379}$ | $L_{B7}$ |
| III-1083 | $L_{A380}$ | $L_{B7}$ |
| III-1084 | $L_{A381}$ | $L_{B7}$ |
| III-1085 | $L_{A382}$ | $L_{B7}$ |
| III-1086 | $L_{A383}$ | $L_{B7}$ |
| III-1087 | $L_{A384}$ | $L_{B7}$ |
| III-1088 | $L_{A385}$ | $L_{B7}$ |
| III-1089 | $L_{A386}$ | $L_{B7}$ |
| III-1090 | $L_{A387}$ | $L_{B7}$ |
| III-1091 | $L_{A388}$ | $L_{B7}$ |
| III-1092 | $L_{A389}$ | $L_{B7}$ |
| III-1093 | $L_{A390}$ | $L_{B7}$ |
| III-1094 | $L_{A391}$ | $L_{B7}$ |
| III-1095 | $L_{A392}$ | $L_{B7}$ |
| III-1096 | $L_{A393}$ | $L_{B7}$ |
| III-1097 | $L_{A394}$ | $L_{B7}$ |
| III-1098 | $L_{A395}$ | $L_{B7}$ |
| III-1099 | $L_{A396}$ | $L_{B7}$ |
| III-1100 | $L_{A397}$ | $L_{B7}$ |
| III-1101 | $L_{A398}$ | $L_{B7}$ |
| III-1102 | $L_{A399}$ | $L_{B7}$ |
| III-1103 | $L_{A400}$ | $L_{B7}$ |
| III-1104 | $L_{A401}$ | $L_{B7}$ |
| III-1105 | $L_{A402}$ | $L_{B7}$ |
| III-1106 | $L_{A403}$ | $L_{B7}$ |
| III-1107 | $L_{A404}$ | $L_{B7}$ |
| III-1108 | $L_{A405}$ | $L_{B7}$ |
| III-1109 | $L_{A406}$ | $L_{B7}$ |
| III-1110 | $L_{A407}$ | $L_{B7}$ |
| III-1111 | $L_{A408}$ | $L_{B7}$ |
| III-1112 | $L_{A409}$ | $L_{B7}$ |
| III-1113 | $L_{A410}$ | $L_{B7}$ |
| III-1114 | $L_{A411}$ | $L_{B7}$ |
| III-1115 | $L_{A412}$ | $L_{B7}$ |
| III-1116 | $L_{A413}$ | $L_{B7}$ |
| III-1117 | $L_{A414}$ | $L_{B7}$ |
| III-1118 | $L_{A415}$ | $L_{B7}$ |
| III-1119 | $L_{A416}$ | $L_{B7}$ |
| III-1120 | $L_{A417}$ | $L_{B7}$ |
| III-1121 | $L_{A418}$ | $L_{B7}$ |
| III-1122 | $L_{A419}$ | $L_{B7}$ |
| III-1123 | $L_{A420}$ | $L_{B7}$ |
| III-1124 | $L_{A421}$ | $L_{B7}$ |
| III-1125 | $L_{A422}$ | $L_{B7}$ |
| III-1126 | $L_{A423}$ | $L_{B7}$ |
| III-1127 | $L_{A424}$ | $L_{B7}$ |
| III-1128 | $L_{A425}$ | $L_{B7}$ |
| III-1129 | $L_{A426}$ | $L_{B7}$ |
| III-1130 | $L_{A427}$ | $L_{B7}$ |
| III-1131 | $L_{A428}$ | $L_{B7}$ |
| III-1132 | $L_{A429}$ | $L_{B7}$ |
| III-1133 | $L_{A430}$ | $L_{B7}$ |
| III-1134 | $L_{A431}$ | $L_{B7}$ |
| III-1135 | $L_{A432}$ | $L_{B7}$ |
| III-1136 | $L_{A433}$ | $L_{B7}$ |
| III-1137 | $L_{A434}$ | $L_{B7}$ |
| III-1138 | $L_{A435}$ | $L_{B7}$ |
| III-1139 | $L_{A436}$ | $L_{B7}$ |
| III-1140 | $L_{A437}$ | $L_{B7}$ |
| III-1141 | $L_{A438}$ | $L_{B7}$ |
| III-1142 | $L_{A439}$ | $L_{B7}$ |
| III-1143 | $L_{A440}$ | $L_{B7}$ |
| III-1144 | $L_{A441}$ | $L_{B7}$ |
| III-1145 | $L_{A442}$ | $L_{B7}$ |
| III-1146 | $L_{A443}$ | $L_{B7}$ |
| III-1147 | $L_{A444}$ | $L_{B7}$ |
| III-1148 | $L_{A445}$ | $L_{B7}$ |
| III-1149 | $L_{A446}$ | $L_{B7}$ |
| III-1150 | $L_{A447}$ | $L_{B7}$ |
| III-1151 | $L_{A448}$ | $L_{B7}$ |
| III-1152 | $L_{A449}$ | $L_{B7}$ |
| III-1153 | $L_{A450}$ | $L_{B7}$ |
| III-1154 | $L_{A451}$ | $L_{B7}$ |
| III-1155 | $L_{A452}$ | $L_{B7}$ |
| III-1156 | $L_{A453}$ | $L_{B7}$ |
| III-1157 | $L_{A454}$ | $L_{B7}$ |

| Compound Number | $L_A$ | $L_B$ |
|---|---|---|
| III-1158 | $L_{A455}$ | $L_{B7}$ |
| III-1159 | $L_{A456}$ | $L_{B7}$ |
| III-1160 | $L_{A457}$ | $L_{B7}$ |
| III-1161 | $L_{A458}$ | $L_{B7}$ |
| III-1162 | $L_{A459}$ | $L_{B7}$ |
| III-1163 | $L_{A460}$ | $L_{B7}$ |
| III-1164 | $L_{A461}$ | $L_{B7}$ |
| III-1165 | $L_{A462}$ | $L_{B7}$ |
| III-1166 | $L_{A463}$ | $L_{B7}$ |
| III-1167 | $L_{A464}$ | $L_{B7}$ |
| III-1168 | $L_{A465}$ | $L_{B7}$ |
| III-1169 | $L_{A466}$ | $L_{B7}$ |
| III-1170 | $L_{A467}$ | $L_{B7}$ |
| III-1171 | $L_{A468}$ | $L_{B7}$ |
| III-1172 | $L_{A469}$ | $L_{B7}$ |
| III-1173 | $L_{A470}$ | $L_{B7}$ |
| III-1174 | $L_{A471}$ | $L_{B7}$ |
| III-1175 | $L_{A472}$ | $L_{B7}$ |
| III-1176 | $L_{A473}$ | $L_{B7}$ |
| III-1177 | $L_{A474}$ | $L_{B7}$ |
| III-1178 | $L_{A475}$ | $L_{B7}$ |
| III-1179 | $L_{A476}$ | $L_{B7}$ |
| III-1180 | $L_{A477}$ | $L_{B7}$ |
| III-1181 | $L_{A478}$ | $L_{B7}$ |
| III-1182 | $L_{A479}$ | $L_{B7}$ |
| III-1183 | $L_{A480}$ | $L_{B7}$ |
| III-1184 | $L_{A481}$ | $L_{B7}$ |
| III-1185 | $L_{A482}$ | $L_{B7}$ |
| III-1186 | $L_{A483}$ | $L_{B7}$ |
| III-1187 | $L_{A484}$ | $L_{B7}$ |
| III-1188 | $L_{A485}$ | $L_{B7}$ |
| III-1189 | $L_{A486}$ | $L_{B7}$ |
| III-1190 | $L_{A487}$ | $L_{B7}$ |
| III-1191 | $L_{A318}$ | $L_{B8}$ |
| III-1192 | $L_{A319}$ | $L_{B8}$ |
| III-1193 | $L_{A320}$ | $L_{B8}$ |
| III-1194 | $L_{A321}$ | $L_{B8}$ |
| III-1195 | $L_{A322}$ | $L_{B8}$ |
| III-1196 | $L_{A323}$ | $L_{B8}$ |
| III-1197 | $L_{A324}$ | $L_{B8}$ |
| III-1198 | $L_{A325}$ | $L_{B8}$ |
| III-1199 | $L_{A326}$ | $L_{B8}$ |
| III-1200 | $L_{A327}$ | $L_{B8}$ |
| III-1201 | $L_{A328}$ | $L_{B8}$ |
| III-1202 | $L_{A329}$ | $L_{B8}$ |
| III-1203 | $L_{A330}$ | $L_{B8}$ |
| III-1204 | $L_{A331}$ | $L_{B8}$ |
| III-1205 | $L_{A332}$ | $L_{B8}$ |
| III-1206 | $L_{A333}$ | $L_{B8}$ |
| III-1207 | $L_{A334}$ | $L_{B8}$ |
| III-1208 | $L_{A335}$ | $L_{B8}$ |
| III-1209 | $L_{A336}$ | $L_{B8}$ |
| III-1210 | $L_{A337}$ | $L_{B8}$ |
| III-1211 | $L_{A338}$ | $L_{B8}$ |
| III-1212 | $L_{A339}$ | $L_{B8}$ |
| III-1213 | $L_{A340}$ | $L_{B8}$ |
| III-1214 | $L_{A341}$ | $L_{B8}$ |
| III-1215 | $L_{A342}$ | $L_{B8}$ |
| III-1216 | $L_{A343}$ | $L_{B8}$ |
| III-1217 | $L_{A344}$ | $L_{B8}$ |
| III-1218 | $L_{A345}$ | $L_{B8}$ |
| III-1219 | $L_{A346}$ | $L_{B8}$ |
| III-1220 | $L_{A347}$ | $L_{B8}$ |
| III-1221 | $L_{A348}$ | $L_{B8}$ |
| III-1222 | $L_{A349}$ | $L_{B8}$ |
| III-1223 | $L_{A350}$ | $L_{B8}$ |
| III-1224 | $L_{A351}$ | $L_{B8}$ |
| III-1225 | $L_{A352}$ | $L_{B8}$ |
| III-1226 | $L_{A353}$ | $L_{B8}$ |
| III-1227 | $L_{A354}$ | $L_{B8}$ |
| III-1228 | $L_{A355}$ | $L_{B8}$ |
| III-1229 | $L_{A356}$ | $L_{B8}$ |
| III-1230 | $L_{A357}$ | $L_{B8}$ |
| III-1231 | $L_{A358}$ | $L_{B8}$ |
| III-1232 | $L_{A359}$ | $L_{B8}$ |
| III-1233 | $L_{A360}$ | $L_{B8}$ |
| III-1234 | $L_{A361}$ | $L_{B8}$ |
| III-1235 | $L_{A362}$ | $L_{B8}$ |
| III-1236 | $L_{A363}$ | $L_{B8}$ |
| III-1237 | $L_{A364}$ | $L_{B8}$ |
| III-1238 | $L_{A365}$ | $L_{B8}$ |
| III-1239 | $L_{A366}$ | $L_{B8}$ |
| III-1240 | $L_{A367}$ | $L_{B8}$ |
| III-1241 | $L_{A368}$ | $L_{B8}$ |
| III-1242 | $L_{A369}$ | $L_{B8}$ |
| III-1243 | $L_{A370}$ | $L_{B8}$ |
| III-1244 | $L_{A371}$ | $L_{B8}$ |
| III-1245 | $L_{A372}$ | $L_{B8}$ |
| III-1246 | $L_{A373}$ | $L_{B8}$ |
| III-1247 | $L_{A374}$ | $L_{B8}$ |
| III-1248 | $L_{A375}$ | $L_{B8}$ |
| III-1249 | $L_{A376}$ | $L_{B8}$ |
| III-1250 | $L_{A377}$ | $L_{B8}$ |
| III-1251 | $L_{A378}$ | $L_{B8}$ |
| III-1252 | $L_{A379}$ | $L_{B8}$ |
| III-1253 | $L_{A380}$ | $L_{B8}$ |
| III-1254 | $L_{A381}$ | $L_{B8}$ |
| III-1255 | $L_{A382}$ | $L_{B8}$ |
| III-1256 | $L_{A383}$ | $L_{B8}$ |
| III-1257 | $L_{A384}$ | $L_{B8}$ |
| III-1258 | $L_{A385}$ | $L_{B8}$ |
| III-1259 | $L_{A386}$ | $L_{B8}$ |
| III-1260 | $L_{A387}$ | $L_{B8}$ |
| III-1261 | $L_{A388}$ | $L_{B8}$ |
| III-1262 | $L_{A389}$ | $L_{B8}$ |
| III-1263 | $L_{A390}$ | $L_{B8}$ |
| III-1264 | $L_{A391}$ | $L_{B8}$ |
| III-1265 | $L_{A392}$ | $L_{B8}$ |
| III-1266 | $L_{A393}$ | $L_{B8}$ |
| III-1267 | $L_{A394}$ | $L_{B8}$ |
| III-1268 | $L_{A395}$ | $L_{B8}$ |
| III-1269 | $L_{A396}$ | $L_{B8}$ |
| III-1270 | $L_{A397}$ | $L_{B8}$ |
| III-1271 | $L_{A398}$ | $L_{B8}$ |
| III-1272 | $L_{A399}$ | $L_{B8}$ |
| III-1273 | $L_{A400}$ | $L_{B8}$ |
| III-1274 | $L_{A401}$ | $L_{B8}$ |
| III-1275 | $L_{A402}$ | $L_{B8}$ |
| III-1276 | $L_{A403}$ | $L_{B8}$ |
| III-1277 | $L_{A404}$ | $L_{B8}$ |
| III-1278 | $L_{A405}$ | $L_{B8}$ |
| III-1279 | $L_{A406}$ | $L_{B8}$ |
| III-1280 | $L_{A407}$ | $L_{B8}$ |
| III-1281 | $L_{A408}$ | $L_{B8}$ |
| III-1282 | $L_{A409}$ | $L_{B8}$ |
| III-1283 | $L_{A410}$ | $L_{B8}$ |
| III-1284 | $L_{A411}$ | $L_{B8}$ |
| III-1285 | $L_{A412}$ | $L_{B8}$ |
| III-1286 | $L_{A413}$ | $L_{B8}$ |
| III-1287 | $L_{A414}$ | $L_{B8}$ |
| III-1288 | $L_{A415}$ | $L_{B8}$ |
| III-1289 | $L_{A416}$ | $L_{B8}$ |
| III-1290 | $L_{A417}$ | $L_{B8}$ |
| III-1291 | $L_{A418}$ | $L_{B8}$ |
| III-1292 | $L_{A419}$ | $L_{B8}$ |
| III-1293 | $L_{A420}$ | $L_{B8}$ |
| III-1294 | $L_{A421}$ | $L_{B8}$ |
| III-1295 | $L_{A422}$ | $L_{B8}$ |
| III-1296 | $L_{A423}$ | $L_{B8}$ |
| III-1297 | $L_{A424}$ | $L_{B8}$ |
| III-1298 | $L_{A425}$ | $L_{B8}$ |
| III-1299 | $L_{A426}$ | $L_{B8}$ |
| III-1300 | $L_{A427}$ | $L_{B8}$ |
| III-1301 | $L_{A428}$ | $L_{B8}$ |
| III-1302 | $L_{A429}$ | $L_{B8}$ |
| III-1303 | $L_{A430}$ | $L_{B8}$ |
| III-1304 | $L_{A431}$ | $L_{B8}$ |
| III-1305 | $L_{A432}$ | $L_{B8}$ |
| III-1306 | $L_{A433}$ | $L_{B8}$ |
| III-1307 | $L_{A434}$ | $L_{B8}$ |
| III-1308 | $L_{A435}$ | $L_{B8}$ |
| III-1309 | $L_{A436}$ | $L_{B8}$ |

| Compound Number | $L_A$ | $L_B$ |
|---|---|---|
| III-1310 | $L_{A437}$ | $L_{B8}$ |
| III-1311 | $L_{A438}$ | $L_{B8}$ |
| III-1312 | $L_{A439}$ | $L_{B8}$ |
| III-1313 | $L_{A440}$ | $L_{B8}$ |
| III-1314 | $L_{A441}$ | $L_{B8}$ |
| III-1315 | $L_{A442}$ | $L_{B8}$ |
| III-1316 | $L_{A443}$ | $L_{B8}$ |
| III-1317 | $L_{A444}$ | $L_{B8}$ |
| III-1318 | $L_{A445}$ | $L_{B8}$ |
| III-1319 | $L_{A446}$ | $L_{B8}$ |
| III-1320 | $L_{A447}$ | $L_{B8}$ |
| III-1321 | $L_{A448}$ | $L_{B8}$ |
| III-1322 | $L_{A449}$ | $L_{B8}$ |
| III-1323 | $L_{A450}$ | $L_{B8}$ |
| III-1324 | $L_{A451}$ | $L_{B8}$ |
| III-1325 | $L_{A452}$ | $L_{B8}$ |
| III-1326 | $L_{A453}$ | $L_{B8}$ |
| III-1327 | $L_{A454}$ | $L_{B8}$ |
| III-1328 | $L_{A455}$ | $L_{B8}$ |
| III-1329 | $L_{A456}$ | $L_{B8}$ |
| III-1330 | $L_{A457}$ | $L_{B8}$ |
| III-1331 | $L_{A458}$ | $L_{B8}$ |
| III-1332 | $L_{A459}$ | $L_{B8}$ |
| III-1333 | $L_{A460}$ | $L_{B8}$ |
| III-1334 | $L_{A461}$ | $L_{B8}$ |
| III-1335 | $L_{A462}$ | $L_{B8}$ |
| III-1336 | $L_{A463}$ | $L_{B8}$ |
| III-1337 | $L_{A464}$ | $L_{B8}$ |
| III-1338 | $L_{A465}$ | $L_{B8}$ |
| III-1339 | $L_{A466}$ | $L_{B8}$ |
| III-1340 | $L_{A467}$ | $L_{B8}$ |
| III-1341 | $L_{A468}$ | $L_{B8}$ |
| III-1342 | $L_{A469}$ | $L_{B8}$ |
| III-1343 | $L_{A470}$ | $L_{B8}$ |
| III-1344 | $L_{A471}$ | $L_{B8}$ |
| III-1345 | $L_{A472}$ | $L_{B8}$ |
| III-1346 | $L_{A473}$ | $L_{B8}$ |
| III-1347 | $L_{A474}$ | $L_{B8}$ |
| III-1348 | $L_{A475}$ | $L_{B8}$ |
| III-1349 | $L_{A476}$ | $L_{B8}$ |
| III-1350 | $L_{A477}$ | $L_{B8}$ |
| III-1351 | $L_{A478}$ | $L_{B8}$ |
| III-1352 | $L_{A479}$ | $L_{B8}$ |
| III-1353 | $L_{A480}$ | $L_{B8}$ |
| III-1354 | $L_{A481}$ | $L_{B8}$ |
| III-1355 | $L_{A482}$ | $L_{B8}$ |
| III-1356 | $L_{A483}$ | $L_{B8}$ |
| III-1357 | $L_{A484}$ | $L_{B8}$ |
| III-1358 | $L_{A485}$ | $L_{B8}$ |
| III-1359 | $L_{A486}$ | $L_{B8}$ |
| III-1360 | $L_{A487}$ | $L_{B8}$ |
| III-1361 | $L_{A318}$ | $L_{B9}$ |
| III-1362 | $L_{A319}$ | $L_{B9}$ |
| III-1363 | $L_{A320}$ | $L_{B9}$ |
| III-1364 | $L_{A321}$ | $L_{B9}$ |
| III-1365 | $L_{A322}$ | $L_{B9}$ |
| III-1366 | $L_{A323}$ | $L_{B9}$ |
| III-1367 | $L_{A324}$ | $L_{B9}$ |
| III-1368 | $L_{A325}$ | $L_{B9}$ |
| III-1369 | $L_{A326}$ | $L_{B9}$ |
| III-1370 | $L_{A327}$ | $L_{B9}$ |
| III-1371 | $L_{A328}$ | $L_{B9}$ |
| III-1372 | $L_{A329}$ | $L_{BS}$ |
| III-1373 | $L_{A330}$ | $L_{B9}$ |
| III-1374 | $L_{A331}$ | $L_{B9}$ |
| III-1375 | $L_{A332}$ | $L_{B9}$ |
| III-1376 | $L_{A333}$ | $L_{B9}$ |
| III-1377 | $L_{A334}$ | $L_{B9}$ |
| III-1378 | $L_{A335}$ | $L_{B9}$ |
| III-1379 | $L_{A336}$ | $L_{B9}$ |
| III-1380 | $L_{A337}$ | $L_{B9}$ |
| III-1381 | $L_{A338}$ | $L_{B9}$ |
| III-1382 | $L_{A339}$ | $L_{B9}$ |
| III-1383 | $L_{A340}$ | $L_{B9}$ |
| III-1384 | $L_{A341}$ | $L_{B9}$ |
| III-1385 | $L_{A342}$ | $L_{B9}$ |
| III-1386 | $L_{A343}$ | $L_{B9}$ |
| III-1387 | $L_{A344}$ | $L_{B9}$ |
| III-1388 | $L_{A345}$ | $L_{B9}$ |
| III-1389 | $L_{A346}$ | $L_{B9}$ |
| III-1390 | $L_{A347}$ | $L_{B9}$ |
| III-1391 | $L_{A348}$ | $L_{B9}$ |
| III-1392 | $L_{A349}$ | $L_{B9}$ |
| III-1393 | $L_{A350}$ | $L_{B9}$ |
| III-1394 | $L_{A351}$ | $L_{B9}$ |
| III-1395 | $L_{A352}$ | $L_{B9}$ |
| III-1396 | $L_{A353}$ | $L_{B9}$ |
| III-1397 | $L_{A354}$ | $L_{B9}$ |
| III-1398 | $L_{A355}$ | $L_{B9}$ |
| III-1399 | $L_{A356}$ | $L_{B9}$ |
| III-1400 | $L_{A357}$ | $L_{B9}$ |
| III-1401 | $L_{A358}$ | $L_{B9}$ |
| III-1402 | $L_{A359}$ | $L_{B9}$ |
| III-1403 | $L_{A360}$ | $L_{B9}$ |
| III-1404 | $L_{A361}$ | $L_{B9}$ |
| III-1405 | $L_{A362}$ | $L_{B9}$ |
| III-1406 | $L_{A363}$ | $L_{B9}$ |
| III-1407 | $L_{A364}$ | $L_{B9}$ |
| III-1408 | $L_{A365}$ | $L_{B9}$ |
| III-1409 | $L_{A366}$ | $L_{B9}$ |
| III-1410 | $L_{A367}$ | $L_{B9}$ |
| III-1411 | $L_{A368}$ | $L_{B9}$ |
| III-1412 | $L_{A369}$ | $L_{B9}$ |
| III-1413 | $L_{A370}$ | $L_{B9}$ |
| III-1414 | $L_{A371}$ | $L_{B9}$ |
| III-1415 | $L_{A372}$ | $L_{B9}$ |
| III-1416 | $L_{A373}$ | $L_{B9}$ |
| III-1417 | $L_{A374}$ | $L_{B9}$ |
| III-1418 | $L_{A375}$ | $L_{B9}$ |
| III-1419 | $L_{A376}$ | $L_{B9}$ |
| III-1420 | $L_{A377}$ | $L_{B9}$ |
| III-1421 | $L_{A378}$ | $L_{B9}$ |
| III-1422 | $L_{A379}$ | $L_{B9}$ |
| III-1423 | $L_{A380}$ | $L_{B9}$ |
| III-1424 | $L_{A381}$ | $L_{B9}$ |
| III-1425 | $L_{A382}$ | $L_{B9}$ |
| III-1426 | $L_{A383}$ | $L_{B9}$ |
| III-1427 | $L_{A384}$ | $L_{B9}$ |
| III-1428 | $L_{A385}$ | $L_{B9}$ |
| III-1429 | $L_{A386}$ | $L_{B9}$ |
| III-1430 | $L_{A387}$ | $L_{B9}$ |
| III-1431 | $L_{A388}$ | $L_{B9}$ |
| III-1432 | $L_{A389}$ | $L_{B9}$ |
| III-1433 | $L_{A390}$ | $L_{B9}$ |
| III-1434 | $L_{A391}$ | $L_{B9}$ |
| III-1435 | $L_{A392}$ | $L_{B9}$ |
| III-1436 | $L_{A393}$ | $L_{B9}$ |
| III-1437 | $L_{A394}$ | $L_{B9}$ |
| III-1438 | $L_{A395}$ | $L_{B9}$ |
| III-1439 | $L_{A396}$ | $L_{B9}$ |
| III-1440 | $L_{A397}$ | $L_{B9}$ |
| III-1441 | $L_{A398}$ | $L_{B9}$ |
| III-1442 | $L_{A399}$ | $L_{B9}$ |
| III-1443 | $L_{A400}$ | $L_{B9}$ |
| III-1444 | $L_{A401}$ | $L_{B9}$ |
| III-1445 | $L_{A402}$ | $L_{B9}$ |
| III-1446 | $L_{A403}$ | $L_{B9}$ |
| III-1447 | $L_{A404}$ | $L_{B9}$ |
| III-1448 | $L_{A405}$ | $L_{B9}$ |
| III-1449 | $L_{A406}$ | $L_{B9}$ |
| III-1450 | $L_{A407}$ | $L_{B9}$ |
| III-1451 | $L_{A408}$ | $L_{B9}$ |
| III-1452 | $L_{A409}$ | $L_{B9}$ |
| III-1453 | $L_{A410}$ | $L_{B9}$ |
| III-1454 | $L_{A411}$ | $L_{B9}$ |
| III-1455 | $L_{A412}$ | $L_{B9}$ |
| III-1456 | $L_{A413}$ | $L_{B9}$ |
| III-1457 | $L_{A414}$ | $L_{B9}$ |
| III-1458 | $L_{A415}$ | $L_{B9}$ |
| III-1459 | $L_{A416}$ | $L_{B9}$ |
| III-1460 | $L_{A417}$ | $L_{B9}$ |
| III-1461 | $L_{A418}$ | $L_{B9}$ |

| Compound Number | $L_A$ | $L_B$ |
|---|---|---|
| III-1462 | $L_{A419}$ | $L_{B9}$ |
| III-1463 | $L_{A420}$ | $L_{B9}$ |
| III-1464 | $L_{A421}$ | $L_{B9}$ |
| III-1465 | $L_{A422}$ | $L_{B9}$ |
| III-1466 | $L_{A423}$ | $L_{B9}$ |
| III-1467 | $L_{A424}$ | $L_{B9}$ |
| III-1468 | $L_{A425}$ | $L_{B9}$ |
| III-1469 | $L_{A426}$ | $L_{B9}$ |
| III-1470 | $L_{A427}$ | $L_{B9}$ |
| III-1471 | $L_{A428}$ | $L_{B9}$ |
| III-1472 | $L_{A429}$ | $L_{B9}$ |
| III-1473 | $L_{A430}$ | $L_{B9}$ |
| III-1474 | $L_{A431}$ | $L_{B9}$ |
| III-1475 | $L_{A432}$ | $L_{B9}$ |
| III-1476 | $L_{A433}$ | $L_{B9}$ |
| III-1477 | $L_{A434}$ | $L_{B9}$ |
| III-1478 | $L_{A435}$ | $L_{B9}$ |
| III-1479 | $L_{A436}$ | $L_{B9}$ |
| III-1480 | $L_{A437}$ | $L_{B9}$ |
| III-1481 | $L_{A438}$ | $L_{B9}$ |
| III-1482 | $L_{A439}$ | $L_{B9}$ |
| III-1483 | $L_{A440}$ | $L_{B9}$ |
| III-1484 | $L_{A441}$ | $L_{B9}$ |
| III-1485 | $L_{A442}$ | $L_{B9}$ |
| III-1486 | $L_{A443}$ | $L_{B9}$ |
| III-1487 | $L_{A444}$ | $L_{B9}$ |
| III-1488 | $L_{A445}$ | $L_{B9}$ |
| III-1489 | $L_{A446}$ | $L_{B9}$ |
| III-1490 | $L_{A447}$ | $L_{B9}$ |
| III-1491 | $L_{A448}$ | $L_{B9}$ |
| III-1492 | $L_{A449}$ | $L_{B9}$ |
| III-1493 | $L_{A450}$ | $L_{B9}$ |
| III-1494 | $L_{A451}$ | $L_{B9}$ |
| III-1495 | $L_{A452}$ | $L_{B9}$ |
| III-1496 | $L_{A453}$ | $L_{B9}$ |
| III-1497 | $L_{A454}$ | $L_{B9}$ |
| III-1498 | $L_{A455}$ | $L_{B9}$ |
| III-1499 | $L_{A456}$ | $L_{B9}$ |
| III-1500 | $L_{A457}$ | $L_{B9}$ |
| III-1501 | $L_{A458}$ | $L_{B9}$ |
| III-1502 | $L_{A459}$ | $L_{B9}$ |
| III-1503 | $L_{A460}$ | $L_{B9}$ |
| III-1504 | $L_{A461}$ | $L_{B9}$ |
| III-1505 | $L_{A462}$ | $L_{B9}$ |
| III-1506 | $L_{A463}$ | $L_{B9}$ |
| III-1507 | $L_{A464}$ | $L_{B9}$ |
| III-1508 | $L_{A465}$ | $L_{B9}$ |
| III-1509 | $L_{A466}$ | $L_{B9}$ |
| III-1510 | $L_{A467}$ | $L_{B9}$ |
| III-1511 | $L_{A468}$ | $L_{B9}$ |
| III-1512 | $L_{A469}$ | $L_{B9}$ |
| III-1513 | $L_{A470}$ | $L_{B9}$ |
| III-1514 | $L_{A471}$ | $L_{B9}$ |
| III-1515 | $L_{A472}$ | $L_{B9}$ |
| III-1516 | $L_{A473}$ | $L_{B9}$ |
| III-1517 | $L_{A474}$ | $L_{B9}$ |
| III-1518 | $L_{A475}$ | $L_{B9}$ |
| III-1519 | $L_{A476}$ | $L_{B9}$ |
| III-1520 | $L_{A477}$ | $L_{B9}$ |
| III-1521 | $L_{A478}$ | $L_{B9}$ |
| III-1522 | $L_{A479}$ | $L_{B9}$ |
| III-1523 | $L_{A480}$ | $L_{B9}$ |
| III-1524 | $L_{A481}$ | $L_{B9}$ |
| III-1525 | $L_{A482}$ | $L_{B9}$ |
| III-1526 | $L_{A483}$ | $L_{B9}$ |
| III-1527 | $L_{A484}$ | $L_{B9}$ |
| III-1528 | $L_{A485}$ | $L_{B9}$ |
| III-1529 | $L_{A486}$ | $L_{B9}$ |
| III-1530 | $L_{A487}$ | $L_{B9}$ |
| III-1531 | $L_{A318}$ | $L_{B10}$ |
| III-1532 | $L_{A319}$ | $L_{B10}$ |
| III-1533 | $L_{A320}$ | $L_{B10}$ |
| III-1534 | $L_{A321}$ | $L_{B10}$ |
| III-1535 | $L_{A322}$ | $L_{B10}$ |
| III-1536 | $L_{A323}$ | $L_{B10}$ |
| III-1537 | $L_{A324}$ | $L_{B10}$ |
| III-1538 | $L_{A325}$ | $L_{B10}$ |
| III-1539 | $L_{A326}$ | $L_{B10}$ |
| III-1540 | $L_{A327}$ | $L_{B10}$ |
| III-1541 | $L_{A328}$ | $L_{B10}$ |
| III-1542 | $L_{A329}$ | $L_{B10}$ |
| III-1543 | $L_{A330}$ | $L_{B10}$ |
| III-1544 | $L_{A331}$ | $L_{B10}$ |
| III-1545 | $L_{A332}$ | $L_{B10}$ |
| III-1546 | $L_{A333}$ | $L_{B10}$ |
| III-1547 | $L_{A334}$ | $L_{B10}$ |
| III-1548 | $L_{A335}$ | $L_{B10}$ |
| III-1549 | $L_{A336}$ | $L_{B10}$ |
| III-1550 | $L_{A337}$ | $L_{B10}$ |
| III-1551 | $L_{A338}$ | $L_{B10}$ |
| III-1552 | $L_{A339}$ | $L_{B10}$ |
| III-1553 | $L_{A340}$ | $L_{B10}$ |
| III-1554 | $L_{A341}$ | $L_{B10}$ |
| III-1555 | $L_{A342}$ | $L_{B10}$ |
| III-1556 | $L_{A343}$ | $L_{B10}$ |
| III-1557 | $L_{A344}$ | $L_{B10}$ |
| III-1558 | $L_{A345}$ | $L_{B10}$ |
| III-1559 | $L_{A346}$ | $L_{B10}$ |
| III-1560 | $L_{A347}$ | $L_{B10}$ |
| III-1561 | $L_{A348}$ | $L_{B10}$ |
| III-1562 | $L_{A349}$ | $L_{B10}$ |
| III-1563 | $L_{A350}$ | $L_{B10}$ |
| III-1564 | $L_{A351}$ | $L_{B10}$ |
| III-1565 | $L_{A352}$ | $L_{B10}$ |
| III-1566 | $L_{A353}$ | $L_{B10}$ |
| III-1567 | $L_{A354}$ | $L_{B10}$ |
| III-1568 | $L_{A355}$ | $L_{B10}$ |
| III-1569 | $L_{A356}$ | $L_{B10}$ |
| III-1570 | $L_{A357}$ | $L_{B10}$ |
| III-1571 | $L_{A358}$ | $L_{B10}$ |
| III-1572 | $L_{A359}$ | $L_{B10}$ |
| III-1573 | $L_{A360}$ | $L_{B10}$ |
| III-1574 | $L_{A361}$ | $L_{B10}$ |
| III-1575 | $L_{A362}$ | $L_{B10}$ |
| III-1576 | $L_{A363}$ | $L_{B10}$ |
| III-1577 | $L_{A364}$ | $L_{B10}$ |
| III-1578 | $L_{A365}$ | $L_{B10}$ |
| III-1579 | $L_{A366}$ | $L_{B10}$ |
| III-1580 | $L_{A367}$ | $L_{B10}$ |
| III-1581 | $L_{A368}$ | $L_{B10}$ |
| III-1582 | $L_{A369}$ | $L_{B10}$ |
| III-1583 | $L_{A370}$ | $L_{B10}$ |
| III-1584 | $L_{A371}$ | $L_{B10}$ |
| III-1585 | $L_{A372}$ | $L_{B10}$ |
| III-1586 | $L_{A373}$ | $L_{B10}$ |
| III-1587 | $L_{A374}$ | $L_{B10}$ |
| III-1588 | $L_{A375}$ | $L_{B10}$ |
| III-1589 | $L_{A376}$ | $L_{B10}$ |
| III-1590 | $L_{A377}$ | $L_{B10}$ |
| III-1591 | $L_{A378}$ | $L_{B10}$ |
| III-1592 | $L_{A379}$ | $L_{B10}$ |
| III-1593 | $L_{A380}$ | $L_{B10}$ |
| III-1594 | $L_{A381}$ | $L_{B10}$ |
| III-1595 | $L_{A382}$ | $L_{B10}$ |
| III-1596 | $L_{A383}$ | $L_{B10}$ |
| III-1597 | $L_{A384}$ | $L_{B10}$ |
| III-1598 | $L_{A385}$ | $L_{B10}$ |
| III-1599 | $L_{A386}$ | $L_{B10}$ |
| III-1600 | $L_{A387}$ | $L_{B10}$ |
| III-1601 | $L_{A388}$ | $L_{B10}$ |
| III-1602 | $L_{A389}$ | $L_{B10}$ |
| III-1603 | $L_{A390}$ | $L_{B10}$ |
| III-1604 | $L_{A391}$ | $L_{B10}$ |
| III-1605 | $L_{A392}$ | $L_{B10}$ |
| III-1606 | $L_{A393}$ | $L_{B10}$ |
| III-1607 | $L_{A394}$ | $L_{B10}$ |
| III-1608 | $L_{A395}$ | $L_{B10}$ |
| III-1609 | $L_{A396}$ | $L_{B10}$ |
| III-1610 | $L_{A397}$ | $L_{B10}$ |
| III-1611 | $L_{A398}$ | $L_{B10}$ |
| III-1612 | $L_{A399}$ | $L_{B10}$ |
| III-1613 | $L_{A400}$ | $L_{B10}$ |

| Compound Number | $L_A$ | $L_B$ |
|---|---|---|
| III-1614 | $L_{A401}$ | $L_{B10}$ |
| III-1615 | $L_{A402}$ | $L_{B10}$ |
| III-1616 | $L_{A403}$ | $L_{B10}$ |
| III-1617 | $L_{A404}$ | $L_{B10}$ |
| III-1618 | $L_{A405}$ | $L_{B10}$ |
| III-1619 | $L_{A406}$ | $L_{B10}$ |
| III-1620 | $L_{A407}$ | $L_{B10}$ |
| III-1621 | $L_{A408}$ | $L_{B10}$ |
| III-1622 | $L_{A409}$ | $L_{B10}$ |
| III-1623 | $L_{A410}$ | $L_{B10}$ |
| III-1624 | $L_{A411}$ | $L_{B10}$ |
| III-1625 | $L_{A412}$ | $L_{B10}$ |
| III-1626 | $L_{A413}$ | $L_{B10}$ |
| III-1627 | $L_{A414}$ | $L_{B10}$ |
| III-1628 | $L_{A415}$ | $L_{B10}$ |
| III-1629 | $L_{A416}$ | $L_{B10}$ |
| III-1630 | $L_{A417}$ | $L_{B10}$ |
| III-1631 | $L_{A418}$ | $L_{B10}$ |
| III-1632 | $L_{A419}$ | $L_{B10}$ |
| III-1633 | $L_{A420}$ | $L_{B10}$ |
| III-1634 | $L_{A421}$ | $L_{B10}$ |
| III-1635 | $L_{A422}$ | $L_{B10}$ |
| III-1636 | $L_{A423}$ | $L_{B10}$ |
| III-1637 | $L_{A424}$ | $L_{B10}$ |
| III-1638 | $L_{A425}$ | $L_{B10}$ |
| III-1639 | $L_{A426}$ | $L_{B10}$ |
| III-1640 | $L_{A427}$ | $L_{B10}$ |
| III-1641 | $L_{A428}$ | $L_{B10}$ |
| III-1642 | $L_{A429}$ | $L_{B10}$ |
| III-1643 | $L_{A430}$ | $L_{B10}$ |
| III-1644 | $L_{A431}$ | $L_{B10}$ |
| III-1645 | $L_{A432}$ | $L_{B10}$ |
| III-1646 | $L_{A433}$ | $L_{B10}$ |
| III-1647 | $L_{A434}$ | $L_{B10}$ |
| III-1648 | $L_{A435}$ | $L_{B10}$ |
| III-1649 | $L_{A436}$ | $L_{B10}$ |
| III-1650 | $L_{A437}$ | $L_{B10}$ |
| III-1651 | $L_{A438}$ | $L_{B10}$ |
| III-1652 | $L_{A439}$ | $L_{B10}$ |
| III-1653 | $L_{A440}$ | $L_{B10}$ |
| III-1654 | $L_{A441}$ | $L_{B10}$ |
| III-1655 | $L_{A442}$ | $L_{B10}$ |
| III-1656 | $L_{A443}$ | $L_{B10}$ |
| III-1657 | $L_{A444}$ | $L_{B10}$ |
| III-1658 | $L_{A445}$ | $L_{B10}$ |
| III-1659 | $L_{A446}$ | $L_{B10}$ |
| III-1660 | $L_{A447}$ | $L_{B10}$ |
| III-1661 | $L_{A448}$ | $L_{B10}$ |
| III-1662 | $L_{A449}$ | $L_{B10}$ |
| III-1663 | $L_{A450}$ | $L_{B10}$ |
| III-1664 | $L_{A451}$ | $L_{B10}$ |
| III-1665 | $L_{A452}$ | $L_{B10}$ |
| III-1666 | $L_{A453}$ | $L_{B10}$ |
| III-1667 | $L_{A454}$ | $L_{B10}$ |
| III-1668 | $L_{A455}$ | $L_{B10}$ |
| III-1669 | $L_{A456}$ | $L_{B10}$ |
| III-1670 | $L_{A457}$ | $L_{B10}$ |
| III-1671 | $L_{A458}$ | $L_{B10}$ |
| III-1672 | $L_{A459}$ | $L_{B10}$ |
| III-1673 | $L_{A460}$ | $L_{B10}$ |
| III-1674 | $L_{A461}$ | $L_{B10}$ |
| III-1675 | $L_{A462}$ | $L_{B10}$ |
| III-1676 | $L_{A463}$ | $L_{B10}$ |
| III-1677 | $L_{A464}$ | $L_{B10}$ |
| III-1678 | $L_{A465}$ | $L_{B10}$ |
| III-1679 | $L_{A466}$ | $L_{B10}$ |
| III-1680 | $L_{A467}$ | $L_{B10}$ |
| III-1681 | $L_{A468}$ | $L_{B10}$ |
| III-1682 | $L_{A469}$ | $L_{B10}$ |
| III-1683 | $L_{A470}$ | $L_{B10}$ |
| III-1684 | $L_{A471}$ | $L_{B10}$ |
| III-1685 | $L_{A472}$ | $L_{B10}$ |
| III-1686 | $L_{A473}$ | $L_{B10}$ |
| III-1687 | $L_{A474}$ | $L_{B10}$ |
| III-1688 | $L_{A475}$ | $L_{B10}$ |
| III-1689 | $L_{A476}$ | $L_{B10}$ |
| III-1690 | $L_{A477}$ | $L_{B10}$ |
| III-1691 | $L_{A478}$ | $L_{B10}$ |
| III-1692 | $L_{A479}$ | $L_{B10}$ |
| III-1693 | $L_{A480}$ | $L_{B10}$ |
| III-1694 | $L_{A481}$ | $L_{B10}$ |
| III-1695 | $L_{A482}$ | $L_{B10}$ |
| III-1696 | $L_{A483}$ | $L_{B10}$ |
| III-1697 | $L_{A484}$ | $L_{B10}$ |
| III-1698 | $L_{A485}$ | $L_{B10}$ |
| III-1699 | $L_{A486}$ | $L_{B10}$ |
| III-1700 | $L_{A487}$ | $L_{B10}$ |
| III-1701 | $L_{A318}$ | $L_{B11}$ |
| III-1702 | $L_{A319}$ | $L_{B11}$ |
| III-1703 | $L_{A320}$ | $L_{B11}$ |
| III-1704 | $L_{A321}$ | $L_{B11}$ |
| III-1705 | $L_{A322}$ | $L_{B11}$ |
| III-1706 | $L_{A323}$ | $L_{B11}$ |
| III-1707 | $L_{A324}$ | $L_{B11}$ |
| III-1708 | $L_{A325}$ | $L_{B11}$ |
| III-1709 | $L_{A326}$ | $L_{B11}$ |
| III-1710 | $L_{A327}$ | $L_{B11}$ |
| III-1711 | $L_{A328}$ | $L_{B11}$ |
| III-1712 | $L_{A329}$ | $L_{B11}$ |
| III-1713 | $L_{A330}$ | $L_{B11}$ |
| III-1714 | $L_{A331}$ | $L_{B11}$ |
| III-1715 | $L_{A332}$ | $L_{B11}$ |
| III-1716 | $L_{A333}$ | $L_{B11}$ |
| III-1717 | $L_{A334}$ | $L_{B11}$ |
| III-1718 | $L_{A335}$ | $L_{B11}$ |
| III-1719 | $L_{A336}$ | $L_{B11}$ |
| III-1720 | $L_{A337}$ | $L_{B11}$ |
| III-1721 | $L_{A338}$ | $L_{B11}$ |
| III-1722 | $L_{A339}$ | $L_{B11}$ |
| III-1723 | $L_{A340}$ | $L_{B11}$ |
| III-1724 | $L_{A341}$ | $L_{B11}$ |
| III-1725 | $L_{A342}$ | $L_{B11}$ |
| III-1726 | $L_{A343}$ | $L_{B11}$ |
| III-1727 | $L_{A344}$ | $L_{B11}$ |
| III-1728 | $L_{A345}$ | $L_{B11}$ |
| III-1729 | $L_{A346}$ | $L_{B11}$ |
| III-1730 | $L_{A347}$ | $L_{B11}$ |
| III-1731 | $L_{A348}$ | $L_{B11}$ |
| III-1732 | $L_{A349}$ | $L_{B11}$ |
| III-1733 | $L_{A350}$ | $L_{B11}$ |
| III-1734 | $L_{A351}$ | $L_{B11}$ |
| III-1735 | $L_{A352}$ | $L_{B11}$ |
| III-1736 | $L_{A353}$ | $L_{B11}$ |
| III-1737 | $L_{A354}$ | $L_{B11}$ |
| III-1738 | $L_{A355}$ | $L_{B11}$ |
| III-1739 | $L_{A356}$ | $L_{B11}$ |
| III-1740 | $L_{A357}$ | $L_{B11}$ |
| III-1741 | $L_{A358}$ | $L_{B11}$ |
| III-1742 | $L_{A359}$ | $L_{B11}$ |
| III-1743 | $L_{A360}$ | $L_{B11}$ |
| III-1744 | $L_{A361}$ | $L_{B11}$ |
| III-1745 | $L_{A362}$ | $L_{B11}$ |
| III-1746 | $L_{A363}$ | $L_{B11}$ |
| III-1747 | $L_{A364}$ | $L_{B11}$ |
| III-1748 | $L_{A365}$ | $L_{B11}$ |
| III-1749 | $L_{A366}$ | $L_{B11}$ |
| III-1750 | $L_{A367}$ | $L_{B11}$ |
| III-1751 | $L_{A368}$ | $L_{B11}$ |
| III-1752 | $L_{A369}$ | $L_{B11}$ |
| III-1753 | $L_{A370}$ | $L_{B11}$ |
| III-1754 | $L_{A371}$ | $L_{B11}$ |
| III-1755 | $L_{A372}$ | $L_{B11}$ |
| III-1756 | $L_{A373}$ | $L_{B11}$ |
| III-1757 | $L_{A374}$ | $L_{B11}$ |
| III-1758 | $L_{A375}$ | $L_{B11}$ |
| III-1759 | $L_{A376}$ | $L_{B11}$ |
| III-1760 | $L_{A377}$ | $L_{B11}$ |
| III-1761 | $L_{A378}$ | $L_{B11}$ |
| III-1762 | $L_{A379}$ | $L_{B11}$ |
| III-1763 | $L_{A380}$ | $L_{B11}$ |
| III-1764 | $L_{A381}$ | $L_{B11}$ |
| III-1765 | $L_{A382}$ | $L_{B11}$ |

| Compound Number | $L_A$ | $L_B$ |
|---|---|---|
| III-1766 | $L_{A383}$ | $L_{B11}$ |
| III-1767 | $L_{A384}$ | $L_{B11}$ |
| III-1768 | $L_{A385}$ | $L_{B11}$ |
| III-1769 | $L_{A386}$ | $L_{B11}$ |
| III-1770 | $L_{A387}$ | $L_{B11}$ |
| III-1771 | $L_{A388}$ | $L_{B11}$ |
| III-1772 | $L_{A389}$ | $L_{B11}$ |
| III-1773 | $L_{A390}$ | $L_{B11}$ |
| III-1774 | $L_{A391}$ | $L_{B11}$ |
| III-1775 | $L_{A392}$ | $L_{B11}$ |
| III-1776 | $L_{A393}$ | $L_{B11}$ |
| III-1777 | $L_{A394}$ | $L_{B11}$ |
| III-1778 | $L_{A395}$ | $L_{B11}$ |
| III-1779 | $L_{A396}$ | $L_{B11}$ |
| III-1780 | $L_{A397}$ | $L_{B11}$ |
| III-1781 | $L_{A398}$ | $L_{B11}$ |
| III-1782 | $L_{A399}$ | $L_{B11}$ |
| III-1783 | $L_{A400}$ | $L_{B11}$ |
| III-1784 | $L_{A401}$ | $L_{B11}$ |
| III-1785 | $L_{A402}$ | $L_{B11}$ |
| III-1786 | $L_{A403}$ | $L_{B11}$ |
| III-1787 | $L_{A404}$ | $L_{B11}$ |
| III-1788 | $L_{A405}$ | $L_{B11}$ |
| III-1789 | $L_{A406}$ | $L_{B11}$ |
| III-1790 | $L_{A407}$ | $L_{B11}$ |
| III-1791 | $L_{A408}$ | $L_{B11}$ |
| III-1792 | $L_{A409}$ | $L_{B11}$ |
| III-1793 | $L_{A410}$ | $L_{B11}$ |
| III-1794 | $L_{A411}$ | $L_{B11}$ |
| III-1795 | $L_{A412}$ | $L_{B11}$ |
| III-1796 | $L_{A413}$ | $L_{B11}$ |
| III-1797 | $L_{A414}$ | $L_{B11}$ |
| III-1798 | $L_{A415}$ | $L_{B11}$ |
| III-1799 | $L_{A416}$ | $L_{B11}$ |
| III-1800 | $L_{A417}$ | $L_{B11}$ |
| III-1801 | $L_{A418}$ | $L_{B11}$ |
| III-1802 | $L_{A419}$ | $L_{B11}$ |
| III-1803 | $L_{A420}$ | $L_{B11}$ |
| III-1804 | $L_{A421}$ | $L_{B11}$ |
| III-1805 | $L_{A422}$ | $L_{B11}$ |
| III-1806 | $L_{A423}$ | $L_{B11}$ |
| III-1807 | $L_{A424}$ | $L_{B11}$ |
| III-1808 | $L_{A425}$ | $L_{B11}$ |
| III-1809 | $L_{A426}$ | $L_{B11}$ |
| III-1810 | $L_{A427}$ | $L_{B11}$ |
| III-1811 | $L_{A428}$ | $L_{B11}$ |
| III-1812 | $L_{A429}$ | $L_{B11}$ |
| III-1813 | $L_{A430}$ | $L_{B11}$ |
| III-1814 | $L_{A431}$ | $L_{B11}$ |
| III-1815 | $L_{A432}$ | $L_{B11}$ |
| III-1816 | $L_{A433}$ | $L_{B11}$ |
| III-1817 | $L_{A434}$ | $L_{B11}$ |
| III-1818 | $L_{A435}$ | $L_{B11}$ |
| III-1819 | $L_{A436}$ | $L_{B11}$ |
| III-1820 | $L_{A437}$ | $L_{B11}$ |
| III-1821 | $L_{A438}$ | $L_{B11}$ |
| III-1822 | $L_{A439}$ | $L_{B11}$ |
| III-1823 | $L_{A440}$ | $L_{B11}$ |
| III-1824 | $L_{A441}$ | $L_{B11}$ |
| III-1825 | $L_{A442}$ | $L_{B11}$ |
| III-1826 | $L_{A443}$ | $L_{B11}$ |
| III-1827 | $L_{A444}$ | $L_{B11}$ |
| III-1828 | $L_{A445}$ | $L_{B11}$ |
| III-1829 | $L_{A446}$ | $L_{B11}$ |
| III-1830 | $L_{A447}$ | $L_{B11}$ |
| III-1831 | $L_{A448}$ | $L_{B11}$ |
| III-1832 | $L_{A449}$ | $L_{B11}$ |
| III-1833 | $L_{A450}$ | $L_{B11}$ |
| III-1834 | $L_{A451}$ | $L_{B11}$ |
| III-1835 | $L_{A452}$ | $L_{B11}$ |
| III-1836 | $L_{A453}$ | $L_{B11}$ |
| III-1837 | $L_{A454}$ | $L_{B11}$ |
| III-1838 | $L_{A455}$ | $L_{B11}$ |
| III-1839 | $L_{A456}$ | $L_{B11}$ |
| III-1840 | $L_{A457}$ | $L_{B11}$ |
| III-1841 | $L_{A458}$ | $L_{B11}$ |
| III-1842 | $L_{A459}$ | $L_{B11}$ |
| III-1843 | $L_{A460}$ | $L_{B11}$ |
| III-1844 | $L_{A461}$ | $L_{B11}$ |
| III-1845 | $L_{A462}$ | $L_{B11}$ |
| III-1846 | $L_{A463}$ | $L_{B11}$ |
| III-1847 | $L_{A464}$ | $L_{B11}$ |
| III-1848 | $L_{A465}$ | $L_{B11}$ |
| III-1849 | $L_{A466}$ | $L_{B11}$ |
| III-1850 | $L_{A467}$ | $L_{B11}$ |
| III-1851 | $L_{A468}$ | $L_{B11}$ |
| III-1852 | $L_{A469}$ | $L_{B11}$ |
| III-1853 | $L_{A470}$ | $L_{B11}$ |
| III-1854 | $L_{A471}$ | $L_{B11}$ |
| III-1855 | $L_{A472}$ | $L_{B11}$ |
| III-1856 | $L_{A473}$ | $L_{B11}$ |
| III-1857 | $L_{A474}$ | $L_{B11}$ |
| III-1858 | $L_{A475}$ | $L_{B11}$ |
| III-1859 | $L_{A476}$ | $L_{B11}$ |
| III-1860 | $L_{A477}$ | $L_{B11}$ |
| III-1861 | $L_{A478}$ | $L_{B11}$ |
| III-1862 | $L_{A479}$ | $L_{B11}$ |
| III-1863 | $L_{A480}$ | $L_{B11}$ |
| III-1864 | $L_{A481}$ | $L_{B11}$ |
| III-1865 | $L_{A482}$ | $L_{B11}$ |
| III-1866 | $L_{A483}$ | $L_{B11}$ |
| III-1867 | $L_{A484}$ | $L_{B11}$ |
| III-1868 | $L_{A485}$ | $L_{B11}$ |
| III-1869 | $L_{A486}$ | $L_{B11}$ |
| III-1870 | $L_{A487}$ | $L_{B11}$ |
| III-1871 | $L_{A318}$ | $L_{B12}$ |
| III-1872 | $L_{A319}$ | $L_{B12}$ |
| III-1873 | $L_{A320}$ | $L_{B12}$ |
| III-1874 | $L_{A321}$ | $L_{B12}$ |
| III-1875 | $L_{A322}$ | $L_{B12}$ |
| III-1876 | $L_{A323}$ | $L_{B12}$ |
| III-1877 | $L_{A324}$ | $L_{B12}$ |
| III-1878 | $L_{A325}$ | $L_{B12}$ |
| III-1879 | $L_{A326}$ | $L_{B12}$ |
| III-1880 | $L_{A327}$ | $L_{B12}$ |
| III-1881 | $L_{A328}$ | $L_{B12}$ |
| III-1882 | $L_{A329}$ | $L_{B12}$ |
| III-1883 | $L_{A330}$ | $L_{B12}$ |
| III-1884 | $L_{A331}$ | $L_{B12}$ |
| III-1885 | $L_{A332}$ | $L_{B12}$ |
| III-1886 | $L_{A333}$ | $L_{B12}$ |
| III-1887 | $L_{A334}$ | $L_{B12}$ |
| III-1888 | $L_{A335}$ | $L_{B12}$ |
| III-1889 | $L_{A336}$ | $L_{B12}$ |
| III-1890 | $L_{A337}$ | $L_{B12}$ |
| III-1891 | $L_{A338}$ | $L_{B12}$ |
| III-1892 | $L_{A339}$ | $L_{B12}$ |
| III-1893 | $L_{A340}$ | $L_{B12}$ |
| III-1894 | $L_{A341}$ | $L_{B12}$ |
| III-1895 | $L_{A342}$ | $L_{B12}$ |
| III-1896 | $L_{A343}$ | $L_{B12}$ |
| III-1897 | $L_{A344}$ | $L_{B12}$ |
| III-1898 | $L_{A345}$ | $L_{B12}$ |
| III-1899 | $L_{A346}$ | $L_{B12}$ |
| III-1900 | $L_{A347}$ | $L_{B12}$ |
| III-1901 | $L_{A348}$ | $L_{B12}$ |
| III-1902 | $L_{A349}$ | $L_{B12}$ |
| III-1903 | $L_{A350}$ | $L_{B12}$ |
| III-1904 | $L_{A351}$ | $L_{B12}$ |
| III-1905 | $L_{A352}$ | $L_{B12}$ |
| III-1906 | $L_{A353}$ | $L_{B12}$ |
| III-1907 | $L_{A354}$ | $L_{B12}$ |
| III-1908 | $L_{A355}$ | $L_{B12}$ |
| III-1909 | $L_{A356}$ | $L_{B12}$ |
| III-1910 | $L_{A357}$ | $L_{B12}$ |
| III-1911 | $L_{A358}$ | $L_{B12}$ |
| III-1912 | $L_{A359}$ | $L_{B12}$ |
| III-1913 | $L_{A360}$ | $L_{B12}$ |
| III-1914 | $L_{A361}$ | $L_{B12}$ |
| III-1915 | $L_{A362}$ | $L_{B12}$ |
| III-1916 | $L_{A363}$ | $L_{B12}$ |
| III-1917 | $L_{A364}$ | $L_{B12}$ |

-continued

| Compound Number | $L_A$ | $L_B$ |
|---|---|---|
| III-1918 | $L_{A365}$ | $L_{B12}$ |
| III-1919 | $L_{A366}$ | $L_{B12}$ |
| III-1920 | $L_{A367}$ | $L_{B12}$ |
| III-1921 | $L_{A368}$ | $L_{B12}$ |
| III-1922 | $L_{A369}$ | $L_{B12}$ |
| III-1923 | $L_{A370}$ | $L_{B12}$ |
| III-1924 | $L_{A371}$ | $L_{B12}$ |
| III-1925 | $L_{A372}$ | $L_{B12}$ |
| III-1926 | $L_{A373}$ | $L_{B12}$ |
| III-1927 | $L_{A374}$ | $L_{B12}$ |
| III-1928 | $L_{A375}$ | $L_{B12}$ |
| III-1929 | $L_{A376}$ | $L_{B12}$ |
| III-1930 | $L_{A377}$ | $L_{B12}$ |
| III-1931 | $L_{A378}$ | $L_{B12}$ |
| III-1932 | $L_{A379}$ | $L_{B12}$ |
| III-1933 | $L_{A380}$ | $L_{B12}$ |
| III-1934 | $L_{A381}$ | $L_{B12}$ |
| III-1935 | $L_{A382}$ | $L_{B12}$ |
| III-1936 | $L_{A383}$ | $L_{B12}$ |
| III-1937 | $L_{A384}$ | $L_{B12}$ |
| III-1938 | $L_{A385}$ | $L_{B12}$ |
| III-1939 | $L_{A386}$ | $L_{B12}$ |
| III-1940 | $L_{A387}$ | $L_{B12}$ |
| III-1941 | $L_{A388}$ | $L_{B12}$ |
| III-1942 | $L_{A389}$ | $L_{B12}$ |
| III-1943 | $L_{A390}$ | $L_{B12}$ |
| III-1944 | $L_{A391}$ | $L_{B12}$ |
| III-1945 | $L_{A392}$ | $L_{B12}$ |
| III-1946 | $L_{A393}$ | $L_{B12}$ |
| III-1947 | $L_{A394}$ | $L_{B12}$ |
| III-1948 | $L_{A395}$ | $L_{B12}$ |
| III-1949 | $L_{A396}$ | $L_{B12}$ |
| III-1950 | $L_{A397}$ | $L_{B12}$ |
| III-1951 | $L_{A398}$ | $L_{B12}$ |
| III-1952 | $L_{A399}$ | $L_{B12}$ |
| III-1953 | $L_{A400}$ | $L_{B12}$ |
| III-1954 | $L_{A401}$ | $L_{B12}$ |
| III-1955 | $L_{A402}$ | $L_{B12}$ |
| III-1956 | $L_{A403}$ | $L_{B12}$ |
| III-1957 | $L_{A404}$ | $L_{B12}$ |
| III-1958 | $L_{A405}$ | $L_{B12}$ |
| III-1959 | $L_{A406}$ | $L_{B12}$ |
| III-1960 | $L_{A407}$ | $L_{B12}$ |
| III-1961 | $L_{A408}$ | $L_{B12}$ |
| III-1962 | $L_{A409}$ | $L_{B12}$ |
| III-1963 | $L_{A410}$ | $L_{B12}$ |
| III-1964 | $L_{A411}$ | $L_{B12}$ |
| III-1965 | $L_{A412}$ | $L_{B12}$ |
| III-1966 | $L_{A413}$ | $L_{B12}$ |
| III-1967 | $L_{A414}$ | $L_{B12}$ |
| III-1968 | $L_{A415}$ | $L_{B12}$ |
| III-1969 | $L_{A416}$ | $L_{B12}$ |
| III-1970 | $L_{A417}$ | $L_{B12}$ |
| III-1971 | $L_{A418}$ | $L_{B12}$ |
| III-1972 | $L_{A419}$ | $L_{B12}$ |
| III-1973 | $L_{A420}$ | $L_{B12}$ |
| III-1974 | $L_{A421}$ | $L_{B12}$ |
| III-1975 | $L_{A422}$ | $L_{B12}$ |
| III-1976 | $L_{A423}$ | $L_{B12}$ |
| III-1977 | $L_{A424}$ | $L_{B12}$ |
| III-1978 | $L_{A425}$ | $L_{B12}$ |
| III-1979 | $L_{A426}$ | $L_{B12}$ |
| III-1980 | $L_{A427}$ | $L_{B12}$ |
| III-1981 | $L_{A428}$ | $L_{B12}$ |
| III-1982 | $L_{A429}$ | $L_{B12}$ |
| III-1983 | $L_{A430}$ | $L_{B12}$ |
| III-1984 | $L_{A431}$ | $L_{B12}$ |
| III-1985 | $L_{A432}$ | $L_{B12}$ |
| III-1986 | $L_{A433}$ | $L_{B12}$ |
| III-1987 | $L_{A434}$ | $L_{B12}$ |
| III-1988 | $L_{A435}$ | $L_{B12}$ |
| III-1989 | $L_{A436}$ | $L_{B12}$ |
| III-1990 | $L_{A437}$ | $L_{B12}$ |
| III-1991 | $L_{A438}$ | $L_{B12}$ |
| III-1992 | $L_{A439}$ | $L_{B12}$ |
| III-1993 | $L_{A440}$ | $L_{B12}$ |
| III-1994 | $L_{A441}$ | $L_{B12}$ |
| III-1995 | $L_{A442}$ | $L_{B12}$ |
| III-1996 | $L_{A443}$ | $L_{B12}$ |
| III-1997 | $L_{A444}$ | $L_{B12}$ |
| III-1998 | $L_{A445}$ | $L_{B12}$ |
| III-1999 | $L_{A446}$ | $L_{B12}$ |
| III-2000 | $L_{A447}$ | $L_{B12}$ |
| III-2001 | $L_{A448}$ | $L_{B12}$ |
| III-2002 | $L_{A449}$ | $L_{B12}$ |
| III-2003 | $L_{A450}$ | $L_{B12}$ |
| III-2004 | $L_{A451}$ | $L_{B12}$ |
| III-2005 | $L_{A452}$ | $L_{B12}$ |
| III-2006 | $L_{A453}$ | $L_{B12}$ |
| III-2007 | $L_{A454}$ | $L_{B12}$ |
| III-2008 | $L_{A455}$ | $L_{B12}$ |
| III-2009 | $L_{A456}$ | $L_{B12}$ |
| III-2010 | $L_{A457}$ | $L_{B12}$ |
| III-2011 | $L_{A458}$ | $L_{B12}$ |
| III-2012 | $L_{A459}$ | $L_{B12}$ |
| III-2013 | $L_{A460}$ | $L_{B12}$ |
| III-2014 | $L_{A461}$ | $L_{B12}$ |
| III-2015 | $L_{A462}$ | $L_{B12}$ |
| III-2016 | $L_{A463}$ | $L_{B12}$ |
| III-2017 | $L_{A464}$ | $L_{B12}$ |
| III-2018 | $L_{A465}$ | $L_{B12}$ |
| III-2019 | $L_{A466}$ | $L_{B12}$ |
| III-2020 | $L_{A467}$ | $L_{B12}$ |
| III-2021 | $L_{A468}$ | $L_{B12}$ |
| III-2022 | $L_{A469}$ | $L_{B12}$ |
| III-2023 | $L_{A470}$ | $L_{B12}$ |
| III-2024 | $L_{A471}$ | $L_{B12}$ |
| III-2025 | $L_{A472}$ | $L_{B12}$ |
| III-2026 | $L_{A473}$ | $L_{B12}$ |
| III-2027 | $L_{A474}$ | $L_{B12}$ |
| III-2028 | $L_{A475}$ | $L_{B12}$ |
| III-2029 | $L_{A476}$ | $L_{B12}$ |
| III-2030 | $L_{A477}$ | $L_{B12}$ |
| III-2031 | $L_{A478}$ | $L_{B12}$ |
| III-2032 | $L_{A479}$ | $L_{B12}$ |
| III-2033 | $L_{A480}$ | $L_{B12}$ |
| III-2034 | $L_{A481}$ | $L_{B12}$ |
| III-2035 | $L_{A482}$ | $L_{B12}$ |
| III-2036 | $L_{A483}$ | $L_{B12}$ |
| III-2037 | $L_{A484}$ | $L_{B12}$ |
| III-2038 | $L_{A485}$ | $L_{B12}$ |
| III-2039 | $L_{A486}$ | $L_{B12}$ |
| III-2040 | $L_{A487}$ | $L_{B12}$ |
| III-2041 | $L_{A318}$ | $L_{B13}$ |
| III-2042 | $L_{A319}$ | $L_{B13}$ |
| III-2043 | $L_{A320}$ | $L_{B13}$ |
| III-2044 | $L_{A321}$ | $L_{B13}$ |
| III-2045 | $L_{A322}$ | $L_{B13}$ |
| III-2046 | $L_{A323}$ | $L_{B13}$ |
| III-2047 | $L_{A324}$ | $L_{B13}$ |
| III-2048 | $L_{A325}$ | $L_{B13}$ |
| III-2049 | $L_{A326}$ | $L_{B13}$ |
| III-2050 | $L_{A327}$ | $L_{B13}$ |
| III-2051 | $L_{A328}$ | $L_{B13}$ |
| III-2052 | $L_{A329}$ | $L_{B13}$ |
| III-2053 | $L_{A330}$ | $L_{B13}$ |
| III-2054 | $L_{A331}$ | $L_{B13}$ |
| III-2055 | $L_{A332}$ | $L_{B13}$ |
| III-2056 | $L_{A333}$ | $L_{B13}$ |
| III-2057 | $L_{A334}$ | $L_{B13}$ |
| III-2058 | $L_{A335}$ | $L_{B13}$ |
| III-2059 | $L_{A336}$ | $L_{B13}$ |
| III-2060 | $L_{A337}$ | $L_{B13}$ |
| III-2061 | $L_{A338}$ | $L_{B13}$ |
| III-2062 | $L_{A339}$ | $L_{B13}$ |
| III-2063 | $L_{A340}$ | $L_{B13}$ |
| III-2064 | $L_{A341}$ | $L_{B13}$ |
| III-2065 | $L_{A342}$ | $L_{B13}$ |
| III-2066 | $L_{A343}$ | $L_{B13}$ |
| III-2067 | $L_{A344}$ | $L_{B13}$ |
| III-2068 | $L_{A345}$ | $L_{B13}$ |
| III-2069 | $L_{A346}$ | $L_{B13}$ |

| Compound Number | $L_A$ | $L_B$ |
|---|---|---|
| III-2070 | $L_{A347}$ | $L_{B13}$ |
| III-2071 | $L_{A348}$ | $L_{B13}$ |
| III-2072 | $L_{A349}$ | $L_{B13}$ |
| III-2073 | $L_{A350}$ | $L_{B13}$ |
| III-2074 | $L_{A351}$ | $L_{B13}$ |
| III-2075 | $L_{A352}$ | $L_{B13}$ |
| III-2076 | $L_{A353}$ | $L_{B13}$ |
| III-2077 | $L_{A354}$ | $L_{B13}$ |
| III-2078 | $L_{A355}$ | $L_{B13}$ |
| III-2079 | $L_{A356}$ | $L_{B13}$ |
| III-2080 | $L_{A357}$ | $L_{B13}$ |
| III-2081 | $L_{A358}$ | $L_{B13}$ |
| III-2082 | $L_{A359}$ | $L_{B13}$ |
| III-2083 | $L_{A360}$ | $L_{B13}$ |
| III-2084 | $L_{A361}$ | $L_{B13}$ |
| III-2085 | $L_{A362}$ | $L_{B13}$ |
| III-2086 | $L_{A363}$ | $L_{B13}$ |
| III-2087 | $L_{A364}$ | $L_{B13}$ |
| III-2088 | $L_{A365}$ | $L_{B13}$ |
| III-2089 | $L_{A366}$ | $L_{B13}$ |
| III-2090 | $L_{A367}$ | $L_{B13}$ |
| III-2091 | $L_{A368}$ | $L_{B13}$ |
| III-2092 | $L_{A369}$ | $L_{B13}$ |
| III-2093 | $L_{A370}$ | $L_{B13}$ |
| III-2094 | $L_{A371}$ | $L_{B13}$ |
| III-2095 | $L_{A372}$ | $L_{B13}$ |
| III-2096 | $L_{A373}$ | $L_{B13}$ |
| III-2097 | $L_{A374}$ | $L_{B13}$ |
| III-2098 | $L_{A375}$ | $L_{B13}$ |
| III-2099 | $L_{A376}$ | $L_{B13}$ |
| III-2100 | $L_{A377}$ | $L_{B13}$ |
| III-2101 | $L_{A378}$ | $L_{B13}$ |
| III-2102 | $L_{A379}$ | $L_{B13}$ |
| III-2103 | $L_{A380}$ | $L_{B13}$ |
| III-2104 | $L_{A381}$ | $L_{B13}$ |
| III-2105 | $L_{A382}$ | $L_{B13}$ |
| III-2106 | $L_{A383}$ | $L_{B13}$ |
| III-2107 | $L_{A384}$ | $L_{B13}$ |
| III-2108 | $L_{A385}$ | $L_{B13}$ |
| III-2109 | $L_{A386}$ | $L_{B13}$ |
| III-2110 | $L_{A387}$ | $L_{B13}$ |
| III-2111 | $L_{A388}$ | $L_{B13}$ |
| III-2112 | $L_{A389}$ | $L_{B13}$ |
| III-2113 | $L_{A390}$ | $L_{B13}$ |
| III-2114 | $L_{A391}$ | $L_{B13}$ |
| III-2115 | $L_{A392}$ | $L_{B13}$ |
| III-2116 | $L_{A393}$ | $L_{B13}$ |
| III-2117 | $L_{A394}$ | $L_{B13}$ |
| III-2118 | $L_{A395}$ | $L_{B13}$ |
| III-2119 | $L_{A396}$ | $L_{B13}$ |
| III-2120 | $L_{A397}$ | $L_{B13}$ |
| III-2121 | $L_{A398}$ | $L_{B13}$ |
| III-2122 | $L_{A399}$ | $L_{B13}$ |
| III-2123 | $L_{A400}$ | $L_{B13}$ |
| III-2124 | $L_{A401}$ | $L_{B13}$ |
| III-2125 | $L_{A402}$ | $L_{B13}$ |
| III-2126 | $L_{A403}$ | $L_{B13}$ |
| III-2127 | $L_{A404}$ | $L_{B13}$ |
| III-2128 | $L_{A405}$ | $L_{B13}$ |
| III-2129 | $L_{A406}$ | $L_{B13}$ |
| III-2130 | $L_{A407}$ | $L_{B13}$ |
| III-2131 | $L_{A408}$ | $L_{B13}$ |
| III-2132 | $L_{A409}$ | $L_{B13}$ |
| III-2133 | $L_{A410}$ | $L_{B13}$ |
| III-2134 | $L_{A411}$ | $L_{B13}$ |
| III-2135 | $L_{A412}$ | $L_{B13}$ |
| III-2136 | $L_{A413}$ | $L_{B13}$ |
| III-2137 | $L_{A414}$ | $L_{B13}$ |
| III-2138 | $L_{A415}$ | $L_{B13}$ |
| III-2139 | $L_{A416}$ | $L_{B13}$ |
| III-2140 | $L_{A417}$ | $L_{B13}$ |
| III-2141 | $L_{A418}$ | $L_{B13}$ |
| III-2142 | $L_{A419}$ | $L_{B13}$ |
| III-2143 | $L_{A420}$ | $L_{B13}$ |
| III-2144 | $L_{A421}$ | $L_{B13}$ |
| III-2145 | $L_{A422}$ | $L_{B13}$ |
| III-2146 | $L_{A423}$ | $L_{B13}$ |
| III-2147 | $L_{A424}$ | $L_{B13}$ |
| III-2148 | $L_{A425}$ | $L_{B13}$ |
| III-2149 | $L_{A426}$ | $L_{B13}$ |
| III-2150 | $L_{A427}$ | $L_{B13}$ |
| III-2151 | $L_{A428}$ | $L_{B13}$ |
| III-2152 | $L_{A429}$ | $L_{B13}$ |
| III-2153 | $L_{A430}$ | $L_{B13}$ |
| III-2154 | $L_{A431}$ | $L_{B13}$ |
| III-2155 | $L_{A432}$ | $L_{B13}$ |
| III-2156 | $L_{A433}$ | $L_{B13}$ |
| III-2157 | $L_{A434}$ | $L_{B13}$ |
| III-2158 | $L_{A435}$ | $L_{B13}$ |
| III-2159 | $L_{A436}$ | $L_{B13}$ |
| III-2160 | $L_{A437}$ | $L_{B13}$ |
| III-2161 | $L_{A438}$ | $L_{B13}$ |
| III-2162 | $L_{A439}$ | $L_{B13}$ |
| III-2163 | $L_{A440}$ | $L_{B13}$ |
| III-2164 | $L_{A441}$ | $L_{B13}$ |
| III-2165 | $L_{A442}$ | $L_{B13}$ |
| III-2166 | $L_{A443}$ | $L_{B13}$ |
| III-2167 | $L_{A444}$ | $L_{B13}$ |
| III-2168 | $L_{A445}$ | $L_{B13}$ |
| III-2169 | $L_{A446}$ | $L_{B13}$ |
| III-2170 | $L_{A447}$ | $L_{B13}$ |
| III-2171 | $L_{A448}$ | $L_{B13}$ |
| III-2172 | $L_{A449}$ | $L_{B13}$ |
| III-2173 | $L_{A450}$ | $L_{B13}$ |
| III-2174 | $L_{A451}$ | $L_{B13}$ |
| III-2175 | $L_{A452}$ | $L_{B13}$ |
| III-2176 | $L_{A453}$ | $L_{B13}$ |
| III-2177 | $L_{A454}$ | $L_{B13}$ |
| III-2178 | $L_{A455}$ | $L_{B13}$ |
| III-2179 | $L_{A456}$ | $L_{B13}$ |
| III-2180 | $L_{A457}$ | $L_{B13}$ |
| III-2181 | $L_{A458}$ | $L_{B13}$ |
| III-2182 | $L_{A459}$ | $L_{B13}$ |
| III-2183 | $L_{A460}$ | $L_{B13}$ |
| III-2184 | $L_{A461}$ | $L_{B13}$ |
| III-2185 | $L_{A462}$ | $L_{B13}$ |
| III-2186 | $L_{A463}$ | $L_{B13}$ |
| III-2187 | $L_{A464}$ | $L_{B13}$ |
| III-2188 | $L_{A465}$ | $L_{B13}$ |
| III-2189 | $L_{A466}$ | $L_{B13}$ |
| III-2190 | $L_{A467}$ | $L_{B13}$ |
| III-2191 | $L_{A468}$ | $L_{B13}$ |
| III-2192 | $L_{A469}$ | $L_{B13}$ |
| III-2193 | $L_{A470}$ | $L_{B13}$ |
| III-2194 | $L_{A471}$ | $L_{B13}$ |
| III-2195 | $L_{A472}$ | $L_{B13}$ |
| III-2196 | $L_{A473}$ | $L_{B13}$ |
| III-2197 | $L_{A474}$ | $L_{B13}$ |
| III-2198 | $L_{A475}$ | $L_{B13}$ |
| III-2199 | $L_{A476}$ | $L_{B13}$ |
| III-2200 | $L_{A477}$ | $L_{B13}$ |
| III-2201 | $L_{A478}$ | $L_{B13}$ |
| III-2202 | $L_{A479}$ | $L_{B13}$ |
| III-2203 | $L_{A480}$ | $L_{B13}$ |
| III-2204 | $L_{A481}$ | $L_{B13}$ |
| III-2205 | $L_{A482}$ | $L_{B13}$ |
| III-2206 | $L_{A483}$ | $L_{B13}$ |
| III-2207 | $L_{A484}$ | $L_{B13}$ |
| III-2208 | $L_{A485}$ | $L_{B13}$ |
| III-2209 | $L_{A486}$ | $L_{B13}$ |
| III-2210 | $L_{A487}$ | $L_{B13}$ |
| III-2211 | $L_{A318}$ | $L_{B14}$ |
| III-2212 | $L_{A319}$ | $L_{B14}$ |
| III-2213 | $L_{A320}$ | $L_{B14}$ |
| III-2214 | $L_{A321}$ | $L_{B14}$ |
| III-2215 | $L_{A322}$ | $L_{B14}$ |
| III-2216 | $L_{A323}$ | $L_{B14}$ |
| III-2217 | $L_{A324}$ | $L_{B14}$ |
| III-2218 | $L_{A325}$ | $L_{B14}$ |
| III-2219 | $L_{A326}$ | $L_{B14}$ |
| III-2220 | $L_{A327}$ | $L_{B14}$ |
| III-2221 | $L_{A328}$ | $L_{B14}$ |

| Compound Number | $L_A$ | $L_B$ |
|---|---|---|
| III-2222 | $L_{A329}$ | $L_{B14}$ |
| III-2223 | $L_{A330}$ | $L_{B14}$ |
| III-2224 | $L_{A331}$ | $L_{B14}$ |
| III-2225 | $L_{A332}$ | $L_{B14}$ |
| III-2226 | $L_{A333}$ | $L_{B14}$ |
| III-2227 | $L_{A334}$ | $L_{B14}$ |
| III-2228 | $L_{A335}$ | $L_{B14}$ |
| III-2229 | $L_{A336}$ | $L_{B14}$ |
| III-2230 | $L_{A337}$ | $L_{B14}$ |
| III-2231 | $L_{A338}$ | $L_{B14}$ |
| III-2232 | $L_{A339}$ | $L_{B14}$ |
| III-2233 | $L_{A340}$ | $L_{B14}$ |
| III-2234 | $L_{A341}$ | $L_{B14}$ |
| III-2235 | $L_{A342}$ | $L_{B14}$ |
| III-2236 | $L_{A343}$ | $L_{B14}$ |
| III-2237 | $L_{A344}$ | $L_{B14}$ |
| III-2238 | $L_{A345}$ | $L_{B14}$ |
| III-2239 | $L_{A346}$ | $L_{B14}$ |
| III-2240 | $L_{A347}$ | $L_{B14}$ |
| III-2241 | $L_{A348}$ | $L_{B14}$ |
| III-2242 | $L_{A349}$ | $L_{B14}$ |
| III-2243 | $L_{A350}$ | $L_{B14}$ |
| III-2244 | $L_{A351}$ | $L_{B14}$ |
| III-2245 | $L_{A352}$ | $L_{B14}$ |
| III-2246 | $L_{A353}$ | $L_{B14}$ |
| III-2247 | $L_{A354}$ | $L_{B14}$ |
| III-2248 | $L_{A355}$ | $L_{B14}$ |
| III-2249 | $L_{A356}$ | $L_{B14}$ |
| III-2250 | $L_{A357}$ | $L_{B14}$ |
| III-2251 | $L_{A358}$ | $L_{B14}$ |
| III-2252 | $L_{A359}$ | $L_{B14}$ |
| III-2253 | $L_{A360}$ | $L_{B14}$ |
| III-2254 | $L_{A361}$ | $L_{B14}$ |
| III-2255 | $L_{A362}$ | $L_{B14}$ |
| III-2256 | $L_{A363}$ | $L_{B14}$ |
| III-2257 | $L_{A364}$ | $L_{B14}$ |
| III-2258 | $L_{A365}$ | $L_{B14}$ |
| III-2259 | $L_{A366}$ | $L_{B14}$ |
| III-2260 | $L_{A367}$ | $L_{B14}$ |
| III-2261 | $L_{A368}$ | $L_{B14}$ |
| III-2262 | $L_{A369}$ | $L_{B14}$ |
| III-2263 | $L_{A370}$ | $L_{B14}$ |
| III-2264 | $L_{A371}$ | $L_{B14}$ |
| III-2265 | $L_{A372}$ | $L_{B14}$ |
| III-2266 | $L_{A373}$ | $L_{B14}$ |
| III-2267 | $L_{A374}$ | $L_{B14}$ |
| III-2268 | $L_{A375}$ | $L_{B14}$ |
| III-2269 | $L_{A376}$ | $L_{B14}$ |
| III-2270 | $L_{A377}$ | $L_{B14}$ |
| III-2271 | $L_{A378}$ | $L_{B14}$ |
| III-2272 | $L_{A379}$ | $L_{B14}$ |
| III-2273 | $L_{A380}$ | $L_{B14}$ |
| III-2274 | $L_{A381}$ | $L_{B14}$ |
| III-2275 | $L_{A382}$ | $L_{B14}$ |
| III-2276 | $L_{A383}$ | $L_{B14}$ |
| III-2277 | $L_{A384}$ | $L_{B14}$ |
| III-2278 | $L_{A385}$ | $L_{B14}$ |
| III-2279 | $L_{A386}$ | $L_{B14}$ |
| III-2280 | $L_{A387}$ | $L_{B14}$ |
| III-2281 | $L_{A388}$ | $L_{B14}$ |
| III-2282 | $L_{A389}$ | $L_{B14}$ |
| III-2283 | $L_{A390}$ | $L_{B14}$ |
| III-2284 | $L_{A391}$ | $L_{B14}$ |
| III-2285 | $L_{A392}$ | $L_{B14}$ |
| III-2286 | $L_{A393}$ | $L_{B14}$ |
| III-2287 | $L_{A394}$ | $L_{B14}$ |
| III-2288 | $L_{A395}$ | $L_{B14}$ |
| III-2289 | $L_{A396}$ | $L_{B14}$ |
| III-2290 | $L_{A397}$ | $L_{B14}$ |
| III-2291 | $L_{A398}$ | $L_{B14}$ |
| III-2292 | $L_{A399}$ | $L_{B14}$ |
| III-2293 | $L_{A400}$ | $L_{B14}$ |
| III-2294 | $L_{A401}$ | $L_{B14}$ |
| III-2295 | $L_{A402}$ | $L_{B14}$ |
| III-2296 | $L_{A403}$ | $L_{B14}$ |
| III-2297 | $L_{A404}$ | $L_{B14}$ |
| III-2298 | $L_{A405}$ | $L_{B14}$ |
| III-2299 | $L_{A406}$ | $L_{B14}$ |
| III-2300 | $L_{A407}$ | $L_{B14}$ |
| III-2301 | $L_{A408}$ | $L_{B14}$ |
| III-2302 | $L_{A409}$ | $L_{B14}$ |
| III-2303 | $L_{A410}$ | $L_{B14}$ |
| III-2304 | $L_{A411}$ | $L_{B14}$ |
| III-2305 | $L_{A412}$ | $L_{B14}$ |
| III-2306 | $L_{A413}$ | $L_{B14}$ |
| III-2307 | $L_{A414}$ | $L_{B14}$ |
| III-2308 | $L_{A415}$ | $L_{B14}$ |
| III-2309 | $L_{A416}$ | $L_{B14}$ |
| III-2310 | $L_{A417}$ | $L_{B14}$ |
| III-2311 | $L_{A418}$ | $L_{B14}$ |
| III-2312 | $L_{A419}$ | $L_{B14}$ |
| III-2313 | $L_{A420}$ | $L_{B14}$ |
| III-2314 | $L_{A421}$ | $L_{B14}$ |
| III-2315 | $L_{A422}$ | $L_{B14}$ |
| III-2316 | $L_{A423}$ | $L_{B14}$ |
| III-2317 | $L_{A424}$ | $L_{B14}$ |
| III-2318 | $L_{A425}$ | $L_{B14}$ |
| III-2319 | $L_{A426}$ | $L_{B14}$ |
| III-2320 | $L_{A427}$ | $L_{B14}$ |
| III-2321 | $L_{A428}$ | $L_{B14}$ |
| III-2322 | $L_{A429}$ | $L_{B14}$ |
| III-2323 | $L_{A430}$ | $L_{B14}$ |
| III-2324 | $L_{A431}$ | $L_{B14}$ |
| III-2325 | $L_{A432}$ | $L_{B14}$ |
| III-2326 | $L_{A433}$ | $L_{B14}$ |
| III-2327 | $L_{A434}$ | $L_{B14}$ |
| III-2328 | $L_{A435}$ | $L_{B14}$ |
| III-2329 | $L_{A436}$ | $L_{B14}$ |
| III-2330 | $L_{A437}$ | $L_{B14}$ |
| III-2331 | $L_{A438}$ | $L_{B14}$ |
| III-2332 | $L_{A439}$ | $L_{B14}$ |
| III-2333 | $L_{A440}$ | $L_{B14}$ |
| III-2334 | $L_{A441}$ | $L_{B14}$ |
| III-2335 | $L_{A442}$ | $L_{B14}$ |
| III-2336 | $L_{A443}$ | $L_{B14}$ |
| III-2337 | $L_{A444}$ | $L_{B14}$ |
| III-2338 | $L_{A445}$ | $L_{B14}$ |
| III-2339 | $L_{A446}$ | $L_{B14}$ |
| III-2340 | $L_{A447}$ | $L_{B14}$ |
| III-2341 | $L_{A448}$ | $L_{B14}$ |
| III-2342 | $L_{A449}$ | $L_{B14}$ |
| III-2343 | $L_{A450}$ | $L_{B14}$ |
| III-2344 | $L_{A451}$ | $L_{B14}$ |
| III-2345 | $L_{A452}$ | $L_{B14}$ |
| III-2346 | $L_{A453}$ | $L_{B14}$ |
| III-2347 | $L_{A454}$ | $L_{B14}$ |
| III-2348 | $L_{A455}$ | $L_{B14}$ |
| III-2349 | $L_{A456}$ | $L_{B14}$ |
| III-2350 | $L_{A457}$ | $L_{B14}$ |
| III-2351 | $L_{A458}$ | $L_{B14}$ |
| III-2352 | $L_{A459}$ | $L_{B14}$ |
| III-2353 | $L_{A460}$ | $L_{B14}$ |
| III-2354 | $L_{A461}$ | $L_{B14}$ |
| III-2355 | $L_{A462}$ | $L_{B14}$ |
| III-2356 | $L_{A463}$ | $L_{B14}$ |
| III-2357 | $L_{A464}$ | $L_{B14}$ |
| III-2358 | $L_{A465}$ | $L_{B14}$ |
| III-2359 | $L_{A466}$ | $L_{B14}$ |
| III-2360 | $L_{A467}$ | $L_{B14}$ |
| III-2361 | $L_{A468}$ | $L_{B14}$ |
| III-2362 | $L_{A469}$ | $L_{B14}$ |
| III-2363 | $L_{A470}$ | $L_{B14}$ |
| III-2364 | $L_{A471}$ | $L_{B14}$ |
| III-2365 | $L_{A472}$ | $L_{B14}$ |
| III-2366 | $L_{A473}$ | $L_{B14}$ |
| III-2367 | $L_{A474}$ | $L_{B14}$ |
| III-2368 | $L_{A475}$ | $L_{B14}$ |
| III-2369 | $L_{A476}$ | $L_{B14}$ |
| III-2370 | $L_{A477}$ | $L_{B14}$ |
| III-2371 | $L_{A478}$ | $L_{B14}$ |
| III-2372 | $L_{A479}$ | $L_{B14}$ |
| III-2373 | $L_{A480}$ | $L_{B14}$ |

-continued

| Compound Number | $L_A$ | $L_B$ |
|---|---|---|
| III-2374 | $L_{A481}$ | $L_{B14}$ |
| III-2375 | $L_{A482}$ | $L_{B14}$ |
| III-2376 | $L_{A483}$ | $L_{B14}$ |
| III-2377 | $L_{A484}$ | $L_{B14}$ |
| III-2378 | $L_{A485}$ | $L_{B14}$ |
| III-2379 | $L_{A486}$ | $L_{B14}$ |
| III-2380 | $L_{A487}$ | $L_{B14}$ |
| III-2381 | $L_{A318}$ | $L_{B15}$ |
| III-2382 | $L_{A319}$ | $L_{B15}$ |
| III-2383 | $L_{A320}$ | $L_{B15}$ |
| III-2384 | $L_{A321}$ | $L_{B15}$ |
| III-2385 | $L_{A322}$ | $L_{B15}$ |
| III-2386 | $L_{A323}$ | $L_{B15}$ |
| III-2387 | $L_{A324}$ | $L_{B15}$ |
| III-2388 | $L_{A325}$ | $L_{B15}$ |
| III-2389 | $L_{A326}$ | $L_{B15}$ |
| III-2390 | $L_{A327}$ | $L_{B15}$ |
| III-2391 | $L_{A328}$ | $L_{B15}$ |
| III-2392 | $L_{A329}$ | $L_{B15}$ |
| III-2393 | $L_{A330}$ | $L_{B15}$ |
| III-2394 | $L_{A331}$ | $L_{B15}$ |
| III-2395 | $L_{A332}$ | $L_{B15}$ |
| III-2396 | $L_{A333}$ | $L_{B15}$ |
| III-2397 | $L_{A334}$ | $L_{B15}$ |
| III-2398 | $L_{A335}$ | $L_{B15}$ |
| III-2399 | $L_{A336}$ | $L_{B15}$ |
| III-2400 | $L_{A337}$ | $L_{B15}$ |
| III-2401 | $L_{A338}$ | $L_{B15}$ |
| III-2402 | $L_{A339}$ | $L_{B15}$ |
| III-2403 | $L_{A340}$ | $L_{B15}$ |
| III-2404 | $L_{A341}$ | $L_{B15}$ |
| III-2405 | $L_{A342}$ | $L_{B15}$ |
| III-2406 | $L_{A343}$ | $L_{B15}$ |
| III-2407 | $L_{A344}$ | $L_{B15}$ |
| III-2408 | $L_{A345}$ | $L_{B15}$ |
| III-2409 | $L_{A346}$ | $L_{B15}$ |
| III-2410 | $L_{A347}$ | $L_{B15}$ |
| III-2411 | $L_{A348}$ | $L_{B15}$ |
| III-2412 | $L_{A349}$ | $L_{B15}$ |
| III-2413 | $L_{A350}$ | $L_{B15}$ |
| III-2414 | $L_{A351}$ | $L_{B15}$ |
| III-2415 | $L_{A352}$ | $L_{B15}$ |
| III-2416 | $L_{A353}$ | $L_{B15}$ |
| III-2417 | $L_{A354}$ | $L_{B15}$ |
| III-2418 | $L_{A355}$ | $L_{B15}$ |
| III-2419 | $L_{A356}$ | $L_{B15}$ |
| III-2420 | $L_{A357}$ | $L_{B15}$ |
| III-2421 | $L_{A358}$ | $L_{B15}$ |
| III-2422 | $L_{A359}$ | $L_{B15}$ |
| III-2423 | $L_{A360}$ | $L_{B15}$ |
| III-2424 | $L_{A361}$ | $L_{B15}$ |
| III-2425 | $L_{A362}$ | $L_{B15}$ |
| III-2426 | $L_{A363}$ | $L_{B15}$ |
| III-2427 | $L_{A364}$ | $L_{B15}$ |
| III-2428 | $L_{A365}$ | $L_{B15}$ |
| III-2429 | $L_{A366}$ | $L_{B15}$ |
| III-2430 | $L_{A367}$ | $L_{B15}$ |
| III-2431 | $L_{A368}$ | $L_{B15}$ |
| III-2432 | $L_{A369}$ | $L_{B15}$ |
| III-2433 | $L_{A370}$ | $L_{B15}$ |
| III-2434 | $L_{A371}$ | $L_{B15}$ |
| III-2435 | $L_{A372}$ | $L_{B15}$ |
| III-2436 | $L_{A373}$ | $L_{B15}$ |
| III-2437 | $L_{A374}$ | $L_{B15}$ |
| III-2438 | $L_{A375}$ | $L_{B15}$ |
| III-2439 | $L_{A376}$ | $L_{B15}$ |
| III-2440 | $L_{A377}$ | $L_{B15}$ |
| III-2441 | $L_{A378}$ | $L_{B15}$ |
| III-2442 | $L_{A379}$ | $L_{B15}$ |
| III-2443 | $L_{A380}$ | $L_{B15}$ |
| III-2444 | $L_{A381}$ | $L_{B15}$ |
| III-2445 | $L_{A382}$ | $L_{B15}$ |
| III-2446 | $L_{A383}$ | $L_{B15}$ |
| III-2447 | $L_{A384}$ | $L_{B15}$ |
| III-2448 | $L_{A385}$ | $L_{B15}$ |
| III-2449 | $L_{A386}$ | $L_{B15}$ |
| III-2450 | $L_{A387}$ | $L_{B15}$ |
| III-2451 | $L_{A388}$ | $L_{B15}$ |
| III-2452 | $L_{A389}$ | $L_{B15}$ |
| III-2453 | $L_{A390}$ | $L_{B15}$ |
| III-2454 | $L_{A391}$ | $L_{B15}$ |
| III-2455 | $L_{A392}$ | $L_{B15}$ |
| III-2456 | $L_{A393}$ | $L_{B15}$ |
| III-2457 | $L_{A394}$ | $L_{B15}$ |
| III-2458 | $L_{A395}$ | $L_{B15}$ |
| III-2459 | $L_{A396}$ | $L_{B15}$ |
| III-2460 | $L_{A397}$ | $L_{B15}$ |
| III-2461 | $L_{A398}$ | $L_{B15}$ |
| III-2462 | $L_{A399}$ | $L_{B15}$ |
| III-2463 | $L_{A400}$ | $L_{B15}$ |
| III-2464 | $L_{A401}$ | $L_{B15}$ |
| III-2465 | $L_{A402}$ | $L_{B15}$ |
| III-2466 | $L_{A403}$ | $L_{B15}$ |
| III-2467 | $L_{A404}$ | $L_{B15}$ |
| III-2468 | $L_{A405}$ | $L_{B15}$ |
| III-2469 | $L_{A406}$ | $L_{B15}$ |
| III-2470 | $L_{A407}$ | $L_{B15}$ |
| III-2471 | $L_{A408}$ | $L_{B15}$ |
| III-2472 | $L_{A409}$ | $L_{B15}$ |
| III-2473 | $L_{A410}$ | $L_{B15}$ |
| III-2474 | $L_{A411}$ | $L_{B15}$ |
| III-2475 | $L_{A412}$ | $L_{B15}$ |
| III-2476 | $L_{A413}$ | $L_{B15}$ |
| III-2477 | $L_{A414}$ | $L_{B15}$ |
| III-2478 | $L_{A415}$ | $L_{B15}$ |
| III-2479 | $L_{A416}$ | $L_{B15}$ |
| III-2480 | $L_{A417}$ | $L_{B15}$ |
| III-2481 | $L_{A418}$ | $L_{B15}$ |
| III-2482 | $L_{A419}$ | $L_{B15}$ |
| III-2483 | $L_{A420}$ | $L_{B15}$ |
| III-2484 | $L_{A421}$ | $L_{B15}$ |
| III-2485 | $L_{A422}$ | $L_{B15}$ |
| III-2486 | $L_{A423}$ | $L_{B15}$ |
| III-2487 | $L_{A424}$ | $L_{B15}$ |
| III-2488 | $L_{A425}$ | $L_{B15}$ |
| III-2489 | $L_{A426}$ | $L_{B15}$ |
| III-2490 | $L_{A427}$ | $L_{B15}$ |
| III-2491 | $L_{A428}$ | $L_{B15}$ |
| III-2492 | $L_{A429}$ | $L_{B15}$ |
| III-2493 | $L_{A430}$ | $L_{B15}$ |
| III-2494 | $L_{A431}$ | $L_{B15}$ |
| III-2495 | $L_{A432}$ | $L_{B15}$ |
| III-2496 | $L_{A433}$ | $L_{B15}$ |
| III-2497 | $L_{A434}$ | $L_{B15}$ |
| III-2498 | $L_{A435}$ | $L_{B15}$ |
| III-2499 | $L_{A436}$ | $L_{B15}$ |
| III-2500 | $L_{A437}$ | $L_{B15}$ |
| III-2501 | $L_{A438}$ | $L_{B15}$ |
| III-2502 | $L_{A439}$ | $L_{B15}$ |
| III-2503 | $L_{A440}$ | $L_{B15}$ |
| III-2504 | $L_{A441}$ | $L_{B15}$ |
| III-2505 | $L_{A442}$ | $L_{B15}$ |
| III-2506 | $L_{A443}$ | $L_{B15}$ |
| III-2507 | $L_{A444}$ | $L_{B15}$ |
| III-2508 | $L_{A445}$ | $L_{B15}$ |
| III-2509 | $L_{A446}$ | $L_{B15}$ |
| III-2510 | $L_{A447}$ | $L_{B15}$ |
| III-2511 | $L_{A448}$ | $L_{B15}$ |
| III-2512 | $L_{A449}$ | $L_{B15}$ |
| III-2513 | $L_{A450}$ | $L_{B15}$ |
| III-2514 | $L_{A451}$ | $L_{B15}$ |
| III-2515 | $L_{A452}$ | $L_{B15}$ |
| III-2516 | $L_{A453}$ | $L_{B15}$ |
| III-2517 | $L_{A454}$ | $L_{B15}$ |
| III-2518 | $L_{A455}$ | $L_{B15}$ |
| III-2519 | $L_{A456}$ | $L_{B15}$ |
| III-2520 | $L_{A457}$ | $L_{B15}$ |
| III-2521 | $L_{A458}$ | $L_{B15}$ |
| III-2522 | $L_{A459}$ | $L_{B15}$ |
| III-2523 | $L_{A460}$ | $L_{B15}$ |
| III-2524 | $L_{A461}$ | $L_{B15}$ |
| III-2525 | $L_{A462}$ | $L_{B15}$ |

| Compound Number | $L_A$ | $L_B$ |
|---|---|---|
| III-2526 | $L_{A463}$ | $L_{B15}$ |
| III-2527 | $L_{A464}$ | $L_{B15}$ |
| III-2528 | $L_{A465}$ | $L_{B15}$ |
| III-2529 | $L_{A466}$ | $L_{B15}$ |
| III-2530 | $L_{A467}$ | $L_{B15}$ |
| III-2531 | $L_{A468}$ | $L_{B15}$ |
| III-2532 | $L_{A469}$ | $L_{B15}$ |
| III-2533 | $L_{A470}$ | $L_{B15}$ |
| III-2534 | $L_{A471}$ | $L_{B15}$ |
| III-2535 | $L_{A472}$ | $L_{B15}$ |
| III-2536 | $L_{A473}$ | $L_{B15}$ |
| III-2537 | $L_{A474}$ | $L_{B15}$ |
| III-2538 | $L_{A475}$ | $L_{B15}$ |
| III-2539 | $L_{A476}$ | $L_{B15}$ |
| III-2540 | $L_{A477}$ | $L_{B15}$ |
| III-2541 | $L_{A478}$ | $L_{B15}$ |
| III-2542 | $L_{A479}$ | $L_{B15}$ |
| III-2543 | $L_{A480}$ | $L_{B15}$ |
| III-2544 | $L_{A481}$ | $L_{B15}$ |
| III-2545 | $L_{A482}$ | $L_{B15}$ |
| III-2546 | $L_{A483}$ | $L_{B15}$ |
| III-2547 | $L_{A484}$ | $L_{B15}$ |
| III-2548 | $L_{A485}$ | $L_{B15}$ |
| III-2549 | $L_{A486}$ | $L_{B15}$ |
| III-2550 | $L_{A487}$ | $L_{B15}$ |
| III-2551 | $L_{A318}$ | $L_{B16}$ |
| III-2552 | $L_{A319}$ | $L_{B16}$ |
| III-2553 | $L_{A320}$ | $L_{B16}$ |
| III-2554 | $L_{A321}$ | $L_{B16}$ |
| III-2555 | $L_{A322}$ | $L_{B16}$ |
| III-2556 | $L_{A323}$ | $L_{B16}$ |
| III-2557 | $L_{A324}$ | $L_{B16}$ |
| III-2558 | $L_{A325}$ | $L_{B16}$ |
| III-2559 | $L_{A326}$ | $L_{B16}$ |
| III-2560 | $L_{A327}$ | $L_{B16}$ |
| III-2561 | $L_{A328}$ | $L_{B16}$ |
| III-2562 | $L_{A329}$ | $L_{B16}$ |
| III-2563 | $L_{A330}$ | $L_{B16}$ |
| III-2564 | $L_{A331}$ | $L_{B16}$ |
| III-2565 | $L_{A332}$ | $L_{B16}$ |
| III-2566 | $L_{A333}$ | $L_{B16}$ |
| III-2567 | $L_{A334}$ | $L_{B16}$ |
| III-2568 | $L_{A335}$ | $L_{B16}$ |
| III-2569 | $L_{A336}$ | $L_{B16}$ |
| III-2570 | $L_{A337}$ | $L_{B16}$ |
| III-2571 | $L_{A338}$ | $L_{B16}$ |
| III-2572 | $L_{A339}$ | $L_{B16}$ |
| III-2573 | $L_{A340}$ | $L_{B16}$ |
| III-2574 | $L_{A341}$ | $L_{B16}$ |
| III-2575 | $L_{A342}$ | $L_{B16}$ |
| III-2576 | $L_{A343}$ | $L_{B16}$ |
| III-2577 | $L_{A344}$ | $L_{B16}$ |
| III-2578 | $L_{A345}$ | $L_{B16}$ |
| III-2579 | $L_{A346}$ | $L_{B16}$ |
| III-2580 | $L_{A347}$ | $L_{B16}$ |
| III-2581 | $L_{A348}$ | $L_{B16}$ |
| III-2582 | $L_{A349}$ | $L_{B16}$ |
| III-2583 | $L_{A350}$ | $L_{B16}$ |
| III-2584 | $L_{A351}$ | $L_{B16}$ |
| III-2585 | $L_{A352}$ | $L_{B16}$ |
| III-2586 | $L_{A353}$ | $L_{B16}$ |
| III-2587 | $L_{A354}$ | $L_{B16}$ |
| III-2588 | $L_{A355}$ | $L_{B16}$ |
| III-2589 | $L_{A356}$ | $L_{B16}$ |
| III-2590 | $L_{A357}$ | $L_{B16}$ |
| III-2591 | $L_{A358}$ | $L_{B16}$ |
| III-2592 | $L_{A359}$ | $L_{B16}$ |
| III-2593 | $L_{A360}$ | $L_{B16}$ |
| III-2594 | $L_{A361}$ | $L_{B16}$ |
| III-2595 | $L_{A362}$ | $L_{B16}$ |
| III-2596 | $L_{A363}$ | $L_{B16}$ |
| III-2597 | $L_{A364}$ | $L_{B16}$ |
| III-2598 | $L_{A365}$ | $L_{B16}$ |
| III-2599 | $L_{A366}$ | $L_{B16}$ |
| III-2600 | $L_{A367}$ | $L_{B16}$ |
| III-2601 | $L_{A368}$ | $L_{B16}$ |
| III-2602 | $L_{A369}$ | $L_{B16}$ |
| III-2603 | $L_{A370}$ | $L_{B16}$ |
| III-2604 | $L_{A371}$ | $L_{B16}$ |
| III-2605 | $L_{A372}$ | $L_{B16}$ |
| III-2606 | $L_{A373}$ | $L_{B16}$ |
| III-2607 | $L_{A374}$ | $L_{B16}$ |
| III-2608 | $L_{A375}$ | $L_{B16}$ |
| III-2609 | $L_{A376}$ | $L_{B16}$ |
| III-2610 | $L_{A377}$ | $L_{B16}$ |
| III-2611 | $L_{A378}$ | $L_{B16}$ |
| III-2612 | $L_{A379}$ | $L_{B16}$ |
| III-2613 | $L_{A380}$ | $L_{B16}$ |
| III-2614 | $L_{A381}$ | $L_{B16}$ |
| III-2615 | $L_{A382}$ | $L_{B16}$ |
| III-2616 | $L_{A383}$ | $L_{B16}$ |
| III-2617 | $L_{A384}$ | $L_{B16}$ |
| III-2618 | $L_{A385}$ | $L_{B16}$ |
| III-2619 | $L_{A386}$ | $L_{B16}$ |
| III-2620 | $L_{A387}$ | $L_{B16}$ |
| III-2621 | $L_{A388}$ | $L_{B16}$ |
| III-2622 | $L_{A389}$ | $L_{B16}$ |
| III-2623 | $L_{A390}$ | $L_{B16}$ |
| III-2624 | $L_{A391}$ | $L_{B16}$ |
| III-2625 | $L_{A392}$ | $L_{B16}$ |
| III-2626 | $L_{A393}$ | $L_{B16}$ |
| III-2627 | $L_{A394}$ | $L_{B16}$ |
| III-2628 | $L_{A395}$ | $L_{B16}$ |
| III-2629 | $L_{A396}$ | $L_{B16}$ |
| III-2630 | $L_{A397}$ | $L_{B16}$ |
| III-2631 | $L_{A398}$ | $L_{B16}$ |
| III-2632 | $L_{A399}$ | $L_{B16}$ |
| III-2633 | $L_{A400}$ | $L_{B16}$ |
| III-2634 | $L_{A401}$ | $L_{B16}$ |
| III-2635 | $L_{A402}$ | $L_{B16}$ |
| III-2636 | $L_{A403}$ | $L_{B16}$ |
| III-2637 | $L_{A404}$ | $L_{B16}$ |
| III-2638 | $L_{A405}$ | $L_{B16}$ |
| III-2639 | $L_{A406}$ | $L_{B16}$ |
| III-2640 | $L_{A407}$ | $L_{B16}$ |
| III-2641 | $L_{A408}$ | $L_{B16}$ |
| III-2642 | $L_{A409}$ | $L_{B16}$ |
| III-2643 | $L_{A410}$ | $L_{B16}$ |
| III-2644 | $L_{A411}$ | $L_{B16}$ |
| III-2645 | $L_{A412}$ | $L_{B16}$ |
| III-2646 | $L_{A413}$ | $L_{B16}$ |
| III-2647 | $L_{A414}$ | $L_{B16}$ |
| III-2648 | $L_{A415}$ | $L_{B16}$ |
| III-2649 | $L_{A416}$ | $L_{B16}$ |
| III-2650 | $L_{A417}$ | $L_{B16}$ |
| III-2651 | $L_{A418}$ | $L_{B16}$ |
| III-2652 | $L_{A419}$ | $L_{B16}$ |
| III-2653 | $L_{A420}$ | $L_{B16}$ |
| III-2654 | $L_{A421}$ | $L_{B16}$ |
| III-2655 | $L_{A422}$ | $L_{B16}$ |
| III-2656 | $L_{A423}$ | $L_{B16}$ |
| III-2657 | $L_{A424}$ | $L_{B16}$ |
| III-2658 | $L_{A425}$ | $L_{B16}$ |
| III-2659 | $L_{A426}$ | $L_{B16}$ |
| III-2660 | $L_{A427}$ | $L_{B16}$ |
| III-2661 | $L_{A428}$ | $L_{B16}$ |
| III-2662 | $L_{A429}$ | $L_{B16}$ |
| III-2663 | $L_{A430}$ | $L_{B16}$ |
| III-2664 | $L_{A431}$ | $L_{B16}$ |
| III-2665 | $L_{A432}$ | $L_{B16}$ |
| III-2666 | $L_{A433}$ | $L_{B16}$ |
| III-2667 | $L_{A434}$ | $L_{B16}$ |
| III-2668 | $L_{A435}$ | $L_{B16}$ |
| III-2669 | $L_{A436}$ | $L_{B16}$ |
| III-2670 | $L_{A437}$ | $L_{B16}$ |
| III-2671 | $L_{A438}$ | $L_{B16}$ |
| III-2672 | $L_{A439}$ | $L_{B16}$ |
| III-2673 | $L_{A440}$ | $L_{B16}$ |
| III-2674 | $L_{A441}$ | $L_{B16}$ |
| III-2675 | $L_{A442}$ | $L_{B16}$ |
| III-2676 | $L_{A443}$ | $L_{B16}$ |
| III-2677 | $L_{A444}$ | $L_{B16}$ |

| Compound Number | $L_A$ | $L_B$ |
|---|---|---|
| III-2678 | $L_{A445}$ | $L_{B16}$ |
| III-2679 | $L_{A446}$ | $L_{B16}$ |
| III-2680 | $L_{A447}$ | $L_{B16}$ |
| III-2681 | $L_{A448}$ | $L_{B16}$ |
| III-2682 | $L_{A449}$ | $L_{B16}$ |
| III-2683 | $L_{A450}$ | $L_{B16}$ |
| III-2684 | $L_{A451}$ | $L_{B16}$ |
| III-2685 | $L_{A452}$ | $L_{B16}$ |
| III-2686 | $L_{A453}$ | $L_{B16}$ |
| III-2687 | $L_{A454}$ | $L_{B16}$ |
| III-2688 | $L_{A455}$ | $L_{B16}$ |
| III-2689 | $L_{A456}$ | $L_{B16}$ |
| III-2690 | $L_{A457}$ | $L_{B16}$ |
| III-2691 | $L_{A458}$ | $L_{B16}$ |
| III-2692 | $L_{A459}$ | $L_{B16}$ |
| III-2693 | $L_{A460}$ | $L_{B16}$ |
| III-2694 | $L_{A461}$ | $L_{B16}$ |
| III-2695 | $L_{A462}$ | $L_{B16}$ |
| III-2696 | $L_{A463}$ | $L_{B16}$ |
| III-2697 | $L_{A464}$ | $L_{B16}$ |
| III-2698 | $L_{A465}$ | $L_{B16}$ |
| III-2699 | $L_{A466}$ | $L_{B16}$ |
| III-2700 | $L_{A467}$ | $L_{B16}$ |
| III-2701 | $L_{A468}$ | $L_{B16}$ |
| III-2702 | $L_{A469}$ | $L_{B16}$ |
| III-2703 | $L_{A470}$ | $L_{B16}$ |
| III-2704 | $L_{A471}$ | $L_{B16}$ |
| III-2705 | $L_{A472}$ | $L_{B16}$ |
| III-2706 | $L_{A473}$ | $L_{B16}$ |
| III-2707 | $L_{A474}$ | $L_{B16}$ |
| III-2708 | $L_{A475}$ | $L_{B16}$ |
| III-2709 | $L_{A476}$ | $L_{B16}$ |
| III-2710 | $L_{A477}$ | $L_{B16}$ |
| III-2711 | $L_{A478}$ | $L_{B16}$ |
| III-2712 | $L_{A479}$ | $L_{B16}$ |
| III-2713 | $L_{A480}$ | $L_{B16}$ |
| III-2714 | $L_{A481}$ | $L_{B16}$ |
| III-2715 | $L_{A482}$ | $L_{B16}$ |
| III-2716 | $L_{A483}$ | $L_{B16}$ |
| III-2717 | $L_{A484}$ | $L_{B16}$ |
| III-2718 | $L_{A485}$ | $L_{B16}$ |
| III-2719 | $L_{A486}$ | $L_{B16}$ |
| III-2720 | $L_{A487}$ | $L_{B16}$ |
| III-2721 | $L_{A318}$ | $L_{B17}$ |
| III-2722 | $L_{A319}$ | $L_{B17}$ |
| III-2723 | $L_{A320}$ | $L_{B17}$ |
| III-2724 | $L_{A321}$ | $L_{B17}$ |
| III-2725 | $L_{A322}$ | $L_{B17}$ |
| III-2726 | $L_{A323}$ | $L_{B17}$ |
| III-2727 | $L_{A324}$ | $L_{B17}$ |
| III-2728 | $L_{A325}$ | $L_{B17}$ |
| III-2729 | $L_{A326}$ | $L_{B17}$ |
| III-2730 | $L_{A327}$ | $L_{B17}$ |
| III-2731 | $L_{A328}$ | $L_{B17}$ |
| III-2732 | $L_{A329}$ | $L_{B17}$ |
| III-2733 | $L_{A330}$ | $L_{B17}$ |
| III-2734 | $L_{A331}$ | $L_{B17}$ |
| III-2735 | $L_{A332}$ | $L_{B17}$ |
| III-2736 | $L_{A333}$ | $L_{B17}$ |
| III-2737 | $L_{A334}$ | $L_{B17}$ |
| III-2738 | $L_{A335}$ | $L_{B17}$ |
| III-2739 | $L_{A336}$ | $L_{B17}$ |
| III-2740 | $L_{A337}$ | $L_{B17}$ |
| III-2741 | $L_{A338}$ | $L_{B17}$ |
| III-2742 | $L_{A339}$ | $L_{B17}$ |
| III-2743 | $L_{A340}$ | $L_{B17}$ |
| III-2744 | $L_{A341}$ | $L_{B17}$ |
| III-2745 | $L_{A342}$ | $L_{B17}$ |
| III-2746 | $L_{A343}$ | $L_{B17}$ |
| III-2747 | $L_{A344}$ | $L_{B17}$ |
| III-2748 | $L_{A345}$ | $L_{B17}$ |
| III-2749 | $L_{A346}$ | $L_{B17}$ |
| III-2750 | $L_{A347}$ | $L_{B17}$ |
| III-2751 | $L_{A348}$ | $L_{B17}$ |
| III-2752 | $L_{A349}$ | $L_{B17}$ |
| III-2753 | $L_{A350}$ | $L_{B17}$ |
| III-2754 | $L_{A351}$ | $L_{B17}$ |
| III-2755 | $L_{A352}$ | $L_{B17}$ |
| III-2756 | $L_{A353}$ | $L_{B17}$ |
| III-2757 | $L_{A354}$ | $L_{B17}$ |
| III-2758 | $L_{A355}$ | $L_{B17}$ |
| III-2759 | $L_{A356}$ | $L_{B17}$ |
| III-2760 | $L_{A357}$ | $L_{B17}$ |
| III-2761 | $L_{A358}$ | $L_{B17}$ |
| III-2762 | $L_{A359}$ | $L_{B17}$ |
| III-2763 | $L_{A360}$ | $L_{B17}$ |
| III-2764 | $L_{A361}$ | $L_{B17}$ |
| III-2765 | $L_{A362}$ | $L_{B17}$ |
| III-2766 | $L_{A363}$ | $L_{B17}$ |
| III-2767 | $L_{A364}$ | $L_{B17}$ |
| III-2768 | $L_{A365}$ | $L_{B17}$ |
| III-2769 | $L_{A366}$ | $L_{B17}$ |
| III-2770 | $L_{A367}$ | $L_{B17}$ |
| III-2771 | $L_{A368}$ | $L_{B17}$ |
| III-2772 | $L_{A369}$ | $L_{B17}$ |
| III-2773 | $L_{A370}$ | $L_{B17}$ |
| III-2774 | $L_{A371}$ | $L_{B17}$ |
| III-2775 | $L_{A372}$ | $L_{B17}$ |
| III-2776 | $L_{A373}$ | $L_{B17}$ |
| III-2777 | $L_{A374}$ | $L_{B17}$ |
| III-2778 | $L_{A375}$ | $L_{B17}$ |
| III-2779 | $L_{A376}$ | $L_{B17}$ |
| III-2780 | $L_{A377}$ | $L_{B17}$ |
| III-2781 | $L_{A378}$ | $L_{B17}$ |
| III-2782 | $L_{A379}$ | $L_{B17}$ |
| III-2783 | $L_{A380}$ | $L_{B17}$ |
| III-2784 | $L_{A381}$ | $L_{B17}$ |
| III-2785 | $L_{A382}$ | $L_{B17}$ |
| III-2786 | $L_{A383}$ | $L_{B17}$ |
| III-2787 | $L_{A384}$ | $L_{B17}$ |
| III-2788 | $L_{A385}$ | $L_{B17}$ |
| III-2789 | $L_{A386}$ | $L_{B17}$ |
| III-2790 | $L_{A387}$ | $L_{B17}$ |
| III-2791 | $L_{A388}$ | $L_{B17}$ |
| III-2792 | $L_{A389}$ | $L_{B17}$ |
| III-2793 | $L_{A390}$ | $L_{B17}$ |
| III-2794 | $L_{A391}$ | $L_{B17}$ |
| III-2795 | $L_{A392}$ | $L_{B17}$ |
| III-2796 | $L_{A393}$ | $L_{B17}$ |
| III-2797 | $L_{A394}$ | $L_{B17}$ |
| III-2798 | $L_{A395}$ | $L_{B17}$ |
| III-2799 | $L_{A396}$ | $L_{B17}$ |
| III-2800 | $L_{A397}$ | $L_{B17}$ |
| III-2801 | $L_{A398}$ | $L_{B17}$ |
| III-2802 | $L_{A399}$ | $L_{B17}$ |
| III-2803 | $L_{A400}$ | $L_{B17}$ |
| III-2804 | $L_{A401}$ | $L_{B17}$ |
| III-2805 | $L_{A402}$ | $L_{B17}$ |
| III-2806 | $L_{A403}$ | $L_{B17}$ |
| III-2807 | $L_{A404}$ | $L_{B17}$ |
| III-2808 | $L_{A405}$ | $L_{B17}$ |
| III-2809 | $L_{A406}$ | $L_{B17}$ |
| III-2810 | $L_{A407}$ | $L_{B17}$ |
| III-2811 | $L_{A408}$ | $L_{B17}$ |
| III-2812 | $L_{A409}$ | $L_{B17}$ |
| III-2813 | $L_{A410}$ | $L_{B17}$ |
| III-2814 | $L_{A411}$ | $L_{B17}$ |
| III-2815 | $L_{A412}$ | $L_{B17}$ |
| III-2816 | $L_{A413}$ | $L_{B17}$ |
| III-2817 | $L_{A414}$ | $L_{B17}$ |
| III-2818 | $L_{A415}$ | $L_{B17}$ |
| III-2819 | $L_{A416}$ | $L_{B17}$ |
| III-2820 | $L_{A417}$ | $L_{B17}$ |
| III-2821 | $L_{A418}$ | $L_{B17}$ |
| III-2822 | $L_{A419}$ | $L_{B17}$ |
| III-2823 | $L_{A420}$ | $L_{B17}$ |
| III-2824 | $L_{A421}$ | $L_{B17}$ |
| III-2825 | $L_{A422}$ | $L_{B17}$ |
| III-2826 | $L_{A423}$ | $L_{B17}$ |
| III-2827 | $L_{A424}$ | $L_{B17}$ |
| III-2828 | $L_{A425}$ | $L_{B17}$ |
| III-2829 | $L_{A426}$ | $L_{B17}$ |

| Compound Number | $L_A$ | $L_B$ |
|---|---|---|
| III-2830 | $L_{A427}$ | $L_{B17}$ |
| III-2831 | $L_{A428}$ | $L_{B17}$ |
| III-2832 | $L_{A429}$ | $L_{B17}$ |
| III-2833 | $L_{A430}$ | $L_{B17}$ |
| III-2834 | $L_{A431}$ | $L_{B17}$ |
| III-2835 | $L_{A432}$ | $L_{B17}$ |
| III-2836 | $L_{A433}$ | $L_{B17}$ |
| III-2837 | $L_{A434}$ | $L_{B17}$ |
| III-2838 | $L_{A435}$ | $L_{B17}$ |
| III-2839 | $L_{A436}$ | $L_{B17}$ |
| III-2840 | $L_{A437}$ | $L_{B17}$ |
| III-2841 | $L_{A438}$ | $L_{B17}$ |
| III-2842 | $L_{A439}$ | $L_{B17}$ |
| III-2843 | $L_{A440}$ | $L_{B17}$ |
| III-2844 | $L_{A441}$ | $L_{B17}$ |
| III-2845 | $L_{A442}$ | $L_{B17}$ |
| III-2846 | $L_{A443}$ | $L_{B17}$ |
| III-2847 | $L_{A444}$ | $L_{B17}$ |
| III-2848 | $L_{A445}$ | $L_{B17}$ |
| III-2849 | $L_{A446}$ | $L_{B17}$ |
| III-2850 | $L_{A447}$ | $L_{B17}$ |
| III-2851 | $L_{A448}$ | $L_{B17}$ |
| III-2852 | $L_{A449}$ | $L_{B17}$ |
| III-2853 | $L_{A450}$ | $L_{B17}$ |
| III-2854 | $L_{A451}$ | $L_{B17}$ |
| III-2855 | $L_{A452}$ | $L_{B17}$ |
| III-2856 | $L_{A453}$ | $L_{B17}$ |
| III-2857 | $L_{A454}$ | $L_{B17}$ |
| III-2858 | $L_{A455}$ | $L_{B17}$ |
| III-2859 | $L_{A456}$ | $L_{B17}$ |
| III-2860 | $L_{A457}$ | $L_{B17}$ |
| III-2861 | $L_{A458}$ | $L_{B17}$ |
| III-2862 | $L_{A459}$ | $L_{B17}$ |
| III-2863 | $L_{A460}$ | $L_{B17}$ |
| III-2864 | $L_{A461}$ | $L_{B17}$ |
| III-2865 | $L_{A462}$ | $L_{B17}$ |
| III-2866 | $L_{A463}$ | $L_{B17}$ |
| III-2867 | $L_{A464}$ | $L_{B17}$ |
| III-2868 | $L_{A465}$ | $L_{B17}$ |
| III-2869 | $L_{A466}$ | $L_{B17}$ |
| III-2870 | $L_{A467}$ | $L_{B17}$ |
| III-2871 | $L_{A468}$ | $L_{B17}$ |
| III-2872 | $L_{A469}$ | $L_{B17}$ |
| III-2873 | $L_{A470}$ | $L_{B17}$ |
| III-2874 | $L_{A471}$ | $L_{B17}$ |
| III-2875 | $L_{A472}$ | $L_{B17}$ |
| III-2876 | $L_{A473}$ | $L_{B17}$ |
| III-2877 | $L_{A474}$ | $L_{B17}$ |
| III-2878 | $L_{A475}$ | $L_{B17}$ |
| III-2879 | $L_{A476}$ | $L_{B17}$ |
| III-2880 | $L_{A477}$ | $L_{B17}$ |
| III-2881 | $L_{A478}$ | $L_{B17}$ |
| III-2882 | $L_{A479}$ | $L_{B17}$ |
| III-2883 | $L_{A480}$ | $L_{B17}$ |
| III-2884 | $L_{A481}$ | $L_{B17}$ |
| III-2885 | $L_{A482}$ | $L_{B17}$ |
| III-2886 | $L_{A483}$ | $L_{B17}$ |
| III-2887 | $L_{A484}$ | $L_{B17}$ |
| III-2888 | $L_{A485}$ | $L_{B17}$ |
| III-2889 | $L_{A486}$ | $L_{B17}$ |
| III-2890 | $L_{A487}$ | $L_{B17}$ |
| III-2891 | $L_{A318}$ | $L_{B18}$ |
| III-2892 | $L_{A319}$ | $L_{B18}$ |
| III-2893 | $L_{A320}$ | $L_{B18}$ |
| III-2894 | $L_{A321}$ | $L_{B18}$ |
| III-2895 | $L_{A322}$ | $L_{B18}$ |
| III-2896 | $L_{A323}$ | $L_{B18}$ |
| III-2897 | $L_{A324}$ | $L_{B18}$ |
| III-2898 | $L_{A325}$ | $L_{B18}$ |
| III-2899 | $L_{A326}$ | $L_{B18}$ |
| III-2900 | $L_{A327}$ | $L_{B18}$ |
| III-2901 | $L_{A328}$ | $L_{B18}$ |
| III-2902 | $L_{A329}$ | $L_{B18}$ |
| III-2903 | $L_{A330}$ | $L_{B18}$ |
| III-2904 | $L_{A331}$ | $L_{B18}$ |
| III-2905 | $L_{A332}$ | $L_{B18}$ |
| III-2906 | $L_{A333}$ | $L_{B18}$ |
| III-2907 | $L_{A334}$ | $L_{B18}$ |
| III-2908 | $L_{A335}$ | $L_{B18}$ |
| III-2909 | $L_{A336}$ | $L_{B18}$ |
| III-2910 | $L_{A337}$ | $L_{B18}$ |
| III-2911 | $L_{A338}$ | $L_{B18}$ |
| III-2912 | $L_{A339}$ | $L_{B18}$ |
| III-2913 | $L_{A340}$ | $L_{B18}$ |
| III-2914 | $L_{A341}$ | $L_{B18}$ |
| III-2915 | $L_{A342}$ | $L_{B18}$ |
| III-2916 | $L_{A343}$ | $L_{B18}$ |
| III-2917 | $L_{A344}$ | $L_{B18}$ |
| III-2918 | $L_{A345}$ | $L_{B18}$ |
| III-2919 | $L_{A346}$ | $L_{B18}$ |
| III-2920 | $L_{A347}$ | $L_{B18}$ |
| III-2921 | $L_{A348}$ | $L_{B18}$ |
| III-2922 | $L_{A349}$ | $L_{B18}$ |
| III-2923 | $L_{A350}$ | $L_{B18}$ |
| III-2924 | $L_{A351}$ | $L_{B18}$ |
| III-2925 | $L_{A352}$ | $L_{B18}$ |
| III-2926 | $L_{A353}$ | $L_{B18}$ |
| III-2927 | $L_{A354}$ | $L_{B18}$ |
| III-2928 | $L_{A355}$ | $L_{B18}$ |
| III-2929 | $L_{A356}$ | $L_{B18}$ |
| III-2930 | $L_{A357}$ | $L_{B18}$ |
| III-2931 | $L_{A358}$ | $L_{B18}$ |
| III-2932 | $L_{A359}$ | $L_{B18}$ |
| III-2933 | $L_{A360}$ | $L_{B18}$ |
| III-2934 | $L_{A361}$ | $L_{B18}$ |
| III-2935 | $L_{A362}$ | $L_{B18}$ |
| III-2936 | $L_{A363}$ | $L_{B18}$ |
| III-2937 | $L_{A364}$ | $L_{B18}$ |
| III-2938 | $L_{A365}$ | $L_{B18}$ |
| III-2939 | $L_{A366}$ | $L_{B18}$ |
| III-2940 | $L_{A367}$ | $L_{B18}$ |
| III-2941 | $L_{A368}$ | $L_{B18}$ |
| III-2942 | $L_{A369}$ | $L_{B18}$ |
| III-2943 | $L_{A370}$ | $L_{B18}$ |
| III-2944 | $L_{A371}$ | $L_{B18}$ |
| III-2945 | $L_{A372}$ | $L_{B18}$ |
| III-2946 | $L_{A373}$ | $L_{B18}$ |
| III-2947 | $L_{A374}$ | $L_{B18}$ |
| III-2948 | $L_{A375}$ | $L_{B18}$ |
| III-2949 | $L_{A376}$ | $L_{B18}$ |
| III-2950 | $L_{A377}$ | $L_{B18}$ |
| III-2951 | $L_{A378}$ | $L_{B18}$ |
| III-2952 | $L_{A379}$ | $L_{B18}$ |
| III-2953 | $L_{A380}$ | $L_{B18}$ |
| III-2954 | $L_{A381}$ | $L_{B18}$ |
| III-2955 | $L_{A382}$ | $L_{B18}$ |
| III-2956 | $L_{A383}$ | $L_{B18}$ |
| III-2957 | $L_{A384}$ | $L_{B18}$ |
| III-2958 | $L_{A385}$ | $L_{B18}$ |
| III-2959 | $L_{A386}$ | $L_{B18}$ |
| III-2960 | $L_{A387}$ | $L_{B18}$ |
| III-2961 | $L_{A388}$ | $L_{B18}$ |
| III-2962 | $L_{A389}$ | $L_{B18}$ |
| III-2963 | $L_{A390}$ | $L_{B18}$ |
| III-2964 | $L_{A391}$ | $L_{B18}$ |
| III-2965 | $L_{A392}$ | $L_{B18}$ |
| III-2966 | $L_{A393}$ | $L_{B18}$ |
| III-2967 | $L_{A394}$ | $L_{B18}$ |
| III-2968 | $L_{A395}$ | $L_{B18}$ |
| III-2969 | $L_{A396}$ | $L_{B18}$ |
| III-2970 | $L_{A397}$ | $L_{B18}$ |
| III-2971 | $L_{A398}$ | $L_{B18}$ |
| III-2972 | $L_{A399}$ | $L_{B18}$ |
| III-2973 | $L_{A400}$ | $L_{B18}$ |
| III-2974 | $L_{A401}$ | $L_{B18}$ |
| III-2975 | $L_{A402}$ | $L_{B18}$ |
| III-2976 | $L_{A403}$ | $L_{B18}$ |
| III-2977 | $L_{A404}$ | $L_{B18}$ |
| III-2978 | $L_{A405}$ | $L_{B18}$ |
| III-2979 | $L_{A406}$ | $L_{B18}$ |
| III-2980 | $L_{A407}$ | $L_{B18}$ |
| III-2981 | $L_{A408}$ | $L_{B18}$ |

| Compound Number | $L_A$ | $L_B$ |
|---|---|---|
| III-2982 | $L_{A409}$ | $L_{B18}$ |
| III-2983 | $L_{A410}$ | $L_{B18}$ |
| III-2984 | $L_{A411}$ | $L_{B18}$ |
| III-2985 | $L_{A412}$ | $L_{B18}$ |
| III-2986 | $L_{A413}$ | $L_{B18}$ |
| III-2987 | $L_{A414}$ | $L_{B18}$ |
| III-2988 | $L_{A415}$ | $L_{B18}$ |
| III-2989 | $L_{A416}$ | $L_{B18}$ |
| III-2990 | $L_{A417}$ | $L_{B18}$ |
| III-2991 | $L_{A418}$ | $L_{B18}$ |
| III-2992 | $L_{A419}$ | $L_{B18}$ |
| III-2993 | $L_{A420}$ | $L_{B18}$ |
| III-2994 | $L_{A421}$ | $L_{B18}$ |
| III-2995 | $L_{A422}$ | $L_{B18}$ |
| III-2996 | $L_{A423}$ | $L_{B18}$ |
| III-2997 | $L_{A424}$ | $L_{B18}$ |
| III-2998 | $L_{A425}$ | $L_{B18}$ |
| III-2999 | $L_{A426}$ | $L_{B18}$ |
| III-3000 | $L_{A427}$ | $L_{B18}$ |
| III-3001 | $L_{A428}$ | $L_{B18}$ |
| III-3002 | $L_{A429}$ | $L_{B18}$ |
| III-3003 | $L_{A430}$ | $L_{B18}$ |
| III-3004 | $L_{A431}$ | $L_{B18}$ |
| III-3005 | $L_{A432}$ | $L_{B18}$ |
| III-3006 | $L_{A433}$ | $L_{B18}$ |
| III-3007 | $L_{A434}$ | $L_{B18}$ |
| III-3008 | $L_{A435}$ | $L_{B18}$ |
| III-3009 | $L_{A436}$ | $L_{B18}$ |
| III-3010 | $L_{A437}$ | $L_{B18}$ |
| III-3011 | $L_{A438}$ | $L_{B18}$ |
| III-3012 | $L_{A439}$ | $L_{B18}$ |
| III-3013 | $L_{A440}$ | $L_{B18}$ |
| III-3014 | $L_{A441}$ | $L_{B18}$ |
| III-3015 | $L_{A442}$ | $L_{B18}$ |
| III-3016 | $L_{A443}$ | $L_{B18}$ |
| III-3017 | $L_{A444}$ | $L_{B18}$ |
| III-3018 | $L_{A445}$ | $L_{B18}$ |
| III-3019 | $L_{A446}$ | $L_{B18}$ |
| III-3020 | $L_{A447}$ | $L_{B18}$ |
| III-3021 | $L_{A448}$ | $L_{B18}$ |
| III-3022 | $L_{A449}$ | $L_{B18}$ |
| III-3023 | $L_{A450}$ | $L_{B18}$ |
| III-3024 | $L_{A451}$ | $L_{B18}$ |
| III-3025 | $L_{A452}$ | $L_{B18}$ |
| III-3026 | $L_{A453}$ | $L_{B18}$ |
| III-3027 | $L_{A454}$ | $L_{B18}$ |
| III-3028 | $L_{A455}$ | $L_{B18}$ |
| III-3029 | $L_{A456}$ | $L_{B18}$ |
| III-3030 | $L_{A457}$ | $L_{B18}$ |
| III-3031 | $L_{A458}$ | $L_{B18}$ |
| III-3032 | $L_{A459}$ | $L_{B18}$ |
| III-3033 | $L_{A460}$ | $L_{B18}$ |
| III-3034 | $L_{A461}$ | $L_{B18}$ |
| III-3035 | $L_{A462}$ | $L_{B18}$ |
| III-3036 | $L_{A463}$ | $L_{B18}$ |
| III-3037 | $L_{A464}$ | $L_{B18}$ |
| III-3038 | $L_{A465}$ | $L_{B18}$ |
| III-3039 | $L_{A466}$ | $L_{B18}$ |
| III-3040 | $L_{A467}$ | $L_{B18}$ |
| III-3041 | $L_{A468}$ | $L_{B18}$ |
| III-3042 | $L_{A469}$ | $L_{B18}$ |
| III-3043 | $L_{A470}$ | $L_{B18}$ |
| III-3044 | $L_{A471}$ | $L_{B18}$ |
| III-3045 | $L_{A472}$ | $L_{B18}$ |
| III-3046 | $L_{A473}$ | $L_{B18}$ |
| III-3047 | $L_{A474}$ | $L_{B18}$ |
| III-3048 | $L_{A475}$ | $L_{B18}$ |
| III-3049 | $L_{A476}$ | $L_{B18}$ |
| III-3050 | $L_{A477}$ | $L_{B18}$ |
| III-3051 | $L_{A478}$ | $L_{B18}$ |
| III-3052 | $L_{A479}$ | $L_{B18}$ |
| III-3053 | $L_{A480}$ | $L_{B18}$ |
| III-3054 | $L_{A481}$ | $L_{B18}$ |
| III-3055 | $L_{A482}$ | $L_{B18}$ |
| III-3056 | $L_{A483}$ | $L_{B18}$ |
| III-3057 | $L_{A484}$ | $L_{B18}$ |
| III-3058 | $L_{A485}$ | $L_{B18}$ |
| III-3059 | $L_{A486}$ | $L_{B18}$ |
| III-3060 | $L_{A487}$ | $L_{B18}$ |
| III-3061 | $L_{A318}$ | $L_{B19}$ |
| III-3062 | $L_{A319}$ | $L_{B19}$ |
| III-3063 | $L_{A320}$ | $L_{B19}$ |
| III-3064 | $L_{A321}$ | $L_{B19}$ |
| III-3065 | $L_{A322}$ | $L_{B19}$ |
| III-3066 | $L_{A323}$ | $L_{B19}$ |
| III-3067 | $L_{A324}$ | $L_{B19}$ |
| III-3068 | $L_{A325}$ | $L_{B19}$ |
| III-3069 | $L_{A326}$ | $L_{B19}$ |
| III-3070 | $L_{A327}$ | $L_{B19}$ |
| III-3071 | $L_{A328}$ | $L_{B19}$ |
| III-3072 | $L_{A329}$ | $L_{B19}$ |
| III-3073 | $L_{A330}$ | $L_{B19}$ |
| III-3074 | $L_{A331}$ | $L_{B19}$ |
| III-3075 | $L_{A332}$ | $L_{B19}$ |
| III-3076 | $L_{A333}$ | $L_{B19}$ |
| III-3077 | $L_{A334}$ | $L_{B19}$ |
| III-3078 | $L_{A335}$ | $L_{B19}$ |
| III-3079 | $L_{A336}$ | $L_{B19}$ |
| III-3080 | $L_{A337}$ | $L_{B19}$ |
| III-3081 | $L_{A338}$ | $L_{B19}$ |
| III-3082 | $L_{A339}$ | $L_{B19}$ |
| III-3083 | $L_{A340}$ | $L_{B19}$ |
| III-3084 | $L_{A341}$ | $L_{B19}$ |
| III-3085 | $L_{A342}$ | $L_{B19}$ |
| III-3086 | $L_{A343}$ | $L_{B19}$ |
| III-3087 | $L_{A344}$ | $L_{B19}$ |
| III-3088 | $L_{A345}$ | $L_{B19}$ |
| III-3089 | $L_{A346}$ | $L_{B19}$ |
| III-3090 | $L_{A347}$ | $L_{B19}$ |
| III-3091 | $L_{A348}$ | $L_{B19}$ |
| III-3092 | $L_{A349}$ | $L_{B19}$ |
| III-3093 | $L_{A350}$ | $L_{B19}$ |
| III-3094 | $L_{A351}$ | $L_{B19}$ |
| III-3095 | $L_{A352}$ | $L_{B19}$ |
| III-3096 | $L_{A353}$ | $L_{B19}$ |
| III-3097 | $L_{A354}$ | $L_{B19}$ |
| III-3098 | $L_{A355}$ | $L_{B19}$ |
| III-3099 | $L_{A356}$ | $L_{B19}$ |
| III-3100 | $L_{A357}$ | $L_{B19}$ |
| III-3101 | $L_{A358}$ | $L_{B19}$ |
| III-3102 | $L_{A359}$ | $L_{B19}$ |
| III-3103 | $L_{A360}$ | $L_{B19}$ |
| III-3104 | $L_{A361}$ | $L_{B19}$ |
| III-3105 | $L_{A362}$ | $L_{B19}$ |
| III-3106 | $L_{A363}$ | $L_{B19}$ |
| III-3107 | $L_{A364}$ | $L_{B19}$ |
| III-3108 | $L_{A365}$ | $L_{B19}$ |
| III-3109 | $L_{A366}$ | $L_{B19}$ |
| III-3110 | $L_{A367}$ | $L_{B19}$ |
| III-3111 | $L_{A368}$ | $L_{B19}$ |
| III-3112 | $L_{A369}$ | $L_{B19}$ |
| III-3113 | $L_{A370}$ | $L_{B19}$ |
| III-3114 | $L_{A371}$ | $L_{B19}$ |
| III-3115 | $L_{A372}$ | $L_{B19}$ |
| III-3116 | $L_{A373}$ | $L_{B19}$ |
| III-3117 | $L_{A374}$ | $L_{B19}$ |
| III-3118 | $L_{A375}$ | $L_{B19}$ |
| III-3119 | $L_{A376}$ | $L_{B19}$ |
| III-3120 | $L_{A377}$ | $L_{B19}$ |
| III-3121 | $L_{A378}$ | $L_{B19}$ |
| III-3122 | $L_{A379}$ | $L_{B19}$ |
| III-3123 | $L_{A380}$ | $L_{B19}$ |
| III-3124 | $L_{A381}$ | $L_{B19}$ |
| III-3125 | $L_{A382}$ | $L_{B19}$ |
| III-3126 | $L_{A383}$ | $L_{B19}$ |
| III-3127 | $L_{A384}$ | $L_{B19}$ |
| III-3128 | $L_{A385}$ | $L_{B19}$ |
| III-3129 | $L_{A386}$ | $L_{B19}$ |
| III-3130 | $L_{A387}$ | $L_{B19}$ |
| III-3131 | $L_{A388}$ | $L_{B19}$ |
| III-3132 | $L_{A389}$ | $L_{B19}$ |
| III-3133 | $L_{A390}$ | $L_{B19}$ |

| Compound Number | $L_A$ | $L_B$ |
|---|---|---|
| III-3134 | $L_{A391}$ | $L_{B19}$ |
| III-3135 | $L_{A392}$ | $L_{B19}$ |
| III-3136 | $L_{A393}$ | $L_{B19}$ |
| III-3137 | $L_{A394}$ | $L_{B19}$ |
| III-3138 | $L_{A395}$ | $L_{B19}$ |
| III-3139 | $L_{A396}$ | $L_{B19}$ |
| III-3140 | $L_{A397}$ | $L_{B19}$ |
| III-3141 | $L_{A398}$ | $L_{B19}$ |
| III-3142 | $L_{A399}$ | $L_{B19}$ |
| III-3143 | $L_{A400}$ | $L_{B19}$ |
| III-3144 | $L_{A401}$ | $L_{B19}$ |
| III-3145 | $L_{A402}$ | $L_{B19}$ |
| III-3146 | $L_{A403}$ | $L_{B19}$ |
| III-3147 | $L_{A404}$ | $L_{B19}$ |
| III-3148 | $L_{A405}$ | $L_{B19}$ |
| III-3149 | $L_{A406}$ | $L_{B19}$ |
| III-3150 | $L_{A407}$ | $L_{B19}$ |
| III-3151 | $L_{A408}$ | $L_{B19}$ |
| III-3152 | $L_{A409}$ | $L_{B19}$ |
| III-3153 | $L_{A410}$ | $L_{B19}$ |
| III-3154 | $L_{A411}$ | $L_{B19}$ |
| III-3155 | $L_{A412}$ | $L_{B19}$ |
| III-3156 | $L_{A413}$ | $L_{B19}$ |
| III-3157 | $L_{A414}$ | $L_{B19}$ |
| III-3158 | $L_{A415}$ | $L_{B19}$ |
| III-3159 | $L_{A416}$ | $L_{B19}$ |
| III-3160 | $L_{A417}$ | $L_{B19}$ |
| III-3161 | $L_{A418}$ | $L_{B19}$ |
| III-3162 | $L_{A419}$ | $L_{B19}$ |
| III-3163 | $L_{A420}$ | $L_{B19}$ |
| III-3164 | $L_{A421}$ | $L_{B19}$ |
| III-3165 | $L_{A422}$ | $L_{B19}$ |
| III-3166 | $L_{A423}$ | $L_{B19}$ |
| III-3167 | $L_{A424}$ | $L_{B19}$ |
| III-3168 | $L_{A425}$ | $L_{B19}$ |
| III-3169 | $L_{A426}$ | $L_{B19}$ |
| III-3170 | $L_{A427}$ | $L_{B19}$ |
| III-3171 | $L_{A428}$ | $L_{B19}$ |
| III-3172 | $L_{A429}$ | $L_{B19}$ |
| III-3173 | $L_{A430}$ | $L_{B19}$ |
| III-3174 | $L_{A431}$ | $L_{B19}$ |
| III-3175 | $L_{A432}$ | $L_{B19}$ |
| III-3176 | $L_{A433}$ | $L_{B19}$ |
| III-3177 | $L_{A434}$ | $L_{B19}$ |
| III-3178 | $L_{A435}$ | $L_{B19}$ |
| III-3179 | $L_{A436}$ | $L_{B19}$ |
| III-3180 | $L_{A437}$ | $L_{B19}$ |
| III-3181 | $L_{A438}$ | $L_{B19}$ |
| III-3182 | $L_{A439}$ | $L_{B19}$ |
| III-3183 | $L_{A440}$ | $L_{B19}$ |
| III-3184 | $L_{A441}$ | $L_{B19}$ |
| III-3185 | $L_{A442}$ | $L_{B19}$ |
| III-3186 | $L_{A443}$ | $L_{B19}$ |
| III-3187 | $L_{A444}$ | $L_{B19}$ |
| III-3188 | $L_{A445}$ | $L_{B19}$ |
| III-3189 | $L_{A446}$ | $L_{B19}$ |
| III-3190 | $L_{A447}$ | $L_{B19}$ |
| III-3191 | $L_{A448}$ | $L_{B19}$ |
| III-3192 | $L_{A449}$ | $L_{B19}$ |
| III-3193 | $L_{A450}$ | $L_{B19}$ |
| III-3194 | $L_{A451}$ | $L_{B19}$ |
| III-3195 | $L_{A452}$ | $L_{B19}$ |
| III-3196 | $L_{A453}$ | $L_{B19}$ |
| III-3197 | $L_{A454}$ | $L_{B19}$ |
| III-3198 | $L_{A455}$ | $L_{B19}$ |
| III-3199 | $L_{A456}$ | $L_{B19}$ |
| III-3200 | $L_{A457}$ | $L_{B19}$ |
| III-3201 | $L_{A458}$ | $L_{B19}$ |
| III-3202 | $L_{A459}$ | $L_{B19}$ |
| III-3203 | $L_{A460}$ | $L_{B19}$ |
| III-3204 | $L_{A461}$ | $L_{B19}$ |
| III-3205 | $L_{A462}$ | $L_{B19}$ |
| III-3206 | $L_{A463}$ | $L_{B19}$ |
| III-3207 | $L_{A464}$ | $L_{B19}$ |
| III-3208 | $L_{A465}$ | $L_{B19}$ |
| III-3209 | $L_{A466}$ | $L_{B19}$ |
| III-3210 | $L_{A467}$ | $L_{B19}$ |
| III-3211 | $L_{A468}$ | $L_{B19}$ |
| III-3212 | $L_{A469}$ | $L_{B19}$ |
| III-3213 | $L_{A470}$ | $L_{B19}$ |
| III-3214 | $L_{A471}$ | $L_{B19}$ |
| III-3215 | $L_{A472}$ | $L_{B19}$ |
| III-3216 | $L_{A473}$ | $L_{B19}$ |
| III-3217 | $L_{A474}$ | $L_{B19}$ |
| III-3218 | $L_{A475}$ | $L_{B19}$ |
| III-3219 | $L_{A476}$ | $L_{B19}$ |
| III-3220 | $L_{A477}$ | $L_{B19}$ |
| III-3221 | $L_{A478}$ | $L_{B19}$ |
| III-3222 | $L_{A479}$ | $L_{B19}$ |
| III-3223 | $L_{A480}$ | $L_{B19}$ |
| III-3224 | $L_{A481}$ | $L_{B19}$ |
| III-3225 | $L_{A482}$ | $L_{B19}$ |
| III-3226 | $L_{A483}$ | $L_{B19}$ |
| III-3227 | $L_{A484}$ | $L_{B19}$ |
| III-3228 | $L_{A485}$ | $L_{B19}$ |
| III-3229 | $L_{A486}$ | $L_{B19}$ |
| III-3230 | $L_{A487}$ | $L_{B19}$ |
| III-3231 | $L_{A318}$ | $L_{B20}$ |
| III-3232 | $L_{A319}$ | $L_{B20}$ |
| III-3233 | $L_{A320}$ | $L_{B20}$ |
| III-3234 | $L_{A321}$ | $L_{B20}$ |
| III-3235 | $L_{A322}$ | $L_{B20}$ |
| III-3236 | $L_{A323}$ | $L_{B20}$ |
| III-3237 | $L_{A324}$ | $L_{B20}$ |
| III-3238 | $L_{A325}$ | $L_{B20}$ |
| III-3239 | $L_{A326}$ | $L_{B20}$ |
| III-3240 | $L_{A327}$ | $L_{B20}$ |
| III-3241 | $L_{A328}$ | $L_{B20}$ |
| III-3242 | $L_{A329}$ | $L_{B20}$ |
| III-3243 | $L_{A330}$ | $L_{B20}$ |
| III-3244 | $L_{A331}$ | $L_{B20}$ |
| III-3245 | $L_{A332}$ | $L_{B20}$ |
| III-3246 | $L_{A333}$ | $L_{B20}$ |
| III-3247 | $L_{A334}$ | $L_{B20}$ |
| III-3248 | $L_{A335}$ | $L_{B20}$ |
| III-3249 | $L_{A336}$ | $L_{B20}$ |
| III-3250 | $L_{A337}$ | $L_{B20}$ |
| III-3251 | $L_{A338}$ | $L_{B20}$ |
| III-3252 | $L_{A339}$ | $L_{B20}$ |
| III-3253 | $L_{A340}$ | $L_{B20}$ |
| III-3254 | $L_{A341}$ | $L_{B20}$ |
| III-3255 | $L_{A342}$ | $L_{B20}$ |
| III-3256 | $L_{A343}$ | $L_{B20}$ |
| III-3257 | $L_{A344}$ | $L_{B20}$ |
| III-3258 | $L_{A345}$ | $L_{B20}$ |
| III-3259 | $L_{A346}$ | $L_{B20}$ |
| III-3260 | $L_{A347}$ | $L_{B20}$ |
| III-3261 | $L_{A348}$ | $L_{B20}$ |
| III-3262 | $L_{A349}$ | $L_{B20}$ |
| III-3263 | $L_{A350}$ | $L_{B20}$ |
| III-3264 | $L_{A351}$ | $L_{B20}$ |
| III-3265 | $L_{A352}$ | $L_{B20}$ |
| III-3266 | $L_{A353}$ | $L_{B20}$ |
| III-3267 | $L_{A354}$ | $L_{B20}$ |
| III-3268 | $L_{A355}$ | $L_{B20}$ |
| III-3269 | $L_{A356}$ | $L_{B20}$ |
| III-3270 | $L_{A357}$ | $L_{B20}$ |
| III-3271 | $L_{A358}$ | $L_{B20}$ |
| III-3272 | $L_{A359}$ | $L_{B20}$ |
| III-3273 | $L_{A360}$ | $L_{B20}$ |
| III-3274 | $L_{A361}$ | $L_{B20}$ |
| III-3275 | $L_{A362}$ | $L_{B20}$ |
| III-3276 | $L_{A363}$ | $L_{B20}$ |
| III-3277 | $L_{A364}$ | $L_{B20}$ |
| III-3278 | $L_{A365}$ | $L_{B20}$ |
| III-3279 | $L_{A366}$ | $L_{B20}$ |
| III-3280 | $L_{A367}$ | $L_{B20}$ |
| III-3281 | $L_{A368}$ | $L_{B20}$ |
| III-3282 | $L_{A369}$ | $L_{B20}$ |
| III-3283 | $L_{A370}$ | $L_{B20}$ |
| III-3284 | $L_{A371}$ | $L_{B20}$ |
| III-3285 | $L_{A372}$ | $L_{B20}$ |

| Compound Number | $L_A$ | $L_B$ |
|---|---|---|
| III-3286 | $L_{A373}$ | $L_{B20}$ |
| III-3287 | $L_{A374}$ | $L_{B20}$ |
| III-3288 | $L_{A375}$ | $L_{B20}$ |
| III-3289 | $L_{A376}$ | $L_{B20}$ |
| III-3290 | $L_{A377}$ | $L_{B20}$ |
| III-3291 | $L_{A378}$ | $L_{B20}$ |
| III-3292 | $L_{A379}$ | $L_{B20}$ |
| III-3293 | $L_{A380}$ | $L_{B20}$ |
| III-3294 | $L_{A381}$ | $L_{B20}$ |
| III-3295 | $L_{A382}$ | $L_{B20}$ |
| III-3296 | $L_{A383}$ | $L_{B20}$ |
| III-3297 | $L_{A384}$ | $L_{B20}$ |
| III-3298 | $L_{A385}$ | $L_{B20}$ |
| III-3299 | $L_{A386}$ | $L_{B20}$ |
| III-3300 | $L_{A387}$ | $L_{B20}$ |
| III-3301 | $L_{A388}$ | $L_{B20}$ |
| III-3302 | $L_{A389}$ | $L_{B20}$ |
| III-3303 | $L_{A390}$ | $L_{B20}$ |
| III-3304 | $L_{A391}$ | $L_{B20}$ |
| III-3305 | $L_{A392}$ | $L_{B20}$ |
| III-3306 | $L_{A393}$ | $L_{B20}$ |
| III-3307 | $L_{A394}$ | $L_{B20}$ |
| III-3308 | $L_{A395}$ | $L_{B20}$ |
| III-3309 | $L_{A396}$ | $L_{B20}$ |
| III-3310 | $L_{A397}$ | $L_{B20}$ |
| III-3311 | $L_{A398}$ | $L_{B20}$ |
| III-3312 | $L_{A399}$ | $L_{B20}$ |
| III-3313 | $L_{A400}$ | $L_{B20}$ |
| III-3314 | $L_{A401}$ | $L_{B20}$ |
| III-3315 | $L_{A402}$ | $L_{B20}$ |
| III-3316 | $L_{A403}$ | $L_{B20}$ |
| III-3317 | $L_{A404}$ | $L_{B20}$ |
| III-3318 | $L_{A405}$ | $L_{B20}$ |
| III-3319 | $L_{A406}$ | $L_{B20}$ |
| III-3320 | $L_{A407}$ | $L_{B20}$ |
| III-3321 | $L_{A408}$ | $L_{B20}$ |
| III-3322 | $L_{A409}$ | $L_{B20}$ |
| III-3323 | $L_{A410}$ | $L_{B20}$ |
| III-3324 | $L_{A411}$ | $L_{B20}$ |
| III-3325 | $L_{A412}$ | $L_{B20}$ |
| III-3326 | $L_{A413}$ | $L_{B20}$ |
| III-3327 | $L_{A414}$ | $L_{B20}$ |
| III-3328 | $L_{A415}$ | $L_{B20}$ |
| III-3329 | $L_{A416}$ | $L_{B20}$ |
| III-3330 | $L_{A417}$ | $L_{B20}$ |
| III-3331 | $L_{A418}$ | $L_{B20}$ |
| III-3332 | $L_{A419}$ | $L_{B20}$ |
| III-3333 | $L_{A420}$ | $L_{B20}$ |
| III-3334 | $L_{A421}$ | $L_{B20}$ |
| III-3335 | $L_{A422}$ | $L_{B20}$ |
| III-3336 | $L_{A423}$ | $L_{B20}$ |
| III-3337 | $L_{A424}$ | $L_{B20}$ |
| III-3338 | $L_{A425}$ | $L_{B20}$ |
| III-3339 | $L_{A426}$ | $L_{B20}$ |
| III-3340 | $L_{A427}$ | $L_{B20}$ |
| III-3341 | $L_{A428}$ | $L_{B20}$ |
| III-3342 | $L_{A429}$ | $L_{B20}$ |
| III-3343 | $L_{A430}$ | $L_{B20}$ |
| III-3344 | $L_{A431}$ | $L_{B20}$ |
| III-3345 | $L_{A432}$ | $L_{B20}$ |
| III-3346 | $L_{A433}$ | $L_{B20}$ |
| III-3347 | $L_{A434}$ | $L_{B20}$ |
| III-3348 | $L_{A435}$ | $L_{B20}$ |
| III-3349 | $L_{A436}$ | $L_{B20}$ |
| III-3350 | $L_{A437}$ | $L_{B20}$ |
| III-3351 | $L_{A438}$ | $L_{B20}$ |
| III-3352 | $L_{A439}$ | $L_{B20}$ |
| III-3353 | $L_{A440}$ | $L_{B20}$ |
| III-3354 | $L_{A441}$ | $L_{B20}$ |
| III-3355 | $L_{A442}$ | $L_{B20}$ |
| III-3356 | $L_{A443}$ | $L_{B20}$ |
| III-3357 | $L_{A444}$ | $L_{B20}$ |
| III-3358 | $L_{A445}$ | $L_{B20}$ |
| III-3359 | $L_{A446}$ | $L_{B20}$ |
| III-3360 | $L_{A447}$ | $L_{B20}$ |
| III-3361 | $L_{A448}$ | $L_{B20}$ |
| III-3362 | $L_{A449}$ | $L_{B20}$ |
| III-3363 | $L_{A450}$ | $L_{B20}$ |
| III-3364 | $L_{A451}$ | $L_{B20}$ |
| III-3365 | $L_{A452}$ | $L_{B20}$ |
| III-3366 | $L_{A453}$ | $L_{B20}$ |
| III-3367 | $L_{A454}$ | $L_{B20}$ |
| III-3368 | $L_{A455}$ | $L_{B20}$ |
| III-3369 | $L_{A456}$ | $L_{B20}$ |
| III-3370 | $L_{A457}$ | $L_{B20}$ |
| III-3371 | $L_{A458}$ | $L_{B20}$ |
| III-3372 | $L_{A459}$ | $L_{B20}$ |
| III-3373 | $L_{A460}$ | $L_{B20}$ |
| III-3374 | $L_{A461}$ | $L_{B20}$ |
| III-3375 | $L_{A462}$ | $L_{B20}$ |
| III-3376 | $L_{A463}$ | $L_{B20}$ |
| III-3377 | $L_{A464}$ | $L_{B20}$ |
| III-3378 | $L_{A465}$ | $L_{B20}$ |
| III-3379 | $L_{A466}$ | $L_{B20}$ |
| III-3380 | $L_{A467}$ | $L_{B20}$ |
| III-3381 | $L_{A468}$ | $L_{B20}$ |
| III-3382 | $L_{A469}$ | $L_{B20}$ |
| III-3383 | $L_{A470}$ | $L_{B20}$ |
| III-3384 | $L_{A471}$ | $L_{B20}$ |
| III-3385 | $L_{A472}$ | $L_{B20}$ |
| III-3386 | $L_{A473}$ | $L_{B20}$ |
| III-3387 | $L_{A474}$ | $L_{B20}$ |
| III-3388 | $L_{A475}$ | $L_{B20}$ |
| III-3389 | $L_{A476}$ | $L_{B20}$ |
| III-3390 | $L_{A477}$ | $L_{B20}$ |
| III-3391 | $L_{A478}$ | $L_{B20}$ |
| III-3392 | $L_{A479}$ | $L_{B20}$ |
| III-3393 | $L_{A480}$ | $L_{B20}$ |
| III-3394 | $L_{A481}$ | $L_{B20}$ |
| III-3395 | $L_{A482}$ | $L_{B20}$ |
| III-3396 | $L_{A483}$ | $L_{B20}$ |
| III-3397 | $L_{A484}$ | $L_{B20}$ |
| III-3398 | $L_{A485}$ | $L_{B20}$ |
| III-3399 | $L_{A486}$ | $L_{B20}$ |
| III-3400 | $L_{A487}$ | $L_{B20}$ |
| III-3401 | $L_{A318}$ | $L_{B21}$ |
| III-3402 | $L_{A319}$ | $L_{B21}$ |
| III-3403 | $L_{A320}$ | $L_{B21}$ |
| III-3404 | $L_{A321}$ | $L_{B21}$ |
| III-3405 | $L_{A322}$ | $L_{B21}$ |
| III-3406 | $L_{A323}$ | $L_{B21}$ |
| III-3407 | $L_{A324}$ | $L_{B21}$ |
| III-3408 | $L_{A325}$ | $L_{B21}$ |
| III-3409 | $L_{A326}$ | $L_{B21}$ |
| III-3410 | $L_{A327}$ | $L_{B21}$ |
| III-3411 | $L_{A328}$ | $L_{B21}$ |
| III-3412 | $L_{A329}$ | $L_{B21}$ |
| III-3413 | $L_{A330}$ | $L_{B21}$ |
| III-3414 | $L_{A331}$ | $L_{B21}$ |
| III-3415 | $L_{A332}$ | $L_{B21}$ |
| III-3416 | $L_{A333}$ | $L_{B21}$ |
| III-3417 | $L_{A334}$ | $L_{B21}$ |
| III-3418 | $L_{A335}$ | $L_{B21}$ |
| III-3419 | $L_{A336}$ | $L_{B21}$ |
| III-3420 | $L_{A337}$ | $L_{B21}$ |
| III-3421 | $L_{A338}$ | $L_{B21}$ |
| III-3422 | $L_{A339}$ | $L_{B21}$ |
| III-3423 | $L_{A340}$ | $L_{B21}$ |
| III-3424 | $L_{A341}$ | $L_{B21}$ |
| III-3425 | $L_{A342}$ | $L_{B21}$ |
| III-3426 | $L_{A343}$ | $L_{B21}$ |
| III-3427 | $L_{A344}$ | $L_{B21}$ |
| III-3428 | $L_{A345}$ | $L_{B21}$ |
| III-3429 | $L_{A346}$ | $L_{B21}$ |
| III-3430 | $L_{A347}$ | $L_{B21}$ |
| III-3431 | $L_{A348}$ | $L_{B21}$ |
| III-3432 | $L_{A349}$ | $L_{B21}$ |
| III-3433 | $L_{A350}$ | $L_{B21}$ |
| III-3434 | $L_{A351}$ | $L_{B21}$ |
| III-3435 | $L_{A352}$ | $L_{B21}$ |
| III-3436 | $L_{A353}$ | $L_{B21}$ |
| III-3437 | $L_{A354}$ | $L_{B21}$ |

-continued

| Compound Number | $L_A$ | $L_B$ |
|---|---|---|
| III-3438 | $L_{A355}$ | $L_{B21}$ |
| III-3439 | $L_{A356}$ | $L_{B21}$ |
| III-3440 | $L_{A357}$ | $L_{B21}$ |
| III-3441 | $L_{A358}$ | $L_{B21}$ |
| III-3442 | $L_{A359}$ | $L_{B21}$ |
| III-3443 | $L_{A360}$ | $L_{B21}$ |
| III-3444 | $L_{A361}$ | $L_{B21}$ |
| III-3445 | $L_{A362}$ | $L_{B21}$ |
| III-3446 | $L_{A363}$ | $L_{B21}$ |
| III-3447 | $L_{A364}$ | $L_{B21}$ |
| III-3448 | $L_{A365}$ | $L_{B21}$ |
| III-3449 | $L_{A366}$ | $L_{B21}$ |
| III-3450 | $L_{A367}$ | $L_{B21}$ |
| III-3451 | $L_{A368}$ | $L_{B21}$ |
| III-3452 | $L_{A369}$ | $L_{B21}$ |
| III-3453 | $L_{A370}$ | $L_{B21}$ |
| III-3454 | $L_{A371}$ | $L_{B21}$ |
| III-3455 | $L_{A372}$ | $L_{B21}$ |
| III-3456 | $L_{A373}$ | $L_{B21}$ |
| III-3457 | $L_{A374}$ | $L_{B21}$ |
| III-3458 | $L_{A375}$ | $L_{B21}$ |
| III-3459 | $L_{A376}$ | $L_{B21}$ |
| III-3460 | $L_{A377}$ | $L_{B21}$ |
| III-3461 | $L_{A378}$ | $L_{B21}$ |
| III-3462 | $L_{A379}$ | $L_{B21}$ |
| III-3463 | $L_{A380}$ | $L_{B21}$ |
| III-3464 | $L_{A381}$ | $L_{B21}$ |
| III-3465 | $L_{A382}$ | $L_{B21}$ |
| III-3466 | $L_{A383}$ | $L_{B21}$ |
| III-3467 | $L_{A384}$ | $L_{B21}$ |
| III-3468 | $L_{A385}$ | $L_{B21}$ |
| III-3469 | $L_{A386}$ | $L_{B21}$ |
| III-3470 | $L_{A387}$ | $L_{B21}$ |
| III-3471 | $L_{A388}$ | $L_{B21}$ |
| III-3472 | $L_{A389}$ | $L_{B21}$ |
| III-3473 | $L_{A390}$ | $L_{B21}$ |
| III-3474 | $L_{A391}$ | $L_{B21}$ |
| III-3475 | $L_{A392}$ | $L_{B21}$ |
| III-3476 | $L_{A393}$ | $L_{B21}$ |
| III-3477 | $L_{A394}$ | $L_{B21}$ |
| III-3478 | $L_{A395}$ | $L_{B21}$ |
| III-3479 | $L_{A396}$ | $L_{B21}$ |
| III-3480 | $L_{A397}$ | $L_{B21}$ |
| III-3481 | $L_{A398}$ | $L_{B21}$ |
| III-3482 | $L_{A399}$ | $L_{B21}$ |
| III-3483 | $L_{A400}$ | $L_{B21}$ |
| III-3484 | $L_{A401}$ | $L_{B21}$ |
| III-3485 | $L_{A402}$ | $L_{B21}$ |
| III-3486 | $L_{A403}$ | $L_{B21}$ |
| III-3487 | $L_{A404}$ | $L_{B21}$ |
| III-3488 | $L_{A405}$ | $L_{B21}$ |
| III-3489 | $L_{A406}$ | $L_{B21}$ |
| III-3490 | $L_{A407}$ | $L_{B21}$ |
| III-3491 | $L_{A408}$ | $L_{B21}$ |
| III-3492 | $L_{A409}$ | $L_{B21}$ |
| III-3493 | $L_{A410}$ | $L_{B21}$ |
| III-3494 | $L_{A411}$ | $L_{B21}$ |
| III-3495 | $L_{A412}$ | $L_{B21}$ |
| III-3496 | $L_{A413}$ | $L_{B21}$ |
| III-3497 | $L_{A414}$ | $L_{B21}$ |
| III-3498 | $L_{A415}$ | $L_{B21}$ |
| III-3499 | $L_{A416}$ | $L_{B21}$ |
| III-3500 | $L_{A417}$ | $L_{B21}$ |
| III-3501 | $L_{A418}$ | $L_{B21}$ |
| III-3502 | $L_{A419}$ | $L_{B21}$ |
| III-3503 | $L_{A420}$ | $L_{B21}$ |
| III-3504 | $L_{A421}$ | $L_{B21}$ |
| III-3505 | $L_{A422}$ | $L_{B21}$ |
| III-3506 | $L_{A423}$ | $L_{B21}$ |
| III-3507 | $L_{A424}$ | $L_{B21}$ |
| III-3508 | $L_{A425}$ | $L_{B21}$ |
| III-3509 | $L_{A426}$ | $L_{B21}$ |
| III-3510 | $L_{A427}$ | $L_{B21}$ |
| III-3511 | $L_{A428}$ | $L_{B21}$ |
| III-3512 | $L_{A429}$ | $L_{B21}$ |
| III-3513 | $L_{A430}$ | $L_{B21}$ |
| III-3514 | $L_{A431}$ | $L_{B21}$ |
| III-3515 | $L_{A432}$ | $L_{B21}$ |
| III-3516 | $L_{A433}$ | $L_{B21}$ |
| III-3517 | $L_{A434}$ | $L_{B21}$ |
| III-3518 | $L_{A435}$ | $L_{B21}$ |
| III-3519 | $L_{A436}$ | $L_{B21}$ |
| III-3520 | $L_{A437}$ | $L_{B21}$ |
| III-3521 | $L_{A438}$ | $L_{B21}$ |
| III-3522 | $L_{A439}$ | $L_{B21}$ |
| III-3523 | $L_{A440}$ | $L_{B21}$ |
| III-3524 | $L_{A441}$ | $L_{B21}$ |
| III-3525 | $L_{A442}$ | $L_{B21}$ |
| III-3526 | $L_{A443}$ | $L_{B21}$ |
| III-3527 | $L_{A444}$ | $L_{B21}$ |
| III-3528 | $L_{A445}$ | $L_{B21}$ |
| III-3529 | $L_{A446}$ | $L_{B21}$ |
| III-3530 | $L_{A447}$ | $L_{B21}$ |
| III-3531 | $L_{A448}$ | $L_{B21}$ |
| III-3532 | $L_{A449}$ | $L_{B21}$ |
| III-3533 | $L_{A450}$ | $L_{B21}$ |
| III-3534 | $L_{A451}$ | $L_{B21}$ |
| III-3535 | $L_{A452}$ | $L_{B21}$ |
| III-3536 | $L_{A453}$ | $L_{B21}$ |
| III-3537 | $L_{A454}$ | $L_{B21}$ |
| III-3538 | $L_{A455}$ | $L_{B21}$ |
| III-3539 | $L_{A456}$ | $L_{B21}$ |
| III-3540 | $L_{A457}$ | $L_{B21}$ |
| III-3541 | $L_{A458}$ | $L_{B21}$ |
| III-3542 | $L_{A459}$ | $L_{B21}$ |
| III-3543 | $L_{A460}$ | $L_{B21}$ |
| III-3544 | $L_{A461}$ | $L_{B21}$ |
| III-3545 | $L_{A462}$ | $L_{B21}$ |
| III-3546 | $L_{A463}$ | $L_{B21}$ |
| III-3547 | $L_{A464}$ | $L_{B21}$ |
| III-3548 | $L_{A465}$ | $L_{B21}$ |
| III-3549 | $L_{A466}$ | $L_{B21}$ |
| III-3550 | $L_{A467}$ | $L_{B21}$ |
| III-3551 | $L_{A468}$ | $L_{B21}$ |
| III-3552 | $L_{A469}$ | $L_{B21}$ |
| III-3553 | $L_{A470}$ | $L_{B21}$ |
| III-3554 | $L_{A471}$ | $L_{B21}$ |
| III-3555 | $L_{A472}$ | $L_{B21}$ |
| III-3556 | $L_{A473}$ | $L_{B21}$ |
| III-3557 | $L_{A474}$ | $L_{B21}$ |
| III-3558 | $L_{A475}$ | $L_{B21}$ |
| III-3559 | $L_{A476}$ | $L_{B21}$ |
| III-3560 | $L_{A477}$ | $L_{B21}$ |
| III-3561 | $L_{A478}$ | $L_{B21}$ |
| III-3562 | $L_{A479}$ | $L_{B21}$ |
| III-3563 | $L_{A480}$ | $L_{B21}$ |
| III-3564 | $L_{A481}$ | $L_{B21}$ |
| III-3565 | $L_{A482}$ | $L_{B21}$ |
| III-3566 | $L_{A483}$ | $L_{B21}$ |
| III-3567 | $L_{A484}$ | $L_{B21}$ |
| III-3568 | $L_{A485}$ | $L_{B21}$ |
| III-3569 | $L_{A486}$ | $L_{B21}$ |
| III-3570 | $L_{A487}$ | $L_{B21}$ |
| III-3571 | $L_{A318}$ | $L_{B22}$ |
| III-3572 | $L_{A319}$ | $L_{B22}$ |
| III-3573 | $L_{A320}$ | $L_{B22}$ |
| III-3574 | $L_{A321}$ | $L_{B22}$ |
| III-3575 | $L_{A322}$ | $L_{B22}$ |
| III-3576 | $L_{A323}$ | $L_{B22}$ |
| III-3577 | $L_{A324}$ | $L_{B22}$ |
| III-3578 | $L_{A325}$ | $L_{B22}$ |
| III-3579 | $L_{A326}$ | $L_{B22}$ |
| III-3580 | $L_{A327}$ | $L_{B22}$ |
| III-3581 | $L_{A328}$ | $L_{B22}$ |
| III-3582 | $L_{A329}$ | $L_{B22}$ |
| III-3583 | $L_{A330}$ | $L_{B22}$ |
| III-3584 | $L_{A331}$ | $L_{B22}$ |
| III-3585 | $L_{A332}$ | $L_{B22}$ |
| III-3586 | $L_{A333}$ | $L_{B22}$ |
| III-3587 | $L_{A334}$ | $L_{B22}$ |
| III-3588 | $L_{A335}$ | $L_{B22}$ |
| III-3589 | $L_{A336}$ | $L_{B22}$ |

-continued

| Compound Number | $L_A$ | $L_B$ |
|---|---|---|
| III-3590 | $L_{A337}$ | $L_{B22}$ |
| III-3591 | $L_{A338}$ | $L_{B22}$ |
| III-3592 | $L_{A339}$ | $L_{B22}$ |
| III-3593 | $L_{A340}$ | $L_{B22}$ |
| III-3594 | $L_{A341}$ | $L_{B22}$ |
| III-3595 | $L_{A342}$ | $L_{B22}$ |
| III-3596 | $L_{A343}$ | $L_{B22}$ |
| III-3597 | $L_{A344}$ | $L_{B22}$ |
| III-3598 | $L_{A345}$ | $L_{B22}$ |
| III-3599 | $L_{A346}$ | $L_{B22}$ |
| III-3600 | $L_{A347}$ | $L_{B22}$ |
| III-3601 | $L_{A348}$ | $L_{B22}$ |
| III-3602 | $L_{A349}$ | $L_{B22}$ |
| III-3603 | $L_{A350}$ | $L_{B22}$ |
| III-3604 | $L_{A351}$ | $L_{B22}$ |
| III-3605 | $L_{A352}$ | $L_{B22}$ |
| III-3606 | $L_{A353}$ | $L_{B22}$ |
| III-3607 | $L_{A354}$ | $L_{B22}$ |
| III-3608 | $L_{A355}$ | $L_{B22}$ |
| III-3609 | $L_{A356}$ | $L_{B22}$ |
| III-3610 | $L_{A357}$ | $L_{B22}$ |
| III-3611 | $L_{A358}$ | $L_{B22}$ |
| III-3612 | $L_{A359}$ | $L_{B22}$ |
| III-3613 | $L_{A360}$ | $L_{B22}$ |
| III-3614 | $L_{A361}$ | $L_{B22}$ |
| III-3615 | $L_{A362}$ | $L_{B22}$ |
| III-3616 | $L_{A363}$ | $L_{B22}$ |
| III-3617 | $L_{A364}$ | $L_{B22}$ |
| III-3618 | $L_{A365}$ | $L_{B22}$ |
| III-3619 | $L_{A366}$ | $L_{B22}$ |
| III-3620 | $L_{A367}$ | $L_{B22}$ |
| III-3621 | $L_{A368}$ | $L_{B22}$ |
| III-3622 | $L_{A369}$ | $L_{B22}$ |
| III-3623 | $L_{A370}$ | $L_{B22}$ |
| III-3624 | $L_{A371}$ | $L_{B22}$ |
| III-3625 | $L_{A372}$ | $L_{B22}$ |
| III-3626 | $L_{A373}$ | $L_{B22}$ |
| III-3627 | $L_{A374}$ | $L_{B22}$ |
| III-3628 | $L_{A375}$ | $L_{B22}$ |
| III-3629 | $L_{A376}$ | $L_{B22}$ |
| III-3630 | $L_{A377}$ | $L_{B22}$ |
| III-3631 | $L_{A378}$ | $L_{B22}$ |
| III-3632 | $L_{A379}$ | $L_{B22}$ |
| III-3633 | $L_{A380}$ | $L_{B22}$ |
| III-3634 | $L_{A381}$ | $L_{B22}$ |
| III-3635 | $L_{A382}$ | $L_{B22}$ |
| III-3636 | $L_{A383}$ | $L_{B22}$ |
| III-3637 | $L_{A384}$ | $L_{B22}$ |
| III-3638 | $L_{A385}$ | $L_{B22}$ |
| III-3639 | $L_{A386}$ | $L_{B22}$ |
| III-3640 | $L_{A387}$ | $L_{B22}$ |
| III-3641 | $L_{A388}$ | $L_{B22}$ |
| III-3642 | $L_{A389}$ | $L_{B22}$ |
| III-3643 | $L_{A390}$ | $L_{B22}$ |
| III-3644 | $L_{A391}$ | $L_{B22}$ |
| III-3645 | $L_{A392}$ | $L_{B22}$ |
| III-3646 | $L_{A393}$ | $L_{B22}$ |
| III-3647 | $L_{A394}$ | $L_{B22}$ |
| III-3648 | $L_{A395}$ | $L_{B22}$ |
| III-3649 | $L_{A396}$ | $L_{B22}$ |
| III-3650 | $L_{A397}$ | $L_{B22}$ |
| III-3651 | $L_{A398}$ | $L_{B22}$ |
| III-3652 | $L_{A399}$ | $L_{B22}$ |
| III-3653 | $L_{A400}$ | $L_{B22}$ |
| III-3654 | $L_{A401}$ | $L_{B22}$ |
| III-3655 | $L_{A402}$ | $L_{B22}$ |
| III-3656 | $L_{A403}$ | $L_{B22}$ |
| III-3657 | $L_{A404}$ | $L_{B22}$ |
| III-3658 | $L_{A405}$ | $L_{B22}$ |
| III-3659 | $L_{A406}$ | $L_{B22}$ |
| III-3660 | $L_{A407}$ | $L_{B22}$ |
| III-3661 | $L_{A408}$ | $L_{B22}$ |
| III-3662 | $L_{A409}$ | $L_{B22}$ |
| III-3663 | $L_{A410}$ | $L_{B22}$ |
| III-3664 | $L_{A411}$ | $L_{B22}$ |
| III-3665 | $L_{A412}$ | $L_{B22}$ |
| III-3666 | $L_{A413}$ | $L_{B22}$ |
| III-3667 | $L_{A414}$ | $L_{B22}$ |
| III-3668 | $L_{A415}$ | $L_{B22}$ |
| III-3669 | $L_{A416}$ | $L_{B22}$ |
| III-3670 | $L_{A417}$ | $L_{B22}$ |
| III-3671 | $L_{A418}$ | $L_{B22}$ |
| III-3672 | $L_{A419}$ | $L_{B22}$ |
| III-3673 | $L_{A420}$ | $L_{B22}$ |
| III-3674 | $L_{A421}$ | $L_{B22}$ |
| III-3675 | $L_{A422}$ | $L_{B22}$ |
| III-3676 | $L_{A423}$ | $L_{B22}$ |
| III-3677 | $L_{A424}$ | $L_{B22}$ |
| III-3678 | $L_{A425}$ | $L_{B22}$ |
| III-3679 | $L_{A426}$ | $L_{B22}$ |
| III-3680 | $L_{A427}$ | $L_{B22}$ |
| III-3681 | $L_{A428}$ | $L_{B22}$ |
| III-3682 | $L_{A429}$ | $L_{B22}$ |
| III-3683 | $L_{A430}$ | $L_{B22}$ |
| III-3684 | $L_{A431}$ | $L_{B22}$ |
| III-3685 | $L_{A432}$ | $L_{B22}$ |
| III-3686 | $L_{A433}$ | $L_{B22}$ |
| III-3687 | $L_{A434}$ | $L_{B22}$ |
| III-3688 | $L_{A435}$ | $L_{B22}$ |
| III-3689 | $L_{A436}$ | $L_{B22}$ |
| III-3690 | $L_{A437}$ | $L_{B22}$ |
| III-3691 | $L_{A438}$ | $L_{B22}$ |
| III-3692 | $L_{A439}$ | $L_{B22}$ |
| III-3693 | $L_{A440}$ | $L_{B22}$ |
| III-3694 | $L_{A441}$ | $L_{B22}$ |
| III-3695 | $L_{A442}$ | $L_{B22}$ |
| III-3696 | $L_{A443}$ | $L_{B22}$ |
| III-3697 | $L_{A444}$ | $L_{B22}$ |
| III-3698 | $L_{A445}$ | $L_{B22}$ |
| III-3699 | $L_{A446}$ | $L_{B22}$ |
| III-3700 | $L_{A447}$ | $L_{B22}$ |
| III-3701 | $L_{A448}$ | $L_{B22}$ |
| III-3702 | $L_{A449}$ | $L_{B22}$ |
| III-3703 | $L_{A450}$ | $L_{B22}$ |
| III-3704 | $L_{A451}$ | $L_{B22}$ |
| III-3705 | $L_{A452}$ | $L_{B22}$ |
| III-3706 | $L_{A453}$ | $L_{B22}$ |
| III-3707 | $L_{A454}$ | $L_{B22}$ |
| III-3708 | $L_{A455}$ | $L_{B22}$ |
| III-3709 | $L_{A456}$ | $L_{B22}$ |
| III-3710 | $L_{A457}$ | $L_{B22}$ |
| III-3711 | $L_{A458}$ | $L_{B22}$ |
| III-3712 | $L_{A459}$ | $L_{B22}$ |
| III-3713 | $L_{A460}$ | $L_{B22}$ |
| III-3714 | $L_{A461}$ | $L_{B22}$ |
| III-3715 | $L_{A462}$ | $L_{B22}$ |
| III-3716 | $L_{A463}$ | $L_{B22}$ |
| III-3717 | $L_{A464}$ | $L_{B22}$ |
| III-3718 | $L_{A465}$ | $L_{B22}$ |
| III-3719 | $L_{A466}$ | $L_{B22}$ |
| III-3720 | $L_{A467}$ | $L_{B22}$ |
| III-3721 | $L_{A468}$ | $L_{B22}$ |
| III-3722 | $L_{A469}$ | $L_{B22}$ |
| III-3723 | $L_{A470}$ | $L_{B22}$ |
| III-3724 | $L_{A471}$ | $L_{B22}$ |
| III-3725 | $L_{A472}$ | $L_{B22}$ |
| III-3726 | $L_{A473}$ | $L_{B22}$ |
| III-3727 | $L_{A474}$ | $L_{B22}$ |
| III-3728 | $L_{A475}$ | $L_{B22}$ |
| III-3729 | $L_{A476}$ | $L_{B22}$ |
| III-3730 | $L_{A477}$ | $L_{B22}$ |
| III-3731 | $L_{A478}$ | $L_{B22}$ |
| III-3732 | $L_{A479}$ | $L_{B22}$ |
| III-3733 | $L_{A480}$ | $L_{B22}$ |
| III-3734 | $L_{A481}$ | $L_{B22}$ |
| III-3735 | $L_{A482}$ | $L_{B22}$ |
| III-3736 | $L_{A483}$ | $L_{B22}$ |
| III-3737 | $L_{A484}$ | $L_{B22}$ |
| III-3738 | $L_{A485}$ | $L_{B22}$ |
| III-3739 | $L_{A486}$ | $L_{B22}$ |
| III-3740 | $L_{A487}$ | $L_{B22}$ |
| III-3741 | $L_{A318}$ | $L_{B23}$ |

-continued

| Compound Number | $L_A$ | $L_B$ |
|---|---|---|
| III-3742 | $L_{A319}$ | $L_{B23}$ |
| III-3743 | $L_{A320}$ | $L_{B23}$ |
| III-3744 | $L_{A321}$ | $L_{B23}$ |
| III-3745 | $L_{A322}$ | $L_{B23}$ |
| III-3746 | $L_{A323}$ | $L_{B23}$ |
| III-3747 | $L_{A324}$ | $L_{B23}$ |
| III-3748 | $L_{A325}$ | $L_{B23}$ |
| III-3749 | $L_{A326}$ | $L_{B23}$ |
| III-3750 | $L_{A327}$ | $L_{B23}$ |
| III-3751 | $L_{A328}$ | $L_{B23}$ |
| III-3752 | $L_{A329}$ | $L_{B23}$ |
| III-3753 | $L_{A330}$ | $L_{B23}$ |
| III-3754 | $L_{A331}$ | $L_{B23}$ |
| III-3755 | $L_{A332}$ | $L_{B23}$ |
| III-3756 | $L_{A333}$ | $L_{B23}$ |
| III-3757 | $L_{A334}$ | $L_{B23}$ |
| III-3758 | $L_{A335}$ | $L_{B23}$ |
| III-3759 | $L_{A336}$ | $L_{B23}$ |
| III-3760 | $L_{A337}$ | $L_{B23}$ |
| III-3761 | $L_{A338}$ | $L_{B23}$ |
| III-3762 | $L_{A339}$ | $L_{B23}$ |
| III-3763 | $L_{A340}$ | $L_{B23}$ |
| III-3764 | $L_{A341}$ | $L_{B23}$ |
| III-3765 | $L_{A342}$ | $L_{B23}$ |
| III-3766 | $L_{A343}$ | $L_{B23}$ |
| III-3767 | $L_{A344}$ | $L_{B23}$ |
| III-3768 | $L_{A345}$ | $L_{B23}$ |
| III-3769 | $L_{A346}$ | $L_{B23}$ |
| III-3770 | $L_{A347}$ | $L_{B23}$ |
| III-3771 | $L_{A348}$ | $L_{B23}$ |
| III-3772 | $L_{A349}$ | $L_{B23}$ |
| III-3773 | $L_{A350}$ | $L_{B23}$ |
| III-3774 | $L_{A351}$ | $L_{B23}$ |
| III-3775 | $L_{A352}$ | $L_{B23}$ |
| III-3776 | $L_{A353}$ | $L_{B23}$ |
| III-3777 | $L_{A354}$ | $L_{B23}$ |
| III-3778 | $L_{A355}$ | $L_{B23}$ |
| III-3779 | $L_{A356}$ | $L_{B23}$ |
| III-3780 | $L_{A357}$ | $L_{B23}$ |
| III-3781 | $L_{A358}$ | $L_{B23}$ |
| III-3782 | $L_{A359}$ | $L_{B23}$ |
| III-3783 | $L_{A360}$ | $L_{B23}$ |
| III-3784 | $L_{A361}$ | $L_{B23}$ |
| III-3785 | $L_{A362}$ | $L_{B23}$ |
| III-3786 | $L_{A363}$ | $L_{B23}$ |
| III-3787 | $L_{A364}$ | $L_{B23}$ |
| III-3788 | $L_{A365}$ | $L_{B23}$ |
| III-3789 | $L_{A366}$ | $L_{B23}$ |
| III-3790 | $L_{A367}$ | $L_{B23}$ |
| III-3791 | $L_{A368}$ | $L_{B23}$ |
| III-3792 | $L_{A369}$ | $L_{B23}$ |
| III-3793 | $L_{A370}$ | $L_{B23}$ |
| III-3794 | $L_{A371}$ | $L_{B23}$ |
| III-3795 | $L_{A372}$ | $L_{B23}$ |
| III-3796 | $L_{A373}$ | $L_{B23}$ |
| III-3797 | $L_{A374}$ | $L_{B23}$ |
| III-3798 | $L_{A375}$ | $L_{B23}$ |
| III-3799 | $L_{A376}$ | $L_{B23}$ |
| III-3800 | $L_{A377}$ | $L_{B23}$ |
| III-3801 | $L_{A378}$ | $L_{B23}$ |
| III-3802 | $L_{A379}$ | $L_{B23}$ |
| III-3803 | $L_{A380}$ | $L_{B23}$ |
| III-3804 | $L_{A381}$ | $L_{B23}$ |
| III-3805 | $L_{A382}$ | $L_{B23}$ |
| III-3806 | $L_{A383}$ | $L_{B23}$ |
| III-3807 | $L_{A384}$ | $L_{B23}$ |
| III-3808 | $L_{A385}$ | $L_{B23}$ |
| III-3809 | $L_{A386}$ | $L_{B23}$ |
| III-3810 | $L_{A387}$ | $L_{B23}$ |
| III-3811 | $L_{A388}$ | $L_{B23}$ |
| III-3812 | $L_{A389}$ | $L_{B23}$ |
| III-3813 | $L_{A390}$ | $L_{B23}$ |
| III-3814 | $L_{A391}$ | $L_{B23}$ |
| III-3815 | $L_{A392}$ | $L_{B23}$ |
| III-3816 | $L_{A393}$ | $L_{B23}$ |
| III-3817 | $L_{A394}$ | $L_{B23}$ |
| III-3818 | $L_{A395}$ | $L_{B23}$ |
| III-3819 | $L_{A396}$ | $L_{B23}$ |
| III-3820 | $L_{A397}$ | $L_{B23}$ |
| III-3821 | $L_{A398}$ | $L_{B23}$ |
| III-3822 | $L_{A399}$ | $L_{B23}$ |
| III-3823 | $L_{A400}$ | $L_{B23}$ |
| III-3824 | $L_{A401}$ | $L_{B23}$ |
| III-3825 | $L_{A402}$ | $L_{B23}$ |
| III-3826 | $L_{A403}$ | $L_{B23}$ |
| III-3827 | $L_{A404}$ | $L_{B23}$ |
| III-3828 | $L_{A405}$ | $L_{B23}$ |
| III-3829 | $L_{A406}$ | $L_{B23}$ |
| III-3830 | $L_{A407}$ | $L_{B23}$ |
| III-3831 | $L_{A408}$ | $L_{B23}$ |
| III-3832 | $L_{A409}$ | $L_{B23}$ |
| III-3833 | $L_{A410}$ | $L_{B23}$ |
| III-3834 | $L_{A411}$ | $L_{B23}$ |
| III-3835 | $L_{A412}$ | $L_{B23}$ |
| III-3836 | $L_{A413}$ | $L_{B23}$ |
| III-3837 | $L_{A414}$ | $L_{B23}$ |
| III-3838 | $L_{A415}$ | $L_{B23}$ |
| III-3839 | $L_{A416}$ | $L_{B23}$ |
| III-3840 | $L_{A417}$ | $L_{B23}$ |
| III-3841 | $L_{A418}$ | $L_{B23}$ |
| III-3842 | $L_{A419}$ | $L_{B23}$ |
| III-3843 | $L_{A420}$ | $L_{B23}$ |
| III-3844 | $L_{A421}$ | $L_{B23}$ |
| III-3845 | $L_{A422}$ | $L_{B23}$ |
| III-3846 | $L_{A423}$ | $L_{B23}$ |
| III-3847 | $L_{A424}$ | $L_{B23}$ |
| III-3848 | $L_{A425}$ | $L_{B23}$ |
| III-3849 | $L_{A426}$ | $L_{B23}$ |
| III-3850 | $L_{A427}$ | $L_{B23}$ |
| III-3851 | $L_{A428}$ | $L_{B23}$ |
| III-3852 | $L_{A429}$ | $L_{B23}$ |
| III-3853 | $L_{A430}$ | $L_{B23}$ |
| III-3854 | $L_{A431}$ | $L_{B23}$ |
| III-3855 | $L_{A432}$ | $L_{B23}$ |
| III-3856 | $L_{A433}$ | $L_{B23}$ |
| III-3857 | $L_{A434}$ | $L_{B23}$ |
| III-3858 | $L_{A435}$ | $L_{B23}$ |
| III-3859 | $L_{A436}$ | $L_{B23}$ |
| III-3860 | $L_{A437}$ | $L_{B23}$ |
| III-3861 | $L_{A438}$ | $L_{B23}$ |
| III-3862 | $L_{A439}$ | $L_{B23}$ |
| III-3863 | $L_{A440}$ | $L_{B23}$ |
| III-3864 | $L_{A441}$ | $L_{B23}$ |
| III-3865 | $L_{A442}$ | $L_{B23}$ |
| III-3866 | $L_{A443}$ | $L_{B23}$ |
| III-3867 | $L_{A444}$ | $L_{B23}$ |
| III-3868 | $L_{A445}$ | $L_{B23}$ |
| III-3869 | $L_{A446}$ | $L_{B23}$ |
| III-3870 | $L_{A447}$ | $L_{B23}$ |
| III-3871 | $L_{A448}$ | $L_{B23}$ |
| III-3872 | $L_{A449}$ | $L_{B23}$ |
| III-3873 | $L_{A450}$ | $L_{B23}$ |
| III-3874 | $L_{A451}$ | $L_{B23}$ |
| III-3875 | $L_{A452}$ | $L_{B23}$ |
| III-3876 | $L_{A453}$ | $L_{B23}$ |
| III-3877 | $L_{A454}$ | $L_{B23}$ |
| III-3878 | $L_{A455}$ | $L_{B23}$ |
| III-3879 | $L_{A456}$ | $L_{B23}$ |
| III-3880 | $L_{A457}$ | $L_{B23}$ |
| III-3881 | $L_{A458}$ | $L_{B23}$ |
| III-3882 | $L_{A459}$ | $L_{B23}$ |
| III-3883 | $L_{A460}$ | $L_{B23}$ |
| III-3884 | $L_{A461}$ | $L_{B23}$ |
| III-3885 | $L_{A462}$ | $L_{B23}$ |
| III-3886 | $L_{A463}$ | $L_{B23}$ |
| III-3887 | $L_{A464}$ | $L_{B23}$ |
| III-3888 | $L_{A465}$ | $L_{B23}$ |
| III-3889 | $L_{A466}$ | $L_{B23}$ |
| III-3890 | $L_{A467}$ | $L_{B23}$ |
| III-3891 | $L_{A468}$ | $L_{B23}$ |
| III-3892 | $L_{A469}$ | $L_{B23}$ |
| III-3893 | $L_{A470}$ | $L_{B23}$ |

-continued

| Compound Number | $L_A$ | $L_B$ |
|---|---|---|
| III-3894 | $L_{A471}$ | $L_{B23}$ |
| III-3895 | $L_{A472}$ | $L_{B23}$ |
| III-3896 | $L_{A473}$ | $L_{B23}$ |
| III-3897 | $L_{A474}$ | $L_{B23}$ |
| III-3898 | $L_{A475}$ | $L_{B23}$ |
| III-3899 | $L_{A476}$ | $L_{B23}$ |
| III-3900 | $L_{A477}$ | $L_{B23}$ |
| III-3901 | $L_{A478}$ | $L_{B23}$ |
| III-3902 | $L_{A479}$ | $L_{B23}$ |
| III-3903 | $L_{A480}$ | $L_{B23}$ |
| III-3904 | $L_{A481}$ | $L_{B23}$ |
| III-3905 | $L_{A482}$ | $L_{B23}$ |
| III-3906 | $L_{A483}$ | $L_{B23}$ |
| III-3907 | $L_{A484}$ | $L_{B23}$ |
| III-3908 | $L_{A485}$ | $L_{B23}$ |
| III-3909 | $L_{A486}$ | $L_{B23}$ |
| III-3910 | $L_{A487}$ | $L_{B23}$ |
| III-3911 | $L_{A318}$ | $L_{B24}$ |
| III-3912 | $L_{A319}$ | $L_{B24}$ |
| III-3913 | $L_{A320}$ | $L_{B24}$ |
| III-3914 | $L_{A321}$ | $L_{B24}$ |
| III-3915 | $L_{A322}$ | $L_{B24}$ |
| III-3916 | $L_{A323}$ | $L_{B24}$ |
| III-3917 | $L_{A324}$ | $L_{B24}$ |
| III-3918 | $L_{A325}$ | $L_{B24}$ |
| III-3919 | $L_{A326}$ | $L_{B24}$ |
| III-3920 | $L_{A327}$ | $L_{B24}$ |
| III-3921 | $L_{A328}$ | $L_{B24}$ |
| III-3922 | $L_{A329}$ | $L_{B24}$ |
| III-3923 | $L_{A330}$ | $L_{B24}$ |
| III-3924 | $L_{A331}$ | $L_{B24}$ |
| III-3925 | $L_{A332}$ | $L_{B24}$ |
| III-3926 | $L_{A333}$ | $L_{B24}$ |
| III-3927 | $L_{A334}$ | $L_{B24}$ |
| III-3928 | $L_{A335}$ | $L_{B24}$ |
| III-3929 | $L_{A336}$ | $L_{B24}$ |
| III-3930 | $L_{A337}$ | $L_{B24}$ |
| III-3931 | $L_{A338}$ | $L_{B24}$ |
| III-3932 | $L_{A339}$ | $L_{B24}$ |
| III-3933 | $L_{A340}$ | $L_{B24}$ |
| III-3934 | $L_{A341}$ | $L_{B24}$ |
| III-3935 | $L_{A342}$ | $L_{B24}$ |
| III-3936 | $L_{A343}$ | $L_{B24}$ |
| III-3937 | $L_{A344}$ | $L_{B24}$ |
| III-3938 | $L_{A345}$ | $L_{B24}$ |
| III-3939 | $L_{A346}$ | $L_{B24}$ |
| III-3940 | $L_{A347}$ | $L_{B24}$ |
| III-3941 | $L_{A348}$ | $L_{B24}$ |
| III-3942 | $L_{A349}$ | $L_{B24}$ |
| III-3943 | $L_{A350}$ | $L_{B24}$ |
| III-3944 | $L_{A351}$ | $L_{B24}$ |
| III-3945 | $L_{A352}$ | $L_{B24}$ |
| III-3946 | $L_{A353}$ | $L_{B24}$ |
| III-3947 | $L_{A354}$ | $L_{B24}$ |
| III-3948 | $L_{A355}$ | $L_{B24}$ |
| III-3949 | $L_{A356}$ | $L_{B24}$ |
| III-3950 | $L_{A357}$ | $L_{B24}$ |
| III-3951 | $L_{A358}$ | $L_{B24}$ |
| III-3952 | $L_{A359}$ | $L_{B24}$ |
| III-3953 | $L_{A360}$ | $L_{B24}$ |
| III-3954 | $L_{A361}$ | $L_{B24}$ |
| III-3955 | $L_{A362}$ | $L_{B24}$ |
| III-3956 | $L_{A363}$ | $L_{B24}$ |
| III-3957 | $L_{A364}$ | $L_{B24}$ |
| III-3958 | $L_{A365}$ | $L_{B24}$ |
| III-3959 | $L_{A366}$ | $L_{B24}$ |
| III-3960 | $L_{A367}$ | $L_{B24}$ |
| III-3961 | $L_{A368}$ | $L_{B24}$ |
| III-3962 | $L_{A369}$ | $L_{B24}$ |
| III-3963 | $L_{A370}$ | $L_{B24}$ |
| III-3964 | $L_{A371}$ | $L_{B24}$ |
| III-3965 | $L_{A372}$ | $L_{B24}$ |
| III-3966 | $L_{A373}$ | $L_{B24}$ |
| III-3967 | $L_{A374}$ | $L_{B24}$ |
| III-3968 | $L_{A375}$ | $L_{B24}$ |
| III-3969 | $L_{A376}$ | $L_{B24}$ |
| III-3970 | $L_{A377}$ | $L_{B24}$ |
| III-3971 | $L_{A378}$ | $L_{B24}$ |
| III-3972 | $L_{A379}$ | $L_{B24}$ |
| III-3973 | $L_{A380}$ | $L_{B24}$ |
| III-3974 | $L_{A381}$ | $L_{B24}$ |
| III-3975 | $L_{A382}$ | $L_{B24}$ |
| III-3976 | $L_{A383}$ | $L_{B24}$ |
| III-3977 | $L_{A384}$ | $L_{B24}$ |
| III-3978 | $L_{A385}$ | $L_{B24}$ |
| III-3979 | $L_{A386}$ | $L_{B24}$ |
| III-3980 | $L_{A387}$ | $L_{B24}$ |
| III-3981 | $L_{A388}$ | $L_{B24}$ |
| III-3982 | $L_{A389}$ | $L_{B24}$ |
| III-3983 | $L_{A390}$ | $L_{B24}$ |
| III-3984 | $L_{A391}$ | $L_{B24}$ |
| III-3985 | $L_{A392}$ | $L_{B24}$ |
| III-3986 | $L_{A393}$ | $L_{B24}$ |
| III-3987 | $L_{A394}$ | $L_{B24}$ |
| III-3988 | $L_{A395}$ | $L_{B24}$ |
| III-3989 | $L_{A396}$ | $L_{B24}$ |
| III-3990 | $L_{A397}$ | $L_{B24}$ |
| III-3991 | $L_{A398}$ | $L_{B24}$ |
| III-3992 | $L_{A399}$ | $L_{B24}$ |
| III-3993 | $L_{A400}$ | $L_{B24}$ |
| III-3994 | $L_{A401}$ | $L_{B24}$ |
| III-3995 | $L_{A402}$ | $L_{B24}$ |
| III-3996 | $L_{A403}$ | $L_{B24}$ |
| III-3997 | $L_{A404}$ | $L_{B24}$ |
| III-3998 | $L_{A405}$ | $L_{B24}$ |
| III-3999 | $L_{A406}$ | $L_{B24}$ |
| III-4000 | $L_{A407}$ | $L_{B24}$ |
| III-4001 | $L_{A408}$ | $L_{B24}$ |
| III-4002 | $L_{A409}$ | $L_{B24}$ |
| III-4003 | $L_{A410}$ | $L_{B24}$ |
| III-4004 | $L_{A411}$ | $L_{B24}$ |
| III-4005 | $L_{A412}$ | $L_{B24}$ |
| III-4006 | $L_{A413}$ | $L_{B24}$ |
| III-4007 | $L_{A414}$ | $L_{B24}$ |
| III-4008 | $L_{A415}$ | $L_{B24}$ |
| III-4009 | $L_{A416}$ | $L_{B24}$ |
| III-4010 | $L_{A417}$ | $L_{B24}$ |
| III-4011 | $L_{A418}$ | $L_{B24}$ |
| III-4012 | $L_{A419}$ | $L_{B24}$ |
| III-4013 | $L_{A420}$ | $L_{B24}$ |
| III-4014 | $L_{A421}$ | $L_{B24}$ |
| III-4015 | $L_{A422}$ | $L_{B24}$ |
| III-4016 | $L_{A423}$ | $L_{B24}$ |
| III-4017 | $L_{A424}$ | $L_{B24}$ |
| III-4018 | $L_{A425}$ | $L_{B24}$ |
| III-4019 | $L_{A426}$ | $L_{B24}$ |
| III-4020 | $L_{A427}$ | $L_{B24}$ |
| III-4021 | $L_{A428}$ | $L_{B24}$ |
| III-4022 | $L_{A429}$ | $L_{B24}$ |
| III-4023 | $L_{A430}$ | $L_{B24}$ |
| III-4024 | $L_{A431}$ | $L_{B24}$ |
| III-4025 | $L_{A432}$ | $L_{B24}$ |
| III-4026 | $L_{A433}$ | $L_{B24}$ |
| III-4027 | $L_{A434}$ | $L_{B24}$ |
| III-4028 | $L_{A435}$ | $L_{B24}$ |
| III-4029 | $L_{A436}$ | $L_{B24}$ |
| III-4030 | $L_{A437}$ | $L_{B24}$ |
| III-4031 | $L_{A438}$ | $L_{B24}$ |
| III-4032 | $L_{A439}$ | $L_{B24}$ |
| III-4033 | $L_{A440}$ | $L_{B24}$ |
| III-4034 | $L_{A441}$ | $L_{B24}$ |
| III-4035 | $L_{A442}$ | $L_{B24}$ |
| III-4036 | $L_{A443}$ | $L_{B24}$ |
| III-4037 | $L_{A444}$ | $L_{B24}$ |
| III-4038 | $L_{A445}$ | $L_{B24}$ |
| III-4039 | $L_{A446}$ | $L_{B24}$ |
| III-4040 | $L_{A447}$ | $L_{B24}$ |
| III-4041 | $L_{A448}$ | $L_{B24}$ |
| III-4042 | $L_{A449}$ | $L_{B24}$ |
| III-4043 | $L_{A450}$ | $L_{B24}$ |
| III-4044 | $L_{A451}$ | $L_{B24}$ |
| III-4045 | $L_{A452}$ | $L_{B24}$ |

-continued

| Compound Number | $L_A$ | $L_B$ |
|---|---|---|
| III-4046 | $L_{A453}$ | $L_{B24}$ |
| III-4047 | $L_{A454}$ | $L_{B24}$ |
| III-4048 | $L_{A455}$ | $L_{B24}$ |
| III-4049 | $L_{A456}$ | $L_{B24}$ |
| III-4050 | $L_{A457}$ | $L_{B24}$ |
| III-4051 | $L_{A458}$ | $L_{B24}$ |
| III-4052 | $L_{A459}$ | $L_{B24}$ |
| III-4053 | $L_{A460}$ | $L_{B24}$ |
| III-4054 | $L_{A461}$ | $L_{B24}$ |
| III-4055 | $L_{A462}$ | $L_{B24}$ |
| III-4056 | $L_{A463}$ | $L_{B24}$ |
| III-4057 | $L_{A464}$ | $L_{B24}$ |
| III-4058 | $L_{A465}$ | $L_{B24}$ |
| III-4059 | $L_{A466}$ | $L_{B24}$ |
| III-4060 | $L_{A467}$ | $L_{B24}$ |
| III-4061 | $L_{A468}$ | $L_{B24}$ |
| III-4062 | $L_{A469}$ | $L_{B24}$ |
| III-4063 | $L_{A470}$ | $L_{B24}$ |
| III-4064 | $L_{A471}$ | $L_{B24}$ |
| III-4065 | $L_{A472}$ | $L_{B24}$ |
| III-4066 | $L_{A473}$ | $L_{B24}$ |
| III-4067 | $L_{A474}$ | $L_{B24}$ |
| III-4068 | $L_{A475}$ | $L_{B24}$ |
| III-4069 | $L_{A476}$ | $L_{B24}$ |
| III-4070 | $L_{A477}$ | $L_{B24}$ |
| III-4071 | $L_{A478}$ | $L_{B24}$ |
| III-4072 | $L_{A479}$ | $L_{B24}$ |
| III-4073 | $L_{A480}$ | $L_{B24}$ |
| III-4074 | $L_{A481}$ | $L_{B24}$ |
| III-4075 | $L_{A482}$ | $L_{B24}$ |
| III-4076 | $L_{A483}$ | $L_{B24}$ |
| III-4077 | $L_{A484}$ | $L_{B24}$ |
| III-4078 | $L_{A485}$ | $L_{B24}$ |
| III-4079 | $L_{A486}$ | $L_{B24}$ |
| III-4080 | $L_{A487}$ | $L_{B24}$ |
| III-4081 | $L_{A318}$ | $L_{B25}$ |
| III-4082 | $L_{A319}$ | $L_{B25}$ |
| III-4083 | $L_{A320}$ | $L_{B25}$ |
| III-4084 | $L_{A321}$ | $L_{B25}$ |
| III-4085 | $L_{A322}$ | $L_{B25}$ |
| III-4086 | $L_{A323}$ | $L_{B25}$ |
| III-4087 | $L_{A324}$ | $L_{B25}$ |
| III-4088 | $L_{A325}$ | $L_{B25}$ |
| III-4089 | $L_{A326}$ | $L_{B25}$ |
| III-4090 | $L_{A327}$ | $L_{B25}$ |
| III-4091 | $L_{A328}$ | $L_{B25}$ |
| III-4092 | $L_{A329}$ | $L_{B25}$ |
| III-4093 | $L_{A330}$ | $L_{B25}$ |
| III-4094 | $L_{A331}$ | $L_{B25}$ |
| III-4095 | $L_{A332}$ | $L_{B25}$ |
| III-4096 | $L_{A333}$ | $L_{B25}$ |
| III-4097 | $L_{A334}$ | $L_{B25}$ |
| III-4098 | $L_{A335}$ | $L_{B25}$ |
| III-4099 | $L_{A336}$ | $L_{B25}$ |
| III-4100 | $L_{A337}$ | $L_{B25}$ |
| III-4101 | $L_{A338}$ | $L_{B25}$ |
| III-4102 | $L_{A339}$ | $L_{B25}$ |
| III-4103 | $L_{A340}$ | $L_{B25}$ |
| III-4104 | $L_{A341}$ | $L_{B25}$ |
| III-4105 | $L_{A342}$ | $L_{B25}$ |
| III-4106 | $L_{A343}$ | $L_{B25}$ |
| III-4107 | $L_{A344}$ | $L_{B25}$ |
| III-4108 | $L_{A345}$ | $L_{B25}$ |
| III-4109 | $L_{A346}$ | $L_{B25}$ |
| III-4110 | $L_{A347}$ | $L_{B25}$ |
| III-4111 | $L_{A348}$ | $L_{B25}$ |
| III-4112 | $L_{A349}$ | $L_{B25}$ |
| III-4113 | $L_{A350}$ | $L_{B25}$ |
| III-4114 | $L_{A351}$ | $L_{B25}$ |
| III-4115 | $L_{A352}$ | $L_{B25}$ |
| III-4116 | $L_{A353}$ | $L_{B25}$ |
| III-4117 | $L_{A354}$ | $L_{B25}$ |
| III-4118 | $L_{A355}$ | $L_{B25}$ |
| III-4119 | $L_{A356}$ | $L_{B25}$ |
| III-4120 | $L_{A357}$ | $L_{B25}$ |
| III-4121 | $L_{A358}$ | $L_{B25}$ |
| III-4122 | $L_{A359}$ | $L_{B25}$ |
| III-4123 | $L_{A360}$ | $L_{B25}$ |
| III-4124 | $L_{A361}$ | $L_{B25}$ |
| III-4125 | $L_{A362}$ | $L_{B25}$ |
| III-4126 | $L_{A363}$ | $L_{B25}$ |
| III-4127 | $L_{A364}$ | $L_{B25}$ |
| III-4128 | $L_{A365}$ | $L_{B25}$ |
| III-4129 | $L_{A366}$ | $L_{B25}$ |
| III-4130 | $L_{A367}$ | $L_{B25}$ |
| III-4131 | $L_{A368}$ | $L_{B25}$ |
| III-4132 | $L_{A369}$ | $L_{B25}$ |
| III-4133 | $L_{A370}$ | $L_{B25}$ |
| III-4134 | $L_{A371}$ | $L_{B25}$ |
| III-4135 | $L_{A372}$ | $L_{B25}$ |
| III-4136 | $L_{A373}$ | $L_{B25}$ |
| III-4137 | $L_{A374}$ | $L_{B25}$ |
| III-4138 | $L_{A375}$ | $L_{B25}$ |
| III-4139 | $L_{A376}$ | $L_{B25}$ |
| III-4140 | $L_{A377}$ | $L_{B25}$ |
| III-4141 | $L_{A378}$ | $L_{B25}$ |
| III-4142 | $L_{A379}$ | $L_{B25}$ |
| III-4143 | $L_{A380}$ | $L_{B25}$ |
| III-4144 | $L_{A381}$ | $L_{B25}$ |
| III-4145 | $L_{A382}$ | $L_{B25}$ |
| III-4146 | $L_{A383}$ | $L_{B25}$ |
| III-4147 | $L_{A384}$ | $L_{B25}$ |
| III-4148 | $L_{A385}$ | $L_{B25}$ |
| III-4149 | $L_{A386}$ | $L_{B25}$ |
| III-4150 | $L_{A387}$ | $L_{B25}$ |
| III-4151 | $L_{A388}$ | $L_{B25}$ |
| III-4152 | $L_{A389}$ | $L_{B25}$ |
| III-4153 | $L_{A390}$ | $L_{B25}$ |
| III-4154 | $L_{A391}$ | $L_{B25}$ |
| III-4155 | $L_{A392}$ | $L_{B25}$ |
| III-4156 | $L_{A393}$ | $L_{B25}$ |
| III-4157 | $L_{A394}$ | $L_{B25}$ |
| III-4158 | $L_{A395}$ | $L_{B25}$ |
| III-4159 | $L_{A396}$ | $L_{B25}$ |
| III-4160 | $L_{A397}$ | $L_{B25}$ |
| III-4161 | $L_{A398}$ | $L_{B25}$ |
| III-4162 | $L_{A399}$ | $L_{B25}$ |
| III-4163 | $L_{A400}$ | $L_{B25}$ |
| III-4164 | $L_{A401}$ | $L_{B25}$ |
| III-4165 | $L_{A402}$ | $L_{B25}$ |
| III-4166 | $L_{A403}$ | $L_{B25}$ |
| III-4167 | $L_{A404}$ | $L_{B25}$ |
| III-4168 | $L_{A405}$ | $L_{B25}$ |
| III-4169 | $L_{A406}$ | $L_{B25}$ |
| III-4170 | $L_{A407}$ | $L_{B25}$ |
| III-4171 | $L_{A408}$ | $L_{B25}$ |
| III-4172 | $L_{A409}$ | $L_{B25}$ |
| III-4173 | $L_{A410}$ | $L_{B25}$ |
| III-4174 | $L_{A411}$ | $L_{B25}$ |
| III-4175 | $L_{A412}$ | $L_{B25}$ |
| III-4176 | $L_{A413}$ | $L_{B25}$ |
| III-4177 | $L_{A414}$ | $L_{B25}$ |
| III-4178 | $L_{A415}$ | $L_{B25}$ |
| III-4179 | $L_{A416}$ | $L_{B25}$ |
| III-4180 | $L_{A417}$ | $L_{B25}$ |
| III-4181 | $L_{A418}$ | $L_{B25}$ |
| III-4182 | $L_{A419}$ | $L_{B25}$ |
| III-4183 | $L_{A420}$ | $L_{B25}$ |
| III-4184 | $L_{A421}$ | $L_{B25}$ |
| III-4185 | $L_{A422}$ | $L_{B25}$ |
| III-4186 | $L_{A423}$ | $L_{B25}$ |
| III-4187 | $L_{A424}$ | $L_{B25}$ |
| III-4188 | $L_{A425}$ | $L_{B25}$ |
| III-4189 | $L_{A426}$ | $L_{B25}$ |
| III-4190 | $L_{A427}$ | $L_{B25}$ |
| III-4191 | $L_{A428}$ | $L_{B25}$ |
| III-4192 | $L_{A429}$ | $L_{B25}$ |
| III-4193 | $L_{A430}$ | $L_{B25}$ |
| III-4194 | $L_{A431}$ | $L_{B25}$ |
| III-4195 | $L_{A432}$ | $L_{B25}$ |
| III-4196 | $L_{A433}$ | $L_{B25}$ |
| III-4197 | $L_{A434}$ | $L_{B25}$ |

-continued

| Compound Number | $L_A$ | $L_B$ |
| --- | --- | --- |
| III-4198 | $L_{A435}$ | $L_{B25}$ |
| III-4199 | $L_{A436}$ | $L_{B25}$ |
| III-4200 | $L_{A437}$ | $L_{B25}$ |
| III-4201 | $L_{A438}$ | $L_{B25}$ |
| III-4202 | $L_{A439}$ | $L_{B25}$ |
| III-4203 | $L_{A440}$ | $L_{B25}$ |
| III-4204 | $L_{A441}$ | $L_{B25}$ |
| III-4205 | $L_{A442}$ | $L_{B25}$ |
| III-4206 | $L_{A443}$ | $L_{B25}$ |
| III-4207 | $L_{A444}$ | $L_{B25}$ |
| III-4208 | $L_{A445}$ | $L_{B25}$ |
| III-4209 | $L_{A446}$ | $L_{B25}$ |
| III-4210 | $L_{A447}$ | $L_{B25}$ |
| III-4211 | $L_{A448}$ | $L_{B25}$ |
| III-4212 | $L_{A449}$ | $L_{B25}$ |
| III-4213 | $L_{A450}$ | $L_{B25}$ |
| III-4214 | $L_{A451}$ | $L_{B25}$ |
| III-4215 | $L_{A452}$ | $L_{B25}$ |
| III-4216 | $L_{A453}$ | $L_{B25}$ |
| III-4217 | $L_{A454}$ | $L_{B25}$ |
| III-4218 | $L_{A455}$ | $L_{B25}$ |
| III-4219 | $L_{A456}$ | $L_{B25}$ |
| III-4220 | $L_{A457}$ | $L_{B25}$ |
| III-4221 | $L_{A458}$ | $L_{B25}$ |
| III-4222 | $L_{A459}$ | $L_{B25}$ |
| III-4223 | $L_{A460}$ | $L_{B25}$ |
| III-4224 | $L_{A461}$ | $L_{B25}$ |
| III-4225 | $L_{A462}$ | $L_{B25}$ |
| III-4226 | $L_{A463}$ | $L_{B25}$ |
| III-4227 | $L_{A464}$ | $L_{B25}$ |
| III-4228 | $L_{A465}$ | $L_{B25}$ |
| III-4229 | $L_{A466}$ | $L_{B25}$ |
| III-4230 | $L_{A467}$ | $L_{B25}$ |
| III-4231 | $L_{A468}$ | $L_{B25}$ |
| III-4232 | $L_{A469}$ | $L_{B25}$ |
| III-4233 | $L_{A470}$ | $L_{B25}$ |
| III-4234 | $L_{A471}$ | $L_{B25}$ |
| III-4235 | $L_{A472}$ | $L_{B25}$ |
| III-4236 | $L_{A473}$ | $L_{B25}$ |
| III-4237 | $L_{A474}$ | $L_{B25}$ |
| III-4238 | $L_{A475}$ | $L_{B25}$ |
| III-4239 | $L_{A476}$ | $L_{B25}$ |
| III-4240 | $L_{A477}$ | $L_{B25}$ |
| III-4241 | $L_{A478}$ | $L_{B25}$ |
| III-4242 | $L_{A479}$ | $L_{B25}$ |
| III-4243 | $L_{A480}$ | $L_{B25}$ |
| III-4244 | $L_{A481}$ | $L_{B25}$ |
| III-4245 | $L_{A482}$ | $L_{B25}$ |
| III-4246 | $L_{A483}$ | $L_{B25}$ |
| III-4247 | $L_{A484}$ | $L_{B25}$ |
| III-4248 | $L_{A485}$ | $L_{B25}$ |
| III-4249 | $L_{A486}$ | $L_{B25}$ |
| III-4250 | $L_{A487}$ | $L_{B25}$ |
| III-4251 | $L_{A318}$ | $L_{B26}$ |
| III-4252 | $L_{A319}$ | $L_{B26}$ |
| III-4253 | $L_{A320}$ | $L_{B26}$ |
| III-4254 | $L_{A321}$ | $L_{B26}$ |
| III-4255 | $L_{A322}$ | $L_{B26}$ |
| III-4256 | $L_{A323}$ | $L_{B26}$ |
| III-4257 | $L_{A324}$ | $L_{B26}$ |
| III-4258 | $L_{A325}$ | $L_{B26}$ |
| III-4259 | $L_{A326}$ | $L_{B26}$ |
| III-4260 | $L_{A327}$ | $L_{B26}$ |
| III-4261 | $L_{A328}$ | $L_{B26}$ |
| III-4262 | $L_{A329}$ | $L_{B26}$ |
| III-4263 | $L_{A330}$ | $L_{B26}$ |
| III-4264 | $L_{A331}$ | $L_{B26}$ |
| III-4265 | $L_{A332}$ | $L_{B26}$ |
| III-4266 | $L_{A333}$ | $L_{B26}$ |
| III-4267 | $L_{A334}$ | $L_{B26}$ |
| III-4268 | $L_{A335}$ | $L_{B26}$ |
| III-4269 | $L_{A336}$ | $L_{B26}$ |
| III-4270 | $L_{A337}$ | $L_{B26}$ |
| III-4271 | $L_{A338}$ | $L_{B26}$ |
| III-4272 | $L_{A339}$ | $L_{B26}$ |
| III-4273 | $L_{A340}$ | $L_{B26}$ |
| III-4274 | $L_{A341}$ | $L_{B26}$ |
| III-4275 | $L_{A342}$ | $L_{B26}$ |
| III-4276 | $L_{A343}$ | $L_{B26}$ |
| III-4277 | $L_{A344}$ | $L_{B26}$ |
| III-4278 | $L_{A345}$ | $L_{B26}$ |
| III-4279 | $L_{A346}$ | $L_{B26}$ |
| III-4280 | $L_{A347}$ | $L_{B26}$ |
| III-4281 | $L_{A348}$ | $L_{B26}$ |
| III-4282 | $L_{A349}$ | $L_{B26}$ |
| III-4283 | $L_{A350}$ | $L_{B26}$ |
| III-4284 | $L_{A351}$ | $L_{B26}$ |
| III-4285 | $L_{A352}$ | $L_{B26}$ |
| III-4286 | $L_{A353}$ | $L_{B26}$ |
| III-4287 | $L_{A354}$ | $L_{B26}$ |
| III-4288 | $L_{A355}$ | $L_{B26}$ |
| III-4289 | $L_{A356}$ | $L_{B26}$ |
| III-4290 | $L_{A357}$ | $L_{B26}$ |
| III-4291 | $L_{A358}$ | $L_{B26}$ |
| III-4292 | $L_{A359}$ | $L_{B26}$ |
| III-4293 | $L_{A360}$ | $L_{B26}$ |
| III-4294 | $L_{A361}$ | $L_{B26}$ |
| III-4295 | $L_{A362}$ | $L_{B26}$ |
| III-4296 | $L_{A363}$ | $L_{B26}$ |
| III-4297 | $L_{A364}$ | $L_{B26}$ |
| III-4298 | $L_{A365}$ | $L_{B26}$ |
| III-4299 | $L_{A366}$ | $L_{B26}$ |
| III-4300 | $L_{A367}$ | $L_{B26}$ |
| III-4301 | $L_{A368}$ | $L_{B26}$ |
| III-4302 | $L_{A369}$ | $L_{B26}$ |
| III-4303 | $L_{A370}$ | $L_{B26}$ |
| III-4304 | $L_{A371}$ | $L_{B26}$ |
| III-4305 | $L_{A372}$ | $L_{B26}$ |
| III-4306 | $L_{A373}$ | $L_{B26}$ |
| III-4307 | $L_{A374}$ | $L_{B26}$ |
| III-4308 | $L_{A375}$ | $L_{B26}$ |
| III-4309 | $L_{A376}$ | $L_{B26}$ |
| III-4310 | $L_{A377}$ | $L_{B26}$ |
| III-4311 | $L_{A378}$ | $L_{B26}$ |
| III-4312 | $L_{A379}$ | $L_{B26}$ |
| III-4313 | $L_{A380}$ | $L_{B26}$ |
| III-4314 | $L_{A381}$ | $L_{B26}$ |
| III-4315 | $L_{A382}$ | $L_{B26}$ |
| III-4316 | $L_{A383}$ | $L_{B26}$ |
| III-4317 | $L_{A384}$ | $L_{B26}$ |
| III-4318 | $L_{A385}$ | $L_{B26}$ |
| III-4319 | $L_{A386}$ | $L_{B26}$ |
| III-4320 | $L_{A387}$ | $L_{B26}$ |
| III-4321 | $L_{A388}$ | $L_{B26}$ |
| III-4322 | $L_{A389}$ | $L_{B26}$ |
| III-4323 | $L_{A390}$ | $L_{B26}$ |
| III-4324 | $L_{A391}$ | $L_{B26}$ |
| III-4325 | $L_{A392}$ | $L_{B26}$ |
| III-4326 | $L_{A393}$ | $L_{B26}$ |
| III-4327 | $L_{A394}$ | $L_{B26}$ |
| III-4328 | $L_{A395}$ | $L_{B26}$ |
| III-4329 | $L_{A396}$ | $L_{B26}$ |
| III-4330 | $L_{A397}$ | $L_{B26}$ |
| III-4331 | $L_{A398}$ | $L_{B26}$ |
| III-4332 | $L_{A399}$ | $L_{B26}$ |
| III-4333 | $L_{A400}$ | $L_{B26}$ |
| III-4334 | $L_{A401}$ | $L_{B26}$ |
| III-4335 | $L_{A402}$ | $L_{B26}$ |
| III-4336 | $L_{A403}$ | $L_{B26}$ |
| III-4337 | $L_{A404}$ | $L_{B26}$ |
| III-4338 | $L_{A405}$ | $L_{B26}$ |
| III-4339 | $L_{A406}$ | $L_{B26}$ |
| III-4340 | $L_{A407}$ | $L_{B26}$ |
| III-4341 | $L_{A408}$ | $L_{B26}$ |
| III-4342 | $L_{A409}$ | $L_{B26}$ |
| III-4343 | $L_{A410}$ | $L_{B26}$ |
| III-4344 | $L_{A411}$ | $L_{B26}$ |
| III-4345 | $L_{A412}$ | $L_{B26}$ |
| III-4346 | $L_{A413}$ | $L_{B26}$ |
| III-4347 | $L_{A414}$ | $L_{B26}$ |
| III-4348 | $L_{A415}$ | $L_{B26}$ |
| III-4349 | $L_{A416}$ | $L_{B26}$ |

-continued

| Compound Number | $L_A$ | $L_B$ |
|---|---|---|
| III-4350 | $L_{A417}$ | $L_{B26}$ |
| III-4351 | $L_{A418}$ | $L_{B26}$ |
| III-4352 | $L_{A419}$ | $L_{B26}$ |
| III-4353 | $L_{A420}$ | $L_{B26}$ |
| III-4354 | $L_{A421}$ | $L_{B26}$ |
| III-4355 | $L_{A422}$ | $L_{B26}$ |
| III-4356 | $L_{A423}$ | $L_{B26}$ |
| III-4357 | $L_{A424}$ | $L_{B26}$ |
| III-4358 | $L_{A425}$ | $L_{B26}$ |
| III-4359 | $L_{A426}$ | $L_{B26}$ |
| III-4360 | $L_{A427}$ | $L_{B26}$ |
| III-4361 | $L_{A428}$ | $L_{B26}$ |
| III-4362 | $L_{A429}$ | $L_{B26}$ |
| III-4363 | $L_{A430}$ | $L_{B26}$ |
| III-4364 | $L_{A431}$ | $L_{B26}$ |
| III-4365 | $L_{A432}$ | $L_{B26}$ |
| III-4366 | $L_{A433}$ | $L_{B26}$ |
| III-4367 | $L_{A434}$ | $L_{B26}$ |
| III-4368 | $L_{A435}$ | $L_{B26}$ |
| III-4369 | $L_{A436}$ | $L_{B26}$ |
| III-4370 | $L_{A437}$ | $L_{B26}$ |
| III-4371 | $L_{A438}$ | $L_{B26}$ |
| III-4372 | $L_{A439}$ | $L_{B26}$ |
| III-4373 | $L_{A440}$ | $L_{B26}$ |
| III-4374 | $L_{A441}$ | $L_{B26}$ |
| III-4375 | $L_{A442}$ | $L_{B26}$ |
| III-4376 | $L_{A443}$ | $L_{B26}$ |
| III-4377 | $L_{A444}$ | $L_{B26}$ |
| III-4378 | $L_{A445}$ | $L_{B26}$ |
| III-4379 | $L_{A446}$ | $L_{B26}$ |
| III-4380 | $L_{A447}$ | $L_{B26}$ |
| III-4381 | $L_{A448}$ | $L_{B26}$ |
| III-4382 | $L_{A449}$ | $L_{B26}$ |
| III-4383 | $L_{A450}$ | $L_{B26}$ |
| III-4384 | $L_{A451}$ | $L_{B26}$ |
| III-4385 | $L_{A452}$ | $L_{B26}$ |
| III-4386 | $L_{A453}$ | $L_{B26}$ |
| III-4387 | $L_{A454}$ | $L_{B26}$ |
| III-4388 | $L_{A455}$ | $L_{B26}$ |
| III-4389 | $L_{A456}$ | $L_{B26}$ |
| III-4390 | $L_{A457}$ | $L_{B26}$ |
| III-4391 | $L_{A458}$ | $L_{B26}$ |
| III-4392 | $L_{A459}$ | $L_{B26}$ |
| III-4393 | $L_{A460}$ | $L_{B26}$ |
| III-4394 | $L_{A461}$ | $L_{B26}$ |
| III-4395 | $L_{A462}$ | $L_{B26}$ |
| III-4396 | $L_{A463}$ | $L_{B26}$ |
| III-4397 | $L_{A464}$ | $L_{B26}$ |
| III-4398 | $L_{A465}$ | $L_{B26}$ |
| III-4399 | $L_{A466}$ | $L_{B26}$ |
| III-4400 | $L_{A467}$ | $L_{B26}$ |
| III-4401 | $L_{A468}$ | $L_{B26}$ |
| III-4402 | $L_{A469}$ | $L_{B26}$ |
| III-4403 | $L_{A470}$ | $L_{B26}$ |
| III-4404 | $L_{A471}$ | $L_{B26}$ |
| III-4405 | $L_{A472}$ | $L_{B26}$ |
| III-4406 | $L_{A473}$ | $L_{B26}$ |
| III-4407 | $L_{A474}$ | $L_{B26}$ |
| III-4408 | $L_{A475}$ | $L_{B26}$ |
| III-4409 | $L_{A476}$ | $L_{B26}$ |
| III-4410 | $L_{A477}$ | $L_{B26}$ |
| III-4411 | $L_{A478}$ | $L_{B26}$ |
| III-4412 | $L_{A479}$ | $L_{B26}$ |
| III-4413 | $L_{A480}$ | $L_{B26}$ |
| III-4414 | $L_{A481}$ | $L_{B26}$ |
| III-4415 | $L_{A482}$ | $L_{B26}$ |
| III-4416 | $L_{A483}$ | $L_{B26}$ |
| III-4417 | $L_{A484}$ | $L_{B26}$ |
| III-4418 | $L_{A485}$ | $L_{B26}$ |
| III-4419 | $L_{A486}$ | $L_{B26}$ |
| III-4420 | $L_{A487}$ | $L_{B26}$ |
| III-4421 | $L_{A318}$ | $L_{B27}$ |
| III-4422 | $L_{A319}$ | $L_{B27}$ |
| III-4423 | $L_{A320}$ | $L_{B27}$ |
| III-4424 | $L_{A321}$ | $L_{B27}$ |
| III-4425 | $L_{A322}$ | $L_{B27}$ |
| III-4426 | $L_{A323}$ | $L_{B27}$ |
| III-4427 | $L_{A324}$ | $L_{B27}$ |
| III-4428 | $L_{A325}$ | $L_{B27}$ |
| III-4429 | $L_{A326}$ | $L_{B27}$ |
| III-4430 | $L_{A327}$ | $L_{B27}$ |
| III-4431 | $L_{A328}$ | $L_{B27}$ |
| III-4432 | $L_{A329}$ | $L_{B27}$ |
| III-4433 | $L_{A330}$ | $L_{B27}$ |
| III-4434 | $L_{A331}$ | $L_{B27}$ |
| III-4435 | $L_{A332}$ | $L_{B27}$ |
| III-4436 | $L_{A333}$ | $L_{B27}$ |
| III-4437 | $L_{A334}$ | $L_{B27}$ |
| III-4438 | $L_{A335}$ | $L_{B27}$ |
| III-4439 | $L_{A336}$ | $L_{B27}$ |
| III-4440 | $L_{A337}$ | $L_{B27}$ |
| III-4441 | $L_{A338}$ | $L_{B27}$ |
| III-4442 | $L_{A339}$ | $L_{B27}$ |
| III-4443 | $L_{A340}$ | $L_{B27}$ |
| III-4444 | $L_{A341}$ | $L_{B27}$ |
| III-4445 | $L_{A342}$ | $L_{B27}$ |
| III-4446 | $L_{A343}$ | $L_{B27}$ |
| III-4447 | $L_{A344}$ | $L_{B27}$ |
| III-4448 | $L_{A345}$ | $L_{B27}$ |
| III-4449 | $L_{A346}$ | $L_{B27}$ |
| III-4450 | $L_{A347}$ | $L_{B27}$ |
| III-4451 | $L_{A348}$ | $L_{B27}$ |
| III-4452 | $L_{A349}$ | $L_{B27}$ |
| III-4453 | $L_{A350}$ | $L_{B27}$ |
| III-4454 | $L_{A351}$ | $L_{B27}$ |
| III-4455 | $L_{A352}$ | $L_{B27}$ |
| III-4456 | $L_{A353}$ | $L_{B27}$ |
| III-4457 | $L_{A354}$ | $L_{B27}$ |
| III-4458 | $L_{A355}$ | $L_{B27}$ |
| III-4459 | $L_{A356}$ | $L_{B27}$ |
| III-4460 | $L_{A357}$ | $L_{B27}$ |
| III-4461 | $L_{A358}$ | $L_{B27}$ |
| III-4462 | $L_{A359}$ | $L_{B27}$ |
| III-4463 | $L_{A360}$ | $L_{B27}$ |
| III-4464 | $L_{A361}$ | $L_{B27}$ |
| III-4465 | $L_{A362}$ | $L_{B27}$ |
| III-4466 | $L_{A363}$ | $L_{B27}$ |
| III-4467 | $L_{A364}$ | $L_{B27}$ |
| III-4468 | $L_{A365}$ | $L_{B27}$ |
| III-4469 | $L_{A366}$ | $L_{B27}$ |
| III-4470 | $L_{A367}$ | $L_{B27}$ |
| III-4471 | $L_{A368}$ | $L_{B27}$ |
| III-4472 | $L_{A369}$ | $L_{B27}$ |
| III-4473 | $L_{A370}$ | $L_{B27}$ |
| III-4474 | $L_{A371}$ | $L_{B27}$ |
| III-4475 | $L_{A372}$ | $L_{B27}$ |
| III-4476 | $L_{A373}$ | $L_{B27}$ |
| III-4477 | $L_{A374}$ | $L_{B27}$ |
| III-4478 | $L_{A375}$ | $L_{B27}$ |
| III-4479 | $L_{A376}$ | $L_{B27}$ |
| III-4480 | $L_{A377}$ | $L_{B27}$ |
| III-4481 | $L_{A378}$ | $L_{B27}$ |
| III-4482 | $L_{A379}$ | $L_{B27}$ |
| III-4483 | $L_{A380}$ | $L_{B27}$ |
| III-4484 | $L_{A381}$ | $L_{B27}$ |
| III-4485 | $L_{A382}$ | $L_{B27}$ |
| III-4486 | $L_{A383}$ | $L_{B27}$ |
| III-4487 | $L_{A384}$ | $L_{B27}$ |
| III-4488 | $L_{A385}$ | $L_{B27}$ |
| III-4489 | $L_{A386}$ | $L_{B27}$ |
| III-4490 | $L_{A387}$ | $L_{B27}$ |
| III-4491 | $L_{A388}$ | $L_{B27}$ |
| III-4492 | $L_{A389}$ | $L_{B27}$ |
| III-4493 | $L_{A390}$ | $L_{B27}$ |
| III-4494 | $L_{A391}$ | $L_{B27}$ |
| III-4495 | $L_{A392}$ | $L_{B27}$ |
| III-4496 | $L_{A393}$ | $L_{B27}$ |
| III-4497 | $L_{A394}$ | $L_{B27}$ |
| III-4498 | $L_{A395}$ | $L_{B27}$ |
| III-4499 | $L_{A396}$ | $L_{B27}$ |
| III-4500 | $L_{A397}$ | $L_{B27}$ |
| III-4501 | $L_{A398}$ | $L_{B27}$ |

| Compound Number | $L_A$ | $L_B$ |
|---|---|---|
| III-4502 | $L_{A399}$ | $L_{B27}$ |
| III-4503 | $L_{A400}$ | $L_{B27}$ |
| III-4504 | $L_{A401}$ | $L_{B27}$ |
| III-4505 | $L_{A402}$ | $L_{B27}$ |
| III-4506 | $L_{A403}$ | $L_{B27}$ |
| III-4507 | $L_{A404}$ | $L_{B27}$ |
| III-4508 | $L_{A405}$ | $L_{B27}$ |
| III-4509 | $L_{A406}$ | $L_{B27}$ |
| III-4510 | $L_{A407}$ | $L_{B27}$ |
| III-4511 | $L_{A408}$ | $L_{B27}$ |
| III-4512 | $L_{A409}$ | $L_{B27}$ |
| III-4513 | $L_{A410}$ | $L_{B27}$ |
| III-4514 | $L_{A411}$ | $L_{B27}$ |
| III-4515 | $L_{A412}$ | $L_{B27}$ |
| III-4516 | $L_{A413}$ | $L_{B27}$ |
| III-4517 | $L_{A414}$ | $L_{B27}$ |
| III-4518 | $L_{A415}$ | $L_{B27}$ |
| III-4519 | $L_{A416}$ | $L_{B27}$ |
| III-4520 | $L_{A417}$ | $L_{B27}$ |
| III-4521 | $L_{A418}$ | $L_{B27}$ |
| III-4522 | $L_{A419}$ | $L_{B27}$ |
| III-4523 | $L_{A420}$ | $L_{B27}$ |
| III-4524 | $L_{A421}$ | $L_{B27}$ |
| III-4525 | $L_{A422}$ | $L_{B27}$ |
| III-4526 | $L_{A423}$ | $L_{B27}$ |
| III-4527 | $L_{A424}$ | $L_{B27}$ |
| III-4528 | $L_{A425}$ | $L_{B27}$ |
| III-4529 | $L_{A426}$ | $L_{B27}$ |
| III-4530 | $L_{A427}$ | $L_{B27}$ |
| III-4531 | $L_{A428}$ | $L_{B27}$ |
| III-4532 | $L_{A429}$ | $L_{B27}$ |
| III-4533 | $L_{A430}$ | $L_{B27}$ |
| III-4534 | $L_{A431}$ | $L_{B27}$ |
| III-4535 | $L_{A432}$ | $L_{B27}$ |
| III-4536 | $L_{A433}$ | $L_{B27}$ |
| III-4537 | $L_{A434}$ | $L_{B27}$ |
| III-4538 | $L_{A435}$ | $L_{B27}$ |
| III-4539 | $L_{A436}$ | $L_{B27}$ |
| III-4540 | $L_{A437}$ | $L_{B27}$ |
| III-4541 | $L_{A438}$ | $L_{B27}$ |
| III-4542 | $L_{A439}$ | $L_{B27}$ |
| III-4543 | $L_{A440}$ | $L_{B27}$ |
| III-4544 | $L_{A441}$ | $L_{B27}$ |
| III-4545 | $L_{A442}$ | $L_{B27}$ |
| III-4546 | $L_{A443}$ | $L_{B27}$ |
| III-4547 | $L_{A444}$ | $L_{B27}$ |
| III-4548 | $L_{A445}$ | $L_{B27}$ |
| III-4549 | $L_{A446}$ | $L_{B27}$ |
| III-4550 | $L_{A447}$ | $L_{B27}$ |
| III-4551 | $L_{A448}$ | $L_{B27}$ |
| III-4552 | $L_{A449}$ | $L_{B27}$ |
| III-4553 | $L_{A450}$ | $L_{B27}$ |
| III-4554 | $L_{A451}$ | $L_{B27}$ |
| III-4555 | $L_{A452}$ | $L_{B27}$ |
| III-4556 | $L_{A453}$ | $L_{B27}$ |
| III-4557 | $L_{A454}$ | $L_{B27}$ |
| III-4558 | $L_{A455}$ | $L_{B27}$ |
| III-4559 | $L_{A456}$ | $L_{B27}$ |
| III-4560 | $L_{A457}$ | $L_{B27}$ |
| III-4561 | $L_{A458}$ | $L_{B27}$ |
| III-4562 | $L_{A459}$ | $L_{B27}$ |
| III-4563 | $L_{A460}$ | $L_{B27}$ |
| III-4564 | $L_{A461}$ | $L_{B27}$ |
| III-4565 | $L_{A462}$ | $L_{B27}$ |
| III-4566 | $L_{A463}$ | $L_{B27}$ |
| III-4567 | $L_{A464}$ | $L_{B27}$ |
| III-4568 | $L_{A465}$ | $L_{B27}$ |
| III-4569 | $L_{A466}$ | $L_{B27}$ |
| III-4570 | $L_{A467}$ | $L_{B27}$ |
| III-4571 | $L_{A468}$ | $L_{B27}$ |
| III-4572 | $L_{A469}$ | $L_{B27}$ |
| III-4573 | $L_{A470}$ | $L_{B27}$ |
| III-4574 | $L_{A471}$ | $L_{B27}$ |
| III-4575 | $L_{A472}$ | $L_{B27}$ |
| III-4576 | $L_{A473}$ | $L_{B27}$ |
| III-4577 | $L_{A474}$ | $L_{B27}$ |
| III-4578 | $L_{A475}$ | $L_{B27}$ |
| III-4579 | $L_{A476}$ | $L_{B27}$ |
| III-4580 | $L_{A477}$ | $L_{B27}$ |
| III-4581 | $L_{A478}$ | $L_{B27}$ |
| III-4582 | $L_{A479}$ | $L_{B27}$ |
| III-4583 | $L_{A480}$ | $L_{B27}$ |
| III-4584 | $L_{A481}$ | $L_{B27}$ |
| III-4585 | $L_{A482}$ | $L_{B27}$ |
| III-4586 | $L_{A483}$ | $L_{B27}$ |
| III-4587 | $L_{A484}$ | $L_{B27}$ |
| III-4588 | $L_{A485}$ | $L_{B27}$ |
| III-4589 | $L_{A486}$ | $L_{B27}$ |
| III-4590 | $L_{A487}$ | $L_{B27}$ |
| III-4591 | $L_{A318}$ | $L_{B28}$ |
| III-4592 | $L_{A319}$ | $L_{B28}$ |
| III-4593 | $L_{A320}$ | $L_{B28}$ |
| III-4594 | $L_{A321}$ | $L_{B28}$ |
| III-4595 | $L_{A322}$ | $L_{B28}$ |
| III-4596 | $L_{A323}$ | $L_{B28}$ |
| III-4597 | $L_{A324}$ | $L_{B28}$ |
| III-4598 | $L_{A325}$ | $L_{B28}$ |
| III-4599 | $L_{A326}$ | $L_{B28}$ |
| III-4600 | $L_{A327}$ | $L_{B28}$ |
| III-4601 | $L_{A328}$ | $L_{B28}$ |
| III-4602 | $L_{A329}$ | $L_{B28}$ |
| III-4603 | $L_{A330}$ | $L_{B28}$ |
| III-4604 | $L_{A331}$ | $L_{B28}$ |
| III-4605 | $L_{A332}$ | $L_{B28}$ |
| III-4606 | $L_{A333}$ | $L_{B28}$ |
| III-4607 | $L_{A334}$ | $L_{B28}$ |
| III-4608 | $L_{A335}$ | $L_{B28}$ |
| III-4609 | $L_{A336}$ | $L_{B28}$ |
| III-4610 | $L_{A337}$ | $L_{B28}$ |
| III-4611 | $L_{A338}$ | $L_{B28}$ |
| III-4612 | $L_{A339}$ | $L_{B28}$ |
| III-4613 | $L_{A340}$ | $L_{B28}$ |
| III-4614 | $L_{A341}$ | $L_{B28}$ |
| III-4615 | $L_{A342}$ | $L_{B28}$ |
| III-4616 | $L_{A343}$ | $L_{B28}$ |
| III-4617 | $L_{A344}$ | $L_{B28}$ |
| III-4618 | $L_{A345}$ | $L_{B28}$ |
| III-4619 | $L_{A346}$ | $L_{B28}$ |
| III-4620 | $L_{A347}$ | $L_{B28}$ |
| III-4621 | $L_{A348}$ | $L_{B28}$ |
| III-4622 | $L_{A349}$ | $L_{B28}$ |
| III-4623 | $L_{A350}$ | $L_{B28}$ |
| III-4624 | $L_{A351}$ | $L_{B28}$ |
| III-4625 | $L_{A352}$ | $L_{B28}$ |
| III-4626 | $L_{A353}$ | $L_{B28}$ |
| III-4627 | $L_{A354}$ | $L_{B28}$ |
| III-4628 | $L_{A355}$ | $L_{B28}$ |
| III-4629 | $L_{A356}$ | $L_{B28}$ |
| III-4630 | $L_{A357}$ | $L_{B28}$ |
| III-4631 | $L_{A358}$ | $L_{B28}$ |
| III-4632 | $L_{A359}$ | $L_{B28}$ |
| III-4633 | $L_{A360}$ | $L_{B28}$ |
| III-4634 | $L_{A361}$ | $L_{B28}$ |
| III-4635 | $L_{A362}$ | $L_{B28}$ |
| III-4636 | $L_{A363}$ | $L_{B28}$ |
| III-4637 | $L_{A364}$ | $L_{B28}$ |
| III-4638 | $L_{A365}$ | $L_{B28}$ |
| III-4639 | $L_{A366}$ | $L_{B28}$ |
| III-4640 | $L_{A367}$ | $L_{B28}$ |
| III-4641 | $L_{A368}$ | $L_{B28}$ |
| III-4642 | $L_{A369}$ | $L_{B28}$ |
| III-4643 | $L_{A370}$ | $L_{B28}$ |
| III-4644 | $L_{A371}$ | $L_{B28}$ |
| III-4645 | $L_{A372}$ | $L_{B28}$ |
| III-4646 | $L_{A373}$ | $L_{B28}$ |
| III-4647 | $L_{A374}$ | $L_{B28}$ |
| III-4648 | $L_{A375}$ | $L_{B28}$ |
| III-4649 | $L_{A376}$ | $L_{B28}$ |
| III-4650 | $L_{A377}$ | $L_{B28}$ |
| III-4651 | $L_{A378}$ | $L_{B28}$ |
| III-4652 | $L_{A379}$ | $L_{B28}$ |
| III-4653 | $L_{A380}$ | $L_{B28}$ |

| Compound Number | $L_A$ | $L_B$ |
|---|---|---|
| III-4654 | $L_{A381}$ | $L_{B28}$ |
| III-4655 | $L_{A382}$ | $L_{B28}$ |
| III-4656 | $L_{A383}$ | $L_{B28}$ |
| III-4657 | $L_{A384}$ | $L_{B28}$ |
| III-4658 | $L_{A385}$ | $L_{B28}$ |
| III-4659 | $L_{A386}$ | $L_{B28}$ |
| III-4660 | $L_{A387}$ | $L_{B28}$ |
| III-4661 | $L_{A388}$ | $L_{B28}$ |
| III-4662 | $L_{A389}$ | $L_{B28}$ |
| III-4663 | $L_{A390}$ | $L_{B28}$ |
| III-4664 | $L_{A391}$ | $L_{B28}$ |
| III-4665 | $L_{A392}$ | $L_{B28}$ |
| III-4666 | $L_{A393}$ | $L_{B28}$ |
| III-4667 | $L_{A394}$ | $L_{B28}$ |
| III-4668 | $L_{A395}$ | $L_{B28}$ |
| III-4669 | $L_{A396}$ | $L_{B28}$ |
| III-4670 | $L_{A397}$ | $L_{B28}$ |
| III-4671 | $L_{A398}$ | $L_{B28}$ |
| III-4672 | $L_{A399}$ | $L_{B28}$ |
| III-4673 | $L_{A400}$ | $L_{B28}$ |
| III-4674 | $L_{A401}$ | $L_{B28}$ |
| III-4675 | $L_{A402}$ | $L_{B28}$ |
| III-4676 | $L_{A403}$ | $L_{B28}$ |
| III-4677 | $L_{A404}$ | $L_{B28}$ |
| III-4678 | $L_{A405}$ | $L_{B28}$ |
| III-4679 | $L_{A406}$ | $L_{B28}$ |
| III-4680 | $L_{A407}$ | $L_{B28}$ |
| III-4681 | $L_{A408}$ | $L_{B28}$ |
| III-4682 | $L_{A409}$ | $L_{B28}$ |
| III-4683 | $L_{A410}$ | $L_{B28}$ |
| III-4684 | $L_{A411}$ | $L_{B28}$ |
| III-4685 | $L_{A412}$ | $L_{B28}$ |
| III-4686 | $L_{A413}$ | $L_{B28}$ |
| III-4687 | $L_{A414}$ | $L_{B28}$ |
| III-4688 | $L_{A415}$ | $L_{B28}$ |
| III-4689 | $L_{A416}$ | $L_{B28}$ |
| III-4690 | $L_{A417}$ | $L_{B28}$ |
| III-4691 | $L_{A418}$ | $L_{B28}$ |
| III-4692 | $L_{A419}$ | $L_{B28}$ |
| III-4693 | $L_{A420}$ | $L_{B28}$ |
| III-4694 | $L_{A421}$ | $L_{B28}$ |
| III-4695 | $L_{A422}$ | $L_{B28}$ |
| III-4696 | $L_{A423}$ | $L_{B28}$ |
| III-4697 | $L_{A424}$ | $L_{B28}$ |
| III-4698 | $L_{A425}$ | $L_{B28}$ |
| III-4699 | $L_{A426}$ | $L_{B28}$ |
| III-4700 | $L_{A427}$ | $L_{B28}$ |
| III-4701 | $L_{A428}$ | $L_{B28}$ |
| III-4702 | $L_{A429}$ | $L_{B28}$ |
| III-4703 | $L_{A430}$ | $L_{B28}$ |
| III-4704 | $L_{A431}$ | $L_{B28}$ |
| III-4705 | $L_{A432}$ | $L_{B28}$ |
| III-4706 | $L_{A433}$ | $L_{B28}$ |
| III-4707 | $L_{A434}$ | $L_{B28}$ |
| III-4708 | $L_{A435}$ | $L_{B28}$ |
| III-4709 | $L_{A436}$ | $L_{B28}$ |
| III-4710 | $L_{A437}$ | $L_{B28}$ |
| III-4711 | $L_{A438}$ | $L_{B28}$ |
| III-4712 | $L_{A439}$ | $L_{B28}$ |
| III-4713 | $L_{A440}$ | $L_{B28}$ |
| III-4714 | $L_{A441}$ | $L_{B28}$ |
| III-4715 | $L_{A442}$ | $L_{B28}$ |
| III-4716 | $L_{A443}$ | $L_{B28}$ |
| III-4717 | $L_{A444}$ | $L_{B28}$ |
| III-4718 | $L_{A445}$ | $L_{B28}$ |
| III-4719 | $L_{A446}$ | $L_{B28}$ |
| III-4720 | $L_{A447}$ | $L_{B28}$ |
| III-4721 | $L_{A448}$ | $L_{B28}$ |
| III-4722 | $L_{A449}$ | $L_{B28}$ |
| III-4723 | $L_{A450}$ | $L_{B28}$ |
| III-4724 | $L_{A451}$ | $L_{B28}$ |
| III-4725 | $L_{A452}$ | $L_{B28}$ |
| III-4726 | $L_{A453}$ | $L_{B28}$ |
| III-4727 | $L_{A454}$ | $L_{B28}$ |
| III-4728 | $L_{A455}$ | $L_{B28}$ |
| III-4729 | $L_{A456}$ | $L_{B28}$ |
| III-4730 | $L_{A457}$ | $L_{B28}$ |
| III-4731 | $L_{A458}$ | $L_{B28}$ |
| III-4732 | $L_{A459}$ | $L_{B28}$ |
| III-4733 | $L_{A460}$ | $L_{B28}$ |
| III-4734 | $L_{A461}$ | $L_{B28}$ |
| III-4735 | $L_{A462}$ | $L_{B28}$ |
| III-4736 | $L_{A463}$ | $L_{B28}$ |
| III-4737 | $L_{A464}$ | $L_{B28}$ |
| III-4738 | $L_{A465}$ | $L_{B28}$ |
| III-4739 | $L_{A466}$ | $L_{B28}$ |
| III-4740 | $L_{A467}$ | $L_{B28}$ |
| III-4741 | $L_{A468}$ | $L_{B28}$ |
| III-4742 | $L_{A469}$ | $L_{B28}$ |
| III-4743 | $L_{A470}$ | $L_{B28}$ |
| III-4744 | $L_{A471}$ | $L_{B28}$ |
| III-4745 | $L_{A472}$ | $L_{B28}$ |
| III-4746 | $L_{A473}$ | $L_{B28}$ |
| III-4747 | $L_{A474}$ | $L_{B28}$ |
| III-4748 | $L_{A475}$ | $L_{B28}$ |
| III-4749 | $L_{A476}$ | $L_{B28}$ |
| III-4750 | $L_{A477}$ | $L_{B28}$ |
| III-4751 | $L_{A478}$ | $L_{B28}$ |
| III-4752 | $L_{A479}$ | $L_{B28}$ |
| III-4753 | $L_{A480}$ | $L_{B28}$ |
| III-4754 | $L_{A481}$ | $L_{B28}$ |
| III-4755 | $L_{A482}$ | $L_{B28}$ |
| III-4756 | $L_{A483}$ | $L_{B28}$ |
| III-4757 | $L_{A484}$ | $L_{B28}$ |
| III-4758 | $L_{A485}$ | $L_{B28}$ |
| III-4759 | $L_{A486}$ | $L_{B28}$ |
| III-4760 | $L_{A487}$ | $L_{B28}$ |
| III-4761 | $L_{A318}$ | $L_{B29}$ |
| III-4762 | $L_{A319}$ | $L_{B29}$ |
| III-4763 | $L_{A320}$ | $L_{B29}$ |
| III-4764 | $L_{A321}$ | $L_{B29}$ |
| III-4765 | $L_{A322}$ | $L_{B29}$ |
| III-4766 | $L_{A323}$ | $L_{B29}$ |
| III-4767 | $L_{A324}$ | $L_{B29}$ |
| III-4768 | $L_{A325}$ | $L_{B29}$ |
| III-4769 | $L_{A326}$ | $L_{B29}$ |
| III-4770 | $L_{A327}$ | $L_{B29}$ |
| III-4771 | $L_{A328}$ | $L_{B29}$ |
| III-4772 | $L_{A329}$ | $L_{B29}$ |
| III-4773 | $L_{A330}$ | $L_{B29}$ |
| III-4774 | $L_{A331}$ | $L_{B29}$ |
| III-4775 | $L_{A332}$ | $L_{B29}$ |
| III-4776 | $L_{A333}$ | $L_{B29}$ |
| III-4777 | $L_{A334}$ | $L_{B29}$ |
| III-4778 | $L_{A335}$ | $L_{B29}$ |
| III-4779 | $L_{A336}$ | $L_{B29}$ |
| III-4780 | $L_{A337}$ | $L_{B29}$ |
| III-4781 | $L_{A338}$ | $L_{B29}$ |
| III-4782 | $L_{A339}$ | $L_{B29}$ |
| III-4783 | $L_{A340}$ | $L_{B29}$ |
| III-4784 | $L_{A341}$ | $L_{B29}$ |
| III-4785 | $L_{A342}$ | $L_{B29}$ |
| III-4786 | $L_{A343}$ | $L_{B29}$ |
| III-4787 | $L_{A344}$ | $L_{B29}$ |
| III-4788 | $L_{A345}$ | $L_{B29}$ |
| III-4789 | $L_{A346}$ | $L_{B29}$ |
| III-4790 | $L_{A347}$ | $L_{B29}$ |
| III-4791 | $L_{A348}$ | $L_{B29}$ |
| III-4792 | $L_{A349}$ | $L_{B29}$ |
| III-4793 | $L_{A350}$ | $L_{B29}$ |
| III-4794 | $L_{A351}$ | $L_{B29}$ |
| III-4795 | $L_{A352}$ | $L_{B29}$ |
| III-4796 | $L_{A353}$ | $L_{B29}$ |
| III-4797 | $L_{A354}$ | $L_{B29}$ |
| III-4798 | $L_{A355}$ | $L_{B29}$ |
| III-4799 | $L_{A356}$ | $L_{B29}$ |
| III-4800 | $L_{A357}$ | $L_{B29}$ |
| III-4801 | $L_{A358}$ | $L_{B29}$ |
| III-4802 | $L_{A359}$ | $L_{B29}$ |
| III-4803 | $L_{A360}$ | $L_{B29}$ |
| III-4804 | $L_{A361}$ | $L_{B29}$ |
| III-4805 | $L_{A362}$ | $L_{B29}$ |

-continued

| Compound Number | $L_A$ | $L_B$ |
|---|---|---|
| III-4806 | $L_{A363}$ | $L_{B29}$ |
| III-4807 | $L_{A364}$ | $L_{B29}$ |
| III-4808 | $L_{A365}$ | $L_{B29}$ |
| III-4809 | $L_{A366}$ | $L_{B29}$ |
| III-4810 | $L_{A367}$ | $L_{B29}$ |
| III-4811 | $L_{A368}$ | $L_{B29}$ |
| III-4812 | $L_{A369}$ | $L_{B29}$ |
| III-4813 | $L_{A370}$ | $L_{B29}$ |
| III-4814 | $L_{A371}$ | $L_{B29}$ |
| III-4815 | $L_{A372}$ | $L_{B29}$ |
| III-4816 | $L_{A373}$ | $L_{B29}$ |
| III-4817 | $L_{A374}$ | $L_{B29}$ |
| III-4818 | $L_{A375}$ | $L_{B29}$ |
| III-4819 | $L_{A376}$ | $L_{B29}$ |
| III-4820 | $L_{A377}$ | $L_{B29}$ |
| III-4821 | $L_{A378}$ | $L_{B29}$ |
| III-4822 | $L_{A379}$ | $L_{B29}$ |
| III-4823 | $L_{A380}$ | $L_{B29}$ |
| III-4824 | $L_{A381}$ | $L_{B29}$ |
| III-4825 | $L_{A382}$ | $L_{B29}$ |
| III-4826 | $L_{A383}$ | $L_{B29}$ |
| III-4827 | $L_{A384}$ | $L_{B29}$ |
| III-4828 | $L_{A385}$ | $L_{B29}$ |
| III-4829 | $L_{A386}$ | $L_{B29}$ |
| III-4830 | $L_{A387}$ | $L_{B29}$ |
| III-4831 | $L_{A388}$ | $L_{B29}$ |
| III-4832 | $L_{A389}$ | $L_{B29}$ |
| III-4833 | $L_{A390}$ | $L_{B29}$ |
| III-4834 | $L_{A391}$ | $L_{B29}$ |
| III-4835 | $L_{A392}$ | $L_{B29}$ |
| III-4836 | $L_{A393}$ | $L_{B29}$ |
| III-4837 | $L_{A394}$ | $L_{B29}$ |
| III-4838 | $L_{A395}$ | $L_{B29}$ |
| III-4839 | $L_{A396}$ | $L_{B29}$ |
| III-4840 | $L_{A397}$ | $L_{B29}$ |
| III-4841 | $L_{A398}$ | $L_{B29}$ |
| III-4842 | $L_{A399}$ | $L_{B29}$ |
| III-4843 | $L_{A400}$ | $L_{B29}$ |
| III-4844 | $L_{A401}$ | $L_{B29}$ |
| III-4845 | $L_{A402}$ | $L_{B29}$ |
| III-4846 | $L_{A403}$ | $L_{B29}$ |
| III-4847 | $L_{A404}$ | $L_{B29}$ |
| III-4848 | $L_{A405}$ | $L_{B29}$ |
| III-4849 | $L_{A406}$ | $L_{B29}$ |
| III-4850 | $L_{A407}$ | $L_{B29}$ |
| III-4851 | $L_{A408}$ | $L_{B29}$ |
| III-4852 | $L_{A409}$ | $L_{B29}$ |
| III-4853 | $L_{A410}$ | $L_{B29}$ |
| III-4854 | $L_{A411}$ | $L_{B29}$ |
| III-4855 | $L_{A412}$ | $L_{B29}$ |
| III-4856 | $L_{A413}$ | $L_{B29}$ |
| III-4857 | $L_{A414}$ | $L_{B29}$ |
| III-4858 | $L_{A415}$ | $L_{B29}$ |
| III-4859 | $L_{A416}$ | $L_{B29}$ |
| III-4860 | $L_{A417}$ | $L_{B29}$ |
| III-4861 | $L_{A418}$ | $L_{B29}$ |
| III-4862 | $L_{A419}$ | $L_{B29}$ |
| III-4863 | $L_{A420}$ | $L_{B29}$ |
| III-4864 | $L_{A421}$ | $L_{B29}$ |
| III-4865 | $L_{A422}$ | $L_{B29}$ |
| III-4866 | $L_{A423}$ | $L_{B29}$ |
| III-4867 | $L_{A424}$ | $L_{B29}$ |
| III-4868 | $L_{A425}$ | $L_{B29}$ |
| III-4869 | $L_{A426}$ | $L_{B29}$ |
| III-4870 | $L_{A427}$ | $L_{B29}$ |
| III-4871 | $L_{A428}$ | $L_{B29}$ |
| III-4872 | $L_{A429}$ | $L_{B29}$ |
| III-4873 | $L_{A430}$ | $L_{B29}$ |
| III-4874 | $L_{A431}$ | $L_{B29}$ |
| III-4875 | $L_{A432}$ | $L_{B29}$ |
| III-4876 | $L_{A433}$ | $L_{B29}$ |
| III-4877 | $L_{A434}$ | $L_{B29}$ |
| III-4878 | $L_{A435}$ | $L_{B29}$ |
| III-4879 | $L_{A436}$ | $L_{B29}$ |
| III-4880 | $L_{A437}$ | $L_{B29}$ |
| III-4881 | $L_{A438}$ | $L_{B29}$ |
| III-4882 | $L_{A439}$ | $L_{B29}$ |
| III-4883 | $L_{A440}$ | $L_{B29}$ |
| III-4884 | $L_{A441}$ | $L_{B29}$ |
| III-4885 | $L_{A442}$ | $L_{B29}$ |
| III-4886 | $L_{A443}$ | $L_{B29}$ |
| III-4887 | $L_{A444}$ | $L_{B29}$ |
| III-4888 | $L_{A445}$ | $L_{B29}$ |
| III-4889 | $L_{A446}$ | $L_{B29}$ |
| III-4890 | $L_{A447}$ | $L_{B29}$ |
| III-4891 | $L_{A448}$ | $L_{B29}$ |
| III-4892 | $L_{A449}$ | $L_{B29}$ |
| III-4893 | $L_{A450}$ | $L_{B29}$ |
| III-4894 | $L_{A451}$ | $L_{B29}$ |
| III-4895 | $L_{A452}$ | $L_{B29}$ |
| III-4896 | $L_{A453}$ | $L_{B29}$ |
| III-4897 | $L_{A454}$ | $L_{B29}$ |
| III-4898 | $L_{A455}$ | $L_{B29}$ |
| III-4899 | $L_{A456}$ | $L_{B29}$ |
| III-4900 | $L_{A457}$ | $L_{B29}$ |
| III-4901 | $L_{A458}$ | $L_{B29}$ |
| III-4902 | $L_{A459}$ | $L_{B29}$ |
| III-4903 | $L_{A460}$ | $L_{B29}$ |
| III-4904 | $L_{A461}$ | $L_{B29}$ |
| III-4905 | $L_{A462}$ | $L_{B29}$ |
| III-4906 | $L_{A463}$ | $L_{B29}$ |
| III-4907 | $L_{A464}$ | $L_{B29}$ |
| III-4908 | $L_{A465}$ | $L_{B29}$ |
| III-4909 | $L_{A466}$ | $L_{B29}$ |
| III-4910 | $L_{A467}$ | $L_{B29}$ |
| III-4911 | $L_{A468}$ | $L_{B29}$ |
| III-4912 | $L_{A469}$ | $L_{B29}$ |
| III-4913 | $L_{A470}$ | $L_{B29}$ |
| III-4914 | $L_{A471}$ | $L_{B29}$ |
| III-4915 | $L_{A472}$ | $L_{B29}$ |
| III-4916 | $L_{A473}$ | $L_{B29}$ |
| III-4917 | $L_{A474}$ | $L_{B29}$ |
| III-4918 | $L_{A475}$ | $L_{B29}$ |
| III-4919 | $L_{A476}$ | $L_{B29}$ |
| III-4920 | $L_{A477}$ | $L_{B29}$ |
| III-4921 | $L_{A478}$ | $L_{B29}$ |
| III-4922 | $L_{A479}$ | $L_{B29}$ |
| III-4923 | $L_{A480}$ | $L_{B29}$ |
| III-4924 | $L_{A481}$ | $L_{B29}$ |
| III-4925 | $L_{A482}$ | $L_{B29}$ |
| III-4926 | $L_{A483}$ | $L_{B29}$ |
| III-4927 | $L_{A484}$ | $L_{B29}$ |
| III-4928 | $L_{A485}$ | $L_{B29}$ |
| III-4929 | $L_{A486}$ | $L_{B29}$ |
| III-4930 | $L_{A487}$ | $L_{B29}$ |
| III-4931 | $L_{A318}$ | $L_{B30}$ |
| III-4932 | $L_{A319}$ | $L_{B30}$ |
| III-4933 | $L_{A320}$ | $L_{B30}$ |
| III-4934 | $L_{A321}$ | $L_{B30}$ |
| III-4935 | $L_{A322}$ | $L_{B30}$ |
| III-4936 | $L_{A323}$ | $L_{B30}$ |
| III-4937 | $L_{A324}$ | $L_{B30}$ |
| III-4938 | $L_{A325}$ | $L_{B30}$ |
| III-4939 | $L_{A326}$ | $L_{B30}$ |
| III-4940 | $L_{A327}$ | $L_{B30}$ |
| III-4941 | $L_{A328}$ | $L_{B30}$ |
| III-4942 | $L_{A329}$ | $L_{B30}$ |
| III-4943 | $L_{A330}$ | $L_{B30}$ |
| III-4944 | $L_{A331}$ | $L_{B30}$ |
| III-4945 | $L_{A332}$ | $L_{B30}$ |
| III-4946 | $L_{A333}$ | $L_{B30}$ |
| III-4947 | $L_{A334}$ | $L_{B30}$ |
| III-4948 | $L_{A335}$ | $L_{B30}$ |
| III-4949 | $L_{A336}$ | $L_{B30}$ |
| III-4950 | $L_{A337}$ | $L_{B30}$ |
| III-4951 | $L_{A338}$ | $L_{B30}$ |
| III-4952 | $L_{A339}$ | $L_{B30}$ |
| III-4953 | $L_{A340}$ | $L_{B30}$ |
| III-4954 | $L_{A341}$ | $L_{B30}$ |
| III-4955 | $L_{A342}$ | $L_{B30}$ |
| III-4956 | $L_{A343}$ | $L_{B30}$ |
| III-4957 | $L_{A344}$ | $L_{B30}$ |

| Compound Number | $L_A$ | $L_B$ |
|---|---|---|
| III-4958 | $L_{A345}$ | $L_{B30}$ |
| III-4959 | $L_{A346}$ | $L_{B30}$ |
| III-4960 | $L_{A347}$ | $L_{B30}$ |
| III-4961 | $L_{A348}$ | $L_{B30}$ |
| III-4962 | $L_{A349}$ | $L_{B30}$ |
| III-4963 | $L_{A350}$ | $L_{B30}$ |
| III-4964 | $L_{A351}$ | $L_{B30}$ |
| III-4965 | $L_{A352}$ | $L_{B30}$ |
| III-4966 | $L_{A353}$ | $L_{B30}$ |
| III-4967 | $L_{A354}$ | $L_{B30}$ |
| III-4968 | $L_{A355}$ | $L_{B30}$ |
| III-4969 | $L_{A356}$ | $L_{B30}$ |
| III-4970 | $L_{A357}$ | $L_{B30}$ |
| III-4971 | $L_{A358}$ | $L_{B30}$ |
| III-4972 | $L_{A359}$ | $L_{B30}$ |
| III-4973 | $L_{A360}$ | $L_{B30}$ |
| III-4974 | $L_{A361}$ | $L_{B30}$ |
| III-4975 | $L_{A362}$ | $L_{B30}$ |
| III-4976 | $L_{A363}$ | $L_{B30}$ |
| III-4977 | $L_{A364}$ | $L_{B30}$ |
| III-4978 | $L_{A365}$ | $L_{B30}$ |
| III-4979 | $L_{A366}$ | $L_{B30}$ |
| III-4980 | $L_{A367}$ | $L_{B30}$ |
| III-4981 | $L_{A368}$ | $L_{B30}$ |
| III-4982 | $L_{A369}$ | $L_{B30}$ |
| III-4983 | $L_{A370}$ | $L_{B30}$ |
| III-4984 | $L_{A371}$ | $L_{B30}$ |
| III-4985 | $L_{A372}$ | $L_{B30}$ |
| III-4986 | $L_{A373}$ | $L_{B30}$ |
| III-4987 | $L_{A374}$ | $L_{B30}$ |
| III-4988 | $L_{A375}$ | $L_{B30}$ |
| III-4989 | $L_{A376}$ | $L_{B30}$ |
| III-4990 | $L_{A377}$ | $L_{B30}$ |
| III-4991 | $L_{A378}$ | $L_{B30}$ |
| III-4992 | $L_{A379}$ | $L_{B30}$ |
| III-4993 | $L_{A380}$ | $L_{B30}$ |
| III-4994 | $L_{A381}$ | $L_{B30}$ |
| III-4995 | $L_{A382}$ | $L_{B30}$ |
| III-4996 | $L_{A383}$ | $L_{B30}$ |
| III-4997 | $L_{A384}$ | $L_{B30}$ |
| III-4998 | $L_{A385}$ | $L_{B30}$ |
| III-4999 | $L_{A386}$ | $L_{B30}$ |
| III-5000 | $L_{A387}$ | $L_{B30}$ |
| III-5001 | $L_{A388}$ | $L_{B30}$ |
| III-5002 | $L_{A389}$ | $L_{B30}$ |
| III-5003 | $L_{A390}$ | $L_{B30}$ |
| III-5004 | $L_{A391}$ | $L_{B30}$ |
| III-5005 | $L_{A392}$ | $L_{B30}$ |
| III-5006 | $L_{A393}$ | $L_{B30}$ |
| III-5007 | $L_{A394}$ | $L_{B30}$ |
| III-5008 | $L_{A395}$ | $L_{B30}$ |
| III-5009 | $L_{A396}$ | $L_{B30}$ |
| III-5010 | $L_{A397}$ | $L_{B30}$ |
| III-5011 | $L_{A398}$ | $L_{B30}$ |
| III-5012 | $L_{A399}$ | $L_{B30}$ |
| III-5013 | $L_{A400}$ | $L_{B30}$ |
| III-5014 | $L_{A401}$ | $L_{B30}$ |
| III-5015 | $L_{A402}$ | $L_{B30}$ |
| III-5016 | $L_{A403}$ | $L_{B30}$ |
| III-5017 | $L_{A404}$ | $L_{B30}$ |
| III-5018 | $L_{A405}$ | $L_{B30}$ |
| III-5019 | $L_{A406}$ | $L_{B30}$ |
| III-5020 | $L_{A407}$ | $L_{B30}$ |
| III-5021 | $L_{A408}$ | $L_{B30}$ |
| III-5022 | $L_{A409}$ | $L_{B30}$ |
| III-5023 | $L_{A410}$ | $L_{B30}$ |
| III-5024 | $L_{A411}$ | $L_{B30}$ |
| III-5025 | $L_{A412}$ | $L_{B30}$ |
| III-5026 | $L_{A413}$ | $L_{B30}$ |
| III-5027 | $L_{A414}$ | $L_{B30}$ |
| III-5028 | $L_{A415}$ | $L_{B30}$ |
| III-5029 | $L_{A416}$ | $L_{B30}$ |
| III-5030 | $L_{A417}$ | $L_{B30}$ |
| III-5031 | $L_{A418}$ | $L_{B30}$ |
| III-5032 | $L_{A419}$ | $L_{B30}$ |
| III-5033 | $L_{A420}$ | $L_{B30}$ |
| III-5034 | $L_{A421}$ | $L_{B30}$ |
| III-5035 | $L_{A422}$ | $L_{B30}$ |
| III-5036 | $L_{A423}$ | $L_{B30}$ |
| III-5037 | $L_{A424}$ | $L_{B30}$ |
| III-5038 | $L_{A425}$ | $L_{B30}$ |
| III-5039 | $L_{A426}$ | $L_{B30}$ |
| III-5040 | $L_{A427}$ | $L_{B30}$ |
| III-5041 | $L_{A428}$ | $L_{B30}$ |
| III-5042 | $L_{A429}$ | $L_{B30}$ |
| III-5043 | $L_{A430}$ | $L_{B30}$ |
| III-5044 | $L_{A431}$ | $L_{B30}$ |
| III-5045 | $L_{A432}$ | $L_{B30}$ |
| III-5046 | $L_{A433}$ | $L_{B30}$ |
| III-5047 | $L_{A434}$ | $L_{B30}$ |
| III-5048 | $L_{A435}$ | $L_{B30}$ |
| III-5049 | $L_{A436}$ | $L_{B30}$ |
| III-5050 | $L_{A437}$ | $L_{B30}$ |
| III-5051 | $L_{A438}$ | $L_{B30}$ |
| III-5052 | $L_{A439}$ | $L_{B30}$ |
| III-5053 | $L_{A440}$ | $L_{B30}$ |
| III-5054 | $L_{A441}$ | $L_{B30}$ |
| III-5055 | $L_{A442}$ | $L_{B30}$ |
| III-5056 | $L_{A443}$ | $L_{B30}$ |
| III-5057 | $L_{A444}$ | $L_{B30}$ |
| III-5058 | $L_{A445}$ | $L_{B30}$ |
| III-5059 | $L_{A446}$ | $L_{B30}$ |
| III-5060 | $L_{A447}$ | $L_{B30}$ |
| III-5061 | $L_{A448}$ | $L_{B30}$ |
| III-5062 | $L_{A449}$ | $L_{B30}$ |
| III-5063 | $L_{A450}$ | $L_{B30}$ |
| III-5064 | $L_{A451}$ | $L_{B30}$ |
| III-5065 | $L_{A452}$ | $L_{B30}$ |
| III-5066 | $L_{A453}$ | $L_{B30}$ |
| III-5067 | $L_{A454}$ | $L_{B30}$ |
| III-5068 | $L_{A455}$ | $L_{B30}$ |
| III-5069 | $L_{A456}$ | $L_{B30}$ |
| III-5070 | $L_{A457}$ | $L_{B30}$ |
| III-5071 | $L_{A458}$ | $L_{B30}$ |
| III-5072 | $L_{A459}$ | $L_{B30}$ |
| III-5073 | $L_{A460}$ | $L_{B30}$ |
| III-5074 | $L_{A461}$ | $L_{B30}$ |
| III-5075 | $L_{A462}$ | $L_{B30}$ |
| III-5076 | $L_{A463}$ | $L_{B30}$ |
| III-5077 | $L_{A464}$ | $L_{B30}$ |
| III-5078 | $L_{A465}$ | $L_{B30}$ |
| III-5079 | $L_{A466}$ | $L_{B30}$ |
| III-5080 | $L_{A467}$ | $L_{B30}$ |
| III-5081 | $L_{A468}$ | $L_{B30}$ |
| III-5082 | $L_{A469}$ | $L_{B30}$ |
| III-5083 | $L_{A470}$ | $L_{B30}$ |
| III-5084 | $L_{A471}$ | $L_{B30}$ |
| III-5085 | $L_{A472}$ | $L_{B30}$ |
| III-5086 | $L_{A473}$ | $L_{B30}$ |
| III-5087 | $L_{A474}$ | $L_{B30}$ |
| III-5088 | $L_{A475}$ | $L_{B30}$ |
| III-5089 | $L_{A476}$ | $L_{B30}$ |
| III-5090 | $L_{A477}$ | $L_{B30}$ |
| III-5091 | $L_{A478}$ | $L_{B30}$ |
| III-5092 | $L_{A479}$ | $L_{B30}$ |
| III-5093 | $L_{A480}$ | $L_{B30}$ |
| III-5094 | $L_{A481}$ | $L_{B30}$ |
| III-5095 | $L_{A482}$ | $L_{B30}$ |
| III-5096 | $L_{A483}$ | $L_{B30}$ |
| III-5097 | $L_{A484}$ | $L_{B30}$ |
| III-5098 | $L_{A485}$ | $L_{B30}$ |
| III-5099 | $L_{A486}$ | $L_{B30}$ |
| III-5100 | $L_{A487}$ | $L_{B30}$ |
| III-5101 | $L_{A318}$ | $L_{B31}$ |
| III-5102 | $L_{A319}$ | $L_{B31}$ |
| III-5103 | $L_{A320}$ | $L_{B31}$ |
| III-5104 | $L_{A321}$ | $L_{B31}$ |
| III-5105 | $L_{A322}$ | $L_{B31}$ |
| III-5106 | $L_{A323}$ | $L_{B31}$ |
| III-5107 | $L_{A324}$ | $L_{B31}$ |
| III-5108 | $L_{A325}$ | $L_{B31}$ |
| III-5109 | $L_{A326}$ | $L_{B31}$ |

-continued

| Compound Number | $L_A$ | $L_B$ |
|---|---|---|
| III-5110 | $L_{A327}$ | $L_{B31}$ |
| III-5111 | $L_{A328}$ | $L_{B31}$ |
| III-5112 | $L_{A329}$ | $L_{B31}$ |
| III-5113 | $L_{A330}$ | $L_{B31}$ |
| III-5114 | $L_{A331}$ | $L_{B31}$ |
| III-5115 | $L_{A332}$ | $L_{B31}$ |
| III-5116 | $L_{A333}$ | $L_{B31}$ |
| III-5117 | $L_{A334}$ | $L_{B31}$ |
| III-5118 | $L_{A335}$ | $L_{B31}$ |
| III-5119 | $L_{A336}$ | $L_{B31}$ |
| III-5120 | $L_{A337}$ | $L_{B31}$ |
| III-5121 | $L_{A338}$ | $L_{B31}$ |
| III-5122 | $L_{A339}$ | $L_{B31}$ |
| III-5123 | $L_{A340}$ | $L_{B31}$ |
| III-5124 | $L_{A341}$ | $L_{B31}$ |
| III-5125 | $L_{A342}$ | $L_{B31}$ |
| III-5126 | $L_{A343}$ | $L_{B31}$ |
| III-5127 | $L_{A344}$ | $L_{B31}$ |
| III-5128 | $L_{A345}$ | $L_{B31}$ |
| III-5129 | $L_{A346}$ | $L_{B31}$ |
| III-5130 | $L_{A347}$ | $L_{B31}$ |
| III-5131 | $L_{A348}$ | $L_{B31}$ |
| III-5132 | $L_{A349}$ | $L_{B31}$ |
| III-5133 | $L_{A350}$ | $L_{B31}$ |
| III-5134 | $L_{A351}$ | $L_{B31}$ |
| III-5135 | $L_{A352}$ | $L_{B31}$ |
| III-5136 | $L_{A353}$ | $L_{B31}$ |
| III-5137 | $L_{A354}$ | $L_{B31}$ |
| III-5138 | $L_{A355}$ | $L_{B31}$ |
| III-5139 | $L_{A356}$ | $L_{B31}$ |
| III-5140 | $L_{A357}$ | $L_{B31}$ |
| III-5141 | $L_{A358}$ | $L_{B31}$ |
| III-5142 | $L_{A359}$ | $L_{B31}$ |
| III-5143 | $L_{A360}$ | $L_{B31}$ |
| III-5144 | $L_{A361}$ | $L_{B31}$ |
| III-5145 | $L_{A362}$ | $L_{B31}$ |
| III-5146 | $L_{A363}$ | $L_{B31}$ |
| III-5147 | $L_{A364}$ | $L_{B31}$ |
| III-5148 | $L_{A365}$ | $L_{B31}$ |
| III-5149 | $L_{A366}$ | $L_{B31}$ |
| III-5150 | $L_{A367}$ | $L_{B31}$ |
| III-5151 | $L_{A368}$ | $L_{B31}$ |
| III-5152 | $L_{A369}$ | $L_{B31}$ |
| III-5153 | $L_{A370}$ | $L_{B31}$ |
| III-5154 | $L_{A371}$ | $L_{B31}$ |
| III-5155 | $L_{A372}$ | $L_{B31}$ |
| III-5156 | $L_{A373}$ | $L_{B31}$ |
| III-5157 | $L_{A374}$ | $L_{B31}$ |
| III-5158 | $L_{A375}$ | $L_{B31}$ |
| III-5159 | $L_{A376}$ | $L_{B31}$ |
| III-5160 | $L_{A377}$ | $L_{B31}$ |
| III-5161 | $L_{A378}$ | $L_{B31}$ |
| III-5162 | $L_{A379}$ | $L_{B31}$ |
| III-5163 | $L_{A380}$ | $L_{B31}$ |
| III-5164 | $L_{A381}$ | $L_{B31}$ |
| III-5165 | $L_{A382}$ | $L_{B31}$ |
| III-5166 | $L_{A383}$ | $L_{B31}$ |
| III-5167 | $L_{A384}$ | $L_{B31}$ |
| III-5168 | $L_{A385}$ | $L_{B31}$ |
| III-5169 | $L_{A386}$ | $L_{B31}$ |
| III-5170 | $L_{A387}$ | $L_{B31}$ |
| III-5171 | $L_{A388}$ | $L_{B31}$ |
| III-5172 | $L_{A389}$ | $L_{B31}$ |
| III-5173 | $L_{A390}$ | $L_{B31}$ |
| III-5174 | $L_{A391}$ | $L_{B31}$ |
| III-5175 | $L_{A392}$ | $L_{B31}$ |
| III-5176 | $L_{A393}$ | $L_{B31}$ |
| III-5177 | $L_{A394}$ | $L_{B31}$ |
| III-5178 | $L_{A395}$ | $L_{B31}$ |
| III-5179 | $L_{A396}$ | $L_{B31}$ |
| III-5180 | $L_{A397}$ | $L_{B31}$ |
| III-5181 | $L_{A398}$ | $L_{B31}$ |
| III-5182 | $L_{A399}$ | $L_{B31}$ |
| III-5183 | $L_{A400}$ | $L_{B31}$ |
| III-5184 | $L_{A401}$ | $L_{B31}$ |
| III-5185 | $L_{A402}$ | $L_{B31}$ |
| III-5186 | $L_{A403}$ | $L_{B31}$ |
| III-5187 | $L_{A404}$ | $L_{B31}$ |
| III-5188 | $L_{A405}$ | $L_{B31}$ |
| III-5189 | $L_{A406}$ | $L_{B31}$ |
| III-5190 | $L_{A407}$ | $L_{B31}$ |
| III-5191 | $L_{A408}$ | $L_{B31}$ |
| III-5192 | $L_{A409}$ | $L_{B31}$ |
| III-5193 | $L_{A410}$ | $L_{B31}$ |
| III-5194 | $L_{A411}$ | $L_{B31}$ |
| III-5195 | $L_{A412}$ | $L_{B31}$ |
| III-5196 | $L_{A413}$ | $L_{B31}$ |
| III-5197 | $L_{A414}$ | $L_{B31}$ |
| III-5198 | $L_{A415}$ | $L_{B31}$ |
| III-5199 | $L_{A416}$ | $L_{B31}$ |
| III-5200 | $L_{A417}$ | $L_{B31}$ |
| III-5201 | $L_{A418}$ | $L_{B31}$ |
| III-5202 | $L_{A419}$ | $L_{B31}$ |
| III-5203 | $L_{A420}$ | $L_{B31}$ |
| III-5204 | $L_{A421}$ | $L_{B31}$ |
| III-5205 | $L_{A422}$ | $L_{B31}$ |
| III-5206 | $L_{A423}$ | $L_{B31}$ |
| III-5207 | $L_{A424}$ | $L_{B31}$ |
| III-5208 | $L_{A425}$ | $L_{B31}$ |
| III-5209 | $L_{A426}$ | $L_{B31}$ |
| III-5210 | $L_{A427}$ | $L_{B31}$ |
| III-5211 | $L_{A428}$ | $L_{B31}$ |
| III-5212 | $L_{A429}$ | $L_{B31}$ |
| III-5213 | $L_{A430}$ | $L_{B31}$ |
| III-5214 | $L_{A431}$ | $L_{B31}$ |
| III-5215 | $L_{A432}$ | $L_{B31}$ |
| III-5216 | $L_{A433}$ | $L_{B31}$ |
| III-5217 | $L_{A434}$ | $L_{B31}$ |
| III-5218 | $L_{A435}$ | $L_{B31}$ |
| III-5219 | $L_{A436}$ | $L_{B31}$ |
| III-5220 | $L_{A437}$ | $L_{B31}$ |
| III-5221 | $L_{A438}$ | $L_{B31}$ |
| III-5222 | $L_{A439}$ | $L_{B31}$ |
| III-5223 | $L_{A440}$ | $L_{B31}$ |
| III-5224 | $L_{A441}$ | $L_{B31}$ |
| III-5225 | $L_{A442}$ | $L_{B31}$ |
| III-5226 | $L_{A443}$ | $L_{B31}$ |
| III-5227 | $L_{A444}$ | $L_{B31}$ |
| III-5228 | $L_{A445}$ | $L_{B31}$ |
| III-5229 | $L_{A446}$ | $L_{B31}$ |
| III-5230 | $L_{A447}$ | $L_{B31}$ |
| III-5231 | $L_{A448}$ | $L_{B31}$ |
| III-5232 | $L_{A449}$ | $L_{B31}$ |
| III-5233 | $L_{A450}$ | $L_{B31}$ |
| III-5234 | $L_{A451}$ | $L_{B31}$ |
| III-5235 | $L_{A452}$ | $L_{B31}$ |
| III-5236 | $L_{A453}$ | $L_{B31}$ |
| III-5237 | $L_{A454}$ | $L_{B31}$ |
| III-5238 | $L_{A455}$ | $L_{B31}$ |
| III-5239 | $L_{A456}$ | $L_{B31}$ |
| III-5240 | $L_{A457}$ | $L_{B31}$ |
| III-5241 | $L_{A458}$ | $L_{B31}$ |
| III-5242 | $L_{A459}$ | $L_{B31}$ |
| III-5243 | $L_{A460}$ | $L_{B31}$ |
| III-5244 | $L_{A461}$ | $L_{B31}$ |
| III-5245 | $L_{A462}$ | $L_{B31}$ |
| III-5246 | $L_{A463}$ | $L_{B31}$ |
| III-5247 | $L_{A464}$ | $L_{B31}$ |
| III-5248 | $L_{A465}$ | $L_{B31}$ |
| III-5249 | $L_{A466}$ | $L_{B31}$ |
| III-5250 | $L_{A467}$ | $L_{B31}$ |
| III-5251 | $L_{A468}$ | $L_{B31}$ |
| III-5252 | $L_{A469}$ | $L_{B31}$ |
| III-5253 | $L_{A470}$ | $L_{B31}$ |
| III-5254 | $L_{A471}$ | $L_{B31}$ |
| III-5255 | $L_{A472}$ | $L_{B31}$ |
| III-5256 | $L_{A473}$ | $L_{B31}$ |
| III-5257 | $L_{A474}$ | $L_{B31}$ |
| III-5258 | $L_{A475}$ | $L_{B31}$ |
| III-5259 | $L_{A476}$ | $L_{B31}$ |
| III-5260 | $L_{A477}$ | $L_{B31}$ |
| III-5261 | $L_{A478}$ | $L_{B31}$ |

| Compound Number | $L_A$ | $L_B$ |
|---|---|---|
| III-5262 | $L_{A479}$ | $L_{B31}$ |
| III-5263 | $L_{A480}$ | $L_{B31}$ |
| III-5264 | $L_{A481}$ | $L_{B31}$ |
| III-5265 | $L_{A482}$ | $L_{B31}$ |
| III-5266 | $L_{A483}$ | $L_{B31}$ |
| III-5267 | $L_{A484}$ | $L_{B31}$ |
| III-5268 | $L_{A485}$ | $L_{B31}$ |
| III-5269 | $L_{A486}$ | $L_{B31}$ |
| III-5270 | $L_{A487}$ | $L_{B31}$ |
| III-5271 | $L_{A318}$ | $L_{B32}$ |
| III-5272 | $L_{A319}$ | $L_{B32}$ |
| III-5273 | $L_{A320}$ | $L_{B32}$ |
| III-5274 | $L_{A321}$ | $L_{B32}$ |
| III-5275 | $L_{A322}$ | $L_{B32}$ |
| III-5276 | $L_{A323}$ | $L_{B32}$ |
| III-5277 | $L_{A324}$ | $L_{B32}$ |
| III-5278 | $L_{A325}$ | $L_{B32}$ |
| III-5279 | $L_{A326}$ | $L_{B32}$ |
| III-5280 | $L_{A327}$ | $L_{B32}$ |
| III-5281 | $L_{A328}$ | $L_{B32}$ |
| III-5282 | $L_{A329}$ | $L_{B32}$ |
| III-5283 | $L_{A330}$ | $L_{B32}$ |
| III-5284 | $L_{A331}$ | $L_{B32}$ |
| III-5285 | $L_{A332}$ | $L_{B32}$ |
| III-5286 | $L_{A333}$ | $L_{B32}$ |
| III-5287 | $L_{A334}$ | $L_{B32}$ |
| III-5288 | $L_{A335}$ | $L_{B32}$ |
| III-5289 | $L_{A336}$ | $L_{B32}$ |
| III-5290 | $L_{A337}$ | $L_{B32}$ |
| III-5291 | $L_{A338}$ | $L_{B32}$ |
| III-5292 | $L_{A339}$ | $L_{B32}$ |
| III-5293 | $L_{A340}$ | $L_{B32}$ |
| III-5294 | $L_{A341}$ | $L_{B32}$ |
| III-5295 | $L_{A342}$ | $L_{B32}$ |
| III-5296 | $L_{A343}$ | $L_{B32}$ |
| III-5297 | $L_{A344}$ | $L_{B32}$ |
| III-5298 | $L_{A345}$ | $L_{B32}$ |
| III-5299 | $L_{A346}$ | $L_{B32}$ |
| III-5300 | $L_{A347}$ | $L_{B32}$ |
| III-5301 | $L_{A348}$ | $L_{B32}$ |
| III-5302 | $L_{A349}$ | $L_{B32}$ |
| III-5303 | $L_{A350}$ | $L_{B32}$ |
| III-5304 | $L_{A351}$ | $L_{B32}$ |
| III-5305 | $L_{A352}$ | $L_{B32}$ |
| III-5306 | $L_{A353}$ | $L_{B32}$ |
| III-5307 | $L_{A354}$ | $L_{B32}$ |
| III-5308 | $L_{A355}$ | $L_{B32}$ |
| III-5309 | $L_{A356}$ | $L_{B32}$ |
| III-5310 | $L_{A357}$ | $L_{B32}$ |
| III-5311 | $L_{A358}$ | $L_{B32}$ |
| III-5312 | $L_{A359}$ | $L_{B32}$ |
| III-5313 | $L_{A360}$ | $L_{B32}$ |
| III-5314 | $L_{A361}$ | $L_{B32}$ |
| III-5315 | $L_{A362}$ | $L_{B32}$ |
| III-5316 | $L_{A363}$ | $L_{B32}$ |
| III-5317 | $L_{A364}$ | $L_{B32}$ |
| III-5318 | $L_{A365}$ | $L_{B32}$ |
| III-5319 | $L_{A366}$ | $L_{B32}$ |
| III-5320 | $L_{A367}$ | $L_{B32}$ |
| III-5321 | $L_{A368}$ | $L_{B32}$ |
| III-5322 | $L_{A369}$ | $L_{B32}$ |
| III-5323 | $L_{A370}$ | $L_{B32}$ |
| III-5324 | $L_{A371}$ | $L_{B32}$ |
| III-5325 | $L_{A372}$ | $L_{B32}$ |
| III-5326 | $L_{A373}$ | $L_{B32}$ |
| III-5327 | $L_{A374}$ | $L_{B32}$ |
| III-5328 | $L_{A375}$ | $L_{B32}$ |
| III-5329 | $L_{A376}$ | $L_{B32}$ |
| III-5330 | $L_{A377}$ | $L_{B32}$ |
| III-5331 | $L_{A378}$ | $L_{B32}$ |
| III-5332 | $L_{A379}$ | $L_{B32}$ |
| III-5333 | $L_{A380}$ | $L_{B32}$ |
| III-5334 | $L_{A381}$ | $L_{B32}$ |
| III-5335 | $L_{A382}$ | $L_{B32}$ |
| III-5336 | $L_{A383}$ | $L_{B32}$ |
| III-5337 | $L_{A384}$ | $L_{B32}$ |
| III-5338 | $L_{A385}$ | $L_{B32}$ |
| III-5339 | $L_{A386}$ | $L_{B32}$ |
| III-5340 | $L_{A387}$ | $L_{B32}$ |
| III-5341 | $L_{A388}$ | $L_{B32}$ |
| III-5342 | $L_{A389}$ | $L_{B32}$ |
| III-5343 | $L_{A390}$ | $L_{B32}$ |
| III-5344 | $L_{A391}$ | $L_{B32}$ |
| III-5345 | $L_{A392}$ | $L_{B32}$ |
| III-5346 | $L_{A393}$ | $L_{B32}$ |
| III-5347 | $L_{A394}$ | $L_{B32}$ |
| III-5348 | $L_{A395}$ | $L_{B32}$ |
| III-5349 | $L_{A396}$ | $L_{B32}$ |
| III-5350 | $L_{A397}$ | $L_{B32}$ |
| III-5351 | $L_{A398}$ | $L_{B32}$ |
| III-5352 | $L_{A399}$ | $L_{B32}$ |
| III-5353 | $L_{A400}$ | $L_{B32}$ |
| III-5354 | $L_{A401}$ | $L_{B32}$ |
| III-5355 | $L_{A402}$ | $L_{B32}$ |
| III-5356 | $L_{A403}$ | $L_{B32}$ |
| III-5357 | $L_{A404}$ | $L_{B32}$ |
| III-5358 | $L_{A405}$ | $L_{B32}$ |
| III-5359 | $L_{A406}$ | $L_{B32}$ |
| III-5360 | $L_{A407}$ | $L_{B32}$ |
| III-5361 | $L_{A408}$ | $L_{B32}$ |
| III-5362 | $L_{A409}$ | $L_{B32}$ |
| III-5363 | $L_{A410}$ | $L_{B32}$ |
| III-5364 | $L_{A411}$ | $L_{B32}$ |
| III-5365 | $L_{A412}$ | $L_{B32}$ |
| III-5366 | $L_{A413}$ | $L_{B32}$ |
| III-5367 | $L_{A414}$ | $L_{B32}$ |
| III-5368 | $L_{A415}$ | $L_{B32}$ |
| III-5369 | $L_{A416}$ | $L_{B32}$ |
| III-5370 | $L_{A417}$ | $L_{B32}$ |
| III-5371 | $L_{A418}$ | $L_{B32}$ |
| III-5372 | $L_{A419}$ | $L_{B32}$ |
| III-5373 | $L_{A420}$ | $L_{B32}$ |
| III-5374 | $L_{A421}$ | $L_{B32}$ |
| III-5375 | $L_{A422}$ | $L_{B32}$ |
| III-5376 | $L_{A423}$ | $L_{B32}$ |
| III-5377 | $L_{A424}$ | $L_{B32}$ |
| III-5378 | $L_{A425}$ | $L_{B32}$ |
| III-5379 | $L_{A426}$ | $L_{B32}$ |
| III-5380 | $L_{A427}$ | $L_{B32}$ |
| III-5381 | $L_{A428}$ | $L_{B32}$ |
| III-5382 | $L_{A429}$ | $L_{B32}$ |
| III-5383 | $L_{A430}$ | $L_{B32}$ |
| III-5384 | $L_{A431}$ | $L_{B32}$ |
| III-5385 | $L_{A432}$ | $L_{B32}$ |
| III-5386 | $L_{A433}$ | $L_{B32}$ |
| III-5387 | $L_{A434}$ | $L_{B32}$ |
| III-5388 | $L_{A435}$ | $L_{B32}$ |
| III-5389 | $L_{A436}$ | $L_{B32}$ |
| III-5390 | $L_{A437}$ | $L_{B32}$ |
| III-5391 | $L_{A438}$ | $L_{B32}$ |
| III-5392 | $L_{A439}$ | $L_{B32}$ |
| III-5393 | $L_{A440}$ | $L_{B32}$ |
| III-5394 | $L_{A441}$ | $L_{B32}$ |
| III-5395 | $L_{A442}$ | $L_{B32}$ |
| III-5396 | $L_{A443}$ | $L_{B32}$ |
| III-5397 | $L_{A444}$ | $L_{B32}$ |
| III-5398 | $L_{A445}$ | $L_{B32}$ |
| III-5399 | $L_{A446}$ | $L_{B32}$ |
| III-5400 | $L_{A447}$ | $L_{B32}$ |
| III-5401 | $L_{A448}$ | $L_{B32}$ |
| III-5402 | $L_{A449}$ | $L_{B32}$ |
| III-5403 | $L_{A450}$ | $L_{B32}$ |
| III-5404 | $L_{A451}$ | $L_{B32}$ |
| III-5405 | $L_{A452}$ | $L_{B32}$ |
| III-5406 | $L_{A453}$ | $L_{B32}$ |
| III-5407 | $L_{A454}$ | $L_{B32}$ |
| III-5408 | $L_{A455}$ | $L_{B32}$ |
| III-5409 | $L_{A456}$ | $L_{B32}$ |
| III-5410 | $L_{A457}$ | $L_{B32}$ |
| III-5411 | $L_{A458}$ | $L_{B32}$ |
| III-5412 | $L_{A459}$ | $L_{B32}$ |
| III-5413 | $L_{A460}$ | $L_{B32}$ |

-continued

| Compound Number | $L_A$ | $L_B$ |
|---|---|---|
| III-5414 | $L_{A461}$ | $L_{B32}$ |
| III-5415 | $L_{A462}$ | $L_{B32}$ |
| III-5416 | $L_{A463}$ | $L_{B32}$ |
| III-5417 | $L_{A464}$ | $L_{B32}$ |
| III-5418 | $L_{A465}$ | $L_{B32}$ |
| III-5419 | $L_{A466}$ | $L_{B32}$ |
| III-5420 | $L_{A467}$ | $L_{B32}$ |
| III-5421 | $L_{A468}$ | $L_{B32}$ |
| III-5422 | $L_{A469}$ | $L_{B32}$ |
| III-5423 | $L_{A470}$ | $L_{B32}$ |
| III-5424 | $L_{A471}$ | $L_{B32}$ |
| III-5425 | $L_{A472}$ | $L_{B32}$ |
| III-5426 | $L_{A473}$ | $L_{B32}$ |
| III-5427 | $L_{A474}$ | $L_{B32}$ |
| III-5428 | $L_{A475}$ | $L_{B32}$ |
| III-5429 | $L_{A476}$ | $L_{B32}$ |
| III-5430 | $L_{A477}$ | $L_{B32}$ |
| III-5431 | $L_{A478}$ | $L_{B32}$ |
| III-5432 | $L_{A479}$ | $L_{B32}$ |
| III-5433 | $L_{A480}$ | $L_{B32}$ |
| III-5434 | $L_{A481}$ | $L_{B32}$ |
| III-5435 | $L_{A482}$ | $L_{B32}$ |
| III-5436 | $L_{A483}$ | $L_{B32}$ |
| III-5437 | $L_{A484}$ | $L_{B32}$ |
| III-5438 | $L_{A485}$ | $L_{B32}$ |
| III-5439 | $L_{A486}$ | $L_{B32}$ |
| III-5440 | $L_{A487}$ | $L_{B32}$ |
| III-5441 | $L_{A318}$ | $L_{B33}$ |
| III-5442 | $L_{A319}$ | $L_{B33}$ |
| III-5443 | $L_{A320}$ | $L_{B33}$ |
| III-5444 | $L_{A321}$ | $L_{B33}$ |
| III-5445 | $L_{A322}$ | $L_{B33}$ |
| III-5446 | $L_{A323}$ | $L_{B33}$ |
| III-5447 | $L_{A324}$ | $L_{B33}$ |
| III-5448 | $L_{A325}$ | $L_{B33}$ |
| III-5449 | $L_{A326}$ | $L_{B33}$ |
| III-5450 | $L_{A327}$ | $L_{B33}$ |
| III-5451 | $L_{A328}$ | $L_{B33}$ |
| III-5452 | $L_{A329}$ | $L_{B33}$ |
| III-5453 | $L_{A330}$ | $L_{B33}$ |
| III-5454 | $L_{A331}$ | $L_{B33}$ |
| III-5455 | $L_{A332}$ | $L_{B33}$ |
| III-5456 | $L_{A333}$ | $L_{B33}$ |
| III-5457 | $L_{A334}$ | $L_{B33}$ |
| III-5458 | $L_{A335}$ | $L_{B33}$ |
| III-5459 | $L_{A336}$ | $L_{B33}$ |
| III-5460 | $L_{A337}$ | $L_{B33}$ |
| III-5461 | $L_{A338}$ | $L_{B33}$ |
| III-5462 | $L_{A339}$ | $L_{B33}$ |
| III-5463 | $L_{A340}$ | $L_{B33}$ |
| III-5464 | $L_{A341}$ | $L_{B33}$ |
| III-5465 | $L_{A342}$ | $L_{B33}$ |
| III-5466 | $L_{A343}$ | $L_{B33}$ |
| III-5467 | $L_{A344}$ | $L_{B33}$ |
| III-5468 | $L_{A345}$ | $L_{B33}$ |
| III-5469 | $L_{A346}$ | $L_{B33}$ |
| III-5470 | $L_{A347}$ | $L_{B33}$ |
| III-5471 | $L_{A348}$ | $L_{B33}$ |
| III-5472 | $L_{A349}$ | $L_{B33}$ |
| III-5473 | $L_{A350}$ | $L_{B33}$ |
| III-5474 | $L_{A351}$ | $L_{B33}$ |
| III-5475 | $L_{A352}$ | $L_{B33}$ |
| III-5476 | $L_{A353}$ | $L_{B33}$ |
| III-5477 | $L_{A354}$ | $L_{B33}$ |
| III-5478 | $L_{A355}$ | $L_{B33}$ |
| III-5479 | $L_{A356}$ | $L_{B33}$ |
| III-5480 | $L_{A357}$ | $L_{B33}$ |
| III-5481 | $L_{A358}$ | $L_{B33}$ |
| III-5482 | $L_{A359}$ | $L_{B33}$ |
| III-5483 | $L_{A360}$ | $L_{B33}$ |
| III-5484 | $L_{A361}$ | $L_{B33}$ |
| III-5485 | $L_{A362}$ | $L_{B33}$ |
| III-5486 | $L_{A363}$ | $L_{B33}$ |
| III-5487 | $L_{A364}$ | $L_{B33}$ |
| III-5488 | $L_{A365}$ | $L_{B33}$ |
| III-5489 | $L_{A366}$ | $L_{B33}$ |
| III-5490 | $L_{A367}$ | $L_{B33}$ |
| III-5491 | $L_{A368}$ | $L_{B33}$ |
| III-5492 | $L_{A369}$ | $L_{B33}$ |
| III-5493 | $L_{A370}$ | $L_{B33}$ |
| III-5494 | $L_{A371}$ | $L_{B33}$ |
| III-5495 | $L_{A372}$ | $L_{B33}$ |
| III-5496 | $L_{A373}$ | $L_{B33}$ |
| III-5497 | $L_{A374}$ | $L_{B33}$ |
| III-5498 | $L_{A375}$ | $L_{B33}$ |
| III-5499 | $L_{A376}$ | $L_{B33}$ |
| III-5500 | $L_{A377}$ | $L_{B33}$ |
| III-5501 | $L_{A378}$ | $L_{B33}$ |
| III-5502 | $L_{A379}$ | $L_{B33}$ |
| III-5503 | $L_{A380}$ | $L_{B33}$ |
| III-5504 | $L_{A381}$ | $L_{B33}$ |
| III-5505 | $L_{A382}$ | $L_{B33}$ |
| III-5506 | $L_{A383}$ | $L_{B33}$ |
| III-5507 | $L_{A384}$ | $L_{B33}$ |
| III-5508 | $L_{A385}$ | $L_{B33}$ |
| III-5509 | $L_{A386}$ | $L_{B33}$ |
| III-5510 | $L_{A387}$ | $L_{B33}$ |
| III-5511 | $L_{A388}$ | $L_{B33}$ |
| III-5512 | $L_{A389}$ | $L_{B33}$ |
| III-5513 | $L_{A390}$ | $L_{B33}$ |
| III-5514 | $L_{A391}$ | $L_{B33}$ |
| III-5515 | $L_{A392}$ | $L_{B33}$ |
| III-5516 | $L_{A393}$ | $L_{B33}$ |
| III-5517 | $L_{A394}$ | $L_{B33}$ |
| III-5518 | $L_{A395}$ | $L_{B33}$ |
| III-5519 | $L_{A396}$ | $L_{B33}$ |
| III-5520 | $L_{A397}$ | $L_{B33}$ |
| III-5521 | $L_{A398}$ | $L_{B33}$ |
| III-5522 | $L_{A399}$ | $L_{B33}$ |
| III-5523 | $L_{A400}$ | $L_{B33}$ |
| III-5524 | $L_{A401}$ | $L_{B33}$ |
| III-5525 | $L_{A402}$ | $L_{B33}$ |
| III-5526 | $L_{A403}$ | $L_{B33}$ |
| III-5527 | $L_{A404}$ | $L_{B33}$ |
| III-5528 | $L_{A405}$ | $L_{B33}$ |
| III-5529 | $L_{A406}$ | $L_{B33}$ |
| III-5530 | $L_{A407}$ | $L_{B33}$ |
| III-5531 | $L_{A408}$ | $L_{B33}$ |
| III-5532 | $L_{A409}$ | $L_{B33}$ |
| III-5533 | $L_{A410}$ | $L_{B33}$ |
| III-5534 | $L_{A411}$ | $L_{B33}$ |
| III-5535 | $L_{A412}$ | $L_{B33}$ |
| III-5536 | $L_{A413}$ | $L_{B33}$ |
| III-5537 | $L_{A414}$ | $L_{B33}$ |
| III-5538 | $L_{A415}$ | $L_{B33}$ |
| III-5539 | $L_{A416}$ | $L_{B33}$ |
| III-5540 | $L_{A417}$ | $L_{B33}$ |
| III-5541 | $L_{A418}$ | $L_{B33}$ |
| III-5542 | $L_{A419}$ | $L_{B33}$ |
| III-5543 | $L_{A420}$ | $L_{B33}$ |
| III-5544 | $L_{A421}$ | $L_{B33}$ |
| III-5545 | $L_{A422}$ | $L_{B33}$ |
| III-5546 | $L_{A423}$ | $L_{B33}$ |
| III-5547 | $L_{A424}$ | $L_{B33}$ |
| III-5548 | $L_{A425}$ | $L_{B33}$ |
| III-5549 | $L_{A426}$ | $L_{B33}$ |
| III-5550 | $L_{A427}$ | $L_{B33}$ |
| III-5551 | $L_{A428}$ | $L_{B33}$ |
| III-5552 | $L_{A429}$ | $L_{B33}$ |
| III-5553 | $L_{A430}$ | $L_{B33}$ |
| III-5554 | $L_{A431}$ | $L_{B33}$ |
| III-5555 | $L_{A432}$ | $L_{B33}$ |
| III-5556 | $L_{A433}$ | $L_{B33}$ |
| III-5557 | $L_{A434}$ | $L_{B33}$ |
| III-5558 | $L_{A435}$ | $L_{B33}$ |
| III-5559 | $L_{A436}$ | $L_{B33}$ |
| III-5560 | $L_{A437}$ | $L_{B33}$ |
| III-5561 | $L_{A438}$ | $L_{B33}$ |
| III-5562 | $L_{A439}$ | $L_{B33}$ |
| III-5563 | $L_{A440}$ | $L_{B33}$ |
| III-5564 | $L_{A441}$ | $L_{B33}$ |
| III-5565 | $L_{A442}$ | $L_{B33}$ |

| Compound Number | $L_A$ | $L_B$ |
|---|---|---|
| III-5566 | $L_{A443}$ | $L_{B33}$ |
| III-5567 | $L_{A444}$ | $L_{B33}$ |
| III-5568 | $L_{A445}$ | $L_{B33}$ |
| III-5569 | $L_{A446}$ | $L_{B33}$ |
| III-5570 | $L_{A447}$ | $L_{B33}$ |
| III-5571 | $L_{A448}$ | $L_{B33}$ |
| III-5572 | $L_{A449}$ | $L_{B33}$ |
| III-5573 | $L_{A450}$ | $L_{B33}$ |
| III-5574 | $L_{A451}$ | $L_{B33}$ |
| III-5575 | $L_{A452}$ | $L_{B33}$ |
| III-5576 | $L_{A453}$ | $L_{B33}$ |
| III-5577 | $L_{A454}$ | $L_{B33}$ |
| III-5578 | $L_{A455}$ | $L_{B33}$ |
| III-5579 | $L_{A456}$ | $L_{B33}$ |
| III-5580 | $L_{A457}$ | $L_{B33}$ |
| III-5581 | $L_{A458}$ | $L_{B33}$ |
| III-5582 | $L_{A459}$ | $L_{B33}$ |
| III-5583 | $L_{A460}$ | $L_{B33}$ |
| III-5584 | $L_{A461}$ | $L_{B33}$ |
| III-5585 | $L_{A462}$ | $L_{B33}$ |
| III-5586 | $L_{A463}$ | $L_{B33}$ |
| III-5587 | $L_{A464}$ | $L_{B33}$ |
| III-5588 | $L_{A465}$ | $L_{B33}$ |
| III-5589 | $L_{A466}$ | $L_{B33}$ |
| III-5590 | $L_{A467}$ | $L_{B33}$ |
| III-5591 | $L_{A468}$ | $L_{B33}$ |
| III-5592 | $L_{A469}$ | $L_{B33}$ |
| III-5593 | $L_{A470}$ | $L_{B33}$ |
| III-5594 | $L_{A471}$ | $L_{B33}$ |
| III-5595 | $L_{A472}$ | $L_{B33}$ |
| III-5596 | $L_{A473}$ | $L_{B33}$ |
| III-5597 | $L_{A474}$ | $L_{B33}$ |
| III-5598 | $L_{A475}$ | $L_{B33}$ |
| III-5599 | $L_{A476}$ | $L_{B33}$ |
| III-5600 | $L_{A477}$ | $L_{B33}$ |
| III-5601 | $L_{A478}$ | $L_{B33}$ |
| III-5602 | $L_{A479}$ | $L_{B33}$ |
| III-5603 | $L_{A480}$ | $L_{B33}$ |
| III-5604 | $L_{A481}$ | $L_{B33}$ |
| III-5605 | $L_{A482}$ | $L_{B33}$ |
| III-5606 | $L_{A483}$ | $L_{B33}$ |
| III-5607 | $L_{A484}$ | $L_{B33}$ |
| III-5608 | $L_{A485}$ | $L_{B33}$ |
| III-5609 | $L_{A486}$ | $L_{B33}$ |
| III-5610 | $L_{A487}$ | $L_{B33}$ |
| III-5611 | $L_{A318}$ | $L_{B34}$ |
| III-5612 | $L_{A319}$ | $L_{B34}$ |
| III-5613 | $L_{A320}$ | $L_{B34}$ |
| III-5614 | $L_{A321}$ | $L_{B34}$ |
| III-5615 | $L_{A322}$ | $L_{B34}$ |
| III-5616 | $L_{A323}$ | $L_{B34}$ |
| III-5617 | $L_{A324}$ | $L_{B34}$ |
| III-5618 | $L_{A325}$ | $L_{B34}$ |
| III-5619 | $L_{A326}$ | $L_{B34}$ |
| III-5620 | $L_{A327}$ | $L_{B34}$ |
| III-5621 | $L_{A328}$ | $L_{B34}$ |
| III-5622 | $L_{A329}$ | $L_{B34}$ |
| III-5623 | $L_{A330}$ | $L_{B34}$ |
| III-5624 | $L_{A331}$ | $L_{B34}$ |
| III-5625 | $L_{A332}$ | $L_{B34}$ |
| III-5626 | $L_{A333}$ | $L_{B34}$ |
| III-5627 | $L_{A334}$ | $L_{B34}$ |
| III-5628 | $L_{A335}$ | $L_{B34}$ |
| III-5629 | $L_{A336}$ | $L_{B34}$ |
| III-5630 | $L_{A337}$ | $L_{B34}$ |
| III-5631 | $L_{A338}$ | $L_{B34}$ |
| III-5632 | $L_{A339}$ | $L_{B34}$ |
| III-5633 | $L_{A340}$ | $L_{B34}$ |
| III-5634 | $L_{A341}$ | $L_{B34}$ |
| III-5635 | $L_{A342}$ | $L_{B34}$ |
| III-5636 | $L_{A343}$ | $L_{B34}$ |
| III-5637 | $L_{A344}$ | $L_{B34}$ |
| III-5638 | $L_{A345}$ | $L_{B34}$ |
| III-5639 | $L_{A346}$ | $L_{B34}$ |
| III-5640 | $L_{A347}$ | $L_{B34}$ |
| III-5641 | $L_{A348}$ | $L_{B34}$ |
| III-5642 | $L_{A349}$ | $L_{B34}$ |
| III-5643 | $L_{A350}$ | $L_{B34}$ |
| III-5644 | $L_{A351}$ | $L_{B34}$ |
| III-5645 | $L_{A352}$ | $L_{B34}$ |
| III-5646 | $L_{A353}$ | $L_{B34}$ |
| III-5647 | $L_{A354}$ | $L_{B34}$ |
| III-5648 | $L_{A355}$ | $L_{B34}$ |
| III-5649 | $L_{A356}$ | $L_{B34}$ |
| III-5650 | $L_{A357}$ | $L_{B34}$ |
| III-5651 | $L_{A358}$ | $L_{B34}$ |
| III-5652 | $L_{A359}$ | $L_{B34}$ |
| III-5653 | $L_{A360}$ | $L_{B34}$ |
| III-5654 | $L_{A361}$ | $L_{B34}$ |
| III-5655 | $L_{A362}$ | $L_{B34}$ |
| III-5656 | $L_{A363}$ | $L_{B34}$ |
| III-5657 | $L_{A364}$ | $L_{B34}$ |
| III-5658 | $L_{A365}$ | $L_{B34}$ |
| III-5659 | $L_{A366}$ | $L_{B34}$ |
| III-5660 | $L_{A367}$ | $L_{B34}$ |
| III-5661 | $L_{A368}$ | $L_{B34}$ |
| III-5662 | $L_{A369}$ | $L_{B34}$ |
| III-5663 | $L_{A370}$ | $L_{B34}$ |
| III-5664 | $L_{A371}$ | $L_{B34}$ |
| III-5665 | $L_{A372}$ | $L_{B34}$ |
| III-5666 | $L_{A373}$ | $L_{B34}$ |
| III-5667 | $L_{A374}$ | $L_{B34}$ |
| III-5668 | $L_{A375}$ | $L_{B34}$ |
| III-5669 | $L_{A376}$ | $L_{B34}$ |
| III-5670 | $L_{A377}$ | $L_{B34}$ |
| III-5671 | $L_{A378}$ | $L_{B34}$ |
| III-5672 | $L_{A379}$ | $L_{B34}$ |
| III-5673 | $L_{A380}$ | $L_{B34}$ |
| III-5674 | $L_{A381}$ | $L_{B34}$ |
| III-5675 | $L_{A382}$ | $L_{B34}$ |
| III-5676 | $L_{A383}$ | $L_{B34}$ |
| III-5677 | $L_{A384}$ | $L_{B34}$ |
| III-5678 | $L_{A385}$ | $L_{B34}$ |
| III-5679 | $L_{A386}$ | $L_{B34}$ |
| III-5680 | $L_{A387}$ | $L_{B34}$ |
| III-5681 | $L_{A388}$ | $L_{B34}$ |
| III-5682 | $L_{A389}$ | $L_{B34}$ |
| III-5683 | $L_{A390}$ | $L_{B34}$ |
| III-5684 | $L_{A391}$ | $L_{B34}$ |
| III-5685 | $L_{A392}$ | $L_{B34}$ |
| III-5686 | $L_{A393}$ | $L_{B34}$ |
| III-5687 | $L_{A394}$ | $L_{B34}$ |
| III-5688 | $L_{A395}$ | $L_{B34}$ |
| III-5689 | $L_{A396}$ | $L_{B34}$ |
| III-5690 | $L_{A397}$ | $L_{B34}$ |
| III-5691 | $L_{A398}$ | $L_{B34}$ |
| III-5692 | $L_{A399}$ | $L_{B34}$ |
| III-5693 | $L_{A400}$ | $L_{B34}$ |
| III-5694 | $L_{A401}$ | $L_{B34}$ |
| III-5695 | $L_{A402}$ | $L_{B34}$ |
| III-5696 | $L_{A403}$ | $L_{B34}$ |
| III-5697 | $L_{A404}$ | $L_{B34}$ |
| III-5698 | $L_{A405}$ | $L_{B34}$ |
| III-5699 | $L_{A406}$ | $L_{B34}$ |
| III-5700 | $L_{A407}$ | $L_{B34}$ |
| III-5701 | $L_{A408}$ | $L_{B34}$ |
| III-5702 | $L_{A409}$ | $L_{B34}$ |
| III-5703 | $L_{A410}$ | $L_{B34}$ |
| III-5704 | $L_{A411}$ | $L_{B34}$ |
| III-5705 | $L_{A412}$ | $L_{B34}$ |
| III-5706 | $L_{A413}$ | $L_{B34}$ |
| III-5707 | $L_{A414}$ | $L_{B34}$ |
| III-5708 | $L_{A415}$ | $L_{B34}$ |
| III-5709 | $L_{A416}$ | $L_{B34}$ |
| III-5710 | $L_{A417}$ | $L_{B34}$ |
| III-5711 | $L_{A418}$ | $L_{B34}$ |
| III-5712 | $L_{A419}$ | $L_{B34}$ |
| III-5713 | $L_{A420}$ | $L_{B34}$ |
| III-5714 | $L_{A421}$ | $L_{B34}$ |
| III-5715 | $L_{A422}$ | $L_{B34}$ |
| III-5716 | $L_{A423}$ | $L_{B34}$ |
| III-5717 | $L_{A424}$ | $L_{B34}$ |

| Compound Number | $L_A$ | $L_B$ |
|---|---|---|
| III-5718 | $L_{A425}$ | $L_{B34}$ |
| III-5719 | $L_{A426}$ | $L_{B34}$ |
| III-5720 | $L_{A427}$ | $L_{B34}$ |
| III-5721 | $L_{A428}$ | $L_{B34}$ |
| III-5722 | $L_{A429}$ | $L_{B34}$ |
| III-5723 | $L_{A430}$ | $L_{B34}$ |
| III-5724 | $L_{A431}$ | $L_{B34}$ |
| III-5725 | $L_{A432}$ | $L_{B34}$ |
| III-5726 | $L_{A433}$ | $L_{B34}$ |
| III-5727 | $L_{A434}$ | $L_{B34}$ |
| III-5728 | $L_{A435}$ | $L_{B34}$ |
| III-5729 | $L_{A436}$ | $L_{B34}$ |
| III-5730 | $L_{A437}$ | $L_{B34}$ |
| III-5731 | $L_{A438}$ | $L_{B34}$ |
| III-5732 | $L_{A439}$ | $L_{B34}$ |
| III-5733 | $L_{A440}$ | $L_{B34}$ |
| III-5734 | $L_{A441}$ | $L_{B34}$ |
| III-5735 | $L_{A442}$ | $L_{B34}$ |
| III-5736 | $L_{A443}$ | $L_{B34}$ |
| III-5737 | $L_{A444}$ | $L_{B34}$ |
| III-5738 | $L_{A445}$ | $L_{B34}$ |
| III-5739 | $L_{A446}$ | $L_{B34}$ |
| III-5740 | $L_{A447}$ | $L_{B34}$ |
| III-5741 | $L_{A448}$ | $L_{B34}$ |
| III-5742 | $L_{A449}$ | $L_{B34}$ |
| III-5743 | $L_{A450}$ | $L_{B34}$ |
| III-5744 | $L_{A451}$ | $L_{B34}$ |
| III-5745 | $L_{A452}$ | $L_{B34}$ |
| III-5746 | $L_{A453}$ | $L_{B34}$ |
| III-5747 | $L_{A454}$ | $L_{B34}$ |
| III-5748 | $L_{A455}$ | $L_{B34}$ |
| III-5749 | $L_{A456}$ | $L_{B34}$ |
| III-5750 | $L_{A457}$ | $L_{B34}$ |
| III-5751 | $L_{A458}$ | $L_{B34}$ |
| III-5752 | $L_{A459}$ | $L_{B34}$ |
| III-5753 | $L_{A460}$ | $L_{B34}$ |
| III-5754 | $L_{A461}$ | $L_{B34}$ |
| III-5755 | $L_{A462}$ | $L_{B34}$ |
| III-5756 | $L_{A463}$ | $L_{B34}$ |
| III-5757 | $L_{A464}$ | $L_{B34}$ |
| III-5758 | $L_{A465}$ | $L_{B34}$ |
| III-5759 | $L_{A466}$ | $L_{B34}$ |
| III-5760 | $L_{A467}$ | $L_{B34}$ |
| III-5761 | $L_{A468}$ | $L_{B34}$ |
| III-5762 | $L_{A469}$ | $L_{B34}$ |
| III-5763 | $L_{A470}$ | $L_{B34}$ |
| III-5764 | $L_{A471}$ | $L_{B34}$ |
| III-5765 | $L_{A472}$ | $L_{B34}$ |
| III-5766 | $L_{A473}$ | $L_{B34}$ |
| III-5767 | $L_{A474}$ | $L_{B34}$ |
| III-5768 | $L_{A475}$ | $L_{B34}$ |
| III-5769 | $L_{A476}$ | $L_{B34}$ |
| III-5770 | $L_{A477}$ | $L_{B34}$ |
| III-5771 | $L_{A478}$ | $L_{B34}$ |
| III-5772 | $L_{A479}$ | $L_{B34}$ |
| III-5773 | $L_{A480}$ | $L_{B34}$ |
| III-5774 | $L_{A481}$ | $L_{B34}$ |
| III-5775 | $L_{A482}$ | $L_{B34}$ |
| III-5776 | $L_{A483}$ | $L_{B34}$ |
| III-5777 | $L_{A484}$ | $L_{B34}$ |
| III-5778 | $L_{A485}$ | $L_{B34}$ |
| III-5779 | $L_{A486}$ | $L_{B34}$ |
| III-5780 | $L_{A487}$ | $L_{B34}$ |
| III-5781 | $L_{A318}$ | $L_{B35}$ |
| III-5782 | $L_{A319}$ | $L_{B35}$ |
| III-5783 | $L_{A320}$ | $L_{B35}$ |
| III-5784 | $L_{A321}$ | $L_{B35}$ |
| III-5785 | $L_{A322}$ | $L_{B35}$ |
| III-5786 | $L_{A323}$ | $L_{B35}$ |
| III-5787 | $L_{A324}$ | $L_{B35}$ |
| III-5788 | $L_{A325}$ | $L_{B35}$ |
| III-5789 | $L_{A326}$ | $L_{B35}$ |
| III-5790 | $L_{A327}$ | $L_{B35}$ |
| III-5791 | $L_{A328}$ | $L_{B35}$ |
| III-5792 | $L_{A329}$ | $L_{B35}$ |
| III-5793 | $L_{A330}$ | $L_{B35}$ |
| III-5794 | $L_{A331}$ | $L_{B35}$ |
| III-5795 | $L_{A332}$ | $L_{B35}$ |
| III-5796 | $L_{A333}$ | $L_{B35}$ |
| III-5797 | $L_{A334}$ | $L_{B35}$ |
| III-5798 | $L_{A335}$ | $L_{B35}$ |
| III-5799 | $L_{A336}$ | $L_{B35}$ |
| III-5800 | $L_{A337}$ | $L_{B35}$ |
| III-5801 | $L_{A338}$ | $L_{B35}$ |
| III-5802 | $L_{A339}$ | $L_{B35}$ |
| III-5803 | $L_{A340}$ | $L_{B35}$ |
| III-5804 | $L_{A341}$ | $L_{B35}$ |
| III-5805 | $L_{A342}$ | $L_{B35}$ |
| III-5806 | $L_{A343}$ | $L_{B35}$ |
| III-5807 | $L_{A344}$ | $L_{B35}$ |
| III-5808 | $L_{A345}$ | $L_{B35}$ |
| III-5809 | $L_{A346}$ | $L_{B35}$ |
| III-5810 | $L_{A347}$ | $L_{B35}$ |
| III-5811 | $L_{A348}$ | $L_{B35}$ |
| III-5812 | $L_{A349}$ | $L_{B35}$ |
| III-5813 | $L_{A350}$ | $L_{B35}$ |
| III-5814 | $L_{A351}$ | $L_{B35}$ |
| III-5815 | $L_{A352}$ | $L_{B35}$ |
| III-5816 | $L_{A353}$ | $L_{B35}$ |
| III-5817 | $L_{A354}$ | $L_{B35}$ |
| III-5818 | $L_{A355}$ | $L_{B35}$ |
| III-5819 | $L_{A356}$ | $L_{B35}$ |
| III-5820 | $L_{A357}$ | $L_{B35}$ |
| III-5821 | $L_{A358}$ | $L_{B35}$ |
| III-5822 | $L_{A359}$ | $L_{B35}$ |
| III-5823 | $L_{A360}$ | $L_{B35}$ |
| III-5824 | $L_{A361}$ | $L_{B35}$ |
| III-5825 | $L_{A362}$ | $L_{B35}$ |
| III-5826 | $L_{A363}$ | $L_{B35}$ |
| III-5827 | $L_{A364}$ | $L_{B35}$ |
| III-5828 | $L_{A365}$ | $L_{B35}$ |
| III-5829 | $L_{A366}$ | $L_{B35}$ |
| III-5830 | $L_{A367}$ | $L_{B35}$ |
| III-5831 | $L_{A368}$ | $L_{B35}$ |
| III-5832 | $L_{A369}$ | $L_{B35}$ |
| III-5833 | $L_{A370}$ | $L_{B35}$ |
| III-5834 | $L_{A371}$ | $L_{B35}$ |
| III-5835 | $L_{A372}$ | $L_{B35}$ |
| III-5836 | $L_{A373}$ | $L_{B35}$ |
| III-5837 | $L_{A374}$ | $L_{B35}$ |
| III-5838 | $L_{A375}$ | $L_{B35}$ |
| III-5839 | $L_{A376}$ | $L_{B35}$ |
| III-5840 | $L_{A377}$ | $L_{B35}$ |
| III-5841 | $L_{A378}$ | $L_{B35}$ |
| III-5842 | $L_{A379}$ | $L_{B35}$ |
| III-5843 | $L_{A380}$ | $L_{B35}$ |
| III-5844 | $L_{A381}$ | $L_{B35}$ |
| III-5845 | $L_{A382}$ | $L_{B35}$ |
| III-5846 | $L_{A383}$ | $L_{B35}$ |
| III-5847 | $L_{A384}$ | $L_{B35}$ |
| III-5848 | $L_{A385}$ | $L_{B35}$ |
| III-5849 | $L_{A386}$ | $L_{B35}$ |
| III-5850 | $L_{A387}$ | $L_{B35}$ |
| III-5851 | $L_{A388}$ | $L_{B35}$ |
| III-5852 | $L_{A389}$ | $L_{B35}$ |
| III-5853 | $L_{A390}$ | $L_{B35}$ |
| III-5854 | $L_{A391}$ | $L_{B35}$ |
| III-5855 | $L_{A392}$ | $L_{B35}$ |
| III-5856 | $L_{A393}$ | $L_{B35}$ |
| III-5857 | $L_{A394}$ | $L_{B35}$ |
| III-5858 | $L_{A395}$ | $L_{B35}$ |
| III-5859 | $L_{A396}$ | $L_{B35}$ |
| III-5860 | $L_{A397}$ | $L_{B35}$ |
| III-5861 | $L_{A398}$ | $L_{B35}$ |
| III-5862 | $L_{A399}$ | $L_{B35}$ |
| III-5863 | $L_{A400}$ | $L_{B35}$ |
| III-5864 | $L_{A401}$ | $L_{B35}$ |
| III-5865 | $L_{A402}$ | $L_{B35}$ |
| III-5866 | $L_{A403}$ | $L_{B35}$ |
| III-5867 | $L_{A404}$ | $L_{B35}$ |
| III-5868 | $L_{A405}$ | $L_{B35}$ |
| III-5869 | $L_{A406}$ | $L_{B35}$ |

-continued

| Compound Number | $L_A$ | $L_B$ |
|---|---|---|
| III-5870 | $L_{A407}$ | $L_{B35}$ |
| III-5871 | $L_{A408}$ | $L_{B35}$ |
| III-5872 | $L_{A409}$ | $L_{B35}$ |
| III-5873 | $L_{A410}$ | $L_{B35}$ |
| III-5874 | $L_{A411}$ | $L_{B35}$ |
| III-5875 | $L_{A412}$ | $L_{B35}$ |
| III-5876 | $L_{A413}$ | $L_{B35}$ |
| III-5877 | $L_{A414}$ | $L_{B35}$ |
| III-5878 | $L_{A415}$ | $L_{B35}$ |
| III-5879 | $L_{A416}$ | $L_{B35}$ |
| III-5880 | $L_{A417}$ | $L_{B35}$ |
| III-5881 | $L_{A418}$ | $L_{B35}$ |
| III-5882 | $L_{A419}$ | $L_{B35}$ |
| III-5883 | $L_{A420}$ | $L_{B35}$ |
| III-5884 | $L_{A421}$ | $L_{B35}$ |
| III-5885 | $L_{A422}$ | $L_{B35}$ |
| III-5886 | $L_{A423}$ | $L_{B35}$ |
| III-5887 | $L_{A424}$ | $L_{B35}$ |
| III-5888 | $L_{A425}$ | $L_{B35}$ |
| III-5889 | $L_{A426}$ | $L_{B35}$ |
| III-5890 | $L_{A427}$ | $L_{B35}$ |
| III-5891 | $L_{A428}$ | $L_{B35}$ |
| III-5892 | $L_{A429}$ | $L_{B35}$ |
| III-5893 | $L_{A430}$ | $L_{B35}$ |
| III-5894 | $L_{A431}$ | $L_{B35}$ |
| III-5895 | $L_{A432}$ | $L_{B35}$ |
| III-5896 | $L_{A433}$ | $L_{B35}$ |
| III-5897 | $L_{A434}$ | $L_{B35}$ |
| III-5898 | $L_{A435}$ | $L_{B35}$ |
| III-5899 | $L_{A436}$ | $L_{B35}$ |
| III-5900 | $L_{A437}$ | $L_{B35}$ |
| III-5901 | $L_{A438}$ | $L_{B35}$ |
| III-5902 | $L_{A439}$ | $L_{B35}$ |
| III-5903 | $L_{A440}$ | $L_{B35}$ |
| III-5904 | $L_{A441}$ | $L_{B35}$ |
| III-5905 | $L_{A442}$ | $L_{B35}$ |
| III-5906 | $L_{A443}$ | $L_{B35}$ |
| III-5907 | $L_{A444}$ | $L_{B35}$ |
| III-5908 | $L_{A445}$ | $L_{B35}$ |
| III-5909 | $L_{A446}$ | $L_{B35}$ |
| III-5910 | $L_{A447}$ | $L_{B35}$ |
| III-5911 | $L_{A448}$ | $L_{B35}$ |
| III-5912 | $L_{A449}$ | $L_{B35}$ |
| III-5913 | $L_{A450}$ | $L_{B35}$ |
| III-5914 | $L_{A451}$ | $L_{B35}$ |
| III-5915 | $L_{A452}$ | $L_{B35}$ |
| III-5916 | $L_{A453}$ | $L_{B35}$ |
| III-5917 | $L_{A454}$ | $L_{B35}$ |
| III-5918 | $L_{A455}$ | $L_{B35}$ |
| III-5919 | $L_{A456}$ | $L_{B35}$ |
| III-5920 | $L_{A457}$ | $L_{B35}$ |
| III-5921 | $L_{A458}$ | $L_{B35}$ |
| III-5922 | $L_{A459}$ | $L_{B35}$ |
| III-5923 | $L_{A460}$ | $L_{B35}$ |
| III-5924 | $L_{A461}$ | $L_{B35}$ |
| III-5925 | $L_{A462}$ | $L_{B35}$ |
| III-5926 | $L_{A463}$ | $L_{B35}$ |
| III-5927 | $L_{A464}$ | $L_{B35}$ |
| III-5928 | $L_{A465}$ | $L_{B35}$ |
| III-5929 | $L_{A466}$ | $L_{B35}$ |
| III-5930 | $L_{A467}$ | $L_{B35}$ |
| III-5931 | $L_{A468}$ | $L_{B35}$ |
| III-5932 | $L_{A469}$ | $L_{B35}$ |
| III-5933 | $L_{A470}$ | $L_{B35}$ |
| III-5934 | $L_{A471}$ | $L_{B35}$ |
| III-5935 | $L_{A472}$ | $L_{B35}$ |
| III-5936 | $L_{A473}$ | $L_{B35}$ |
| III-5937 | $L_{A474}$ | $L_{B35}$ |
| III-5938 | $L_{A475}$ | $L_{B35}$ |
| III-5939 | $L_{A476}$ | $L_{B35}$ |
| III-5940 | $L_{A477}$ | $L_{B35}$ |
| III-5941 | $L_{A478}$ | $L_{B35}$ |
| III-5942 | $L_{A479}$ | $L_{B35}$ |
| III-5943 | $L_{A480}$ | $L_{B35}$ |
| III-5944 | $L_{A481}$ | $L_{B35}$ |
| III-5945 | $L_{A482}$ | $L_{B35}$ |
| III-5946 | $L_{A483}$ | $L_{B35}$ |
| III-5947 | $L_{A484}$ | $L_{B35}$ |
| III-5948 | $L_{A485}$ | $L_{B35}$ |
| III-5949 | $L_{A486}$ | $L_{B35}$ |
| III-5950 | $L_{A487}$ | $L_{B35}$ |
| III-5951 | $L_{A318}$ | $L_{B36}$ |
| III-5952 | $L_{A319}$ | $L_{B36}$ |
| III-5953 | $L_{A320}$ | $L_{B36}$ |
| III-5954 | $L_{A321}$ | $L_{B36}$ |
| III-5955 | $L_{A322}$ | $L_{B36}$ |
| III-5956 | $L_{A323}$ | $L_{B36}$ |
| III-5957 | $L_{A324}$ | $L_{B36}$ |
| III-5958 | $L_{A325}$ | $L_{B36}$ |
| III-5959 | $L_{A326}$ | $L_{B36}$ |
| III-5960 | $L_{A327}$ | $L_{B36}$ |
| III-5961 | $L_{A328}$ | $L_{B36}$ |
| III-5962 | $L_{A329}$ | $L_{B36}$ |
| III-5963 | $L_{A330}$ | $L_{B36}$ |
| III-5964 | $L_{A331}$ | $L_{B36}$ |
| III-5965 | $L_{A332}$ | $L_{B36}$ |
| III-5966 | $L_{A333}$ | $L_{B36}$ |
| III-5967 | $L_{A334}$ | $L_{B36}$ |
| III-5968 | $L_{A335}$ | $L_{B36}$ |
| III-5969 | $L_{A336}$ | $L_{B36}$ |
| III-5970 | $L_{A337}$ | $L_{B36}$ |
| III-5971 | $L_{A338}$ | $L_{B36}$ |
| III-5972 | $L_{A339}$ | $L_{B36}$ |
| III-5973 | $L_{A340}$ | $L_{B36}$ |
| III-5974 | $L_{A341}$ | $L_{B36}$ |
| III-5975 | $L_{A342}$ | $L_{B36}$ |
| III-5976 | $L_{A343}$ | $L_{B36}$ |
| III-5977 | $L_{A344}$ | $L_{B36}$ |
| III-5978 | $L_{A345}$ | $L_{B36}$ |
| III-5979 | $L_{A346}$ | $L_{B36}$ |
| III-5980 | $L_{A347}$ | $L_{B36}$ |
| III-5981 | $L_{A348}$ | $L_{B36}$ |
| III-5982 | $L_{A349}$ | $L_{B36}$ |
| III-5983 | $L_{A350}$ | $L_{B36}$ |
| III-5984 | $L_{A351}$ | $L_{B36}$ |
| III-5985 | $L_{A352}$ | $L_{B36}$ |
| III-5986 | $L_{A353}$ | $L_{B36}$ |
| III-5987 | $L_{A354}$ | $L_{B36}$ |
| III-5988 | $L_{A355}$ | $L_{B36}$ |
| III-5989 | $L_{A356}$ | $L_{B36}$ |
| III-5990 | $L_{A357}$ | $L_{B36}$ |
| III-5991 | $L_{A358}$ | $L_{B36}$ |
| III-5992 | $L_{A359}$ | $L_{B36}$ |
| III-5993 | $L_{A360}$ | $L_{B36}$ |
| III-5994 | $L_{A361}$ | $L_{B36}$ |
| III-5995 | $L_{A362}$ | $L_{B36}$ |
| III-5996 | $L_{A363}$ | $L_{B36}$ |
| III-5997 | $L_{A364}$ | $L_{B36}$ |
| III-5998 | $L_{A365}$ | $L_{B36}$ |
| III-5999 | $L_{A366}$ | $L_{B36}$ |
| III-6000 | $L_{A367}$ | $L_{B36}$ |
| III-6001 | $L_{A368}$ | $L_{B36}$ |
| III-6002 | $L_{A369}$ | $L_{B36}$ |
| III-6003 | $L_{A370}$ | $L_{B36}$ |
| III-6004 | $L_{A371}$ | $L_{B36}$ |
| III-6005 | $L_{A372}$ | $L_{B36}$ |
| III-6006 | $L_{A373}$ | $L_{B36}$ |
| III-6007 | $L_{A374}$ | $L_{B36}$ |
| III-6008 | $L_{A375}$ | $L_{B36}$ |
| III-6009 | $L_{A376}$ | $L_{B36}$ |
| III-6010 | $L_{A377}$ | $L_{B36}$ |
| III-6011 | $L_{A378}$ | $L_{B36}$ |
| III-6012 | $L_{A379}$ | $L_{B36}$ |
| III-6013 | $L_{A380}$ | $L_{B36}$ |
| III-6014 | $L_{A381}$ | $L_{B36}$ |
| III-6015 | $L_{A382}$ | $L_{B36}$ |
| III-6016 | $L_{A383}$ | $L_{B36}$ |
| III-6017 | $L_{A384}$ | $L_{B36}$ |
| III-6018 | $L_{A385}$ | $L_{B36}$ |
| III-6019 | $L_{A386}$ | $L_{B36}$ |
| III-6020 | $L_{A387}$ | $L_{B36}$ |
| III-6021 | $L_{A388}$ | $L_{B36}$ |

-continued

| Compound Number | $L_A$ | $L_B$ |
|---|---|---|
| III-6022 | $L_{A389}$ | $L_{B36}$ |
| III-6023 | $L_{A390}$ | $L_{B36}$ |
| III-6024 | $L_{A391}$ | $L_{B36}$ |
| III-6025 | $L_{A392}$ | $L_{B36}$ |
| III-6026 | $L_{A393}$ | $L_{B36}$ |
| III-6027 | $L_{A394}$ | $L_{B36}$ |
| III-6028 | $L_{A395}$ | $L_{B36}$ |
| III-6029 | $L_{A396}$ | $L_{B36}$ |
| III-6030 | $L_{A397}$ | $L_{B36}$ |
| III-6031 | $L_{A398}$ | $L_{B36}$ |
| III-6032 | $L_{A399}$ | $L_{B36}$ |
| III-6033 | $L_{A400}$ | $L_{B36}$ |
| III-6034 | $L_{A401}$ | $L_{B36}$ |
| III-6035 | $L_{A402}$ | $L_{B36}$ |
| III-6036 | $L_{A403}$ | $L_{B36}$ |
| III-6037 | $L_{A404}$ | $L_{B36}$ |
| III-6038 | $L_{A405}$ | $L_{B36}$ |
| III-6039 | $L_{A406}$ | $L_{B36}$ |
| III-6040 | $L_{A407}$ | $L_{B36}$ |
| III-6041 | $L_{A408}$ | $L_{B36}$ |
| III-6042 | $L_{A409}$ | $L_{B36}$ |
| III-6043 | $L_{A410}$ | $L_{B36}$ |
| III-6044 | $L_{A411}$ | $L_{B36}$ |
| III-6045 | $L_{A412}$ | $L_{B36}$ |
| III-6046 | $L_{A413}$ | $L_{B36}$ |
| III-6047 | $L_{A414}$ | $L_{B36}$ |
| III-6048 | $L_{A415}$ | $L_{B36}$ |
| III-6049 | $L_{A416}$ | $L_{B36}$ |
| III-6050 | $L_{A417}$ | $L_{B36}$ |
| III-6051 | $L_{A418}$ | $L_{B36}$ |
| III-6052 | $L_{A419}$ | $L_{B36}$ |
| III-6053 | $L_{A420}$ | $L_{B36}$ |
| III-6054 | $L_{A421}$ | $L_{B36}$ |
| III-6055 | $L_{A422}$ | $L_{B36}$ |
| III-6056 | $L_{A423}$ | $L_{B36}$ |
| III-6057 | $L_{A424}$ | $L_{B36}$ |
| III-6058 | $L_{A425}$ | $L_{B36}$ |
| III-6059 | $L_{A426}$ | $L_{B36}$ |
| III-6060 | $L_{A427}$ | $L_{B36}$ |
| III-6061 | $L_{A428}$ | $L_{B36}$ |
| III-6062 | $L_{A429}$ | $L_{B36}$ |
| III-6063 | $L_{A430}$ | $L_{B36}$ |
| III-6064 | $L_{A431}$ | $L_{B36}$ |
| III-6065 | $L_{A432}$ | $L_{B36}$ |
| III-6066 | $L_{A433}$ | $L_{B36}$ |
| III-6067 | $L_{A434}$ | $L_{B36}$ |
| III-6068 | $L_{A435}$ | $L_{B36}$ |
| III-6069 | $L_{A436}$ | $L_{B36}$ |
| III-6070 | $L_{A437}$ | $L_{B36}$ |
| III-6071 | $L_{A438}$ | $L_{B36}$ |
| III-6072 | $L_{A439}$ | $L_{B36}$ |
| III-6073 | $L_{A440}$ | $L_{B36}$ |
| III-6074 | $L_{A441}$ | $L_{B36}$ |
| III-6075 | $L_{A442}$ | $L_{B36}$ |
| III-6076 | $L_{A443}$ | $L_{B36}$ |
| III-6077 | $L_{A444}$ | $L_{B36}$ |
| III-6078 | $L_{A445}$ | $L_{B36}$ |
| III-6079 | $L_{A446}$ | $L_{B36}$ |
| III-6080 | $L_{A447}$ | $L_{B36}$ |
| III-6081 | $L_{A448}$ | $L_{B36}$ |
| III-6082 | $L_{A449}$ | $L_{B36}$ |
| III-6083 | $L_{A450}$ | $L_{B36}$ |
| III-6084 | $L_{A451}$ | $L_{B36}$ |
| III-6085 | $L_{A452}$ | $L_{B36}$ |
| III-6086 | $L_{A453}$ | $L_{B36}$ |
| III-6087 | $L_{A454}$ | $L_{B36}$ |
| III-6088 | $L_{A455}$ | $L_{B36}$ |
| III-6089 | $L_{A456}$ | $L_{B36}$ |
| III-6090 | $L_{A457}$ | $L_{B36}$ |
| III-6091 | $L_{A458}$ | $L_{B36}$ |
| III-6092 | $L_{A459}$ | $L_{B36}$ |
| III-6093 | $L_{A460}$ | $L_{B36}$ |
| III-6094 | $L_{A461}$ | $L_{B36}$ |
| III-6095 | $L_{A462}$ | $L_{B36}$ |
| III-6096 | $L_{A463}$ | $L_{B36}$ |
| III-6097 | $L_{A464}$ | $L_{B36}$ |

-continued

| Compound Number | $L_A$ | $L_B$ |
|---|---|---|
| III-6098 | $L_{A465}$ | $L_{B36}$ |
| III-6099 | $L_{A466}$ | $L_{B36}$ |
| III-6100 | $L_{A467}$ | $L_{B36}$ |
| III-6101 | $L_{A468}$ | $L_{B36}$ |
| III-6102 | $L_{A469}$ | $L_{B36}$ |
| III-6103 | $L_{A470}$ | $L_{B36}$ |
| III-6104 | $L_{A471}$ | $L_{B36}$ |
| III-6105 | $L_{A472}$ | $L_{B36}$ |
| III-6106 | $L_{A473}$ | $L_{B36}$ |
| III-6107 | $L_{A474}$ | $L_{B36}$ |
| III-6108 | $L_{A475}$ | $L_{B36}$ |
| III-6109 | $L_{A476}$ | $L_{B36}$ |
| III-6110 | $L_{A477}$ | $L_{B36}$ |
| III-6111 | $L_{A478}$ | $L_{B36}$ |
| III-6112 | $L_{A479}$ | $L_{B36}$ |
| III-6113 | $L_{A480}$ | $L_{B36}$ |
| III-6114 | $L_{A481}$ | $L_{B36}$ |
| III-6115 | $L_{A482}$ | $L_{B36}$ |
| III-6116 | $L_{A483}$ | $L_{B36}$ |
| III-6117 | $L_{A484}$ | $L_{B36}$ |
| III-6118 | $L_{A485}$ | $L_{B36}$ |
| III-6119 | $L_{A486}$ | $L_{B36}$ |
| III-6120 | $L_{A487}$ | $L_{B36}$ |
| III-6121 | $L_{A318}$ | $L_{B37}$ |
| III-6122 | $L_{A319}$ | $L_{B37}$ |
| III-6123 | $L_{A320}$ | $L_{B37}$ |
| III-6124 | $L_{A321}$ | $L_{B37}$ |
| III-6125 | $L_{A322}$ | $L_{B37}$ |
| III-6126 | $L_{A323}$ | $L_{B37}$ |
| III-6127 | $L_{A324}$ | $L_{B37}$ |
| III-6128 | $L_{A325}$ | $L_{B37}$ |
| III-6129 | $L_{A326}$ | $L_{B37}$ |
| III-6130 | $L_{A327}$ | $L_{B37}$ |
| III-6131 | $L_{A328}$ | $L_{B37}$ |
| III-6132 | $L_{A329}$ | $L_{B37}$ |
| III-6133 | $L_{A330}$ | $L_{B37}$ |
| III-6134 | $L_{A331}$ | $L_{B37}$ |
| III-6135 | $L_{A332}$ | $L_{B37}$ |
| III-6136 | $L_{A333}$ | $L_{B37}$ |
| III-6137 | $L_{A334}$ | $L_{B37}$ |
| III-6138 | $L_{A335}$ | $L_{B37}$ |
| III-6139 | $L_{A336}$ | $L_{B37}$ |
| III-6140 | $L_{A337}$ | $L_{B37}$ |
| III-6141 | $L_{A338}$ | $L_{B37}$ |
| III-6142 | $L_{A339}$ | $L_{B37}$ |
| III-6143 | $L_{A340}$ | $L_{B37}$ |
| III-6144 | $L_{A341}$ | $L_{B37}$ |
| III-6145 | $L_{A342}$ | $L_{B37}$ |
| III-6146 | $L_{A343}$ | $L_{B37}$ |
| III-6147 | $L_{A344}$ | $L_{B37}$ |
| III-6148 | $L_{A345}$ | $L_{B37}$ |
| III-6149 | $L_{A346}$ | $L_{B37}$ |
| III-6150 | $L_{A347}$ | $L_{B37}$ |
| III-6151 | $L_{A348}$ | $L_{B37}$ |
| III-6152 | $L_{A349}$ | $L_{B37}$ |
| III-6153 | $L_{A350}$ | $L_{B37}$ |
| III-6154 | $L_{A351}$ | $L_{B37}$ |
| III-6155 | $L_{A352}$ | $L_{B37}$ |
| III-6156 | $L_{A353}$ | $L_{B37}$ |
| III-6157 | $L_{A354}$ | $L_{B37}$ |
| III-6158 | $L_{A355}$ | $L_{B37}$ |
| III-6159 | $L_{A356}$ | $L_{B37}$ |
| III-6160 | $L_{A357}$ | $L_{B37}$ |
| III-6161 | $L_{A358}$ | $L_{B37}$ |
| III-6162 | $L_{A359}$ | $L_{B37}$ |
| III-6163 | $L_{A360}$ | $L_{B37}$ |
| III-6164 | $L_{A361}$ | $L_{B37}$ |
| III-6165 | $L_{A362}$ | $L_{B37}$ |
| III-6166 | $L_{A363}$ | $L_{B37}$ |
| III-6167 | $L_{A364}$ | $L_{B37}$ |
| III-6168 | $L_{A365}$ | $L_{B37}$ |
| III-6169 | $L_{A366}$ | $L_{B37}$ |
| III-6170 | $L_{A367}$ | $L_{B37}$ |
| III-6171 | $L_{A368}$ | $L_{B37}$ |
| III-6172 | $L_{A369}$ | $L_{B37}$ |
| III-6173 | $L_{A370}$ | $L_{B37}$ |

| Compound Number | $L_A$ | $L_B$ |
| --- | --- | --- |
| III-6174 | $L_{A371}$ | $L_{B37}$ |
| III-6175 | $L_{A372}$ | $L_{B37}$ |
| III-6176 | $L_{A373}$ | $L_{B37}$ |
| III-6177 | $L_{A374}$ | $L_{B37}$ |
| III-6178 | $L_{A375}$ | $L_{B37}$ |
| III-6179 | $L_{A376}$ | $L_{B37}$ |
| III-6180 | $L_{A377}$ | $L_{B37}$ |
| III-6181 | $L_{A378}$ | $L_{B37}$ |
| III-6182 | $L_{A379}$ | $L_{B37}$ |
| III-6183 | $L_{A380}$ | $L_{B37}$ |
| III-6184 | $L_{A381}$ | $L_{B37}$ |
| III-6185 | $L_{A382}$ | $L_{B37}$ |
| III-6186 | $L_{A383}$ | $L_{B37}$ |
| III-6187 | $L_{A384}$ | $L_{B37}$ |
| III-6188 | $L_{A385}$ | $L_{B37}$ |
| III-6189 | $L_{A386}$ | $L_{B37}$ |
| III-6190 | $L_{A387}$ | $L_{B37}$ |
| III-6191 | $L_{A388}$ | $L_{B37}$ |
| III-6192 | $L_{A389}$ | $L_{B37}$ |
| III-6193 | $L_{A390}$ | $L_{B37}$ |
| III-6194 | $L_{A391}$ | $L_{B37}$ |
| III-6195 | $L_{A392}$ | $L_{B37}$ |
| III-6196 | $L_{A393}$ | $L_{B37}$ |
| III-6197 | $L_{A394}$ | $L_{B37}$ |
| III-6198 | $L_{A395}$ | $L_{B37}$ |
| III-6199 | $L_{A396}$ | $L_{B37}$ |
| III-6200 | $L_{A397}$ | $L_{B37}$ |
| III-6201 | $L_{A398}$ | $L_{B37}$ |
| III-6202 | $L_{A399}$ | $L_{B37}$ |
| III-6203 | $L_{A400}$ | $L_{B37}$ |
| III-6204 | $L_{A401}$ | $L_{B37}$ |
| III-6205 | $L_{A402}$ | $L_{B37}$ |
| III-6206 | $L_{A403}$ | $L_{B37}$ |
| III-6207 | $L_{A404}$ | $L_{B37}$ |
| III-6208 | $L_{A405}$ | $L_{B37}$ |
| III-6209 | $L_{A406}$ | $L_{B37}$ |
| III-6210 | $L_{A407}$ | $L_{B37}$ |
| III-6211 | $L_{A408}$ | $L_{B37}$ |
| III-6212 | $L_{A409}$ | $L_{B37}$ |
| III-6213 | $L_{A410}$ | $L_{B37}$ |
| III-6214 | $L_{A411}$ | $L_{B37}$ |
| III-6215 | $L_{A412}$ | $L_{B37}$ |
| III-6216 | $L_{A413}$ | $L_{B37}$ |
| III-6217 | $L_{A414}$ | $L_{B37}$ |
| III-6218 | $L_{A415}$ | $L_{B37}$ |
| III-6219 | $L_{A416}$ | $L_{B37}$ |
| III-6220 | $L_{A417}$ | $L_{B37}$ |
| III-6221 | $L_{A418}$ | $L_{B37}$ |
| III-6222 | $L_{A419}$ | $L_{B37}$ |
| III-6223 | $L_{A420}$ | $L_{B37}$ |
| III-6224 | $L_{A421}$ | $L_{B37}$ |
| III-6225 | $L_{A422}$ | $L_{B37}$ |
| III-6226 | $L_{A423}$ | $L_{B37}$ |
| III-6227 | $L_{A424}$ | $L_{B37}$ |
| III-6228 | $L_{A425}$ | $L_{B37}$ |
| III-6229 | $L_{A426}$ | $L_{B37}$ |
| III-6230 | $L_{A427}$ | $L_{B37}$ |
| III-6231 | $L_{A428}$ | $L_{B37}$ |
| III-6232 | $L_{A429}$ | $L_{B37}$ |
| III-6233 | $L_{A430}$ | $L_{B37}$ |
| III-6234 | $L_{A431}$ | $L_{B37}$ |
| III-6235 | $L_{A432}$ | $L_{B37}$ |
| III-6236 | $L_{A433}$ | $L_{B37}$ |
| III-6237 | $L_{A434}$ | $L_{B37}$ |
| III-6238 | $L_{A435}$ | $L_{B37}$ |
| III-6239 | $L_{A436}$ | $L_{B37}$ |
| III-6240 | $L_{A437}$ | $L_{B37}$ |
| III-6241 | $L_{A438}$ | $L_{B37}$ |
| III-6242 | $L_{A439}$ | $L_{B37}$ |
| III-6243 | $L_{A440}$ | $L_{B37}$ |
| III-6244 | $L_{A441}$ | $L_{B37}$ |
| III-6245 | $L_{A442}$ | $L_{B37}$ |
| III-6246 | $L_{A443}$ | $L_{B37}$ |
| III-6247 | $L_{A444}$ | $L_{B37}$ |
| III-6248 | $L_{A445}$ | $L_{B37}$ |
| III-6249 | $L_{A446}$ | $L_{B37}$ |
| III-6250 | $L_{A447}$ | $L_{B37}$ |
| III-6251 | $L_{A448}$ | $L_{B37}$ |
| III-6252 | $L_{A449}$ | $L_{B37}$ |
| III-6253 | $L_{A450}$ | $L_{B37}$ |
| III-6254 | $L_{A451}$ | $L_{B37}$ |
| III-6255 | $L_{A452}$ | $L_{B37}$ |
| III-6256 | $L_{A453}$ | $L_{B37}$ |
| III-6257 | $L_{A454}$ | $L_{B37}$ |
| III-6258 | $L_{A455}$ | $L_{B37}$ |
| III-6259 | $L_{A456}$ | $L_{B37}$ |
| III-6260 | $L_{A457}$ | $L_{B37}$ |
| III-6261 | $L_{A458}$ | $L_{B37}$ |
| III-6262 | $L_{A459}$ | $L_{B37}$ |
| III-6263 | $L_{A460}$ | $L_{B37}$ |
| III-6264 | $L_{A461}$ | $L_{B37}$ |
| III-6265 | $L_{A462}$ | $L_{B37}$ |
| III-6266 | $L_{A463}$ | $L_{B37}$ |
| III-6267 | $L_{A464}$ | $L_{B37}$ |
| III-6268 | $L_{A465}$ | $L_{B37}$ |
| III-6269 | $L_{A466}$ | $L_{B37}$ |
| III-6270 | $L_{A467}$ | $L_{B37}$ |
| III-6271 | $L_{A468}$ | $L_{B37}$ |
| III-6272 | $L_{A469}$ | $L_{B37}$ |
| III-6273 | $L_{A470}$ | $L_{B37}$ |
| III-6274 | $L_{A471}$ | $L_{B37}$ |
| III-6275 | $L_{A472}$ | $L_{B37}$ |
| III-6276 | $L_{A473}$ | $L_{B37}$ |
| III-6277 | $L_{A474}$ | $L_{B37}$ |
| III-6278 | $L_{A475}$ | $L_{B37}$ |
| III-6279 | $L_{A476}$ | $L_{B37}$ |
| III-6280 | $L_{A477}$ | $L_{B37}$ |
| III-6281 | $L_{A478}$ | $L_{B37}$ |
| III-6282 | $L_{A479}$ | $L_{B37}$ |
| III-6283 | $L_{A480}$ | $L_{B37}$ |
| III-6284 | $L_{A481}$ | $L_{B37}$ |
| III-6285 | $L_{A482}$ | $L_{B37}$ |
| III-6286 | $L_{A483}$ | $L_{B37}$ |
| III-6287 | $L_{A484}$ | $L_{B37}$ |
| III-6288 | $L_{A485}$ | $L_{B37}$ |
| III-6289 | $L_{A486}$ | $L_{B37}$ |
| III-6290 | $L_{A487}$ | $L_{B37}$ |

In one embodiment, a first device comprising a first organic light emitting device is provided. The first device further comprises an anode, a cathode, and an organic layer, disposed between the anode and the cathode. The organic layer comprises a compound having the formula $Ir(L_A)_n(L_B)_{3-n}$, and having the structure according to Formula I and the variables as defined herein.

According to an embodiment, the organic layer of the first organic light emitting device comprises a compound having the formula $Ir(L_A)_n(L_B)_{3-n}$, and having the structure according to Formula III and the variables as defined herein.

In one embodiment, the first device is a consumer product. In one embodiment, the first device is an organic light-emitting device. In one embodiment, the first device comprises a lighting panel.

In another embodiment, the organic layer in the first organic light emitting device is an emissive layer and the compound is an emissive dopant. In one embodiment, the organic layer is an emissive layer and the compound is a non-emissive dopant.

In one embodiment, the organic layer further comprises a host. In one embodiment, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC-H_{2n+1}$, $Ar_1$, $Ar_1$-$Ar_2$, $C_nH_{2n}-Ar_1$, or no substitution, wherein n is from 1 to 10; and wherein $Ar_1$ and $Ar_2$ are independently selected from the group consisting of benzene, biphenyl, naphthalene, triphenylene, carbazole, and heteroaromatic analogs thereof In one embodiment, the host comprises at least one chemical group selected from the group consisting of carbazole, dibenzothiphene, dibenzofuran, dibenzoselenophene, azacarbazole, aza-dibenzothiophene, aza-dibenzofuran, and aza-dibenzoselenophene.

The "aza" designation in the fragments described above, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[fh]quinoxaline and dibenzo[fh]quinoline. One of ordinary skill in the art can readily envision other nitrogen analogs of the aza-derivatives described above, and all such analogs are intended to be encompassed by the terms as set forth herein.

In one embodiment, the host is selected from a group of compounds, the Host Group, consisting of:

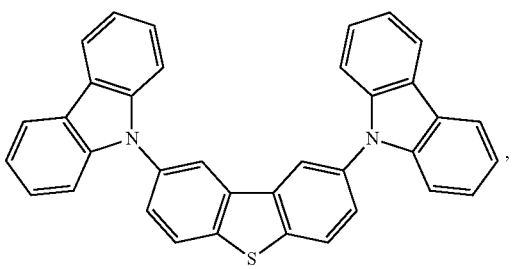

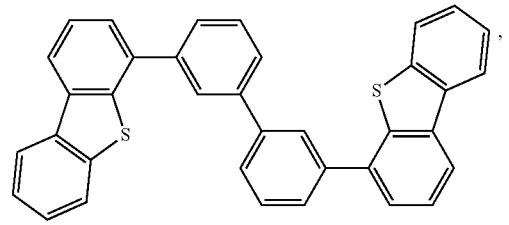

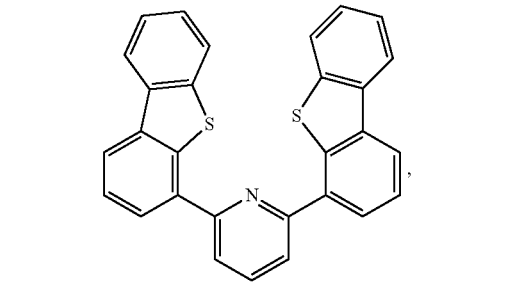

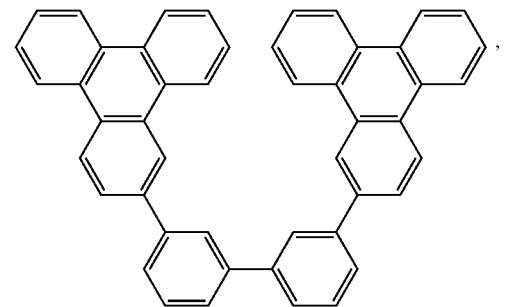

-continued

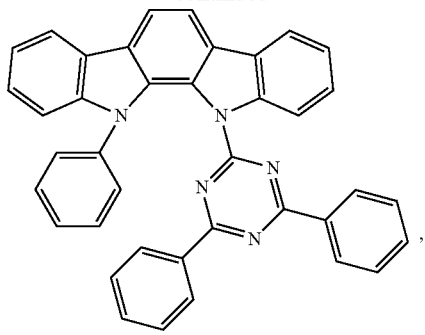

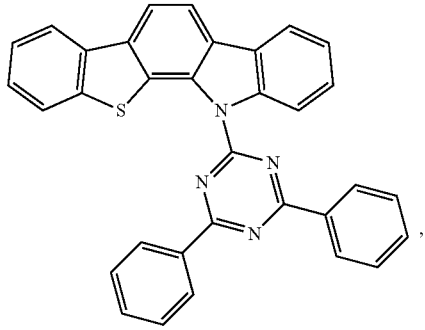 [SMILES: c1ccc(-c2nc(-c3ccccc3)nc(-n3c4ccccc4c4ccc5c6ccccc6sc5c43)n2)cc1]

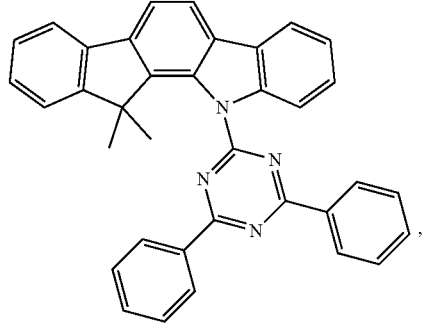

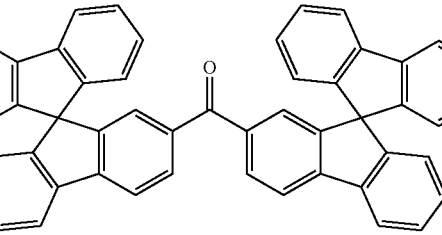

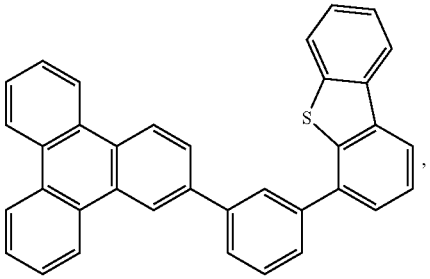

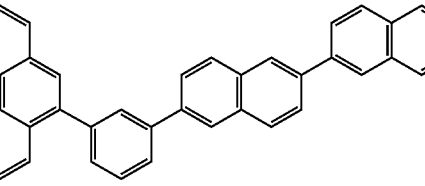

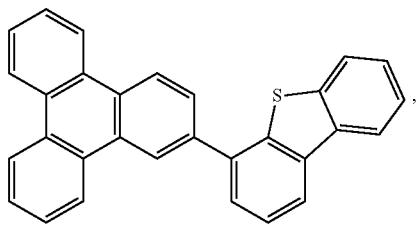

and combinations thereof.

In one embodiment, the host comprises a metal complex.

According to another aspect, the organic layer in the first device described above can comprise a compound having the formula $Ir(L_A)_n(L_B)_{3-n}$, having the structure according Formula II as defined above.

According to another aspect, a formulation comprising the compound of Formula I and/or Formula II is also within the scope of the present disclosure.

Device Examples

All example devices were fabricated by high vacuum ($<10^{-7}$ Torr) thermal evaporation. The anode electrode is 1200 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of the device examples consisted of sequentially, from the ITO surface, 100 Å of Compound A as the hole injection layer (HIL), 300 Å of 4,4'-bis[N-(1-naphthyl)-N-phenylamino]biphenyl (α-NPD) as the hole transporting layer (HTL), 300 Å of the invention compound doped in Compound B as a host with 7 wt % of the iridium phosphorescent compound as the emissive layer (EML), 50 Å of Compound B as a blocking layer (BL), 450 Å of tris-8-hydroxyquinoline aluminum (Alq) as the ETL. The comparative Example with Compound C was fabricated similarly to the Device Examples.

The device results and data from those devices are summarized in Tables 2 and 3. As used herein, NPD, Alq, Compounds A, B, and comparative Compound C, and the inventive compounds III-32, III-44, and III-74 have the following structures:

Compound B

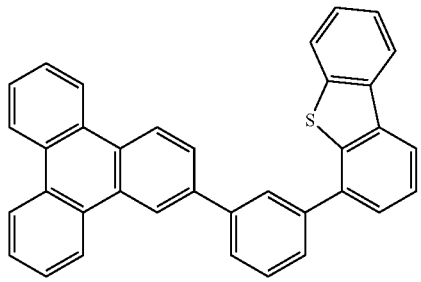

Compound A

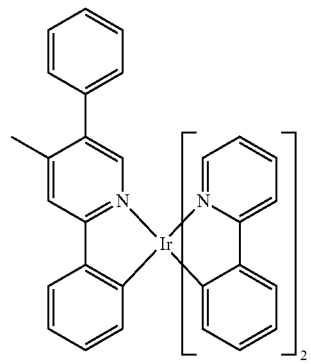

Compound C

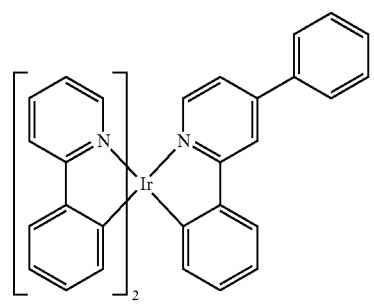

Compound III-32

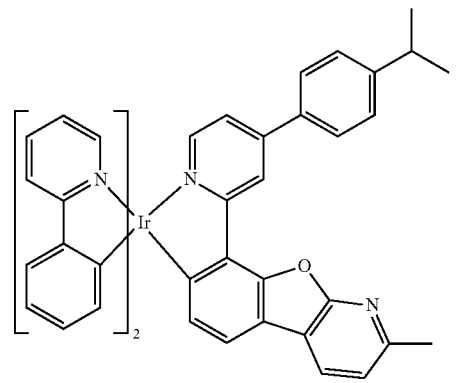

Compound III-44

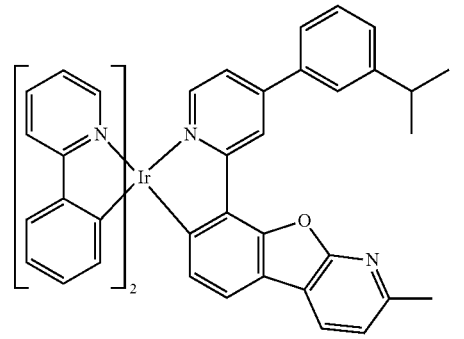

Compound III-74

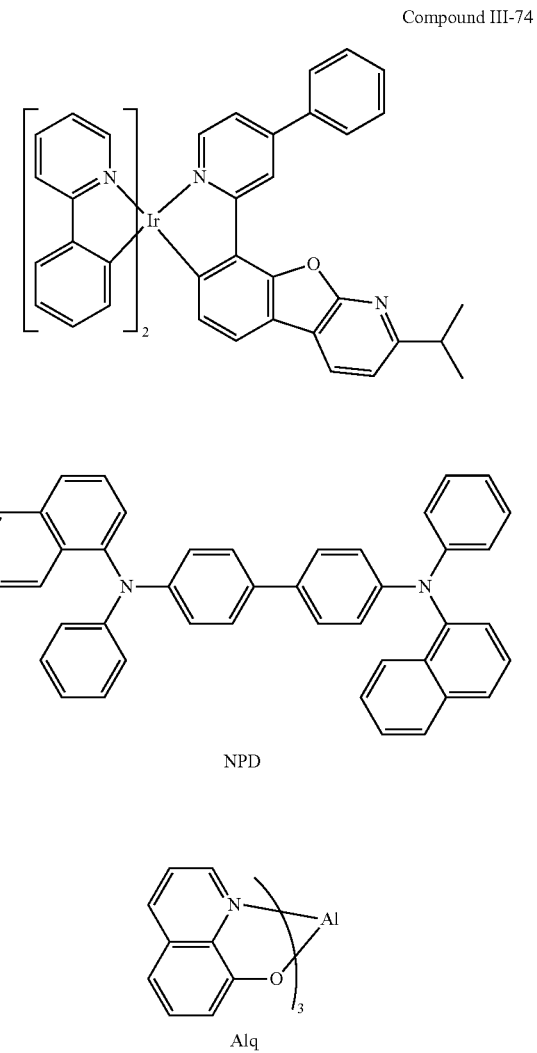

NPD

Alq

TABLE 2 device Structures of Inventive Compound and Comparative Compound

| Devices | HIL | HTL | EML (300 Å, doping %) | BL | ETL | | |
|---|---|---|---|---|---|---|---|
| Comparative Example 1 | Compound A 100 Å | NPD 300 Å | Compound B | Compound C 7% | Compound B 50 Å | Alq 450 Å | |
| Inventive Example 1 | Compound A 100 Å | NPD 300 Å | Compound B | Compound III-32 7% | Compound B 50 Å | Alq 450 Å | |
| Inventive Example 2 | Compound A 100 Å | NPD 300 Å | Compound B | Compound III-44, 7% | Compound B 50 Å | Alq 450 Å | |
| Inventive Example 3 | Compound A 100 Å | NPD 300 Å | Compound B | Compound III-74 7% | Compound B 50 Å | Alq 450 Å | |

TABLE 3

Device Results

| | At 10 mA/cm$^2$ | | | |
|---|---|---|---|---|
| Devices | CIE (x, y) | V | LE (cd/A) | EQE (%) |
| Comparative Example 1 | (0.43, 0.55) | 8.3 | 54.2 | 20.6 |
| Inventive Example 1 | (0.42, 0.57) | 8.3 | 73.6 | 27.7 |
| Inventive Example 2 | (0.43, 0.57) | 8.2 | 67.6 | 25.9 |
| Inventive Example 3 | (0.43, 0.56) | 8.5 | 63.4 | 23.3 |

Table 3 summarizes the performance of the devices. The CIE color coordinate, driving voltage (V), luminous efficiency (LE) were measured at a fixed current density, 10 mA/cm$^2$. According to the CIE color coordinate, all example devices were yellow emitting but the inventive device Examples 1, 2, and 3 exhibited better efficiencies than the comparative device Example 1 in term of LE (63.4~73.6 cd/A vs 54.2 cd/A) and EQE (23.3~27.7% vs 20.6%).

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as MoO$_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

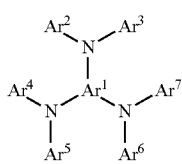

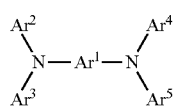

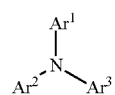

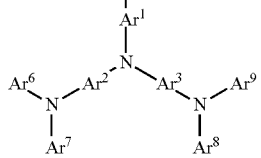

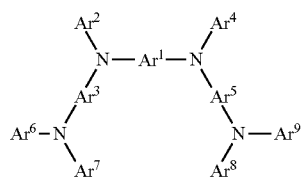

Each of Ar$^1$ to Ar$^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, Ar$^1$ to Ar$^9$ is independently selected from the group consisting of:

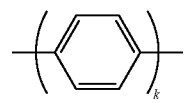

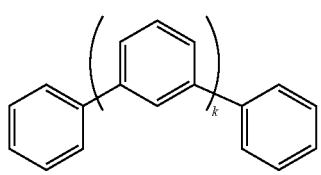

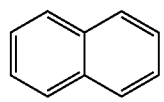

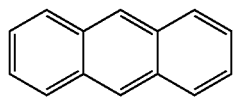

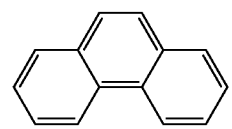

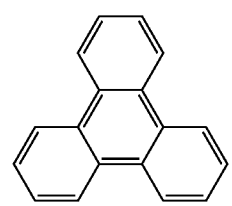 [SMILES: c1ccc2c(c1)c1ccccc1c1ccccc21]

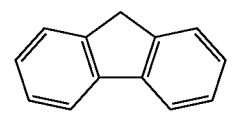 [SMILES: c1ccc2c(c1)Cc1ccccc1-2]

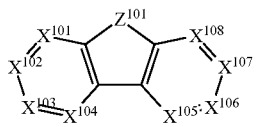

k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

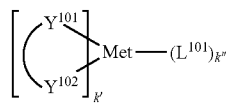

Met is a metal; ($Y^{101}$-$Y^{102}$) is a bidentate ligand, $Y^{101}$ and $Y^{102}$ are independently selected from C, N, O, P, and S; $L^{101}$ is another ligand; k' is an integer value from 1 to the maximum number of ligands that may be attached to the metal; and k'+k'' is the maximum number of ligands that may be attached to the metal.

In one aspect, ($Y^{101}$-$Y^{102}$) is a 2-phenylpyridine derivative.
In another aspect, ($Y^{101}$-$Y^{102}$) is a carbene ligand.
In another aspect, Met is selected from Ir, Pt, Os, and Zn.
In a further aspect, the metal complex has a smallest oxidation potential in solution vs. $Fc^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table 4 below categorizes host materials as preferred for devices that emit various colors, any host material may be used with any dopant so long as the triplet criteria is satisfied.

Examples of metal complexes used as host are preferred to have the following general formula:

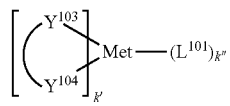

Met is a metal; ($Y^{103}$-$Y^{104}$) is a bidentate ligand, $Y^{103}$ and $Y^{104}$ are independently selected from C, N, O, P, and S; $L^{101}$ is another ligand; k' is an integer value from 1 to the maximum number of ligands that may be attached to the metal; and k'+k'' is the maximum number of ligands that may be attached to the metal.

In one aspect, the metal complexes are:

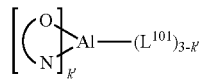

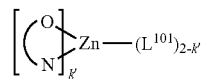

(O—N) is a bidentate ligand, having metal coordinated to atoms O and N.

In another aspect, Met is selected from Ir and Pt.

In a further aspect, ($Y^{103}$-$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

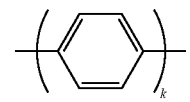

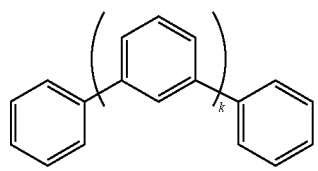

153                                    154
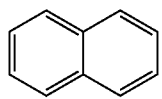
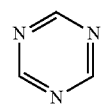
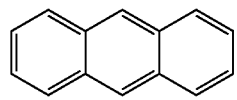 [SMILES: c1ccc2cc3ccccc3cc2c1]
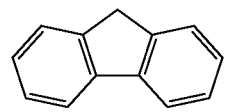
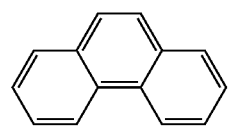
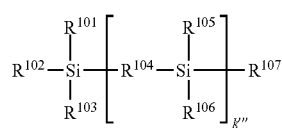
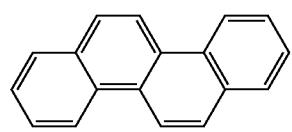
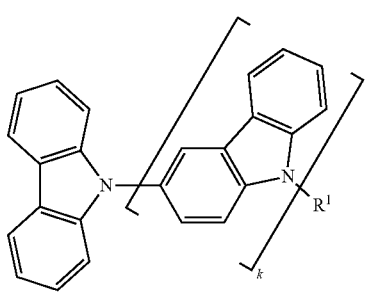
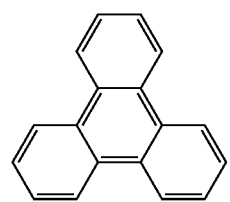 [SMILES: c1ccc2c(c1)c1ccccc1c1ccccc21]
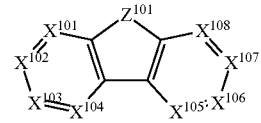
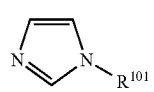
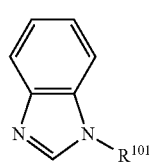
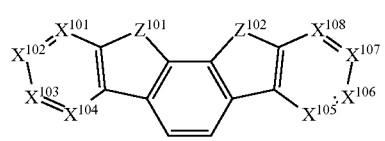
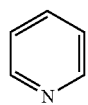
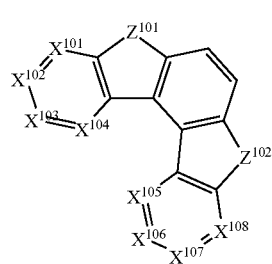

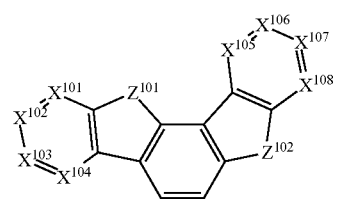

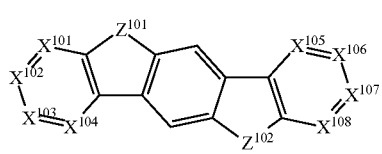

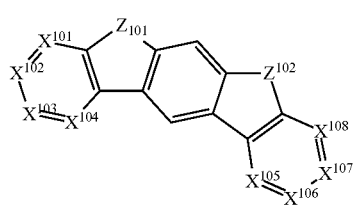

R$^{101}$ to R$^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 1 to 20; k''' is an integer from 0 to 20.

X$^{101}$ to X$^{108}$ is selected from C (including CH) or N.

Z$^{101}$ and Z$^{102}$ is selected from NR$^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

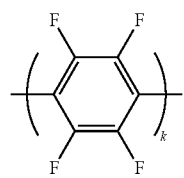

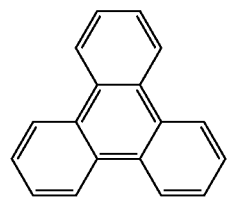 [SMILES: c1ccc2c(c1)c1ccccc1c1ccccc21]

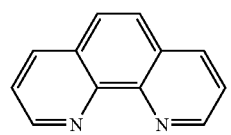 [SMILES: c1cnc2c(c1)ccc1cccnc12]

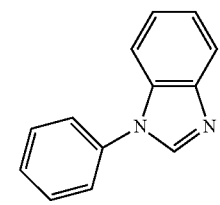 [SMILES: c1ccc(-n2cnc3ccccc32)cc1]

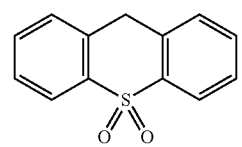 [SMILES: O=S1(=O)c2ccccc2Cc2ccccc21]

k is an integer from 1 to 20; L$^{101}$ is another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

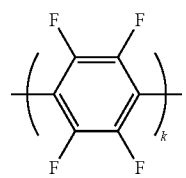

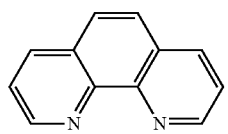 [SMILES: c1cnc2c(c1)ccc1cccnc12]

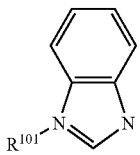

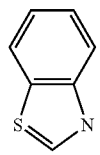

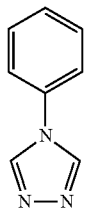 [SMILES: c1ccc(-n2cnnc2)cc1]

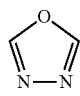

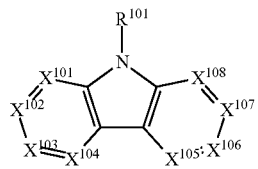

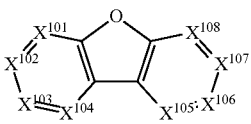

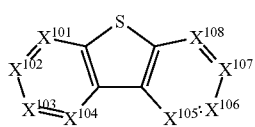

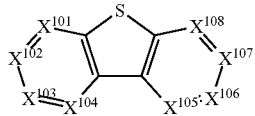

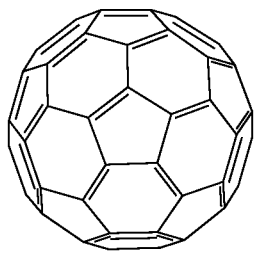

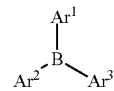

$R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 1 to 20.

$X^{101}$ to $X^{108}$ is selected from C (including CH) or N.

In another aspect, the metal complexes used in ETL contains, but not limit to the following general formula:

$$\left[\left(\begin{array}{c}O\\N\end{array}\right)Al\right]_{k'}-(L^{101})_{3-k'}$$

$$\left[\left(\begin{array}{c}O\\N\end{array}\right)Be\right]_{k'}-(L^{101})_{2-k'}$$

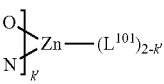

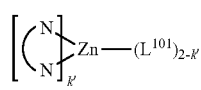

(O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table 4 below. Table 4 lists non-limiting classes of materials, non-limiting examples of compounds for each class, and references that disclose the materials.

TABLE 4

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | | Synth. Met. 87, 171 (1997) WO2007002683 |

TABLE 4-continued

| MATERIAL | EXAMPLES OF MATERIAL | PUBLICATIONS |
| --- | --- | --- |
| Phosphonic acid and sliane SAMs | | US20030162053 |
| Triarylamine or polythiophene polymers with conductivity dopants | | EP1725079A1 |
| Organic compounds with conductive inorganic compounds, such as molybdenum and tungsten oxides | | US20050123751<br>SID Symposium Digest, 37, 923 (2006)<br>WO2009018009 |

TABLE 4-continued
| MATERIAL | EXAMPLES OF MATERIAL | PUBLICATIONS |
| --- | --- | --- |
| n-type semiconducting organic complexes | | US20020158242 |
| Metal organometallic complexes | | US20060240279 |
| Cross-linkable compounds | | US20080220265 |
| Polythiophene based polymers and copolymers | 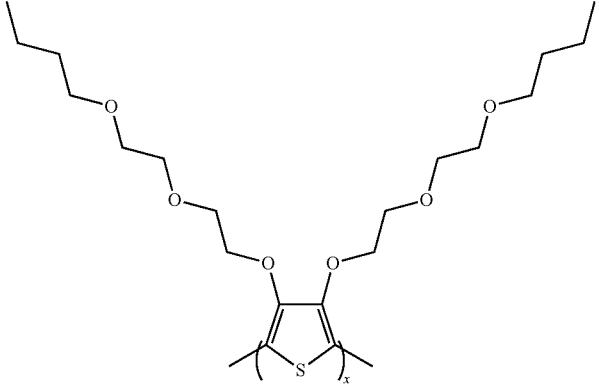 | WO 2011075644 EP2350216 |
| Hole transporting materials | | |
| Triarylamines (e.g., TPD, α-NPD) | 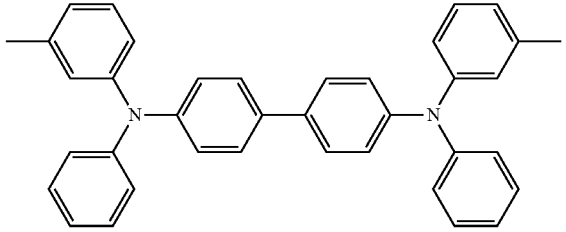 | Appl. Phys. Lett. 51, 913 (1987) |
| | 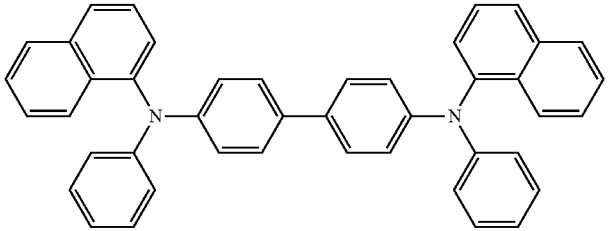 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 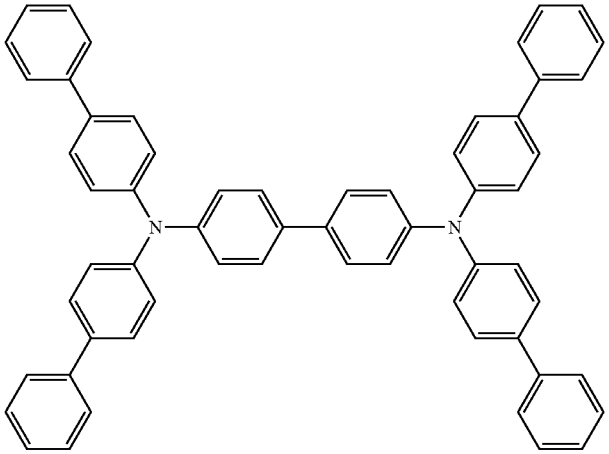 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |

TABLE 4-continued
| MATERIAL | EXAMPLES OF MATERIAL | PUBLICATIONS |
|---|---|---|
| | 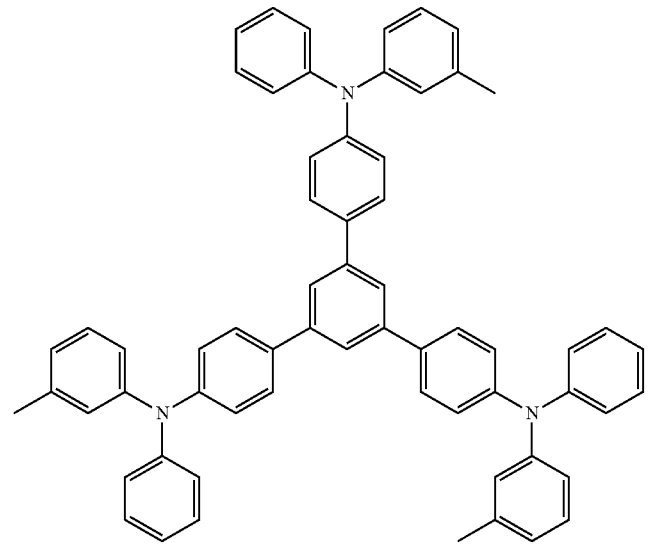 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 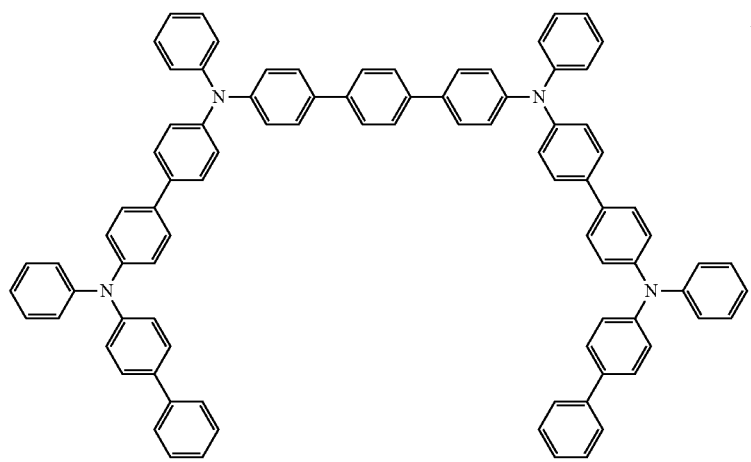 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |
| | 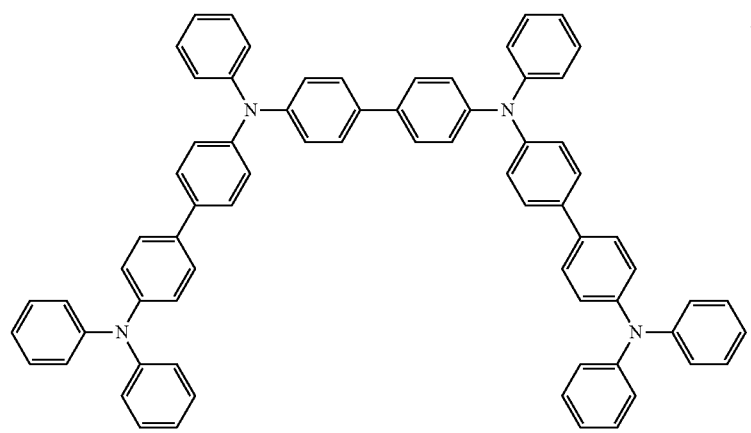 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |

TABLE 4-continued

| MATERIAL | EXAMPLES OF MATERIAL | PUBLICATIONS |
| --- | --- | --- |
| Triaylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |
| Indolocarbazoles | | Synth. Met. 111, 421 (2000) |

TABLE 4-continued

| MATERIAL | EXAMPLES OF MATERIAL | PUBLICATIONS |
| --- | --- | --- |
| Isoindole compounds | | Chem. Mater. 15, 3148 (2003) |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |
| Metal 8-hydroxyquinolates (e.g., Alq₃, BAlq) | | Nature 395, 151 (1998) |
| | | US20060202194 |

TABLE 4-continued

| MATERIAL | EXAMPLES OF MATERIAL | PUBLICATIONS |
|---|---|---|
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

TABLE 4-continued
| MATERIAL | EXAMPLES OF MATERIAL | PUBLICATIONS |
|---|---|---|
| | Green hosts | |
| Arylcarbazoles | 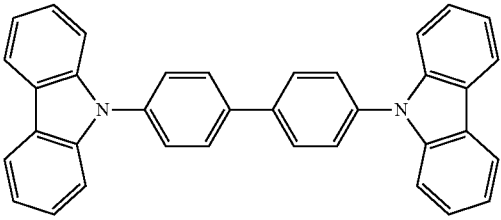 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 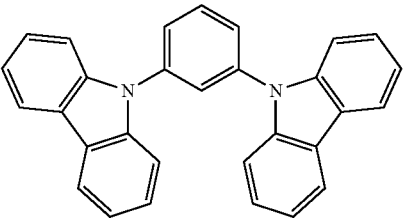 [SMILES: c1cc(-n2c3ccccc3c3ccccc32)cc(-n2c3ccccc3c3ccccc32)c1] | US20030175553 |
| | 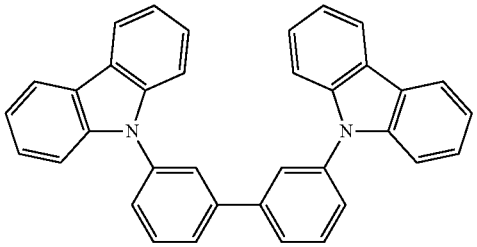 [SMILES: c1cc(-c2cccc(-n3c4ccccc4c4ccccc43)c2)cc(-n2c3ccccc3c3ccccc32)c1] | WO2001039234 |
| Aryltriphenylene compounds | 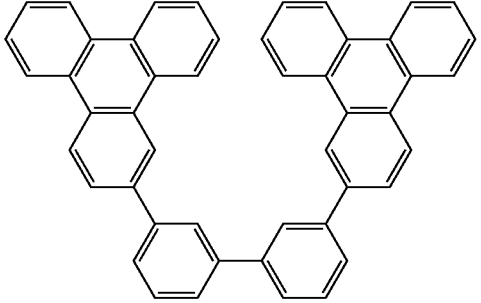 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 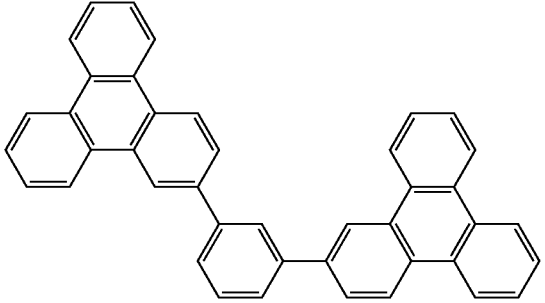 [SMILES: c1cc(-c2ccc3c4ccccc4c4ccccc4c3c2)cc(-c2ccc3c4ccccc4c4ccccc4c3c2)c1] | US20060280965 |
| | 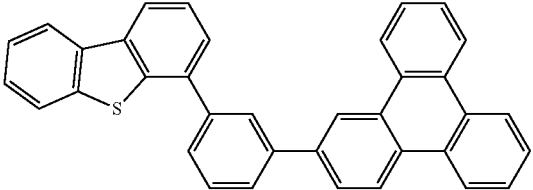 [SMILES: c1cc(-c2ccc3c4ccccc4c4ccccc4c3c2)cc(-c2cccc3c2sc2ccccc23)c1] | WO2009021126 |

TABLE 4-continued
| MATERIAL | EXAMPLES OF MATERIAL | PUBLICATIONS |
|---|---|---|
| Poly-fused heteroaryl compounds | 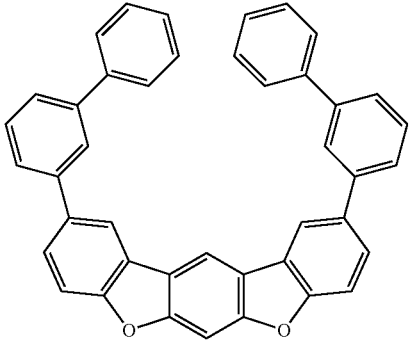 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type/ molecules | 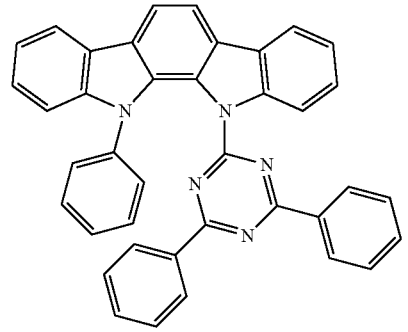 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 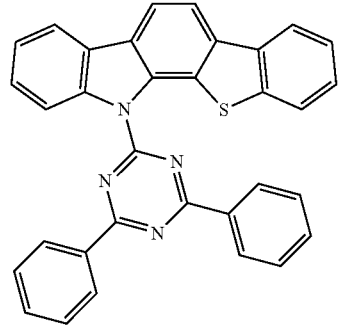 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 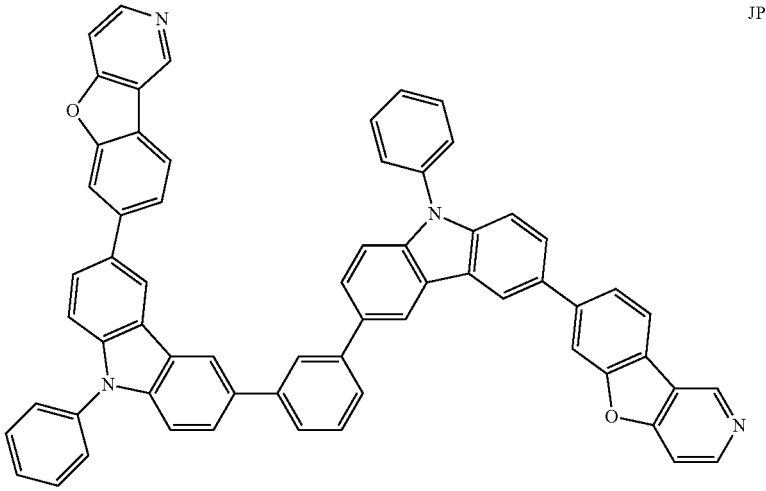 | JP2008074939 |

TABLE 4-continued
| MATERIAL | EXAMPLES OF MATERIAL | PUBLICATIONS |
|---|---|---|
| | 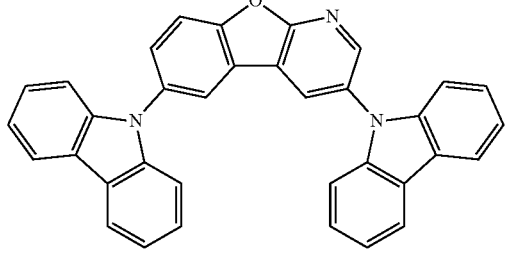 | US20100187984 |
| Polymers (e.g., PVK) | 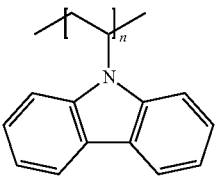 | Appl. Phys. Lett. 77, 2280 (2000) |
| Spirofluorene compounds | 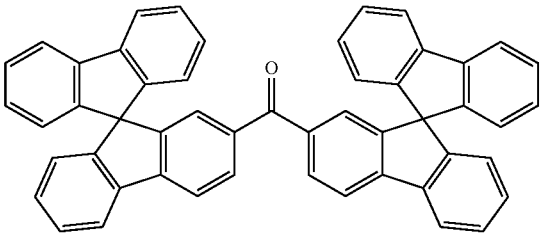 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 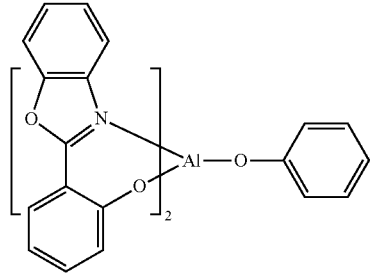 | WO2005089025 |
| | 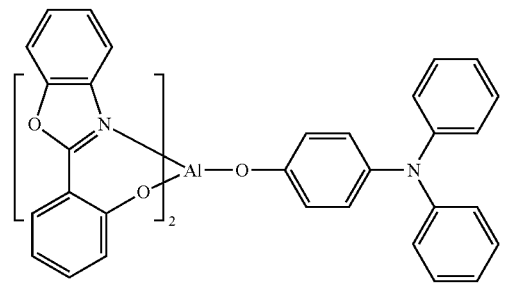 | WO2006132173 |
| | 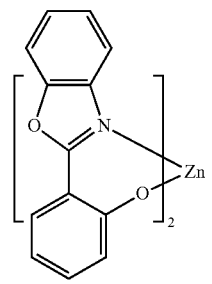 | JP200511610 |

TABLE 4-continued

| MATERIAL | EXAMPLES OF MATERIAL | PUBLICATIONS |
|---|---|---|
| Spirofluorene-carbazole compounds | | JP2007254297 |
| | | JP2007254297 |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |

| MATERIAL | EXAMPLES OF MATERIAL | PUBLICATIONS |
|---|---|---|
| | 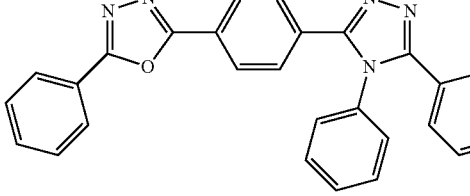 | WO2004107822 |
| Tetraphenylene complexes | 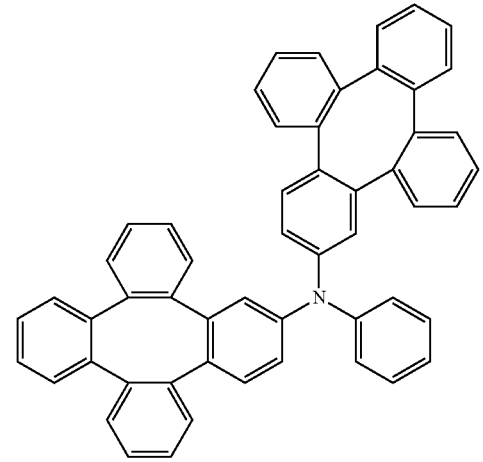 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 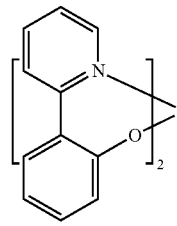 | WO2005030900 |
| Metal coordination complexes (e.g., Zn, Al with N^N ligands) | 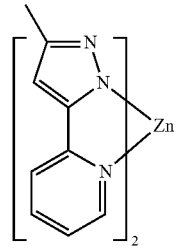 | US20040137268, US20040137267 |
Blue hosts
| Arylcarbazoles | 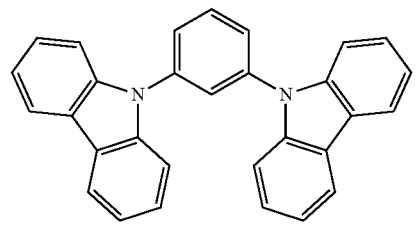 [SMILES: c1cc(-n2c3ccccc3c3ccccc32)cc(-n2c3ccccc3c3ccccc32)c1] | Appl. Phys. Lett, 82, 2422 (2003) |

TABLE 4-continued
| MATERIAL | EXAMPLES OF MATERIAL | PUBLICATIONS |
|---|---|---|
| | 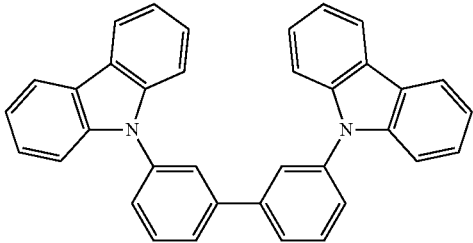 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofuran-carbazole compounds | 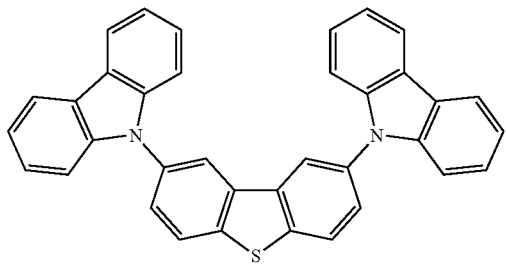 [SMILES: c1ccc2c(c1)c1ccccc1n2-c1ccc2sc3ccc(-n4c5ccccc5c5ccccc54)cc3c2c1] | WO2006114966, US20090167162 |
| | 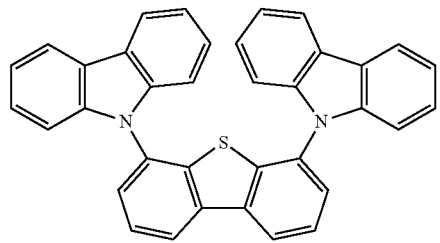 [SMILES: c1cc(-n2c3ccccc3c3ccccc32)c2sc3c(-n4c5ccccc5c5ccccc54)cccc3c2c1] | US20090167162 |
| | 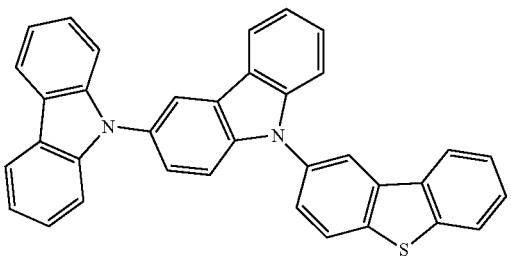 [SMILES: c1ccc2c(c1)sc1ccc(-n3c4ccccc4c4cc(-n5c6ccccc6c6ccccc65)ccc43)cc12] | WO2009086028 |
| | 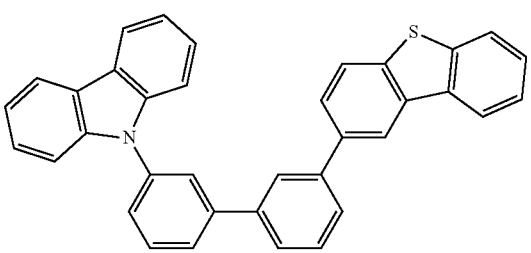 [SMILES: c1cc(-c2cccc(-n3c4ccccc4c4ccccc43)c2)cc(-c2ccc3sc4ccccc4c3c2)c1] | US20090030202, US20090017330 |
| | 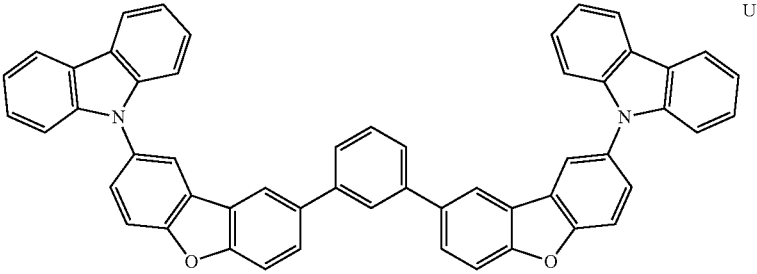 | US20100084966 |

TABLE 4-continued
| MATERIAL | EXAMPLES OF MATERIAL | PUBLICATIONS |
|---|---|---|
| Silicon aryl compounds | 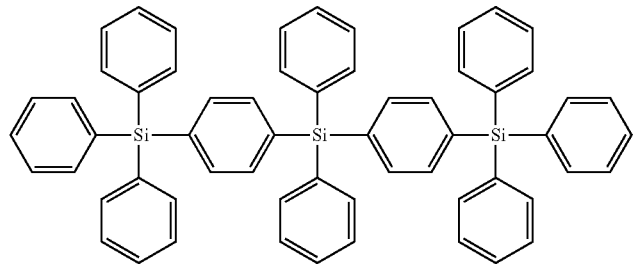 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 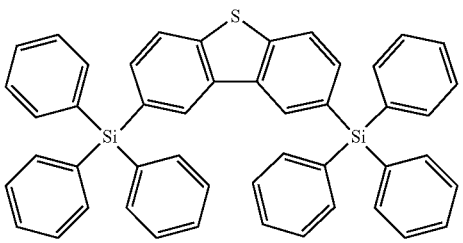 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 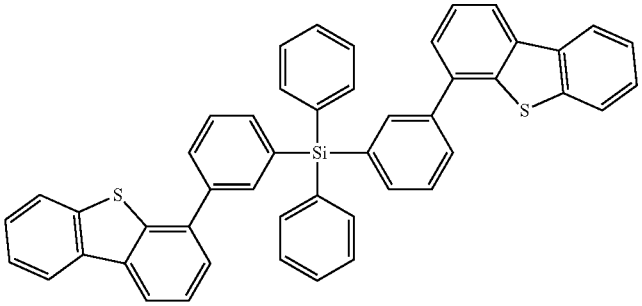 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 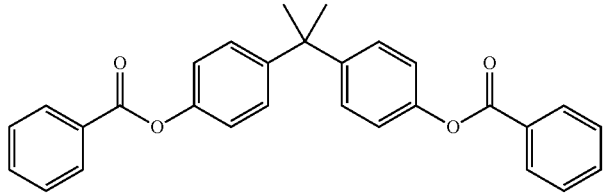 [SMILES: CC(C)(c1ccc(OC(=O)c2ccccc2)cc1)c1ccc(OC(=O)c2ccccc2)cc1] | WO2006100298 |
| Carbazole linked by non-conjugated groups | 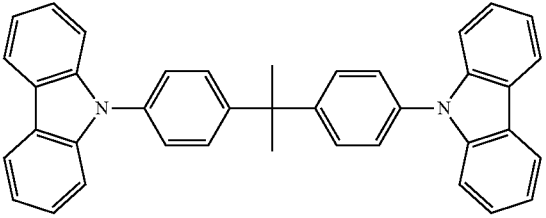 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 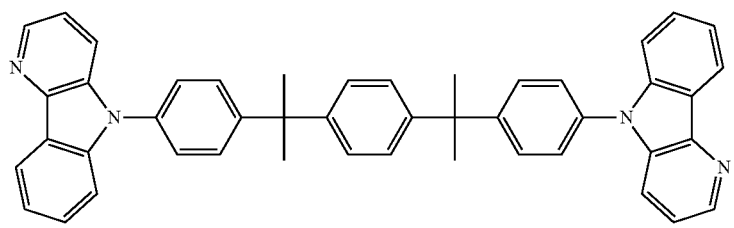 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |

TABLE 4-continued

| MATERIAL | EXAMPLES OF MATERIAL | PUBLICATIONS |
|---|---|---|
| High triplet metal organometallic complex | | U.S. Pat. No. 7,154,114 |

Phosphorescent dopants
Red dopants

| | | |
|---|---|---|
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |

TABLE 4-continued

| MATERIAL | EXAMPLES OF MATERIAL | PUBLICATIONS |
|---|---|---|
|  |  | US20060202194 |
|  |  | US20060202194 |
|  |  | US20070087321 |
|  |  | US20080261076<br>US20100090591 |
|  |  | US20070087321 |

| MATERIAL | EXAMPLES OF MATERIAL | PUBLICATIONS |
|---|---|---|
| | 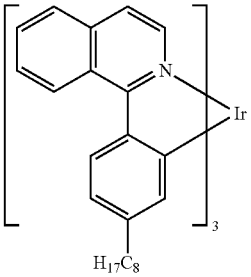 | Adv. Mater. 19, 739 (2007) |
| | 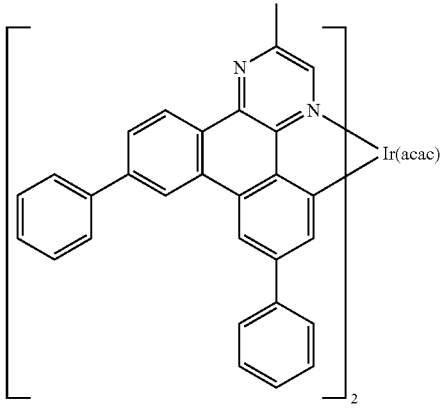 | WO2009100991 |
| | 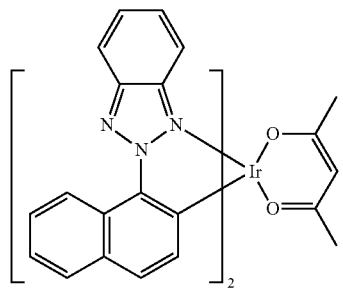 | WO2008101842 |
| | 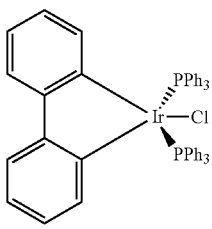 | U.S. Pat. No. 7,232,618 |
| Platinum(II) organometallic complexes | 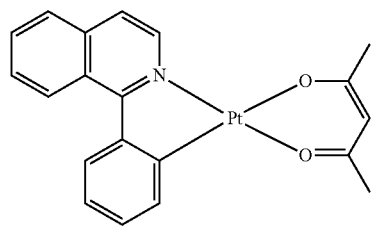 | WO2003040257 |

TABLE 4-continued

| MATERIAL | EXAMPLES OF MATERIAL | PUBLICATIONS |
| --- | --- | --- |
|  |  | US20070103060 |
| Osminum(III) complexes |  | Chem. Mater. 17, 3532 (2005) |
| Ruthenium(II) complexes |  | Adv. Mater. 17, 1059 (2005) |
| Rhenium (I), (II), and (III) complexes |  | US20050244673 |
|  | Green dopants |  |
| Iridium(III) organometallic complexes | and its derivatives | Inorg. Chem. 40, 1704 (2001) |

TABLE 4-continued
| MATERIAL | EXAMPLES OF MATERIAL | PUBLICATIONS |
|---|---|---|
| | 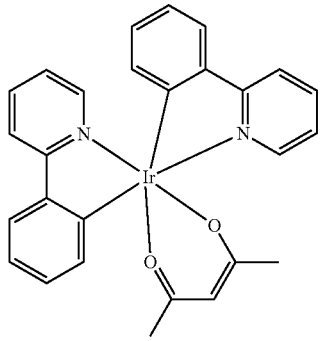 | US20020034656 |
| | 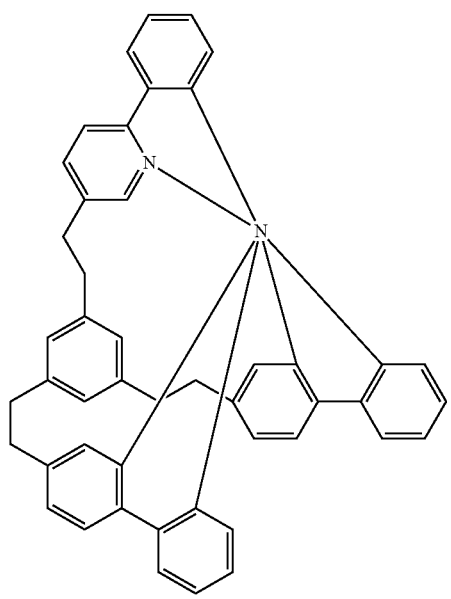 | U.S. Pat. No. 7,332,232 |
| | 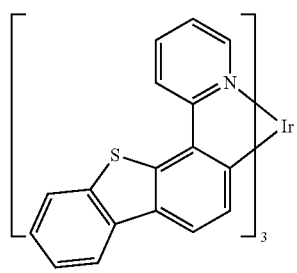 | US20090108737<br>WO2010028151<br>EP1841834B<br>US20060127696<br>US20090039776<br>U.S. Pat. No. 6,921,915 |
| | 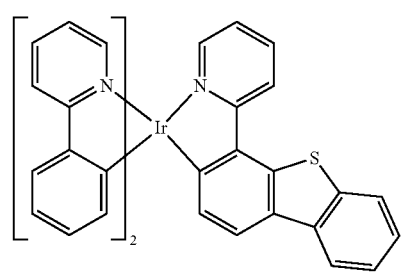 | US20100244004 |

TABLE 4-continued
| MATERIAL | EXAMPLES OF MATERIAL | PUBLICATIONS |
|---|---|---|
| | 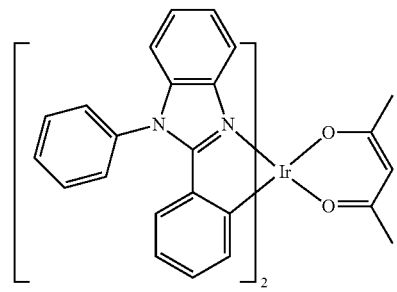 | U.S. Pat. No. 6,687,266 |
| | 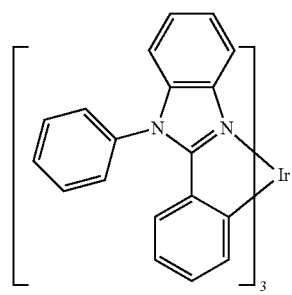 | Chem. Mater. 16, 2480 (2004) |
| | 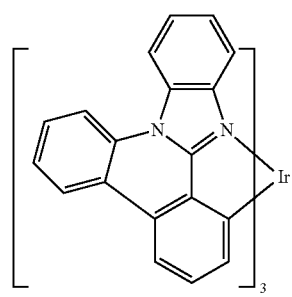 | US20070190359 |
| | 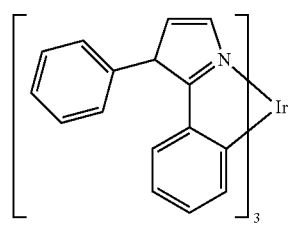 | US 20060008670 JP2007123392 |
| | 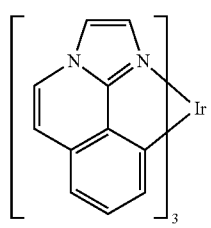 | WO2010086089, WO2011044988 |
| | 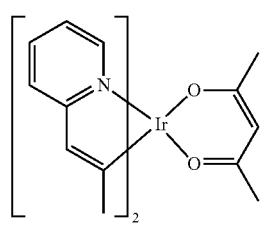 | Adv. Mater. 16, 2003 (2004) |

TABLE 4-continued
| MATERIAL | EXAMPLES OF MATERIAL | PUBLICATIONS |
|---|---|---|
| | 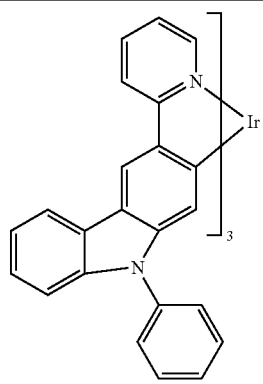 | Angew. Chem. Int. Ed. 2006, 45, 7800 |
| | 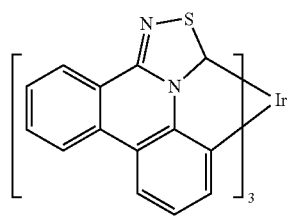 | WO2009050290 |
| | 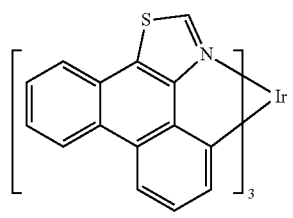 | US20090165846 |
| | 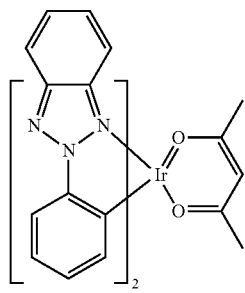 | US20080015355 |
| | 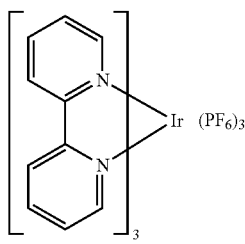 | US20010015432 |
| | 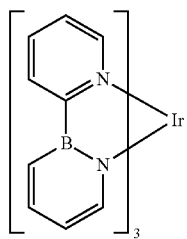 | US20100295032 |

TABLE 4-continued
| MATERIAL | EXAMPLES OF MATERIAL | PUBLICATIONS |
|---|---|---|
| Monomer for polymeric metal organometallic compounds | 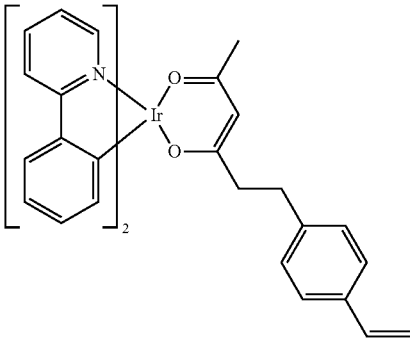 | U.S. Pat. No. 7,250,226, U.S. Pat. No. 7,396,598 |
| Pt(II) organometallic complexes, including polydentated ligands | 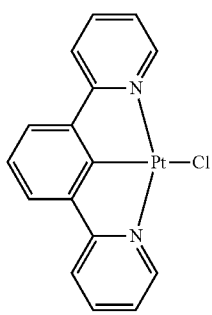 | Appl. Phys. Lett. 86, 153505 (2005) |
| | 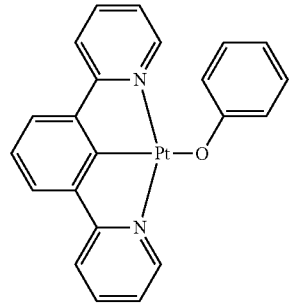 | Appl. Phys. Lett. 86, 153505 (2005) |
| | 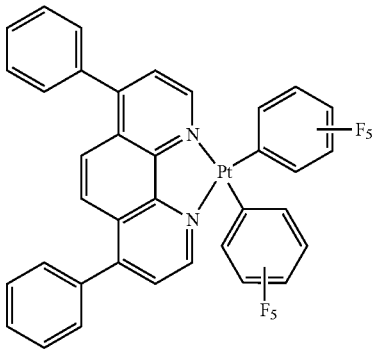 | Chem. Lett. 34, 592 (2005) |
| | 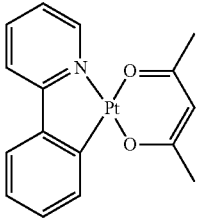 | WO2002015645 |

TABLE 4-continued
| MATERIAL | EXAMPLES OF MATERIAL | PUBLICATIONS |
|---|---|---|
| | 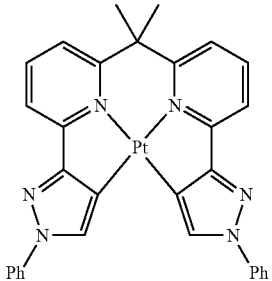 | US20060263635 |
| | 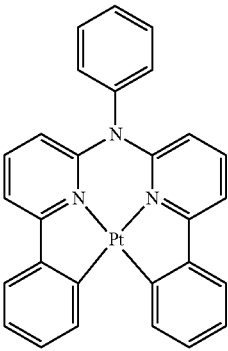 | US20060182992<br>US20070103060 |
| Cu complexes | 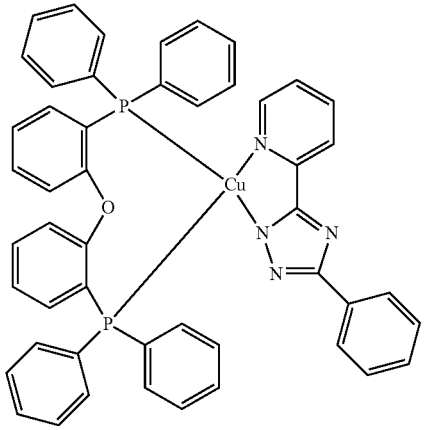 | WO2009000673 |
| | 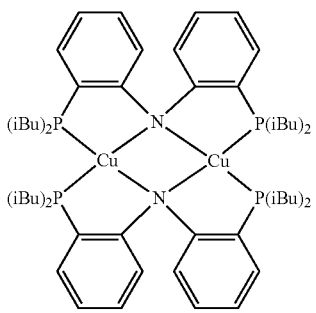 | US20070111026 |

TABLE 4-continued
| MATERIAL | EXAMPLES OF MATERIAL | PUBLICATIONS |
|---|---|---|
| Gold complexes | 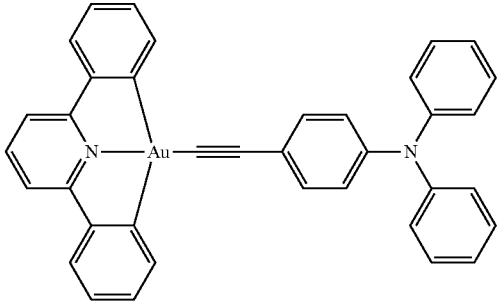 | Chem. Commun. 2906 (2005) |
| Rhenium(III) complexes | 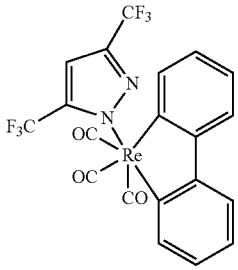 | Inorg. Chem. 42, 1248 (2003) |
| Osmium(II) complexes | 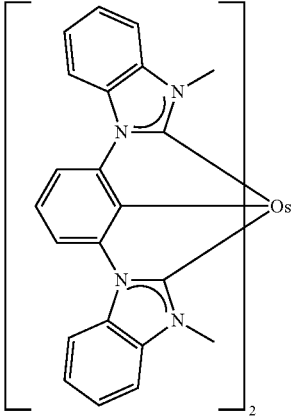 | U.S. Pat. No. 7,279,704 |
| Deuterated organometallic complexes | | US20030138657 |
| Organometallic complexes with two or more metal centers | 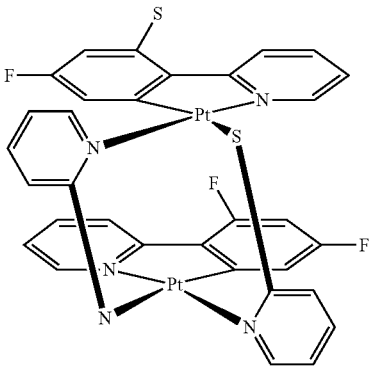 | US20030152802<br>U.S. Pat. No. 7,090,928 |

TABLE 4-continued

| MATERIAL | EXAMPLES OF MATERIAL | PUBLICATIONS |
| --- | --- | --- |
| Blue dopants | | |
| Iridium(III) organometallic complexes | | WO2002002714 |
| | | WO2006009024 |
| | | US20060251923<br>US20110057559<br>US20110204333 |
| | | U.S. Pat. No. 7,393,599,<br>WO2006056418,<br>US20050260441,<br>WO2005019373 |
| | | U.S. Pat. No. 7,534,505 |
| | | WO2011051404 |

TABLE 4-continued

| MATERIAL | EXAMPLES OF MATERIAL | PUBLICATIONS |
| --- | --- | --- |
| | | U.S. Pat. No. 7,445,855 |
| | | US20070190359, US20080297033 US20100148663 |
| | | U.S. Pat. No. 7,338,722 |
| | | US20020134984 |
| | | Angew. Chem. Int. Ed. 47, 1 (2008) |

TABLE 4-continued

| MATERIAL | EXAMPLES OF MATERIAL | PUBLICATIONS |
|---|---|---|
| | | Chem. Mater. 18, 5119 (2006) |
| | | Inorg. Chem. 46, 4308 (2007) |
| | | WO2005123873 |
| | | WO2005123873 |
| | | WO2007004380 |

TABLE 4-continued

| MATERIAL | EXAMPLES OF MATERIAL | PUBLICATIONS |
| --- | --- | --- |
| | | WO2006082742 |
| Osmium(II) complexes | | U.S. Pat. No. 7,279,704 |
| | | Organometallics 23, 3745 (2004) |
| Gold complexes | | Appl. Phys. Lett. 74, 1361 (1999) |
| Platinum(II) complexes | | WO2006098120, WO2006103874 |

TABLE 4-continued

| MATERIAL | EXAMPLES OF MATERIAL | PUBLICATIONS |
|---|---|---|
| Pt tetradentate complexes with at least one metal-carbene bond | 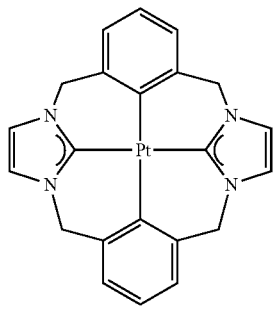 | U.S. Pat. No. 7,655,323 |
| Exciton/hole blocking layer materials | | |
| Bathocuprine compounds (e.g., BCP, BPhen) | 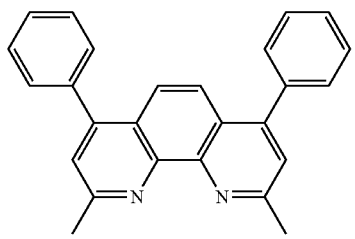 [SMILES: Cc1cc(-c2ccccc2)c2ccc3c(-c4ccccc4)cc(C)nc3c2n1] | Appl. Phys. Lett. 75, 4 (1999) |
| | 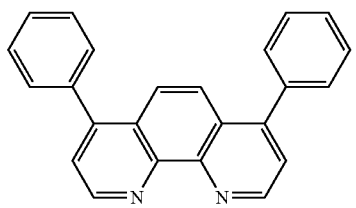 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 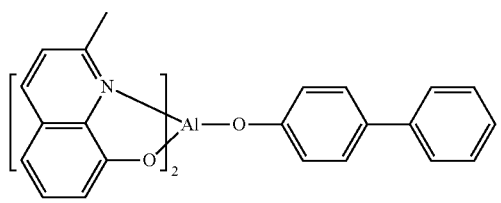 | Appl. Phys. Lett. 81, 162 (2002) |
| 5-member ring electron deficient heterocycles such as triazole, oxadiazole, imidazole, benzoimidazole | 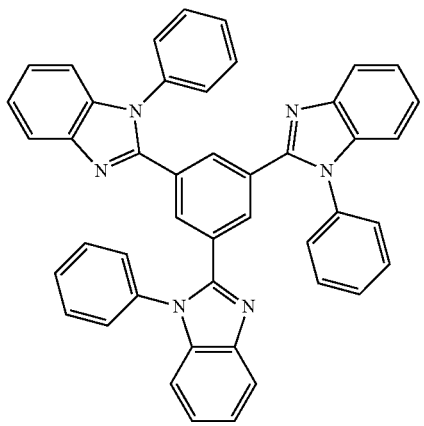 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 4-continued
| MATERIAL | EXAMPLES OF MATERIAL | PUBLICATIONS |
|---|---|---|
| Triphenylene compounds | 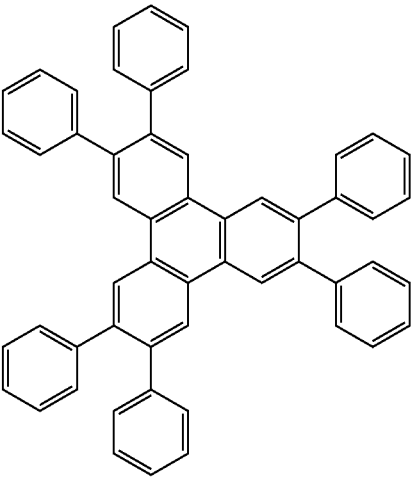 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 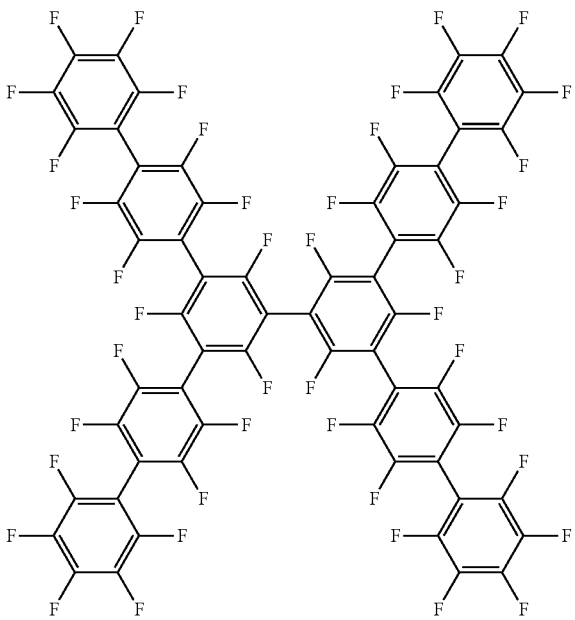 [SMILES: Fc1c(F)c(F)c(-c2c(F)c(F)c(-c3c(F)c(-c4c(F)c(F)c(-c5c(F)c(F)c(F)c(F)c5F)c(F)c4F)c(F)c(-c4c(F)c(-c5c(F)c(F)c(-c6c(F)c(F)c(F)c(F)c6F)c(F)c5F)c(F)c(-c5c(F)c(F)c(-c6c(F)c(F)c(F)c(F)c6F)c(F)c5F)c4F)c3F)c(F)c2F)c(F)c1F] | Appl. Phys. Lett. 79, 156 (2001) |
| Phenothiazine-S-oxide | 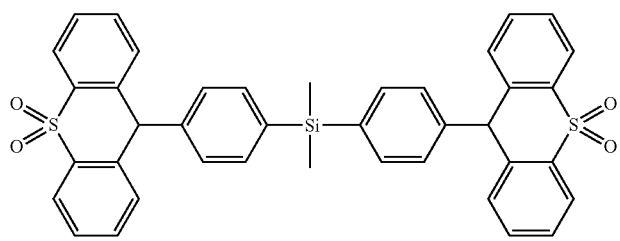 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 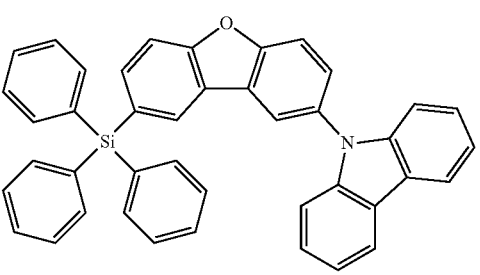 [SMILES: c1ccc([Si](c2ccccc2)(c2ccccc2)c2ccc3oc4ccc(-n5c6ccccc6c6ccccc65)cc4c3c2)cc1] | WO2010079051 |

TABLE 4-continued
| MATERIAL | EXAMPLES OF MATERIAL | PUBLICATIONS |
|---|---|---|
| Aza-carbazoles | 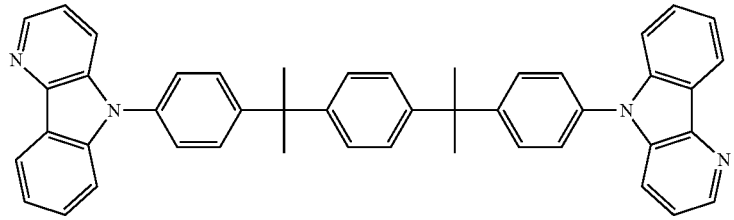 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 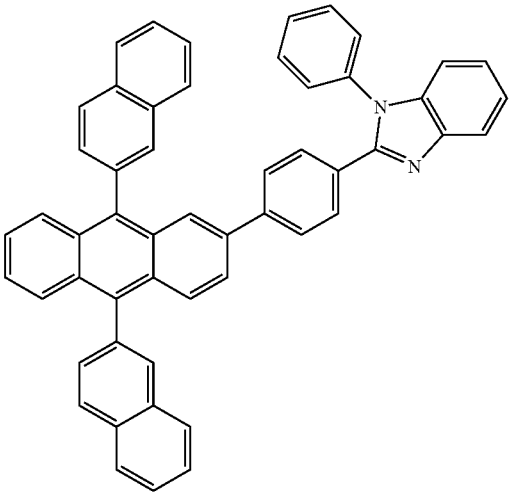 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 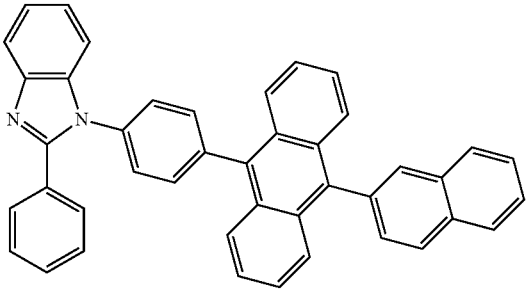 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 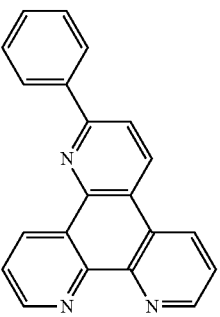 [SMILES: c1ccc(-c2ccc3c4cccnc4c4ncccc4c3n2)cc1] | US20090115316 |

TABLE 4-continued

| MATERIAL | EXAMPLES OF MATERIAL | PUBLICATIONS |
| --- | --- | --- |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987)<br>U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |

TABLE 4-continued

| MATERIAL | EXAMPLES OF MATERIAL | PUBLICATIONS |
|---|---|---|
| | | Appl. Phys. Lett. 55, 1489 (1989) |
| | | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |
| Fullerene (e.g., C60) | | US20090101870 |

TABLE 4-continued

| MATERIAL | EXAMPLES OF MATERIAL | PUBLICATIONS |
|---|---|---|
| Triazine complexes | 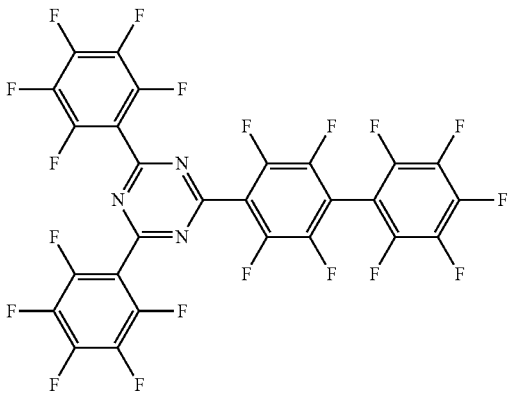 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 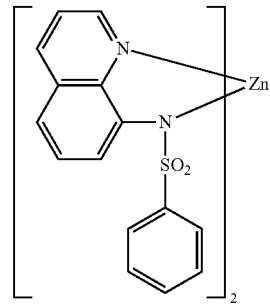 | U.S. Pat. No. 6,528,187 |

Experimental

1. Synthesis of Compound III-32

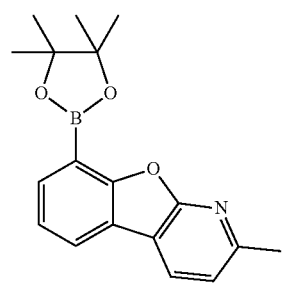

+

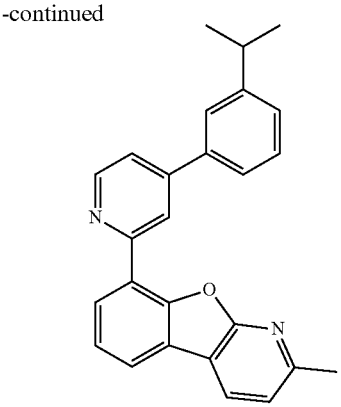

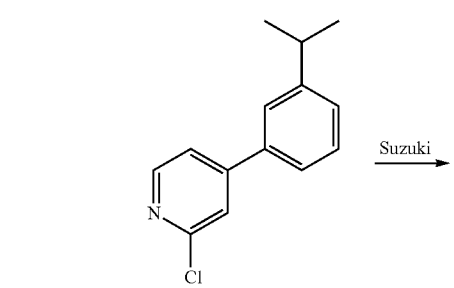 Suzuki→

A mixture of phenylpyridine iridium complex (2.1 g, 2.94 mmol), 8-(4-(4-isopropylphenyl)pyridin-2-yl)-2-methylbenzofuro[2,3-b]pyridine (2.23 g, 5.88 mmol), 2-ethoxyethanol (60 mL) and DMF (60 mL) was heated at 130° C. overnight. The solvent mixture was evaporated under vacuum. The residue was run through a short silica plug with dichloromethane (DCM). The reaction mixture was further purified by silica gel column with DCM/heptane as elute to obtain 1.3 g desired product (50.3% yield) which was confirmed by LC-MS.

2. Synthesis of Compound III-44

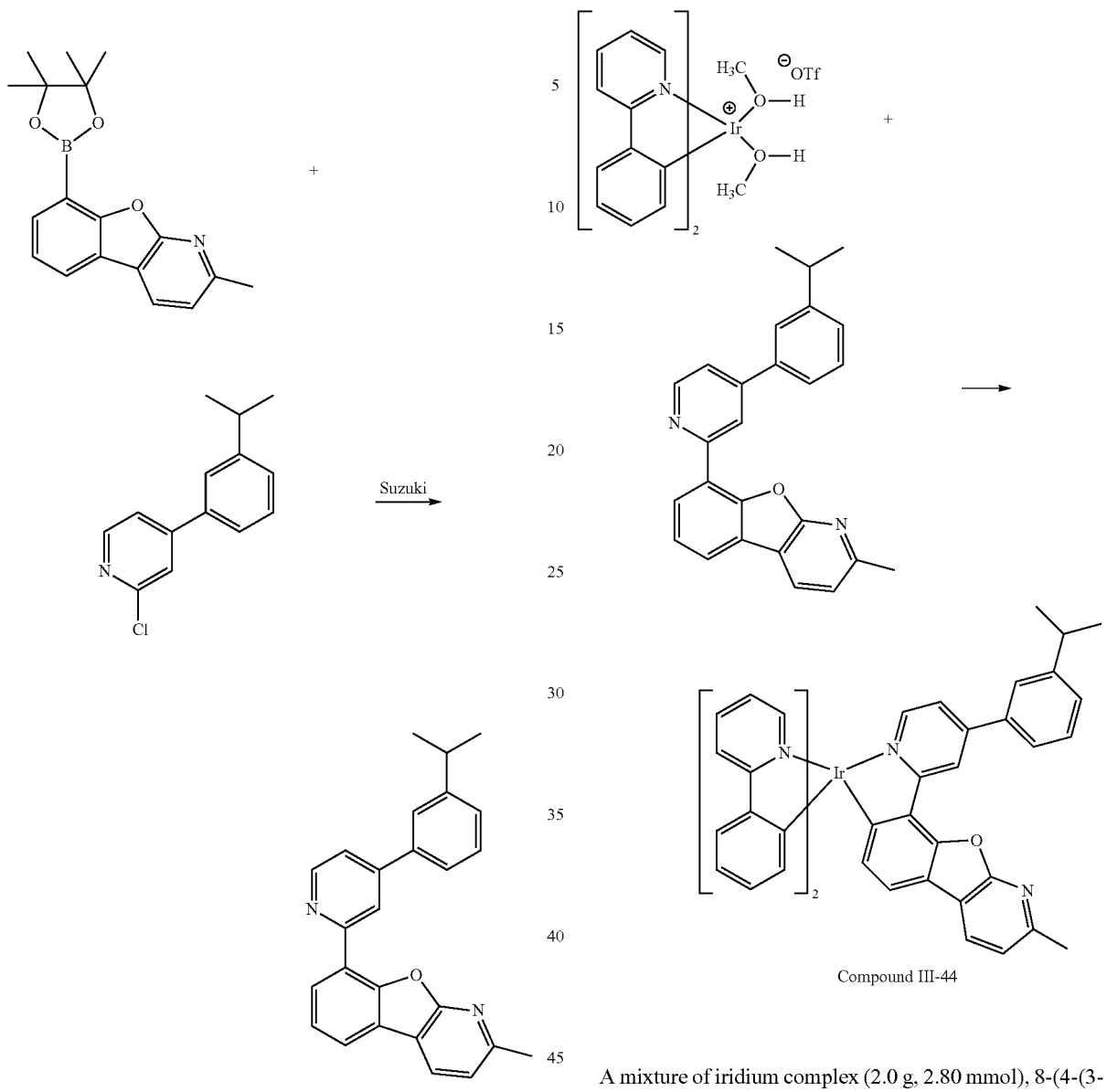

Synthesis of 8-(4-(3-isopropylphenyl)pyridine-2-yl)-
2-methylbenzofuro[2,3-b]pyridine A mixture of 2-methyl-8-(4,4,5,5-tetramethyl-1,3,2-dioxaborolan-2-yl)benzofuro[2,3-b]pyridine (3.15 g, 10.2 mmol), 2-chloro-4-(3-isopropylphenyl)pyridine (2.60 g, 11.2 mmol), $Pd_2(dba)_3$ (0.187 g 0.204 mmol), dicyclohexyl(2',6'-dimethoxy-[1,1'-biphenyl]-2-yl)phosphine (0.335 g, 0.815 mmol), potassium phosphate (7.57 g, 35.7 mmol), toluene (90 mL) and water (9 mL) was degassed with nitrogen and then refluxed overnight. The toluene layer was dried on $Na_2SO_4$ and then further purified by column chromatography using dichloromethane in hexanes and then vacuum distilled to give 8-(4-(3-Isopropylphenyl)pyridine-2-yl)-2-methylbenzofuro[2,3-b]pyridine (2.2 g, 57% yield).

A mixture of iridium complex (2.0 g, 2.80 mmol), 8-(4-(3-isopropylphenyl)pyridine-2-yl)-2methylbenzofuro[2,3-b] pyridine (2.2 g, 5.81 mmol), 2-ethoxyethanol (60 mL) and DMF (60 mL) was heated at 130° C. overnight. The reaction mixture was concentrated to remove solvents and filtered through a small plug of silica gel and further chromatographed to give 1.08 g desired product (44% yield).

3. Synthesis of Compound III-74

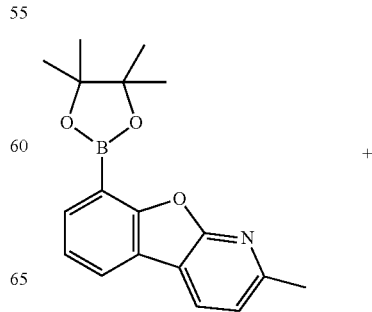

-continued

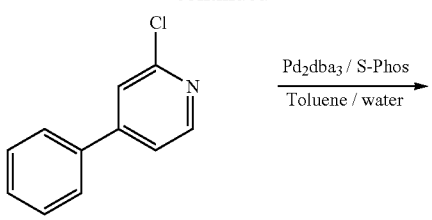

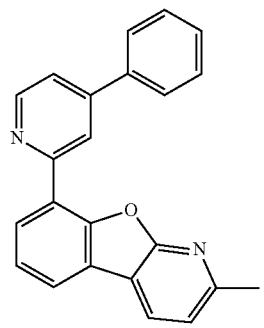

Synthesis of 2-methyl-8-(4-phenylpyridin-2-yl)benzofuro[2,3-b]pyridine 2-methyl-8-(4,4,5,5-tetramethyl-1,3,2-dioxaborolan-2-yl)benzofuro[2,3-b]pyridine (5.96 g, 19.28 mmol), 2-chloro-4-phenylpyridine (4.39 g, 23.13 mmol), tris(dibenzylideneacetone)palladium(0) (0.353 g, 0.386 mmol) and 2-Dicyclohexylphosphino-2',6'-dimethoxybiphenyl (0.8 g, 1.951 mmol) were charged into a 500 mL 2-neck flask. Potassium phosphate tribasic (12.26 g, 57.8 mmol) was then dissolved in 45 mL of water. This solution was charged into the reaction mixture. The reaction mixture was degassed with nitrogen then was heated to reflux overnight. The reaction mixture was cooled to room temperature. The toluene layer was separated and was dried over magnesium sulfate. These organics were filtered and concentrated under vacuum. The crude product was passed through a silica gel column using 70-99% toluene/heptanes followed by 5-15% ethyl acetate/toluene. Some of the impure product fractions were columned on silica gel using 5-15% ethyl acetate/DCM. All the clean product fractions were combined yielding 2-methyl-8-(4-phenylpyridin-2-yl)benzofuro[2,3-b]pyridine (5.3 g, 15.76 mmol, 82% yield).

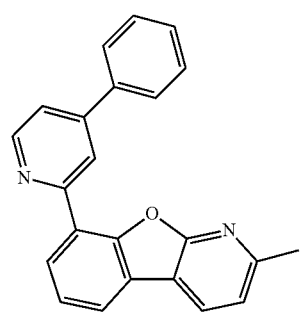

-continued

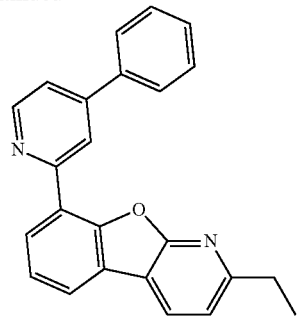

Synthesis of 2-ethyl-8-(4-phenylpyridin-2-yl)benzofuro[2,3-b]pyridine 2-methyl-8-(4-phenylpyridin-2-yl)benzofuro[2,3-b]pyridine (5.3 g, 15.76 mmol) was dissolved in 130 mL of THF. This solution was cooled in a dry ice bath to −78° C. Lithium diisopropylamide in THF (9.85 mL, 19.69 mmol) was added dropwise to the reaction mixture over a 10 minute period maintaining the temperature below −73° C. The reaction mixture was stirred at −78° C. for 2 hours. Iodomethane (3.35 g, 23.63 mmol) was dissolved in 20 mL of THF then was added dropwise via syringe to the cold reaction mixture. Stirring was continued as the reaction mixture gradually warmed to room temperature overnight. The reaction mixture was quenched with aqueous ammonium chloride then was extracted 2×300 mL ethyl acetate. The organics were combined, were washed with aqueous LiCl then were dried over magnesium sulfate. These organics were then filtered and concentrated under vacuum. The crude residue was dissolved in DCM and was loaded onto a silica gel column. The column was eluted with 5-8% ethyl acetate/DCM. The main set of product fractions were combined and concentrated under vacuum yielding 2-ethyl-8-(4-phenylpyridin-2-yl)benzofuro[2,3-b]pyridine (5.15 g, 14.70 mmol, 93% yield)

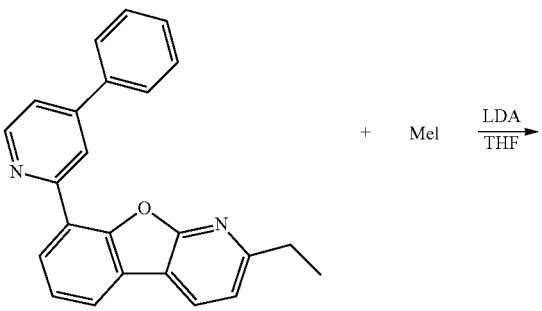

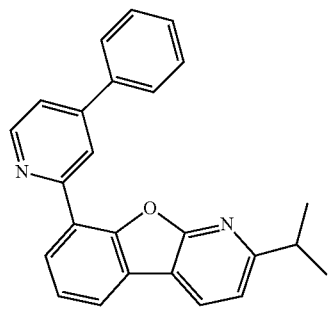

Synthesis of 2-isopropyl-8-(4-phenylpyridin-2-yl) benzofuro[2,3-b]pyridine 2-ethyl-8-(4-phenylpyridin-2-yl)benzofuro[2,3-b]pyridine (5.15 g, 14.70 mmol) was charged into the reaction mixture with 120 mL of THF. This mixture was cooled to −78° C. Lithium diisopropylamide in THF (9.19 mL, 18.37 mmol) was added dropwise to the cooled reaction mixture over a 10 minute period. The reaction mixture was then stirred for 2 hours at −78° C. Iodomethane (3.13 g, 22.05 mmol) was then dissolved in 10 mL of THF. This solution was then added via syringe to the cold reaction mixture. Stirring was continued as the reaction mixture was allowed to gradually warm to room temperature overnight. The reaction mixture was quenched with aqueous ammonium chloride then was extracted 2×300 mL ethyl acetate. The organics were combined, were washed with aqueous LiCl then were dried over magnesium sulfate. These organics were then filtered and concentrated under vacuum. The crude residue was dissolved in DCM and was loaded onto a silica gel column. The column was eluted with 3-4% ethyl acetate/DCM. Clean product fractions were combined and solvents were evaporated yielding 2-isopropyl-8-(4-phenylpyridin-2-yl)benzofuro[2,3-b]pyridine (4.1 g, 11.25 mmol, 77% yield).

2-isopropyl-8-(4-phenylpyridin-2-yl)benzofuro[2,3-b]pyridine (2.2 g, 6.04 mmol) and iridium complex (2.1 g, 2.94 mmol) were combined with 60 mL of DMF and 60 mL of 2-ethoxyethanol. This heterogeneous mixture was placed under a nitrogen atmosphere then was heated to reflux overnight. The reaction mixture was cooled to room temperature. The solvents were removed under vacuum. The crude residue was dissolved in 300 mL of DCM. This mixture was passed through a short silica gel plug. The plug was rinsed with 500 mL of DCM. The DCM filtrate was evaporated under vacuum then was loaded onto a silica gel column. The column was 1st eluted with 60% DCM/heptanes then 50% DCM/heptanes. The eluant was gradually increased to 57% DCM/heptanes. Clean product fractions yielded the desired product (1.4 g, 1.972 mmol, 67.0% yield).

5. Synthesis of Compound III-1604

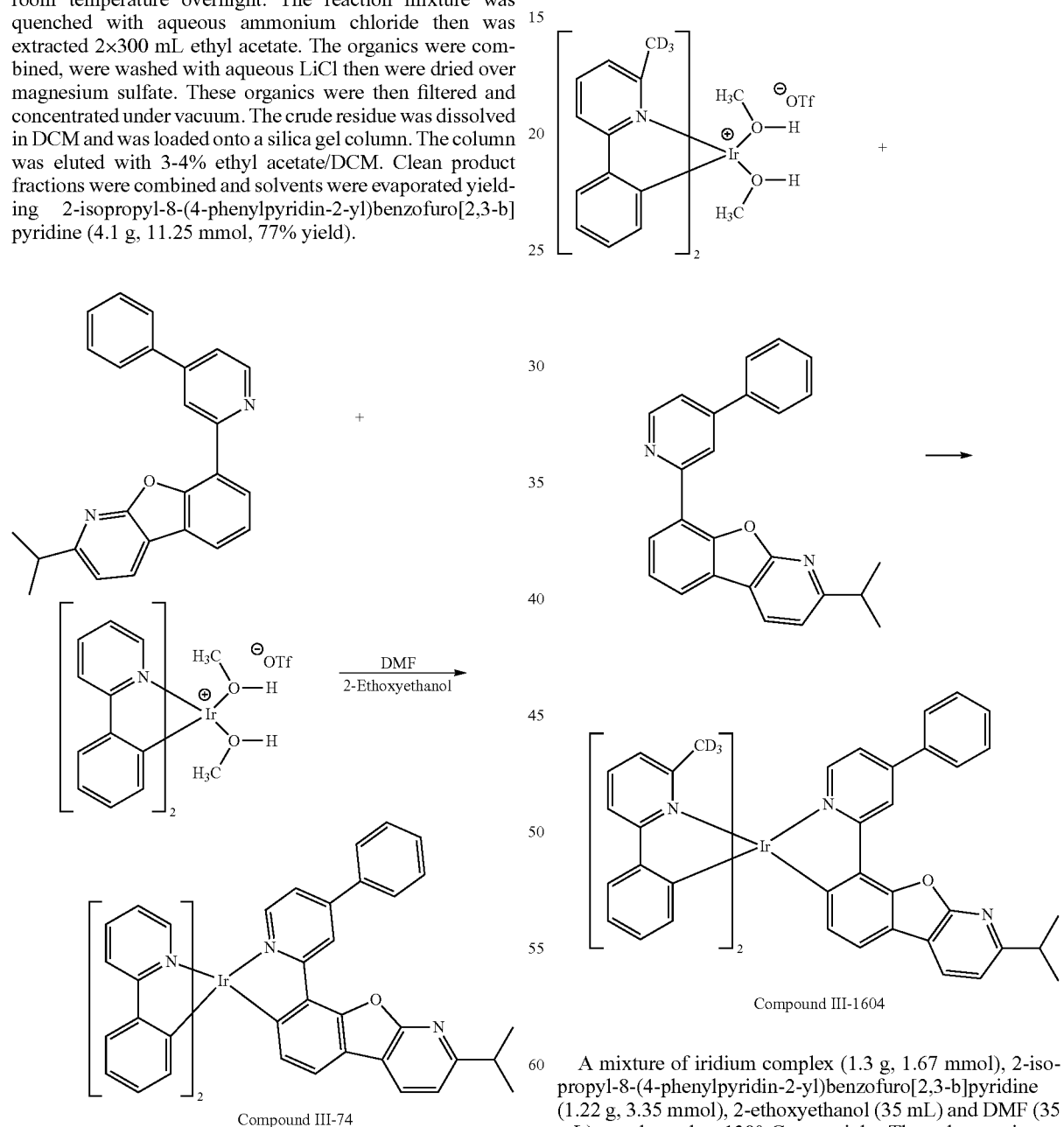

Compound III-74

Compound III-1604

A mixture of iridium complex (1.3 g, 1.67 mmol), 2-isopropyl-8-(4-phenylpyridin-2-yl)benzofuro[2,3-b]pyridine (1.22 g, 3.35 mmol), 2-ethoxyethanol (35 mL) and DMF (35 mL) was heated at 130° C. overnight. The solvent mixture was evaporated under vacuum. The residue was run through a short silica plug. The mixture was further purified by silica gel column with DCM/heptane as elute to obtain 1.25 g desired product (83% yield).

6. Synthesis of Compound III-35

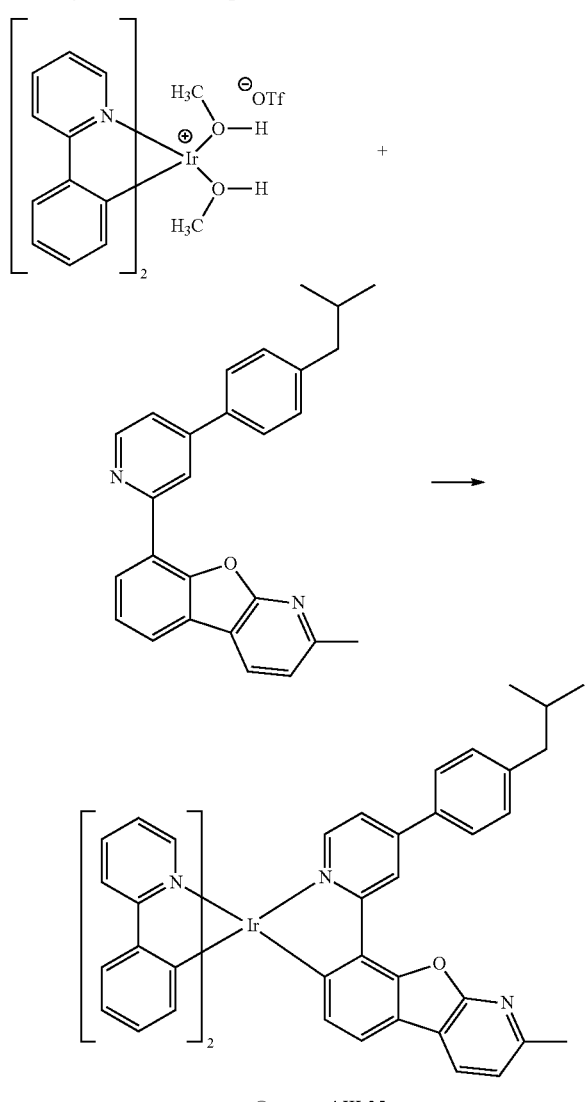

Compound III-35

A mixture of iridium complex (2.3 g, 3.22 mmol), 8-(4-(4-isobutylphenyl)pyridin-2-yl)-2-methylbenzofuro[2,3-b]pyridine (2.53 g, 6.44 mmol), 2-ethoxyethanol (60 mL) and DMF (60 mL) was heated at 130° C. overnight. The solvent mixture was evaporated under vacuum. The residue was run through a short silica plug. The reaction mixture was further purified by silica gel column with DCM/heptane as elute to obtain 1.8 g desired product (62.6% yield).

7. Synthesis of Compound III-50

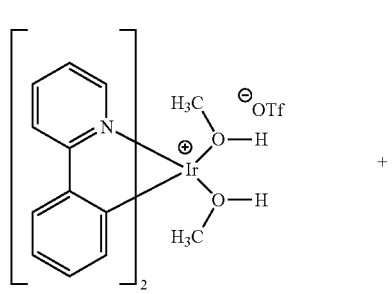

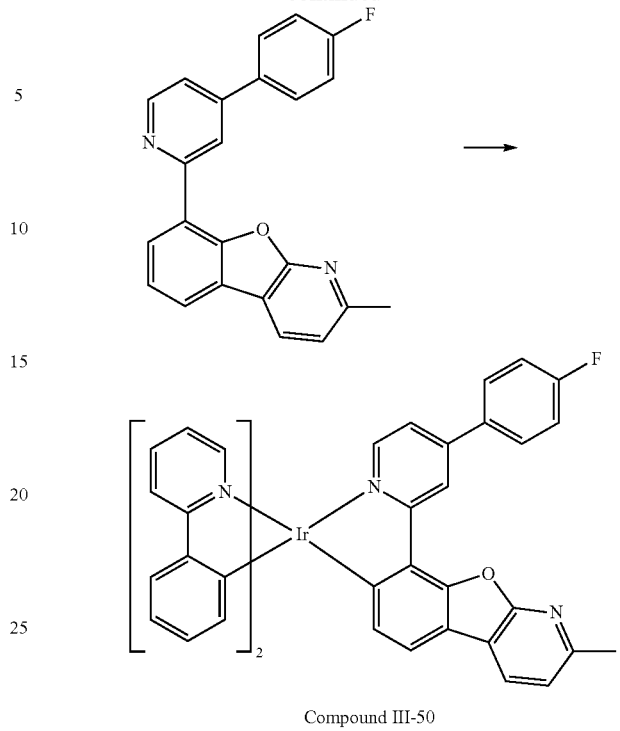

Compound III-50

A mixture of iridium complex (2.3 g, 3.22 mmol), 8-(4-(4-fluorophenyl)pyridin-2-yl)-2-methylbenzofuro[2,3-b]pyridine (2.28 g, 6.44 mmol), 2-ethoxyethanol (60 mL) and DMF (60 mL) was heated at 130° C. overnight. The solvent mixture was evaporated under vacuum. The residue was run through a short silica plug. The reaction mixture was further purified by silica gel column with DCM/heptane as elute to obtain 1.6 g desired product (56.1% yield) which was confirmed by LC-MS.

8. Synthesis of Compound III-38

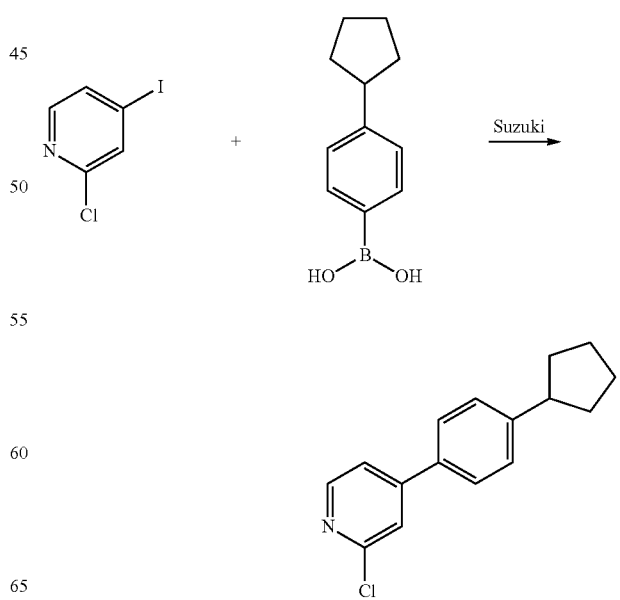

Synthesis of 2-Chloro-4-(4-cyclopentylphenyl)pyridine

A mixture of 2-chloro-4-iodopyridine (6.43 g, 26.3 mmol), (4-cyclopentylphenyl)boronic acid (5.0 g, 26.3 mmol), Pd(Ph$_3$P)$_4$ (0.0.91 g 0.79 mmol), sodium carbonate (8.37 g, 79 mmol), DME (257 mL) and water (64 mL) was degassed with nitrogen and then refluxed overnight. The reaction mixture was concentrated and extracted with ethyl acetate. The the ethyl acetate layer was dried on Na$_2$SO$_4$ and then further purified by column chromatography using dichloromethane in hexanes and then vacuum distilled to give 2-Chloro-4-(4-cyclopentylphenyl)pyridine (4.6 g, 68% yield).

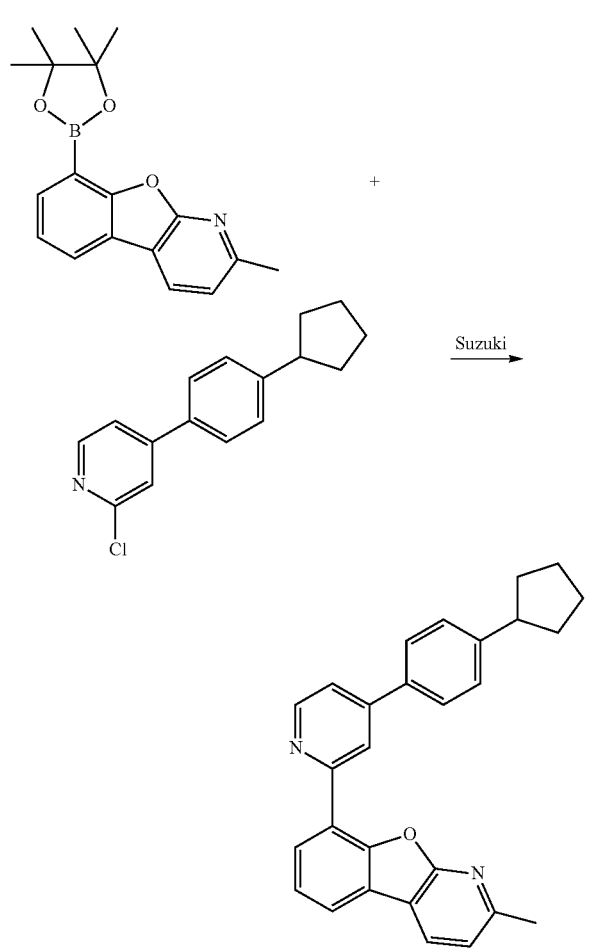

Synthesis of 8-(4-(4-cyclopentylphenyl)pyridine-2-yl)-2-methylbenzofuro[2,3-b]pyridine A mixture of 2-methyl-8-(4,4,5,5-tetramethyl-1,3,2-dioxaborolan-2-yl)benzofuro[2,3-b]pyridine (2.5 g, 8.09 mmol), 2-chloro-4-(4-cyclopentylphenyl)pyridine (2.29 g, 8.89 mmol), Pd$_2$(dba)$_3$ (0.148 g 0.162 mmol), dicyclohexyl(2',6'-dimethoxy-[1,1'-biphenyl]-2-yl)phosphine (0.266 g, 0.647 mmol), potassium phosphate (6.01 g, 28.3 mmol), DME (70 mL) and water (7 mL) was degassed with nitrogen and then refluxed overnight. The mixture was concentrated and extracted with ethyl acetate. The ethyl acetate layer was dried on Na$_2$SO$_4$ and then further purified by column chromatography using ethyl acetate in hexanes to give 8-(4-(4-cyclopentylphenyl)pyridine-2-yl)-2-methylbenzofuro[2,3-b]pyridine (2.4 g, 73% yield).

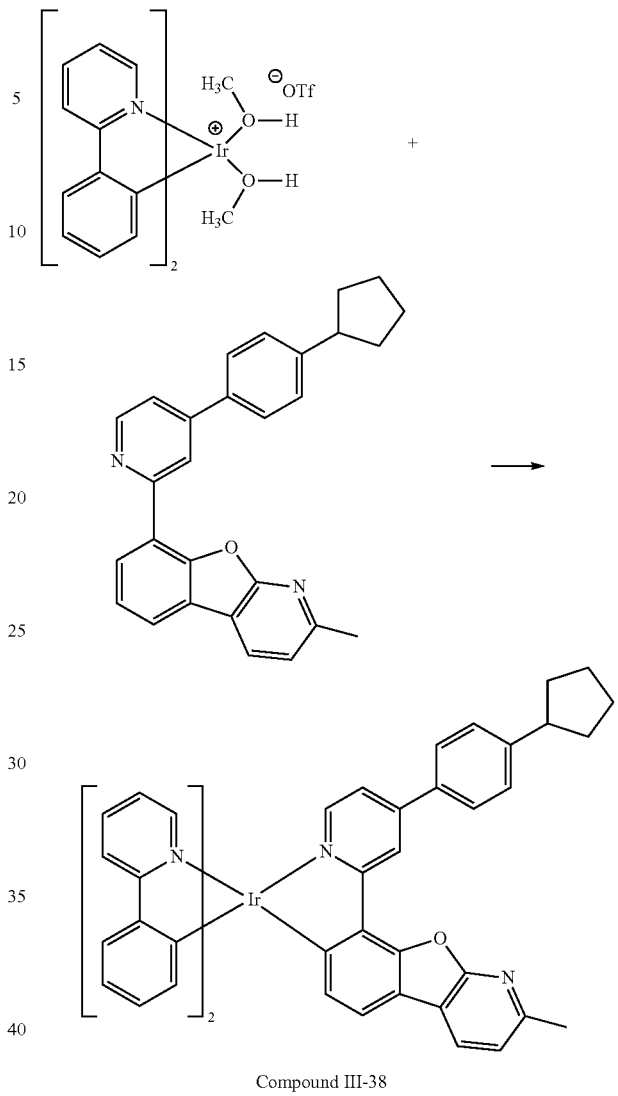

Compound III-38

A mixture of iridium complex (1.2 g, 1.68 mmol), 8-(4-(4-cyclopentylphenyl)pyridine-2-yl)-2methylbenzofuro[2,3-b]pyridine (1.36 g, 3.36 mmol), ethoxyethanol (40 mL) and DMF (40 mL) was heated at 130° C. overnight. The reaction mixture was concentrated to remove solvents and filtered through a small plug of silica gel and further chromatographed to give 0.60 g product. After sublimation, it yielded the product (0.4 g, 27% yield).

9. Synthesis of Compound III-1738

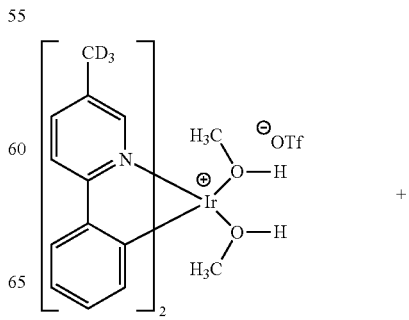

-continued

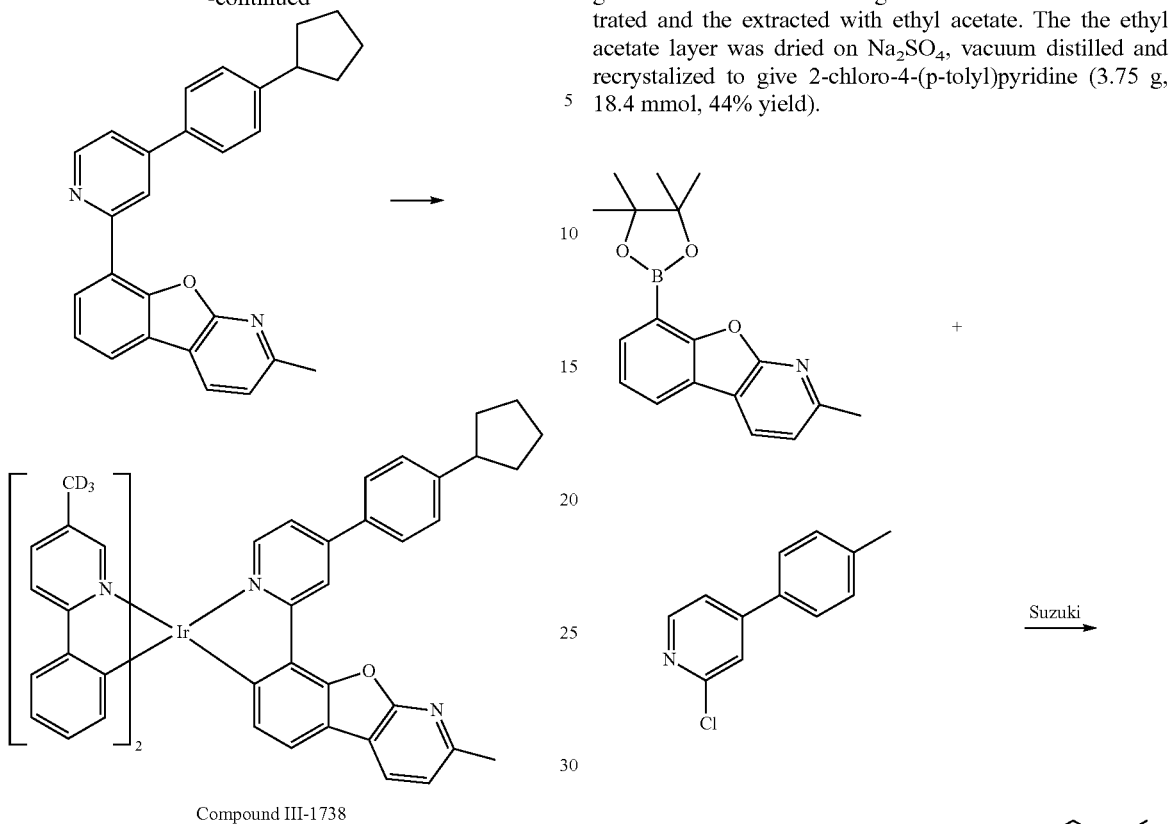

Compound III-1738

A mixture of iridium complex (1.257 g, 1.68 mmol), 8-(4-(4-cyclopentylphenyl)pyridine-2-yl)-2methylbenzofuro[2,3-b]pyridine (1.36 g, 3.36 mmol), ethoxyethanol (40 mL) and DMF (40 mL) was heated at 130° C. overnight. The reaction was concentrated to remove solvents and filtered through a small plug of silica gel and further chromatographed. After sublimation, it gave the product (0.45 g, 29% yield).

10. Synthesis of Compound III-5979

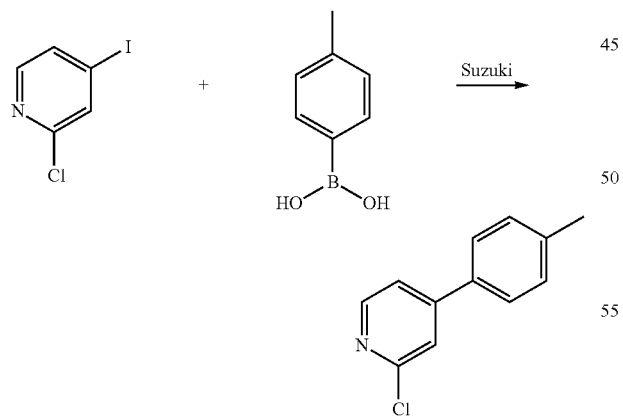

Synthesis of 2-Chloro-4-(p-tolyl)pyridine

A mixture of 2-chloro-4-iodopyridine (10.0 g, 41.8 mmol), p-tolylphenylboronic acid (5.68 g, 41.8 mmol), Pd(Ph₃P)₄ (1.45 g 1.25 mmol), sodium carbonate (13.3 g, 125 mmol), DME (300 mL) and water (75 mL) was degassed with nitrogen and then refluxed overnight. The mixture was concentrated and the extracted with ethyl acetate. The the ethyl acetate layer was dried on Na₂SO₄, vacuum distilled and recrystalized to give 2-chloro-4-(p-tolyl)pyridine (3.75 g, 18.4 mmol, 44% yield).

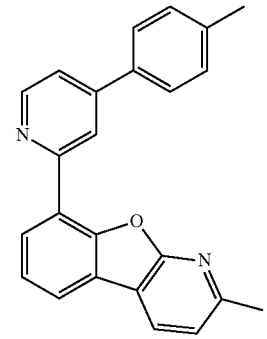

Synthesis of 2-methyl-8-(4-(p-tolyl)(pyridin-2-yl) benzofuro[2,3-b]pyridine

A mixture of 2-methyl-8-(4,4,5,5-tetramethyl-1,3,2-dioxaborolan-2-yl)benzofuro[2,3-b]pyridine (2.5 g, 8.03 mmol), 2-chloro-4-(p-tolyl)pyridine (1.80 g, 8.83 mmol), Pd₂(dba)₃ (0.147 g 0.161 mmol), dicyclohexyl(2',6'-dimethoxy-[1,1'-biphenyl]-2-yl)phosphine (0.264 g, 0.642 mmol), potassium phosphate (5.96 g, 28.1 mmol), toluene (100 mL) and water (10 mL) was degassed with nitrogen and then refluxed overnight. The mixture was concentrated and extracted with ethyl acetate. The ethyl acetate layer was dried on Na₂SO₄ and then further purified by column chromatography using ethyl acetate in hexanes and washed with methanol to give 2-methyl-8-(4-(p-tolyl)pyridin-2-yl)benzofuro[2,3-b]pyridine (2.0 g, 5.71 mmol, 71% yield).

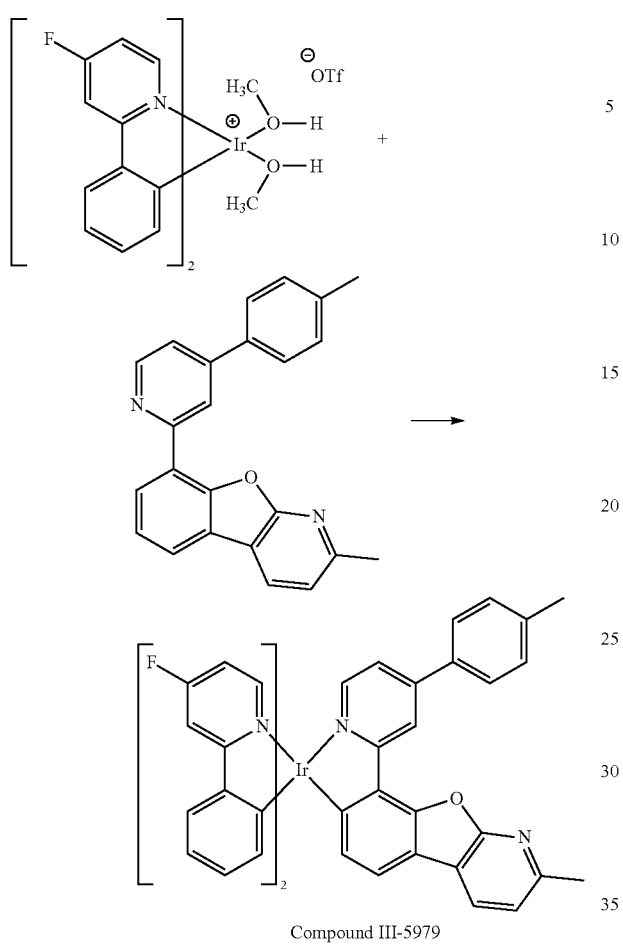

Compound III-5979

To a 250 mL flask, the two starting materials, solvents 2-ethoxyethanol 50 mL and DMF 50 mL were charged. The reaction mixture was heated up to 130° C. under $N_2$ for 27 hours. The reaction was cooled down and solvents were evoparted and run silica gel column with DCM/heptane to obtain about 0.68 g desired product which is confirmed by LC-MS and sublimed to get 0.38 g.

11. Synthesis of Compound III-53

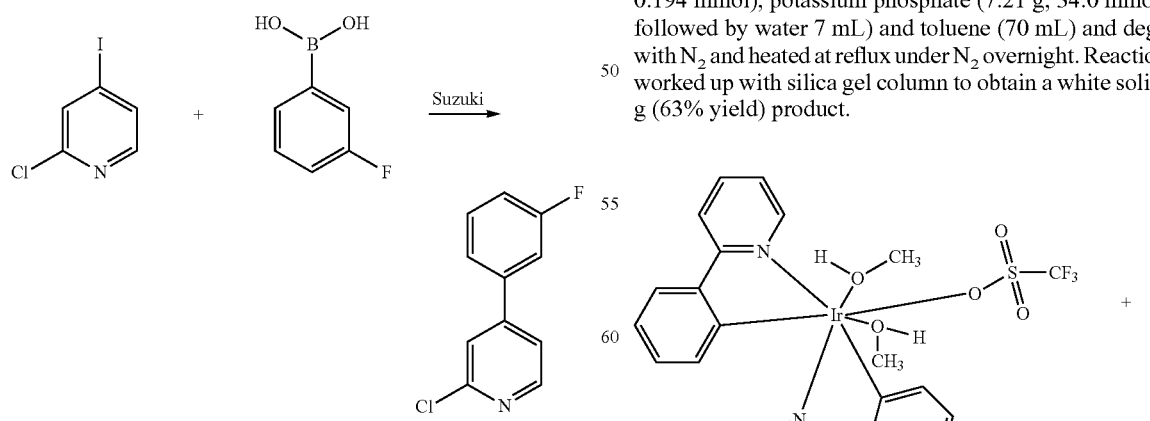

To a 1 liter, 3-necked flask added sodium carbonate (18.18 g, 172 mmol), 2-chloro-4-iodopyridine (13.69 g, 57.2 mmol), (3-fluorophenyl)boronic acid (8 g, 57.2 mmol), DME (400 mL), water (100 mL). The reaction was degassed with $N_2$ for 30 minutes and added with palladiumtetrakistriphenylphosphine (1.982 g, 1.715 mmol) and again degassed with $N_2$. The reaction was heated at reflux under $N_2$ overnight and worked up with silica gel chromatographed using 50-65% DCM/heptane and got about 11.09 g product (93% yield).

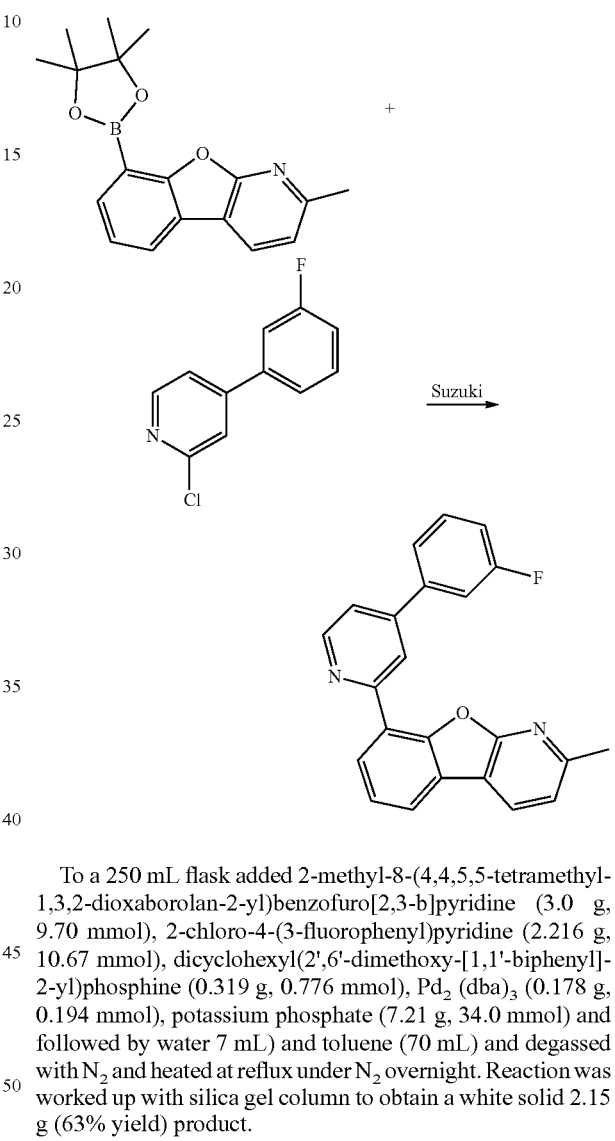

To a 250 mL flask added 2-methyl-8-(4,4,5,5-tetramethyl-1,3,2-dioxaborolan-2-yl)benzofuro[2,3-b]pyridine (3.0 g, 9.70 mmol), 2-chloro-4-(3-fluorophenyl)pyridine (2.216 g, 10.67 mmol), dicyclohexyl(2',6'-dimethoxy-[1,1'-biphenyl]-2-yl)phosphine (0.319 g, 0.776 mmol), $Pd_2(dba)_3$ (0.178 g, 0.194 mmol), potassium phosphate (7.21 g, 34.0 mmol) and followed by water 7 mL) and toluene (70 mL) and degassed with $N_2$ and heated at reflux under $N_2$ overnight. Reaction was worked up with silica gel column to obtain a white solid 2.15 g (63% yield) product.

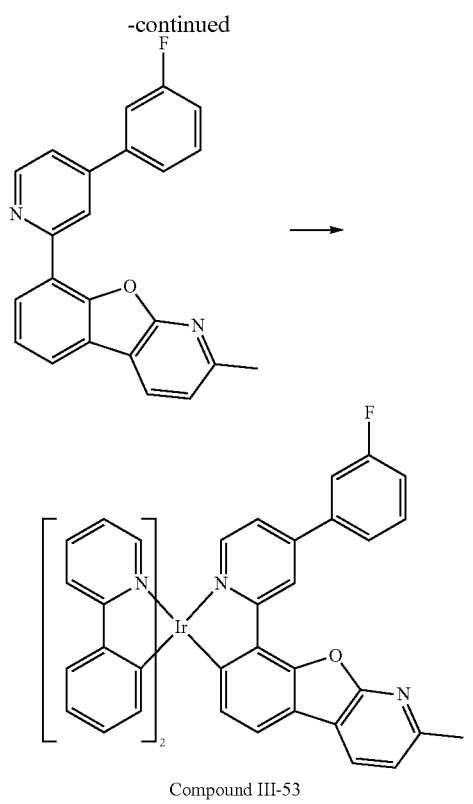

Compound III-53

To a 250 mL flask added iridium complex (2.16 g, 3.03 mmol) and 8-(4-(3-fluorophenyl)pyridin-2-yl)-2-methylbenzofuro[2,3-b]pyridine (2.15 g, 6.07 mmol) and followed by 2-ethoxyethanol (50 mL) and DMF (50 mL). The reaction was heated at 130° C. overnight. An aliquot by HPLC showed completion. The reaction was worked up with silica gel column with 50% DCM in heptane as elute then followed by 100% DCM to get 1.45 g (67% yield) orange solid which LC/MS showed desired MS.

12. Synthesis of Compound III-25

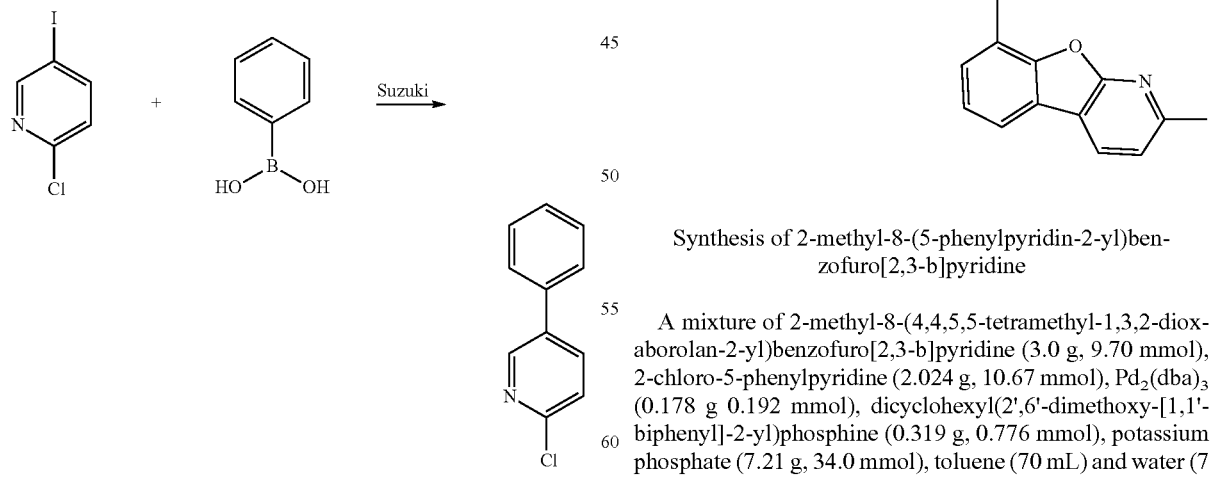

Synthesis of 2-Chloro-5-phenylpyridine

A mixture of 2-chloro-5-iodopyridine (5.0 g, 20.9 mmol), phenylboronic acid (2.6 g, 20.9 mmol), Pd(Ph$_3$P)$_4$ (1.45 g 1.25 mmol), sodium carbonate (6.64 g, 62.6 mmol), DME (20 mL) and water (5 mL) was degassed with nitrogen and then refluxed overnight. The mixture was concentrated and extracted with ethyl acetate. The ethyl acetate layer was dried on Na$_2$SO$_4$ and then vacuum distilled to give 2-chloro-5-phenylpyridine (2.79 g, 14.71 mmol (70.5% yield).

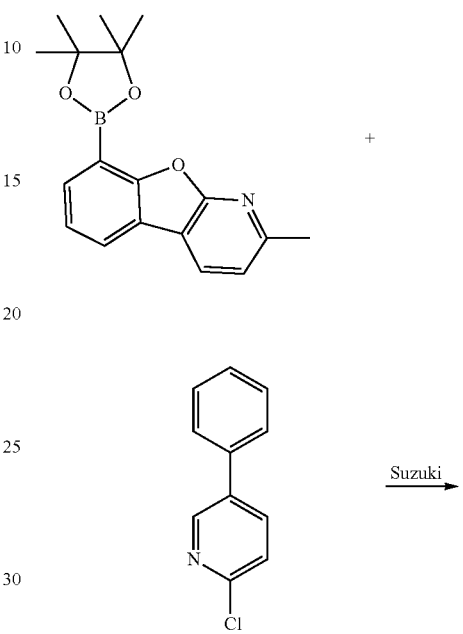

Synthesis of 2-methyl-8-(5-phenylpyridin-2-yl)benzofuro[2,3-b]pyridine

A mixture of 2-methyl-8-(4,4,5,5-tetramethyl-1,3,2-dioxaborolan-2-yl)benzofuro[2,3-b]pyridine (3.0 g, 9.70 mmol), 2-chloro-5-phenylpyridine (2.024 g, 10.67 mmol), Pd$_2$(dba)$_3$ (0.178 g 0.192 mmol), dicyclohexyl(2',6'-dimethoxy-[1,1'-biphenyl]-2-yl)phosphine (0.319 g, 0.776 mmol), potassium phosphate (7.21 g, 34.0 mmol), toluene (70 mL) and water (7 mL) was degassed with nitrogen and then refluxed overnight. It was concentrated and extracted with ethyl acetate. The ethyl acetate layer was dried on Na$_2$SO$_4$ and then further purified by column chromatography using ethyl acetate in hexanes to give 2-methyl-8-(5-phenylpyridin-2-yl)benzofuro[2,3-b]pyridine (1.38 g, 4.10 mmol, 42.3% yield).

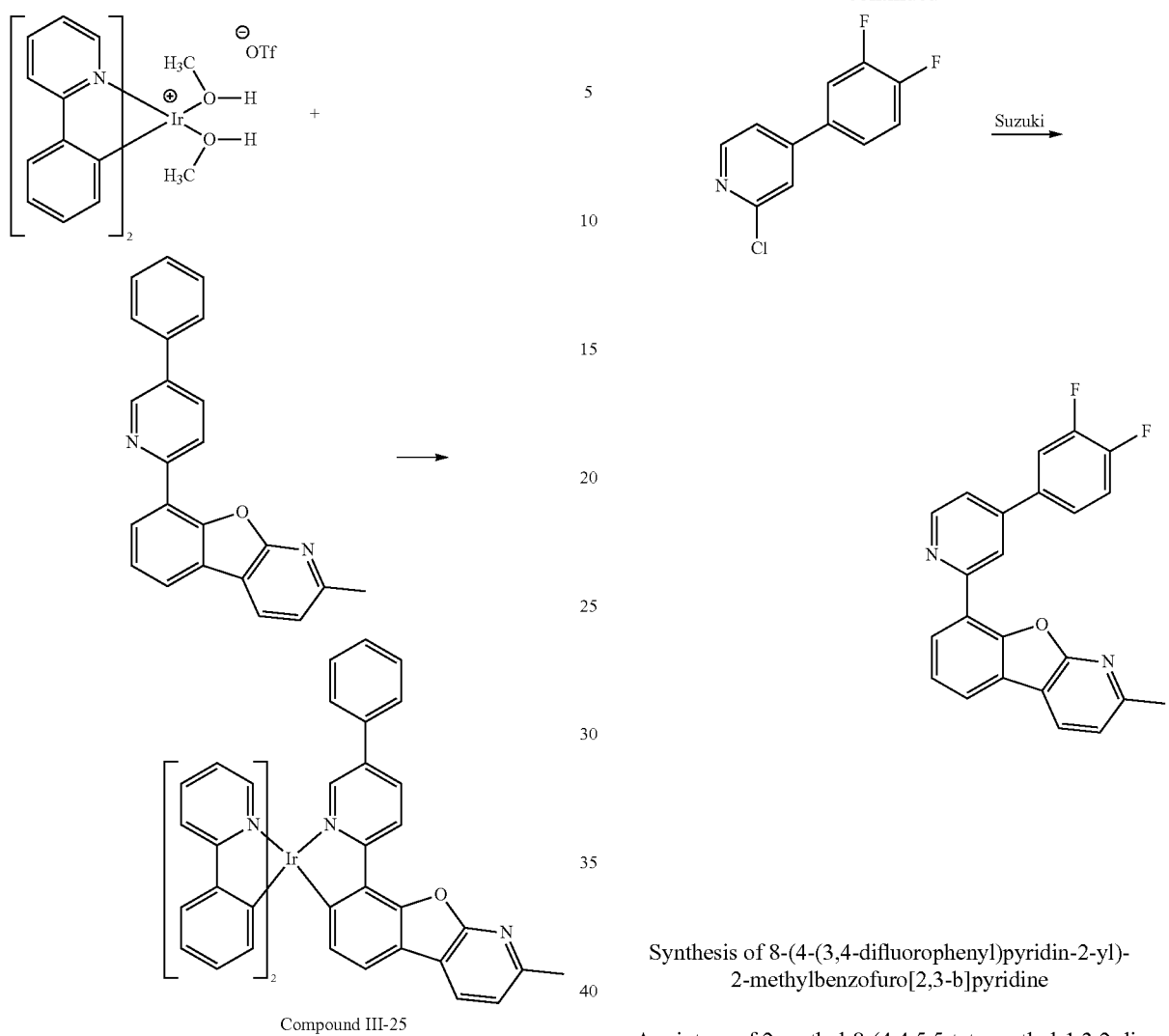

Compound III-25

A mixture of iridium complex (1.6 g, 2.28 mmol),1 2-methyl-8-(5-phenylpyridin-2-yl)benzofuro[2,3-b]pyridine (1.38 g, 4.10 mmol),),2-ethoxyethanol (40 mL) and DMF (40 mL) was heated at 130° C. overnight. The reaction mixture was concentrated to remove solvents and filtered through a small plug of silica gel and further chromatographed (1:1 heptane:DCM) to give 0.60 g and sublimed to give the desired product (0.41 g, 21.5% yield).

13. Synthesis of Compound III-62

Synthesis of 8-(4-(3,4-difluorophenyl)pyridin-2-yl)-2-methylbenzofuro[2,3-b]pyridine A mixture of 2-methyl-8-(4,4,5,5-tetramethyl-1,3,2-dioxaborolan-2-yl)benzofuro[2,3-b]pyridine (3.0 g, 9.70 mmol), 2-chloro-4-(3,4-difluorophenyl)pyridine (2.41 g, 10.67 mmol), Pd$_2$(dba)$_3$ (0.178 g 0.194 mmol), dicyclohexyl(2',6'-dimethoxy-[1,1'-biphenyl]-2-yl)phosphine (0.319 g, 0.776 mmol), potassium phosphate (7.21 g, 34.0 mmol), toluene (70 mL) and water (7 mL) was degassed with nitrogen and then refluxed overnight. The mixture was concentrated and extracted with ethyl acetate. The ethyl acetate layer was dried on Na$_2$SO$_4$ and then further purified by column chromatography using ethyl acetate in dichloromethane to give 8-(4-(3,4-difluorophenyl)pyridin-2-yl)-2-methylbenzofuro[2,3-b]pyridine (2.36 g, 6.34 mmol, 65.3% yield).

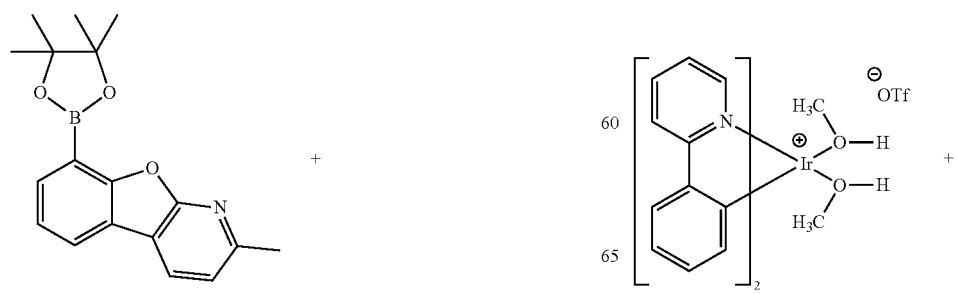

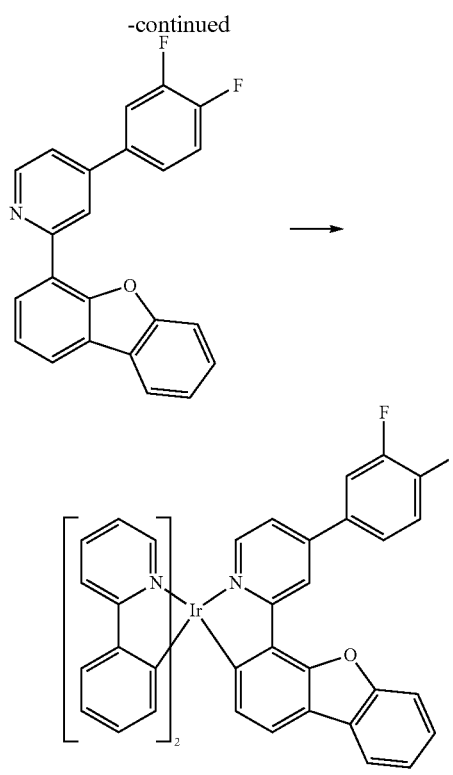

Compound III-62

A mixture of iridium complex (2.26 g, 3.17 mmol), 8 8-(4-(3,4-difluorophenyl)pyridin-2-yl)-2-methylbenzofuro[2,3-b]pyridine (2.36 g, 6.34 mmol), 2-ethoxyethanol (70 mL) and DMF (70 mL) was heated at 130° C. overnight. It was concentrated to remove solvents and filtered through a small plug of silica gel and further chromatographed (1:1 heptane:DCM) to give 0.9 g and sublimed to give the desired product (0.75 g, 27% yield).

14. Synthesis of Compound III-68

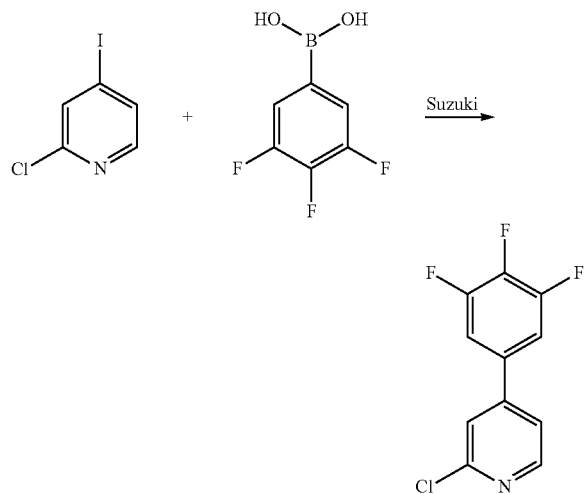

To a 1 liter 3-necked flask added sodium carbonate (10.62 g, 100 mmol), 2-chloro-4-iodopyridine (8.0 g, 33.4 mmol), (3,4,5-trifluorophenyl)boronic acid (5.88 g, 33.4 mmol), DME (300 mL), water (75 mL). The mixture was degassed with $N_2$ for 30 minutes and added palladiumtetrakistriph- enylphosphine (1.158 g, 1.002 mmol) and again degassed with $N_2$. Then the reaction was heated at reflux under $N_2$ overnight and cooled down to workup to give 4.5 g (55% yield) light yellow solid after column.

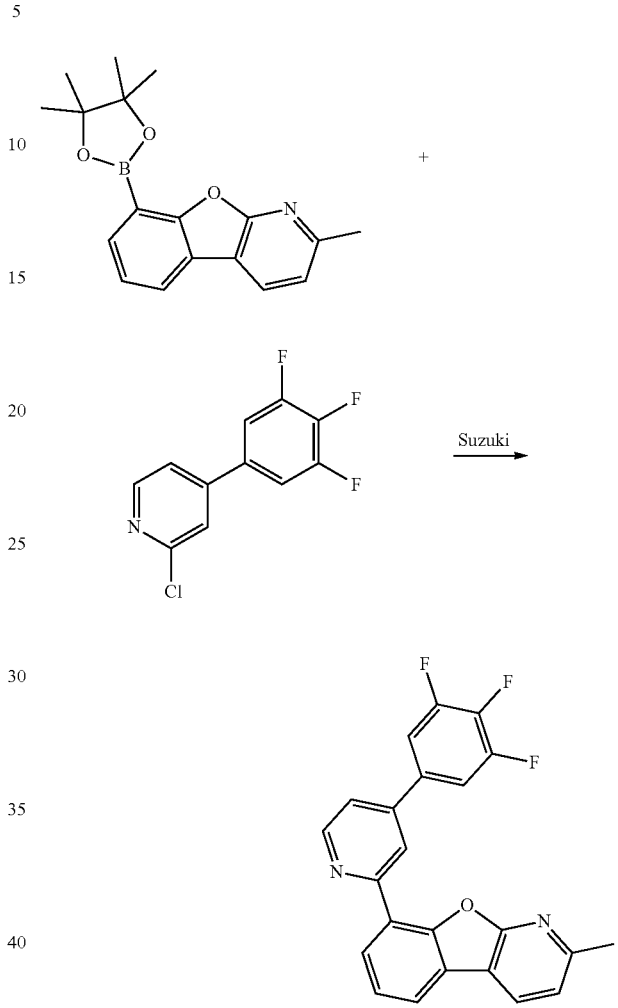

To a 250 ml flask added 2-methyl-8-(4,4,5,5-tetramethyl-1,3,2-dioxaborolan-2-yl)benzofuro[2,3-b]pyridine (3.0 g, 9.70 mmol), 2-chloro-4-(3,4,5-trifluorophenyl)pyridine (2.60 g, 10.67 mmol), dicyclohexyl(2',6'-dimethoxy-[1,1'-biphenyl]-2-yl)phosphine (0.319 g, 0.776 mmol), $Pd_2$ (dba)3 (0.178 g, 0.194 mmol), potassium phosphate (7.21 g, 34.0 mmol) followed by water (7 mL) and toluene (70 mL). The reaction was degassed with $N_2$ and heated at reflux under $N_2$ overnight. An aliquot by GC shows completion. The reaction mixture was worked up to give 2.35 g white solid (62% yield) product.

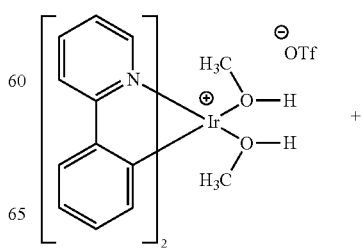

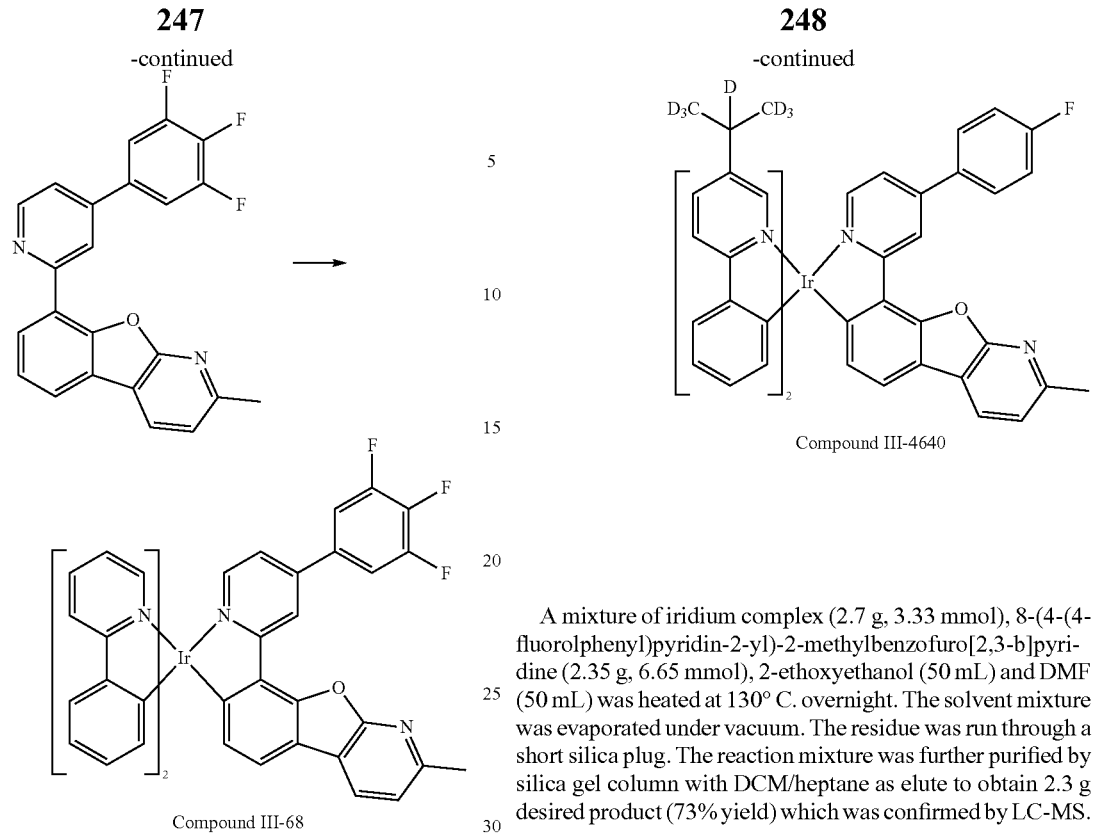

Compound III-68

To a 250 mL flask added iridium complex (2.148 g, 3.01 mmol) and 2-methyl-8-(4-(3,4,5-trifluorophenyl)pyridin-2-yl)benzofuro[2,3-b]pyridine (2.35 g, 6.02 mmol) followed by 2-ethoxyethanol (50 mL) and DMF (50 mL) and heated at 130° C. overnight. The reaction was allowed to cool down and evaporated the solvents. It was dissolved in DCM and passed through a short silica gel plug eluted with DCM and then run a silica gel column to give a 1.25 g (47% yield) orange solid which LC/MS shows desired mass.

15. Synthesis of Compound III-4640

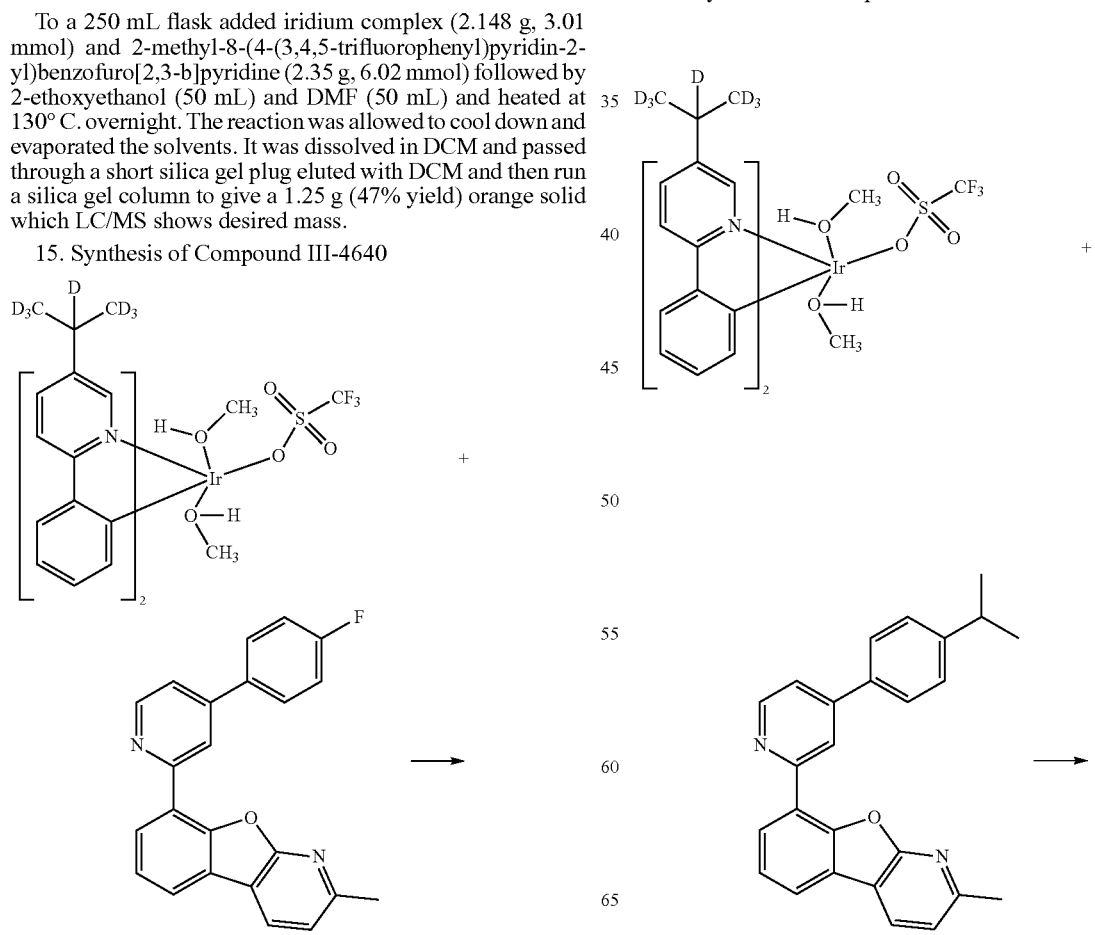

Compound III-4640

A mixture of iridium complex (2.7 g, 3.33 mmol), 8-(4-(4-fluorolphenyl)pyridin-2-yl)-2-methylbenzofuro[2,3-b]pyridine (2.35 g, 6.65 mmol), 2-ethoxyethanol (50 mL) and DMF (50 mL) was heated at 130° C. overnight. The solvent mixture was evaporated under vacuum. The residue was run through a short silica plug. The reaction mixture was further purified by silica gel column with DCM/heptane as elute to obtain 2.3 g desired product (73% yield) which was confirmed by LC-MS.

16. Synthesis of Compound III-4622

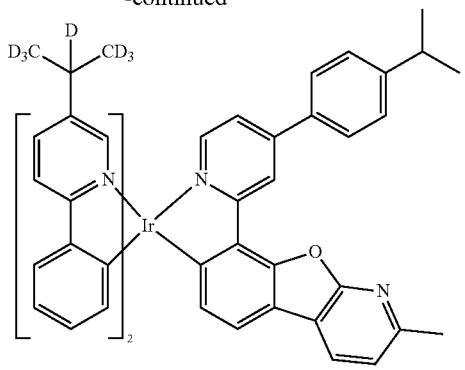

Compound III-4622

A mixture of phenylpyridine iridium complex (2.4 g, 2.96 mmol), 8-(4-(4-isopropylphenyl)pyridin-2-yl)-2-methylbenzofuro[2,3-b]pyridine (2.237 g, 5.91 mmol), 2-ethoxyethanol (50 mL) and DMF (50 mL) was heated at 130° C. overnight. The solvent mixture was evaporated under vacuum. The residue was run through a short silica plug with dichloromethane (DCM). The reaction mixture was further purified by silica gel column with DCM/heptane as elute to obtain 2.4 g desired product (83% yield), which was confirmed by LC-MS.

17. Synthesis of Compound III-56

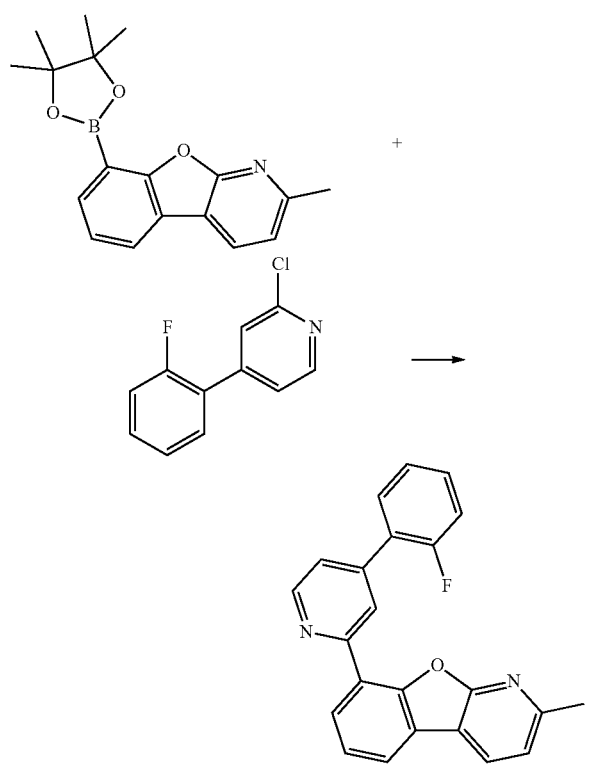

Synthesis of 8-(4-(2-fluorophenyl)pyridin-2-yl)-2-methylbenzofuro[2,3-b]pyridine 2-methyl-8-(4,4,5,5-tetramethyl-1,3,2-dioxaborolan-2-yl)benzofuro[2,3-b]pyridine (2.8 g, 9.06 mmol), 2-chloro-4-(2-fluorophenyl)pyridine (2.25 g, 10.84 mmol), tris(dibenzylideneacetone)palladium(0) (0.166 g, 0.181 mmol) and 2-Dicyclohexylphosphino-2',6'-dimethoxybiphenyl (0.297 g, 0.725 mmol) were charged into the reaction vessel with 200 mL of toluene. Potassium phosphate tribasic (6 g, 28.3 mmol) was then dissolved in 25 mL of water and was added to the reaction mixture. The reaction mixture was degassed with nitrogen then was heated to reflux overnight. The reaction mixture was cooled to room temperature. The toluene layer was separated and was dried over magnesium sulfate. This mixture was filtered and concentrated under vacuum. The crude residue was passed through a silica gel column using 15-22.5% ethyl acetate/heptanes. The clean product fractions were evaporated under reduced pressure yielding 8-(4-(2-fluorophenyl)pyridin-2-yl)-2-methylbenzofuro[2,3-b]pyridine (2.247 g, 6.34 mmol, 70% yield) as a white solid.

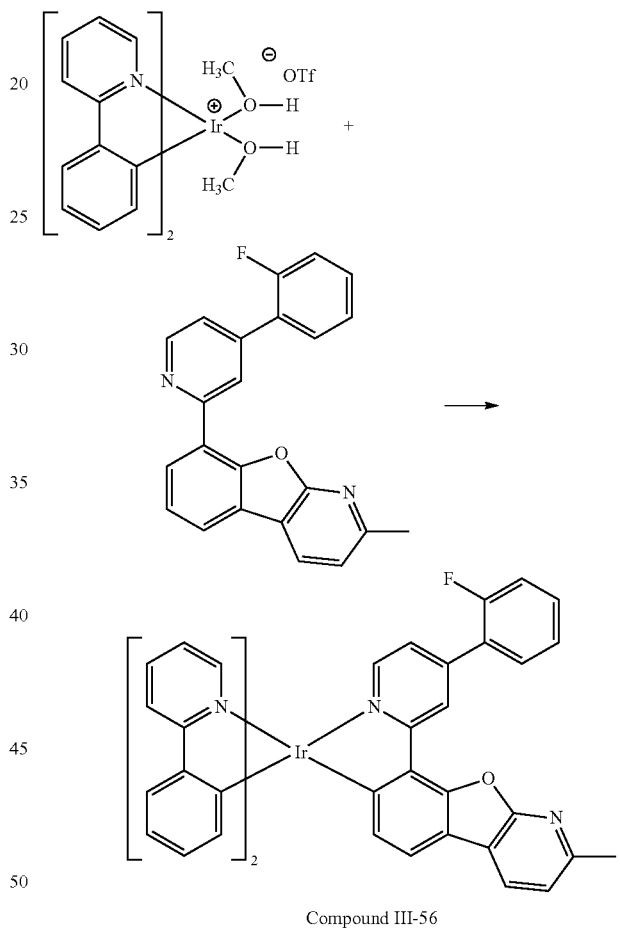

Compound III-56

8-(4-(2-fluorophenyl)pyridin-2-yl)-2-methylbenzofuro[2,3-b]pyridine (1.9 g, 5.36 mmol) and Iridium complex (1.913 g, 2.68 mmol) were charged into the reaction mixture with 50 mL of DMF and 50 mL of 2-ethoxyethanol. This reaction mixture was degassed with nitrogen then was heated at an oil bath temperature of 130° C. for 18 hours. The reaction mixture was cooled to room temperature then was evaporated under reduced pressure. The crude product was dissolved in 300 mL of DCM then was passed through a silica gel plug eluting the plug with 1.5 L of DCM. This DCM filtrated was evaporated and the crude product was passed through a silica gel column eluting the column with 55-65% DCM/heptanes. Clean product fractions yielded 1.2 g (32% yield) of the desired product.

18. Synthesis of Compound III-59

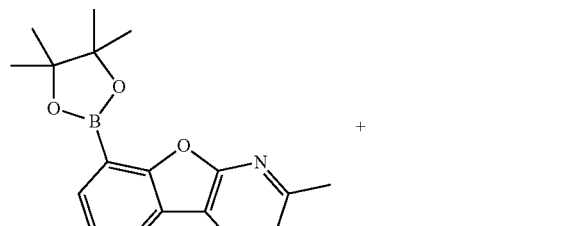

+

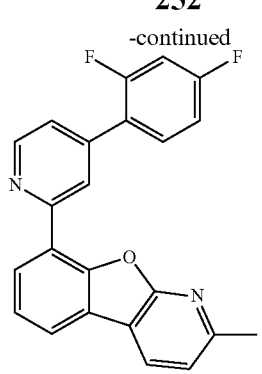

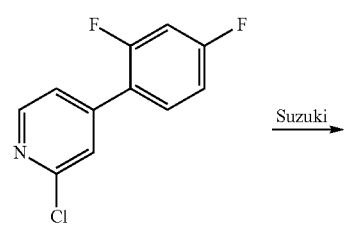 Suzuki→

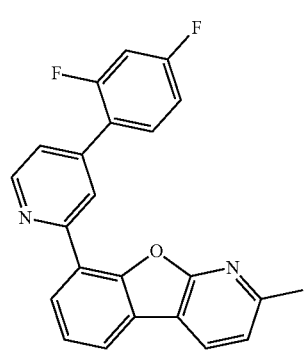

To a 250 mL flask added 2-methyl-8-(4,4,5,5-tetramethyl-1,3,2-dioxaborolan-2-yl) benzofuro[2,3-b]pyridine (3.0 g, 9.70 mmol), 2-chloro-4-(2,4-difluorophenyl)pyridine (2.63 g, 11.64 mmol), dicyclohexyl(2',6'-dimethoxy-[1,1'-biphenyl]-2-yl)phosphine (0.319 g, 0.776 mmol), Pd$_2$(dba)$_3$ (0.178 g, 0.194 mmol), potassium phosphate (7.21 g, 34.0 mmol) followed by water (7 mL) and toluene (volume: 70 mL). The reaction was degassed with N$_2$ and heated at reflux under N$_2$ overnight. The reaction was worked up with silica gel column to give 2.45 g (68%) clean product.

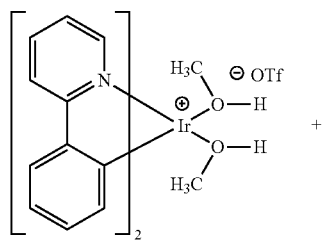

+

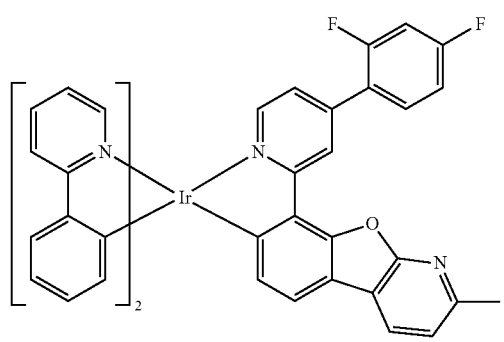

Compound III-59

To a 250 mL flask added iridium complex (2.348 g, 3.29 mmol), 8-(4-(2,4-difluorophenyl)pyridin-2-yl)-2-methyl-benzofuro[2,3-b]pyridine (2.45 g, 6.58 mmol), 2-ethoxyethanol (60 mL), DMF (60 mL). The mixture was heated in an oil bath at 130° C. overnight under N$_2$ and allowed to cool and evaporated the solvents to leave a red/orange solid which was further purified by silica gel column to give orange solid 1.7 g (61% yield) desired product which was confirmed by LC-MS.

19. Synthesis of Compound III-65

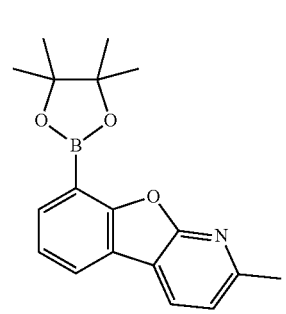

+

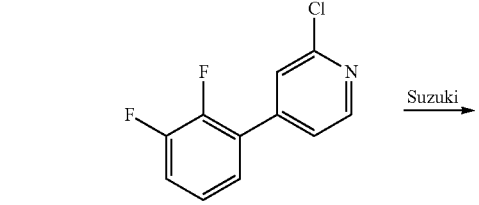 Suzuki→

-continued

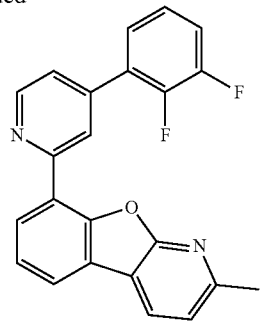

Synthesis of: 8-(4-(2,3-difluorophenyl)pyridin-2-yl)-2-methylbenzofuro[2,3-b]pyridine 2-methyl-8-(4,4,5,5-tetramethyl-1,3,2-dioxaborolan-2-yl)benzofuro[2,3-b]pyridine (2.8 g, 9.06 mmol), 2-chloro-4-(2,3-difluorophenyl)pyridine (2.452 g, 10.87 mmol), tris(dibenzylideneacetone)palladium(0) (0.166 g, 0.181 mmol) and 2-dicyclohexylphosphino-2',6'-dimethoxybiphenyl (0.297 g, 0.725 mmol) were charged into the reaction mixture with 200 mL of toluene. Potassium phosphate tribasic (5.76 g, 27.2 mmol) was dissolved in 25 mL of water then was charged into the reaction mixture. This mixture was degassed then heated to reflux for 18 hours. The reaction mixture was cooled to room temperature. The toluene layer was separated and was dried over magnesium sulfate. This mixture was filtered and concentrated under vacuum. The crude residue was passed through a silica gel column using 15-22.5% ethyl acetate/heptanes. The clean product fractions were evaporated under reduced pressure yielding 8-(4-(2,3-difluorophenyl)pyridin-2-yl)-2-methylbenzofuro[2,3-b]pyridine (1.2 g, 3.22 mmol, 35.6% yield) as a white solid.

-continued

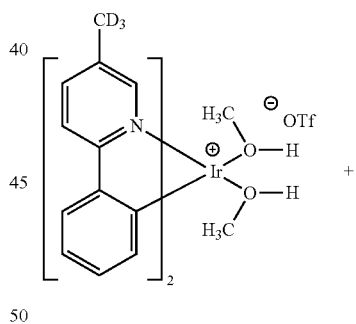

Compound III-65

8-(4-(2,3-difluorophenyl)pyridin-2-yl)-2-methylbenzofuro[2,3-b]pyridine (1.2 g, 3.22 mmol) and iridium complex (2.30 g, 3.22 mmol) were charged into the reaction mixture with 30 mL of DMF and 30 mL of 2-ethoxyethanol. This reaction mixture was degassed with nitrogen then was heated at an oil bath temperature of 130° C. for 18 hours. The reaction mixture was cooled to room temperature then was evaporated under reduced pressure. The crude product was dissolved in 300 mL of DCM then was passed through a silica gel plug eluting the plug with 1.5 L of DCM. This DCM filtrated was evaporated and the crude product was passed through a silica gel column eluting the column with 55-65% DCM/heptanes. Clean product fractions yielded 0.69 g (30% yield) of the desired product.

20. Synthesis of Compound III-1750

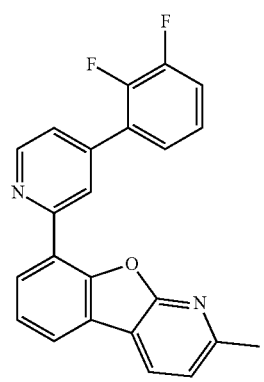

+

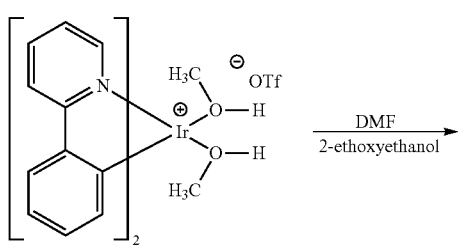

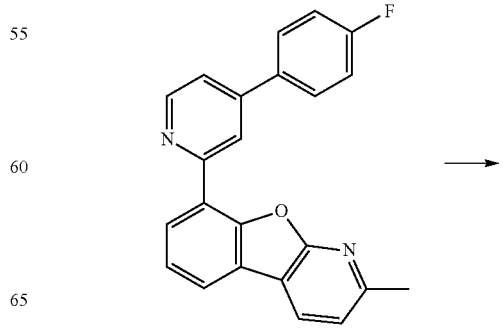

-continued

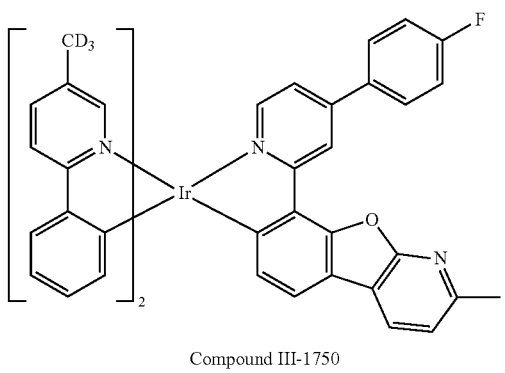

Compound III-1750

A mixture of iridium complex (2.1 g, 2.81 mmol), 8-(4-(4-fluorolphenyl)pyridin-2-yl)-2-methylbenzofuro[2,3-b]pyridine (1.99 g, 5.62 mmol), 2-ethoxyethanol (50 mL) and DMF (50 mL) was heated at 130° C. overnight under nitrogen. The solvent mixture was evaporated under vacuum. The residue was run through a short silica plug. The reaction mixture was further purified by silica gel column with DCM/heptane as elute to obtain 2.1 g desired product (84% yield) which was confirmed by LC-MS.

21. Synthesis of Compound III-1559

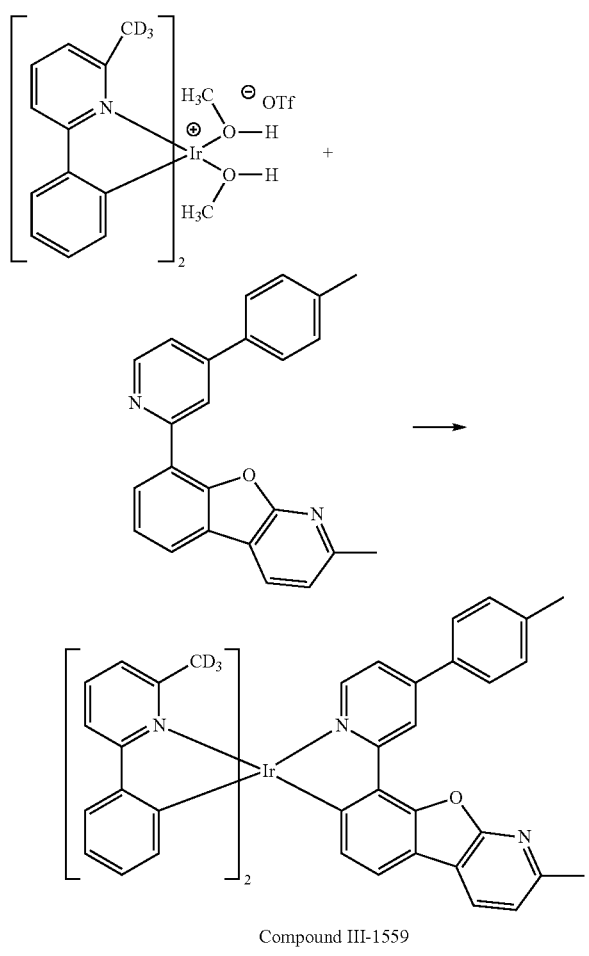

Compound III-1559

A mixture of iridium complex (2.214 g, 2.58 mmol), 8-(4-(4-methylphenyl)pyridin-2-yl)-2-methylbenzofuro[2,3-b]pyridine (1.8 g, 5.14 mmol), 2-ethoxyethanol (50 mL) and DMF (50 mL) was heated at 130° C. overnight. The solvent mixture was evaporated under vacuum. The residue was run through a short silica plug. The reaction mixture was further purified by silica gel column to give 1.8 g (71% yield) desired product which was confirmed by LC-MS.

22. Synthesis of Compound III-26

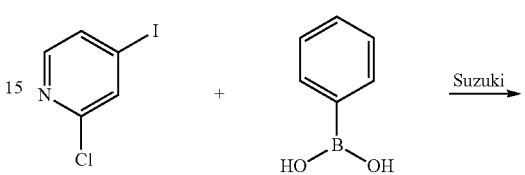

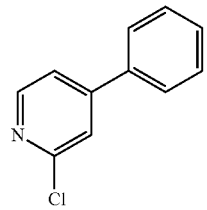

Synthesis of 2-Chloro-4-phenylpyridine

A mixture of 2-chloro-4-iodopyridine (20.0 g, 82 mmol), phenylboronic acid (10.2 g, 82 mmol), Pd(Ph$_3$P)$_4$ (2.84 g 2.46 mmol), sodium carbonate (26.0 g, 246 mmol), DME (600 mL) and water (150 mL) was degassed with nitrogen and then refluxed overnight. The reaction was concentrated and the extracted with ethyl acetate. The ethyl acetate layer was dried on Na$_2$SO$_4$ and then vacuum distilled to give 2-chloro-4-phenylpyridine (2.79 g. 12.7 mmol. 82% yield).

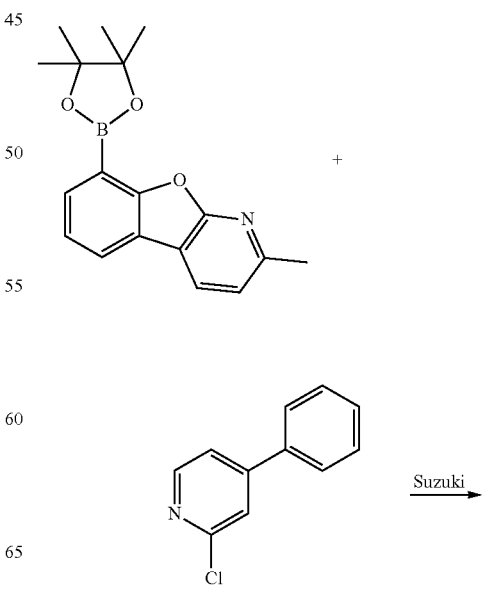

-continued

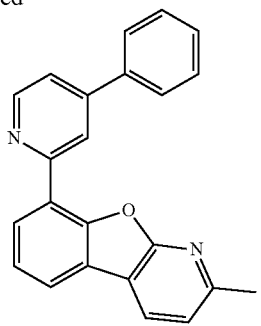

Synthesis of 2-methyl-8-(4-phenylpyridin-2-yl)ben-zofuro[2,3-b]pyridine

A mixture of 2-methyl-8-(4,4,5,5-tetramethyl-1,3,2-dioxaborolan-2-yl)benzofuro[2,3-b]pyridine (4.34 g, 14.03 mmol), 2-chloro-4-phenylpyridine (2.66 g, 14.03 mmol), Pd$_2$(dba)$_3$ (0.257 g 0.281 mmol), dicyclohexyl(2',6'-dimethoxy-[1,1'-biphenyl]-2-yl)phosphine (0.582 g, 1.42 mmol), potassium phosphate (8.93 g, 42.1 mmol), toluene (180 mL) and water (28 mL) was degassed with nitrogen and then refluxed overnight. The mixture was concentrated and extracted with ethyl acetate. The ethyl acetate layer was dried on Na$_2$SO$_4$ and then further purified by column chromatography using ethyl acetate in hexanes to give 2-methyl-8-(4-phenylpyridin-2-yl)benzofuro[2,3-b]pyridine (3.66 g, 10.88 mmol, 78% yield).

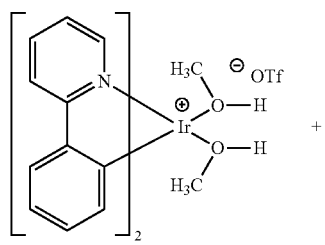 +

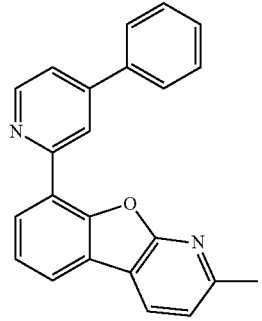 

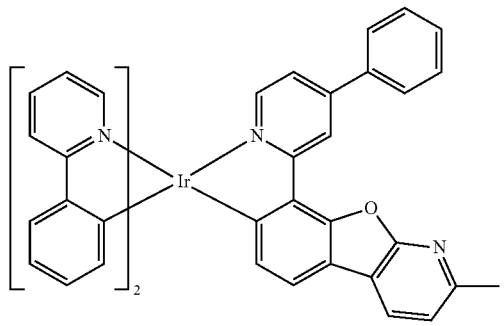

Compound III-26

A mixture of iridium complex (2 g, 2.8 mmol), 1 2-methyl-8-(4-phenylpyridin-2-yl)benzofuro[2,3-b]pyridine (1.89 g, 5.60 mmol,), ethoxyethanol (40 ml) and DMF (40 mL) was heated at 130° C. overnight. The reaction mixture was concentrated to remove solvents and filtered through a small plug of silica gel and further chromatographed to give 0.98 g product. After sublimation, it gave the desired product (0.85 g, 36.3% yield).

23. Synthesis of Compound III-196

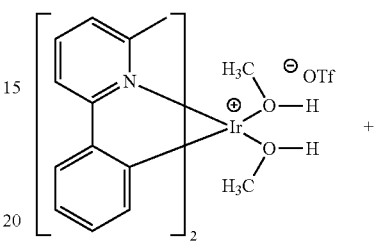 +

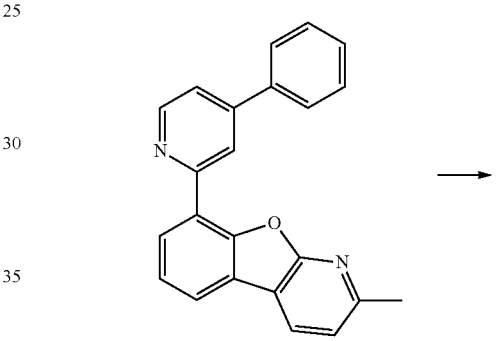 →

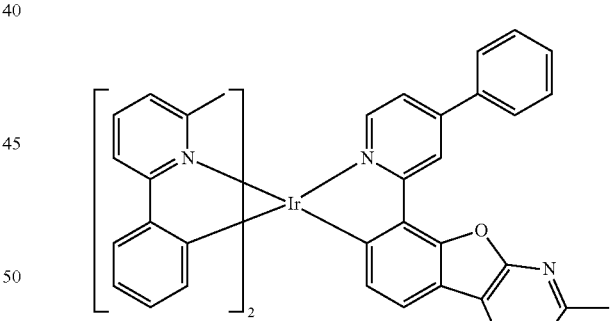

Compound III-196

A mixture of iridium complex (2.0 g, 2.69 mmol),), 2-methyl-8-(4-phenylpyridin-2-yl)benzofuro[2,3-b]pyridine (1.807 g, 5.37 mmol), 2-ethoxyethanol (50 mL) and DMF (50 mL) was heated at 130° C. overnight under nitrogen. The solvent mixture was evaporated under vacuum. The residue was run through a short silica plug with DCM as elute. The reaction mixture was further purified by silica gel column with DCM/heptane as elute to obtain 1.1 g desired product (47% yield) which was confirmed by LC-MS.

24. Synthesis of Compound III-220

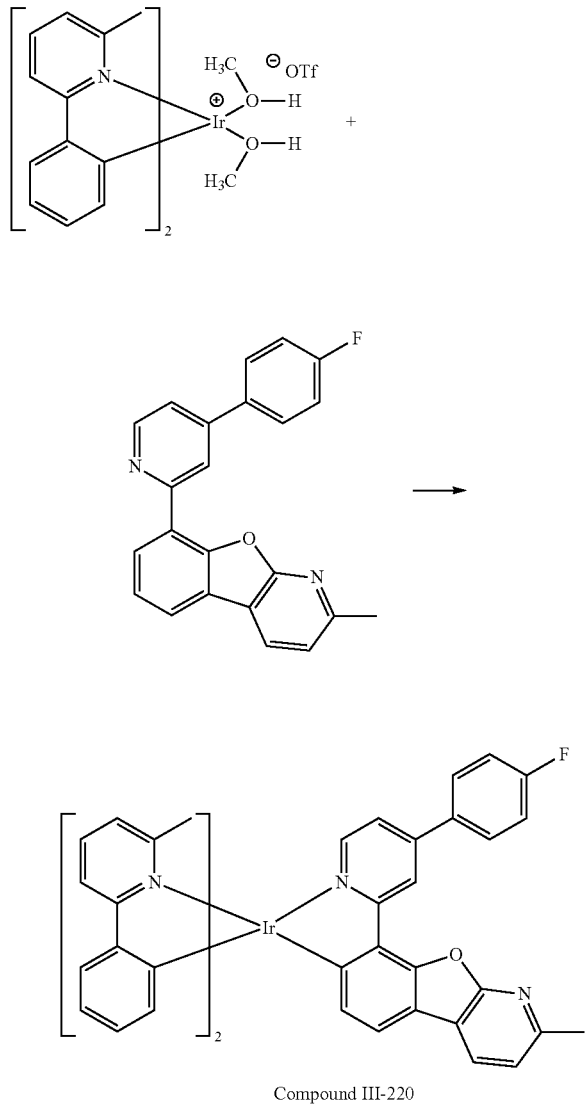

Compound III-220

A mixture of iridium complex (2.0 g, 2.70 mmol), 8-(4-(4-fluorolphenyl)pyridin-2-yl)-2-methylbenzofuro[2,3-b]pyridine (1.911 g, 5.39 mmol), 2-ethoxyethanol 60 mL was heated at 130° C. overnight under nitrogen. The reaction was cooled down and filtered and washed with methanol. The obtained crud product was purified by silica gel column with DCM/heptane as elute to obtain 1.6 g desired product (67%, yield) which was confirmed by LC-MS.

25. Synthesis of Compound III-29

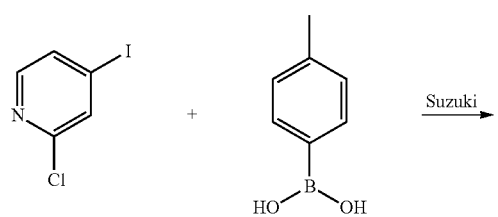 Suzuki

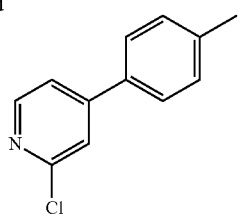

Synthesis of 2-Chloro-4-(p-tolyl)pyridine

A mixture of 2-chloro-4-iodopyridine (10.0 g, 41.8 mmol), p-tolylphenylboronic acid (5.68 g, 41.8 mmol), Pd(Ph₃P)₄ (1.45 g 1.25 mmol), sodium carbonate (13.3 g, 125 mmol), DME (300 mL) and water (75 mL) was degassed with nitrogen and then refluxed overnight. The reaction mixture was concentrated and extracted with ethyl acetate. The ethyl acetate layer was dried on Na₂SO₄ and vacuum distilled and recrystallized to give 2-chloro-4-(p-tolyl)pyridine (3.75 g, 18.4 mmol, 44% yield).

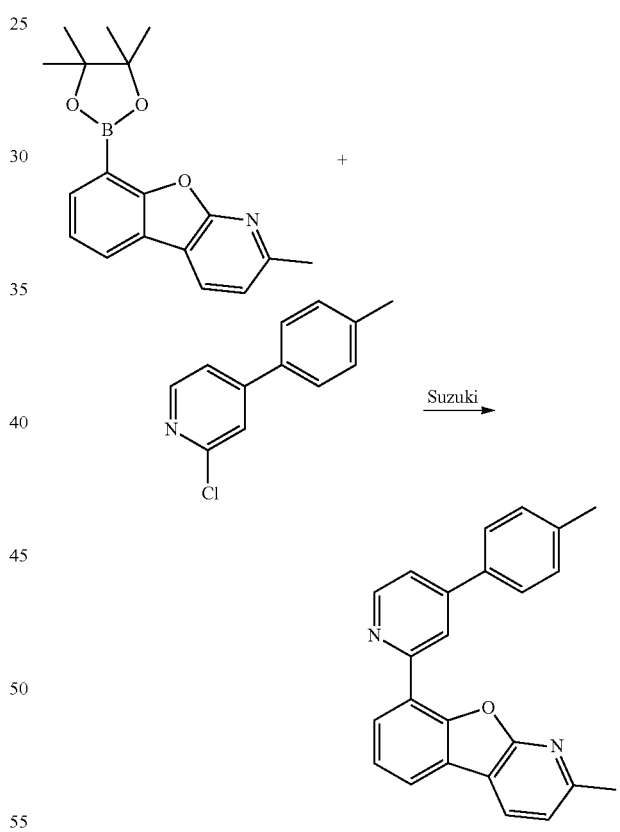

Synthesis of 2-methyl-8-(4-(p-tolyl)(pyridin-2-yl) benzofuro[2,3-b]pyridine A mixture of 2-methyl-8-(4,4,5,5-tetramethyl-1,3,2-dioxaborolan-2-yl)benzofuro[2,3-b]pyridine (2.5 g, 8.03 mmol), 2-chloro-4-(p-tolyl)pyridine (1.80 g, 8.83 mmol), Pd₂(dba)₃ (0.147 g 0.161 mmol), dicyclohexyl(2',6'-dimethoxy-[1,1'-biphenyl]-2-yl)phosphine (0.264 g, 0.642 mmol), potassium phosphate (5.96 g, 28.1 mmol), toluene (100 mL) and water (10 mL) was degassed with nitrogen and then refluxed overnight. The reaction mixture was concentrated and extracted with ethyl acetate. The ethyl acetate layer was dried on Na$_2$SO$_4$ and then further purified by column chromatography using ethyl acetate in hexanes to give 2-methyl-8-(4-(p-tolyl)pyridin-2-yl)benzofuro[2,3-b]pyridine (2.0 g, 5.71 mmol, 71% yield).

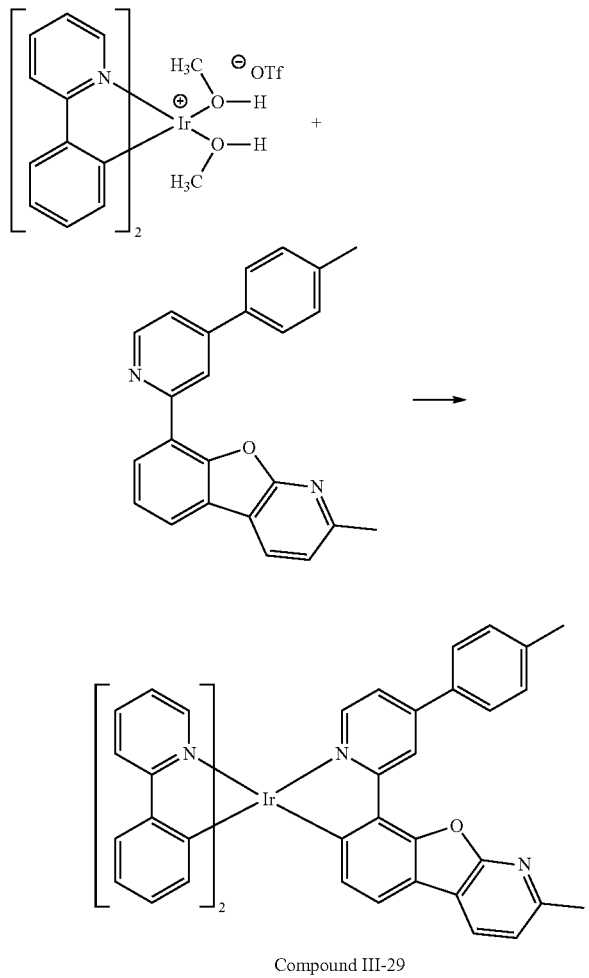

Compound III-29

A mixture of iridium complex (2.26 g, 3.17 mmol),1 2-methyl-8-(4-(p-tolyl)pyridin-2-yl)benzofuro[2,3-b]pyridine (2.0 g, 5.71 mmol),), 2-ethoxyethanol (45 mL) and DMF (45 mL) was heated at 130° C. overnight. The reaction mixture was concentrated to remove solvents and filtered through a small plug of silica gel with DCM and further chromatographed to give 1.54 g product. After sublimation, it yielded 1.0 g (37% yield) desired product which was confirmed by LC-MS.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. A compound having the formula Ir(L$_A$)$_n$(L$_B$)$_{3-n}$, having the structure:

Formula I

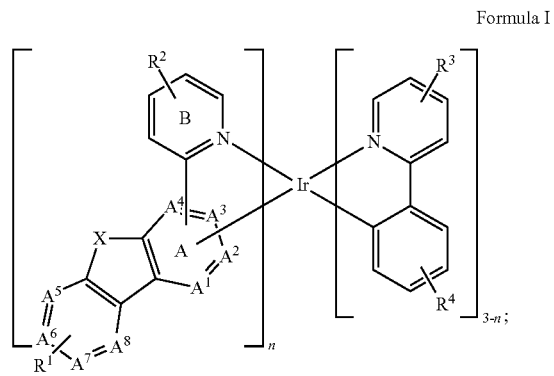

wherein A$^1$, A$^2$, A$^3$, A$^4$, A$^5$, A$^6$, A$^7$, and A$^8$ comprise carbon or nitrogen;

wherein at least one of A$^1$, A$^2$, A$^3$, A$^4$, A$^5$, A$^6$, A$^7$, and A$^8$ is nitrogen;

wherein ring B is bonded to ring A through a C—C bond;

wherein the iridium is bonded to ring A through a Ir—C bond;

wherein X is O, S, or Se;

wherein R$^1$, R$^2$, R$^3$, and R$^4$ independently represent mono-, di-, tri-, tetra-substitution, or no substitution;

wherein any adjacent substitutions in R$^1$, R$^2$, R$^3$, and R$^4$ are optionally linked together to form a ring;

wherein R$^1$, R$^3$, and R$^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein R$^2$ is selected from the group consisting of aryl, substituted aryl, heteroaryl, and substituted heteroaryl; and wherein n is an integer from 1 to 3.

2. The compound of claim 1, wherein R$^2$ is phenyl or substituted phenyl.

3. The compound of claim 1, wherein R$^2$ is pyridine or substituted pyridine.

4. The compound of claim 1, wherein R$^2$ represents mono-substitution.

5. The compound of claim 1, wherein n is 1.

6. The compound of claim 1, wherein the compound has the structure according to Formula II below:

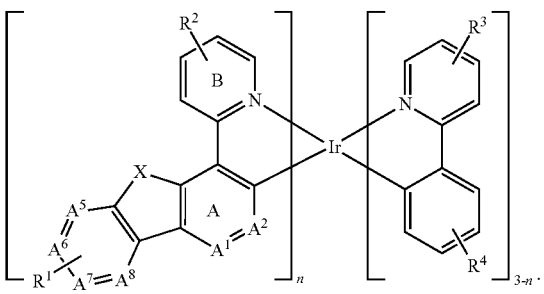

7. The compound of claim 6, wherein n is 1.

8. The compound of claim 1, wherein only one of $A^1$ to $A^8$ is nitrogen.

9. The compound of claim 8, wherein only one of $A^5$ to $A^8$ is nitrogen.

10. The compound of claim 1, wherein X is O.

11. The compound of claim 1, wherein $R^1$, $R^3$, and $R^4$ are independently selected from the group consisting of hydrogen, deuterium, alkyl, and combinations thereof.

12. The compound of claim 1, wherein $R^3$ is alkyl.

13. The compound of claim 12, wherein the alkyl is deuterated or partially deuterated.

14. The compound of claim 1, wherein $L_A$ is selected from the group consisting of:

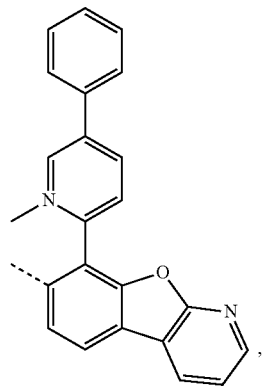
$L_{A318}$

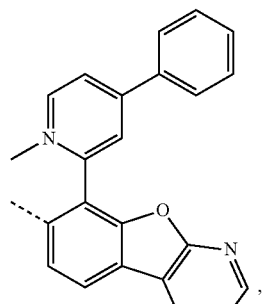
$L_{A319}$

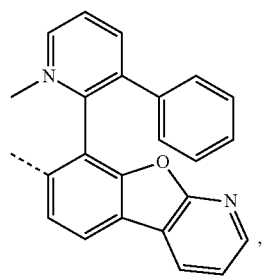
$L_{A320}$

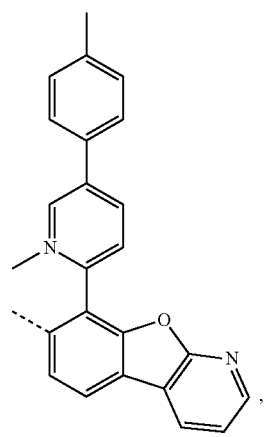
$L_{A321}$

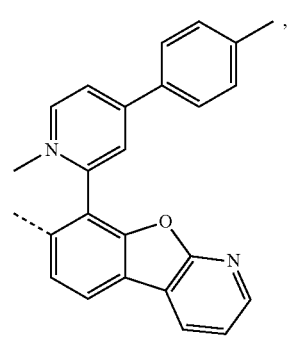
$L_{A322}$

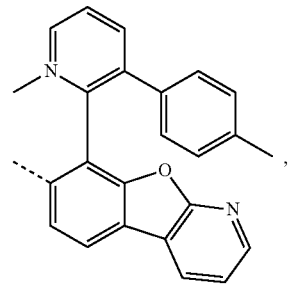
$L_{A323}$

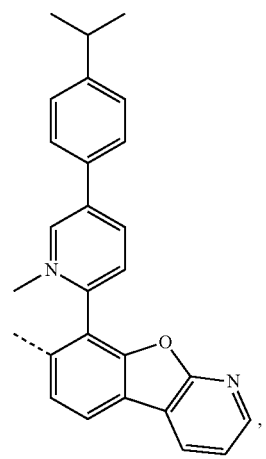
$L_{A324}$

265
-continued
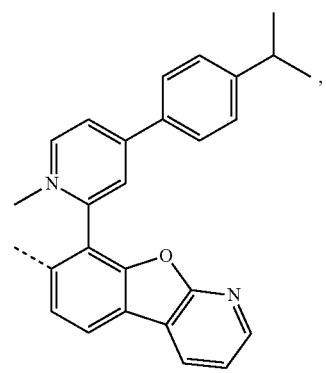
L<sub>A325</sub>
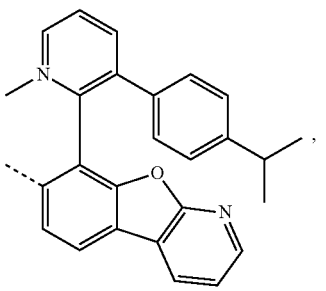
L<sub>A326</sub>
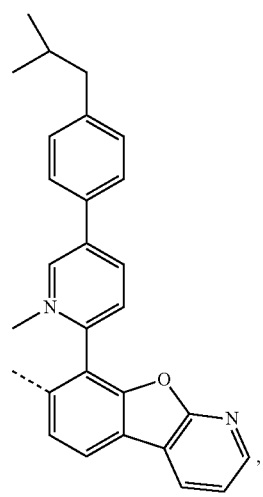
L<sub>A327</sub>
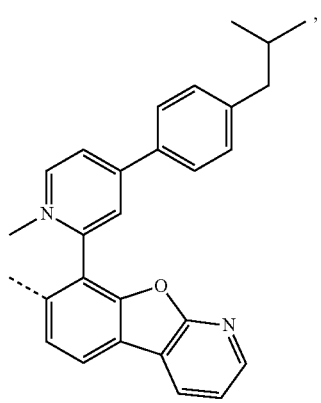
L<sub>A328</sub>
266
-continued
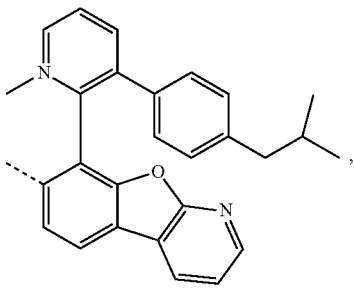
L<sub>A329</sub>
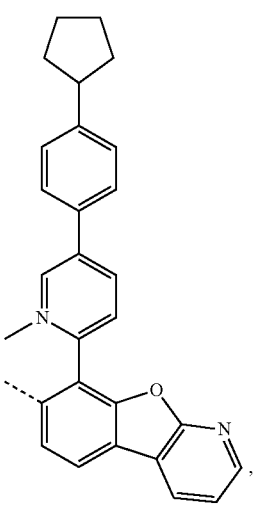
L<sub>A330</sub>
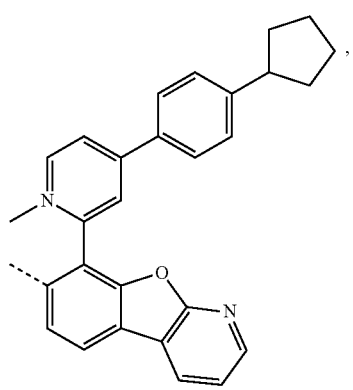
L<sub>A331</sub>
L<sub>A332</sub>

267
-continued
L_{A333}
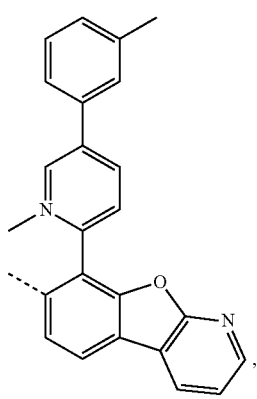
L_{A334}
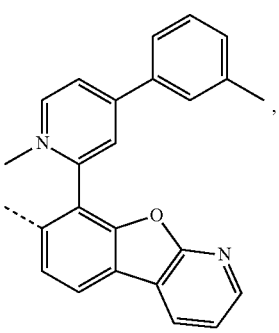
L_{A335}
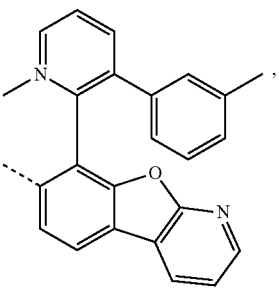
L_{A336}
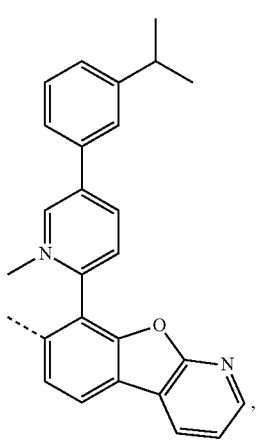
268
-continued
L_{A337}
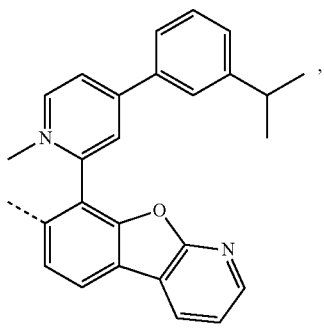
L_{A338}
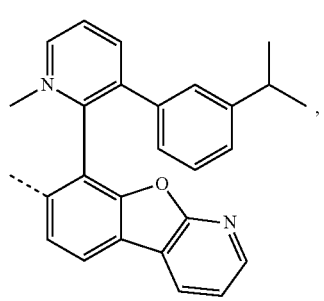
L_{A339}
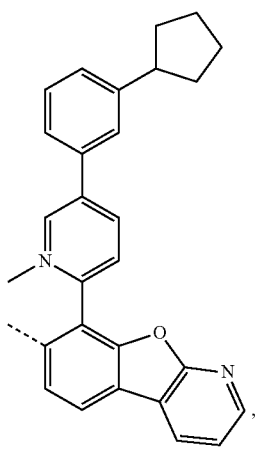
L_{A340}
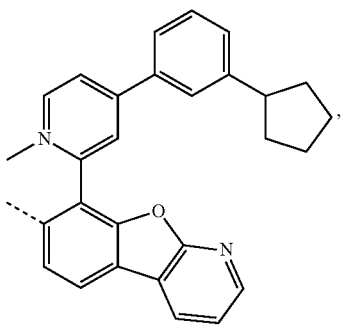

269
-continued
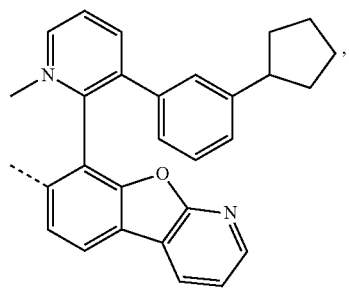
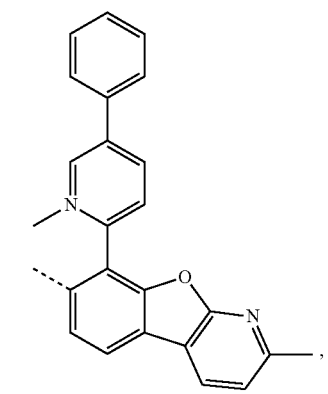
L_{A343}
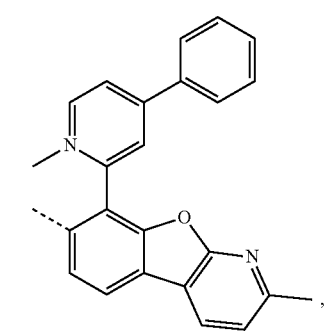
L_{A344}
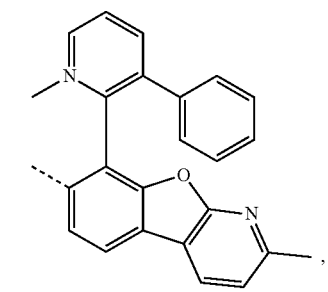
270
-continued
L_{A341}
L_{A345}
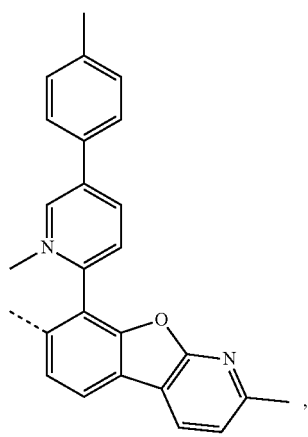
L_{A342}
L_{A346}
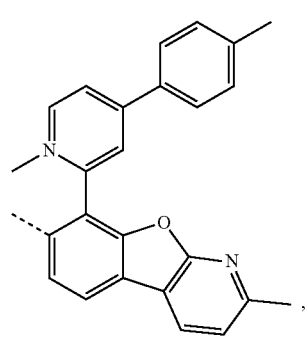
L_{A347}
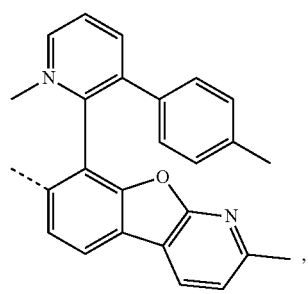
L_{A348}
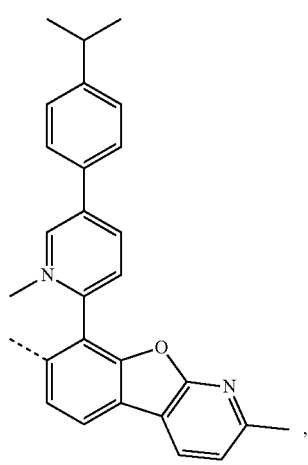

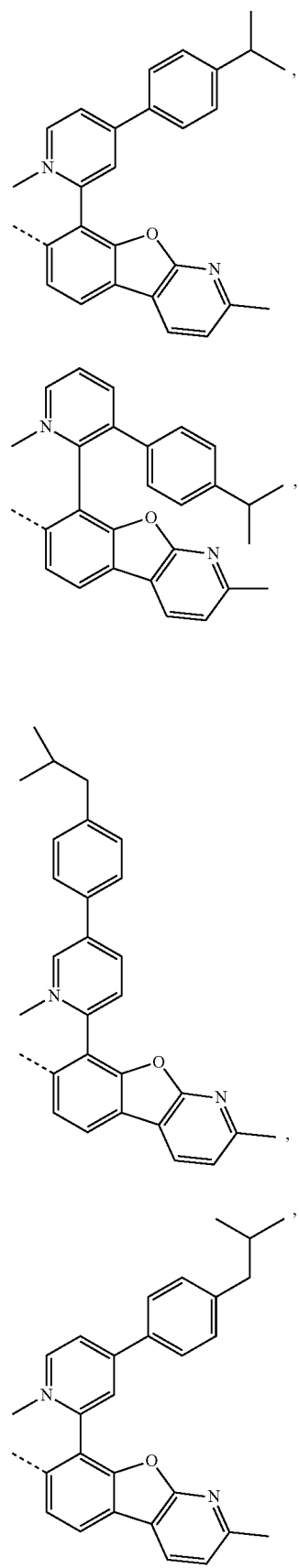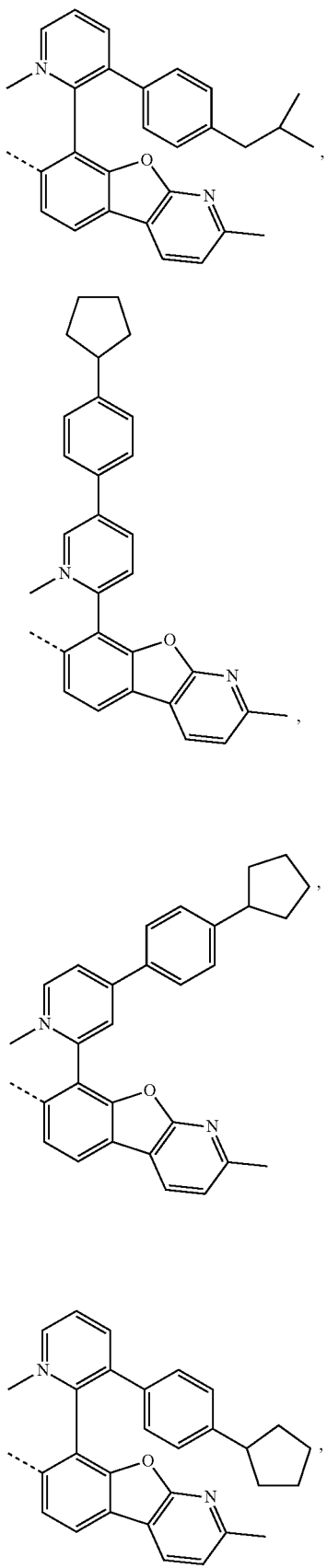

L_{A357}
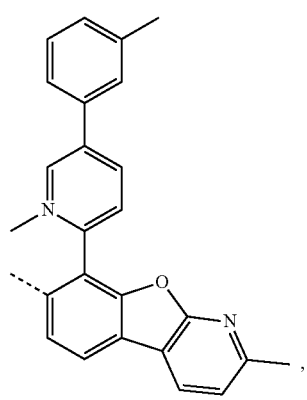
L_{A358}
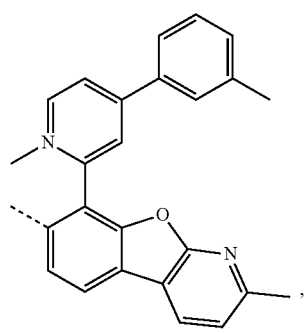
L_{A359}
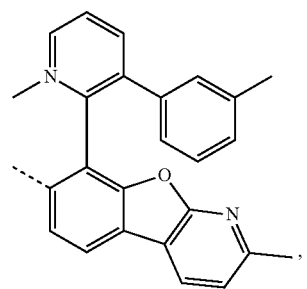
L_{A360}
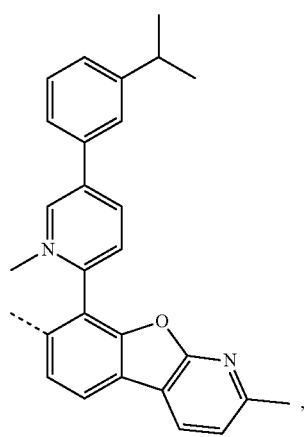
L_{A361}
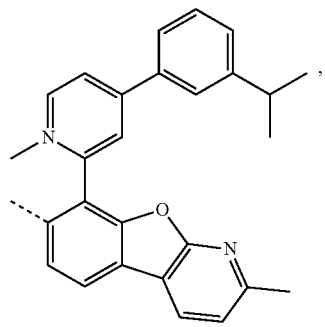
L_{A362}
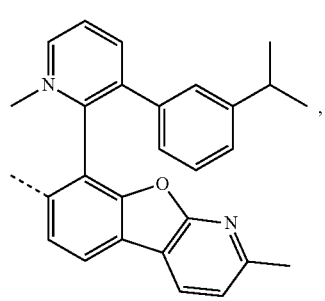
L_{A363}
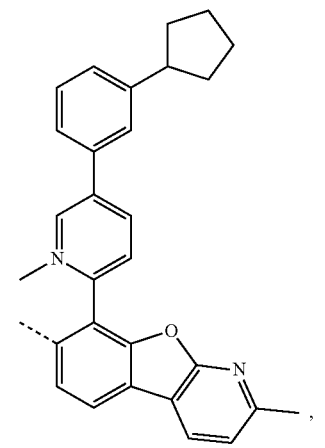
L_{A364}
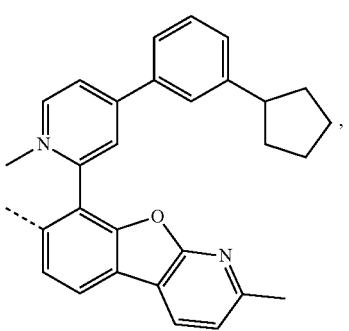

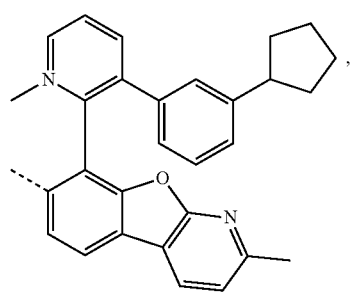
L_{A365}
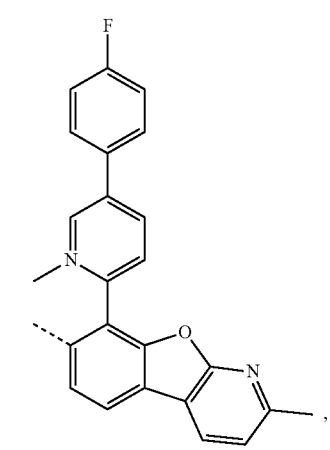
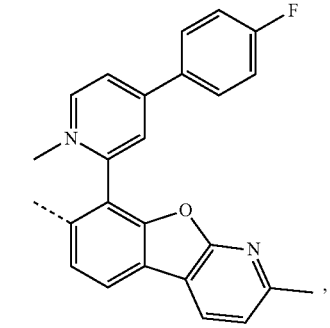
L_{A367}
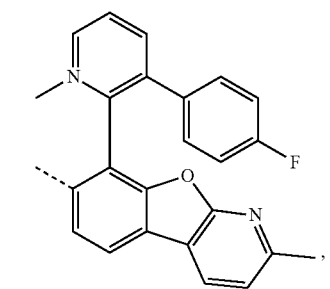
L_{A368}
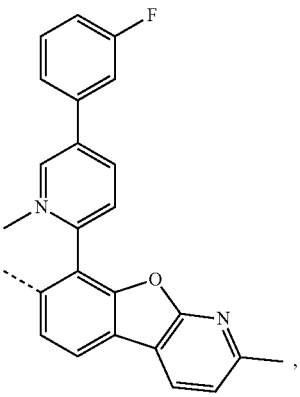
L_{A369}
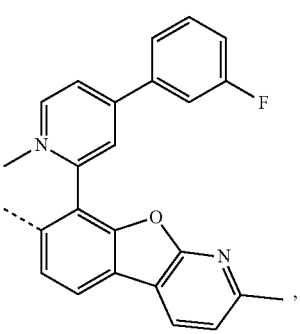
L_{A370}
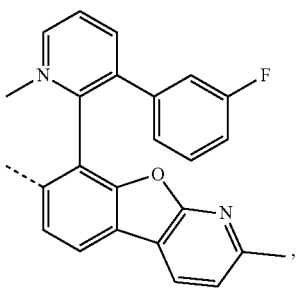
L_{A371}
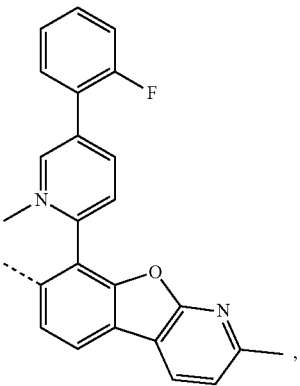
L_{A372}

277
-continued
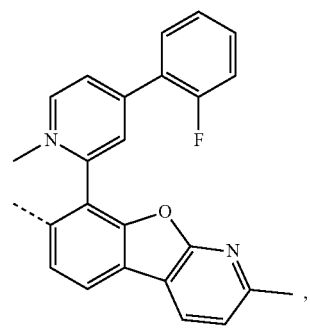
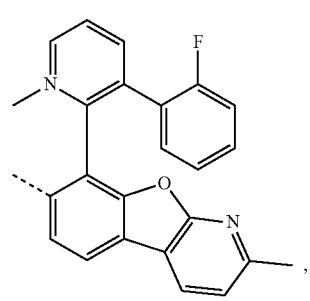
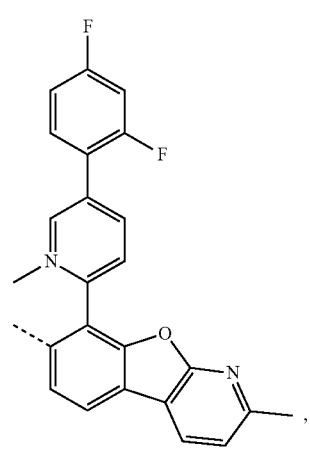
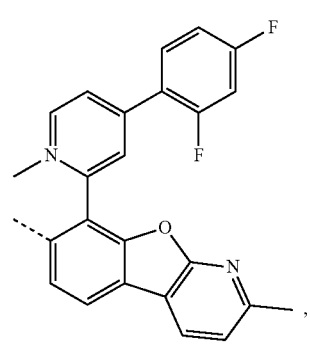
278
-continued
L_{A373}
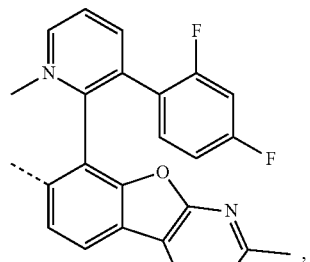
L_{A374}
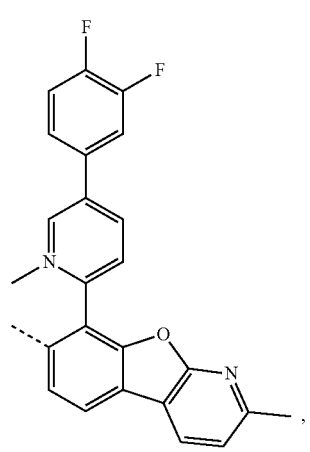
L_{A375}
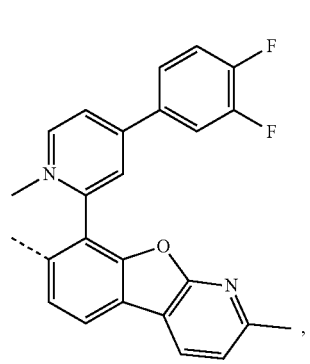
L_{A376}
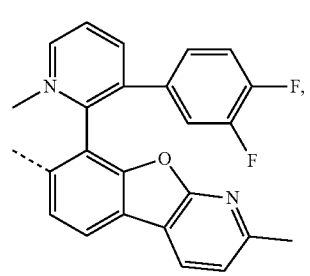
L_{A377}
L_{A378}
L_{A379}
L_{A380}

L<sub>A381</sub> 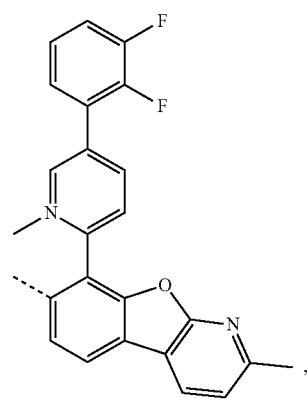
L<sub>A382</sub> 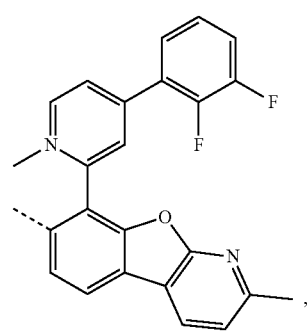
L<sub>A383</sub> 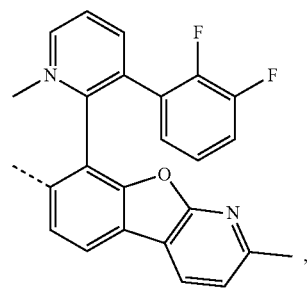
L<sub>A384</sub> 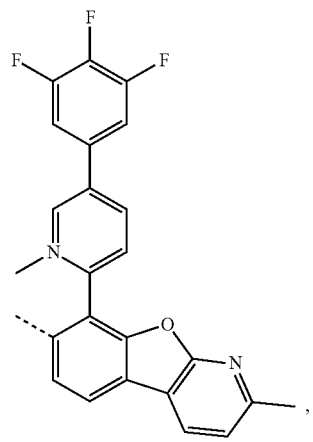
L<sub>A384</sub> 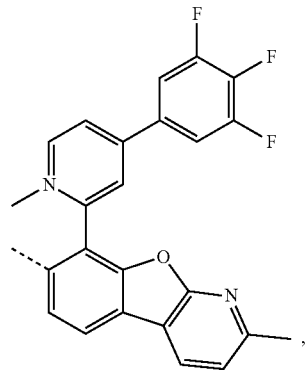
L<sub>A386</sub> 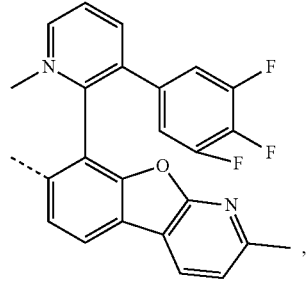
L<sub>A387</sub> 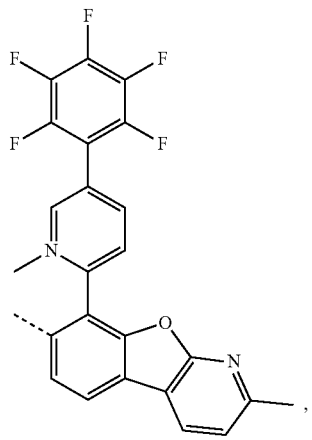
L<sub>A388</sub> 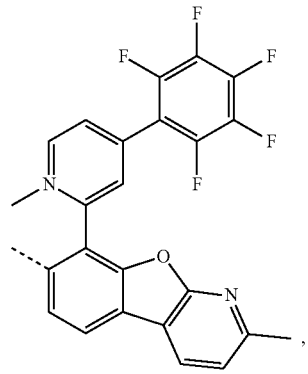

L_{A389} 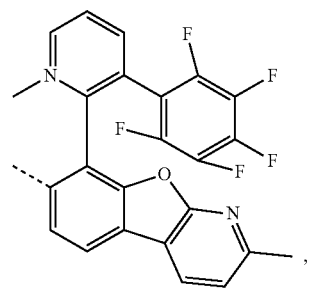
L_{A390} 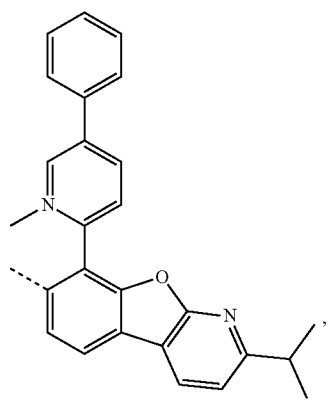
L_{A391} 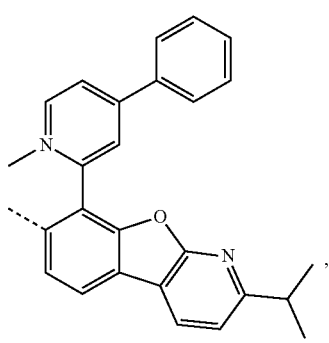
L_{A392} 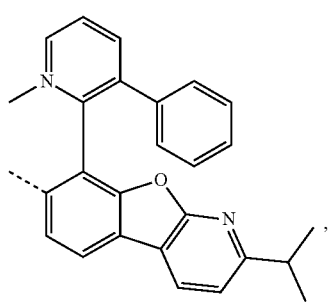
L_{A393} 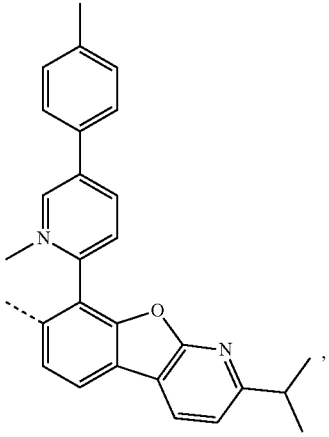
L_{A394} 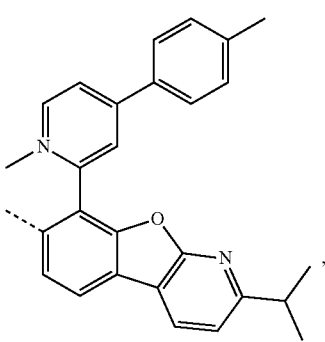
L_{A395} 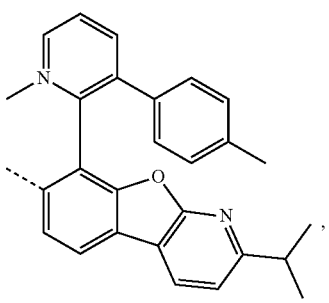
L_{A396} 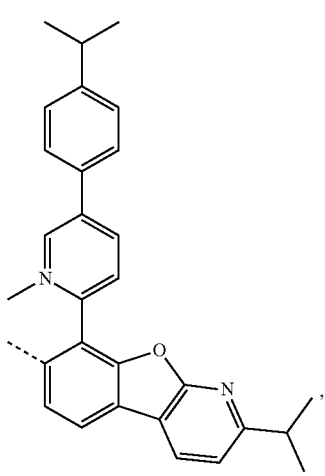

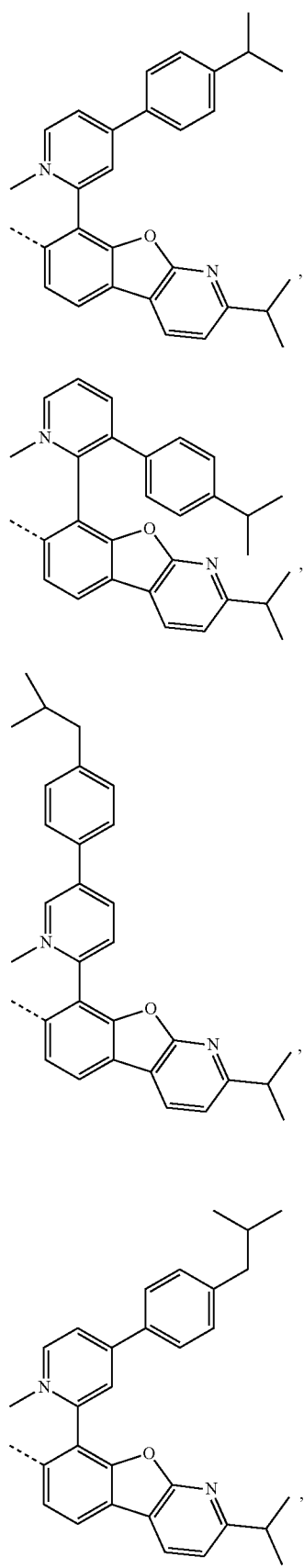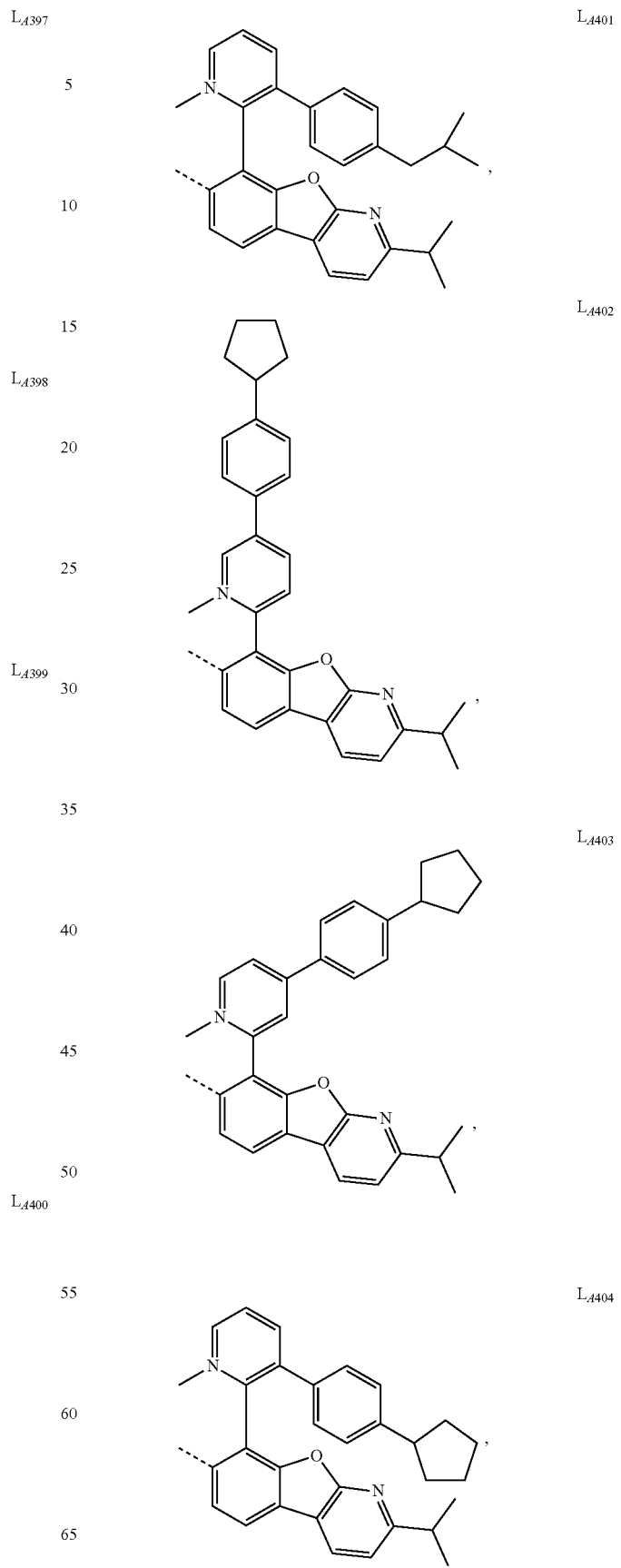

285
-continued
L$_{A405}$
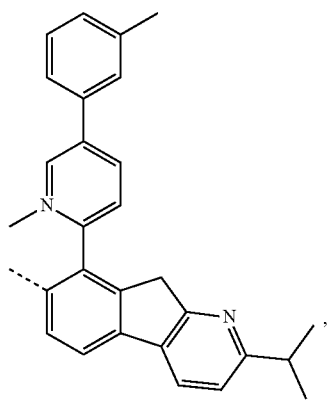
L$_{A406}$
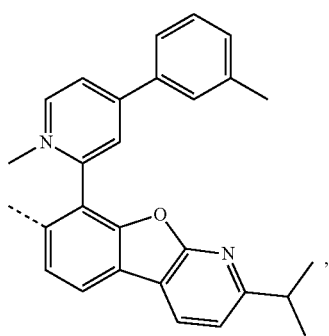
L$_{A407}$
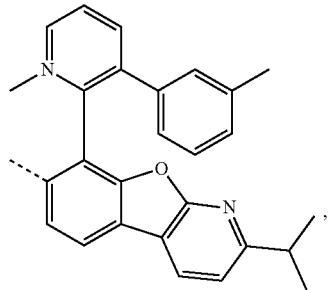
L$_{A408}$
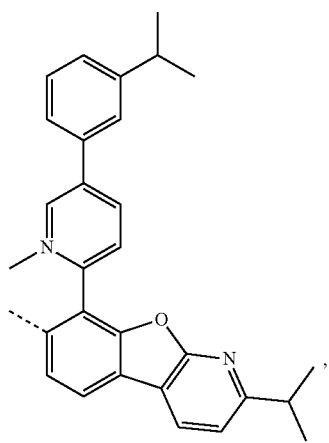
286
-continued
L$_{A409}$
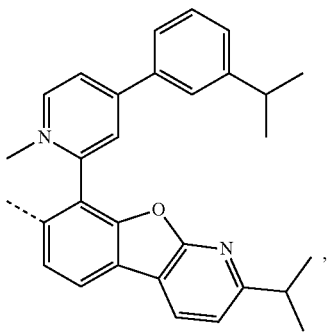
L$_{A410}$
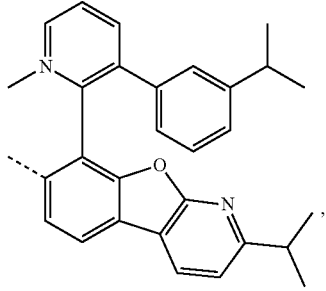
L$_{A411}$
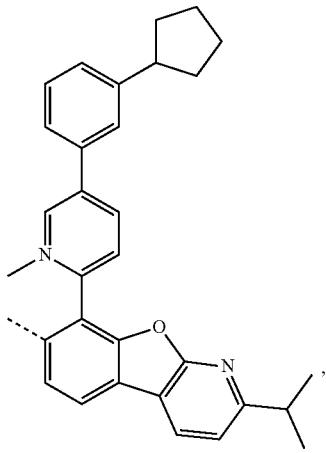
L$_{A412}$
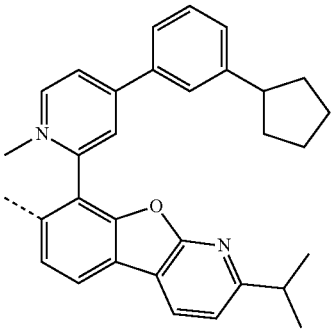

L_{A413}
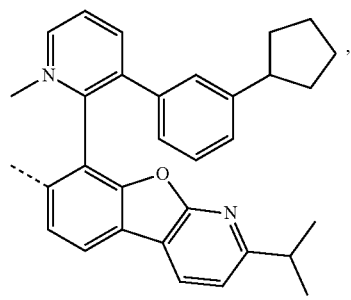
L_{A414}
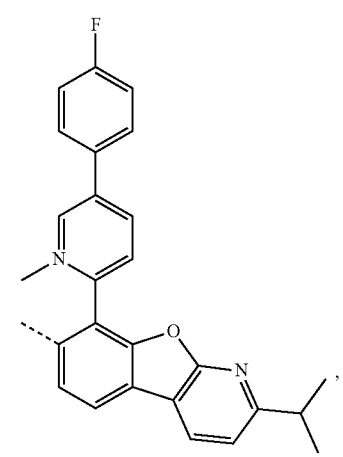
L_{A415}
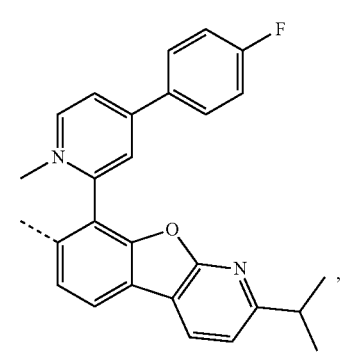
L_{A416}
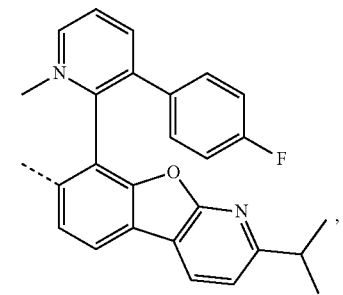
L_{A417}
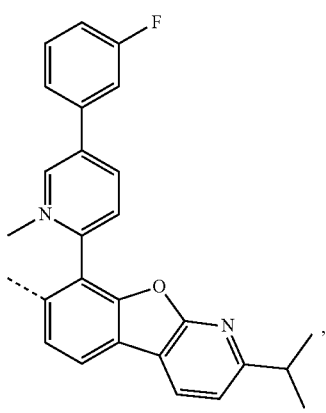
L_{A418}
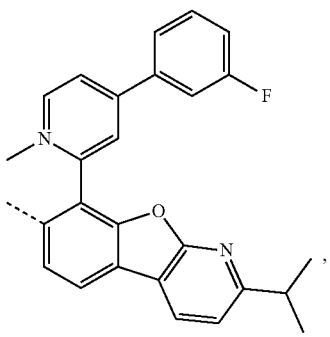
L_{A419}
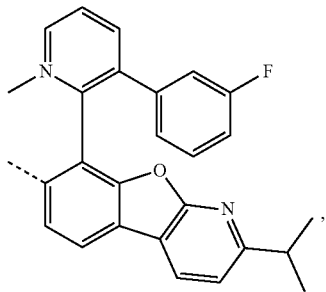
L_{A420}
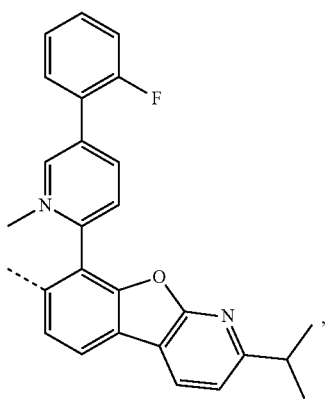

-continued $L_{A421}$ $L_{A422}$ $L_{A423}$ $L_{A424}$

-continued $L_{A425}$ $L_{A426}$ $L_{A427}$ $L_{A428}$

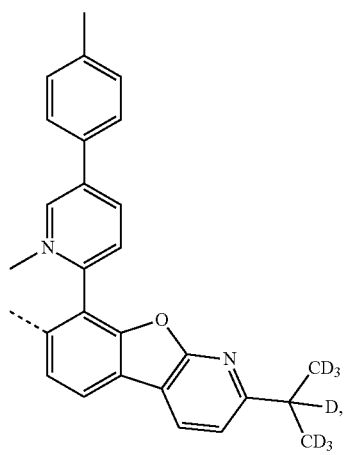
$L_{A429}$
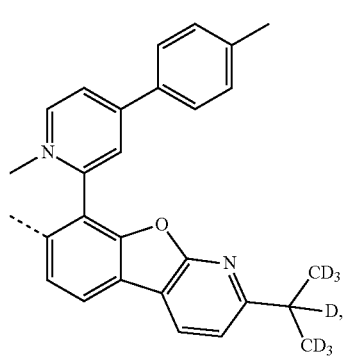
$L_{A430}$
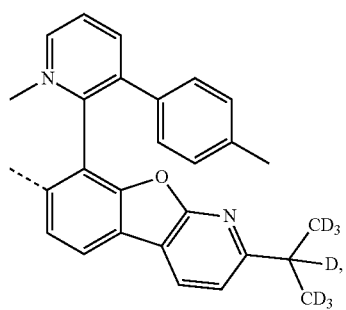
$L_{A431}$
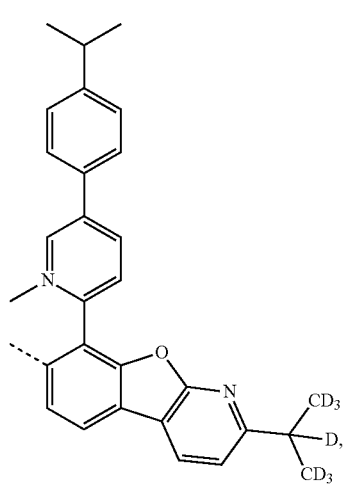
$L_{A432}$
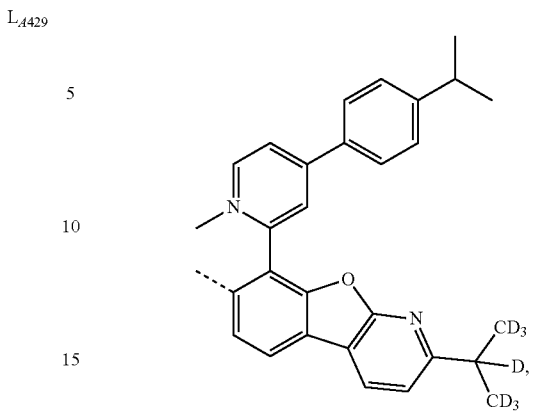
$L_{A433}$
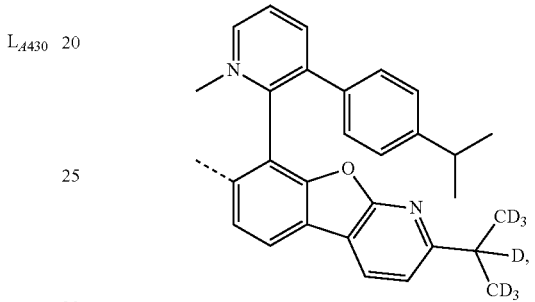
$L_{A434}$
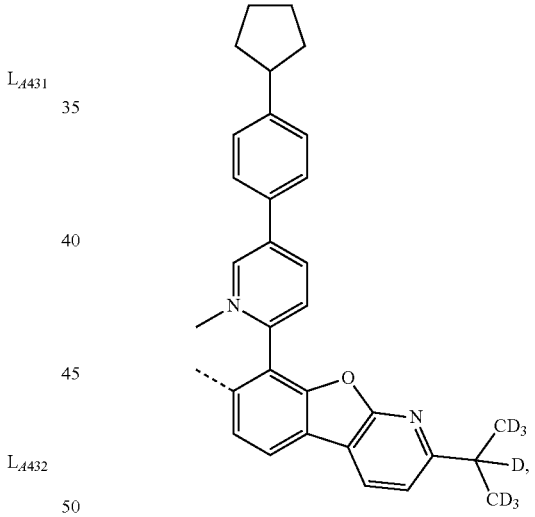
$L_{A435}$
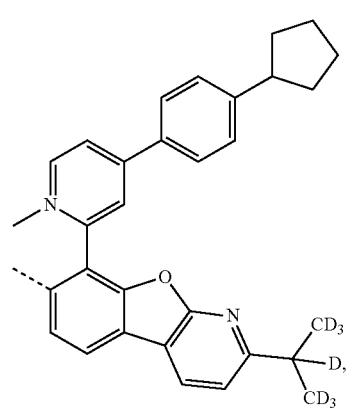
$L_{A436}$

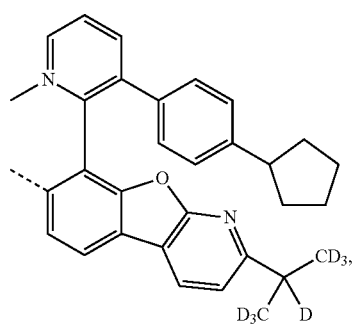
L_A437
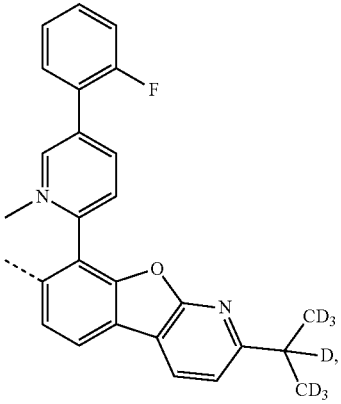
L_A441
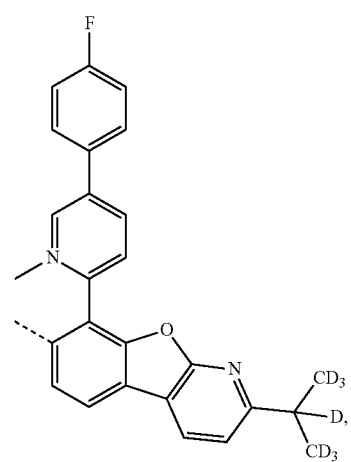
L_A438
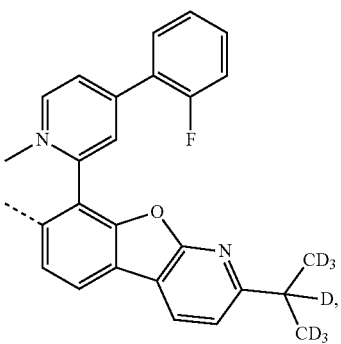
L_A442
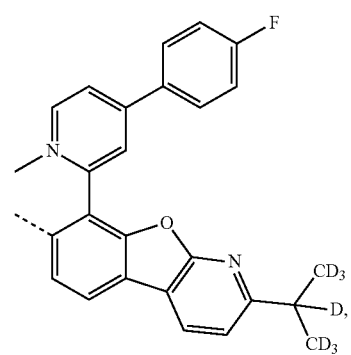
L_A439
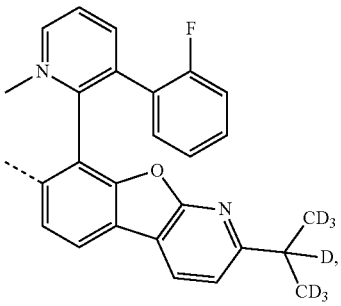
L_A443
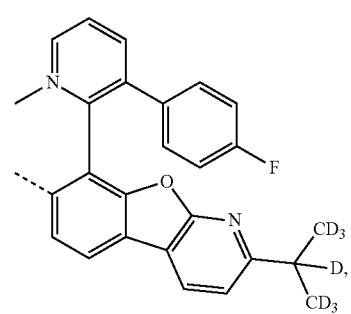
L_A440
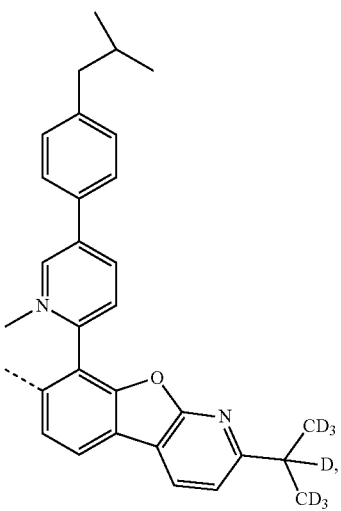
L_A444

L_{A445}
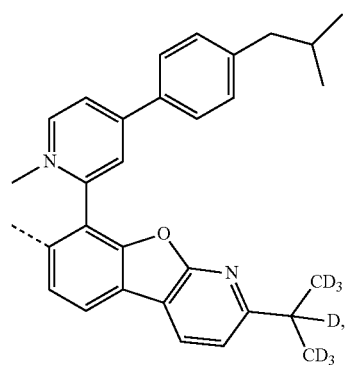
L_{A446}
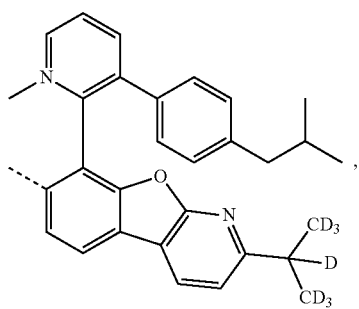
L_{A447}
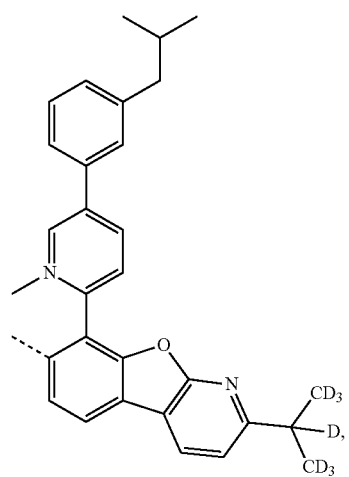
L_{A448}
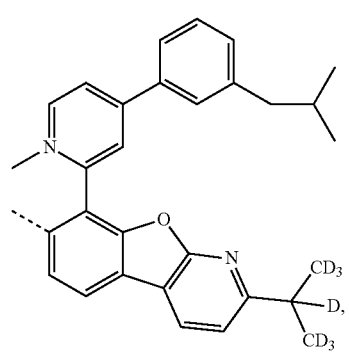
L_{A449}
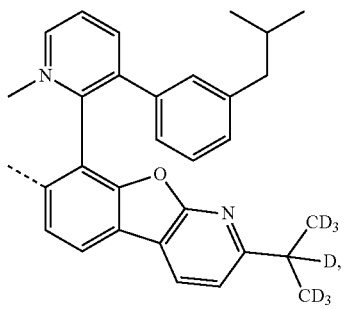
L_{A450}
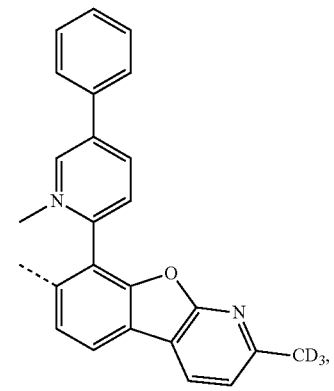
L_{A451}
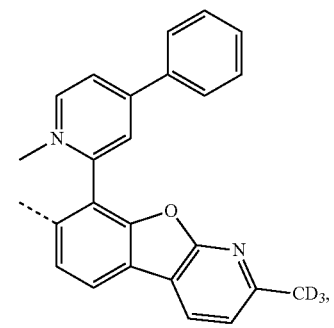
L_{A452}
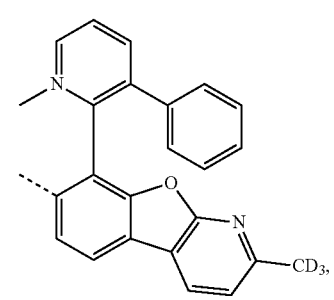

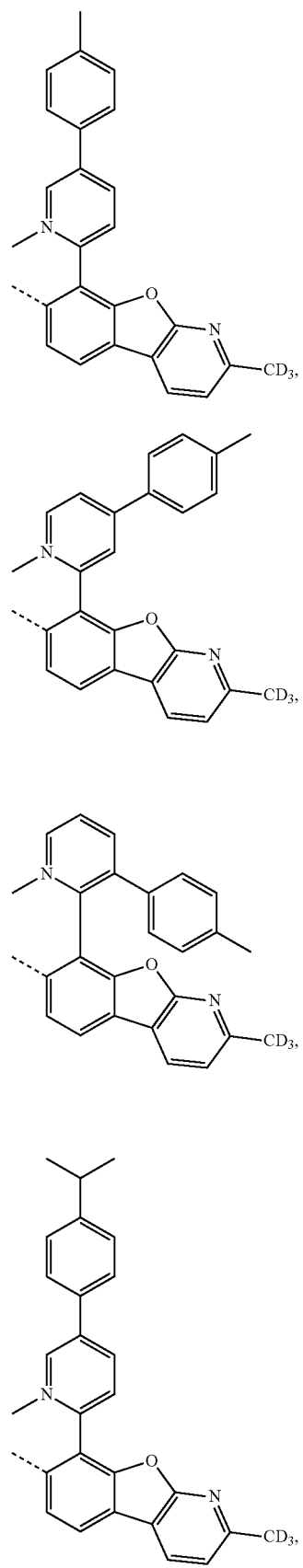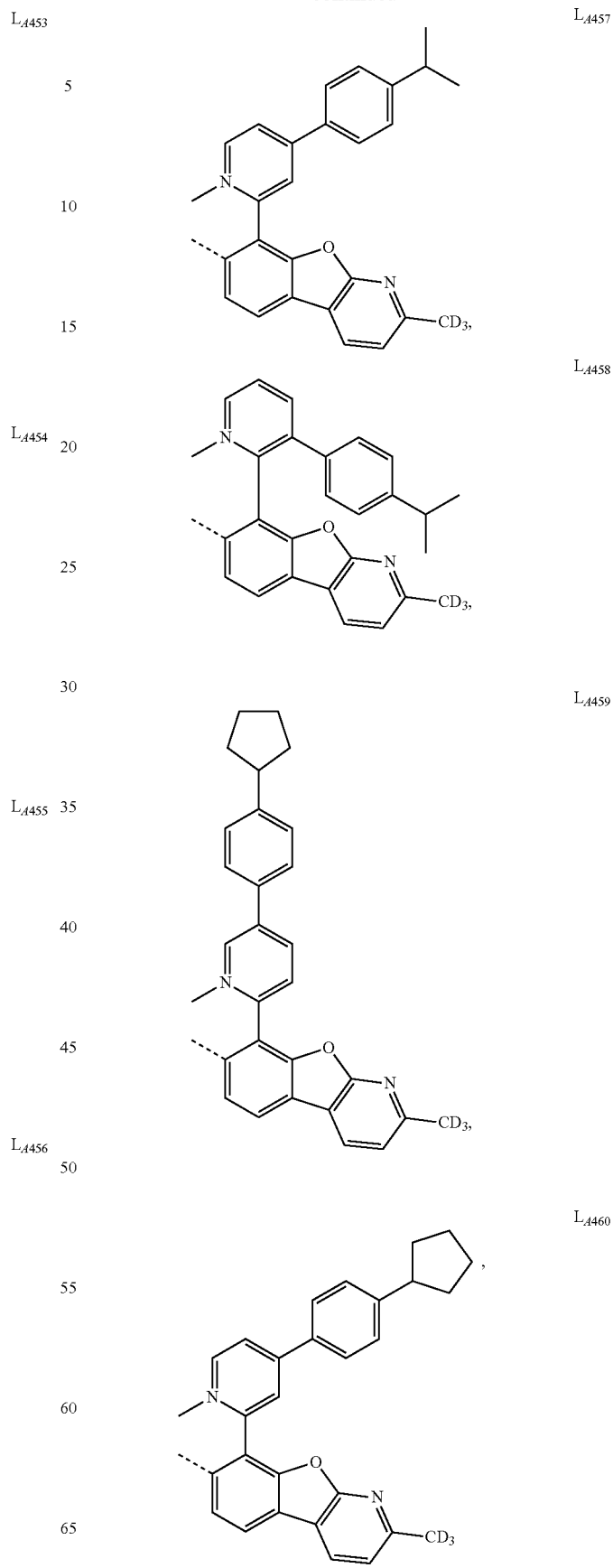

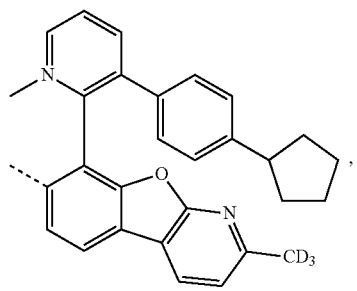
L_{A461}
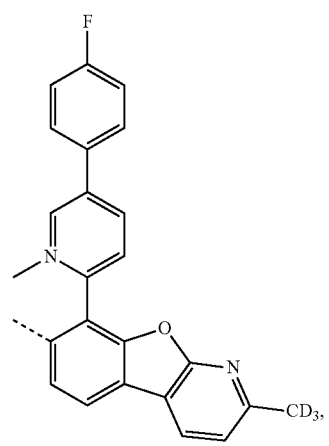
L_{A462}
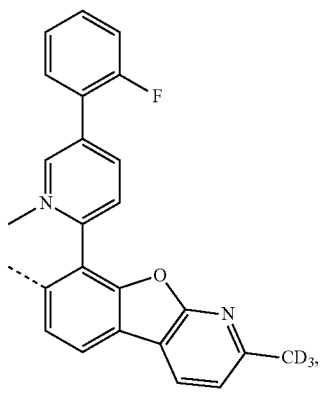
L_{A465}
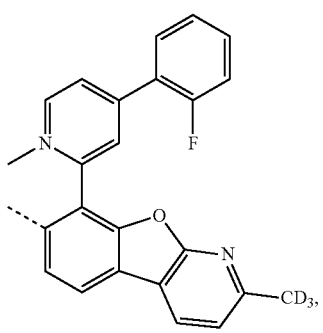
L_{A466}
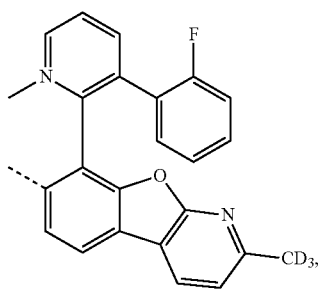
L_{A467}
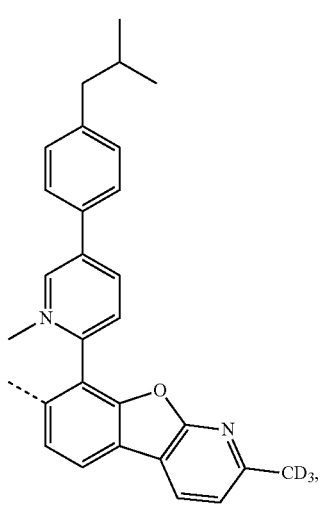
L_{A468}

301
-continued
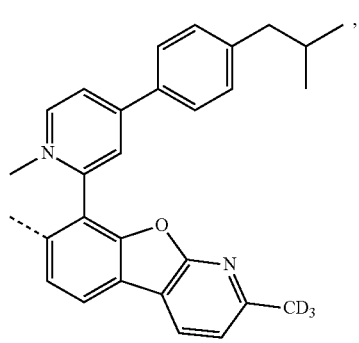
L_{A469},
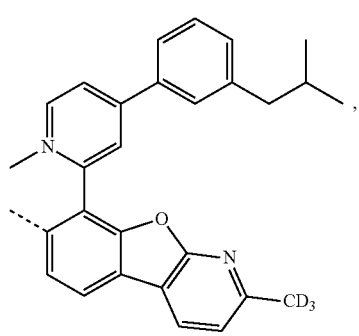
L_{A470},
(unlabeled structure) L_{A471},
(unlabeled structure) L_{A472},
302
-continued
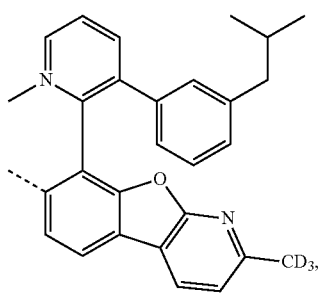
L_{A473},
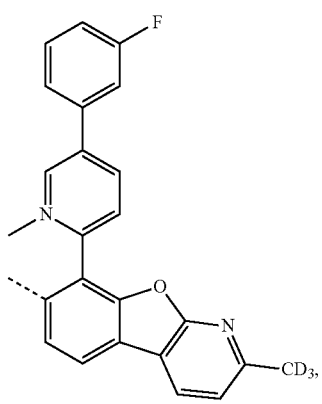
L_{A474},
(structure) L_{A475},
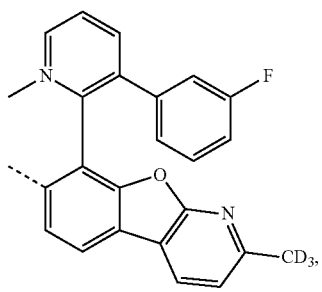
L_{A476},

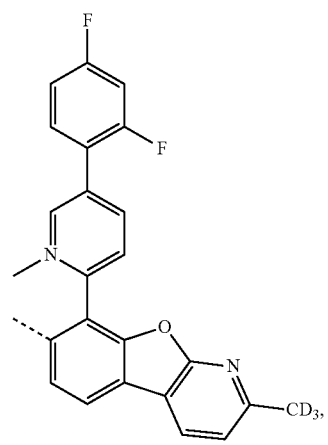
L_{A477}
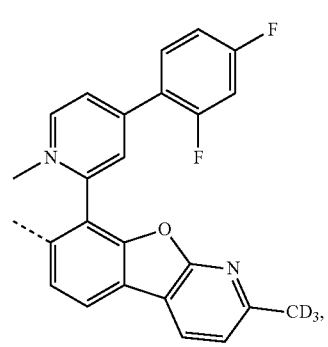
L_{A478}
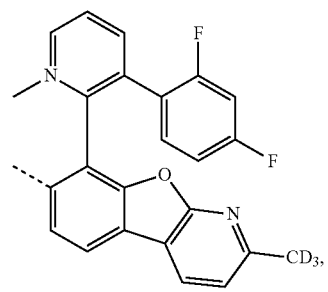
L_{A479}
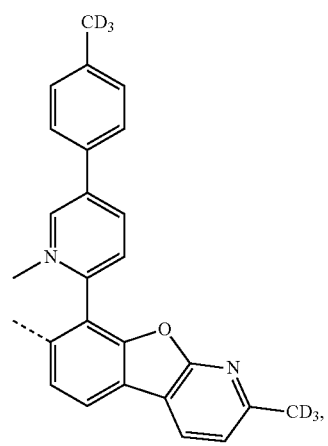
L_{A480}
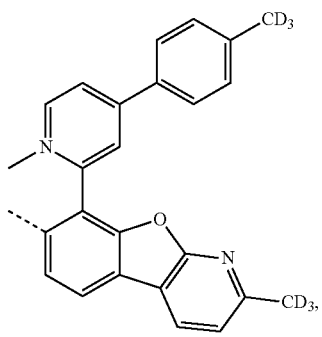
L_{A481}
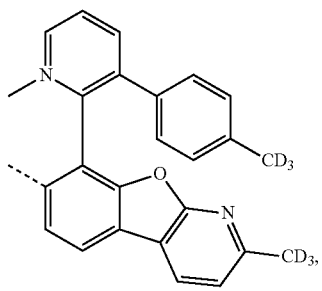
L_{A482}
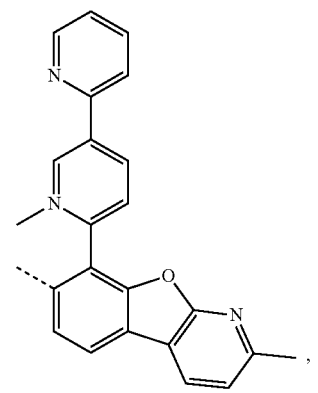
L_{A483}
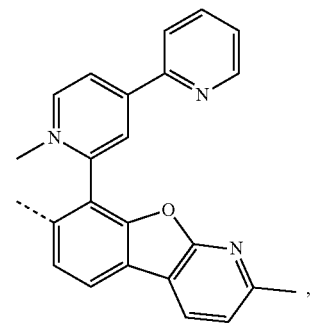
L_{A484}

L_{A485}
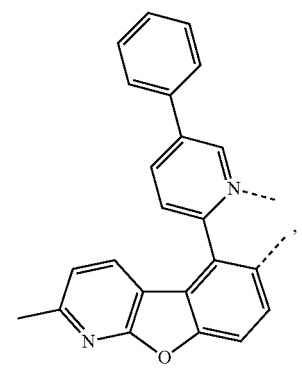
L_{A486}
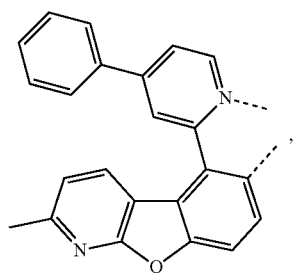
and
L_{A487}
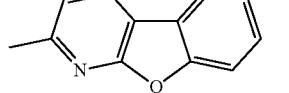
15. The compound of claim 14, wherein $L_B$ is selected from the group consisting of:
L_{B1}
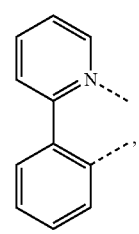
L_{B2}
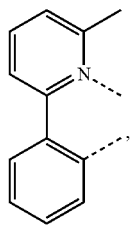
L_{B3}
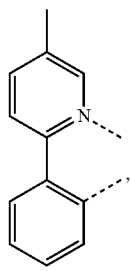
L_{B4}
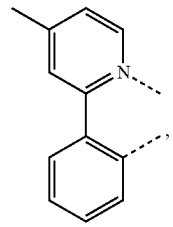
L_{B5}
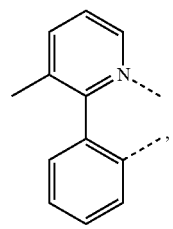
L_{B6}
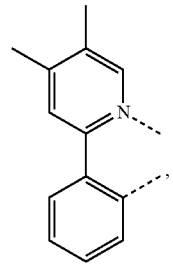
L_{B7}
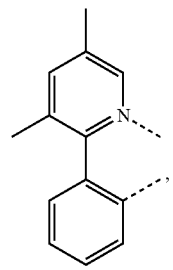

307
-continued
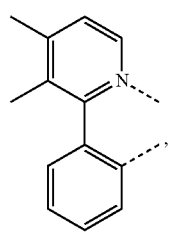
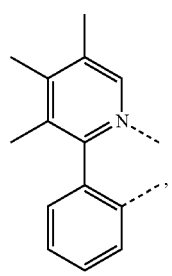
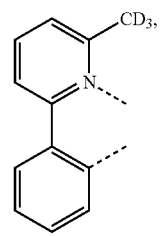
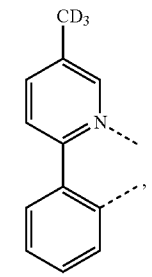
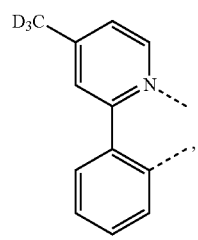
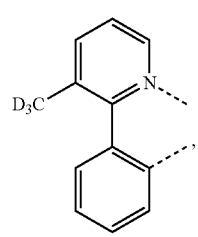
308
-continued
$L_{B8}$
$L_{B9}$
$L_{B10}$
$L_{B11}$
$L_{B12}$
$L_{B13}$
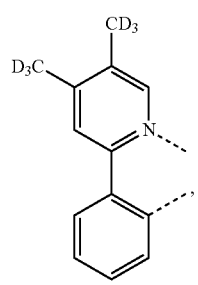 $L_{B14}$
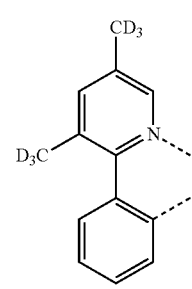 $L_{B15}$
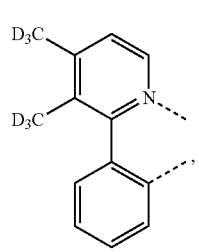 $L_{B16}$
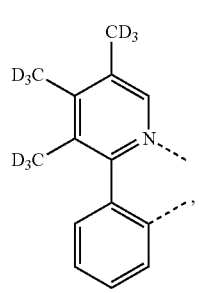 $L_{B17}$
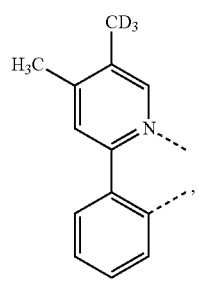 $L_{B18}$
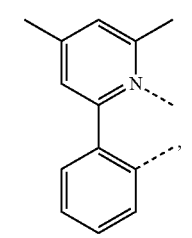 $L_{B19}$ L_{B20} 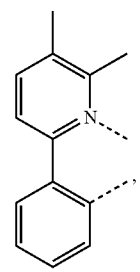
L_{B21} 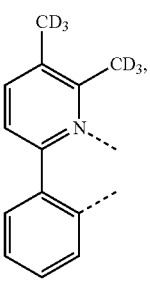
L_{B22} 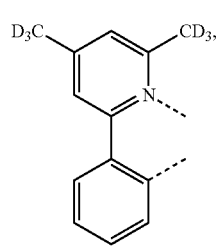
L_{B23} 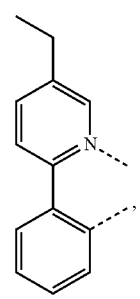
L_{B24} 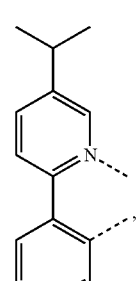
L_{B25} 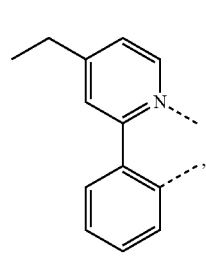
L_{B26} 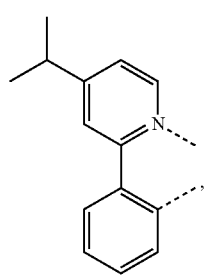
L_{B27} 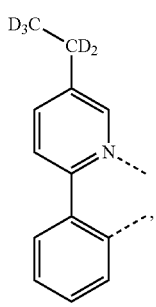
L_{B28} 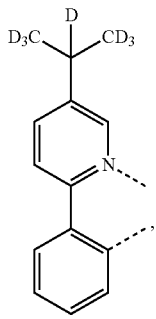
L_{B29} 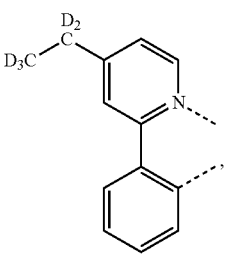
L_{B30} 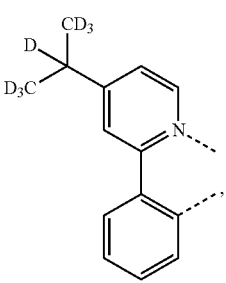

311
-continued

L$_{B31}$
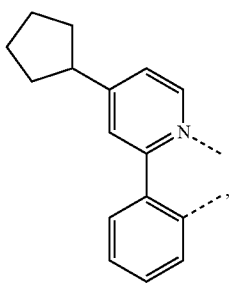

L$_{B32}$
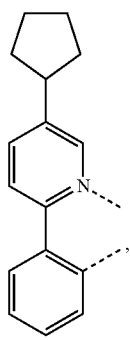

L$_{B33}$
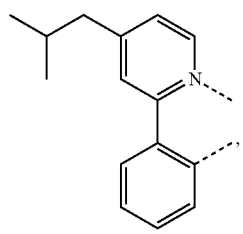

L$_{B34}$
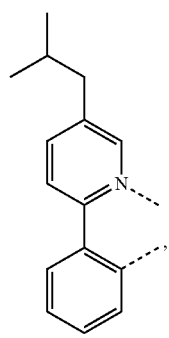

L$_{B35}$
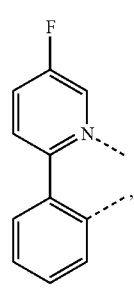

312
-continued

L$_{B36}$
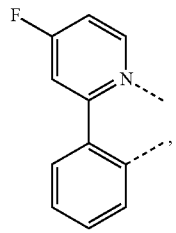
and

L$_{B37}$
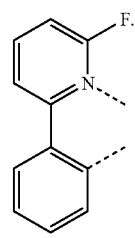

16. The compound of claim 15, wherein the compound is selected from the group consisting of:

| Compound Number | L$_A$ | L$_B$ | Compound Number | L$_A$ | L$_B$ |
|---|---|---|---|---|---|
| III-1 | L$_{A318}$ | L$_{B1}$ | III-3146 | L$_{A4403}$ | L$_{B19}$ |
| III-2 | L$_{A319}$ | L$_{B1}$ | III-3147 | L$_{A4404}$ | L$_{B19}$ |
| III-3 | L$_{A320}$ | L$_{B1}$ | III-3148 | L$_{A4405}$ | L$_{B19}$ |
| III-4 | L$_{A321}$ | L$_{B1}$ | III-3149 | L$_{A4406}$ | L$_{B19}$ |
| III-5 | L$_{A322}$ | L$_{B1}$ | III-3150 | L$_{A4407}$ | L$_{B19}$ |
| III-6 | L$_{A323}$ | L$_{B1}$ | III-3151 | L$_{A4408}$ | L$_{B19}$ |
| III-7 | L$_{A324}$ | L$_{B1}$ | III-3152 | L$_{A4409}$ | L$_{B19}$ |
| III-8 | L$_{A325}$ | L$_{B1}$ | III-3153 | L$_{A4410}$ | L$_{B19}$ |
| III-9 | L$_{A326}$ | L$_{B1}$ | III-3154 | L$_{A4411}$ | L$_{B19}$ |
| III-10 | L$_{A327}$ | L$_{B1}$ | III-3155 | L$_{A4412}$ | L$_{B19}$ |
| III-11 | L$_{A328}$ | L$_{B1}$ | III-3156 | L$_{A4413}$ | L$_{B19}$ |
| III-12 | L$_{A329}$ | L$_{B1}$ | III-3157 | L$_{A4414}$ | L$_{B19}$ |
| III-13 | L$_{A330}$ | L$_{B1}$ | III-3158 | L$_{A4415}$ | L$_{B19}$ |
| III-14 | L$_{A331}$ | L$_{B1}$ | III-3159 | L$_{A4416}$ | L$_{B19}$ |
| III-15 | L$_{A332}$ | L$_{B1}$ | III-3160 | L$_{A4417}$ | L$_{B19}$ |
| III-16 | L$_{A333}$ | L$_{B1}$ | III-3161 | L$_{A4418}$ | L$_{B19}$ |
| III-17 | L$_{A334}$ | L$_{B1}$ | III-3162 | L$_{A4419}$ | L$_{B19}$ |
| III-18 | L$_{A335}$ | L$_{B1}$ | III-3163 | L$_{A4420}$ | L$_{B19}$ |
| III-19 | L$_{A336}$ | L$_{B1}$ | III-3164 | L$_{A4421}$ | L$_{B19}$ |
| III-20 | L$_{A337}$ | L$_{B1}$ | III-3165 | L$_{A4422}$ | L$_{B19}$ |
| III-21 | L$_{A338}$ | L$_{B1}$ | III-3166 | L$_{A4423}$ | L$_{B19}$ |
| III-22 | L$_{A339}$ | L$_{B1}$ | III-3167 | L$_{A4424}$ | L$_{B19}$ |
| III-23 | L$_{A340}$ | L$_{B1}$ | III-3168 | L$_{A4425}$ | L$_{B19}$ |
| III-24 | L$_{A341}$ | L$_{B1}$ | III-3169 | L$_{A4426}$ | L$_{B19}$ |
| III-25 | L$_{A342}$ | L$_{B1}$ | III-3170 | L$_{A4427}$ | L$_{B19}$ |
| III-26 | L$_{A343}$ | L$_{B1}$ | III-3171 | L$_{A4428}$ | L$_{B19}$ |
| III-27 | L$_{A344}$ | L$_{B1}$ | III-3172 | L$_{A4429}$ | L$_{B19}$ |
| III-28 | L$_{A345}$ | L$_{B1}$ | III-3173 | L$_{A4430}$ | L$_{B19}$ |
| III-29 | L$_{A346}$ | L$_{B1}$ | III-3174 | L$_{A4431}$ | L$_{B19}$ |
| III-30 | L$_{A347}$ | L$_{B1}$ | III-3175 | L$_{A4432}$ | L$_{B19}$ |
| III-31 | L$_{A348}$ | L$_{B1}$ | III-3176 | L$_{A4433}$ | L$_{B19}$ |
| III-32 | L$_{A349}$ | L$_{B1}$ | III-3177 | L$_{A4434}$ | L$_{B19}$ |
| III-33 | L$_{A350}$ | L$_{B1}$ | III-3178 | L$_{A4435}$ | L$_{B19}$ |
| III-34 | L$_{A351}$ | L$_{B1}$ | III-3179 | L$_{A4436}$ | L$_{B19}$ |
| III-35 | L$_{A352}$ | L$_{B1}$ | III-3180 | L$_{A4437}$ | L$_{B19}$ |
| III-36 | L$_{A353}$ | L$_{B1}$ | III-3181 | L$_{A4438}$ | L$_{B19}$ |
| III-37 | L$_{A354}$ | L$_{B1}$ | III-3182 | L$_{A4439}$ | L$_{B19}$ |
| III-38 | L$_{A355}$ | L$_{B1}$ | III-3183 | L$_{A4440}$ | L$_{B19}$ |
| III-39 | L$_{A356}$ | L$_{B1}$ | III-3184 | L$_{A4441}$ | L$_{B19}$ |
| III-40 | L$_{A357}$ | L$_{B1}$ | III-3185 | L$_{A4442}$ | L$_{B19}$ |
| III-41 | L$_{A358}$ | L$_{B1}$ | III-3186 | L$_{A4443}$ | L$_{B19}$ |
| III-42 | L$_{A359}$ | L$_{B1}$ | III-3187 | L$_{A4444}$ | L$_{B19}$ |
| III-43 | L$_{A360}$ | L$_{B1}$ | III-3188 | L$_{A4445}$ | L$_{B19}$ |
| III-44 | L$_{A361}$ | L$_{B1}$ | III-3189 | L$_{A4446}$ | L$_{B19}$ |
| III-45 | L$_{A362}$ | L$_{B1}$ | III-3190 | L$_{A4447}$ | L$_{B19}$ |
| III-46 | L$_{A363}$ | L$_{B1}$ | III-3191 | L$_{A4448}$ | L$_{B19}$ |
| III-47 | L$_{A364}$ | L$_{B1}$ | III-3192 | L$_{A4449}$ | L$_{B19}$ |

-continued

| Compound Number | $L_A$ | $L_B$ | Compound Number | $L_A$ | $L_B$ |
|---|---|---|---|---|---|
| III-48 | $L_{A365}$ | $L_{B1}$ | III-3193 | $L_{A450}$ | $L_{B19}$ |
| III-49 | $L_{A366}$ | $L_{B1}$ | III-3194 | $L_{A451}$ | $L_{B19}$ |
| III-50 | $L_{A367}$ | $L_{B1}$ | III-3195 | $L_{A452}$ | $L_{B19}$ |
| III-51 | $L_{A368}$ | $L_{B1}$ | III-3196 | $L_{A453}$ | $L_{B19}$ |
| III-52 | $L_{A369}$ | $L_{B1}$ | III-3197 | $L_{A454}$ | $L_{B19}$ |
| III-53 | $L_{A370}$ | $L_{B1}$ | III-3198 | $L_{A455}$ | $L_{B19}$ |
| III-54 | $L_{A371}$ | $L_{B1}$ | III-3199 | $L_{A456}$ | $L_{B19}$ |
| III-55 | $L_{A372}$ | $L_{B1}$ | III-3200 | $L_{A457}$ | $L_{B19}$ |
| III-56 | $L_{A373}$ | $L_{B1}$ | III-3201 | $L_{A458}$ | $L_{B19}$ |
| III-57 | $L_{A374}$ | $L_{B1}$ | III-3202 | $L_{A459}$ | $L_{B19}$ |
| III-58 | $L_{A375}$ | $L_{B1}$ | III-3203 | $L_{A460}$ | $L_{B19}$ |
| III-59 | $L_{A376}$ | $L_{B1}$ | III-3204 | $L_{A461}$ | $L_{B19}$ |
| III-60 | $L_{A377}$ | $L_{B1}$ | III-3205 | $L_{A462}$ | $L_{B19}$ |
| III-61 | $L_{A378}$ | $L_{B1}$ | III-3206 | $L_{A463}$ | $L_{B19}$ |
| III-62 | $L_{A379}$ | $L_{B1}$ | III-3207 | $L_{A464}$ | $L_{B19}$ |
| III-63 | $L_{A380}$ | $L_{B1}$ | III-3208 | $L_{A465}$ | $L_{B19}$ |
| III-64 | $L_{A381}$ | $L_{B1}$ | III-3209 | $L_{A466}$ | $L_{B19}$ |
| III-65 | $L_{A382}$ | $L_{B1}$ | III-3210 | $L_{A467}$ | $L_{B19}$ |
| III-66 | $L_{A383}$ | $L_{B1}$ | III-3211 | $L_{A468}$ | $L_{B19}$ |
| III-67 | $L_{A384}$ | $L_{B1}$ | III-3212 | $L_{A469}$ | $L_{B19}$ |
| III-68 | $L_{A385}$ | $L_{B1}$ | III-3213 | $L_{A470}$ | $L_{B19}$ |
| III-69 | $L_{A386}$ | $L_{B1}$ | III-3214 | $L_{A471}$ | $L_{B19}$ |
| III-70 | $L_{A387}$ | $L_{B1}$ | III-3215 | $L_{A472}$ | $L_{B19}$ |
| III-71 | $L_{A388}$ | $L_{B1}$ | III-3216 | $L_{A473}$ | $L_{B19}$ |
| III-72 | $L_{A389}$ | $L_{B1}$ | III-3217 | $L_{A474}$ | $L_{B19}$ |
| III-73 | $L_{A390}$ | $L_{B1}$ | III-3218 | $L_{A475}$ | $L_{B19}$ |
| III-74 | $L_{A391}$ | $L_{B1}$ | III-3219 | $L_{A476}$ | $L_{B19}$ |
| III-75 | $L_{A392}$ | $L_{B1}$ | III-3220 | $L_{A477}$ | $L_{B19}$ |
| III-76 | $L_{A393}$ | $L_{B1}$ | III-3221 | $L_{A478}$ | $L_{B19}$ |
| III-77 | $L_{A394}$ | $L_{B1}$ | III-3222 | $L_{A479}$ | $L_{B19}$ |
| III-78 | $L_{A395}$ | $L_{B1}$ | III-3223 | $L_{A480}$ | $L_{B19}$ |
| III-79 | $L_{A396}$ | $L_{B1}$ | III-3224 | $L_{A481}$ | $L_{B19}$ |
| III-80 | $L_{A397}$ | $L_{B1}$ | III-3225 | $L_{A482}$ | $L_{B19}$ |
| III-81 | $L_{A398}$ | $L_{B1}$ | III-3226 | $L_{A483}$ | $L_{B19}$ |
| III-82 | $L_{A399}$ | $L_{B1}$ | III-3227 | $L_{A484}$ | $L_{B19}$ |
| III-83 | $L_{A400}$ | $L_{B1}$ | III-3228 | $L_{A485}$ | $L_{B19}$ |
| III-84 | $L_{A401}$ | $L_{B1}$ | III-3229 | $L_{A486}$ | $L_{B19}$ |
| III-85 | $L_{A402}$ | $L_{B1}$ | III-3230 | $L_{A487}$ | $L_{B19}$ |
| III-86 | $L_{A403}$ | $L_{B1}$ | III-3231 | $L_{A318}$ | $L_{B20}$ |
| III-87 | $L_{A404}$ | $L_{B1}$ | III-3232 | $L_{A319}$ | $L_{B20}$ |
| III-88 | $L_{A405}$ | $L_{B1}$ | III-3233 | $L_{A320}$ | $L_{B20}$ |
| III-89 | $L_{A406}$ | $L_{B1}$ | III-3234 | $L_{A321}$ | $L_{B20}$ |
| III-90 | $L_{A407}$ | $L_{B1}$ | III-3235 | $L_{A322}$ | $L_{B20}$ |
| III-91 | $L_{A408}$ | $L_{B1}$ | III-3236 | $L_{A323}$ | $L_{B20}$ |
| III-92 | $L_{A409}$ | $L_{B1}$ | III-3237 | $L_{A324}$ | $L_{B20}$ |
| III-93 | $L_{A410}$ | $L_{B1}$ | III-3238 | $L_{A325}$ | $L_{B20}$ |
| III-94 | $L_{A411}$ | $L_{B1}$ | III-3239 | $L_{A326}$ | $L_{B20}$ |
| III-95 | $L_{A412}$ | $L_{B1}$ | III-3240 | $L_{A327}$ | $L_{B20}$ |
| III-96 | $L_{A413}$ | $L_{B1}$ | III-3241 | $L_{A328}$ | $L_{B20}$ |
| III-97 | $L_{A414}$ | $L_{B1}$ | III-3242 | $L_{A329}$ | $L_{B20}$ |
| III-98 | $L_{A415}$ | $L_{B1}$ | III-3243 | $L_{A330}$ | $L_{B20}$ |
| III-99 | $L_{A416}$ | $L_{B1}$ | III-3244 | $L_{A331}$ | $L_{B20}$ |
| III-100 | $L_{A417}$ | $L_{B1}$ | III-3245 | $L_{A332}$ | $L_{B20}$ |
| III-101 | $L_{A418}$ | $L_{B1}$ | III-3246 | $L_{A333}$ | $L_{B20}$ |
| III-102 | $L_{A419}$ | $L_{B1}$ | II-3247 | $L_{A334}$ | $L_{B20}$ |
| III-103 | $L_{A420}$ | $L_{B1}$ | III-3248 | $L_{A335}$ | $L_{B20}$ |
| III-104 | $L_{A421}$ | $L_{B1}$ | III-3249 | $L_{A336}$ | $L_{B20}$ |
| III-105 | $L_{A422}$ | $L_{B1}$ | III-3250 | $L_{A337}$ | $L_{B20}$ |
| III-106 | $L_{A423}$ | $L_{B1}$ | III-3251 | $L_{A338}$ | $L_{B20}$ |
| III-107 | $L_{A424}$ | $L_{B1}$ | III-3252 | $L_{A339}$ | $L_{B20}$ |
| III-108 | $L_{A425}$ | $L_{B1}$ | III-3253 | $L_{A340}$ | $L_{B20}$ |
| III-109 | $L_{A426}$ | $L_{B1}$ | III-3254 | $L_{A341}$ | $L_{B20}$ |
| III-110 | $L_{A427}$ | $L_{B1}$ | III-3255 | $L_{A342}$ | $L_{B20}$ |
| III-111 | $L_{A428}$ | $L_{B1}$ | III-3256 | $L_{A343}$ | $L_{B20}$ |
| III-112 | $L_{A429}$ | $L_{B1}$ | III-3257 | $L_{A344}$ | $L_{B20}$ |
| III-113 | $L_{A430}$ | $L_{B1}$ | III-3258 | $L_{A345}$ | $L_{B20}$ |
| III-114 | $L_{A431}$ | $L_{B1}$ | III-3259 | $L_{A346}$ | $L_{B20}$ |
| III-115 | $L_{A432}$ | $L_{B1}$ | III-3260 | $L_{A347}$ | $L_{B20}$ |
| III-116 | $L_{A433}$ | $L_{B1}$ | III-3261 | $L_{A348}$ | $L_{B20}$ |
| III-117 | $L_{A434}$ | $L_{B1}$ | III-3262 | $L_{A349}$ | $L_{B20}$ |
| III-118 | $L_{A435}$ | $L_{B1}$ | III-3263 | $L_{A350}$ | $L_{B20}$ |
| III-119 | $L_{A436}$ | $L_{B1}$ | III-3264 | $L_{A351}$ | $L_{B20}$ |
| III-120 | $L_{A437}$ | $L_{B1}$ | III-3265 | $L_{A352}$ | $L_{B20}$ |
| III-121 | $L_{A438}$ | $L_{B1}$ | III-3266 | $L_{A353}$ | $L_{B20}$ |
| III-122 | $L_{A439}$ | $L_{B1}$ | III-3267 | $L_{A354}$ | $L_{B20}$ |
| III-123 | $L_{A440}$ | $L_{B1}$ | III-3268 | $L_{A355}$ | $L_{B20}$ |
| III-124 | $L_{A441}$ | $L_{B1}$ | III-3269 | $L_{A356}$ | $L_{B20}$ |
| III-125 | $L_{A442}$ | $L_{B1}$ | III-3270 | $L_{A357}$ | $L_{B20}$ |
| III-126 | $L_{A443}$ | $L_{B1}$ | III-3271 | $L_{A358}$ | $L_{B20}$ |
| III-127 | $L_{A444}$ | $L_{B1}$ | III-3272 | $L_{A359}$ | $L_{B20}$ |
| III-128 | $L_{A445}$ | $L_{B1}$ | III-3273 | $L_{A360}$ | $L_{B20}$ |
| III-129 | $L_{A446}$ | $L_{B1}$ | III-3274 | $L_{A361}$ | $L_{B20}$ |
| III-130 | $L_{A447}$ | $L_{B1}$ | III-3275 | $L_{A362}$ | $L_{B20}$ |
| III-131 | $L_{A448}$ | $L_{B1}$ | III-3276 | $L_{A363}$ | $L_{B20}$ |
| III-132 | $L_{A449}$ | $L_{B1}$ | III-3277 | $L_{A364}$ | $L_{B20}$ |
| III-133 | $L_{A450}$ | $L_{B1}$ | III-3278 | $L_{A365}$ | $L_{B20}$ |
| III-134 | $L_{A451}$ | $L_{B1}$ | III-3279 | $L_{A366}$ | $L_{B20}$ |
| III-135 | $L_{A452}$ | $L_{B1}$ | III-3280 | $L_{A367}$ | $L_{B20}$ |
| III-136 | $L_{A453}$ | $L_{B1}$ | III-3281 | $L_{A368}$ | $L_{B20}$ |
| III-137 | $L_{A454}$ | $L_{B1}$ | III-3282 | $L_{A369}$ | $L_{B20}$ |
| III-138 | $L_{A455}$ | $L_{B1}$ | III-3283 | $L_{A370}$ | $L_{B20}$ |
| III-139 | $L_{A456}$ | $L_{B1}$ | III-3284 | $L_{A371}$ | $L_{B20}$ |
| III-140 | $L_{A457}$ | $L_{B1}$ | III-3285 | $L_{A372}$ | $L_{B20}$ |
| III-141 | $L_{A458}$ | $L_{B1}$ | III-3286 | $L_{A373}$ | $L_{B20}$ |
| III-142 | $L_{A459}$ | $L_{B1}$ | III-3287 | $L_{A374}$ | $L_{B20}$ |
| III-143 | $L_{A460}$ | $L_{B1}$ | III-3288 | $L_{A375}$ | $L_{B20}$ |
| III-144 | $L_{A461}$ | $L_{B1}$ | III-3289 | $L_{A376}$ | $L_{B20}$ |
| III-145 | $L_{A462}$ | $L_{B1}$ | III-3290 | $L_{A377}$ | $L_{B20}$ |
| III-146 | $L_{A463}$ | $L_{B1}$ | III-3291 | $L_{A378}$ | $L_{B20}$ |
| III-147 | $L_{A464}$ | $L_{B1}$ | III-3292 | $L_{A379}$ | $L_{B20}$ |
| III-148 | $L_{A465}$ | $L_{B1}$ | III-3293 | $L_{A380}$ | $L_{B20}$ |
| III-149 | $L_{A466}$ | $L_{B1}$ | III-3294 | $L_{A381}$ | $L_{B20}$ |
| III-150 | $L_{A467}$ | $L_{B1}$ | III-3295 | $L_{A382}$ | $L_{B20}$ |
| III-151 | $L_{A468}$ | $L_{B1}$ | III-3296 | $L_{A383}$ | $L_{B20}$ |
| III-152 | $L_{A469}$ | $L_{B1}$ | III-3297 | $L_{A384}$ | $L_{B20}$ |
| III-153 | $L_{A470}$ | $L_{B1}$ | III-3298 | $L_{A385}$ | $L_{B20}$ |
| III-154 | $L_{A471}$ | $L_{B1}$ | III-3299 | $L_{A386}$ | $L_{B20}$ |
| III-155 | $L_{A472}$ | $L_{B1}$ | III-3300 | $L_{A387}$ | $L_{B20}$ |
| III-156 | $L_{A473}$ | $L_{B1}$ | III-3301 | $L_{A388}$ | $L_{B20}$ |
| III-157 | $L_{A474}$ | $L_{B1}$ | III-3302 | $L_{A389}$ | $L_{B20}$ |
| III-158 | $L_{A475}$ | $L_{B1}$ | III-3303 | $L_{A390}$ | $L_{B20}$ |
| III-159 | $L_{A476}$ | $L_{B1}$ | III-3304 | $L_{A391}$ | $L_{B20}$ |
| III-160 | $L_{A477}$ | $L_{B1}$ | III-3305 | $L_{A392}$ | $L_{B20}$ |
| III-161 | $L_{A478}$ | $L_{B1}$ | III-3306 | $L_{A393}$ | $L_{B20}$ |
| III-162 | $L_{A479}$ | $L_{B1}$ | III-3307 | $L_{A394}$ | $L_{B20}$ |
| III-163 | $L_{A480}$ | $L_{B1}$ | III-3308 | $L_{A395}$ | $L_{B20}$ |
| III-164 | $L_{A481}$ | $L_{B1}$ | III-3309 | $L_{A396}$ | $L_{B20}$ |
| III-165 | $L_{A482}$ | $L_{B1}$ | III-3310 | $L_{A397}$ | $L_{B20}$ |
| III-166 | $L_{A483}$ | $L_{B1}$ | III-3311 | $L_{A398}$ | $L_{B20}$ |
| III-167 | $L_{A484}$ | $L_{B1}$ | III-3312 | $L_{A399}$ | $L_{B20}$ |
| III-168 | $L_{A485}$ | $L_{B1}$ | III-3313 | $L_{A400}$ | $L_{B20}$ |
| III-169 | $L_{A486}$ | $L_{B1}$ | III-3314 | $L_{A401}$ | $L_{B20}$ |
| III-170 | $L_{A487}$ | $L_{B1}$ | III-3315 | $L_{A402}$ | $L_{B20}$ |
| III-171 | $L_{A318}$ | $L_{B2}$ | III-3316 | $L_{A403}$ | $L_{B20}$ |
| III-172 | $L_{A319}$ | $L_{B2}$ | III-3317 | $L_{A404}$ | $L_{B20}$ |
| III-173 | $L_{A320}$ | $L_{B2}$ | III-3318 | $L_{A405}$ | $L_{B20}$ |
| III-174 | $L_{A321}$ | $L_{B2}$ | III-3319 | $L_{A406}$ | $L_{B20}$ |
| III-175 | $L_{A322}$ | $L_{B2}$ | III-3320 | $L_{A407}$ | $L_{B20}$ |
| III-176 | $L_{A323}$ | $L_{B2}$ | III-3321 | $L_{A408}$ | $L_{B20}$ |
| III-177 | $L_{A324}$ | $L_{B2}$ | III-3322 | $L_{A409}$ | $L_{B20}$ |
| III-178 | $L_{A325}$ | $L_{B2}$ | III-3323 | $L_{A410}$ | $L_{B20}$ |
| III-179 | $L_{A326}$ | $L_{B2}$ | III-3324 | $L_{A411}$ | $L_{B20}$ |
| III-180 | $L_{A327}$ | $L_{B2}$ | III-3325 | $L_{A412}$ | $L_{B20}$ |
| III-181 | $L_{A328}$ | $L_{B2}$ | III-3326 | $L_{A413}$ | $L_{B20}$ |
| III-182 | $L_{A329}$ | $L_{B2}$ | III-3327 | $L_{A414}$ | $L_{B20}$ |
| III-183 | $L_{A330}$ | $L_{B2}$ | III-3328 | $L_{A415}$ | $L_{B20}$ |
| III-184 | $L_{A331}$ | $L_{B2}$ | III-3329 | $L_{A416}$ | $L_{B20}$ |
| III-185 | $L_{A332}$ | $L_{B2}$ | III-3330 | $L_{A417}$ | $L_{B20}$ |
| III-186 | $L_{A333}$ | $L_{B2}$ | III-3331 | $L_{A418}$ | $L_{B20}$ |
| III-187 | $L_{A334}$ | $L_{B2}$ | III-3332 | $L_{A419}$ | $L_{B20}$ |
| III-188 | $L_{A335}$ | $L_{B2}$ | III-3333 | $L_{A420}$ | $L_{B20}$ |
| III-189 | $L_{A336}$ | $L_{B2}$ | III-3334 | $L_{A421}$ | $L_{B20}$ |
| III-190 | $L_{A337}$ | $L_{B2}$ | III-3335 | $L_{A422}$ | $L_{B20}$ |
| III-191 | $L_{A338}$ | $L_{B2}$ | III-3336 | $L_{A423}$ | $L_{B20}$ |
| III-192 | $L_{A339}$ | $L_{B2}$ | III-3337 | $L_{A424}$ | $L_{B20}$ |
| III-193 | $L_{A340}$ | $L_{B2}$ | III-3338 | $L_{A425}$ | $L_{B20}$ |
| III-194 | $L_{A341}$ | $L_{B2}$ | III-3339 | $L_{A426}$ | $L_{B20}$ |
| III-195 | $L_{A342}$ | $L_{B2}$ | III-3340 | $L_{A427}$ | $L_{B20}$ |
| III-196 | $L_{A343}$ | $L_{B2}$ | III-3341 | $L_{A428}$ | $L_{B20}$ |
| III-197 | $L_{A344}$ | $L_{B2}$ | III-3342 | $L_{A429}$ | $L_{B20}$ |
| III-198 | $L_{A345}$ | $L_{B2}$ | III-3343 | $L_{A430}$ | $L_{B20}$ |
| III-199 | $L_{A346}$ | $L_{B2}$ | III-3344 | $L_{A431}$ | $L_{B20}$ |

-continued

| Compound Number | $L_A$ | $L_B$ | Compound Number | $L_A$ | $L_B$ | Compound Number | $L_A$ | $L_B$ | Compound Number | $L_A$ | $L_B$ |
|---|---|---|---|---|---|---|---|---|---|---|---|
| III-200 | $L_{A347}$ | $L_{B2}$ | III-3345 | $L_{A432}$ | $L_{B20}$ | III-276 | $L_{A423}$ | $L_{B2}$ | III-3421 | $L_{A338}$ | $L_{B21}$ |
| III-201 | $L_{A348}$ | $L_{B2}$ | III-3346 | $L_{A433}$ | $L_{B20}$ | III-277 | $L_{A424}$ | $L_{B2}$ | III-3422 | $L_{A339}$ | $L_{B21}$ |
| III-202 | $L_{A349}$ | $L_{B2}$ | III-3347 | $L_{A434}$ | $L_{B20}$ | III-278 | $L_{A425}$ | $L_{B2}$ | III-3423 | $L_{A340}$ | $L_{B21}$ |
| III-203 | $L_{A350}$ | $L_{B2}$ | III-3348 | $L_{A435}$ | $L_{B20}$ | III-279 | $L_{A426}$ | $L_{B2}$ | III-3424 | $L_{A341}$ | $L_{B21}$ |
| III-204 | $L_{A351}$ | $L_{B2}$ | III-3349 | $L_{A436}$ | $L_{B20}$ | III-280 | $L_{A427}$ | $L_{B2}$ | III-3425 | $L_{A342}$ | $L_{B21}$ |
| III-205 | $L_{A352}$ | $L_{B2}$ | III-3350 | $L_{A437}$ | $L_{B20}$ | III-281 | $L_{A428}$ | $L_{B2}$ | III-3426 | $L_{A343}$ | $L_{B21}$ |
| III-206 | $L_{A353}$ | $L_{B2}$ | III-3351 | $L_{A438}$ | $L_{B20}$ | III-282 | $L_{A429}$ | $L_{B2}$ | III-3427 | $L_{A344}$ | $L_{B21}$ |
| III-207 | $L_{A354}$ | $L_{B2}$ | III-3352 | $L_{A439}$ | $L_{B20}$ | III-283 | $L_{A430}$ | $L_{B2}$ | III-3428 | $L_{A345}$ | $L_{B21}$ |
| III-208 | $L_{A355}$ | $L_{B2}$ | III-3353 | $L_{A440}$ | $L_{B20}$ | III-284 | $L_{A431}$ | $L_{B2}$ | III-3429 | $L_{A346}$ | $L_{B21}$ |
| III-209 | $L_{A356}$ | $L_{B2}$ | III-3354 | $L_{A441}$ | $L_{B20}$ | III-285 | $L_{A432}$ | $L_{B2}$ | III-3430 | $L_{A347}$ | $L_{B21}$ |
| III-210 | $L_{A357}$ | $L_{B2}$ | III-3355 | $L_{A442}$ | $L_{B20}$ | III-286 | $L_{A433}$ | $L_{B2}$ | III-3431 | $L_{A348}$ | $L_{B21}$ |
| III-211 | $L_{A358}$ | $L_{B2}$ | III-3356 | $L_{A443}$ | $L_{B20}$ | III-287 | $L_{A434}$ | $L_{B2}$ | III-3432 | $L_{A349}$ | $L_{B21}$ |
| III-212 | $L_{A359}$ | $L_{B2}$ | III-3357 | $L_{A444}$ | $L_{B20}$ | III-288 | $L_{A435}$ | $L_{B2}$ | III-3433 | $L_{A350}$ | $L_{B21}$ |
| III-213 | $L_{A360}$ | $L_{B2}$ | III-3358 | $L_{A445}$ | $L_{B20}$ | III-289 | $L_{A436}$ | $L_{B2}$ | III-3434 | $L_{A351}$ | $L_{B21}$ |
| III-214 | $L_{A361}$ | $L_{B2}$ | III-3359 | $L_{A446}$ | $L_{B20}$ | III-290 | $L_{A437}$ | $L_{B2}$ | III-3435 | $L_{A352}$ | $L_{B21}$ |
| III-215 | $L_{A362}$ | $L_{B2}$ | III-3360 | $L_{A447}$ | $L_{B20}$ | III-291 | $L_{A438}$ | $L_{B2}$ | III-3436 | $L_{A353}$ | $L_{B21}$ |
| III-216 | $L_{A363}$ | $L_{B2}$ | III-3361 | $L_{A448}$ | $L_{B20}$ | III-292 | $L_{A439}$ | $L_{B2}$ | III-3437 | $L_{A354}$ | $L_{B21}$ |
| III-217 | $L_{A364}$ | $L_{B2}$ | III-3362 | $L_{A449}$ | $L_{B20}$ | III-293 | $L_{A440}$ | $L_{B2}$ | III-3438 | $L_{A355}$ | $L_{B21}$ |
| III-218 | $L_{A365}$ | $L_{B2}$ | III-3363 | $L_{A450}$ | $L_{B20}$ | III-294 | $L_{A441}$ | $L_{B2}$ | III-3439 | $L_{A356}$ | $L_{B21}$ |
| III-219 | $L_{A366}$ | $L_{B2}$ | III-3364 | $L_{A451}$ | $L_{B20}$ | III-295 | $L_{A442}$ | $L_{B2}$ | III-3440 | $L_{A357}$ | $L_{B21}$ |
| III-220 | $L_{A367}$ | $L_{B2}$ | III-3365 | $L_{A452}$ | $L_{B20}$ | III-296 | $L_{A443}$ | $L_{B2}$ | III-3441 | $L_{A358}$ | $L_{B21}$ |
| III-221 | $L_{A368}$ | $L_{B2}$ | III-3366 | $L_{A453}$ | $L_{B20}$ | III-297 | $L_{A444}$ | $L_{B2}$ | III-3442 | $L_{A359}$ | $L_{B21}$ |
| III-222 | $L_{A369}$ | $L_{B2}$ | III-3367 | $L_{A454}$ | $L_{B20}$ | III-298 | $L_{A445}$ | $L_{B2}$ | III-3443 | $L_{A360}$ | $L_{B21}$ |
| III-223 | $L_{A370}$ | $L_{B2}$ | III-3368 | $L_{A455}$ | $L_{B20}$ | III-299 | $L_{A446}$ | $L_{B2}$ | III-3444 | $L_{A361}$ | $L_{B21}$ |
| III-224 | $L_{A371}$ | $L_{B2}$ | III-3369 | $L_{A456}$ | $L_{B20}$ | III-300 | $L_{A447}$ | $L_{B2}$ | III-3445 | $L_{A362}$ | $L_{B21}$ |
| III-225 | $L_{A372}$ | $L_{B2}$ | III-3370 | $L_{A457}$ | $L_{B20}$ | III-301 | $L_{A448}$ | $L_{B2}$ | III-3446 | $L_{A363}$ | $L_{B21}$ |
| III-226 | $L_{A373}$ | $L_{B2}$ | III-3371 | $L_{A458}$ | $L_{B20}$ | III-302 | $L_{A449}$ | $L_{B2}$ | III-3447 | $L_{A364}$ | $L_{B21}$ |
| III-227 | $L_{A374}$ | $L_{B2}$ | III-3372 | $L_{A459}$ | $L_{B20}$ | III-303 | $L_{A450}$ | $L_{B2}$ | III-3448 | $L_{A365}$ | $L_{B21}$ |
| III-228 | $L_{A375}$ | $L_{B2}$ | III-3373 | $L_{A460}$ | $L_{B20}$ | III-304 | $L_{A451}$ | $L_{B2}$ | III-3449 | $L_{A366}$ | $L_{B21}$ |
| III-229 | $L_{A376}$ | $L_{B2}$ | III-3374 | $L_{A461}$ | $L_{B20}$ | III-305 | $L_{A452}$ | $L_{B2}$ | III-3450 | $L_{A367}$ | $L_{B21}$ |
| III-230 | $L_{A377}$ | $L_{B2}$ | III-3375 | $L_{A462}$ | $L_{B20}$ | III-306 | $L_{A453}$ | $L_{B2}$ | III-3451 | $L_{A368}$ | $L_{B21}$ |
| III-231 | $L_{A378}$ | $L_{B2}$ | III-3376 | $L_{A463}$ | $L_{B20}$ | III-307 | $L_{A454}$ | $L_{B2}$ | III-3452 | $L_{A369}$ | $L_{B21}$ |
| III-232 | $L_{A379}$ | $L_{B2}$ | III-3377 | $L_{A464}$ | $L_{B20}$ | III-308 | $L_{A455}$ | $L_{B2}$ | III-3453 | $L_{A370}$ | $L_{B21}$ |
| III-233 | $L_{A380}$ | $L_{B2}$ | III-3378 | $L_{A465}$ | $L_{B20}$ | III-309 | $L_{A456}$ | $L_{B2}$ | III-3454 | $L_{A371}$ | $L_{B21}$ |
| III-234 | $L_{A381}$ | $L_{B2}$ | III-3379 | $L_{A466}$ | $L_{B20}$ | III-310 | $L_{A457}$ | $L_{B2}$ | III-3455 | $L_{A372}$ | $L_{B21}$ |
| III-235 | $L_{A382}$ | $L_{B2}$ | III-3380 | $L_{A467}$ | $L_{B20}$ | III-311 | $L_{A458}$ | $L_{B2}$ | III-3456 | $L_{A373}$ | $L_{B21}$ |
| III-236 | $L_{A383}$ | $L_{B2}$ | III-3381 | $L_{A468}$ | $L_{B20}$ | III-312 | $L_{A459}$ | $L_{B2}$ | III-3457 | $L_{A374}$ | $L_{B21}$ |
| III-237 | $L_{A384}$ | $L_{B2}$ | III-3382 | $L_{A469}$ | $L_{B20}$ | III-313 | $L_{A460}$ | $L_{B2}$ | III-3458 | $L_{A375}$ | $L_{B21}$ |
| III-238 | $L_{A385}$ | $L_{B2}$ | III-3383 | $L_{A470}$ | $L_{B20}$ | III-314 | $L_{A461}$ | $L_{B2}$ | III-3459 | $L_{A376}$ | $L_{B21}$ |
| III-239 | $L_{A386}$ | $L_{B2}$ | III-3384 | $L_{A471}$ | $L_{B20}$ | III-315 | $L_{A462}$ | $L_{B2}$ | III-3460 | $L_{A377}$ | $L_{B21}$ |
| III-240 | $L_{A387}$ | $L_{B2}$ | III-3385 | $L_{A472}$ | $L_{B20}$ | III-316 | $L_{A463}$ | $L_{B2}$ | III-3461 | $L_{A378}$ | $L_{B21}$ |
| III-241 | $L_{A388}$ | $L_{B2}$ | III-3386 | $L_{A473}$ | $L_{B20}$ | III-317 | $L_{A464}$ | $L_{B2}$ | III-3462 | $L_{A379}$ | $L_{B21}$ |
| III-242 | $L_{A389}$ | $L_{B2}$ | III-3387 | $L_{A474}$ | $L_{B20}$ | III-318 | $L_{A465}$ | $L_{B2}$ | III-3463 | $L_{A380}$ | $L_{B21}$ |
| III-243 | $L_{A390}$ | $L_{B2}$ | III-3388 | $L_{A475}$ | $L_{B20}$ | III-319 | $L_{A466}$ | $L_{B2}$ | III-3464 | $L_{A381}$ | $L_{B21}$ |
| III-244 | $L_{A391}$ | $L_{B2}$ | III-3389 | $L_{A476}$ | $L_{B20}$ | III-320 | $L_{A467}$ | $L_{B2}$ | III-3465 | $L_{A382}$ | $L_{B21}$ |
| III-245 | $L_{A392}$ | $L_{B2}$ | III-3390 | $L_{A477}$ | $L_{B20}$ | III-321 | $L_{A468}$ | $L_{B2}$ | III-3466 | $L_{A383}$ | $L_{B21}$ |
| III-246 | $L_{A393}$ | $L_{B2}$ | III-3391 | $L_{A478}$ | $L_{B20}$ | III-322 | $L_{A469}$ | $L_{B2}$ | III-3467 | $L_{A384}$ | $L_{B21}$ |
| III-247 | $L_{A394}$ | $L_{B2}$ | III-3392 | $L_{A479}$ | $L_{B20}$ | III-323 | $L_{A470}$ | $L_{B2}$ | III-3468 | $L_{A385}$ | $L_{B21}$ |
| III-248 | $L_{A395}$ | $L_{B2}$ | III-3393 | $L_{A480}$ | $L_{B20}$ | III-324 | $L_{A471}$ | $L_{B2}$ | III-3469 | $L_{A386}$ | $L_{B21}$ |
| III-249 | $L_{A396}$ | $L_{B2}$ | III-3394 | $L_{A481}$ | $L_{B20}$ | III-325 | $L_{A472}$ | $L_{B2}$ | III-3470 | $L_{A387}$ | $L_{B21}$ |
| III-250 | $L_{A397}$ | $L_{B2}$ | III-3395 | $L_{A482}$ | $L_{B20}$ | III-326 | $L_{A473}$ | $L_{B2}$ | III-3471 | $L_{A388}$ | $L_{B21}$ |
| III-251 | $L_{A398}$ | $L_{B2}$ | III-3396 | $L_{A483}$ | $L_{B20}$ | III-327 | $L_{A474}$ | $L_{B2}$ | III-3472 | $L_{A389}$ | $L_{B21}$ |
| III-252 | $L_{A399}$ | $L_{B2}$ | III-3397 | $L_{A484}$ | $L_{B20}$ | III-328 | $L_{A475}$ | $L_{B2}$ | III-3473 | $L_{A390}$ | $L_{B21}$ |
| III-253 | $L_{A400}$ | $L_{B2}$ | III-3398 | $L_{A485}$ | $L_{B20}$ | III-329 | $L_{A476}$ | $L_{B2}$ | III-3474 | $L_{A391}$ | $L_{B21}$ |
| III-254 | $L_{A401}$ | $L_{B2}$ | III-3399 | $L_{A486}$ | $L_{B20}$ | III-330 | $L_{A477}$ | $L_{B2}$ | III-3475 | $L_{A392}$ | $L_{B21}$ |
| III-255 | $L_{A402}$ | $L_{B2}$ | III-3400 | $L_{A487}$ | $L_{B20}$ | III-331 | $L_{A478}$ | $L_{B2}$ | III-3476 | $L_{A393}$ | $L_{B21}$ |
| III-256 | $L_{A403}$ | $L_{B2}$ | III-3401 | $L_{A318}$ | $L_{B21}$ | III-332 | $L_{A479}$ | $L_{B2}$ | III-3477 | $L_{A394}$ | $L_{B21}$ |
| III-257 | $L_{A404}$ | $L_{B2}$ | III-3402 | $L_{A319}$ | $L_{B21}$ | III-333 | $L_{A480}$ | $L_{B2}$ | III-3478 | $L_{A395}$ | $L_{B21}$ |
| III-258 | $L_{A405}$ | $L_{B2}$ | III-3403 | $L_{A320}$ | $L_{B21}$ | III-334 | $L_{A481}$ | $L_{B2}$ | III-3479 | $L_{A396}$ | $L_{B21}$ |
| III-259 | $L_{A406}$ | $L_{B2}$ | III-3404 | $L_{A321}$ | $L_{B21}$ | III-335 | $L_{A482}$ | $L_{B2}$ | III-3480 | $L_{A397}$ | $L_{B21}$ |
| III-260 | $L_{A407}$ | $L_{B2}$ | III-3405 | $L_{A322}$ | $L_{B21}$ | III-336 | $L_{A483}$ | $L_{B2}$ | III-3481 | $L_{A398}$ | $L_{B21}$ |
| III-261 | $L_{A408}$ | $L_{B2}$ | III-3406 | $L_{A323}$ | $L_{B21}$ | III-337 | $L_{A484}$ | $L_{B2}$ | III-3482 | $L_{A399}$ | $L_{B21}$ |
| III-262 | $L_{A409}$ | $L_{B2}$ | III-3407 | $L_{A324}$ | $L_{B21}$ | III-338 | $L_{A485}$ | $L_{B2}$ | III-3483 | $L_{A400}$ | $L_{B21}$ |
| III-263 | $L_{A410}$ | $L_{B2}$ | III-3408 | $L_{A325}$ | $L_{B21}$ | III-339 | $L_{A486}$ | $L_{B2}$ | III-3484 | $L_{A401}$ | $L_{B21}$ |
| III-264 | $L_{A411}$ | $L_{B2}$ | III-3409 | $L_{A326}$ | $L_{B21}$ | III-340 | $L_{A487}$ | $L_{B2}$ | III-3485 | $L_{A402}$ | $L_{B21}$ |
| III-265 | $L_{A412}$ | $L_{B2}$ | III-3410 | $L_{A327}$ | $L_{B21}$ | III-341 | $L_{A318}$ | $L_{B3}$ | III-3486 | $L_{A403}$ | $L_{B21}$ |
| III-266 | $L_{A413}$ | $L_{B2}$ | III-3411 | $L_{A328}$ | $L_{B21}$ | III-342 | $L_{A319}$ | $L_{B3}$ | III-3487 | $L_{A404}$ | $L_{B21}$ |
| III-267 | $L_{A414}$ | $L_{B2}$ | III-3412 | $L_{A329}$ | $L_{B21}$ | III-343 | $L_{A320}$ | $L_{B3}$ | III-3488 | $L_{A405}$ | $L_{B21}$ |
| III-268 | $L_{A415}$ | $L_{B2}$ | III-3413 | $L_{A330}$ | $L_{B21}$ | III-344 | $L_{A321}$ | $L_{B3}$ | III-3489 | $L_{A406}$ | $L_{B21}$ |
| III-269 | $L_{A416}$ | $L_{B2}$ | III-3414 | $L_{A331}$ | $L_{B21}$ | III-345 | $L_{A322}$ | $L_{B3}$ | III-3490 | $L_{A407}$ | $L_{B21}$ |
| III-270 | $L_{A417}$ | $L_{B2}$ | III-3415 | $L_{A332}$ | $L_{B21}$ | III-346 | $L_{A323}$ | $L_{B3}$ | III-3491 | $L_{A408}$ | $L_{B21}$ |
| III-271 | $L_{A418}$ | $L_{B2}$ | III-3416 | $L_{A333}$ | $L_{B21}$ | III-347 | $L_{A324}$ | $L_{B3}$ | III-3492 | $L_{A409}$ | $L_{B21}$ |
| III-272 | $L_{A419}$ | $L_{B2}$ | III-3417 | $L_{A334}$ | $L_{B21}$ | III-348 | $L_{A325}$ | $L_{B3}$ | III-3493 | $L_{A410}$ | $L_{B21}$ |
| III-273 | $L_{A420}$ | $L_{B2}$ | III-3418 | $L_{A335}$ | $L_{B21}$ | III-349 | $L_{A326}$ | $L_{B3}$ | III-3494 | $L_{A411}$ | $L_{B21}$ |
| III-274 | $L_{A421}$ | $L_{B2}$ | III-3419 | $L_{A336}$ | $L_{B21}$ | III-350 | $L_{A327}$ | $L_{B3}$ | III-3495 | $L_{A412}$ | $L_{B21}$ |
| III-275 | $L_{A422}$ | $L_{B2}$ | III-3420 | $L_{A337}$ | $L_{B21}$ | III-351 | $L_{A328}$ | $L_{B3}$ | III-3496 | $L_{A413}$ | $L_{B21}$ |

-continued

| Compound Number | $L_A$ | $L_B$ | Compound Number | $L_A$ | $L_B$ |
|---|---|---|---|---|---|
| III-352 | $L_{A329}$ | $L_{B3}$ | III-3497 | $L_{A414}$ | $L_{B21}$ |
| III-353 | $L_{A330}$ | $L_{B3}$ | III-3498 | $L_{A415}$ | $L_{B21}$ |
| III-354 | $L_{A331}$ | $L_{B3}$ | III-3499 | $L_{A416}$ | $L_{B21}$ |
| III-355 | $L_{A332}$ | $L_{B3}$ | III-3500 | $L_{A417}$ | $L_{B21}$ |
| III-356 | $L_{A333}$ | $L_{B3}$ | III-3501 | $L_{A418}$ | $L_{B21}$ |
| III-357 | $L_{A334}$ | $L_{B3}$ | III-3502 | $L_{A419}$ | $L_{B21}$ |
| III-358 | $L_{A335}$ | $L_{B3}$ | III-3503 | $L_{A420}$ | $L_{B21}$ |
| III-359 | $L_{A336}$ | $L_{B3}$ | III-3504 | $L_{A421}$ | $L_{B21}$ |
| III-360 | $L_{A337}$ | $L_{B3}$ | III-3505 | $L_{A422}$ | $L_{B21}$ |
| III-361 | $L_{A338}$ | $L_{B3}$ | III-3506 | $L_{A423}$ | $L_{B21}$ |
| III-362 | $L_{A339}$ | $L_{B3}$ | III-3507 | $L_{A424}$ | $L_{B21}$ |
| III-363 | $L_{A340}$ | $L_{B3}$ | III-3508 | $L_{A425}$ | $L_{B21}$ |
| III-364 | $L_{A341}$ | $L_{B3}$ | III-3509 | $L_{A426}$ | $L_{B21}$ |
| III-365 | $L_{A342}$ | $L_{B3}$ | III-3510 | $L_{A427}$ | $L_{B21}$ |
| III-366 | $L_{A343}$ | $L_{B3}$ | III-3511 | $L_{A428}$ | $L_{B21}$ |
| III-367 | $L_{A344}$ | $L_{B3}$ | III-3512 | $L_{A429}$ | $L_{B21}$ |
| III-368 | $L_{A345}$ | $L_{B3}$ | III-3513 | $L_{A430}$ | $L_{B21}$ |
| III-369 | $L_{A346}$ | $L_{B3}$ | III-3514 | $L_{A431}$ | $L_{B21}$ |
| III-370 | $L_{A347}$ | $L_{B3}$ | III-3515 | $L_{A432}$ | $L_{B21}$ |
| III-371 | $L_{A348}$ | $L_{B3}$ | III-3516 | $L_{A433}$ | $L_{B21}$ |
| III-372 | $L_{A349}$ | $L_{B3}$ | III-3517 | $L_{A434}$ | $L_{B21}$ |
| III-373 | $L_{A350}$ | $L_{B3}$ | III-3518 | $L_{A435}$ | $L_{B21}$ |
| III-374 | $L_{A351}$ | $L_{B3}$ | III-3519 | $L_{A436}$ | $L_{B21}$ |
| III-375 | $L_{A352}$ | $L_{B3}$ | III-3520 | $L_{A437}$ | $L_{B21}$ |
| III-376 | $L_{A353}$ | $L_{B3}$ | III-3521 | $L_{A438}$ | $L_{B21}$ |
| III-377 | $L_{A354}$ | $L_{B3}$ | III-3522 | $L_{A439}$ | $L_{B21}$ |
| III-378 | $L_{A355}$ | $L_{B3}$ | III-3523 | $L_{A440}$ | $L_{B21}$ |
| III-379 | $L_{A356}$ | $L_{B3}$ | III-3524 | $L_{A441}$ | $L_{B21}$ |
| III-380 | $L_{A357}$ | $L_{B3}$ | III-3525 | $L_{A442}$ | $L_{B21}$ |
| III-381 | $L_{A358}$ | $L_{B3}$ | III-3526 | $L_{A443}$ | $L_{B21}$ |
| III-382 | $L_{A359}$ | $L_{B3}$ | III-3527 | $L_{A444}$ | $L_{B21}$ |
| III-383 | $L_{A360}$ | $L_{B3}$ | III-3528 | $L_{A445}$ | $L_{B21}$ |
| III-384 | $L_{A361}$ | $L_{B3}$ | III-3529 | $L_{A446}$ | $L_{B21}$ |
| III-385 | $L_{A362}$ | $L_{B3}$ | III-3530 | $L_{A447}$ | $L_{B21}$ |
| III-386 | $L_{A363}$ | $L_{B3}$ | III-3531 | $L_{A448}$ | $L_{B21}$ |
| III-387 | $L_{A364}$ | $L_{B3}$ | III-3532 | $L_{A449}$ | $L_{B21}$ |
| III-388 | $L_{A365}$ | $L_{B3}$ | III-3533 | $L_{A450}$ | $L_{B21}$ |
| III-389 | $L_{A366}$ | $L_{B3}$ | III-3534 | $L_{A451}$ | $L_{B21}$ |
| III-390 | $L_{A367}$ | $L_{B3}$ | III-3535 | $L_{A452}$ | $L_{B21}$ |
| III-391 | $L_{A368}$ | $L_{B3}$ | III-3536 | $L_{A453}$ | $L_{B21}$ |
| III-392 | $L_{A369}$ | $L_{B3}$ | III-3537 | $L_{A454}$ | $L_{B21}$ |
| III-393 | $L_{A370}$ | $L_{B3}$ | III-3538 | $L_{A455}$ | $L_{B21}$ |
| III-394 | $L_{A371}$ | $L_{B3}$ | III-3539 | $L_{A456}$ | $L_{B21}$ |
| III-395 | $L_{A372}$ | $L_{B3}$ | III-3540 | $L_{A457}$ | $L_{B21}$ |
| III-396 | $L_{A373}$ | $L_{B3}$ | III-3541 | $L_{A458}$ | $L_{B21}$ |
| III-397 | $L_{A374}$ | $L_{B3}$ | III-3542 | $L_{A459}$ | $L_{B21}$ |
| III-398 | $L_{A375}$ | $L_{B3}$ | III-3543 | $L_{A460}$ | $L_{B21}$ |
| III-399 | $L_{A376}$ | $L_{B3}$ | III-3544 | $L_{A461}$ | $L_{B21}$ |
| III-400 | $L_{A377}$ | $L_{B3}$ | III-3545 | $L_{A462}$ | $L_{B21}$ |
| III-401 | $L_{A378}$ | $L_{B3}$ | III-3546 | $L_{A463}$ | $L_{B21}$ |
| III-402 | $L_{A379}$ | $L_{B3}$ | III-3547 | $L_{A464}$ | $L_{B21}$ |
| III-403 | $L_{A380}$ | $L_{B3}$ | III-3548 | $L_{A465}$ | $L_{B21}$ |
| III-404 | $L_{A381}$ | $L_{B3}$ | III-3549 | $L_{A466}$ | $L_{B21}$ |
| III-405 | $L_{A382}$ | $L_{B3}$ | III-3550 | $L_{A467}$ | $L_{B21}$ |
| III-406 | $L_{A383}$ | $L_{B3}$ | III-3551 | $L_{A468}$ | $L_{B21}$ |
| III-407 | $L_{A384}$ | $L_{B3}$ | III-3552 | $L_{A469}$ | $L_{B21}$ |
| III-408 | $L_{A385}$ | $L_{B3}$ | III-3553 | $L_{A470}$ | $L_{B21}$ |
| III-409 | $L_{A386}$ | $L_{B3}$ | III-3554 | $L_{A471}$ | $L_{B21}$ |
| III-410 | $L_{A387}$ | $L_{B3}$ | III-3555 | $L_{A472}$ | $L_{B21}$ |
| III-411 | $L_{A388}$ | $L_{B3}$ | III-3556 | $L_{A473}$ | $L_{B21}$ |
| III-412 | $L_{A389}$ | $L_{B3}$ | III-3557 | $L_{A474}$ | $L_{B21}$ |
| III-413 | $L_{A390}$ | $L_{B3}$ | III-3558 | $L_{A475}$ | $L_{B21}$ |
| III-414 | $L_{A391}$ | $L_{B3}$ | III-3559 | $L_{A476}$ | $L_{B21}$ |
| III-415 | $L_{A392}$ | $L_{B3}$ | III-3560 | $L_{A477}$ | $L_{B21}$ |
| III-416 | $L_{A393}$ | $L_{B3}$ | III-3561 | $L_{A478}$ | $L_{B21}$ |
| III-417 | $L_{A394}$ | $L_{B3}$ | III-3562 | $L_{A479}$ | $L_{B21}$ |
| III-418 | $L_{A395}$ | $L_{B3}$ | III-3563 | $L_{A480}$ | $L_{B21}$ |
| III-419 | $L_{A396}$ | $L_{B3}$ | III-3564 | $L_{A481}$ | $L_{B21}$ |
| III-420 | $L_{A397}$ | $L_{B3}$ | III-3565 | $L_{A482}$ | $L_{B21}$ |
| III-421 | $L_{A398}$ | $L_{B3}$ | III-3566 | $L_{A483}$ | $L_{B21}$ |
| III-422 | $L_{A399}$ | $L_{B3}$ | III-3567 | $L_{A484}$ | $L_{B21}$ |
| III-423 | $L_{A400}$ | $L_{B3}$ | III-3568 | $L_{A485}$ | $L_{B21}$ |
| III-424 | $L_{A401}$ | $L_{B3}$ | III-3569 | $L_{A486}$ | $L_{B21}$ |
| III-425 | $L_{A402}$ | $L_{B3}$ | III-3570 | $L_{A487}$ | $L_{B21}$ |
| III-426 | $L_{A403}$ | $L_{B3}$ | III-3571 | $L_{A318}$ | $L_{B22}$ |
| III-427 | $L_{A404}$ | $L_{B3}$ | III-3572 | $L_{A319}$ | $L_{B22}$ |
| III-428 | $L_{A405}$ | $L_{B3}$ | III-3573 | $L_{A320}$ | $L_{B22}$ |
| III-429 | $L_{A406}$ | $L_{B3}$ | III-3574 | $L_{A321}$ | $L_{B22}$ |
| III-430 | $L_{A407}$ | $L_{B3}$ | III-3575 | $L_{A322}$ | $L_{B22}$ |
| III-431 | $L_{A408}$ | $L_{B3}$ | III-3576 | $L_{A323}$ | $L_{B22}$ |
| III-432 | $L_{A409}$ | $L_{B3}$ | III-3577 | $L_{A324}$ | $L_{B22}$ |
| III-433 | $L_{A410}$ | $L_{B3}$ | III-3578 | $L_{A325}$ | $L_{B22}$ |
| III-434 | $L_{A411}$ | $L_{B3}$ | III-3579 | $L_{A326}$ | $L_{B22}$ |
| III-435 | $L_{A412}$ | $L_{B3}$ | III-3580 | $L_{A327}$ | $L_{B22}$ |
| III-436 | $L_{A413}$ | $L_{B3}$ | III-3581 | $L_{A328}$ | $L_{B22}$ |
| III-437 | $L_{A414}$ | $L_{B3}$ | III-3582 | $L_{A329}$ | $L_{B22}$ |
| III-438 | $L_{A415}$ | $L_{B3}$ | III-3583 | $L_{A330}$ | $L_{B22}$ |
| III-439 | $L_{A416}$ | $L_{B3}$ | III-3584 | $L_{A331}$ | $L_{B22}$ |
| III-440 | $L_{A417}$ | $L_{B3}$ | III-3585 | $L_{A332}$ | $L_{B22}$ |
| III-441 | $L_{A418}$ | $L_{B3}$ | III-3586 | $L_{A333}$ | $L_{B22}$ |
| III-442 | $L_{A419}$ | $L_{B3}$ | III-3587 | $L_{A334}$ | $L_{B22}$ |
| III-443 | $L_{A420}$ | $L_{B3}$ | III-3588 | $L_{A335}$ | $L_{B22}$ |
| III-444 | $L_{A421}$ | $L_{B3}$ | III-3589 | $L_{A336}$ | $L_{B22}$ |
| III-445 | $L_{A422}$ | $L_{B3}$ | III-3590 | $L_{A337}$ | $L_{B22}$ |
| III-446 | $L_{A423}$ | $L_{B3}$ | III-3591 | $L_{A338}$ | $L_{B22}$ |
| III-447 | $L_{A424}$ | $L_{B3}$ | III-3592 | $L_{A339}$ | $L_{B22}$ |
| III-448 | $L_{A425}$ | $L_{B3}$ | III-3593 | $L_{A340}$ | $L_{B22}$ |
| III-449 | $L_{A426}$ | $L_{B3}$ | III-3594 | $L_{A341}$ | $L_{B22}$ |
| III-450 | $L_{A427}$ | $L_{B3}$ | III-3595 | $L_{A342}$ | $L_{B22}$ |
| III-451 | $L_{A428}$ | $L_{B3}$ | III-3596 | $L_{A343}$ | $L_{B22}$ |
| III-452 | $L_{A429}$ | $L_{B3}$ | III-3597 | $L_{A344}$ | $L_{B22}$ |
| III-453 | $L_{A430}$ | $L_{B3}$ | III-3598 | $L_{A345}$ | $L_{B22}$ |
| III-454 | $L_{A431}$ | $L_{B3}$ | III-3599 | $L_{A346}$ | $L_{B22}$ |
| III-455 | $L_{A432}$ | $L_{B3}$ | III-3600 | $L_{A347}$ | $L_{B22}$ |
| III-456 | $L_{A433}$ | $L_{B3}$ | III-3601 | $L_{A348}$ | $L_{B22}$ |
| III-457 | $L_{A434}$ | $L_{B3}$ | III-3602 | $L_{A349}$ | $L_{B22}$ |
| III-458 | $L_{A435}$ | $L_{B3}$ | III-3603 | $L_{A350}$ | $L_{B22}$ |
| III-459 | $L_{A436}$ | $L_{B3}$ | III-3604 | $L_{A351}$ | $L_{B22}$ |
| III-460 | $L_{A437}$ | $L_{B3}$ | III-3605 | $L_{A352}$ | $L_{B22}$ |
| III-461 | $L_{A438}$ | $L_{B3}$ | III-3606 | $L_{A353}$ | $L_{B22}$ |
| III-462 | $L_{A439}$ | $L_{B3}$ | III-3607 | $L_{A354}$ | $L_{B22}$ |
| III-463 | $L_{A440}$ | $L_{B3}$ | III-3608 | $L_{A355}$ | $L_{B22}$ |
| III-464 | $L_{A441}$ | $L_{B3}$ | III-3609 | $L_{A356}$ | $L_{B22}$ |
| III-465 | $L_{A442}$ | $L_{B3}$ | III-3610 | $L_{A357}$ | $L_{B22}$ |
| III-466 | $L_{A443}$ | $L_{B3}$ | III-3611 | $L_{A358}$ | $L_{B22}$ |
| III-467 | $L_{A444}$ | $L_{B3}$ | III-3612 | $L_{A359}$ | $L_{B22}$ |
| III-468 | $L_{A445}$ | $L_{B3}$ | III-3613 | $L_{A360}$ | $L_{B22}$ |
| III-469 | $L_{A446}$ | $L_{B3}$ | III-3614 | $L_{A361}$ | $L_{B22}$ |
| III-470 | $L_{A447}$ | $L_{B3}$ | III-3615 | $L_{A362}$ | $L_{B22}$ |
| III-471 | $L_{A448}$ | $L_{B3}$ | III-3616 | $L_{A363}$ | $L_{B22}$ |
| III-472 | $L_{A449}$ | $L_{B3}$ | III-3617 | $L_{A364}$ | $L_{B22}$ |
| III-473 | $L_{A450}$ | $L_{B3}$ | III-3618 | $L_{A365}$ | $L_{B22}$ |
| III-474 | $L_{A451}$ | $L_{B3}$ | III-3619 | $L_{A366}$ | $L_{B22}$ |
| III-475 | $L_{A452}$ | $L_{B3}$ | III-3620 | $L_{A367}$ | $L_{B22}$ |
| III-476 | $L_{A453}$ | $L_{B3}$ | III-3621 | $L_{A368}$ | $L_{B22}$ |
| III-477 | $L_{A454}$ | $L_{B3}$ | III-3622 | $L_{A369}$ | $L_{B22}$ |
| III-478 | $L_{A455}$ | $L_{B3}$ | III-3623 | $L_{A370}$ | $L_{B22}$ |
| III-479 | $L_{A456}$ | $L_{B3}$ | III-3624 | $L_{A371}$ | $L_{B22}$ |
| III-480 | $L_{A457}$ | $L_{B3}$ | III-3625 | $L_{A372}$ | $L_{B22}$ |
| III-481 | $L_{A458}$ | $L_{B3}$ | III-3626 | $L_{A373}$ | $L_{B22}$ |
| III-482 | $L_{A459}$ | $L_{B3}$ | III-3627 | $L_{A374}$ | $L_{B22}$ |
| III-483 | $L_{A460}$ | $L_{B3}$ | III-3628 | $L_{A375}$ | $L_{B22}$ |
| III-484 | $L_{A461}$ | $L_{B3}$ | III-3629 | $L_{A376}$ | $L_{B22}$ |
| III-485 | $L_{A462}$ | $L_{B3}$ | III-3630 | $L_{A377}$ | $L_{B22}$ |
| III-486 | $L_{A463}$ | $L_{B3}$ | III-3631 | $L_{A378}$ | $L_{B22}$ |
| III-487 | $L_{A464}$ | $L_{B3}$ | III-3632 | $L_{A379}$ | $L_{B22}$ |
| III-488 | $L_{A465}$ | $L_{B3}$ | III-3633 | $L_{A380}$ | $L_{B22}$ |
| III-489 | $L_{A466}$ | $L_{B3}$ | III-3634 | $L_{A381}$ | $L_{B22}$ |
| III-490 | $L_{A467}$ | $L_{B3}$ | III-3635 | $L_{A382}$ | $L_{B22}$ |
| III-491 | $L_{A468}$ | $L_{B3}$ | III-3636 | $L_{A383}$ | $L_{B22}$ |
| III-492 | $L_{A469}$ | $L_{B3}$ | III-3637 | $L_{A384}$ | $L_{B22}$ |
| III-493 | $L_{A470}$ | $L_{B3}$ | III-3638 | $L_{A385}$ | $L_{B22}$ |
| III-494 | $L_{A471}$ | $L_{B3}$ | III-3639 | $L_{A386}$ | $L_{B22}$ |
| III-495 | $L_{A472}$ | $L_{B3}$ | III-3640 | $L_{A387}$ | $L_{B22}$ |
| III-496 | $L_{A473}$ | $L_{B3}$ | III-3641 | $L_{A388}$ | $L_{B22}$ |
| III-497 | $L_{A474}$ | $L_{B3}$ | III-3642 | $L_{A389}$ | $L_{B22}$ |
| III-498 | $L_{A475}$ | $L_{B3}$ | III-3643 | $L_{A390}$ | $L_{B22}$ |
| III-499 | $L_{A476}$ | $L_{B3}$ | III-3644 | $L_{A391}$ | $L_{B22}$ |
| III-500 | $L_{A477}$ | $L_{B3}$ | III-3645 | $L_{A392}$ | $L_{B22}$ |
| III-501 | $L_{A478}$ | $L_{B3}$ | III-3646 | $L_{A393}$ | $L_{B22}$ |
| III-502 | $L_{A479}$ | $L_{B3}$ | III-3647 | $L_{A394}$ | $L_{B22}$ |
| III-503 | $L_{A480}$ | $L_{B3}$ | III-3648 | $L_{A395}$ | $L_{B22}$ |

-continued

| Compound Number | $L_A$ | $L_B$ | Compound Number | $L_A$ | $L_B$ |
|---|---|---|---|---|---|
| III-504 | $L_{A481}$ | $L_{B3}$ | III-3649 | $L_{A396}$ | $L_{B22}$ |
| III-505 | $L_{A482}$ | $L_{B3}$ | III-3650 | $L_{A397}$ | $L_{B22}$ |
| III-506 | $L_{A483}$ | $L_{B3}$ | III-3651 | $L_{A398}$ | $L_{B22}$ |
| III-507 | $L_{A484}$ | $L_{B3}$ | III-3652 | $L_{A399}$ | $L_{B22}$ |
| III-508 | $L_{A485}$ | $L_{B3}$ | III-3653 | $L_{A400}$ | $L_{B22}$ |
| III-509 | $L_{A486}$ | $L_{B3}$ | III-3654 | $L_{A401}$ | $L_{B22}$ |
| III-510 | $L_{A487}$ | $L_{B3}$ | III-3655 | $L_{A402}$ | $L_{B22}$ |
| III-511 | $L_{A318}$ | $L_{B4}$ | III-3656 | $L_{A403}$ | $L_{B22}$ |
| III-512 | $L_{A319}$ | $L_{B4}$ | III-3657 | $L_{A404}$ | $L_{B22}$ |
| III-513 | $L_{A320}$ | $L_{B4}$ | III-3658 | $L_{A405}$ | $L_{B22}$ |
| III-514 | $L_{A321}$ | $L_{B4}$ | III-3659 | $L_{A406}$ | $L_{B22}$ |
| III-515 | $L_{A322}$ | $L_{B4}$ | III-3660 | $L_{A407}$ | $L_{B22}$ |
| III-516 | $L_{A323}$ | $L_{B4}$ | III-3661 | $L_{A408}$ | $L_{B22}$ |
| III-517 | $L_{A324}$ | $L_{B4}$ | III-3662 | $L_{A409}$ | $L_{B22}$ |
| III-518 | $L_{A325}$ | $L_{B4}$ | III-3663 | $L_{A410}$ | $L_{B22}$ |
| III-519 | $L_{A326}$ | $L_{B4}$ | III-3664 | $L_{A411}$ | $L_{B22}$ |
| III-520 | $L_{A327}$ | $L_{B4}$ | III-3665 | $L_{A412}$ | $L_{B22}$ |
| III-521 | $L_{A328}$ | $L_{B4}$ | III-3666 | $L_{A413}$ | $L_{B22}$ |
| III-522 | $L_{A329}$ | $L_{B4}$ | III-3667 | $L_{A414}$ | $L_{B22}$ |
| III-523 | $L_{A330}$ | $L_{B4}$ | III-3668 | $L_{A415}$ | $L_{B22}$ |
| III-524 | $L_{A331}$ | $L_{B4}$ | III-3669 | $L_{A416}$ | $L_{B22}$ |
| III-525 | $L_{A332}$ | $L_{B4}$ | III-3670 | $L_{A417}$ | $L_{B22}$ |
| III-526 | $L_{A333}$ | $L_{B4}$ | III-3671 | $L_{A418}$ | $L_{B22}$ |
| III-527 | $L_{A334}$ | $L_{B4}$ | III-3672 | $L_{A419}$ | $L_{B22}$ |
| III-528 | $L_{A335}$ | $L_{B4}$ | III-3673 | $L_{A420}$ | $L_{B22}$ |
| III-529 | $L_{A336}$ | $L_{B4}$ | III-3674 | $L_{A421}$ | $L_{B22}$ |
| III-530 | $L_{A337}$ | $L_{B4}$ | III-3675 | $L_{A422}$ | $L_{B22}$ |
| III-531 | $L_{A338}$ | $L_{B4}$ | III-3676 | $L_{A423}$ | $L_{B22}$ |
| III-532 | $L_{A339}$ | $L_{B4}$ | III-3677 | $L_{A424}$ | $L_{B22}$ |
| III-533 | $L_{A340}$ | $L_{B4}$ | III-3678 | $L_{A425}$ | $L_{B22}$ |
| III-534 | $L_{A341}$ | $L_{B4}$ | III-3679 | $L_{A426}$ | $L_{B22}$ |
| III-535 | $L_{A342}$ | $L_{B4}$ | III-3680 | $L_{A427}$ | $L_{B22}$ |
| III-536 | $L_{A343}$ | $L_{B4}$ | III-3681 | $L_{A428}$ | $L_{B22}$ |
| III-537 | $L_{A344}$ | $L_{B4}$ | III-3682 | $L_{A429}$ | $L_{B22}$ |
| III-538 | $L_{A345}$ | $L_{B4}$ | III-3683 | $L_{A430}$ | $L_{B22}$ |
| III-539 | $L_{A346}$ | $L_{B4}$ | III-3684 | $L_{A431}$ | $L_{B22}$ |
| III-540 | $L_{A347}$ | $L_{B4}$ | III-3685 | $L_{A432}$ | $L_{B22}$ |
| III-541 | $L_{A348}$ | $L_{B4}$ | III-3686 | $L_{A433}$ | $L_{B22}$ |
| III-542 | $L_{A349}$ | $L_{B4}$ | III-3687 | $L_{A434}$ | $L_{B22}$ |
| III-543 | $L_{A350}$ | $L_{B4}$ | III-3688 | $L_{A435}$ | $L_{B22}$ |
| III-544 | $L_{A351}$ | $L_{B4}$ | III-3689 | $L_{A436}$ | $L_{B22}$ |
| III-545 | $L_{A352}$ | $L_{B4}$ | III-3690 | $L_{A437}$ | $L_{B22}$ |
| III-546 | $L_{A353}$ | $L_{B4}$ | III-3691 | $L_{A438}$ | $L_{B22}$ |
| III-547 | $L_{A354}$ | $L_{B4}$ | III-3692 | $L_{A439}$ | $L_{B22}$ |
| III-548 | $L_{A355}$ | $L_{B4}$ | III-3693 | $L_{A440}$ | $L_{B22}$ |
| III-549 | $L_{A356}$ | $L_{B4}$ | III-3694 | $L_{A441}$ | $L_{B22}$ |
| III-550 | $L_{A357}$ | $L_{B4}$ | III-3695 | $L_{A442}$ | $L_{B22}$ |
| III-551 | $L_{A358}$ | $L_{B4}$ | III-3696 | $L_{A443}$ | $L_{B22}$ |
| III-552 | $L_{A359}$ | $L_{B4}$ | III-3697 | $L_{A444}$ | $L_{B22}$ |
| III-553 | $L_{A360}$ | $L_{B4}$ | III-3698 | $L_{A445}$ | $L_{B22}$ |
| III-554 | $L_{A361}$ | $L_{B4}$ | III-3699 | $L_{A446}$ | $L_{B22}$ |
| III-555 | $L_{A362}$ | $L_{B4}$ | III-3700 | $L_{A447}$ | $L_{B22}$ |
| III-556 | $L_{A363}$ | $L_{B4}$ | III-3701 | $L_{A448}$ | $L_{B22}$ |
| III-557 | $L_{A364}$ | $L_{B4}$ | III-3702 | $L_{A449}$ | $L_{B22}$ |
| III-558 | $L_{A365}$ | $L_{B4}$ | III-3703 | $L_{A450}$ | $L_{B22}$ |
| III-559 | $L_{A366}$ | $L_{B4}$ | III-3704 | $L_{A451}$ | $L_{B22}$ |
| III-560 | $L_{A367}$ | $L_{B4}$ | III-3705 | $L_{A452}$ | $L_{B22}$ |
| III-561 | $L_{A368}$ | $L_{B4}$ | III-3706 | $L_{A453}$ | $L_{B22}$ |
| III-562 | $L_{A369}$ | $L_{B4}$ | III-3707 | $L_{A454}$ | $L_{B22}$ |
| III-563 | $L_{A370}$ | $L_{B4}$ | III-3708 | $L_{A455}$ | $L_{B22}$ |
| III-564 | $L_{A371}$ | $L_{B4}$ | III-3709 | $L_{A456}$ | $L_{B22}$ |
| III-565 | $L_{A372}$ | $L_{B4}$ | III-3710 | $L_{A457}$ | $L_{B22}$ |
| III-566 | $L_{A373}$ | $L_{B4}$ | III-3711 | $L_{A458}$ | $L_{B22}$ |
| III-567 | $L_{A374}$ | $L_{B4}$ | III-3712 | $L_{A459}$ | $L_{B22}$ |
| III-568 | $L_{A375}$ | $L_{B4}$ | III-3713 | $L_{A460}$ | $L_{B22}$ |
| III-569 | $L_{A376}$ | $L_{B4}$ | III-3714 | $L_{A461}$ | $L_{B22}$ |
| III-570 | $L_{A377}$ | $L_{B4}$ | III-3715 | $L_{A462}$ | $L_{B22}$ |
| III-571 | $L_{A378}$ | $L_{B4}$ | III-3716 | $L_{A463}$ | $L_{B22}$ |
| III-572 | $L_{A379}$ | $L_{B4}$ | III-3717 | $L_{A464}$ | $L_{B22}$ |
| III-573 | $L_{A380}$ | $L_{B4}$ | III-3718 | $L_{A465}$ | $L_{B22}$ |
| III-574 | $L_{A381}$ | $L_{B4}$ | III-3719 | $L_{A466}$ | $L_{B22}$ |
| III-575 | $L_{A382}$ | $L_{B4}$ | III-3720 | $L_{A467}$ | $L_{B22}$ |
| III-576 | $L_{A383}$ | $L_{B4}$ | III-3721 | $L_{A468}$ | $L_{B22}$ |
| III-577 | $L_{A384}$ | $L_{B4}$ | III-3722 | $L_{A469}$ | $L_{B22}$ |
| III-578 | $L_{A385}$ | $L_{B4}$ | III-3723 | $L_{A470}$ | $L_{B22}$ |
| III-579 | $L_{A386}$ | $L_{B4}$ | III-3724 | $L_{A471}$ | $L_{B22}$ |
| III-580 | $L_{A387}$ | $L_{B4}$ | III-3725 | $L_{A472}$ | $L_{B22}$ |
| III-581 | $L_{A388}$ | $L_{B4}$ | III-3726 | $L_{A473}$ | $L_{B22}$ |
| III-582 | $L_{A389}$ | $L_{B4}$ | III-3727 | $L_{A474}$ | $L_{B22}$ |
| III-583 | $L_{A390}$ | $L_{B4}$ | III-3728 | $L_{A475}$ | $L_{B22}$ |
| III-584 | $L_{A391}$ | $L_{B4}$ | III-3729 | $L_{A476}$ | $L_{B22}$ |
| III-585 | $L_{A392}$ | $L_{B4}$ | III-3730 | $L_{A477}$ | $L_{B22}$ |
| III-586 | $L_{A393}$ | $L_{B4}$ | III-3731 | $L_{A478}$ | $L_{B22}$ |
| III-587 | $L_{A394}$ | $L_{B4}$ | III-3732 | $L_{A479}$ | $L_{B22}$ |
| III-588 | $L_{A395}$ | $L_{B4}$ | III-3733 | $L_{A480}$ | $L_{B22}$ |
| III-589 | $L_{A396}$ | $L_{B4}$ | III-3734 | $L_{A481}$ | $L_{B22}$ |
| III-590 | $L_{A397}$ | $L_{B4}$ | III-3735 | $L_{A482}$ | $L_{B22}$ |
| III-591 | $L_{A398}$ | $L_{B4}$ | III-3736 | $L_{A483}$ | $L_{B22}$ |
| III-592 | $L_{A399}$ | $L_{B4}$ | III-3737 | $L_{A484}$ | $L_{B22}$ |
| III-593 | $L_{A400}$ | $L_{B4}$ | III-3738 | $L_{A485}$ | $L_{B22}$ |
| III-594 | $L_{A401}$ | $L_{B4}$ | III-3739 | $L_{A486}$ | $L_{B22}$ |
| III-595 | $L_{A402}$ | $L_{B4}$ | III-3740 | $L_{A487}$ | $L_{B22}$ |
| III-596 | $L_{A403}$ | $L_{B4}$ | III-3741 | $L_{A318}$ | $L_{B23}$ |
| III-597 | $L_{A404}$ | $L_{B4}$ | III-3742 | $L_{A319}$ | $L_{B23}$ |
| III-598 | $L_{A405}$ | $L_{B4}$ | III-3743 | $L_{A320}$ | $L_{B23}$ |
| III-599 | $L_{A406}$ | $L_{B4}$ | III-3744 | $L_{A321}$ | $L_{B23}$ |
| III-600 | $L_{A407}$ | $L_{B4}$ | III-3745 | $L_{A322}$ | $L_{B23}$ |
| III-601 | $L_{A408}$ | $L_{B4}$ | III-3746 | $L_{A323}$ | $L_{B23}$ |
| III-602 | $L_{A409}$ | $L_{B4}$ | III-3747 | $L_{A324}$ | $L_{B23}$ |
| III-603 | $L_{A410}$ | $L_{B4}$ | III-3748 | $L_{A325}$ | $L_{B23}$ |
| III-604 | $L_{A411}$ | $L_{B4}$ | III-3749 | $L_{A326}$ | $L_{B23}$ |
| III-605 | $L_{A412}$ | $L_{B4}$ | III-3750 | $L_{A327}$ | $L_{B23}$ |
| III-606 | $L_{A413}$ | $L_{B4}$ | III-3751 | $L_{A328}$ | $L_{B23}$ |
| III-607 | $L_{A414}$ | $L_{B4}$ | III-3752 | $L_{A329}$ | $L_{B23}$ |
| III-608 | $L_{A415}$ | $L_{B4}$ | III-3753 | $L_{A330}$ | $L_{B23}$ |
| III-609 | $L_{A416}$ | $L_{B4}$ | III-3754 | $L_{A331}$ | $L_{B23}$ |
| III-610 | $L_{A412}$ | $L_{B4}$ | III-3755 | $L_{A332}$ | $L_{B23}$ |
| III-611 | $L_{A418}$ | $L_{B4}$ | III-3756 | $L_{A333}$ | $L_{B23}$ |
| III-612 | $L_{A413}$ | $L_{B4}$ | III-3757 | $L_{A334}$ | $L_{B23}$ |
| III-613 | $L_{A420}$ | $L_{B4}$ | III-3758 | $L_{A335}$ | $L_{B23}$ |
| III-614 | $L_{A421}$ | $L_{B4}$ | III-3759 | $L_{A336}$ | $L_{B23}$ |
| III-615 | $L_{A422}$ | $L_{B4}$ | III-3760 | $L_{A337}$ | $L_{B23}$ |
| III-616 | $L_{A423}$ | $L_{B4}$ | III-3761 | $L_{A338}$ | $L_{B23}$ |
| III-617 | $L_{A424}$ | $L_{B4}$ | III-3762 | $L_{A339}$ | $L_{B23}$ |
| III-618 | $L_{A425}$ | $L_{B4}$ | III-3763 | $L_{A340}$ | $L_{B23}$ |
| III-619 | $L_{A426}$ | $L_{B4}$ | III-3764 | $L_{A341}$ | $L_{B23}$ |
| III-620 | $L_{A427}$ | $L_{B4}$ | III-3765 | $L_{A342}$ | $L_{B23}$ |
| III-621 | $L_{A428}$ | $L_{B4}$ | III-3766 | $L_{A343}$ | $L_{B23}$ |
| III-622 | $L_{A429}$ | $L_{B4}$ | III-3767 | $L_{A344}$ | $L_{B23}$ |
| III-623 | $L_{A430}$ | $L_{B4}$ | III-3768 | $L_{A345}$ | $L_{B23}$ |
| III-624 | $L_{A431}$ | $L_{B4}$ | III-3769 | $L_{A346}$ | $L_{B23}$ |
| III-625 | $L_{A432}$ | $L_{B4}$ | III-3770 | $L_{A347}$ | $L_{B23}$ |
| III-626 | $L_{A433}$ | $L_{B4}$ | III-3771 | $L_{A348}$ | $L_{B23}$ |
| III-627 | $L_{A434}$ | $L_{B4}$ | III-3772 | $L_{A349}$ | $L_{B23}$ |
| III-628 | $L_{A435}$ | $L_{B4}$ | III-3773 | $L_{A350}$ | $L_{B23}$ |
| III-629 | $L_{A436}$ | $L_{B4}$ | III-3774 | $L_{A351}$ | $L_{B23}$ |
| III-630 | $L_{A437}$ | $L_{B4}$ | III-3775 | $L_{A352}$ | $L_{B23}$ |
| III-631 | $L_{A438}$ | $L_{B4}$ | III-3776 | $L_{A353}$ | $L_{B23}$ |
| III-632 | $L_{A439}$ | $L_{B4}$ | III-3777 | $L_{A354}$ | $L_{B23}$ |
| III-633 | $L_{A440}$ | $L_{B4}$ | III-3778 | $L_{A355}$ | $L_{B23}$ |
| III-634 | $L_{A441}$ | $L_{B4}$ | III-3779 | $L_{A356}$ | $L_{B23}$ |
| III-635 | $L_{A442}$ | $L_{B4}$ | III-3780 | $L_{A357}$ | $L_{B23}$ |
| III-636 | $L_{A443}$ | $L_{B4}$ | III-3781 | $L_{A358}$ | $L_{B23}$ |
| III-637 | $L_{A444}$ | $L_{B4}$ | III-3782 | $L_{A359}$ | $L_{B23}$ |
| III-638 | $L_{A445}$ | $L_{B4}$ | III-3783 | $L_{A360}$ | $L_{B23}$ |
| III-639 | $L_{A446}$ | $L_{B4}$ | III-3784 | $L_{A361}$ | $L_{B23}$ |
| III-640 | $L_{A447}$ | $L_{B4}$ | III-3785 | $L_{A362}$ | $L_{B23}$ |
| III-641 | $L_{A448}$ | $L_{B4}$ | III-3786 | $L_{A363}$ | $L_{B23}$ |
| III-642 | $L_{A443}$ | $L_{B4}$ | III-3787 | $L_{A364}$ | $L_{B23}$ |
| III-643 | $L_{A450}$ | $L_{B4}$ | III-3788 | $L_{A365}$ | $L_{B23}$ |
| III-644 | $L_{A451}$ | $L_{B4}$ | III-3789 | $L_{A366}$ | $L_{B23}$ |
| III-645 | $L_{A452}$ | $L_{B4}$ | III-3790 | $L_{A367}$ | $L_{B23}$ |
| III-646 | $L_{A453}$ | $L_{B4}$ | III-3791 | $L_{A368}$ | $L_{B23}$ |
| III-647 | $L_{A454}$ | $L_{B4}$ | III-3792 | $L_{A369}$ | $L_{B23}$ |
| III-648 | $L_{A455}$ | $L_{B4}$ | III-3793 | $L_{A370}$ | $L_{B23}$ |
| III-649 | $L_{A456}$ | $L_{B4}$ | III-3794 | $L_{A371}$ | $L_{B23}$ |
| III-650 | $L_{A457}$ | $L_{B4}$ | III-3795 | $L_{A372}$ | $L_{B23}$ |
| III-651 | $L_{A458}$ | $L_{B4}$ | III-3796 | $L_{A373}$ | $L_{B23}$ |
| III-652 | $L_{A453}$ | $L_{B4}$ | III-3797 | $L_{A374}$ | $L_{B23}$ |
| III-653 | $L_{A460}$ | $L_{B4}$ | III-3798 | $L_{A375}$ | $L_{B23}$ |
| III-654 | $L_{A461}$ | $L_{B4}$ | III-3799 | $L_{A376}$ | $L_{B23}$ |
| III-655 | $L_{A462}$ | $L_{B4}$ | III-3800 | $L_{A377}$ | $L_{B23}$ |

| Compound Number | $L_A$ | $L_B$ |
|---|---|---|
| III-656 | $L_{A463}$ | $L_{B4}$ |
| III-657 | $L_{A464}$ | $L_{B4}$ |
| III-658 | $L_{A465}$ | $L_{B4}$ |
| III-659 | $L_{A466}$ | $L_{B4}$ |
| III-660 | $L_{A467}$ | $L_{B4}$ |
| III-661 | $L_{A468}$ | $L_{B4}$ |
| III-662 | $L_{A469}$ | $L_{B4}$ |
| III-663 | $L_{A470}$ | $L_{B4}$ |
| III-664 | $L_{A471}$ | $L_{B4}$ |
| III-665 | $L_{A472}$ | $L_{B4}$ |
| III-666 | $L_{A473}$ | $L_{B4}$ |
| III-667 | $L_{A474}$ | $L_{B4}$ |
| III-668 | $L_{A475}$ | $L_{B4}$ |
| III-669 | $L_{A476}$ | $L_{B4}$ |
| III-670 | $L_{A477}$ | $L_{B4}$ |
| III-671 | $L_{A478}$ | $L_{B4}$ |
| III-672 | $L_{A479}$ | $L_{B4}$ |
| III-673 | $L_{A480}$ | $L_{B4}$ |
| III-674 | $L_{A481}$ | $L_{B4}$ |
| III-675 | $L_{A482}$ | $L_{B4}$ |
| III-676 | $L_{A483}$ | $L_{B4}$ |
| III-677 | $L_{A484}$ | $L_{B4}$ |
| III-678 | $L_{A485}$ | $L_{B4}$ |
| III-679 | $L_{A486}$ | $L_{B4}$ |
| III-680 | $L_{A487}$ | $L_{B4}$ |
| III-681 | $L_{A318}$ | $L_{B5}$ |
| III-682 | $L_{A319}$ | $L_{B5}$ |
| III-683 | $L_{A320}$ | $L_{B5}$ |
| III-684 | $L_{A321}$ | $L_{B5}$ |
| III-685 | $L_{A322}$ | $L_{B5}$ |
| III-686 | $L_{A323}$ | $L_{B5}$ |
| III-687 | $L_{A324}$ | $L_{B5}$ |
| III-688 | $L_{A325}$ | $L_{B5}$ |
| III-689 | $L_{A326}$ | $L_{B5}$ |
| III-690 | $L_{A327}$ | $L_{B5}$ |
| III-691 | $L_{A328}$ | $L_{B5}$ |
| III-692 | $L_{A329}$ | $L_{B5}$ |
| III-693 | $L_{A330}$ | $L_{B5}$ |
| III-694 | $L_{A331}$ | $L_{B5}$ |
| III-695 | $L_{A332}$ | $L_{B5}$ |
| III-696 | $L_{A333}$ | $L_{B5}$ |
| III-697 | $L_{A334}$ | $L_{B5}$ |
| III-698 | $L_{A335}$ | $L_{B5}$ |
| III-699 | $L_{A336}$ | $L_{B5}$ |
| III-700 | $L_{A337}$ | $L_{B5}$ |
| III-701 | $L_{A338}$ | $L_{B5}$ |
| III-702 | $L_{A339}$ | $L_{B5}$ |
| III-703 | $L_{A340}$ | $L_{B5}$ |
| III-704 | $L_{A341}$ | $L_{B5}$ |
| III-705 | $L_{A342}$ | $L_{B5}$ |
| III-706 | $L_{A343}$ | $L_{B5}$ |
| III-707 | $L_{A344}$ | $L_{B5}$ |
| III-708 | $L_{A345}$ | $L_{B5}$ |
| III-709 | $L_{A346}$ | $L_{B5}$ |
| III-710 | $L_{A347}$ | $L_{B5}$ |
| III-711 | $L_{A348}$ | $L_{B5}$ |
| III-712 | $L_{A349}$ | $L_{B5}$ |
| III-713 | $L_{A350}$ | $L_{B5}$ |
| III-714 | $L_{A351}$ | $L_{B5}$ |
| III-715 | $L_{A352}$ | $L_{B5}$ |
| III-716 | $L_{A353}$ | $L_{B5}$ |
| III-717 | $L_{A354}$ | $L_{B5}$ |
| III-718 | $L_{A355}$ | $L_{B5}$ |
| III-719 | $L_{A356}$ | $L_{B5}$ |
| III-720 | $L_{A357}$ | $L_{B5}$ |
| III-721 | $L_{A358}$ | $L_{B5}$ |
| III-722 | $L_{A359}$ | $L_{B5}$ |
| III-723 | $L_{A360}$ | $L_{B5}$ |
| III-724 | $L_{A361}$ | $L_{B5}$ |
| III-725 | $L_{A362}$ | $L_{B5}$ |
| III-726 | $L_{A363}$ | $L_{B5}$ |
| III-727 | $L_{A364}$ | $L_{B5}$ |
| III-728 | $L_{A365}$ | $L_{B5}$ |
| III-729 | $L_{A366}$ | $L_{B5}$ |
| III-730 | $L_{A367}$ | $L_{B5}$ |
| III-731 | $L_{A368}$ | $L_{B5}$ |
| III-732 | $L_{A369}$ | $L_{B5}$ |
| III-733 | $L_{A370}$ | $L_{B5}$ |
| III-734 | $L_{A371}$ | $L_{B5}$ |
| III-735 | $L_{A372}$ | $L_{B5}$ |
| III-736 | $L_{A373}$ | $L_{B5}$ |
| III-737 | $L_{A374}$ | $L_{B5}$ |
| III-738 | $L_{A375}$ | $L_{B5}$ |
| III-739 | $L_{A376}$ | $L_{B5}$ |
| III-740 | $L_{A377}$ | $L_{B5}$ |
| III-741 | $L_{A378}$ | $L_{B5}$ |
| III-742 | $L_{A379}$ | $L_{B5}$ |
| III-743 | $L_{A380}$ | $L_{B5}$ |
| III-744 | $L_{A381}$ | $L_{B5}$ |
| III-745 | $L_{A382}$ | $L_{B5}$ |
| III-746 | $L_{A383}$ | $L_{B5}$ |
| III-747 | $L_{A384}$ | $L_{B5}$ |
| III-748 | $L_{A385}$ | $L_{B5}$ |
| III-749 | $L_{A386}$ | $L_{B5}$ |
| III-750 | $L_{A387}$ | $L_{B5}$ |
| III-751 | $L_{A388}$ | $L_{B5}$ |
| III-752 | $L_{A389}$ | $L_{B5}$ |
| III-753 | $L_{A390}$ | $L_{B5}$ |
| III-754 | $L_{A391}$ | $L_{B5}$ |
| III-755 | $L_{A392}$ | $L_{B5}$ |
| III-756 | $L_{A393}$ | $L_{B5}$ |
| III-757 | $L_{A394}$ | $L_{B5}$ |
| III-758 | $L_{A395}$ | $L_{B5}$ |
| III-759 | $L_{A396}$ | $L_{B5}$ |
| III-760 | $L_{A397}$ | $L_{B5}$ |
| III-761 | $L_{A398}$ | $L_{B5}$ |
| III-762 | $L_{A399}$ | $L_{B5}$ |
| III-763 | $L_{A400}$ | $L_{B5}$ |
| III-764 | $L_{A401}$ | $L_{B5}$ |
| III-765 | $L_{A402}$ | $L_{B5}$ |
| III-766 | $L_{A403}$ | $L_{B5}$ |
| III-767 | $L_{A404}$ | $L_{B5}$ |
| III-768 | $L_{A405}$ | $L_{B5}$ |
| III-769 | $L_{A406}$ | $L_{B5}$ |
| III-770 | $L_{A407}$ | $L_{B5}$ |
| III-771 | $L_{A408}$ | $L_{B5}$ |
| III-772 | $L_{A409}$ | $L_{B5}$ |
| III-773 | $L_{A410}$ | $L_{B5}$ |
| III-774 | $L_{A411}$ | $L_{B5}$ |
| III-775 | $L_{A412}$ | $L_{B5}$ |
| III-776 | $L_{A413}$ | $L_{B5}$ |
| III-777 | $L_{A414}$ | $L_{B5}$ |
| III-778 | $L_{A415}$ | $L_{B5}$ |
| III-779 | $L_{A416}$ | $L_{B5}$ |
| III-780 | $L_{A417}$ | $L_{B5}$ |
| III-781 | $L_{A418}$ | $L_{B5}$ |
| III-782 | $L_{A419}$ | $L_{B5}$ |
| III-783 | $L_{A420}$ | $L_{B5}$ |
| III-784 | $L_{A421}$ | $L_{B5}$ |
| III-785 | $L_{A422}$ | $L_{B5}$ |
| III-786 | $L_{A423}$ | $L_{B5}$ |
| III-787 | $L_{A424}$ | $L_{B5}$ |
| III-788 | $L_{A425}$ | $L_{B5}$ |
| III-789 | $L_{A426}$ | $L_{B5}$ |
| III-790 | $L_{A427}$ | $L_{B5}$ |
| III-791 | $L_{A428}$ | $L_{B5}$ |
| III-792 | $L_{A429}$ | $L_{B5}$ |
| III-793 | $L_{A430}$ | $L_{B5}$ |
| III-794 | $L_{A431}$ | $L_{B5}$ |
| III-795 | $L_{A432}$ | $L_{B5}$ |
| III-796 | $L_{A433}$ | $L_{B5}$ |
| III-797 | $L_{A434}$ | $L_{B5}$ |
| III-798 | $L_{A435}$ | $L_{B5}$ |
| III-799 | $L_{A436}$ | $L_{B5}$ |
| III-800 | $L_{A437}$ | $L_{B5}$ |
| III-801 | $L_{A438}$ | $L_{B5}$ |
| III-802 | $L_{A439}$ | $L_{B5}$ |
| III-803 | $L_{A440}$ | $L_{B5}$ |
| III-804 | $L_{A441}$ | $L_{B5}$ |
| III-805 | $L_{A442}$ | $L_{B5}$ |
| III-806 | $L_{A443}$ | $L_{B5}$ |
| III-807 | $L_{A444}$ | $L_{B5}$ |
| III-3801 | $L_{A378}$ | $L_{B23}$ |
| III-3802 | $L_{A379}$ | $L_{B23}$ |
| III-3803 | $L_{A380}$ | $L_{B23}$ |
| III-3804 | $L_{A381}$ | $L_{B23}$ |
| III-3805 | $L_{A382}$ | $L_{B23}$ |
| III-3806 | $L_{A383}$ | $L_{B23}$ |
| III-3807 | $L_{A384}$ | $L_{B23}$ |
| III-3808 | $L_{A385}$ | $L_{B23}$ |
| III-3809 | $L_{A386}$ | $L_{B23}$ |
| III-3810 | $L_{A387}$ | $L_{B23}$ |
| III-3811 | $L_{A388}$ | $L_{B23}$ |
| III-3812 | $L_{A389}$ | $L_{B23}$ |
| III-3813 | $L_{A390}$ | $L_{B23}$ |
| III-3814 | $L_{A391}$ | $L_{B23}$ |
| III-3815 | $L_{A392}$ | $L_{B23}$ |
| III-3816 | $L_{A393}$ | $L_{B23}$ |
| III-3817 | $L_{A394}$ | $L_{B23}$ |
| III-3818 | $L_{A395}$ | $L_{B23}$ |
| III-3819 | $L_{A396}$ | $L_{B23}$ |
| III-3820 | $L_{A397}$ | $L_{B23}$ |
| III-3821 | $L_{A398}$ | $L_{B23}$ |
| III-3822 | $L_{A399}$ | $L_{B23}$ |
| III-3823 | $L_{A400}$ | $L_{B23}$ |
| III-3824 | $L_{A401}$ | $L_{B23}$ |
| III-3825 | $L_{A402}$ | $L_{B23}$ |
| III-3826 | $L_{A403}$ | $L_{B23}$ |
| III-3827 | $L_{A404}$ | $L_{B23}$ |
| III-3828 | $L_{A405}$ | $L_{B23}$ |
| III-3829 | $L_{A406}$ | $L_{B23}$ |
| III-3830 | $L_{A407}$ | $L_{B23}$ |
| III-3831 | $L_{A408}$ | $L_{B23}$ |
| III-3832 | $L_{A409}$ | $L_{B23}$ |
| III-3833 | $L_{A410}$ | $L_{B23}$ |
| III-3834 | $L_{A411}$ | $L_{B23}$ |
| III-3835 | $L_{A412}$ | $L_{B23}$ |
| III-3836 | $L_{A413}$ | $L_{B23}$ |
| III-3837 | $L_{A414}$ | $L_{B23}$ |
| III-3838 | $L_{A415}$ | $L_{B23}$ |
| III-3839 | $L_{A416}$ | $L_{B23}$ |
| III-3840 | $L_{A417}$ | $L_{B23}$ |
| III-3841 | $L_{A418}$ | $L_{B23}$ |
| III-3842 | $L_{A419}$ | $L_{B23}$ |
| III-3843 | $L_{A420}$ | $L_{B23}$ |
| III-3844 | $L_{A421}$ | $L_{B23}$ |
| III-3845 | $L_{A422}$ | $L_{B23}$ |
| III-3846 | $L_{A423}$ | $L_{B23}$ |
| III-3847 | $L_{A424}$ | $L_{B23}$ |
| III-3848 | $L_{A425}$ | $L_{B23}$ |
| III-3849 | $L_{A426}$ | $L_{B23}$ |
| III-3850 | $L_{A427}$ | $L_{B23}$ |
| III-3851 | $L_{A428}$ | $L_{B23}$ |
| III-3852 | $L_{A429}$ | $L_{B23}$ |
| III-3853 | $L_{A430}$ | $L_{B23}$ |
| III-3854 | $L_{A431}$ | $L_{B23}$ |
| III-3855 | $L_{A432}$ | $L_{B23}$ |
| III-3856 | $L_{A433}$ | $L_{B23}$ |
| III-3857 | $L_{A434}$ | $L_{B23}$ |
| III-3858 | $L_{A435}$ | $L_{B23}$ |
| III-3859 | $L_{A436}$ | $L_{B23}$ |
| III-3860 | $L_{A437}$ | $L_{B23}$ |
| III-3861 | $L_{A438}$ | $L_{B23}$ |
| III-3862 | $L_{A439}$ | $L_{B23}$ |
| III-3863 | $L_{A440}$ | $L_{B23}$ |
| III-3864 | $L_{A441}$ | $L_{B23}$ |
| III-3865 | $L_{A442}$ | $L_{B23}$ |
| III-3866 | $L_{A443}$ | $L_{B23}$ |
| III-3867 | $L_{A444}$ | $L_{B23}$ |
| III-3868 | $L_{A445}$ | $L_{B23}$ |
| III-3869 | $L_{A446}$ | $L_{B23}$ |
| III-3870 | $L_{A447}$ | $L_{B23}$ |
| III-3871 | $L_{A448}$ | $L_{B23}$ |
| III-3872 | $L_{A449}$ | $L_{B23}$ |
| III-3873 | $L_{A450}$ | $L_{B23}$ |
| III-3874 | $L_{A451}$ | $L_{B23}$ |
| III-3875 | $L_{A452}$ | $L_{B23}$ |
| III-3876 | $L_{A453}$ | $L_{B23}$ |
| III-3877 | $L_{A454}$ | $L_{B23}$ |
| III-3878 | $L_{A455}$ | $L_{B23}$ |
| III-3879 | $L_{A456}$ | $L_{B23}$ |
| III-3880 | $L_{A457}$ | $L_{B23}$ |
| III-3881 | $L_{A458}$ | $L_{B23}$ |
| III-3882 | $L_{A459}$ | $L_{B23}$ |
| III-3883 | $L_{A460}$ | $L_{B23}$ |
| III-3884 | $L_{A461}$ | $L_{B23}$ |
| III-3885 | $L_{A462}$ | $L_{B23}$ |
| III-3886 | $L_{A463}$ | $L_{B23}$ |
| III-3887 | $L_{A464}$ | $L_{B23}$ |
| III-3888 | $L_{A465}$ | $L_{B23}$ |
| III-3889 | $L_{A466}$ | $L_{B23}$ |
| III-3890 | $L_{A467}$ | $L_{B23}$ |
| III-3891 | $L_{A468}$ | $L_{B23}$ |
| III-3892 | $L_{A469}$ | $L_{B23}$ |
| III-3893 | $L_{A470}$ | $L_{B23}$ |
| III-3894 | $L_{A471}$ | $L_{B23}$ |
| III-3895 | $L_{A472}$ | $L_{B23}$ |
| III-3896 | $L_{A473}$ | $L_{B23}$ |
| III-3897 | $L_{A474}$ | $L_{B23}$ |
| III-3898 | $L_{A475}$ | $L_{B23}$ |
| III-3899 | $L_{A476}$ | $L_{B23}$ |
| III-3900 | $L_{A477}$ | $L_{B23}$ |
| III-3901 | $L_{A478}$ | $L_{B23}$ |
| III-3902 | $L_{A479}$ | $L_{B23}$ |
| III-3903 | $L_{A480}$ | $L_{B23}$ |
| III-3904 | $L_{A481}$ | $L_{B23}$ |
| III-3905 | $L_{A482}$ | $L_{B23}$ |
| III-3906 | $L_{A483}$ | $L_{B23}$ |
| III-3907 | $L_{A484}$ | $L_{B23}$ |
| III-3908 | $L_{A485}$ | $L_{B23}$ |
| III-3909 | $L_{A486}$ | $LB_{23}$ |
| III-3910 | $L_{A487}$ | $L_{B23}$ |
| III-3911 | $L_{A318}$ | $L_{B24}$ |
| III-3912 | $L_{A319}$ | $L_{B24}$ |
| III-3913 | $L_{A320}$ | $L_{B24}$ |
| III-3914 | $L_{A321}$ | $L_{B24}$ |
| III-3915 | $L_{A322}$ | $L_{B24}$ |
| III-3916 | $L_{A323}$ | $L_{B24}$ |
| III-3917 | $L_{A324}$ | $L_{B24}$ |
| III-3918 | $L_{A325}$ | $L_{B24}$ |
| III-3919 | $L_{A326}$ | $L_{B24}$ |
| III-3920 | $L_{A327}$ | $L_{B24}$ |
| III-3921 | $L_{A328}$ | $L_{B24}$ |
| III-3922 | $L_{A329}$ | $L_{B24}$ |
| III-3923 | $L_{A330}$ | $L_{B24}$ |
| III-3924 | $L_{A331}$ | $L_{B24}$ |
| III-3925 | $L_{A332}$ | $L_{B24}$ |
| III-3926 | $L_{A333}$ | $L_{B24}$ |
| III-3927 | $L_{A334}$ | $L_{B24}$ |
| III-3928 | $L_{A335}$ | $L_{B24}$ |
| III-3929 | $L_{A336}$ | $L_{B24}$ |
| III-3930 | $L_{A337}$ | $L_{B24}$ |
| III-3931 | $L_{A338}$ | $L_{B24}$ |
| III-3932 | $L_{A339}$ | $L_{B24}$ |
| III-3933 | $L_{A340}$ | $L_{B24}$ |
| III-3934 | $L_{A341}$ | $L_{B24}$ |
| III-3935 | $L_{A342}$ | $L_{B24}$ |
| III-3936 | $L_{A343}$ | $L_{B24}$ |
| III-3937 | $L_{A344}$ | $L_{B24}$ |
| III-3938 | $L_{A345}$ | $L_{B24}$ |
| III-3939 | $L_{A346}$ | $L_{B24}$ |
| III-3940 | $L_{A347}$ | $L_{B24}$ |
| III-3941 | $L_{A348}$ | $L_{B24}$ |
| III-3942 | $L_{A349}$ | $L_{B24}$ |
| III-3943 | $L_{A350}$ | $L_{B24}$ |
| III-3944 | $L_{A351}$ | $L_{B24}$ |
| III-3945 | $L_{A352}$ | $L_{B24}$ |
| III-3946 | $L_{A353}$ | $L_{B24}$ |
| III-3947 | $L_{A354}$ | $L_{B24}$ |
| III-3948 | $L_{A355}$ | $L_{B24}$ |
| III-3949 | $L_{A356}$ | $L_{B24}$ |
| III-3950 | $L_{A357}$ | $L_{B24}$ |
| III-3951 | $L_{A358}$ | $L_{B24}$ |
| III-3952 | $L_{A359}$ | $L_{B24}$ |

| Compound Number | $L_A$ | $L_B$ | Compound Number | $L_A$ | $L_B$ | Compound Number | $L_A$ | $L_B$ | Compound Number | $L_A$ | $L_B$ |
|---|---|---|---|---|---|---|---|---|---|---|---|
| III-808 | $L_{A445}$ | $L_{B5}$ | III-3953 | $L_{A360}$ | $L_{B24}$ | III-884 | $L_{A351}$ | $L_{B6}$ | III-4029 | $L_{A436}$ | $L_{B24}$ |
| III-809 | $L_{A446}$ | $L_{B5}$ | III-3954 | $L_{A361}$ | $L_{B24}$ | III-885 | $L_{A352}$ | $L_{B6}$ | III-4030 | $L_{A437}$ | $L_{B24}$ |
| III-810 | $L_{A447}$ | $L_{B5}$ | III-3955 | $L_{A362}$ | $L_{B24}$ | III-886 | $L_{A353}$ | $L_{B6}$ | III-4031 | $L_{A438}$ | $L_{B24}$ |
| III-811 | $L_{A448}$ | $L_{B5}$ | III-3956 | $L_{A363}$ | $L_{B24}$ | III-887 | $L_{A354}$ | $L_{B6}$ | III-4032 | $L_{A439}$ | $L_{B24}$ |
| III-812 | $L_{A449}$ | $L_{B5}$ | III-3957 | $L_{A364}$ | $L_{B24}$ | III-888 | $L_{A355}$ | $L_{B6}$ | III-4033 | $L_{A440}$ | $L_{B24}$ |
| III-813 | $L_{A450}$ | $L_{B5}$ | III-3958 | $L_{A365}$ | $L_{B24}$ | III-889 | $L_{A356}$ | $L_{B6}$ | III-4034 | $L_{A441}$ | $L_{B24}$ |
| III-814 | $L_{A451}$ | $L_{B5}$ | III-3959 | $L_{A366}$ | $L_{B24}$ | III-890 | $L_{A357}$ | $L_{B6}$ | III-4035 | $L_{A442}$ | $L_{B24}$ |
| III-815 | $L_{A452}$ | $L_{B5}$ | III-3960 | $L_{A367}$ | $L_{B24}$ | III-891 | $L_{A358}$ | $L_{B6}$ | III-4036 | $L_{A443}$ | $L_{B24}$ |
| III-816 | $L_{A453}$ | $L_{B5}$ | III-3961 | $L_{A368}$ | $L_{B24}$ | III-892 | $L_{A359}$ | $L_{B6}$ | III-4037 | $L_{A444}$ | $L_{B24}$ |
| III-817 | $L_{A454}$ | $L_{B5}$ | III-3962 | $L_{A369}$ | $L_{B24}$ | III-893 | $L_{A360}$ | $L_{B6}$ | III-4038 | $L_{A445}$ | $L_{B24}$ |
| III-818 | $L_{A455}$ | $L_{B5}$ | III-3963 | $L_{A370}$ | $L_{B24}$ | III-894 | $L_{A361}$ | $L_{B6}$ | III-4039 | $L_{A446}$ | $L_{B24}$ |
| III-819 | $L_{A456}$ | $L_{B5}$ | III-3964 | $L_{A371}$ | $L_{B24}$ | III-895 | $L_{A362}$ | $L_{B6}$ | III-4040 | $L_{A447}$ | $L_{B24}$ |
| III-820 | $L_{A457}$ | $L_{B5}$ | III-3965 | $L_{A372}$ | $L_{B24}$ | III-896 | $L_{A363}$ | $L_{B6}$ | III-4041 | $L_{A448}$ | $L_{B24}$ |
| III-821 | $L_{A458}$ | $L_{B5}$ | III-3966 | $L_{A373}$ | $L_{B24}$ | III-897 | $L_{A364}$ | $L_{B6}$ | III-4042 | $L_{A449}$ | $L_{B24}$ |
| III-822 | $L_{A459}$ | $L_{B5}$ | III-3967 | $L_{A374}$ | $L_{B24}$ | III-898 | $L_{A365}$ | $L_{B6}$ | III-4043 | $L_{A450}$ | $L_{B24}$ |
| III-823 | $L_{A460}$ | $L_{B5}$ | III-3968 | $L_{A375}$ | $L_{B24}$ | III-899 | $L_{A366}$ | $L_{B6}$ | III-4044 | $L_{A451}$ | $L_{B24}$ |
| III-824 | $L_{A461}$ | $L_{B5}$ | III-3969 | $L_{A376}$ | $L_{B24}$ | III-900 | $L_{A367}$ | $L_{B6}$ | III-4045 | $L_{A452}$ | $L_{B24}$ |
| III-825 | $L_{A462}$ | $L_{B5}$ | III-3970 | $L_{A377}$ | $L_{B24}$ | III-901 | $L_{A368}$ | $L_{B6}$ | III-4046 | $L_{A453}$ | $L_{B24}$ |
| III-826 | $L_{A463}$ | $L_{B5}$ | III-3971 | $L_{A378}$ | $L_{B24}$ | III-902 | $L_{A369}$ | $L_{B6}$ | III-4047 | $L_{A454}$ | $L_{B24}$ |
| III-827 | $L_{A464}$ | $L_{B5}$ | III-3972 | $L_{A379}$ | $L_{B24}$ | III-903 | $L_{A370}$ | $L_{B6}$ | III-4048 | $L_{A455}$ | $L_{B24}$ |
| III-828 | $L_{A465}$ | $L_{B5}$ | III-3973 | $L_{A380}$ | $L_{B24}$ | III-904 | $L_{A371}$ | $L_{B6}$ | III-4049 | $L_{A456}$ | $L_{B24}$ |
| III-829 | $L_{A466}$ | $L_{B5}$ | III-3974 | $L_{A381}$ | $L_{B24}$ | III-905 | $L_{A372}$ | $L_{B6}$ | III-4050 | $L_{A457}$ | $L_{B24}$ |
| III-830 | $L_{A467}$ | $L_{B5}$ | III-3975 | $L_{A382}$ | $L_{B24}$ | III-906 | $L_{A373}$ | $L_{B6}$ | III-4051 | $L_{A458}$ | $L_{B24}$ |
| III-831 | $L_{A468}$ | $L_{B5}$ | III-3976 | $L_{A383}$ | $L_{B24}$ | III-907 | $L_{A374}$ | $L_{B6}$ | III-4052 | $L_{A459}$ | $L_{B24}$ |
| III-832 | $L_{A469}$ | $L_{B5}$ | III-3977 | $L_{A384}$ | $L_{B24}$ | III-908 | $L_{A375}$ | $L_{B6}$ | III-4053 | $L_{A460}$ | $L_{B24}$ |
| III-833 | $L_{A470}$ | $L_{B5}$ | III-3978 | $L_{A385}$ | $L_{B24}$ | III-909 | $L_{A376}$ | $L_{B6}$ | III-4054 | $L_{A461}$ | $L_{B24}$ |
| III-834 | $L_{A471}$ | $L_{B5}$ | III-3979 | $L_{A386}$ | $L_{B24}$ | III-910 | $L_{A377}$ | $L_{B6}$ | III-4055 | $L_{A462}$ | $L_{B24}$ |
| III-835 | $L_{A472}$ | $L_{B5}$ | III-3980 | $L_{A387}$ | $L_{B24}$ | III-911 | $L_{A378}$ | $L_{B6}$ | III-4056 | $L_{A463}$ | $L_{B24}$ |
| III-836 | $L_{A473}$ | $L_{B5}$ | III-3981 | $L_{A388}$ | $L_{B24}$ | III-912 | $L_{A379}$ | $L_{B6}$ | III-4057 | $L_{A464}$ | $L_{B24}$ |
| III-837 | $L_{A474}$ | $L_{B5}$ | III-3982 | $L_{A389}$ | $L_{B24}$ | III-913 | $L_{A380}$ | $L_{B6}$ | III-4058 | $L_{A465}$ | $L_{B24}$ |
| III-838 | $L_{A475}$ | $L_{B5}$ | III-3983 | $L_{A390}$ | $L_{B24}$ | III-914 | $L_{A381}$ | $L_{B6}$ | III-4059 | $L_{A466}$ | $L_{B24}$ |
| III-839 | $L_{A476}$ | $L_{B5}$ | III-3984 | $L_{A391}$ | $L_{B24}$ | III-915 | $L_{A382}$ | $L_{B6}$ | III-4060 | $L_{A467}$ | $L_{B24}$ |
| III-840 | $L_{A477}$ | $L_{B5}$ | III-3985 | $L_{A392}$ | $L_{B24}$ | III-916 | $L_{A383}$ | $L_{B6}$ | III-4061 | $L_{A468}$ | $L_{B24}$ |
| III-841 | $L_{A478}$ | $L_{B5}$ | III-3986 | $L_{A393}$ | $L_{B24}$ | III-917 | $L_{A384}$ | $L_{B6}$ | III-4062 | $L_{A469}$ | $L_{B24}$ |
| III-842 | $L_{A479}$ | $L_{B5}$ | III-3987 | $L_{A394}$ | $L_{B24}$ | III-918 | $L_{A385}$ | $L_{B6}$ | III-4063 | $L_{A470}$ | $L_{B24}$ |
| III-843 | $L_{A480}$ | $L_{B5}$ | III-3988 | $L_{A395}$ | $L_{B24}$ | III-919 | $L_{A386}$ | $L_{B6}$ | III-4064 | $L_{A471}$ | $L_{B24}$ |
| III-844 | $L_{A481}$ | $L_{B5}$ | III-3989 | $L_{A396}$ | $L_{B24}$ | III-920 | $L_{A387}$ | $L_{B6}$ | III-4065 | $L_{A472}$ | $L_{B24}$ |
| III-845 | $L_{A482}$ | $L_{B5}$ | III-3990 | $L_{A397}$ | $L_{B24}$ | III-921 | $L_{A388}$ | $L_{B6}$ | III-4066 | $L_{A473}$ | $L_{B24}$ |
| III-846 | $L_{A483}$ | $L_{B5}$ | III-3991 | $L_{A398}$ | $L_{B24}$ | III-922 | $L_{A389}$ | $L_{B6}$ | III-4067 | $L_{A474}$ | $L_{B24}$ |
| III-847 | $L_{A484}$ | $L_{B5}$ | III-3992 | $L_{A399}$ | $L_{B24}$ | III-923 | $L_{A390}$ | $L_{B6}$ | III-4068 | $L_{A475}$ | $L_{B24}$ |
| III-848 | $L_{A485}$ | $L_{B5}$ | III-3993 | $L_{A400}$ | $L_{B24}$ | III-924 | $L_{A391}$ | $L_{B6}$ | III-4069 | $L_{A476}$ | $L_{B24}$ |
| III-849 | $L_{A486}$ | $L_{B5}$ | III-3994 | $L_{A401}$ | $L_{B24}$ | III-925 | $L_{A392}$ | $L_{B6}$ | III-4070 | $L_{A477}$ | $L_{B24}$ |
| III-850 | $L_{A487}$ | $L_{B5}$ | III-3995 | $L_{A402}$ | $L_{B24}$ | III-926 | $L_{A393}$ | $L_{B6}$ | III-4071 | $L_{A478}$ | $L_{B24}$ |
| III-851 | $L_{A318}$ | $L_{B6}$ | III-3996 | $L_{A403}$ | $L_{B24}$ | III-927 | $L_{A394}$ | $L_{B6}$ | III-4072 | $L_{A479}$ | $L_{B24}$ |
| III-852 | $L_{A319}$ | $L_{B6}$ | III-3997 | $L_{A404}$ | $L_{B24}$ | III-928 | $L_{A395}$ | $L_{B6}$ | III-4073 | $L_{A480}$ | $L_{B24}$ |
| III-853 | $L_{A320}$ | $L_{B6}$ | III-3998 | $L_{A405}$ | $L_{B24}$ | III-929 | $L_{A396}$ | $L_{B6}$ | III-4074 | $L_{A481}$ | $L_{B24}$ |
| III-854 | $L_{A321}$ | $L_{B6}$ | III-3999 | $L_{A406}$ | $L_{B24}$ | III-930 | $L_{A397}$ | $L_{B6}$ | III-4075 | $L_{A482}$ | $L_{B24}$ |
| III-855 | $L_{A322}$ | $L_{B6}$ | III-4000 | $L_{A407}$ | $L_{B24}$ | III-931 | $L_{A398}$ | $L_{B6}$ | III-4076 | $L_{A483}$ | $L_{B24}$ |
| III-856 | $L_{A323}$ | $L_{B6}$ | III-4001 | $L_{A408}$ | $L_{B24}$ | III-932 | $L_{A399}$ | $L_{B6}$ | III-4077 | $L_{A484}$ | $L_{B24}$ |
| III-857 | $L_{A324}$ | $L_{B6}$ | III-4002 | $L_{A409}$ | $L_{B24}$ | III-933 | $L_{A400}$ | $L_{B6}$ | III-4078 | $L_{A485}$ | $L_{B24}$ |
| III-858 | $L_{A325}$ | $L_{B6}$ | III-4003 | $L_{A410}$ | $L_{B24}$ | III-934 | $L_{A401}$ | $L_{B6}$ | III-4079 | $L_{A486}$ | $L_{B24}$ |
| III-859 | $L_{A326}$ | $L_{B6}$ | III-4004 | $L_{A411}$ | $L_{B24}$ | III-935 | $L_{A402}$ | $L_{B6}$ | III-4080 | $L_{A487}$ | $L_{B24}$ |
| III-860 | $L_{A327}$ | $L_{B6}$ | III-4005 | $L_{A412}$ | $L_{B24}$ | III-936 | $L_{A403}$ | $L_{B6}$ | III-4081 | $L_{A318}$ | $L_{B25}$ |
| III-861 | $L_{A328}$ | $L_{B6}$ | III-4006 | $L_{A413}$ | $L_{B24}$ | III-937 | $L_{A404}$ | $L_{B6}$ | III-4082 | $L_{A319}$ | $L_{B25}$ |
| III-862 | $L_{A329}$ | $L_{B6}$ | III-4007 | $L_{A414}$ | $L_{B24}$ | III-938 | $L_{A405}$ | $L_{B6}$ | III-4083 | $L_{A320}$ | $L_{B25}$ |
| III-863 | $L_{A330}$ | $L_{B6}$ | III-4008 | $L_{A415}$ | $L_{B24}$ | III-939 | $L_{A406}$ | $L_{B6}$ | III-4084 | $L_{A321}$ | $L_{B25}$ |
| III-864 | $L_{A331}$ | $L_{B6}$ | III-4009 | $L_{A416}$ | $L_{B24}$ | III-940 | $L_{A407}$ | $L_{B6}$ | III-4085 | $L_{A322}$ | $L_{B25}$ |
| III-865 | $L_{A332}$ | $L_{B6}$ | III-4010 | $L_{A417}$ | $L_{B24}$ | III-941 | $L_{A408}$ | $L_{B6}$ | III-4086 | $L_{A323}$ | $L_{B25}$ |
| III-866 | $L_{A333}$ | $L_{B6}$ | III-4011 | $L_{A418}$ | $L_{B24}$ | III-942 | $L_{A409}$ | $L_{B6}$ | III-4087 | $L_{A324}$ | $L_{B25}$ |
| III-867 | $L_{A334}$ | $L_{B6}$ | III-4012 | $L_{A419}$ | $L_{B24}$ | III-943 | $L_{A410}$ | $L_{B6}$ | III-4088 | $L_{A325}$ | $L_{B25}$ |
| III-868 | $L_{A335}$ | $L_{B6}$ | III-4013 | $L_{A420}$ | $L_{B24}$ | III-944 | $L_{A411}$ | $L_{B6}$ | III-4089 | $L_{A326}$ | $L_{B25}$ |
| III-869 | $L_{A336}$ | $L_{B6}$ | III-4014 | $L_{A421}$ | $L_{B24}$ | III-945 | $L_{A412}$ | $L_{B6}$ | III-4090 | $L_{A327}$ | $L_{B25}$ |
| III-870 | $L_{A337}$ | $L_{B6}$ | III-4015 | $L_{A422}$ | $L_{B24}$ | III-946 | $L_{A413}$ | $L_{B6}$ | III-4091 | $L_{A328}$ | $L_{B25}$ |
| III-871 | $L_{A338}$ | $L_{B6}$ | III-4016 | $L_{A423}$ | $L_{B24}$ | III-947 | $L_{A414}$ | $L_{B6}$ | III-4092 | $L_{A329}$ | $L_{B25}$ |
| III-872 | $L_{A339}$ | $L_{B6}$ | III-4017 | $L_{A424}$ | $L_{B24}$ | III-948 | $L_{A415}$ | $L_{B6}$ | III-4093 | $L_{A330}$ | $L_{B25}$ |
| III-873 | $L_{A340}$ | $L_{B6}$ | III-4018 | $L_{A425}$ | $L_{B24}$ | III-949 | $L_{A416}$ | $L_{B6}$ | III-4094 | $L_{A331}$ | $L_{B25}$ |
| III-874 | $L_{A341}$ | $L_{B6}$ | III-4019 | $L_{A426}$ | $L_{B24}$ | III-950 | $L_{A417}$ | $L_{B6}$ | III-4095 | $L_{A332}$ | $L_{B25}$ |
| III-875 | $L_{A342}$ | $L_{B6}$ | III-4020 | $L_{A427}$ | $L_{B24}$ | III-951 | $L_{A418}$ | $L_{B6}$ | III-4096 | $L_{A333}$ | $L_{B25}$ |
| III-876 | $L_{A343}$ | $L_{B6}$ | III-4021 | $L_{A428}$ | $L_{B24}$ | III-952 | $L_{A419}$ | $L_{B6}$ | III-4097 | $L_{A334}$ | $L_{B25}$ |
| III-877 | $L_{A344}$ | $L_{B6}$ | III-4022 | $L_{A429}$ | $L_{B24}$ | III-953 | $L_{A420}$ | $L_{B6}$ | III-4098 | $L_{A335}$ | $L_{B25}$ |
| III-878 | $L_{A345}$ | $L_{B6}$ | III-4023 | $L_{A430}$ | $L_{B24}$ | III-954 | $L_{A421}$ | $L_{B6}$ | III-4099 | $L_{A336}$ | $L_{B25}$ |
| III-879 | $L_{A346}$ | $L_{B6}$ | III-4024 | $L_{A431}$ | $L_{B24}$ | III-955 | $L_{A422}$ | $L_{B6}$ | III-4100 | $L_{A337}$ | $L_{B25}$ |
| III-880 | $L_{A347}$ | $L_{B6}$ | III-4025 | $L_{A432}$ | $L_{B24}$ | III-956 | $L_{A423}$ | $L_{B6}$ | III-4101 | $L_{A338}$ | $L_{B25}$ |
| III-881 | $L_{A348}$ | $L_{B6}$ | III-4026 | $L_{A433}$ | $L_{B24}$ | III-957 | $L_{A424}$ | $L_{B6}$ | III-4102 | $L_{A339}$ | $L_{B25}$ |
| III-882 | $L_{A349}$ | $L_{B6}$ | III-4027 | $L_{A434}$ | $L_{B24}$ | III-958 | $L_{A425}$ | $L_{B6}$ | III-4103 | $L_{A340}$ | $L_{B25}$ |
| III-883 | $L_{A350}$ | $L_{B6}$ | III-4028 | $L_{A435}$ | $L_{B24}$ | III-959 | $L_{A426}$ | $L_{B6}$ | III-4104 | $L_{A341}$ | $L_{B25}$ |

| Compound Number | $L_A$ | $L_B$ | Compound Number | $L_A$ | $L_B$ | Compound Number | $L_A$ | $L_B$ | Compound Number | $L_A$ | $L_B$ |
|---|---|---|---|---|---|---|---|---|---|---|---|
| III-960 | $L_{A427}$ | $L_{B6}$ | III-4105 | $L_{A342}$ | $L_{B25}$ | III-1036 | $L_{A333}$ | $L_{B7}$ | III-4181 | $L_{A418}$ | $L_{B25}$ |
| III-961 | $L_{A428}$ | $L_{B6}$ | III-4106 | $L_{A343}$ | $L_{B25}$ | III-1037 | $L_{A334}$ | $L_{B7}$ | III-4182 | $L_{A419}$ | $L_{B25}$ |
| III-962 | $L_{A429}$ | $L_{B6}$ | III-4107 | $L_{A344}$ | $L_{B25}$ | III-1038 | $L_{A335}$ | $L_{B7}$ | III-4183 | $L_{A420}$ | $L_{B25}$ |
| III-963 | $L_{A430}$ | $L_{B6}$ | III-4108 | $L_{A345}$ | $L_{B25}$ | III-1039 | $L_{A336}$ | $L_{B7}$ | III-4184 | $L_{A421}$ | $L_{B25}$ |
| III-964 | $L_{A431}$ | $L_{B6}$ | III-4109 | $L_{A346}$ | $L_{B25}$ | III-1040 | $L_{A337}$ | $L_{B7}$ | III-4185 | $L_{A422}$ | $L_{B25}$ |
| III-965 | $L_{A432}$ | $L_{B6}$ | III-4110 | $L_{A347}$ | $L_{B25}$ | III-1041 | $L_{A338}$ | $L_{B7}$ | III-4186 | $L_{A423}$ | $L_{B25}$ |
| III-966 | $L_{A433}$ | $L_{B6}$ | III-4111 | $L_{A348}$ | $L_{B25}$ | III-1042 | $L_{A339}$ | $L_{B7}$ | III-4187 | $L_{A424}$ | $L_{B25}$ |
| III-967 | $L_{A434}$ | $L_{B6}$ | III-4112 | $L_{A349}$ | $L_{B25}$ | III-1043 | $L_{A340}$ | $L_{B7}$ | III-4188 | $L_{A425}$ | $L_{B25}$ |
| III-968 | $L_{A435}$ | $L_{B6}$ | III-4113 | $L_{A350}$ | $L_{B25}$ | III-1044 | $L_{A341}$ | $L_{B7}$ | III-4189 | $L_{A426}$ | $L_{B25}$ |
| III-969 | $L_{A436}$ | $L_{B6}$ | III-4114 | $L_{A351}$ | $L_{B25}$ | III-1045 | $L_{A342}$ | $L_{B7}$ | III-4190 | $L_{A427}$ | $L_{B25}$ |
| III-970 | $L_{A437}$ | $L_{B6}$ | III-4115 | $L_{A352}$ | $L_{B25}$ | III-1046 | $L_{A343}$ | $L_{B7}$ | III-4191 | $L_{A428}$ | $L_{B25}$ |
| III-971 | $L_{A438}$ | $L_{B6}$ | III-4116 | $L_{A353}$ | $L_{B25}$ | III-1047 | $L_{A344}$ | $L_{B7}$ | III-4192 | $L_{A429}$ | $L_{B25}$ |
| III-972 | $L_{A439}$ | $L_{B6}$ | III-4117 | $L_{A354}$ | $L_{B25}$ | III-1048 | $L_{A345}$ | $L_{B7}$ | III-4193 | $L_{A430}$ | $L_{B25}$ |
| III-973 | $L_{A440}$ | $L_{B6}$ | III-4118 | $L_{A355}$ | $L_{B25}$ | III-1049 | $L_{A346}$ | $L_{B7}$ | III-4194 | $L_{A431}$ | $L_{B25}$ |
| III-974 | $L_{A441}$ | $L_{B6}$ | III-4119 | $L_{A356}$ | $L_{B25}$ | III-1050 | $L_{A347}$ | $L_{B7}$ | III-4195 | $L_{A432}$ | $L_{B25}$ |
| III-975 | $L_{A442}$ | $L_{B6}$ | III-4120 | $L_{A357}$ | $L_{B25}$ | III-1051 | $L_{A348}$ | $L_{B7}$ | III-4196 | $L_{A433}$ | $L_{B25}$ |
| III-976 | $L_{A443}$ | $L_{B6}$ | III-4121 | $L_{A358}$ | $L_{B25}$ | III-1052 | $L_{A349}$ | $L_{B7}$ | III-4197 | $L_{A434}$ | $L_{B25}$ |
| III-977 | $L_{A444}$ | $L_{B6}$ | III-4122 | $L_{A359}$ | $L_{B25}$ | III-1053 | $L_{A350}$ | $L_{B7}$ | III-4198 | $L_{A435}$ | $L_{B25}$ |
| III-978 | $L_{A445}$ | $L_{B6}$ | III-4123 | $L_{A360}$ | $L_{B25}$ | III-1054 | $L_{A351}$ | $L_{B7}$ | III-4199 | $L_{A436}$ | $L_{B25}$ |
| III-979 | $L_{A446}$ | $L_{B6}$ | III-4124 | $L_{A361}$ | $L_{B25}$ | III-1055 | $L_{A352}$ | $L_{B7}$ | III-4200 | $L_{A437}$ | $L_{B25}$ |
| III-980 | $L_{A447}$ | $L_{B6}$ | III-4125 | $L_{A362}$ | $L_{B25}$ | III-1056 | $L_{A353}$ | $L_{B7}$ | III-4201 | $L_{A438}$ | $L_{B25}$ |
| III-981 | $L_{A448}$ | $L_{B6}$ | III-4126 | $L_{A363}$ | $L_{B25}$ | III-1057 | $L_{A354}$ | $L_{B7}$ | III-4202 | $L_{A439}$ | $L_{B25}$ |
| III-982 | $L_{A449}$ | $L_{B6}$ | III-4127 | $L_{A364}$ | $L_{B25}$ | III-1058 | $L_{A355}$ | $L_{B7}$ | III-4203 | $L_{A440}$ | $L_{B25}$ |
| III-983 | $L_{A450}$ | $L_{B6}$ | III-4128 | $L_{A365}$ | $L_{B25}$ | III-1059 | $L_{A356}$ | $L_{B7}$ | III-4204 | $L_{A441}$ | $L_{B25}$ |
| III-984 | $L_{A451}$ | $L_{B6}$ | III-4129 | $L_{A366}$ | $L_{B25}$ | III-1060 | $L_{A357}$ | $L_{B7}$ | III-4205 | $L_{A442}$ | $L_{B25}$ |
| III-985 | $L_{A452}$ | $L_{B6}$ | III-4130 | $L_{A367}$ | $L_{B25}$ | III-1061 | $L_{A358}$ | $L_{B7}$ | III-4206 | $L_{A443}$ | $L_{B25}$ |
| III-986 | $L_{A453}$ | $L_{B6}$ | III-4131 | $L_{A368}$ | $L_{B25}$ | III-1062 | $L_{A359}$ | $L_{B7}$ | III-4207 | $L_{A444}$ | $L_{B25}$ |
| III-987 | $L_{A454}$ | $L_{B6}$ | III-4132 | $L_{A369}$ | $L_{B25}$ | III-1063 | $L_{A360}$ | $L_{B7}$ | III-4208 | $L_{A445}$ | $L_{B25}$ |
| III-988 | $L_{A455}$ | $L_{B6}$ | III-4133 | $L_{A370}$ | $L_{B25}$ | III-1064 | $L_{A361}$ | $L_{B7}$ | III-4209 | $L_{A446}$ | $L_{B25}$ |
| III-989 | $L_{A456}$ | $L_{B6}$ | III-4134 | $L_{A371}$ | $L_{B25}$ | III-1065 | $L_{A362}$ | $L_{B7}$ | III-4210 | $L_{A447}$ | $L_{B25}$ |
| III-990 | $L_{A457}$ | $L_{B6}$ | III-4135 | $L_{A372}$ | $L_{B25}$ | III-1066 | $L_{A363}$ | $L_{B7}$ | III-4211 | $L_{A448}$ | $L_{B25}$ |
| III-991 | $L_{A458}$ | $L_{B6}$ | III-4136 | $L_{A373}$ | $L_{B25}$ | III-1067 | $L_{A364}$ | $L_{B7}$ | III-4212 | $L_{A449}$ | $L_{B25}$ |
| III-992 | $L_{A459}$ | $L_{B6}$ | III-4137 | $L_{A374}$ | $L_{B25}$ | III-1068 | $L_{A365}$ | $L_{B7}$ | III-4213 | $L_{A450}$ | $L_{B25}$ |
| III-993 | $L_{A460}$ | $L_{B6}$ | III-4138 | $L_{A375}$ | $L_{B25}$ | III-1069 | $L_{A366}$ | $L_{B7}$ | III-4214 | $L_{A451}$ | $L_{B25}$ |
| III-994 | $L_{A461}$ | $L_{B6}$ | III-4139 | $L_{A376}$ | $L_{B25}$ | III-1070 | $L_{A367}$ | $L_{B7}$ | III-4215 | $L_{A452}$ | $L_{B25}$ |
| III-995 | $L_{A462}$ | $L_{B6}$ | III-4140 | $L_{A377}$ | $L_{B25}$ | III-1071 | $L_{A368}$ | $L_{B7}$ | III-4216 | $L_{A453}$ | $L_{B25}$ |
| III-996 | $L_{A463}$ | $L_{B6}$ | III-4141 | $L_{A378}$ | $L_{B25}$ | III-1072 | $L_{A369}$ | $L_{B7}$ | III-4217 | $L_{A454}$ | $L_{B25}$ |
| III-997 | $L_{A464}$ | $L_{B6}$ | III-4142 | $L_{A379}$ | $L_{B25}$ | III-1073 | $L_{A370}$ | $L_{B7}$ | III-4218 | $L_{A455}$ | $L_{B25}$ |
| III-998 | $L_{A465}$ | $L_{B6}$ | III-4143 | $L_{A380}$ | $L_{B25}$ | III-1074 | $L_{A371}$ | $L_{B7}$ | III-4219 | $L_{A456}$ | $L_{B25}$ |
| III-999 | $L_{A466}$ | $L_{B6}$ | III-4144 | $L_{A381}$ | $L_{B25}$ | III-1075 | $L_{A372}$ | $L_{B7}$ | III-4220 | $L_{A457}$ | $L_{B25}$ |
| III-1000 | $L_{A467}$ | $L_{B6}$ | III-4145 | $L_{A382}$ | $L_{B25}$ | III-1076 | $L_{A373}$ | $L_{B7}$ | III-4221 | $L_{A458}$ | $L_{B25}$ |
| III-1001 | $L_{A468}$ | $L_{B6}$ | III-4146 | $L_{A383}$ | $L_{B25}$ | III-1077 | $L_{A374}$ | $L_{B7}$ | III-4222 | $L_{A459}$ | $L_{B25}$ |
| III-1002 | $L_{A469}$ | $L_{B6}$ | III-4147 | $L_{A384}$ | $L_{B25}$ | III-1078 | $L_{A375}$ | $L_{B7}$ | III-4223 | $L_{A460}$ | $L_{B25}$ |
| III-1003 | $L_{A470}$ | $L_{B6}$ | III-4148 | $L_{A385}$ | $L_{B25}$ | III-1079 | $L_{A376}$ | $L_{B7}$ | III-4224 | $L_{A461}$ | $L_{B25}$ |
| III-1004 | $L_{A471}$ | $L_{B6}$ | III-4149 | $L_{A386}$ | $L_{B25}$ | III-1080 | $L_{A377}$ | $L_{B7}$ | III-4225 | $L_{A462}$ | $L_{B25}$ |
| III-1005 | $L_{A472}$ | $L_{B6}$ | III-4150 | $L_{A387}$ | $L_{B25}$ | III-1081 | $L_{A378}$ | $L_{B7}$ | III-4226 | $L_{A463}$ | $L_{B25}$ |
| III-1006 | $L_{A473}$ | $L_{B6}$ | III-4151 | $L_{A388}$ | $L_{B25}$ | III-1082 | $L_{A379}$ | $L_{B7}$ | III-4227 | $L_{A464}$ | $L_{B25}$ |
| III-1007 | $L_{A474}$ | $L_{B6}$ | III-4152 | $L_{A389}$ | $L_{B25}$ | III-1083 | $L_{A380}$ | $L_{B7}$ | III-4228 | $L_{A465}$ | $L_{B25}$ |
| III-1008 | $L_{A475}$ | $L_{B6}$ | III-4153 | $L_{A390}$ | $L_{B25}$ | III-1084 | $L_{A381}$ | $L_{B7}$ | III-4229 | $L_{A466}$ | $L_{B25}$ |
| III-1009 | $L_{A476}$ | $L_{B6}$ | III-4154 | $L_{A391}$ | $L_{B25}$ | III-1085 | $L_{A382}$ | $L_{B7}$ | III-4230 | $L_{A467}$ | $L_{B25}$ |
| III-1010 | $L_{A477}$ | $L_{B6}$ | III-4155 | $L_{A392}$ | $L_{B25}$ | III-1086 | $L_{A383}$ | $L_{B7}$ | III-4231 | $L_{A468}$ | $L_{B25}$ |
| III-1011 | $L_{A478}$ | $L_{B6}$ | III-4156 | $L_{A393}$ | $L_{B25}$ | III-1087 | $L_{A384}$ | $L_{B7}$ | III-4232 | $L_{A469}$ | $L_{B25}$ |
| III-1012 | $L_{A479}$ | $L_{B6}$ | III-4157 | $L_{A394}$ | $L_{B25}$ | III-1088 | $L_{A385}$ | $L_{B7}$ | III-4233 | $L_{A470}$ | $L_{B25}$ |
| III-1013 | $L_{A480}$ | $L_{B6}$ | III-4158 | $L_{A395}$ | $L_{B25}$ | III-1089 | $L_{A386}$ | $L_{B7}$ | III-4234 | $L_{A471}$ | $L_{B25}$ |
| III-1014 | $L_{A481}$ | $L_{B6}$ | III-4159 | $L_{A396}$ | $L_{B25}$ | III-1090 | $L_{A387}$ | $L_{B7}$ | III-4235 | $L_{A472}$ | $L_{B25}$ |
| III-1015 | $L_{A482}$ | $L_{B6}$ | III-4160 | $L_{A397}$ | $L_{B25}$ | III-1091 | $L_{A388}$ | $L_{B7}$ | III-4236 | $L_{A473}$ | $L_{B25}$ |
| III-1016 | $L_{A483}$ | $L_{B6}$ | III-4161 | $L_{A398}$ | $L_{B25}$ | III-1092 | $L_{A389}$ | $L_{B7}$ | III-4237 | $L_{A474}$ | $L_{B25}$ |
| III-1017 | $L_{A484}$ | $L_{B6}$ | III-4162 | $L_{A399}$ | $L_{B25}$ | III-1093 | $L_{A390}$ | $L_{B7}$ | III-4238 | $L_{A475}$ | $L_{B25}$ |
| III-1018 | $L_{A485}$ | $L_{B6}$ | III-4163 | $L_{A400}$ | $L_{B25}$ | III-1094 | $L_{A391}$ | $L_{B7}$ | III-4239 | $L_{A476}$ | $L_{B25}$ |
| III-1019 | $L_{A486}$ | $L_{B6}$ | III-4164 | $L_{A401}$ | $L_{B25}$ | III-1095 | $L_{A392}$ | $L_{B7}$ | III-4240 | $L_{A477}$ | $L_{B25}$ |
| III-1020 | $L_{A487}$ | $L_{B6}$ | III-4165 | $L_{A402}$ | $L_{B25}$ | III-1096 | $L_{A393}$ | $L_{B7}$ | III-4241 | $L_{A478}$ | $L_{B25}$ |
| III-1021 | $L_{A318}$ | $L_{B7}$ | III-4166 | $L_{A403}$ | $L_{B25}$ | III-1097 | $L_{A394}$ | $L_{B7}$ | III-4242 | $L_{A479}$ | $L_{B25}$ |
| III-1022 | $L_{A319}$ | $L_{B7}$ | III-4167 | $L_{A404}$ | $L_{B25}$ | III-1098 | $L_{A395}$ | $L_{B7}$ | III-4243 | $L_{A480}$ | $L_{B25}$ |
| III-1023 | $L_{A320}$ | $L_{B7}$ | III-4168 | $L_{A405}$ | $L_{B25}$ | III-1099 | $L_{A396}$ | $L_{B7}$ | III-4244 | $L_{A481}$ | $L_{B25}$ |
| III-1024 | $L_{A321}$ | $L_{B7}$ | III-4169 | $L_{A406}$ | $L_{B25}$ | III-1100 | $L_{A397}$ | $L_{B7}$ | III-4245 | $L_{A482}$ | $L_{B25}$ |
| III-1025 | $L_{A322}$ | $L_{B7}$ | III-4170 | $L_{A407}$ | $L_{B25}$ | III-1101 | $L_{A398}$ | $L_{B7}$ | III-4246 | $L_{A483}$ | $L_{B25}$ |
| III-1026 | $L_{A323}$ | $L_{B7}$ | III-4171 | $L_{A408}$ | $L_{B25}$ | III-1102 | $L_{A399}$ | $L_{B7}$ | III-4247 | $L_{A484}$ | $L_{B25}$ |
| III-1027 | $L_{A324}$ | $L_{B7}$ | III-4172 | $L_{A409}$ | $L_{B25}$ | III-1103 | $L_{A400}$ | $L_{B7}$ | III-4248 | $L_{A485}$ | $L_{B25}$ |
| III-1028 | $L_{A325}$ | $L_{B7}$ | III-4173 | $L_{A410}$ | $L_{B25}$ | III-1104 | $L_{A401}$ | $L_{B7}$ | III-4249 | $L_{A486}$ | $L_{B25}$ |
| III-1029 | $L_{A326}$ | $L_{B7}$ | III-4174 | $L_{A411}$ | $L_{B25}$ | III-1105 | $L_{A402}$ | $L_{B7}$ | III-4250 | $L_{A487}$ | $L_{B25}$ |
| III-1030 | $L_{A327}$ | $L_{B7}$ | III-4175 | $L_{A412}$ | $L_{B25}$ | III-1106 | $L_{A403}$ | $L_{B7}$ | III-4251 | $L_{A318}$ | $L_{B26}$ |
| III-1031 | $L_{A328}$ | $L_{B7}$ | III-4176 | $L_{A413}$ | $L_{B25}$ | III-1107 | $L_{A404}$ | $L_{B7}$ | III-4252 | $L_{A319}$ | $L_{B26}$ |
| III-1032 | $L_{A329}$ | $L_{B7}$ | III-4177 | $L_{A414}$ | $L_{B25}$ | III-1108 | $L_{A405}$ | $L_{B7}$ | III-4253 | $L_{A320}$ | $L_{B26}$ |
| III-1033 | $L_{A330}$ | $L_{B7}$ | III-4178 | $L_{A415}$ | $L_{B25}$ | III-1109 | $L_{A406}$ | $L_{B7}$ | III-4254 | $L_{A321}$ | $L_{B26}$ |
| III-1034 | $L_{A331}$ | $L_{B7}$ | III-4179 | $L_{A416}$ | $L_{B25}$ | III-1110 | $L_{A407}$ | $L_{B7}$ | III-4255 | $L_{A322}$ | $L_{B26}$ |
| III-1035 | $L_{A332}$ | $L_{B7}$ | III-4180 | $L_{A417}$ | $L_{B25}$ | III-1111 | $L_{A408}$ | $L_{B7}$ | III-4256 | $L_{A323}$ | $L_{B26}$ |

| Compound Number | $L_A$ | $L_B$ | Compound Number | $L_A$ | $L_B$ | Compound Number | $L_A$ | $L_B$ | Compound Number | $L_A$ | $L_B$ |
|---|---|---|---|---|---|---|---|---|---|---|---|
| III-1112 | $L_{A409}$ | $L_{B7}$ | III-4257 | $L_{A324}$ | $L_{B26}$ | III-1188 | $L_{A485}$ | $L_{B7}$ | III-4333 | $L_{A400}$ | $L_{B26}$ |
| III-1113 | $L_{A410}$ | $L_{B7}$ | III-4258 | $L_{A325}$ | $L_{B26}$ | III-1189 | $L_{A486}$ | $L_{B7}$ | III-4334 | $L_{A401}$ | $L_{B26}$ |
| III-1114 | $L_{A411}$ | $L_{B7}$ | III-4259 | $L_{A326}$ | $L_{B26}$ | III-1190 | $L_{A487}$ | $L_{B7}$ | III-4335 | $L_{A402}$ | $L_{B26}$ |
| III-1115 | $L_{A412}$ | $L_{B7}$ | III-4260 | $L_{A327}$ | $L_{B26}$ | III-1191 | $L_{A318}$ | $L_{B8}$ | III-4336 | $L_{A403}$ | $L_{B26}$ |
| III-1116 | $L_{A413}$ | $L_{B7}$ | III-4261 | $L_{A328}$ | $L_{B26}$ | III-1192 | $L_{A319}$ | $L_{B8}$ | III-4337 | $L_{A404}$ | $L_{B26}$ |
| III-1117 | $L_{A414}$ | $L_{B7}$ | III-4262 | $L_{A329}$ | $L_{B26}$ | III-1193 | $L_{A320}$ | $L_{B8}$ | III-4338 | $L_{A405}$ | $L_{B26}$ |
| III-1118 | $L_{A415}$ | $L_{B7}$ | III-4263 | $L_{A330}$ | $L_{B26}$ | III-1194 | $L_{A321}$ | $L_{B8}$ | III-4339 | $L_{A406}$ | $L_{B26}$ |
| III-1119 | $L_{A416}$ | $L_{B7}$ | III-4264 | $L_{A331}$ | $L_{B26}$ | III-1195 | $L_{A322}$ | $L_{B8}$ | III-4340 | $L_{A407}$ | $L_{B26}$ |
| III-1120 | $L_{A417}$ | $L_{B7}$ | III-4265 | $L_{A332}$ | $L_{B26}$ | III-1196 | $L_{A323}$ | $L_{B8}$ | III-4341 | $L_{A408}$ | $L_{B26}$ |
| III-1121 | $L_{A418}$ | $L_{B7}$ | III-4266 | $L_{A333}$ | $L_{B26}$ | III-1197 | $L_{A324}$ | $L_{B8}$ | III-4342 | $L_{A409}$ | $L_{B26}$ |
| III-1122 | $L_{A419}$ | $L_{B7}$ | III-4267 | $L_{A334}$ | $L_{B26}$ | III-1198 | $L_{A325}$ | $L_{B8}$ | III-4343 | $L_{A410}$ | $L_{B26}$ |
| III-1123 | $L_{A420}$ | $L_{B7}$ | III-4268 | $L_{A335}$ | $L_{B26}$ | III-1199 | $L_{A326}$ | $L_{B8}$ | III-4344 | $L_{A411}$ | $L_{B26}$ |
| III-1124 | $L_{A421}$ | $L_{B7}$ | III-4269 | $L_{A336}$ | $L_{B26}$ | III-1200 | $L_{A327}$ | $L_{B8}$ | III-4345 | $L_{A412}$ | $L_{B26}$ |
| III-1125 | $L_{A422}$ | $L_{B7}$ | III-4270 | $L_{A337}$ | $L_{B26}$ | III-1201 | $L_{A328}$ | $L_{B8}$ | III-4346 | $L_{A413}$ | $L_{B26}$ |
| III-1126 | $L_{A423}$ | $L_{B7}$ | III-4271 | $L_{A338}$ | $L_{B26}$ | III-1202 | $L_{A329}$ | $L_{B8}$ | III-4347 | $L_{A414}$ | $L_{B26}$ |
| III-1127 | $L_{A424}$ | $L_{B7}$ | III-4272 | $L_{A339}$ | $L_{B26}$ | III-1203 | $L_{A330}$ | $L_{B8}$ | III-4348 | $L_{A415}$ | $L_{B26}$ |
| III-1128 | $L_{A425}$ | $L_{B7}$ | III-4273 | $L_{A340}$ | $L_{B26}$ | III-1204 | $L_{A331}$ | $L_{B8}$ | III-4349 | $L_{A416}$ | $L_{B26}$ |
| III-1129 | $L_{A426}$ | $L_{B7}$ | III-4274 | $L_{A341}$ | $L_{B26}$ | III-1205 | $L_{A332}$ | $L_{B8}$ | III-4350 | $L_{A417}$ | $L_{B26}$ |
| III-1130 | $L_{A427}$ | $L_{B7}$ | III-4275 | $L_{A342}$ | $L_{B26}$ | III-1206 | $L_{A333}$ | $L_{B8}$ | III-4351 | $L_{A418}$ | $L_{B26}$ |
| III-1131 | $L_{A428}$ | $L_{B7}$ | III-4276 | $L_{A343}$ | $L_{B26}$ | III-1207 | $L_{A334}$ | $L_{B8}$ | III-4352 | $L_{A419}$ | $L_{B26}$ |
| III-1132 | $L_{A429}$ | $L_{B7}$ | III-4277 | $L_{A344}$ | $L_{B26}$ | III-1208 | $L_{A335}$ | $L_{B8}$ | III-4353 | $L_{A420}$ | $L_{B26}$ |
| III-1133 | $L_{A430}$ | $L_{B7}$ | III-4278 | $L_{A345}$ | $L_{B26}$ | III-1209 | $L_{A336}$ | $L_{B8}$ | III-4354 | $L_{A421}$ | $L_{B26}$ |
| III-1134 | $L_{A431}$ | $L_{B7}$ | III-4279 | $L_{A346}$ | $L_{B26}$ | III-1210 | $L_{A337}$ | $L_{B8}$ | III-4355 | $L_{A422}$ | $L_{B26}$ |
| III-1135 | $L_{A432}$ | $L_{B7}$ | III-4280 | $L_{A347}$ | $L_{B26}$ | III-1211 | $L_{A338}$ | $L_{B8}$ | III-4356 | $L_{A423}$ | $L_{B26}$ |
| III-1136 | $L_{A433}$ | $L_{B7}$ | III-4281 | $L_{A348}$ | $L_{B26}$ | III-1212 | $L_{A339}$ | $L_{B8}$ | III-4357 | $L_{A424}$ | $L_{B26}$ |
| III-1137 | $L_{A434}$ | $L_{B7}$ | III-4282 | $L_{A349}$ | $L_{B26}$ | III-1213 | $L_{A340}$ | $L_{B8}$ | III-4358 | $L_{A425}$ | $L_{B26}$ |
| III-1138 | $L_{A435}$ | $L_{B7}$ | III-4283 | $L_{A350}$ | $L_{B26}$ | III-1214 | $L_{A341}$ | $L_{B8}$ | III-4359 | $L_{A426}$ | $L_{B26}$ |
| III-1139 | $L_{A436}$ | $L_{B7}$ | III-4284 | $L_{A351}$ | $L_{B26}$ | III-1215 | $L_{A342}$ | $L_{B8}$ | III-4360 | $L_{A427}$ | $L_{B26}$ |
| III-1140 | $L_{A437}$ | $L_{B7}$ | III-4285 | $L_{A352}$ | $L_{B26}$ | III-1216 | $L_{A343}$ | $L_{B8}$ | III-4361 | $L_{A428}$ | $L_{B26}$ |
| III-1141 | $L_{A438}$ | $L_{B7}$ | III-4286 | $L_{A353}$ | $L_{B26}$ | III-1217 | $L_{A344}$ | $L_{B8}$ | III-4362 | $L_{A429}$ | $L_{B26}$ |
| III-1142 | $L_{A439}$ | $L_{B7}$ | III-4287 | $L_{A354}$ | $L_{B26}$ | III-1218 | $L_{A345}$ | $L_{B8}$ | III-4363 | $L_{A430}$ | $L_{B26}$ |
| III-1143 | $L_{A440}$ | $L_{B7}$ | III-4288 | $L_{A355}$ | $L_{B26}$ | III-1219 | $L_{A346}$ | $L_{B8}$ | III-4364 | $L_{A431}$ | $L_{B26}$ |
| III-1144 | $L_{A441}$ | $L_{B7}$ | III-4289 | $L_{A356}$ | $L_{B26}$ | III-1220 | $L_{A347}$ | $L_{B8}$ | III-4365 | $L_{A432}$ | $L_{B26}$ |
| III-1145 | $L_{A442}$ | $L_{B7}$ | III-4290 | $L_{A357}$ | $L_{B26}$ | III-1221 | $L_{A348}$ | $L_{B8}$ | III-4366 | $L_{A433}$ | $L_{B26}$ |
| III-1146 | $L_{A443}$ | $L_{B7}$ | III-4291 | $L_{A358}$ | $L_{B26}$ | III-1222 | $L_{A349}$ | $L_{B8}$ | III-4367 | $L_{A434}$ | $L_{B26}$ |
| III-1147 | $L_{A444}$ | $L_{B7}$ | III-4292 | $L_{A359}$ | $L_{B26}$ | III-1223 | $L_{A350}$ | $L_{B8}$ | III-4368 | $L_{A435}$ | $L_{B26}$ |
| III-1148 | $L_{A445}$ | $L_{B7}$ | III-4293 | $L_{A360}$ | $L_{B26}$ | III-1224 | $L_{A351}$ | $L_{B8}$ | III-4369 | $L_{A436}$ | $L_{B26}$ |
| III-1149 | $L_{A446}$ | $L_{B7}$ | III-4294 | $L_{A361}$ | $L_{B26}$ | III-1225 | $L_{A352}$ | $L_{B8}$ | III-4370 | $L_{A437}$ | $L_{B26}$ |
| III-1150 | $L_{A447}$ | $L_{B7}$ | III-4295 | $L_{A362}$ | $L_{B26}$ | III-1226 | $L_{A353}$ | $L_{B8}$ | III-4371 | $L_{A438}$ | $L_{B26}$ |
| III-1151 | $L_{A448}$ | $L_{B7}$ | III-4296 | $L_{A363}$ | $L_{B26}$ | III-1227 | $L_{A354}$ | $L_{B8}$ | III-4372 | $L_{A439}$ | $L_{B26}$ |
| III-1152 | $L_{A449}$ | $L_{B7}$ | III-4297 | $L_{A364}$ | $L_{B26}$ | III-1228 | $L_{A355}$ | $L_{B8}$ | III-4373 | $L_{A440}$ | $L_{B26}$ |
| III-1153 | $L_{A450}$ | $L_{B7}$ | III-4298 | $L_{A365}$ | $L_{B26}$ | III-1229 | $L_{A356}$ | $L_{B8}$ | III-4374 | $L_{A441}$ | $L_{B26}$ |
| III-1154 | $L_{A451}$ | $L_{B7}$ | III-4299 | $L_{A366}$ | $L_{B26}$ | III-1230 | $L_{A357}$ | $L_{B8}$ | III-4375 | $L_{A442}$ | $L_{B26}$ |
| III-1155 | $L_{A452}$ | $L_{B7}$ | III-4300 | $L_{A367}$ | $L_{B26}$ | III-1231 | $L_{A358}$ | $L_{B8}$ | III-4376 | $L_{A443}$ | $L_{B26}$ |
| III-1156 | $L_{A453}$ | $L_{B7}$ | III-4301 | $L_{A368}$ | $L_{B26}$ | III-1232 | $L_{A359}$ | $L_{B8}$ | III-4377 | $L_{A444}$ | $L_{B26}$ |
| III-1157 | $L_{A454}$ | $L_{B7}$ | III-4302 | $L_{A369}$ | $L_{B26}$ | III-1233 | $L_{A360}$ | $L_{B8}$ | III-4378 | $L_{A445}$ | $L_{B26}$ |
| III-1158 | $L_{A455}$ | $L_{B7}$ | III-4303 | $L_{A370}$ | $L_{B26}$ | III-1234 | $L_{A361}$ | $L_{B8}$ | III-4379 | $L_{A446}$ | $L_{B26}$ |
| III-1159 | $L_{A456}$ | $L_{B7}$ | III-4304 | $L_{A371}$ | $L_{B26}$ | III-1235 | $L_{A362}$ | $L_{B8}$ | III-4380 | $L_{A447}$ | $L_{B26}$ |
| III-1160 | $L_{A457}$ | $L_{B7}$ | III-4305 | $L_{A372}$ | $L_{B26}$ | III-1236 | $L_{A363}$ | $L_{B8}$ | III-4381 | $L_{A448}$ | $L_{B26}$ |
| III-1161 | $L_{A458}$ | $L_{B7}$ | III-4306 | $L_{A373}$ | $L_{B26}$ | III-1237 | $L_{A364}$ | $L_{B8}$ | III-4382 | $L_{A449}$ | $L_{B26}$ |
| III-1162 | $L_{A459}$ | $L_{B7}$ | III-4307 | $L_{A374}$ | $L_{B26}$ | III-1238 | $L_{A365}$ | $L_{B8}$ | III-4383 | $L_{A450}$ | $L_{B26}$ |
| III-1163 | $L_{A460}$ | $L_{B7}$ | III-4308 | $L_{A375}$ | $L_{B26}$ | III-1239 | $L_{A366}$ | $L_{B8}$ | III-4384 | $L_{A451}$ | $L_{B26}$ |
| III-1164 | $L_{A461}$ | $L_{B7}$ | III-4309 | $L_{A376}$ | $L_{B26}$ | III-1240 | $L_{A367}$ | $L_{B8}$ | III-4385 | $L_{A452}$ | $L_{B26}$ |
| III-1165 | $L_{A462}$ | $L_{B7}$ | III-4310 | $L_{A377}$ | $L_{B26}$ | III-1241 | $L_{A368}$ | $L_{B8}$ | III-4386 | $L_{A453}$ | $L_{B26}$ |
| III-1166 | $L_{A463}$ | $L_{B7}$ | III-4311 | $L_{A378}$ | $L_{B26}$ | III-1242 | $L_{A369}$ | $L_{B8}$ | III-4387 | $L_{A454}$ | $L_{B26}$ |
| III-1167 | $L_{A464}$ | $L_{B7}$ | III-4312 | $L_{A379}$ | $L_{B26}$ | III-1243 | $L_{A370}$ | $L_{B8}$ | III-4388 | $L_{A455}$ | $L_{B26}$ |
| III-1168 | $L_{A465}$ | $L_{B7}$ | III-4313 | $L_{A380}$ | $L_{B26}$ | III-1244 | $L_{A371}$ | $L_{B8}$ | III-4389 | $L_{A456}$ | $L_{B26}$ |
| III-1169 | $L_{A466}$ | $L_{B7}$ | III-4314 | $L_{A381}$ | $L_{B26}$ | III-1245 | $L_{A372}$ | $L_{B8}$ | III-4390 | $L_{A457}$ | $L_{B26}$ |
| III-1170 | $L_{A467}$ | $L_{B7}$ | III-4315 | $L_{A382}$ | $L_{B26}$ | III-1246 | $L_{A373}$ | $L_{B8}$ | III-4391 | $L_{A458}$ | $L_{B26}$ |
| III-1171 | $L_{A468}$ | $L_{B7}$ | III-4316 | $L_{A383}$ | $L_{B26}$ | III-1247 | $L_{A374}$ | $L_{B8}$ | III-4392 | $L_{A459}$ | $L_{B26}$ |
| III-1172 | $L_{A469}$ | $L_{B7}$ | III-4317 | $L_{A384}$ | $L_{B26}$ | III-1248 | $L_{A375}$ | $L_{B8}$ | III-4393 | $L_{A460}$ | $L_{B26}$ |
| III-1173 | $L_{A470}$ | $L_{B7}$ | III-4318 | $L_{A385}$ | $L_{B26}$ | III-1249 | $L_{A376}$ | $L_{B8}$ | III-4394 | $L_{A461}$ | $L_{B26}$ |
| III-1174 | $L_{A471}$ | $L_{B7}$ | III-4319 | $L_{A386}$ | $L_{B26}$ | III-1250 | $L_{A377}$ | $L_{B8}$ | III-4395 | $L_{A462}$ | $L_{B26}$ |
| III-1175 | $L_{A472}$ | $L_{B7}$ | III-4320 | $L_{A387}$ | $L_{B26}$ | III-1251 | $L_{A378}$ | $L_{B8}$ | III-4396 | $L_{A463}$ | $L_{B26}$ |
| III-1176 | $L_{A473}$ | $L_{B7}$ | III-4321 | $L_{A388}$ | $L_{B26}$ | III-1252 | $L_{A379}$ | $L_{B8}$ | III-4397 | $L_{A464}$ | $L_{B26}$ |
| III-1177 | $L_{A474}$ | $L_{B7}$ | III-4322 | $L_{A389}$ | $L_{B26}$ | III-1253 | $L_{A380}$ | $L_{B8}$ | III-4398 | $L_{A465}$ | $L_{B26}$ |
| III-1178 | $L_{A475}$ | $L_{B7}$ | III-4323 | $L_{A390}$ | $L_{B26}$ | III-1254 | $L_{A381}$ | $L_{B8}$ | III-4399 | $L_{A466}$ | $L_{B26}$ |
| III-1179 | $L_{A476}$ | $L_{B7}$ | III-4324 | $L_{A391}$ | $L_{B26}$ | III-1255 | $L_{A382}$ | $L_{B8}$ | III-4400 | $L_{A467}$ | $L_{B26}$ |
| III-1180 | $L_{A477}$ | $L_{B7}$ | III-4325 | $L_{A392}$ | $L_{B26}$ | III-1256 | $L_{A383}$ | $L_{B8}$ | III-4401 | $L_{A468}$ | $L_{B26}$ |
| III-1181 | $L_{A478}$ | $L_{B7}$ | III-4326 | $L_{A393}$ | $L_{B26}$ | III-1257 | $L_{A384}$ | $L_{B8}$ | III-4402 | $L_{A469}$ | $L_{B26}$ |
| III-1182 | $L_{A479}$ | $L_{B7}$ | III-4327 | $L_{A394}$ | $L_{B26}$ | III-1258 | $L_{A385}$ | $L_{B8}$ | III-4403 | $L_{A470}$ | $L_{B26}$ |
| III-1183 | $L_{A480}$ | $L_{B7}$ | III-4328 | $L_{A395}$ | $L_{B26}$ | III-1259 | $L_{A386}$ | $L_{B8}$ | III-4404 | $L_{A471}$ | $L_{B26}$ |
| III-1184 | $L_{A481}$ | $L_{B7}$ | III-4329 | $L_{A396}$ | $L_{B26}$ | III-1260 | $L_{A387}$ | $L_{B8}$ | III-4405 | $L_{A472}$ | $L_{B26}$ |
| III-1185 | $L_{A482}$ | $L_{B7}$ | III-4330 | $L_{A397}$ | $L_{B26}$ | III-1261 | $L_{A388}$ | $L_{B8}$ | III-4406 | $L_{A473}$ | $L_{B26}$ |
| III-1186 | $L_{A483}$ | $L_{B7}$ | III-4331 | $L_{A398}$ | $L_{B26}$ | III-1262 | $L_{A389}$ | $L_{B8}$ | III-4407 | $L_{A474}$ | $L_{B26}$ |
| III-1187 | $L_{A484}$ | $L_{B7}$ | III-4332 | $L_{A399}$ | $L_{B26}$ | III-1263 | $L_{A390}$ | $L_{B8}$ | III-4408 | $L_{A475}$ | $L_{B26}$ |

| Compound Number | $L_A$ | $L_B$ | Compound Number | $L_A$ | $L_B$ | Compound Number | $L_A$ | $L_B$ | Compound Number | $L_A$ | $L_B$ |
|---|---|---|---|---|---|---|---|---|---|---|---|
| III-1264 | $L_{A391}$ | $L_{B8}$ | III-4409 | $L_{A476}$ | $L_{B26}$ | III-1340 | $L_{A467}$ | $L_{B8}$ | III-4485 | $L_{A382}$ | $L_{B27}$ |
| III-1265 | $L_{A392}$ | $L_{B8}$ | III-4410 | $L_{A477}$ | $L_{B26}$ | III-1341 | $L_{A468}$ | $L_{B8}$ | III-4486 | $L_{A383}$ | $L_{B27}$ |
| III-1266 | $L_{A393}$ | $L_{B8}$ | III-4411 | $L_{A478}$ | $L_{B26}$ | III-1342 | $L_{A469}$ | $L_{B8}$ | III-4487 | $L_{A384}$ | $L_{B27}$ |
| III-1267 | $L_{A394}$ | $L_{B8}$ | III-4412 | $L_{A479}$ | $L_{B26}$ | III-1343 | $L_{A470}$ | $L_{B8}$ | III-4488 | $L_{A385}$ | $L_{B27}$ |
| III-1268 | $L_{A395}$ | $L_{B8}$ | III-4413 | $L_{A480}$ | $L_{B26}$ | III-1344 | $L_{A471}$ | $L_{B8}$ | III-4489 | $L_{A386}$ | $L_{B27}$ |
| III-1269 | $L_{A396}$ | $L_{B8}$ | III-4414 | $L_{A481}$ | $L_{B26}$ | III-1345 | $L_{A472}$ | $L_{B8}$ | III-4490 | $L_{A387}$ | $L_{B27}$ |
| III-1270 | $L_{A397}$ | $L_{B8}$ | III-4415 | $L_{A482}$ | $L_{B26}$ | III-1346 | $L_{A473}$ | $L_{B8}$ | III-4491 | $L_{A388}$ | $L_{B27}$ |
| III-1271 | $L_{A398}$ | $L_{B8}$ | III-4416 | $L_{A483}$ | $L_{B26}$ | III-1347 | $L_{A474}$ | $L_{B8}$ | III-4492 | $L_{A389}$ | $L_{B27}$ |
| III-1272 | $L_{A399}$ | $L_{B8}$ | III-4417 | $L_{A484}$ | $L_{B26}$ | III-1348 | $L_{A475}$ | $L_{B8}$ | III-4493 | $L_{A390}$ | $L_{B27}$ |
| III-1273 | $L_{A400}$ | $L_{B8}$ | III-4418 | $L_{A485}$ | $L_{B26}$ | III-1349 | $L_{A476}$ | $L_{B8}$ | III-4494 | $L_{A391}$ | $L_{B27}$ |
| III-1274 | $L_{A401}$ | $L_{B8}$ | III-4419 | $L_{A486}$ | $L_{B26}$ | III-1350 | $L_{A477}$ | $L_{B8}$ | III-4495 | $L_{A392}$ | $L_{B27}$ |
| III-1275 | $L_{A402}$ | $L_{B8}$ | III-4420 | $L_{A487}$ | $L_{B26}$ | III-1351 | $L_{A478}$ | $L_{B8}$ | III-4496 | $L_{A393}$ | $L_{B27}$ |
| III-1276 | $L_{A403}$ | $L_{B8}$ | III-4421 | $L_{A318}$ | $L_{B27}$ | III-1352 | $L_{A479}$ | $L_{B8}$ | III-4497 | $L_{A394}$ | $L_{B27}$ |
| III-1277 | $L_{A404}$ | $L_{B8}$ | III-4422 | $L_{A319}$ | $L_{B27}$ | III-1353 | $L_{A480}$ | $L_{B8}$ | III-4498 | $L_{A395}$ | $L_{B27}$ |
| III-1278 | $L_{A405}$ | $L_{B8}$ | III-4423 | $L_{A320}$ | $L_{B27}$ | III-1354 | $L_{A481}$ | $L_{B8}$ | III-4499 | $L_{A396}$ | $L_{B27}$ |
| III-1279 | $L_{A406}$ | $L_{B8}$ | III-4424 | $L_{A321}$ | $L_{B27}$ | III-1355 | $L_{A482}$ | $L_{B8}$ | III-4500 | $L_{A397}$ | $L_{B27}$ |
| III-1280 | $L_{A407}$ | $L_{B8}$ | III-4425 | $L_{A322}$ | $L_{B27}$ | III-1356 | $L_{A483}$ | $L_{B8}$ | III-4501 | $L_{A398}$ | $L_{B27}$ |
| III-1281 | $L_{A408}$ | $L_{B8}$ | III-4426 | $L_{A323}$ | $L_{B27}$ | III-1357 | $L_{A484}$ | $L_{B8}$ | III-4502 | $L_{A399}$ | $L_{B27}$ |
| III-1282 | $L_{A409}$ | $L_{B8}$ | III-4427 | $L_{A324}$ | $L_{B27}$ | III-1358 | $L_{A485}$ | $L_{B8}$ | III-4503 | $L_{A400}$ | $L_{B27}$ |
| III-1283 | $L_{A410}$ | $L_{B8}$ | III-4428 | $L_{A325}$ | $L_{B27}$ | III-1359 | $L_{A486}$ | $L_{B8}$ | III-4504 | $L_{A401}$ | $L_{B27}$ |
| III-1284 | $L_{A411}$ | $L_{B8}$ | III-4429 | $L_{A326}$ | $L_{B27}$ | III-1360 | $L_{A487}$ | $L_{B8}$ | III-4505 | $L_{A402}$ | $L_{B27}$ |
| III-1285 | $L_{A412}$ | $L_{B8}$ | III-4430 | $L_{A327}$ | $L_{B27}$ | III-1361 | $L_{A318}$ | $L_{B9}$ | III-4506 | $L_{A403}$ | $L_{B27}$ |
| III-1286 | $L_{A413}$ | $L_{B8}$ | III-4431 | $L_{A328}$ | $L_{B27}$ | III-1362 | $L_{A319}$ | $L_{B9}$ | III-4507 | $L_{A404}$ | $L_{B27}$ |
| III-1287 | $L_{A414}$ | $L_{B8}$ | III-4432 | $L_{A329}$ | $L_{B27}$ | III-1363 | $L_{A320}$ | $L_{B9}$ | III-4508 | $L_{A405}$ | $L_{B27}$ |
| III-1288 | $L_{A415}$ | $L_{B8}$ | III-4433 | $L_{A330}$ | $L_{B27}$ | III-1364 | $L_{A321}$ | $L_{B9}$ | III-4509 | $L_{A406}$ | $L_{B27}$ |
| III-1289 | $L_{A416}$ | $L_{B8}$ | III-4434 | $L_{A331}$ | $L_{B27}$ | III-1365 | $L_{A322}$ | $L_{B9}$ | III-4510 | $L_{A407}$ | $L_{B27}$ |
| III-1290 | $L_{A417}$ | $L_{B8}$ | III-4435 | $L_{A332}$ | $L_{B27}$ | III-1366 | $L_{A323}$ | $L_{B9}$ | III-4511 | $L_{A408}$ | $L_{B27}$ |
| III-1291 | $L_{A418}$ | $L_{B8}$ | III-4436 | $L_{A333}$ | $L_{B27}$ | III-1367 | $L_{A324}$ | $L_{B9}$ | III-4512 | $L_{A409}$ | $L_{B27}$ |
| III-1292 | $L_{A419}$ | $L_{B8}$ | III-4437 | $L_{A334}$ | $L_{B27}$ | III-1368 | $L_{A325}$ | $L_{B9}$ | III-4513 | $L_{A410}$ | $L_{B27}$ |
| III-1293 | $L_{A420}$ | $L_{B8}$ | III-4438 | $L_{A335}$ | $L_{B27}$ | III-1369 | $L_{A326}$ | $L_{B9}$ | III-4514 | $L_{A411}$ | $L_{B27}$ |
| III-1294 | $L_{A421}$ | $L_{B8}$ | III-4439 | $L_{A336}$ | $L_{B27}$ | III-1370 | $L_{A327}$ | $L_{B9}$ | III-4515 | $L_{A412}$ | $L_{B27}$ |
| III-1295 | $L_{A422}$ | $L_{B8}$ | III-4440 | $L_{A337}$ | $L_{B27}$ | III-1371 | $L_{A328}$ | $L_{B9}$ | III-4516 | $L_{A413}$ | $L_{B27}$ |
| III-1296 | $L_{A423}$ | $L_{B8}$ | III-4441 | $L_{A338}$ | $L_{B27}$ | III-1372 | $L_{A329}$ | $L_{B9}$ | III-4517 | $L_{A414}$ | $L_{B27}$ |
| III-1297 | $L_{A424}$ | $L_{B8}$ | III-4442 | $L_{A339}$ | $L_{B27}$ | III-1373 | $L_{A330}$ | $L_{B9}$ | III-4518 | $L_{A415}$ | $L_{B27}$ |
| III-1298 | $L_{A425}$ | $L_{B8}$ | III-4443 | $L_{A340}$ | $L_{B27}$ | III-1374 | $L_{A331}$ | $L_{B9}$ | III-4519 | $L_{A416}$ | $L_{B27}$ |
| III-1299 | $L_{A426}$ | $L_{B8}$ | III-4444 | $L_{A341}$ | $L_{B27}$ | III-1375 | $L_{A332}$ | $L_{B9}$ | III-4520 | $L_{A417}$ | $L_{B27}$ |
| III-1300 | $L_{A427}$ | $L_{B8}$ | III-4445 | $L_{A342}$ | $L_{B27}$ | III-1376 | $L_{A333}$ | $L_{B9}$ | III-4521 | $L_{A418}$ | $L_{B27}$ |
| III-1301 | $L_{A428}$ | $L_{B8}$ | III-4446 | $L_{A343}$ | $L_{B27}$ | III-1377 | $L_{A334}$ | $L_{B9}$ | III-4522 | $L_{A419}$ | $L_{B27}$ |
| III-1302 | $L_{A429}$ | $L_{B8}$ | III-4447 | $L_{A344}$ | $L_{B27}$ | III-1378 | $L_{A335}$ | $L_{B9}$ | III-4523 | $L_{A420}$ | $L_{B27}$ |
| III-1303 | $L_{A430}$ | $L_{B8}$ | III-4448 | $L_{A345}$ | $L_{B27}$ | III-1379 | $L_{A336}$ | $L_{B9}$ | III-4524 | $L_{A421}$ | $L_{B27}$ |
| III-1304 | $L_{A431}$ | $L_{B8}$ | III-4449 | $L_{A346}$ | $L_{B27}$ | III-1380 | $L_{A337}$ | $L_{B9}$ | III-4525 | $L_{A422}$ | $L_{B27}$ |
| III-1305 | $L_{A432}$ | $L_{B8}$ | III-4450 | $L_{A347}$ | $L_{B27}$ | III-1381 | $L_{A338}$ | $L_{B9}$ | III-4526 | $L_{A423}$ | $L_{B27}$ |
| III-1306 | $L_{A433}$ | $L_{B8}$ | III-4451 | $L_{A348}$ | $L_{B27}$ | III-1382 | $L_{A339}$ | $L_{B9}$ | III-4527 | $L_{A424}$ | $L_{B27}$ |
| III-1307 | $L_{A434}$ | $L_{B8}$ | III-4452 | $L_{A349}$ | $L_{B27}$ | III-1383 | $L_{A340}$ | $L_{B9}$ | III-4528 | $L_{A425}$ | $L_{B27}$ |
| III-1308 | $L_{A435}$ | $L_{B8}$ | III-4453 | $L_{A350}$ | $L_{B27}$ | III-1384 | $L_{A341}$ | $L_{B9}$ | III-4529 | $L_{A426}$ | $L_{B27}$ |
| III-1309 | $L_{A436}$ | $L_{B8}$ | III-4454 | $L_{A351}$ | $L_{B27}$ | III-1385 | $L_{A342}$ | $L_{B9}$ | III-4530 | $L_{A427}$ | $L_{B27}$ |
| III-1310 | $L_{A437}$ | $L_{B8}$ | III-4455 | $L_{A352}$ | $L_{B27}$ | III-1386 | $L_{A343}$ | $L_{B9}$ | III-4531 | $L_{A428}$ | $L_{B27}$ |
| III-1311 | $L_{A438}$ | $L_{B8}$ | III-4456 | $L_{A353}$ | $L_{B27}$ | III-1387 | $L_{A344}$ | $L_{B9}$ | III-4532 | $L_{A429}$ | $L_{B27}$ |
| III-1312 | $L_{A439}$ | $L_{B8}$ | III-4457 | $L_{A354}$ | $L_{B27}$ | III-1388 | $L_{A345}$ | $L_{B9}$ | III-4533 | $L_{A430}$ | $L_{B27}$ |
| III-1313 | $L_{A440}$ | $L_{B8}$ | III-4458 | $L_{A355}$ | $L_{B27}$ | III-1389 | $L_{A346}$ | $L_{B9}$ | III-4534 | $L_{A431}$ | $L_{B27}$ |
| III-1314 | $L_{A441}$ | $L_{B8}$ | III-4459 | $L_{A356}$ | $L_{B27}$ | III-1390 | $L_{A347}$ | $L_{B9}$ | III-4535 | $L_{A432}$ | $L_{B27}$ |
| III-1315 | $L_{A442}$ | $L_{B8}$ | III-4460 | $L_{A357}$ | $L_{B27}$ | III-1391 | $L_{A348}$ | $L_{B9}$ | III-4536 | $L_{A433}$ | $L_{B27}$ |
| III-1316 | $L_{A443}$ | $L_{B8}$ | III-4461 | $L_{A358}$ | $L_{B27}$ | III-1392 | $L_{A349}$ | $L_{B9}$ | III-4537 | $L_{A434}$ | $L_{B27}$ |
| III-1317 | $L_{A444}$ | $L_{B8}$ | III-4462 | $L_{A359}$ | $L_{B27}$ | III-1393 | $L_{A350}$ | $L_{B9}$ | III-4538 | $L_{A435}$ | $L_{B27}$ |
| III-1318 | $L_{A445}$ | $L_{B8}$ | III-4463 | $L_{A360}$ | $L_{B27}$ | III-1394 | $L_{A351}$ | $L_{B9}$ | III-4539 | $L_{A436}$ | $L_{B27}$ |
| III-1319 | $L_{A446}$ | $L_{B8}$ | III-4464 | $L_{A361}$ | $L_{B27}$ | III-1395 | $L_{A352}$ | $L_{B9}$ | III-4540 | $L_{A437}$ | $L_{B27}$ |
| III-1320 | $L_{A447}$ | $L_{B8}$ | III-4465 | $L_{A362}$ | $L_{B27}$ | III-1396 | $L_{A353}$ | $L_{B9}$ | III-4541 | $L_{A438}$ | $L_{B27}$ |
| III-1321 | $L_{A448}$ | $L_{B8}$ | III-4466 | $L_{A363}$ | $L_{B27}$ | III-1397 | $L_{A354}$ | $L_{B9}$ | III-4542 | $L_{A439}$ | $L_{B27}$ |
| III-1322 | $L_{A449}$ | $L_{B8}$ | III-4467 | $L_{A364}$ | $L_{B27}$ | III-1398 | $L_{A355}$ | $L_{B9}$ | III-4543 | $L_{A440}$ | $L_{B27}$ |
| III-1323 | $L_{A450}$ | $L_{B8}$ | III-4468 | $L_{A365}$ | $L_{B27}$ | III-1399 | $L_{A356}$ | $L_{B9}$ | III-4544 | $L_{A441}$ | $L_{B27}$ |
| III-1324 | $L_{A451}$ | $L_{B8}$ | III-4469 | $L_{A366}$ | $L_{B27}$ | III-1400 | $L_{A357}$ | $L_{B9}$ | III-4545 | $L_{A442}$ | $L_{B27}$ |
| III-1325 | $L_{A452}$ | $L_{B8}$ | III-4470 | $L_{A367}$ | $L_{B27}$ | III-1401 | $L_{A358}$ | $L_{B9}$ | III-4546 | $L_{A443}$ | $L_{B27}$ |
| III-1326 | $L_{A453}$ | $L_{B8}$ | III-4471 | $L_{A368}$ | $L_{B27}$ | III-1402 | $L_{A359}$ | $L_{B9}$ | III-4547 | $L_{A444}$ | $L_{B27}$ |
| III-1327 | $L_{A454}$ | $L_{B8}$ | III-4472 | $L_{A369}$ | $L_{B27}$ | III-1403 | $L_{A360}$ | $L_{B9}$ | III-4548 | $L_{A445}$ | $L_{B27}$ |
| III-1328 | $L_{A455}$ | $L_{B8}$ | III-4473 | $L_{A370}$ | $L_{B27}$ | III-1404 | $L_{A361}$ | $L_{B9}$ | III-4549 | $L_{A446}$ | $L_{B27}$ |
| III-1329 | $L_{A456}$ | $L_{B8}$ | III-4474 | $L_{A371}$ | $L_{B27}$ | III-1405 | $L_{A362}$ | $L_{B9}$ | III-4550 | $L_{A447}$ | $L_{B27}$ |
| III-1330 | $L_{A457}$ | $L_{B8}$ | III-4475 | $L_{A372}$ | $L_{B27}$ | III-1406 | $L_{A363}$ | $L_{B9}$ | III-4551 | $L_{A448}$ | $L_{B27}$ |
| III-1331 | $L_{A458}$ | $L_{B8}$ | III-4476 | $L_{A373}$ | $L_{B27}$ | III-1407 | $L_{A364}$ | $L_{B9}$ | III-4552 | $L_{A449}$ | $L_{B27}$ |
| III-1332 | $L_{A459}$ | $L_{B8}$ | III-4477 | $L_{A374}$ | $L_{B27}$ | III-1408 | $L_{A365}$ | $L_{B9}$ | III-4553 | $L_{A450}$ | $L_{B27}$ |
| III-1333 | $L_{A460}$ | $L_{B8}$ | III-4478 | $L_{A375}$ | $L_{B27}$ | III-1409 | $L_{A366}$ | $L_{B9}$ | III-4554 | $L_{A451}$ | $L_{B27}$ |
| III-1334 | $L_{A461}$ | $L_{B8}$ | III-4479 | $L_{A376}$ | $L_{B27}$ | III-1410 | $L_{A367}$ | $L_{B9}$ | III-4555 | $L_{A452}$ | $L_{B27}$ |
| III-1335 | $L_{A462}$ | $L_{B8}$ | III-4480 | $L_{A377}$ | $L_{B27}$ | III-1411 | $L_{A368}$ | $L_{B9}$ | III-4556 | $L_{A453}$ | $L_{B27}$ |
| III-1336 | $L_{A463}$ | $L_{B8}$ | III-4481 | $L_{A378}$ | $L_{B27}$ | III-1412 | $L_{A369}$ | $L_{B9}$ | III-4557 | $L_{A454}$ | $L_{B27}$ |
| III-1337 | $L_{A464}$ | $L_{B8}$ | III-4482 | $L_{A379}$ | $L_{B27}$ | III-1413 | $L_{A370}$ | $L_{B9}$ | III-4558 | $L_{A455}$ | $L_{B27}$ |
| III-1338 | $L_{A465}$ | $L_{B8}$ | III-4483 | $L_{A380}$ | $L_{B27}$ | III-1414 | $L_{A371}$ | $L_{B9}$ | III-4559 | $L_{A456}$ | $L_{B27}$ |
| III-1339 | $L_{A466}$ | $L_{B8}$ | III-4484 | $L_{A381}$ | $L_{B27}$ | III-1415 | $L_{A372}$ | $L_{B9}$ | III-4560 | $L_{A457}$ | $L_{B27}$ |

-continued

| Compound Number | $L_A$ | $L_B$ | Compound Number | $L_A$ | $L_B$ |
|---|---|---|---|---|---|
| III-1416 | $L_{A373}$ | $L_{B9}$ | III-4561 | $L_{A458}$ | $L_{B27}$ |
| III-1417 | $L_{A374}$ | $L_{B9}$ | III-4562 | $L_{A459}$ | $L_{B27}$ |
| III-1418 | $L_{A375}$ | $L_{B9}$ | III-4563 | $L_{A460}$ | $L_{B27}$ |
| III-1419 | $L_{A376}$ | $L_{B9}$ | III-4564 | $L_{A461}$ | $L_{B27}$ |
| III-1420 | $L_{A377}$ | $L_{B9}$ | III-4565 | $L_{A462}$ | $L_{B27}$ |
| III-1421 | $L_{A378}$ | $L_{B9}$ | III-4566 | $L_{A463}$ | $L_{B27}$ |
| III-1422 | $L_{A379}$ | $L_{B9}$ | III-4567 | $L_{A464}$ | $L_{B27}$ |
| III-1423 | $L_{A380}$ | $L_{B9}$ | III-4568 | $L_{A465}$ | $L_{B27}$ |
| III-1424 | $L_{A381}$ | $L_{B9}$ | III-4569 | $L_{A466}$ | $L_{B27}$ |
| III-1425 | $L_{A382}$ | $L_{B9}$ | III-4570 | $L_{A467}$ | $L_{B27}$ |
| III-1426 | $L_{A383}$ | $L_{B9}$ | III-4571 | $L_{A468}$ | $L_{B27}$ |
| III-1427 | $L_{A384}$ | $L_{B9}$ | III-4572 | $L_{A469}$ | $L_{B27}$ |
| III-1428 | $L_{A385}$ | $L_{B9}$ | III-4573 | $L_{A470}$ | $L_{B27}$ |
| III-1429 | $L_{A386}$ | $L_{B9}$ | III-4574 | $L_{A471}$ | $L_{B27}$ |
| III-1430 | $L_{A387}$ | $L_{B9}$ | III-4575 | $L_{A472}$ | $L_{B27}$ |
| III-1431 | $L_{A388}$ | $L_{B9}$ | III-4576 | $L_{A473}$ | $L_{B27}$ |
| III-1432 | $L_{A389}$ | $L_{B9}$ | III-4577 | $L_{A474}$ | $L_{B27}$ |
| III-1433 | $L_{A390}$ | $L_{B9}$ | III-4578 | $L_{A475}$ | $L_{B27}$ |
| III-1434 | $L_{A391}$ | $L_{B9}$ | III-4579 | $L_{A476}$ | $L_{B27}$ |
| III-1435 | $L_{A392}$ | $L_{B9}$ | III-4580 | $L_{A477}$ | $L_{B27}$ |
| III-1436 | $L_{A393}$ | $L_{B9}$ | III-4581 | $L_{A478}$ | $L_{B27}$ |
| III-1437 | $L_{A394}$ | $L_{B9}$ | III-4582 | $L_{A479}$ | $L_{B27}$ |
| III-1438 | $L_{A395}$ | $L_{B9}$ | III-4583 | $L_{A480}$ | $L_{B27}$ |
| III-1439 | $L_{A396}$ | $L_{B9}$ | III-4584 | $L_{A481}$ | $L_{B27}$ |
| III-1440 | $L_{A397}$ | $L_{B9}$ | III-4585 | $L_{A482}$ | $L_{B27}$ |
| III-1441 | $L_{A398}$ | $L_{B9}$ | III-4586 | $L_{A483}$ | $L_{B27}$ |
| III-1442 | $L_{A399}$ | $L_{B9}$ | III-4587 | $L_{A484}$ | $L_{B27}$ |
| III-1443 | $L_{A400}$ | $L_{B9}$ | III-4588 | $L_{A485}$ | $L_{B27}$ |
| III-1444 | $L_{A401}$ | $L_{B9}$ | III-4589 | $L_{A486}$ | $L_{B27}$ |
| III-1445 | $L_{A402}$ | $L_{B9}$ | III-4590 | $L_{A487}$ | $L_{B27}$ |
| III-1446 | $L_{A403}$ | $L_{B9}$ | III-4591 | $L_{A318}$ | $L_{B28}$ |
| III-1447 | $L_{A404}$ | $L_{B9}$ | III-4592 | $L_{A319}$ | $L_{B28}$ |
| III-1448 | $L_{A405}$ | $L_{B9}$ | III-4593 | $L_{A320}$ | $L_{B28}$ |
| III-1449 | $L_{A406}$ | $L_{B9}$ | III-4594 | $L_{A321}$ | $L_{B28}$ |
| III-1450 | $L_{A407}$ | $L_{B9}$ | III-4595 | $L_{A322}$ | $L_{B28}$ |
| III-1451 | $L_{A408}$ | $L_{B9}$ | III-4596 | $L_{A323}$ | $L_{B28}$ |
| III-1452 | $L_{A409}$ | $L_{B9}$ | III-4597 | $L_{A324}$ | $L_{B28}$ |
| III-1453 | $L_{A410}$ | $L_{B9}$ | III-4598 | $L_{A325}$ | $L_{B28}$ |
| III-1454 | $L_{A411}$ | $L_{B9}$ | III-4599 | $L_{A326}$ | $L_{B28}$ |
| III-1455 | $L_{A412}$ | $L_{B9}$ | III-4600 | $L_{A327}$ | $L_{B28}$ |
| III-1456 | $L_{A413}$ | $L_{B9}$ | III-4601 | $L_{A328}$ | $L_{B28}$ |
| III-1457 | $L_{A414}$ | $L_{B9}$ | III-4602 | $L_{A329}$ | $L_{B28}$ |
| III-1458 | $L_{A415}$ | $L_{B9}$ | III-4603 | $L_{A330}$ | $L_{B28}$ |
| III-1459 | $L_{A416}$ | $L_{B9}$ | III-4604 | $L_{A331}$ | $L_{B28}$ |
| III-1460 | $L_{A417}$ | $L_{B9}$ | III-4605 | $L_{A332}$ | $L_{B28}$ |
| III-1461 | $L_{A418}$ | $L_{B9}$ | III-4606 | $L_{A333}$ | $L_{B28}$ |
| III-1462 | $L_{A419}$ | $L_{B9}$ | III-4607 | $L_{A334}$ | $L_{B28}$ |
| III-1463 | $L_{A420}$ | $L_{B9}$ | III-4608 | $L_{A335}$ | $L_{B28}$ |
| III-1464 | $L_{A421}$ | $L_{B9}$ | III-4609 | $L_{A336}$ | $L_{B28}$ |
| III-1465 | $L_{A422}$ | $L_{B9}$ | III-4610 | $L_{A337}$ | $L_{B28}$ |
| III-1466 | $L_{A423}$ | $L_{B9}$ | III-4611 | $L_{A338}$ | $L_{B28}$ |
| III-1467 | $L_{A424}$ | $L_{B9}$ | III-4612 | $L_{A339}$ | $L_{B28}$ |
| III-1468 | $L_{A425}$ | $L_{B9}$ | III-4613 | $L_{A340}$ | $L_{B28}$ |
| III-1469 | $L_{A426}$ | $L_{B9}$ | III-4614 | $L_{A341}$ | $L_{B28}$ |
| III-1470 | $L_{A427}$ | $L_{B9}$ | III-4615 | $L_{A342}$ | $L_{B28}$ |
| III-1471 | $L_{A428}$ | $L_{B9}$ | III-4616 | $L_{A343}$ | $L_{B28}$ |
| III-1472 | $L_{A429}$ | $L_{B9}$ | III-4617 | $L_{A344}$ | $L_{B28}$ |
| III-1473 | $L_{A430}$ | $L_{B9}$ | III-4618 | $L_{A345}$ | $L_{B28}$ |
| III-1474 | $L_{A431}$ | $L_{B9}$ | III-4619 | $L_{A346}$ | $L_{B28}$ |
| III-1475 | $L_{A432}$ | $L_{B9}$ | III-4620 | $L_{A347}$ | $L_{B28}$ |
| III-1476 | $L_{A433}$ | $L_{B9}$ | III-4621 | $L_{A348}$ | $L_{B28}$ |
| III-1477 | $L_{A434}$ | $L_{B9}$ | III-4622 | $L_{A349}$ | $L_{B28}$ |
| III-1478 | $L_{A435}$ | $L_{B9}$ | III-4623 | $L_{A350}$ | $L_{B28}$ |
| III-1479 | $L_{A436}$ | $L_{B9}$ | III-4624 | $L_{A351}$ | $L_{B28}$ |
| III-1480 | $L_{A437}$ | $L_{B9}$ | III-4625 | $L_{A352}$ | $L_{B28}$ |
| III-1481 | $L_{A438}$ | $L_{B9}$ | III-4626 | $L_{A353}$ | $L_{B28}$ |
| III-1482 | $L_{A439}$ | $L_{B9}$ | III-4627 | $L_{A354}$ | $L_{B28}$ |
| III-1483 | $L_{A440}$ | $L_{B9}$ | III-4628 | $L_{A355}$ | $L_{B28}$ |
| III-1484 | $L_{A441}$ | $L_{B9}$ | III-4629 | $L_{A356}$ | $L_{B28}$ |
| III-1485 | $L_{A442}$ | $L_{B9}$ | III-4630 | $L_{A357}$ | $L_{B28}$ |
| III-1486 | $L_{A443}$ | $L_{B9}$ | III-4631 | $L_{A358}$ | $L_{B28}$ |
| III-1487 | $L_{A444}$ | $L_{B9}$ | III-4632 | $L_{A359}$ | $L_{B28}$ |
| III-1488 | $L_{A445}$ | $L_{B9}$ | III-4633 | $L_{A360}$ | $L_{B28}$ |
| III-1489 | $L_{A446}$ | $L_{B9}$ | III-4634 | $L_{A361}$ | $L_{B28}$ |
| III-1490 | $L_{A447}$ | $L_{B9}$ | III-4635 | $L_{A362}$ | $L_{B28}$ |
| III-1491 | $L_{A448}$ | $L_{B9}$ | III-4636 | $L_{A363}$ | $L_{B28}$ |
| III-1492 | $L_{A449}$ | $L_{B9}$ | III-4637 | $L_{A364}$ | $L_{B28}$ |
| III-1493 | $L_{A450}$ | $L_{B9}$ | III-4638 | $L_{A365}$ | $L_{B28}$ |
| III-1494 | $L_{A451}$ | $L_{B9}$ | III-4639 | $L_{A366}$ | $L_{B28}$ |
| III-1495 | $L_{A452}$ | $L_{B9}$ | III-4640 | $L_{A367}$ | $L_{B28}$ |
| III-1496 | $L_{A453}$ | $L_{B9}$ | III-4641 | $L_{A368}$ | $L_{B28}$ |
| III-1497 | $L_{A454}$ | $L_{B9}$ | III-4642 | $L_{A369}$ | $L_{B28}$ |
| III-1498 | $L_{A455}$ | $L_{B9}$ | III-4643 | $L_{A370}$ | $L_{B28}$ |
| III-1499 | $L_{A456}$ | $L_{B9}$ | III-4644 | $L_{A371}$ | $L_{B28}$ |
| III-1500 | $L_{A457}$ | $L_{B9}$ | III-4645 | $L_{A372}$ | $L_{B28}$ |
| III-1501 | $L_{A458}$ | $L_{B9}$ | III-4646 | $L_{A373}$ | $L_{B28}$ |
| III-1502 | $L_{A459}$ | $L_{B9}$ | III-4647 | $L_{A374}$ | $L_{B28}$ |
| III-1503 | $L_{A460}$ | $L_{B9}$ | III-4648 | $L_{A375}$ | $L_{B28}$ |
| III-1504 | $L_{A461}$ | $L_{B9}$ | III-4649 | $L_{A376}$ | $L_{B28}$ |
| III-1505 | $L_{A462}$ | $L_{B9}$ | III-4650 | $L_{A377}$ | $L_{B28}$ |
| III-1506 | $L_{A463}$ | $L_{B9}$ | III-4651 | $L_{A378}$ | $L_{B28}$ |
| III-1507 | $L_{A464}$ | $L_{B9}$ | III-4652 | $L_{A379}$ | $L_{B28}$ |
| III-1508 | $L_{A465}$ | $L_{B9}$ | III-4653 | $L_{A380}$ | $L_{B28}$ |
| III-1509 | $L_{A466}$ | $L_{B9}$ | III-4654 | $L_{A381}$ | $L_{B28}$ |
| III-1510 | $L_{A467}$ | $L_{B9}$ | III-4655 | $L_{A382}$ | $L_{B28}$ |
| III-1511 | $L_{A468}$ | $L_{B9}$ | III-4656 | $L_{A383}$ | $L_{B28}$ |
| III-1512 | $L_{A469}$ | $L_{B9}$ | III-4657 | $L_{A384}$ | $L_{B28}$ |
| III-1513 | $L_{A470}$ | $L_{B9}$ | III-4658 | $L_{A385}$ | $L_{B28}$ |
| III-1514 | $L_{A471}$ | $L_{B9}$ | III-4659 | $L_{A386}$ | $L_{B28}$ |
| III-1515 | $L_{A472}$ | $L_{B9}$ | III-4660 | $L_{A387}$ | $L_{B28}$ |
| III-1516 | $L_{A473}$ | $L_{B9}$ | III-4661 | $L_{A388}$ | $L_{B28}$ |
| III-1517 | $L_{A474}$ | $L_{B9}$ | III-4662 | $L_{A389}$ | $L_{B28}$ |
| III-1518 | $L_{A475}$ | $L_{B9}$ | III-4663 | $L_{A390}$ | $L_{B28}$ |
| III-1519 | $L_{A476}$ | $L_{B9}$ | III-4664 | $L_{A391}$ | $L_{B28}$ |
| III-1520 | $L_{A477}$ | $L_{B9}$ | III-4665 | $L_{A392}$ | $L_{B28}$ |
| III-1521 | $L_{A478}$ | $L_{B9}$ | III-4666 | $L_{A393}$ | $L_{B28}$ |
| III-1522 | $L_{A479}$ | $L_{B9}$ | III-4667 | $L_{A394}$ | $L_{B28}$ |
| III-1523 | $L_{A480}$ | $L_{B9}$ | III-4668 | $L_{A395}$ | $L_{B28}$ |
| III-1524 | $L_{A481}$ | $L_{B9}$ | III-4669 | $L_{A396}$ | $L_{B28}$ |
| III-1525 | $L_{A482}$ | $L_{B9}$ | III-4670 | $L_{A397}$ | $L_{B28}$ |
| III-1526 | $L_{A483}$ | $L_{B9}$ | III-4671 | $L_{A398}$ | $L_{B28}$ |
| III-1527 | $L_{A484}$ | $L_{B9}$ | III-4672 | $L_{A399}$ | $L_{B28}$ |
| III-1528 | $L_{A485}$ | $L_{B9}$ | III-4673 | $L_{A400}$ | $L_{B28}$ |
| III-1529 | $L_{A486}$ | $L_{B9}$ | III-4674 | $L_{A401}$ | $L_{B28}$ |
| III-1530 | $L_{A487}$ | $L_{B9}$ | III-4675 | $L_{A402}$ | $L_{B28}$ |
| III-1531 | $L_{A318}$ | $L_{B10}$ | III-4676 | $L_{A403}$ | $L_{B28}$ |
| III-1532 | $L_{A319}$ | $L_{B10}$ | III-4677 | $L_{A404}$ | $L_{B28}$ |
| III-1533 | $L_{A320}$ | $L_{B10}$ | III-4678 | $L_{A405}$ | $L_{B28}$ |
| III-1534 | $L_{A321}$ | $L_{B10}$ | III-4679 | $L_{A406}$ | $L_{B28}$ |
| III-1535 | $L_{A322}$ | $L_{B10}$ | III-4680 | $L_{A407}$ | $L_{B28}$ |
| III-1536 | $L_{A323}$ | $L_{B10}$ | III-4681 | $L_{A408}$ | $L_{B28}$ |
| III-1537 | $L_{A324}$ | $L_{B10}$ | III-4682 | $L_{A409}$ | $L_{B28}$ |
| III-1538 | $L_{A325}$ | $L_{B10}$ | III-4683 | $L_{A410}$ | $L_{B28}$ |
| III-1539 | $L_{A326}$ | $L_{B10}$ | III-4684 | $L_{A411}$ | $L_{B28}$ |
| III-1540 | $L_{A327}$ | $L_{B10}$ | III-4685 | $L_{A412}$ | $L_{B28}$ |
| III-1541 | $L_{A328}$ | $L_{B10}$ | III-4686 | $L_{A413}$ | $L_{B28}$ |
| III-1542 | $L_{A329}$ | $L_{B10}$ | III-4687 | $L_{A414}$ | $L_{B28}$ |
| III-1543 | $L_{A330}$ | $L_{B10}$ | III-4688 | $L_{A415}$ | $L_{B28}$ |
| III-1544 | $L_{A331}$ | $L_{B10}$ | III-4689 | $L_{A416}$ | $L_{B28}$ |
| III-1545 | $L_{A332}$ | $L_{B10}$ | III-4690 | $L_{A417}$ | $L_{B28}$ |
| III-1546 | $L_{A333}$ | $L_{B10}$ | III-4691 | $L_{A418}$ | $L_{B28}$ |
| III-1547 | $L_{A334}$ | $L_{B10}$ | III-4692 | $L_{A419}$ | $L_{B28}$ |
| III-1548 | $L_{A335}$ | $L_{B10}$ | III-4693 | $L_{A420}$ | $L_{B28}$ |
| III-1549 | $L_{A336}$ | $L_{B10}$ | III-4694 | $L_{A421}$ | $L_{B28}$ |
| III-1550 | $L_{A337}$ | $L_{B10}$ | III-4695 | $L_{A422}$ | $L_{B28}$ |
| III-1551 | $L_{A338}$ | $L_{B10}$ | III-4696 | $L_{A423}$ | $L_{B28}$ |
| III-1552 | $L_{A339}$ | $L_{B10}$ | III-4697 | $L_{A424}$ | $L_{B28}$ |
| III-1553 | $L_{A340}$ | $L_{B10}$ | III-4698 | $L_{A425}$ | $L_{B28}$ |
| III-1554 | $L_{A341}$ | $L_{B10}$ | III-4699 | $L_{A426}$ | $L_{B28}$ |
| III-1555 | $L_{A342}$ | $L_{B10}$ | III-4700 | $L_{A427}$ | $L_{B28}$ |
| III-1556 | $L_{A343}$ | $L_{B10}$ | III-4701 | $L_{A428}$ | $L_{B28}$ |
| III-1557 | $L_{A344}$ | $L_{B10}$ | III-4702 | $L_{A429}$ | $L_{B28}$ |
| III-1558 | $L_{A345}$ | $L_{B10}$ | III-4703 | $L_{A430}$ | $L_{B28}$ |
| III-1559 | $L_{A346}$ | $L_{B10}$ | III-4704 | $L_{A431}$ | $L_{B28}$ |
| III-1560 | $L_{A347}$ | $L_{B10}$ | III-4705 | $L_{A432}$ | $L_{B28}$ |
| III-1561 | $L_{A348}$ | $L_{B10}$ | III-4706 | $L_{A433}$ | $L_{B28}$ |
| III-1562 | $L_{A349}$ | $L_{B10}$ | III-4707 | $L_{A434}$ | $L_{B28}$ |
| III-1563 | $L_{A350}$ | $L_{B10}$ | III-4708 | $L_{A435}$ | $L_{B28}$ |
| III-1564 | $L_{A351}$ | $L_{B10}$ | III-4709 | $L_{A436}$ | $L_{B28}$ |
| III-1565 | $L_{A352}$ | $L_{B10}$ | III-4710 | $L_{A437}$ | $L_{B28}$ |
| III-1566 | $L_{A353}$ | $L_{B10}$ | III-4711 | $L_{A438}$ | $L_{B28}$ |
| III-1567 | $L_{A354}$ | $L_{B10}$ | III-4712 | $L_{A439}$ | $L_{B28}$ |

-continued

| Compound Number | $L_A$ | $L_B$ | Compound Number | $L_A$ | $L_B$ | Compound Number | $L_A$ | $L_B$ | Compound Number | $L_A$ | $L_B$ |
|---|---|---|---|---|---|---|---|---|---|---|---|
| III-1568 | $L_{A355}$ | $L_{B10}$ | III-4713 | $L_{A440}$ | $L_{B28}$ | III-1644 | $L_{A431}$ | $L_{B10}$ | III-4789 | $L_{A346}$ | $L_{B29}$ |
| III-1569 | $L_{A356}$ | $L_{B10}$ | III-4714 | $L_{A441}$ | $L_{B28}$ | III-1645 | $L_{A432}$ | $L_{B10}$ | III-4790 | $L_{A347}$ | $L_{B29}$ |
| III-1570 | $L_{A357}$ | $L_{B10}$ | III-4715 | $L_{A442}$ | $L_{B28}$ | III-1646 | $L_{A433}$ | $L_{B10}$ | III-4791 | $L_{A348}$ | $L_{B29}$ |
| III-1571 | $L_{A358}$ | $L_{B10}$ | III-4716 | $L_{A443}$ | $L_{B28}$ | III-1647 | $L_{A434}$ | $L_{B10}$ | III-4792 | $L_{A349}$ | $L_{B29}$ |
| III-1572 | $L_{A359}$ | $L_{B10}$ | III-4717 | $L_{A444}$ | $L_{B28}$ | III-1648 | $L_{A435}$ | $L_{B10}$ | III-4793 | $L_{A350}$ | $L_{B29}$ |
| III-1573 | $L_{A360}$ | $L_{B10}$ | III-4718 | $L_{A445}$ | $L_{B28}$ | III-1649 | $L_{A436}$ | $L_{B10}$ | III-4794 | $L_{A351}$ | $L_{B29}$ |
| III-1574 | $L_{A361}$ | $L_{B10}$ | III-4719 | $L_{A446}$ | $L_{B28}$ | III-1650 | $L_{A437}$ | $L_{B10}$ | III-4795 | $L_{A352}$ | $L_{B29}$ |
| III-1575 | $L_{A362}$ | $L_{B10}$ | III-4720 | $L_{A447}$ | $L_{B28}$ | III-1651 | $L_{A438}$ | $L_{B10}$ | III-4796 | $L_{A353}$ | $L_{B29}$ |
| III-1576 | $L_{A363}$ | $L_{B10}$ | III-4721 | $L_{A448}$ | $L_{B28}$ | III-1652 | $L_{A439}$ | $L_{B10}$ | III-4797 | $L_{A354}$ | $L_{B29}$ |
| III-1577 | $L_{A364}$ | $L_{B10}$ | III-4722 | $L_{A449}$ | $L_{B28}$ | III-1653 | $L_{A440}$ | $L_{B10}$ | III-4798 | $L_{A355}$ | $L_{B29}$ |
| III-1578 | $L_{A365}$ | $L_{B10}$ | III-4723 | $L_{A450}$ | $L_{B28}$ | III-1654 | $L_{A441}$ | $L_{B10}$ | III-4799 | $L_{A356}$ | $L_{B29}$ |
| III-1579 | $L_{A366}$ | $L_{B10}$ | III-4724 | $L_{A451}$ | $L_{B28}$ | III-1655 | $L_{A442}$ | $L_{B10}$ | III-4800 | $L_{A357}$ | $L_{B29}$ |
| III-1580 | $L_{A367}$ | $L_{B10}$ | III-4725 | $L_{A452}$ | $L_{B28}$ | III-1656 | $L_{A443}$ | $L_{B10}$ | III-4801 | $L_{A358}$ | $L_{B29}$ |
| III-1581 | $L_{A368}$ | $L_{B10}$ | III-4726 | $L_{A453}$ | $L_{B28}$ | III-1657 | $L_{A444}$ | $L_{B10}$ | III-4802 | $L_{A359}$ | $L_{B29}$ |
| III-1582 | $L_{A369}$ | $L_{B10}$ | III-4727 | $L_{A454}$ | $L_{B28}$ | III-1658 | $L_{A445}$ | $L_{B10}$ | III-4803 | $L_{A360}$ | $L_{B29}$ |
| III-1583 | $L_{A370}$ | $L_{B10}$ | III-4728 | $L_{A455}$ | $L_{B28}$ | III-1659 | $L_{A446}$ | $L_{B10}$ | III-4804 | $L_{A361}$ | $L_{B29}$ |
| III-1584 | $L_{A371}$ | $L_{B10}$ | III-4729 | $L_{A456}$ | $L_{B28}$ | III-1660 | $L_{A447}$ | $L_{B10}$ | III-4805 | $L_{A362}$ | $L_{B29}$ |
| III-1585 | $L_{A372}$ | $L_{B10}$ | III-4730 | $L_{A457}$ | $L_{B28}$ | III-1661 | $L_{A448}$ | $L_{B10}$ | III-4806 | $L_{A363}$ | $L_{B29}$ |
| III-1586 | $L_{A373}$ | $L_{B10}$ | III-4731 | $L_{A458}$ | $L_{B28}$ | III-1662 | $L_{A449}$ | $L_{B10}$ | III-4807 | $L_{A364}$ | $L_{B29}$ |
| III-1587 | $L_{A374}$ | $L_{B10}$ | III-4732 | $L_{A459}$ | $L_{B28}$ | III-1663 | $L_{A450}$ | $L_{B10}$ | III-4808 | $L_{A365}$ | $L_{B29}$ |
| III-1588 | $L_{A375}$ | $L_{B10}$ | III-4733 | $L_{A460}$ | $L_{B28}$ | III-1664 | $L_{A451}$ | $L_{B10}$ | III-4809 | $L_{A366}$ | $L_{B29}$ |
| III-1589 | $L_{A376}$ | $L_{B10}$ | III-4734 | $L_{A461}$ | $L_{B28}$ | III-1665 | $L_{A452}$ | $L_{B10}$ | III-4810 | $L_{A367}$ | $L_{B29}$ |
| III-1590 | $L_{A377}$ | $L_{B10}$ | III-4735 | $L_{A462}$ | $L_{B28}$ | III-1666 | $L_{A453}$ | $L_{B10}$ | III-4811 | $L_{A368}$ | $L_{B29}$ |
| III-1591 | $L_{A378}$ | $L_{B10}$ | III-4736 | $L_{A463}$ | $L_{B28}$ | III-1667 | $L_{A454}$ | $L_{B10}$ | III-4812 | $L_{A369}$ | $L_{B29}$ |
| III-1592 | $L_{A379}$ | $L_{B10}$ | III-4737 | $L_{A464}$ | $L_{B28}$ | III-1668 | $L_{A455}$ | $L_{B10}$ | III-4813 | $L_{A370}$ | $L_{B29}$ |
| III-1593 | $L_{A380}$ | $L_{B10}$ | III-4738 | $L_{A465}$ | $L_{B28}$ | III-1669 | $L_{A456}$ | $L_{B10}$ | III-4814 | $L_{A371}$ | $L_{B29}$ |
| III-1594 | $L_{A381}$ | $L_{B10}$ | III-4739 | $L_{A466}$ | $L_{B28}$ | III-1670 | $L_{A457}$ | $L_{B10}$ | III-4815 | $L_{A372}$ | $L_{B29}$ |
| III-1595 | $L_{A382}$ | $L_{B10}$ | III-4740 | $L_{A467}$ | $L_{B28}$ | III-1671 | $L_{A458}$ | $L_{B10}$ | III-4816 | $L_{A373}$ | $L_{B29}$ |
| III-1596 | $L_{A383}$ | $L_{B10}$ | III-4741 | $L_{A468}$ | $L_{B28}$ | III-1672 | $L_{A459}$ | $L_{B10}$ | III-4817 | $L_{A374}$ | $L_{B29}$ |
| III-1597 | $L_{A384}$ | $L_{B10}$ | III-4742 | $L_{A469}$ | $L_{B28}$ | III-1673 | $L_{A460}$ | $L_{B10}$ | III-4818 | $L_{A375}$ | $L_{B29}$ |
| III-1598 | $L_{A385}$ | $L_{B10}$ | III-4743 | $L_{A470}$ | $L_{B28}$ | III-1674 | $L_{A461}$ | $L_{B10}$ | III-4819 | $L_{A376}$ | $L_{B29}$ |
| III-1599 | $L_{A386}$ | $L_{B10}$ | III-4744 | $L_{A471}$ | $L_{B28}$ | III-1675 | $L_{A462}$ | $L_{B10}$ | III-4820 | $L_{A377}$ | $L_{B29}$ |
| III-1600 | $L_{A387}$ | $L_{B10}$ | III-4745 | $L_{A472}$ | $L_{B28}$ | III-1676 | $L_{A463}$ | $L_{B10}$ | III-4821 | $L_{A378}$ | $L_{B29}$ |
| III-1601 | $L_{A388}$ | $L_{B10}$ | III-4746 | $L_{A473}$ | $L_{B28}$ | III-1677 | $L_{A464}$ | $L_{B10}$ | III-4822 | $L_{A379}$ | $L_{B29}$ |
| III-1602 | $L_{A389}$ | $L_{B10}$ | III-4747 | $L_{A474}$ | $L_{B28}$ | III-1678 | $L_{A465}$ | $L_{B10}$ | III-4823 | $L_{A380}$ | $L_{B29}$ |
| III-1603 | $L_{A390}$ | $L_{B10}$ | III-4748 | $L_{A475}$ | $L_{B28}$ | III-1679 | $L_{A466}$ | $L_{B10}$ | III-4824 | $L_{A381}$ | $L_{B29}$ |
| III-1604 | $L_{A391}$ | $L_{B10}$ | III-4749 | $L_{A476}$ | $L_{B28}$ | III-1680 | $L_{A467}$ | $L_{B10}$ | III-4825 | $L_{A382}$ | $L_{B29}$ |
| III-1605 | $L_{A392}$ | $L_{B10}$ | III-4750 | $L_{A477}$ | $L_{B28}$ | III-1681 | $L_{A468}$ | $L_{B10}$ | III-4826 | $L_{A383}$ | $L_{B29}$ |
| III-1606 | $L_{A393}$ | $L_{B10}$ | III-4751 | $L_{A478}$ | $L_{B28}$ | III-1682 | $L_{A469}$ | $L_{B10}$ | III-4827 | $L_{A384}$ | $L_{B29}$ |
| III-1607 | $L_{A394}$ | $L_{B10}$ | III-4752 | $L_{A479}$ | $L_{B28}$ | III-1683 | $L_{A470}$ | $L_{B10}$ | III-4828 | $L_{A385}$ | $L_{B29}$ |
| III-1608 | $L_{A395}$ | $L_{B10}$ | III-4753 | $L_{A480}$ | $L_{B28}$ | III-1684 | $L_{A471}$ | $L_{B10}$ | III-4829 | $L_{A386}$ | $L_{B29}$ |
| III-1609 | $L_{A396}$ | $L_{B10}$ | III-4754 | $L_{A481}$ | $L_{B28}$ | III-1685 | $L_{A472}$ | $L_{B10}$ | III-4830 | $L_{A387}$ | $L_{B29}$ |
| III-1610 | $L_{A397}$ | $L_{B10}$ | III-4755 | $L_{A482}$ | $L_{B28}$ | III-1686 | $L_{A473}$ | $L_{B10}$ | III-4831 | $L_{A388}$ | $L_{B29}$ |
| III-1611 | $L_{A398}$ | $L_{B10}$ | III-4756 | $L_{A483}$ | $L_{B28}$ | III-1687 | $L_{A474}$ | $L_{B10}$ | III-4832 | $L_{A389}$ | $L_{B29}$ |
| III-1612 | $L_{A399}$ | $L_{B10}$ | III-4757 | $L_{A484}$ | $L_{B28}$ | III-1688 | $L_{A475}$ | $L_{B10}$ | III-4833 | $L_{A390}$ | $L_{B29}$ |
| III-1613 | $L_{A400}$ | $L_{B10}$ | III-4758 | $L_{A485}$ | $L_{B28}$ | III-1689 | $L_{A476}$ | $L_{B10}$ | III-4834 | $L_{A391}$ | $L_{B29}$ |
| III-1614 | $L_{A401}$ | $L_{B10}$ | III-4759 | $L_{A486}$ | $L_{B28}$ | III-1690 | $L_{A477}$ | $L_{B10}$ | III-4835 | $L_{A392}$ | $L_{B29}$ |
| III-1615 | $L_{A402}$ | $L_{B10}$ | III-4760 | $L_{A487}$ | $L_{B28}$ | III-1691 | $L_{A478}$ | $L_{B10}$ | III-4836 | $L_{A393}$ | $L_{B29}$ |
| III-1616 | $L_{A403}$ | $L_{B10}$ | III-4761 | $L_{A318}$ | $L_{B29}$ | III-1692 | $L_{A479}$ | $L_{B10}$ | III-4837 | $L_{A394}$ | $L_{B29}$ |
| III-1617 | $L_{A404}$ | $L_{B10}$ | III-4762 | $L_{A319}$ | $L_{B29}$ | III-1693 | $L_{A480}$ | $L_{B10}$ | III-4838 | $L_{A395}$ | $L_{B29}$ |
| III-1618 | $L_{A405}$ | $L_{B10}$ | III-4763 | $L_{A320}$ | $L_{B29}$ | III-1694 | $L_{A481}$ | $L_{B10}$ | III-4839 | $L_{A396}$ | $L_{B29}$ |
| III-1619 | $L_{A406}$ | $L_{B10}$ | III-4764 | $L_{A321}$ | $L_{B29}$ | III-1695 | $L_{A482}$ | $L_{B10}$ | III-4840 | $L_{A397}$ | $L_{B29}$ |
| III-1620 | $L_{A407}$ | $L_{B10}$ | III-4765 | $L_{A322}$ | $L_{B29}$ | III-1696 | $L_{A483}$ | $L_{B10}$ | III-4841 | $L_{A398}$ | $L_{B29}$ |
| III-1621 | $L_{A408}$ | $L_{B10}$ | III-4766 | $L_{A323}$ | $L_{B29}$ | III-1697 | $L_{A484}$ | $L_{B10}$ | III-4842 | $L_{A399}$ | $L_{B29}$ |
| III-1622 | $L_{A409}$ | $L_{B10}$ | III-4767 | $L_{A324}$ | $L_{B29}$ | III-1698 | $L_{A485}$ | $L_{B10}$ | III-4843 | $L_{A400}$ | $L_{B29}$ |
| III-1623 | $L_{A410}$ | $L_{B10}$ | III-4768 | $L_{A325}$ | $L_{B29}$ | III-1699 | $L_{A486}$ | $L_{B10}$ | III-4844 | $L_{A401}$ | $L_{B29}$ |
| III-1624 | $L_{A411}$ | $L_{B10}$ | III-4769 | $L_{A326}$ | $L_{B29}$ | III-1700 | $L_{A487}$ | $L_{B10}$ | III-4845 | $L_{A402}$ | $L_{B29}$ |
| III-1625 | $L_{A412}$ | $L_{B10}$ | III-4770 | $L_{A327}$ | $L_{B29}$ | III-1701 | $L_{A318}$ | $L_{B11}$ | III-4846 | $L_{A403}$ | $L_{B29}$ |
| III-1626 | $L_{A413}$ | $L_{B10}$ | III-4771 | $L_{A328}$ | $L_{B29}$ | III-1702 | $L_{A319}$ | $L_{B11}$ | III-4847 | $L_{A404}$ | $L_{B29}$ |
| III-1627 | $L_{A414}$ | $L_{B10}$ | III-4772 | $L_{A329}$ | $L_{B29}$ | III-1703 | $L_{A320}$ | $L_{B11}$ | III-4848 | $L_{A405}$ | $L_{B29}$ |
| III-1628 | $L_{A415}$ | $L_{B10}$ | III-4773 | $L_{A330}$ | $L_{B29}$ | III-1704 | $L_{A321}$ | $L_{B11}$ | III-4849 | $L_{A406}$ | $L_{B29}$ |
| III-1629 | $L_{A416}$ | $L_{B10}$ | III-4774 | $L_{A331}$ | $L_{B29}$ | III-1705 | $L_{A322}$ | $L_{B11}$ | III-4850 | $L_{A407}$ | $L_{B29}$ |
| III-1630 | $L_{A417}$ | $L_{B10}$ | III-4775 | $L_{A332}$ | $L_{B29}$ | III-1706 | $L_{A323}$ | $L_{B11}$ | III-4851 | $L_{A408}$ | $L_{B29}$ |
| III-1631 | $L_{A418}$ | $L_{B10}$ | III-4776 | $L_{A333}$ | $L_{B29}$ | III-1707 | $L_{A324}$ | $L_{B11}$ | III-4852 | $L_{A409}$ | $L_{B29}$ |
| III-1632 | $L_{A419}$ | $L_{B10}$ | III-4777 | $L_{A334}$ | $L_{B29}$ | III-1708 | $L_{A325}$ | $L_{B11}$ | III-4853 | $L_{A410}$ | $L_{B29}$ |
| III-1633 | $L_{A420}$ | $L_{B10}$ | III-4778 | $L_{A335}$ | $L_{B29}$ | III-1709 | $L_{A326}$ | $L_{B11}$ | III-4854 | $L_{A411}$ | $L_{B29}$ |
| III-1634 | $L_{A421}$ | $L_{B10}$ | III-4779 | $L_{A336}$ | $L_{B29}$ | III-1710 | $L_{A327}$ | $L_{B11}$ | III-4855 | $L_{A412}$ | $L_{B29}$ |
| III-1635 | $L_{A422}$ | $L_{B10}$ | III-4780 | $L_{A337}$ | $L_{B29}$ | III-1711 | $L_{A328}$ | $L_{B11}$ | III-4856 | $L_{A413}$ | $L_{B29}$ |
| III-1636 | $L_{A423}$ | $L_{B10}$ | III-4781 | $L_{A338}$ | $L_{B29}$ | III-1712 | $L_{A329}$ | $L_{B11}$ | III-4857 | $L_{A414}$ | $L_{B29}$ |
| III-1637 | $L_{A424}$ | $L_{B10}$ | III-4782 | $L_{A339}$ | $L_{B29}$ | III-1713 | $L_{A330}$ | $L_{B11}$ | III-4858 | $L_{A415}$ | $L_{B29}$ |
| III-1638 | $L_{A425}$ | $L_{B10}$ | III-4783 | $L_{A340}$ | $L_{B29}$ | III-1714 | $L_{A331}$ | $L_{B11}$ | III-4859 | $L_{A416}$ | $L_{B29}$ |
| III-1639 | $L_{A426}$ | $L_{B10}$ | III-4784 | $L_{A341}$ | $L_{B29}$ | III-1715 | $L_{A332}$ | $L_{B11}$ | III-4860 | $L_{A417}$ | $L_{B29}$ |
| III-1640 | $L_{A427}$ | $L_{B10}$ | III-4785 | $L_{A342}$ | $L_{B29}$ | III-1716 | $L_{A333}$ | $L_{B11}$ | III-4861 | $L_{A418}$ | $L_{B29}$ |
| III-1641 | $L_{A428}$ | $L_{B10}$ | III-4786 | $L_{A343}$ | $L_{B29}$ | III-1717 | $L_{A334}$ | $L_{B11}$ | III-4862 | $L_{A419}$ | $L_{B29}$ |
| III-1642 | $L_{A429}$ | $L_{B10}$ | III-4787 | $L_{A344}$ | $L_{B29}$ | III-1718 | $L_{A335}$ | $L_{B11}$ | III-4863 | $L_{A420}$ | $L_{B29}$ |
| III-1643 | $L_{A430}$ | $L_{B10}$ | III-4788 | $L_{A345}$ | $L_{B29}$ | III-1719 | $L_{A336}$ | $L_{B11}$ | III-4864 | $L_{A421}$ | $L_{B29}$ |

-continued

| Compound Number | $L_A$ | $L_B$ | Compound Number | $L_A$ | $L_B$ |
|---|---|---|---|---|---|
| III-1720 | $L_{A337}$ | $L_{B11}$ | III-4865 | $L_{A422}$ | $L_{B29}$ |
| III-1721 | $L_{A338}$ | $L_{B11}$ | III-4866 | $L_{A423}$ | $L_{B29}$ |
| III-1722 | $L_{A339}$ | $L_{B11}$ | III-4867 | $L_{A424}$ | $L_{B29}$ |
| III-1723 | $L_{A340}$ | $L_{B11}$ | III-4868 | $L_{A425}$ | $L_{B29}$ |
| III-1724 | $L_{A341}$ | $L_{B11}$ | III-4869 | $L_{A426}$ | $L_{B29}$ |
| III-1725 | $L_{A342}$ | $L_{B11}$ | III-4870 | $L_{A427}$ | $L_{B29}$ |
| III-1726 | $L_{A343}$ | $L_{B11}$ | III-4871 | $L_{A428}$ | $L_{B29}$ |
| III-1727 | $L_{A344}$ | $L_{B11}$ | III-4872 | $L_{A429}$ | $L_{B29}$ |
| III-1728 | $L_{A345}$ | $L_{B11}$ | III-4873 | $L_{A430}$ | $L_{B29}$ |
| III-1729 | $L_{A346}$ | $L_{B11}$ | III-4874 | $L_{A431}$ | $L_{B29}$ |
| III-1730 | $L_{A347}$ | $L_{B11}$ | III-4875 | $L_{A432}$ | $L_{B29}$ |
| III-1731 | $L_{A348}$ | $L_{B11}$ | III-4876 | $L_{A433}$ | $L_{B29}$ |
| III-1732 | $L_{A349}$ | $L_{B11}$ | III-4877 | $L_{A434}$ | $L_{B29}$ |
| III-1733 | $L_{A350}$ | $L_{B11}$ | III-4878 | $L_{A435}$ | $L_{B29}$ |
| III-1734 | $L_{A351}$ | $L_{B11}$ | III-4879 | $L_{A436}$ | $L_{B29}$ |
| III-1735 | $L_{A352}$ | $L_{B11}$ | III-4880 | $L_{A437}$ | $L_{B29}$ |
| III-1736 | $L_{A353}$ | $L_{B11}$ | III-4881 | $L_{A438}$ | $L_{B29}$ |
| III-1737 | $L_{A354}$ | $L_{B11}$ | III-4882 | $L_{A439}$ | $L_{B29}$ |
| III-1738 | $L_{A355}$ | $L_{B11}$ | III-4883 | $L_{A440}$ | $L_{B29}$ |
| III-1739 | $L_{A356}$ | $L_{B11}$ | III-4884 | $L_{A441}$ | $L_{B29}$ |
| III-1740 | $L_{A357}$ | $L_{B11}$ | III-4885 | $L_{A442}$ | $L_{B29}$ |
| III-1741 | $L_{A358}$ | $L_{B11}$ | III-4886 | $L_{A443}$ | $L_{B29}$ |
| III-1742 | $L_{A359}$ | $L_{B11}$ | III-4887 | $L_{A444}$ | $L_{B29}$ |
| III-1743 | $L_{A360}$ | $L_{B11}$ | III-4888 | $L_{A445}$ | $L_{B29}$ |
| III-1744 | $L_{A361}$ | $L_{B11}$ | III-4889 | $L_{A446}$ | $L_{B29}$ |
| III-1745 | $L_{A362}$ | $L_{B11}$ | III-4890 | $L_{A447}$ | $L_{B29}$ |
| III-1746 | $L_{A363}$ | $L_{B11}$ | III-4891 | $L_{A448}$ | $L_{B29}$ |
| III-1747 | $L_{A364}$ | $L_{B11}$ | III-4892 | $L_{A449}$ | $L_{B29}$ |
| III-1748 | $L_{A365}$ | $L_{B11}$ | III-4893 | $L_{A450}$ | $L_{B29}$ |
| III-1749 | $L_{A366}$ | $L_{B11}$ | III-4894 | $L_{A451}$ | $L_{B29}$ |
| III-1750 | $L_{A367}$ | $L_{B11}$ | III-4895 | $L_{A452}$ | $L_{B29}$ |
| III-1751 | $L_{A368}$ | $L_{B11}$ | III-4896 | $L_{A453}$ | $L_{B29}$ |
| III-1752 | $L_{A369}$ | $L_{B11}$ | III-4897 | $L_{A454}$ | $L_{B29}$ |
| III-1753 | $L_{A370}$ | $L_{B11}$ | III-4898 | $L_{A455}$ | $L_{B29}$ |
| III-1754 | $L_{A371}$ | $L_{B11}$ | III-4899 | $L_{A456}$ | $L_{B29}$ |
| III-1755 | $L_{A372}$ | $L_{B11}$ | III-4900 | $L_{A457}$ | $L_{B29}$ |
| III-1756 | $L_{A373}$ | $L_{B11}$ | III-4901 | $L_{A458}$ | $L_{B29}$ |
| III-1757 | $L_{A374}$ | $L_{B11}$ | III-4902 | $L_{A459}$ | $L_{B29}$ |
| III-1758 | $L_{A375}$ | $L_{B11}$ | III-4903 | $L_{A460}$ | $L_{B29}$ |
| III-1759 | $L_{A376}$ | $L_{B11}$ | III-4904 | $L_{A461}$ | $L_{B29}$ |
| III-1760 | $L_{A377}$ | $L_{B11}$ | III-4905 | $L_{A462}$ | $L_{B29}$ |
| III-1761 | $L_{A378}$ | $L_{B11}$ | III-4906 | $L_{A463}$ | $L_{B29}$ |
| III-1762 | $L_{A379}$ | $L_{B11}$ | III-4907 | $L_{A464}$ | $L_{B29}$ |
| III-1763 | $L_{A380}$ | $L_{B11}$ | III-4908 | $L_{A465}$ | $L_{B29}$ |
| III-1764 | $L_{A381}$ | $L_{B11}$ | III-4909 | $L_{A466}$ | $L_{B29}$ |
| III-1765 | $L_{A382}$ | $L_{B11}$ | III-4910 | $L_{A467}$ | $L_{B29}$ |
| III-1766 | $L_{A383}$ | $L_{B11}$ | III-4911 | $L_{A468}$ | $L_{B29}$ |
| III-1767 | $L_{A384}$ | $L_{B11}$ | III-4912 | $L_{A469}$ | $L_{B29}$ |
| III-1768 | $L_{A385}$ | $L_{B11}$ | III-4913 | $L_{A470}$ | $L_{B29}$ |
| III-1769 | $L_{A386}$ | $L_{B11}$ | III-4914 | $L_{A471}$ | $L_{B29}$ |
| III-1770 | $L_{A387}$ | $L_{B11}$ | III-4915 | $L_{A472}$ | $L_{B29}$ |
| III-1771 | $L_{A388}$ | $L_{B11}$ | III-4916 | $L_{A473}$ | $L_{B29}$ |
| III-1772 | $L_{A389}$ | $L_{B11}$ | III-4917 | $L_{A474}$ | $L_{B29}$ |
| III-1773 | $L_{A390}$ | $L_{B11}$ | III-4918 | $L_{A475}$ | $L_{B29}$ |
| III-1774 | $L_{A391}$ | $L_{B11}$ | III-4919 | $L_{A476}$ | $L_{B29}$ |
| III-1775 | $L_{A392}$ | $L_{B11}$ | III-4920 | $L_{A477}$ | $L_{B29}$ |
| III-1776 | $L_{A393}$ | $L_{B11}$ | III-4921 | $L_{A478}$ | $L_{B29}$ |
| III-1777 | $L_{A394}$ | $L_{B11}$ | III-4922 | $L_{A479}$ | $L_{B29}$ |
| III-1778 | $L_{A395}$ | $L_{B11}$ | III-4923 | $L_{A480}$ | $L_{B29}$ |
| III-1779 | $L_{A396}$ | $L_{B11}$ | III-4924 | $L_{A481}$ | $L_{B29}$ |
| III-1780 | $L_{A397}$ | $L_{B11}$ | III-4925 | $L_{A482}$ | $L_{B29}$ |
| III-1781 | $L_{A398}$ | $L_{B11}$ | III-4926 | $L_{A483}$ | $L_{B29}$ |
| III-1782 | $L_{A399}$ | $L_{B11}$ | III-4927 | $L_{A484}$ | $L_{B29}$ |
| III-1783 | $L_{A400}$ | $L_{B11}$ | III-4928 | $L_{A485}$ | $L_{B29}$ |
| III-1784 | $L_{A401}$ | $L_{B11}$ | III-4929 | $L_{A486}$ | $L_{B29}$ |
| III-1785 | $L_{A402}$ | $L_{B11}$ | III-4930 | $L_{A487}$ | $L_{B29}$ |
| III-1786 | $L_{A403}$ | $L_{B11}$ | III-4931 | $L_{A318}$ | $L_{B30}$ |
| III-1787 | $L_{A404}$ | $L_{B11}$ | III-4932 | $L_{A319}$ | $L_{B30}$ |
| III-1788 | $L_{A405}$ | $L_{B11}$ | III-4933 | $L_{A320}$ | $L_{B30}$ |
| III-1789 | $L_{A406}$ | $L_{B11}$ | III-4934 | $L_{A321}$ | $L_{B30}$ |
| III-1790 | $L_{A407}$ | $L_{B11}$ | III-4935 | $L_{A322}$ | $L_{B30}$ |
| III-1791 | $L_{A408}$ | $L_{B11}$ | III-4936 | $L_{A323}$ | $L_{B30}$ |
| III-1792 | $L_{A409}$ | $L_{B11}$ | III-4937 | $L_{A324}$ | $L_{B30}$ |
| III-1793 | $L_{A410}$ | $L_{B11}$ | III-4938 | $L_{A325}$ | $L_{B30}$ |
| III-1794 | $L_{A411}$ | $L_{B11}$ | III-4939 | $L_{A326}$ | $L_{B30}$ |
| III-1795 | $L_{A412}$ | $L_{B11}$ | III-4940 | $L_{A327}$ | $L_{B30}$ |
| III-1796 | $L_{A413}$ | $L_{B11}$ | III-4941 | $L_{A328}$ | $L_{B30}$ |
| III-1797 | $L_{A414}$ | $L_{B11}$ | III-4942 | $L_{A329}$ | $L_{B30}$ |
| III-1798 | $L_{A415}$ | $L_{B11}$ | III-4943 | $L_{A330}$ | $L_{B30}$ |
| III-1799 | $L_{A416}$ | $L_{B11}$ | III-4944 | $L_{A331}$ | $L_{B30}$ |
| III-1800 | $L_{A417}$ | $L_{B11}$ | III-4945 | $L_{A332}$ | $L_{B30}$ |
| III-1801 | $L_{A418}$ | $L_{B11}$ | III-4946 | $L_{A333}$ | $L_{B30}$ |
| III-1802 | $L_{A419}$ | $L_{B11}$ | III-4947 | $L_{A334}$ | $L_{B30}$ |
| III-1803 | $L_{A420}$ | $L_{B11}$ | III-4948 | $L_{A335}$ | $L_{B30}$ |
| III-1804 | $L_{A421}$ | $L_{B11}$ | III-4949 | $L_{A336}$ | $L_{B30}$ |
| III-1805 | $L_{A422}$ | $L_{B11}$ | III-4950 | $L_{A337}$ | $L_{B30}$ |
| III-1806 | $L_{A423}$ | $L_{B11}$ | III-4951 | $L_{A338}$ | $L_{B30}$ |
| III-1807 | $L_{A424}$ | $L_{B11}$ | III-4952 | $L_{A339}$ | $L_{B30}$ |
| III-1808 | $L_{A425}$ | $L_{B11}$ | III-4953 | $L_{A340}$ | $L_{B30}$ |
| III-1809 | $L_{A426}$ | $L_{B11}$ | III-4954 | $L_{A341}$ | $L_{B30}$ |
| III-1810 | $L_{A427}$ | $L_{B11}$ | III-4955 | $L_{A342}$ | $L_{B30}$ |
| III-1811 | $L_{A428}$ | $L_{B11}$ | III-4956 | $L_{A343}$ | $L_{B30}$ |
| III-1812 | $L_{A429}$ | $L_{B11}$ | III-4957 | $L_{A344}$ | $L_{B30}$ |
| III-1813 | $L_{A430}$ | $L_{B11}$ | III-4958 | $L_{A345}$ | $L_{B30}$ |
| III-1814 | $L_{A431}$ | $L_{B11}$ | III-4959 | $L_{A346}$ | $L_{B30}$ |
| III-1815 | $L_{A432}$ | $L_{B11}$ | III-4960 | $L_{A347}$ | $L_{B30}$ |
| III-1816 | $L_{A433}$ | $L_{B11}$ | III-4961 | $L_{A348}$ | $L_{B30}$ |
| III-1817 | $L_{A434}$ | $L_{B11}$ | III-4962 | $L_{A349}$ | $L_{B30}$ |
| III-1818 | $L_{A435}$ | $L_{B11}$ | III-4963 | $L_{A350}$ | $L_{B30}$ |
| III-1819 | $L_{A436}$ | $L_{B11}$ | III-4964 | $L_{A351}$ | $L_{B30}$ |
| III-1820 | $L_{A437}$ | $L_{B11}$ | III-4965 | $L_{A352}$ | $L_{B30}$ |
| III-1821 | $L_{A438}$ | $L_{B11}$ | III-4966 | $L_{A353}$ | $L_{B30}$ |
| III-1822 | $L_{A439}$ | $L_{B11}$ | III-4967 | $L_{A354}$ | $L_{B30}$ |
| III-1823 | $L_{A440}$ | $L_{B11}$ | III-4968 | $L_{A355}$ | $L_{B30}$ |
| III-1824 | $L_{A441}$ | $L_{B11}$ | III-4969 | $L_{A356}$ | $L_{B30}$ |
| III-1825 | $L_{A442}$ | $L_{B11}$ | III-4970 | $L_{A357}$ | $L_{B30}$ |
| III-1826 | $L_{A443}$ | $L_{B11}$ | III-4971 | $L_{A358}$ | $L_{B30}$ |
| III-1827 | $L_{A444}$ | $L_{B11}$ | III-4972 | $L_{A359}$ | $L_{B30}$ |
| III-1828 | $L_{A445}$ | $L_{B11}$ | III-4973 | $L_{A360}$ | $L_{B30}$ |
| III-1829 | $L_{A446}$ | $L_{B11}$ | III-4974 | $L_{A361}$ | $L_{B30}$ |
| III-1830 | $L_{A447}$ | $L_{B11}$ | III-4975 | $L_{A362}$ | $L_{B30}$ |
| III-1831 | $L_{A448}$ | $L_{B11}$ | III-4976 | $L_{A363}$ | $L_{B30}$ |
| III-1832 | $L_{A449}$ | $L_{B11}$ | III-4977 | $L_{A364}$ | $L_{B30}$ |
| III-1833 | $L_{A450}$ | $L_{B11}$ | III-4978 | $L_{A365}$ | $L_{B30}$ |
| III-1834 | $L_{A451}$ | $L_{B11}$ | III-4979 | $L_{A366}$ | $L_{B30}$ |
| III-1835 | $L_{A452}$ | $L_{B11}$ | III-4980 | $L_{A367}$ | $L_{B30}$ |
| III-1836 | $L_{A453}$ | $L_{B11}$ | III-4981 | $L_{A368}$ | $L_{B30}$ |
| III-1837 | $L_{A454}$ | $L_{B11}$ | III-4982 | $L_{A369}$ | $L_{B30}$ |
| III-1838 | $L_{A455}$ | $L_{B11}$ | III-4983 | $L_{A370}$ | $L_{B30}$ |
| III-1839 | $L_{A456}$ | $L_{B11}$ | III-4984 | $L_{A371}$ | $L_{B30}$ |
| III-1840 | $L_{A457}$ | $L_{B11}$ | III-4985 | $L_{A372}$ | $L_{B30}$ |
| III-1841 | $L_{A458}$ | $L_{B11}$ | III-4986 | $L_{A373}$ | $L_{B30}$ |
| III-1842 | $L_{A459}$ | $L_{B11}$ | III-4987 | $L_{A374}$ | $L_{B30}$ |
| III-1843 | $L_{A460}$ | $L_{B11}$ | III-4988 | $L_{A375}$ | $L_{B30}$ |
| III-1844 | $L_{A461}$ | $L_{B11}$ | III-4989 | $L_{A376}$ | $L_{B30}$ |
| III-1845 | $L_{A462}$ | $L_{B11}$ | III-4990 | $L_{A377}$ | $L_{B30}$ |
| III-1846 | $L_{A463}$ | $L_{B11}$ | III-4991 | $L_{A378}$ | $L_{B30}$ |
| III-1847 | $L_{A464}$ | $L_{B11}$ | III-4992 | $L_{A379}$ | $L_{B30}$ |
| III-1848 | $L_{A465}$ | $L_{B11}$ | III-4993 | $L_{A380}$ | $L_{B30}$ |
| III-1849 | $L_{A466}$ | $L_{B11}$ | III-4994 | $L_{A381}$ | $L_{B30}$ |
| III-1850 | $L_{A467}$ | $L_{B11}$ | III-4995 | $L_{A382}$ | $L_{B30}$ |
| III-1851 | $L_{A468}$ | $L_{B11}$ | III-4996 | $L_{A383}$ | $L_{B30}$ |
| III-1852 | $L_{A469}$ | $L_{B11}$ | III-4997 | $L_{A384}$ | $L_{B30}$ |
| III-1853 | $L_{A470}$ | $L_{B11}$ | III-4998 | $L_{A385}$ | $L_{B30}$ |
| III-1854 | $L_{A471}$ | $L_{B11}$ | III-4999 | $L_{A386}$ | $L_{B30}$ |
| III-1855 | $L_{A472}$ | $L_{B11}$ | III-5000 | $L_{A387}$ | $L_{B30}$ |
| III-1856 | $L_{A473}$ | $L_{B11}$ | III-5001 | $L_{A388}$ | $L_{B30}$ |
| III-1857 | $L_{A474}$ | $L_{B11}$ | III-5002 | $L_{A389}$ | $L_{B30}$ |
| III-1858 | $L_{A475}$ | $L_{B11}$ | III-5003 | $L_{A390}$ | $L_{B30}$ |
| III-1859 | $L_{A476}$ | $L_{B11}$ | III-5004 | $L_{A391}$ | $L_{B30}$ |
| III-1860 | $L_{A477}$ | $L_{B11}$ | III-5005 | $L_{A392}$ | $L_{B30}$ |
| III-1861 | $L_{A478}$ | $L_{B11}$ | III-5006 | $L_{A393}$ | $L_{B30}$ |
| III-1862 | $L_{A479}$ | $L_{B11}$ | III-5007 | $L_{A394}$ | $L_{B30}$ |
| III-1863 | $L_{A480}$ | $L_{B11}$ | III-5008 | $L_{A395}$ | $L_{B30}$ |
| III-1864 | $L_{A481}$ | $L_{B11}$ | III-5009 | $L_{A396}$ | $L_{B30}$ |
| III-1865 | $L_{A482}$ | $L_{B11}$ | III-5010 | $L_{A397}$ | $L_{B30}$ |
| III-1866 | $L_{A483}$ | $L_{B11}$ | III-5011 | $L_{A398}$ | $L_{B30}$ |
| III-1867 | $L_{A484}$ | $L_{B11}$ | III-5012 | $L_{A399}$ | $L_{B30}$ |
| III-1868 | $L_{A485}$ | $L_{B11}$ | III-5013 | $L_{A400}$ | $L_{B30}$ |
| III-1869 | $L_{A486}$ | $L_{B11}$ | III-5014 | $L_{A401}$ | $L_{B30}$ |
| III-1870 | $L_{A487}$ | $L_{B11}$ | III-5015 | $L_{A402}$ | $L_{B30}$ |
| III-1871 | $L_{A318}$ | $L_{B12}$ | III-5016 | $L_{A403}$ | $L_{B30}$ |

| Compound Number | $L_A$ | $L_B$ | Compound Number | $L_A$ | $L_B$ | Compound Number | $L_A$ | $L_B$ | Compound Number | $L_A$ | $L_B$ |
|---|---|---|---|---|---|---|---|---|---|---|---|
| III-1872 | $L_{A319}$ | $L_{B12}$ | III-5017 | $L_{A404}$ | $L_{B30}$ | III-1948 | $L_{A395}$ | $L_{B12}$ | III-5093 | $L_{A480}$ | $L_{B30}$ |
| III-1873 | $L_{A320}$ | $L_{B12}$ | III-5018 | $L_{A405}$ | $L_{B30}$ | III-1949 | $L_{A396}$ | $L_{B12}$ | III-5094 | $L_{A481}$ | $L_{B30}$ |
| III-1874 | $L_{A321}$ | $L_{B12}$ | III-5019 | $L_{A406}$ | $L_{B30}$ | III-1950 | $L_{A397}$ | $L_{B12}$ | III-5095 | $L_{A482}$ | $L_{B30}$ |
| III-1875 | $L_{A322}$ | $L_{B12}$ | III-5020 | $L_{A407}$ | $L_{B30}$ | III-1951 | $L_{A398}$ | $L_{B12}$ | III-5096 | $L_{A483}$ | $L_{B30}$ |
| III-1876 | $L_{A323}$ | $L_{B12}$ | III-5021 | $L_{A408}$ | $L_{B30}$ | III-1952 | $L_{A399}$ | $L_{B12}$ | III-5097 | $L_{A484}$ | $L_{B30}$ |
| III-1877 | $L_{A324}$ | $L_{B12}$ | III-5022 | $L_{A409}$ | $L_{B30}$ | III-1953 | $L_{A400}$ | $L_{B12}$ | III-5098 | $L_{A485}$ | $L_{B30}$ |
| III-1878 | $L_{A325}$ | $L_{B12}$ | III-5023 | $L_{A410}$ | $L_{B30}$ | III-1954 | $L_{A401}$ | $L_{B12}$ | III-5099 | $L_{A486}$ | $L_{B30}$ |
| III-1879 | $L_{A326}$ | $L_{B12}$ | III-5024 | $L_{A411}$ | $L_{B30}$ | III-1955 | $L_{A402}$ | $L_{B12}$ | III-5100 | $L_{A487}$ | $L_{B30}$ |
| III-1880 | $L_{A327}$ | $L_{B12}$ | III-5025 | $L_{A412}$ | $L_{B30}$ | III-1956 | $L_{A403}$ | $L_{B12}$ | III-5101 | $L_{A318}$ | $L_{B31}$ |
| III-1881 | $L_{A328}$ | $L_{B12}$ | III-5026 | $L_{A413}$ | $L_{B30}$ | III-1957 | $L_{A404}$ | $L_{B12}$ | III-5102 | $L_{A319}$ | $L_{B31}$ |
| III-1882 | $L_{A329}$ | $L_{B12}$ | III-5027 | $L_{A414}$ | $L_{B30}$ | III-1958 | $L_{A405}$ | $L_{B12}$ | III-5103 | $L_{A320}$ | $L_{B31}$ |
| III-1883 | $L_{A330}$ | $L_{B12}$ | III-5028 | $L_{A415}$ | $L_{B30}$ | III-1959 | $L_{A406}$ | $L_{B12}$ | III-5104 | $L_{A321}$ | $L_{B31}$ |
| III-1884 | $L_{A331}$ | $L_{B12}$ | III-5029 | $L_{A416}$ | $L_{B30}$ | III-1960 | $L_{A407}$ | $L_{B12}$ | III-5105 | $L_{A322}$ | $L_{B31}$ |
| III-1885 | $L_{A332}$ | $L_{B12}$ | III-5030 | $L_{A417}$ | $L_{B30}$ | III-1961 | $L_{A408}$ | $L_{B12}$ | III-5106 | $L_{A323}$ | $L_{B31}$ |
| III-1886 | $L_{A333}$ | $L_{B12}$ | III-5031 | $L_{A418}$ | $L_{B30}$ | III-1962 | $L_{A409}$ | $L_{B12}$ | III-5107 | $L_{A324}$ | $L_{B31}$ |
| III-1887 | $L_{A334}$ | $L_{B12}$ | III-5032 | $L_{A419}$ | $L_{B30}$ | III-1963 | $L_{A410}$ | $L_{B12}$ | III-5108 | $L_{A325}$ | $L_{B31}$ |
| III-1888 | $L_{A335}$ | $L_{B12}$ | III-5033 | $L_{A420}$ | $L_{B30}$ | III-1964 | $L_{A411}$ | $L_{B12}$ | III-5109 | $L_{A326}$ | $L_{B31}$ |
| III-1889 | $L_{A336}$ | $L_{B12}$ | III-5034 | $L_{A421}$ | $L_{B30}$ | III-1965 | $L_{A412}$ | $L_{B12}$ | III-5110 | $L_{A327}$ | $L_{B31}$ |
| III-1890 | $L_{A337}$ | $L_{B12}$ | III-5035 | $L_{A422}$ | $L_{B30}$ | III-1966 | $L_{A413}$ | $L_{B12}$ | III-5111 | $L_{A328}$ | $L_{B31}$ |
| III-1891 | $L_{A338}$ | $L_{B12}$ | III-5036 | $L_{A423}$ | $L_{B30}$ | III-1967 | $L_{A414}$ | $L_{B12}$ | III-5112 | $L_{A329}$ | $L_{B31}$ |
| III-1892 | $L_{A339}$ | $L_{B12}$ | III-5037 | $L_{A424}$ | $L_{B30}$ | III-1968 | $L_{A415}$ | $L_{B12}$ | III-5113 | $L_{A330}$ | $L_{B31}$ |
| III-1893 | $L_{A340}$ | $L_{B12}$ | III-5038 | $L_{A425}$ | $L_{B30}$ | III-1969 | $L_{A416}$ | $L_{B12}$ | III-5114 | $L_{A331}$ | $L_{B31}$ |
| III-1894 | $L_{A341}$ | $L_{B12}$ | III-5039 | $L_{A426}$ | $L_{B30}$ | III-1970 | $L_{A417}$ | $L_{B12}$ | III-5115 | $L_{A332}$ | $L_{B31}$ |
| III-1895 | $L_{A342}$ | $L_{B12}$ | III-5040 | $L_{A427}$ | $L_{B30}$ | III-1971 | $L_{A418}$ | $L_{B12}$ | III-5116 | $L_{A333}$ | $L_{B31}$ |
| III-1896 | $L_{A343}$ | $L_{B12}$ | III-5041 | $L_{A428}$ | $L_{B30}$ | III-1972 | $L_{A419}$ | $L_{B12}$ | III-5117 | $L_{A334}$ | $L_{B31}$ |
| III-1897 | $L_{A344}$ | $L_{B12}$ | III-5042 | $L_{A429}$ | $L_{B30}$ | III-1973 | $L_{A420}$ | $L_{B12}$ | III-5118 | $L_{A335}$ | $L_{B31}$ |
| III-1898 | $L_{A345}$ | $L_{B12}$ | III-5043 | $L_{A430}$ | $L_{B30}$ | III-1974 | $L_{A421}$ | $L_{B12}$ | III-5119 | $L_{A336}$ | $L_{B31}$ |
| III-1899 | $L_{A346}$ | $L_{B12}$ | III-5044 | $L_{A431}$ | $L_{B30}$ | III-1975 | $L_{A422}$ | $L_{B12}$ | III-5120 | $L_{A337}$ | $L_{B31}$ |
| III-1900 | $L_{A347}$ | $L_{B12}$ | III-5045 | $L_{A432}$ | $L_{B30}$ | III-1976 | $L_{A423}$ | $L_{B12}$ | III-5121 | $L_{A338}$ | $L_{B31}$ |
| III-1901 | $L_{A348}$ | $L_{B12}$ | III-5046 | $L_{A433}$ | $L_{B30}$ | III-1977 | $L_{A424}$ | $L_{B12}$ | III-5122 | $L_{A339}$ | $L_{B31}$ |
| III-1902 | $L_{A349}$ | $L_{B12}$ | III-5047 | $L_{A434}$ | $L_{B30}$ | III-1978 | $L_{A425}$ | $L_{B12}$ | III-5123 | $L_{A340}$ | $L_{B31}$ |
| III-1903 | $L_{A350}$ | $L_{B12}$ | III-5048 | $L_{A435}$ | $L_{B30}$ | III-1979 | $L_{A426}$ | $L_{B12}$ | III-5124 | $L_{A341}$ | $L_{B31}$ |
| III-1904 | $L_{A351}$ | $L_{B12}$ | III-5049 | $L_{A436}$ | $L_{B30}$ | III-1980 | $L_{A427}$ | $L_{B12}$ | III-5125 | $L_{A342}$ | $L_{B31}$ |
| III-1905 | $L_{A352}$ | $L_{B12}$ | III-5050 | $L_{A437}$ | $L_{B30}$ | III-1981 | $L_{A428}$ | $L_{B12}$ | III-5126 | $L_{A343}$ | $L_{B31}$ |
| III-1906 | $L_{A353}$ | $L_{B12}$ | III-5051 | $L_{A438}$ | $L_{B30}$ | III-1982 | $L_{A429}$ | $L_{B12}$ | III-5127 | $L_{A344}$ | $L_{B31}$ |
| III-1907 | $L_{A354}$ | $L_{B12}$ | III-5052 | $L_{A439}$ | $L_{B30}$ | III-1983 | $L_{A430}$ | $L_{B12}$ | III-5128 | $L_{A345}$ | $L_{B31}$ |
| III-1908 | $L_{A355}$ | $L_{B12}$ | III-5053 | $L_{A440}$ | $L_{B30}$ | III-1984 | $L_{A431}$ | $L_{B12}$ | III-5129 | $L_{A346}$ | $L_{B31}$ |
| III-1909 | $L_{A356}$ | $L_{B12}$ | III-5054 | $L_{A441}$ | $L_{B30}$ | III-1985 | $L_{A432}$ | $L_{B12}$ | III-5130 | $L_{A347}$ | $L_{B31}$ |
| III-1910 | $L_{A357}$ | $L_{B12}$ | III-5055 | $L_{A442}$ | $L_{B30}$ | III-1986 | $L_{A433}$ | $L_{B12}$ | III-5131 | $L_{A348}$ | $L_{B31}$ |
| III-1911 | $L_{A358}$ | $L_{B12}$ | III-5056 | $L_{A443}$ | $L_{B30}$ | III-1987 | $L_{A434}$ | $L_{B12}$ | III-5132 | $L_{A349}$ | $L_{B31}$ |
| III-1912 | $L_{A359}$ | $L_{B12}$ | III-5057 | $L_{A444}$ | $L_{B30}$ | III-1988 | $L_{A435}$ | $L_{B12}$ | III-5133 | $L_{A350}$ | $L_{B31}$ |
| III-1913 | $L_{A360}$ | $L_{B12}$ | III-5058 | $L_{A445}$ | $L_{B30}$ | III-1989 | $L_{A436}$ | $L_{B12}$ | III-5134 | $L_{A351}$ | $L_{B31}$ |
| III-1914 | $L_{A361}$ | $L_{B12}$ | III-5059 | $L_{A446}$ | $L_{B30}$ | III-1990 | $L_{A437}$ | $L_{B12}$ | III-5135 | $L_{A352}$ | $L_{B31}$ |
| III-1915 | $L_{A362}$ | $L_{B12}$ | III-5060 | $L_{A447}$ | $L_{B30}$ | III-1991 | $L_{A438}$ | $L_{B12}$ | III-5136 | $L_{A353}$ | $L_{B31}$ |
| III-1916 | $L_{A363}$ | $L_{B12}$ | III-5061 | $L_{A448}$ | $L_{B30}$ | III-1992 | $L_{A439}$ | $L_{B12}$ | III-5137 | $L_{A354}$ | $L_{B31}$ |
| III-1917 | $L_{A364}$ | $L_{B12}$ | III-5062 | $L_{A449}$ | $L_{B30}$ | III-1993 | $L_{A440}$ | $L_{B12}$ | III-5138 | $L_{A355}$ | $L_{B31}$ |
| III-1918 | $L_{A365}$ | $L_{B12}$ | III-5063 | $L_{A450}$ | $L_{B30}$ | III-1994 | $L_{A441}$ | $L_{B12}$ | III-5139 | $L_{A356}$ | $L_{B31}$ |
| III-1919 | $L_{A366}$ | $L_{B12}$ | III-5064 | $L_{A451}$ | $L_{B30}$ | III-1995 | $L_{A442}$ | $L_{B12}$ | III-5140 | $L_{A357}$ | $L_{B31}$ |
| III-1920 | $L_{A367}$ | $L_{B12}$ | III-5065 | $L_{A452}$ | $L_{B30}$ | III-1996 | $L_{A443}$ | $L_{B12}$ | III-5141 | $L_{A358}$ | $L_{B31}$ |
| III-1921 | $L_{A368}$ | $L_{B12}$ | III-5066 | $L_{A453}$ | $L_{B30}$ | III-1997 | $L_{A444}$ | $L_{B12}$ | III-5142 | $L_{A359}$ | $L_{B31}$ |
| III-1922 | $L_{A369}$ | $L_{B12}$ | III-5067 | $L_{A454}$ | $L_{B30}$ | III-1998 | $L_{A445}$ | $L_{B12}$ | III-5143 | $L_{A360}$ | $L_{B31}$ |
| III-1923 | $L_{A370}$ | $L_{B12}$ | III-5068 | $L_{A455}$ | $L_{B30}$ | III-1999 | $L_{A446}$ | $L_{B12}$ | III-5144 | $L_{A361}$ | $L_{B31}$ |
| III-1924 | $L_{A371}$ | $L_{B12}$ | III-5069 | $L_{A456}$ | $L_{B30}$ | III-2000 | $L_{A447}$ | $L_{B12}$ | III-5145 | $L_{A362}$ | $L_{B31}$ |
| III-1925 | $L_{A372}$ | $L_{B12}$ | III-5070 | $L_{A457}$ | $L_{B30}$ | III-2001 | $L_{A448}$ | $L_{B12}$ | III-5146 | $L_{A363}$ | $L_{B31}$ |
| III-1926 | $L_{A373}$ | $L_{B12}$ | III-5071 | $L_{A458}$ | $L_{B30}$ | III-2002 | $L_{A449}$ | $L_{B12}$ | III-5147 | $L_{A364}$ | $L_{B31}$ |
| III-1927 | $L_{A374}$ | $L_{B12}$ | III-5072 | $L_{A459}$ | $L_{B30}$ | III-2003 | $L_{A450}$ | $L_{B12}$ | III-5148 | $L_{A365}$ | $L_{B31}$ |
| III-1928 | $L_{A375}$ | $L_{B12}$ | III-5073 | $L_{A460}$ | $L_{B30}$ | III-2004 | $L_{A451}$ | $L_{B12}$ | III-5149 | $L_{A366}$ | $L_{B31}$ |
| III-1929 | $L_{A376}$ | $L_{B12}$ | III-5074 | $L_{A461}$ | $L_{B30}$ | III-2005 | $L_{A452}$ | $L_{B12}$ | III-5150 | $L_{A367}$ | $L_{B31}$ |
| III-1930 | $L_{A377}$ | $L_{B12}$ | III-5075 | $L_{A462}$ | $L_{B30}$ | III-2006 | $L_{A453}$ | $L_{B12}$ | III-5151 | $L_{A368}$ | $L_{B31}$ |
| III-1931 | $L_{A378}$ | $L_{B12}$ | III-5076 | $L_{A463}$ | $L_{B30}$ | III-2007 | $L_{A454}$ | $L_{B12}$ | III-5152 | $L_{A369}$ | $L_{B31}$ |
| III-1932 | $L_{A379}$ | $L_{B12}$ | III-5077 | $L_{A464}$ | $L_{B30}$ | III-2008 | $L_{A455}$ | $L_{B12}$ | III-5153 | $L_{A370}$ | $L_{B31}$ |
| III-1933 | $L_{A380}$ | $L_{B12}$ | III-5078 | $L_{A465}$ | $L_{B30}$ | III-2009 | $L_{A456}$ | $L_{B12}$ | III-5154 | $L_{A371}$ | $L_{B31}$ |
| III-1934 | $L_{A381}$ | $L_{B12}$ | III-5079 | $L_{A466}$ | $L_{B30}$ | III-2010 | $L_{A457}$ | $L_{B12}$ | III-5155 | $L_{A372}$ | $L_{B31}$ |
| III-1935 | $L_{A382}$ | $L_{B12}$ | III-5080 | $L_{A467}$ | $L_{B30}$ | III-2011 | $L_{A458}$ | $L_{B12}$ | III-5156 | $L_{A373}$ | $L_{B31}$ |
| III-1936 | $L_{A383}$ | $L_{B12}$ | III-5081 | $L_{A468}$ | $L_{B30}$ | III-2012 | $L_{A459}$ | $L_{B12}$ | III-5157 | $L_{A374}$ | $L_{B31}$ |
| III-1937 | $L_{A384}$ | $L_{B12}$ | III-5082 | $L_{A469}$ | $L_{B30}$ | III-2013 | $L_{A460}$ | $L_{B12}$ | III-5158 | $L_{A375}$ | $L_{B31}$ |
| III-1938 | $L_{A385}$ | $L_{B12}$ | III-5083 | $L_{A470}$ | $L_{B30}$ | III-2014 | $L_{A461}$ | $L_{B12}$ | III-5159 | $L_{A376}$ | $L_{B31}$ |
| III-1939 | $L_{A386}$ | $L_{B12}$ | III-5084 | $L_{A471}$ | $L_{B30}$ | III-2015 | $L_{A462}$ | $L_{B12}$ | III-5160 | $L_{A377}$ | $L_{B31}$ |
| III-1940 | $L_{A387}$ | $L_{B12}$ | III-5085 | $L_{A472}$ | $L_{B30}$ | III-2016 | $L_{A463}$ | $L_{B12}$ | III-5161 | $L_{A378}$ | $L_{B31}$ |
| III-1941 | $L_{A388}$ | $L_{B12}$ | III-5086 | $L_{A473}$ | $L_{B30}$ | III-2017 | $L_{A464}$ | $L_{B12}$ | III-5162 | $L_{A379}$ | $L_{B31}$ |
| III-1942 | $L_{A389}$ | $L_{B12}$ | III-5087 | $L_{A474}$ | $L_{B30}$ | III-2018 | $L_{A465}$ | $L_{B12}$ | III-5163 | $L_{A380}$ | $L_{B31}$ |
| III-1943 | $L_{A390}$ | $L_{B12}$ | III-5088 | $L_{A475}$ | $L_{B30}$ | III-2019 | $L_{A466}$ | $L_{B12}$ | III-5164 | $L_{A381}$ | $L_{B31}$ |
| III-1944 | $L_{A391}$ | $L_{B12}$ | III-5089 | $L_{A476}$ | $L_{B30}$ | III-2020 | $L_{A467}$ | $L_{B12}$ | III-5165 | $L_{A382}$ | $L_{B31}$ |
| III-1945 | $L_{A392}$ | $L_{B12}$ | III-5090 | $L_{A477}$ | $L_{B30}$ | III-2021 | $L_{A468}$ | $L_{B12}$ | III-5166 | $L_{A383}$ | $L_{B31}$ |
| III-1946 | $L_{A393}$ | $L_{B12}$ | III-5091 | $L_{A478}$ | $L_{B30}$ | III-2022 | $L_{A469}$ | $L_{B12}$ | III-5167 | $L_{A384}$ | $L_{B31}$ |
| III-1947 | $L_{A394}$ | $L_{B12}$ | III-5092 | $L_{A479}$ | $L_{B30}$ | III-2023 | $L_{A470}$ | $L_{B12}$ | III-5168 | $L_{A385}$ | $L_{B31}$ |

| Compound Number | $L_A$ | $L_B$ | Compound Number | $L_A$ | $L_B$ | Compound Number | $L_A$ | $L_B$ | Compound Number | $L_A$ | $L_B$ |
|---|---|---|---|---|---|---|---|---|---|---|---|
| III-2024 | $L_{A471}$ | $L_{B12}$ | III-5169 | $L_{A386}$ | $L_{B31}$ | III-2100 | $L_{A377}$ | $L_{B13}$ | III-5245 | $L_{A462}$ | $L_{B31}$ |
| III-2025 | $L_{A472}$ | $L_{B12}$ | III-5170 | $L_{A387}$ | $L_{B31}$ | III-2101 | $L_{A378}$ | $L_{B13}$ | III-5246 | $L_{A463}$ | $L_{B31}$ |
| III-2026 | $L_{A473}$ | $L_{B12}$ | III-5171 | $L_{A388}$ | $L_{B31}$ | III-2102 | $L_{A379}$ | $L_{B13}$ | III-5247 | $L_{A464}$ | $L_{B31}$ |
| III-2027 | $L_{A474}$ | $L_{B12}$ | III-5172 | $L_{A389}$ | $L_{B31}$ | III-2103 | $L_{A380}$ | $L_{B13}$ | III-5248 | $L_{A465}$ | $L_{B31}$ |
| III-2028 | $L_{A475}$ | $L_{B12}$ | III-5173 | $L_{A390}$ | $L_{B31}$ | III-2104 | $L_{A381}$ | $L_{B13}$ | III-5249 | $L_{A466}$ | $L_{B31}$ |
| III-2029 | $L_{A476}$ | $L_{B12}$ | III-5174 | $L_{A391}$ | $L_{B31}$ | III-2105 | $L_{A382}$ | $L_{B13}$ | III-5250 | $L_{A467}$ | $L_{B31}$ |
| III-2030 | $L_{A477}$ | $L_{B12}$ | III-5175 | $L_{A392}$ | $L_{B31}$ | III-2106 | $L_{A383}$ | $L_{B13}$ | III-5251 | $L_{A468}$ | $L_{B31}$ |
| III-2031 | $L_{A478}$ | $L_{B12}$ | III-5176 | $L_{A393}$ | $L_{B31}$ | III-2107 | $L_{A384}$ | $L_{B13}$ | III-5252 | $L_{A469}$ | $L_{B31}$ |
| III-2032 | $L_{A479}$ | $L_{B12}$ | III-5177 | $L_{A394}$ | $L_{B31}$ | III-2108 | $L_{A385}$ | $L_{B13}$ | III-5253 | $L_{A470}$ | $L_{B31}$ |
| III-2033 | $L_{A480}$ | $L_{B12}$ | III-5178 | $L_{A395}$ | $L_{B31}$ | III-2109 | $L_{A386}$ | $L_{B13}$ | III-5254 | $L_{A471}$ | $L_{B31}$ |
| III-2034 | $L_{A481}$ | $L_{B12}$ | III-5179 | $L_{A396}$ | $L_{B31}$ | III-2110 | $L_{A387}$ | $L_{B13}$ | III-5255 | $L_{A472}$ | $L_{B31}$ |
| III-2035 | $L_{A482}$ | $L_{B12}$ | III-5180 | $L_{A397}$ | $L_{B31}$ | III-2111 | $L_{A388}$ | $L_{B13}$ | III-5256 | $L_{A473}$ | $L_{B31}$ |
| III-2036 | $L_{A483}$ | $L_{B12}$ | III-5181 | $L_{A398}$ | $L_{B31}$ | III-2112 | $L_{A389}$ | $L_{B13}$ | III-5257 | $L_{A474}$ | $L_{B31}$ |
| III-2037 | $L_{A484}$ | $L_{B12}$ | III-5182 | $L_{A399}$ | $L_{B31}$ | III-2113 | $L_{A390}$ | $L_{B13}$ | III-5258 | $L_{A475}$ | $L_{B31}$ |
| III-2038 | $L_{A485}$ | $L_{B12}$ | III-5183 | $L_{A400}$ | $L_{B31}$ | III-2114 | $L_{A391}$ | $L_{B13}$ | III-5259 | $L_{A476}$ | $L_{B31}$ |
| III-2039 | $L_{A486}$ | $L_{B12}$ | III-5184 | $L_{A401}$ | $L_{B31}$ | III-2115 | $L_{A392}$ | $L_{B13}$ | III-5260 | $L_{A477}$ | $L_{B31}$ |
| III-2040 | $L_{A487}$ | $L_{B12}$ | III-5185 | $L_{A402}$ | $L_{B31}$ | III-2116 | $L_{A393}$ | $L_{B13}$ | III-5261 | $L_{A478}$ | $L_{B31}$ |
| III-2041 | $L_{A318}$ | $L_{B13}$ | III-5186 | $L_{A403}$ | $L_{B31}$ | III-2117 | $L_{A394}$ | $L_{B13}$ | III-5262 | $L_{A479}$ | $L_{B31}$ |
| III-2042 | $L_{A319}$ | $L_{B13}$ | III-5187 | $L_{A404}$ | $L_{B31}$ | III-2118 | $L_{A395}$ | $L_{B13}$ | III-5263 | $L_{A480}$ | $L_{B31}$ |
| III-2043 | $L_{A320}$ | $L_{B13}$ | III-5188 | $L_{A405}$ | $L_{B31}$ | III-2119 | $L_{A396}$ | $L_{B13}$ | III-5264 | $L_{A481}$ | $L_{B31}$ |
| III-2044 | $L_{A321}$ | $L_{B13}$ | III-5189 | $L_{A406}$ | $L_{B31}$ | III-2120 | $L_{A397}$ | $L_{B13}$ | III-5265 | $L_{A482}$ | $L_{B31}$ |
| III-2045 | $L_{A322}$ | $L_{B13}$ | III-5190 | $L_{A407}$ | $L_{B31}$ | III-2121 | $L_{A398}$ | $L_{B13}$ | III-5266 | $L_{A483}$ | $L_{B31}$ |
| III-2046 | $L_{A323}$ | $L_{B13}$ | III-5191 | $L_{A408}$ | $L_{B31}$ | III-2122 | $L_{A399}$ | $L_{B13}$ | III-5267 | $L_{A484}$ | $L_{B31}$ |
| III-2047 | $L_{A324}$ | $L_{B13}$ | III-5192 | $L_{A409}$ | $L_{B31}$ | III-2123 | $L_{A400}$ | $L_{B13}$ | III-5268 | $L_{A485}$ | $L_{B31}$ |
| III-2048 | $L_{A325}$ | $L_{B13}$ | III-5193 | $L_{A410}$ | $L_{B31}$ | III-2124 | $L_{A401}$ | $L_{B13}$ | III-5269 | $L_{A486}$ | $L_{B31}$ |
| III-2049 | $L_{A326}$ | $L_{B13}$ | III-5194 | $L_{A411}$ | $L_{B31}$ | III-2125 | $L_{A402}$ | $L_{B13}$ | III-5270 | $L_{A487}$ | $L_{B31}$ |
| III-2050 | $L_{A327}$ | $L_{B13}$ | III-5195 | $L_{A412}$ | $L_{B31}$ | III-2126 | $L_{A403}$ | $L_{B13}$ | III-5271 | $L_{A318}$ | $L_{B32}$ |
| III-2051 | $L_{A328}$ | $L_{B13}$ | III-5196 | $L_{A413}$ | $L_{B31}$ | III-2127 | $L_{A404}$ | $L_{B13}$ | III-5272 | $L_{A319}$ | $L_{B32}$ |
| III-2052 | $L_{A329}$ | $L_{B13}$ | III-5197 | $L_{A414}$ | $L_{B31}$ | III-2128 | $L_{A405}$ | $L_{B13}$ | III-5273 | $L_{A320}$ | $L_{B32}$ |
| III-2053 | $L_{A330}$ | $L_{B13}$ | III-5198 | $L_{A415}$ | $L_{B31}$ | III-2129 | $L_{A406}$ | $L_{B13}$ | III-5274 | $L_{A321}$ | $L_{B32}$ |
| III-2054 | $L_{A331}$ | $L_{B13}$ | III-5199 | $L_{A416}$ | $L_{B31}$ | III-2130 | $L_{A407}$ | $L_{B13}$ | III-5275 | $L_{A322}$ | $L_{B32}$ |
| III-2055 | $L_{A332}$ | $L_{B13}$ | III-5200 | $L_{A417}$ | $L_{B31}$ | III-2131 | $L_{A408}$ | $L_{B13}$ | III-5276 | $L_{A323}$ | $L_{B32}$ |
| III-2056 | $L_{A333}$ | $L_{B13}$ | III-5201 | $L_{A418}$ | $L_{B31}$ | III-2132 | $L_{A409}$ | $L_{B13}$ | III-5277 | $L_{A324}$ | $L_{B32}$ |
| III-2057 | $L_{A334}$ | $L_{B13}$ | III-5202 | $L_{A419}$ | $L_{B31}$ | III-2133 | $L_{A410}$ | $L_{B13}$ | III-5278 | $L_{A325}$ | $L_{B32}$ |
| III-2058 | $L_{A335}$ | $L_{B13}$ | III-5203 | $L_{A420}$ | $L_{B31}$ | III-2134 | $L_{A411}$ | $L_{B13}$ | III-5279 | $L_{A326}$ | $L_{B32}$ |
| III-2059 | $L_{A336}$ | $L_{B13}$ | III-5204 | $L_{A421}$ | $L_{B31}$ | III-2135 | $L_{A412}$ | $L_{B13}$ | III-5280 | $L_{A327}$ | $L_{B32}$ |
| III-2060 | $L_{A337}$ | $L_{B13}$ | III-5205 | $L_{A422}$ | $L_{B31}$ | III-2136 | $L_{A413}$ | $L_{B13}$ | III-5281 | $L_{A328}$ | $L_{B32}$ |
| III-2061 | $L_{A338}$ | $L_{B13}$ | III-5206 | $L_{A423}$ | $L_{B31}$ | III-2137 | $L_{A414}$ | $L_{B13}$ | III-5282 | $L_{A329}$ | $L_{B32}$ |
| III-2062 | $L_{A339}$ | $L_{B13}$ | III-5207 | $L_{A424}$ | $L_{B31}$ | III-2138 | $L_{A415}$ | $L_{B13}$ | III-5283 | $L_{A330}$ | $L_{B32}$ |
| III-2063 | $L_{A340}$ | $L_{B13}$ | III-5208 | $L_{A425}$ | $L_{B31}$ | III-2139 | $L_{A416}$ | $L_{B13}$ | III-5284 | $L_{A331}$ | $L_{B32}$ |
| III-2064 | $L_{A341}$ | $L_{B13}$ | III-5209 | $L_{A426}$ | $L_{B31}$ | III-2140 | $L_{A417}$ | $L_{B13}$ | III-5285 | $L_{A332}$ | $L_{B32}$ |
| III-2065 | $L_{A342}$ | $L_{B13}$ | III-5210 | $L_{A427}$ | $L_{B31}$ | III-2141 | $L_{A418}$ | $L_{B13}$ | III-5286 | $L_{A333}$ | $L_{B32}$ |
| III-2066 | $L_{A343}$ | $L_{B13}$ | III-5211 | $L_{A428}$ | $L_{B31}$ | III-2142 | $L_{A419}$ | $L_{B13}$ | III-5287 | $L_{A334}$ | $L_{B32}$ |
| III-2067 | $L_{A344}$ | $L_{B13}$ | III-5212 | $L_{A429}$ | $L_{B31}$ | III-2143 | $L_{A420}$ | $L_{B13}$ | III-5288 | $L_{A335}$ | $L_{B32}$ |
| III-2068 | $L_{A345}$ | $L_{B13}$ | III-5213 | $L_{A430}$ | $L_{B31}$ | III-2144 | $L_{A421}$ | $L_{B13}$ | III-5289 | $L_{A336}$ | $L_{B32}$ |
| III-2069 | $L_{A346}$ | $L_{B13}$ | III-5214 | $L_{A431}$ | $L_{B31}$ | III-2145 | $L_{A422}$ | $L_{B13}$ | III-5290 | $L_{A337}$ | $L_{B32}$ |
| III-2070 | $L_{A347}$ | $L_{B13}$ | III-5215 | $L_{A432}$ | $L_{B31}$ | III-2146 | $L_{A423}$ | $L_{B13}$ | III-5291 | $L_{A338}$ | $L_{B32}$ |
| III-2071 | $L_{A348}$ | $L_{B13}$ | III-5216 | $L_{A433}$ | $L_{B31}$ | III-2147 | $L_{A424}$ | $L_{B13}$ | III-5292 | $L_{A339}$ | $L_{B32}$ |
| III-2072 | $L_{A349}$ | $L_{B13}$ | III-5217 | $L_{A434}$ | $L_{B31}$ | III-2148 | $L_{A425}$ | $L_{B13}$ | III-5293 | $L_{A340}$ | $L_{B32}$ |
| III-2073 | $L_{A350}$ | $L_{B13}$ | III-5218 | $L_{A435}$ | $L_{B31}$ | III-2149 | $L_{A426}$ | $L_{B13}$ | III-5294 | $L_{A341}$ | $L_{B32}$ |
| III-2074 | $L_{A351}$ | $L_{B13}$ | III-5219 | $L_{A436}$ | $L_{B31}$ | III-2150 | $L_{A427}$ | $L_{B13}$ | III-5295 | $L_{A342}$ | $L_{B32}$ |
| III-2075 | $L_{A352}$ | $L_{B13}$ | III-5220 | $L_{A437}$ | $L_{B31}$ | III-2151 | $L_{A428}$ | $L_{B13}$ | III-5296 | $L_{A343}$ | $L_{B32}$ |
| III-2076 | $L_{A353}$ | $L_{B13}$ | III-5221 | $L_{A438}$ | $L_{B31}$ | III-2152 | $L_{A429}$ | $L_{B13}$ | III-5297 | $L_{A344}$ | $L_{B32}$ |
| III-2077 | $L_{A354}$ | $L_{B13}$ | III-5222 | $L_{A439}$ | $L_{B31}$ | III-2153 | $L_{A430}$ | $L_{B13}$ | III-5298 | $L_{A345}$ | $L_{B32}$ |
| III-2078 | $L_{A355}$ | $L_{B13}$ | III-5223 | $L_{A440}$ | $L_{B31}$ | III-2154 | $L_{A431}$ | $L_{B13}$ | III-5299 | $L_{A346}$ | $L_{B32}$ |
| III-2079 | $L_{A356}$ | $L_{B13}$ | III-5224 | $L_{A441}$ | $L_{B31}$ | III-2155 | $L_{A432}$ | $L_{B13}$ | III-5300 | $L_{A347}$ | $L_{B32}$ |
| III-2080 | $L_{A357}$ | $L_{B13}$ | III-5225 | $L_{A442}$ | $L_{B31}$ | III-2156 | $L_{A433}$ | $L_{B13}$ | III-5301 | $L_{A348}$ | $L_{B32}$ |
| III-2081 | $L_{A358}$ | $L_{B13}$ | III-5226 | $L_{A443}$ | $L_{B31}$ | III-2157 | $L_{A434}$ | $L_{B13}$ | III-5302 | $L_{A349}$ | $L_{B32}$ |
| III-2082 | $L_{A359}$ | $L_{B13}$ | III-5227 | $L_{A444}$ | $L_{B31}$ | III-2158 | $L_{A435}$ | $L_{B13}$ | III-5303 | $L_{A350}$ | $L_{B32}$ |
| III-2083 | $L_{A360}$ | $L_{B13}$ | III-5228 | $L_{A445}$ | $L_{B31}$ | III-2159 | $L_{A436}$ | $L_{B13}$ | III-5304 | $L_{A351}$ | $L_{B32}$ |
| III-2084 | $L_{A361}$ | $L_{B13}$ | III-5229 | $L_{A446}$ | $L_{B31}$ | III-2160 | $L_{A437}$ | $L_{B13}$ | III-5305 | $L_{A352}$ | $L_{B32}$ |
| III-2085 | $L_{A362}$ | $L_{B13}$ | III-5230 | $L_{A447}$ | $L_{B31}$ | III-2161 | $L_{A438}$ | $L_{B13}$ | III-5306 | $L_{A353}$ | $L_{B32}$ |
| III-2086 | $L_{A363}$ | $L_{B13}$ | III-5231 | $L_{A448}$ | $L_{B31}$ | III-2162 | $L_{A439}$ | $L_{B13}$ | III-5307 | $L_{A354}$ | $L_{B32}$ |
| III-2087 | $L_{A364}$ | $L_{B13}$ | III-5232 | $L_{A449}$ | $L_{B31}$ | III-2163 | $L_{A440}$ | $L_{B13}$ | III-5308 | $L_{A355}$ | $L_{B32}$ |
| III-2088 | $L_{A365}$ | $L_{B13}$ | III-5233 | $L_{A450}$ | $L_{B31}$ | III-2164 | $L_{A441}$ | $L_{B13}$ | III-5309 | $L_{A356}$ | $L_{B32}$ |
| III-2089 | $L_{A366}$ | $L_{B13}$ | III-5234 | $L_{A451}$ | $L_{B31}$ | III-2165 | $L_{A442}$ | $L_{B13}$ | III-5310 | $L_{A357}$ | $L_{B32}$ |
| III-2090 | $L_{A367}$ | $L_{B13}$ | III-5235 | $L_{A452}$ | $L_{B31}$ | III-2166 | $L_{A443}$ | $L_{B13}$ | III-5311 | $L_{A358}$ | $L_{B32}$ |
| III-2091 | $L_{A368}$ | $L_{B13}$ | III-5236 | $L_{A453}$ | $L_{B31}$ | III-2167 | $L_{A444}$ | $L_{B13}$ | III-5312 | $L_{A359}$ | $L_{B32}$ |
| III-2092 | $L_{A369}$ | $L_{B13}$ | III-5237 | $L_{A454}$ | $L_{B31}$ | III-2168 | $L_{A445}$ | $L_{B13}$ | III-5313 | $L_{A360}$ | $L_{B32}$ |
| III-2093 | $L_{A370}$ | $L_{B13}$ | III-5238 | $L_{A455}$ | $L_{B31}$ | III-2169 | $L_{A446}$ | $L_{B13}$ | III-5314 | $L_{A361}$ | $L_{B32}$ |
| III-2094 | $L_{A371}$ | $L_{B13}$ | III-5239 | $L_{A456}$ | $L_{B31}$ | III-2170 | $L_{A447}$ | $L_{B13}$ | III-5315 | $L_{A362}$ | $L_{B32}$ |
| III-2095 | $L_{A372}$ | $L_{B13}$ | III-5240 | $L_{A457}$ | $L_{B31}$ | III-2171 | $L_{A448}$ | $L_{B13}$ | III-5316 | $L_{A363}$ | $L_{B32}$ |
| III-2096 | $L_{A373}$ | $L_{B13}$ | III-5241 | $L_{A458}$ | $L_{B31}$ | III-2172 | $L_{A449}$ | $L_{B13}$ | III-5317 | $L_{A364}$ | $L_{B32}$ |
| III-2097 | $L_{A374}$ | $L_{B13}$ | III-5242 | $L_{A459}$ | $L_{B31}$ | III-2173 | $L_{A450}$ | $L_{B13}$ | III-5318 | $L_{A365}$ | $L_{B32}$ |
| III-2098 | $L_{A375}$ | $L_{B13}$ | III-5243 | $L_{A460}$ | $L_{B31}$ | III-2174 | $L_{A451}$ | $L_{B13}$ | III-5319 | $L_{A366}$ | $L_{B32}$ |
| III-2099 | $L_{A376}$ | $L_{B13}$ | III-5244 | $L_{A461}$ | $L_{B31}$ | III-2175 | $L_{A452}$ | $L_{B13}$ | III-5320 | $L_{A367}$ | $L_{B32}$ |

-continued

| Compound Number | $L_A$ | $L_B$ | Compound Number | $L_A$ | $L_B$ |
|---|---|---|---|---|---|
| III-2176 | $L_{A453}$ | $L_{B13}$ | III-5321 | $L_{A368}$ | $L_{B32}$ |
| III-2177 | $L_{A454}$ | $L_{B13}$ | III-5322 | $L_{A369}$ | $L_{B32}$ |
| III-2178 | $L_{A455}$ | $L_{B13}$ | III-5323 | $L_{A370}$ | $L_{B32}$ |
| III-2179 | $L_{A456}$ | $L_{B13}$ | III-5324 | $L_{A371}$ | $L_{B32}$ |
| III-2180 | $L_{A457}$ | $L_{B13}$ | III-5325 | $L_{A372}$ | $L_{B32}$ |
| III-2181 | $L_{A458}$ | $L_{B13}$ | III-5326 | $L_{A373}$ | $L_{B32}$ |
| III-2182 | $L_{A459}$ | $L_{B13}$ | III-5327 | $L_{A374}$ | $L_{B32}$ |
| III-2183 | $L_{A460}$ | $L_{B13}$ | III-5328 | $L_{A375}$ | $L_{B32}$ |
| III-2184 | $L_{A461}$ | $L_{B13}$ | III-5329 | $L_{A376}$ | $L_{B32}$ |
| III-2185 | $L_{A462}$ | $L_{B13}$ | III-5330 | $L_{A377}$ | $L_{B32}$ |
| III-2186 | $L_{A463}$ | $L_{B13}$ | III-5331 | $L_{A378}$ | $L_{B32}$ |
| III-2187 | $L_{A464}$ | $L_{B13}$ | III-5332 | $L_{A379}$ | $L_{B32}$ |
| III-2188 | $L_{A465}$ | $L_{B13}$ | III-5333 | $L_{A380}$ | $L_{B32}$ |
| III-2189 | $L_{A466}$ | $L_{B13}$ | III-5334 | $L_{A381}$ | $L_{B32}$ |
| III-2190 | $L_{A467}$ | $L_{B13}$ | III-5335 | $L_{A382}$ | $L_{B32}$ |
| III-2191 | $L_{A468}$ | $L_{B13}$ | III-5336 | $L_{A383}$ | $L_{B32}$ |
| III-2192 | $L_{A469}$ | $L_{B13}$ | III-5337 | $L_{A384}$ | $L_{B32}$ |
| III-2193 | $L_{A470}$ | $L_{B13}$ | III-5338 | $L_{A385}$ | $L_{B32}$ |
| III-2194 | $L_{A471}$ | $L_{B13}$ | III-5339 | $L_{A386}$ | $L_{B32}$ |
| III-2195 | $L_{A472}$ | $L_{B13}$ | III-5340 | $L_{A387}$ | $L_{B32}$ |
| III-2196 | $L_{A473}$ | $L_{B13}$ | III-5341 | $L_{A388}$ | $L_{B32}$ |
| III-2197 | $L_{A474}$ | $L_{B13}$ | III-5342 | $L_{A389}$ | $L_{B32}$ |
| III-2198 | $L_{A475}$ | $L_{B13}$ | III-5343 | $L_{A390}$ | $L_{B32}$ |
| III-2199 | $L_{A476}$ | $L_{B13}$ | III-5344 | $L_{A391}$ | $L_{B32}$ |
| III-2200 | $L_{A477}$ | $L_{B13}$ | III-5345 | $L_{A392}$ | $L_{B32}$ |
| III-2201 | $L_{A478}$ | $L_{B13}$ | III-5346 | $L_{A393}$ | $L_{B32}$ |
| III-2202 | $L_{A479}$ | $L_{B13}$ | III-5347 | $L_{A394}$ | $L_{B32}$ |
| III-2203 | $L_{A480}$ | $L_{B13}$ | III-5348 | $L_{A395}$ | $L_{B32}$ |
| III-2204 | $L_{A481}$ | $L_{B13}$ | III-5349 | $L_{A396}$ | $L_{B32}$ |
| III-2205 | $L_{A482}$ | $L_{B13}$ | III-5350 | $L_{A397}$ | $L_{B32}$ |
| III-2206 | $L_{A483}$ | $L_{B13}$ | III-5351 | $L_{A398}$ | $L_{B32}$ |
| III-2207 | $L_{A484}$ | $L_{B13}$ | III-5352 | $L_{A399}$ | $L_{B32}$ |
| III-2208 | $L_{A485}$ | $L_{B13}$ | III-5353 | $L_{A400}$ | $L_{B32}$ |
| III-2209 | $L_{A486}$ | $L_{B13}$ | III-5354 | $L_{A401}$ | $L_{B32}$ |
| III-2210 | $L_{A487}$ | $L_{B13}$ | III-5355 | $L_{A402}$ | $L_{B32}$ |
| III-2211 | $L_{A318}$ | $L_{B14}$ | III-5356 | $L_{A403}$ | $L_{B32}$ |
| III-2212 | $L_{A319}$ | $L_{B14}$ | III-5357 | $L_{A404}$ | $L_{B32}$ |
| III-2213 | $L_{A320}$ | $L_{B14}$ | III-5358 | $L_{A405}$ | $L_{B32}$ |
| III-2214 | $L_{A321}$ | $L_{B14}$ | III-5359 | $L_{A406}$ | $L_{B32}$ |
| III-2215 | $L_{A322}$ | $L_{B14}$ | III-5360 | $L_{A407}$ | $L_{B32}$ |
| III-2216 | $L_{A323}$ | $L_{B14}$ | III-5361 | $L_{A408}$ | $L_{B32}$ |
| III-2217 | $L_{A324}$ | $L_{B14}$ | III-5362 | $L_{A409}$ | $L_{B32}$ |
| III-2218 | $L_{A325}$ | $L_{B14}$ | III-5363 | $L_{A410}$ | $L_{B32}$ |
| III-2219 | $L_{A326}$ | $L_{B14}$ | III-5364 | $L_{A411}$ | $L_{B32}$ |
| III-2220 | $L_{A327}$ | $L_{B14}$ | III-5365 | $L_{A412}$ | $L_{B32}$ |
| III-2221 | $L_{A328}$ | $L_{B14}$ | III-5366 | $L_{A413}$ | $L_{B32}$ |
| III-2222 | $L_{A329}$ | $L_{B14}$ | III-5367 | $L_{A414}$ | $L_{B32}$ |
| III-2223 | $L_{A330}$ | $L_{B14}$ | III-5368 | $L_{A415}$ | $L_{B32}$ |
| III-2224 | $L_{A331}$ | $L_{B14}$ | III-5369 | $L_{A416}$ | $L_{B32}$ |
| III-2225 | $L_{A332}$ | $L_{B14}$ | III-5370 | $L_{A417}$ | $L_{B32}$ |
| III-2226 | $L_{A333}$ | $L_{B14}$ | III-5371 | $L_{A418}$ | $L_{B32}$ |
| III-2227 | $L_{A334}$ | $L_{B14}$ | III-5372 | $L_{A419}$ | $L_{B32}$ |
| III-2228 | $L_{A335}$ | $L_{B14}$ | III-5373 | $L_{A420}$ | $L_{B32}$ |
| III-2229 | $L_{A336}$ | $L_{B14}$ | III-5374 | $L_{A421}$ | $L_{B32}$ |
| III-2230 | $L_{A337}$ | $L_{B14}$ | III-5375 | $L_{A422}$ | $L_{B32}$ |
| III-2231 | $L_{A338}$ | $L_{B14}$ | III-5376 | $L_{A423}$ | $L_{B32}$ |
| III-2232 | $L_{A339}$ | $L_{B14}$ | III-5377 | $L_{A424}$ | $L_{B32}$ |
| III-2233 | $L_{A340}$ | $L_{B14}$ | III-5378 | $L_{A425}$ | $L_{B32}$ |
| III-2234 | $L_{A341}$ | $L_{B14}$ | III-5379 | $L_{A426}$ | $L_{B32}$ |
| III-2235 | $L_{A342}$ | $L_{B14}$ | III-5380 | $L_{A427}$ | $L_{B32}$ |
| III-2236 | $L_{A343}$ | $L_{B14}$ | III-5381 | $L_{A428}$ | $L_{B32}$ |
| III-2237 | $L_{A344}$ | $L_{B14}$ | III-5382 | $L_{A429}$ | $L_{B32}$ |
| III-2238 | $L_{A345}$ | $L_{B14}$ | III-5383 | $L_{A430}$ | $L_{B32}$ |
| III-2239 | $L_{A346}$ | $L_{B14}$ | III-5384 | $L_{A431}$ | $L_{B32}$ |
| III-2240 | $L_{A347}$ | $L_{B14}$ | III-5385 | $L_{A432}$ | $L_{B32}$ |
| III-2241 | $L_{A348}$ | $L_{B14}$ | III-5386 | $L_{A433}$ | $L_{B32}$ |
| III-2242 | $L_{A349}$ | $L_{B14}$ | III-5387 | $L_{A434}$ | $L_{B32}$ |
| III-2243 | $L_{A350}$ | $L_{B14}$ | III-5388 | $L_{A435}$ | $L_{B32}$ |
| III-2244 | $L_{A351}$ | $L_{B14}$ | III-5389 | $L_{A436}$ | $L_{B32}$ |
| III-2245 | $L_{A352}$ | $L_{B14}$ | III-5390 | $L_{A437}$ | $L_{B32}$ |
| III-2246 | $L_{A353}$ | $L_{B14}$ | III-5391 | $L_{A438}$ | $L_{B32}$ |
| III-2247 | $L_{A354}$ | $L_{B14}$ | III-5392 | $L_{A439}$ | $L_{B32}$ |
| III-2248 | $L_{A355}$ | $L_{B14}$ | III-5393 | $L_{A440}$ | $L_{B32}$ |
| III-2249 | $L_{A356}$ | $L_{B14}$ | III-5394 | $L_{A441}$ | $L_{B32}$ |
| III-2250 | $L_{A357}$ | $L_{B14}$ | III-5395 | $L_{A442}$ | $L_{B32}$ |
| III-2251 | $L_{A358}$ | $L_{B14}$ | III-5396 | $L_{A443}$ | $L_{B32}$ |

-continued

| Compound Number | $L_A$ | $L_B$ | Compound Number | $L_A$ | $L_B$ |
|---|---|---|---|---|---|
| III-2252 | $L_{A359}$ | $L_{B14}$ | III-5397 | $L_{A444}$ | $L_{B32}$ |
| III-2253 | $L_{A360}$ | $L_{B14}$ | III-5398 | $L_{A445}$ | $L_{B32}$ |
| III-2254 | $L_{A361}$ | $L_{B14}$ | III-5399 | $L_{A446}$ | $L_{B32}$ |
| III-2255 | $L_{A362}$ | $L_{B14}$ | III-5400 | $L_{A447}$ | $L_{B32}$ |
| III-2256 | $L_{A363}$ | $L_{B14}$ | III-5401 | $L_{A448}$ | $L_{B32}$ |
| III-2257 | $L_{A364}$ | $L_{B14}$ | III-5402 | $L_{A449}$ | $L_{B32}$ |
| III-2258 | $L_{A365}$ | $L_{B14}$ | III-5403 | $L_{A450}$ | $L_{B32}$ |
| III-2259 | $L_{A366}$ | $L_{B14}$ | III-5404 | $L_{A451}$ | $L_{B32}$ |
| III-2260 | $L_{A367}$ | $L_{B14}$ | III-5405 | $L_{A452}$ | $L_{B32}$ |
| III-2261 | $L_{A368}$ | $L_{B14}$ | III-5406 | $L_{A453}$ | $L_{B32}$ |
| III-2262 | $L_{A369}$ | $L_{B14}$ | III-5407 | $L_{A454}$ | $L_{B32}$ |
| III-2263 | $L_{A370}$ | $L_{B14}$ | III-5408 | $L_{A455}$ | $L_{B32}$ |
| III-2264 | $L_{A371}$ | $L_{B14}$ | III-5409 | $L_{A456}$ | $L_{B32}$ |
| III-2265 | $L_{A372}$ | $L_{B14}$ | III-5410 | $L_{A457}$ | $L_{B32}$ |
| III-2266 | $L_{A373}$ | $L_{B14}$ | III-5411 | $L_{A458}$ | $L_{B32}$ |
| III-2267 | $L_{A374}$ | $L_{B14}$ | III-5412 | $L_{A459}$ | $L_{B32}$ |
| III-2268 | $L_{A375}$ | $L_{B14}$ | III-5413 | $L_{A460}$ | $L_{B32}$ |
| III-2269 | $L_{A376}$ | $L_{B14}$ | III-5414 | $L_{A461}$ | $L_{B32}$ |
| III-2270 | $L_{A377}$ | $L_{B14}$ | III-5415 | $L_{A462}$ | $L_{B32}$ |
| III-2271 | $L_{A378}$ | $L_{B14}$ | III-5416 | $L_{A463}$ | $L_{B32}$ |
| III-2272 | $L_{A379}$ | $L_{B14}$ | III-5417 | $L_{A464}$ | $L_{B32}$ |
| III-2273 | $L_{A380}$ | $L_{B14}$ | III-5418 | $L_{A465}$ | $L_{B32}$ |
| III-2274 | $L_{A381}$ | $L_{B14}$ | III-5419 | $L_{A466}$ | $L_{B32}$ |
| III-2275 | $L_{A382}$ | $L_{B14}$ | III-5420 | $L_{A467}$ | $L_{B32}$ |
| III-2276 | $L_{A383}$ | $L_{B14}$ | III-5421 | $L_{A468}$ | $L_{B32}$ |
| III-2277 | $L_{A384}$ | $L_{B14}$ | III-5422 | $L_{A469}$ | $L_{B32}$ |
| III-2278 | $L_{A385}$ | $L_{B14}$ | III-5423 | $L_{A470}$ | $L_{B32}$ |
| III-2279 | $L_{A386}$ | $L_{B14}$ | III-5424 | $L_{A471}$ | $L_{B32}$ |
| III-2280 | $L_{A387}$ | $L_{B14}$ | III-5425 | $L_{A472}$ | $L_{B32}$ |
| III-2281 | $L_{A388}$ | $L_{B14}$ | III-5426 | $L_{A473}$ | $L_{B32}$ |
| III-2282 | $L_{A389}$ | $L_{B14}$ | III-5427 | $L_{A474}$ | $L_{B32}$ |
| III-2283 | $L_{A390}$ | $L_{B14}$ | III-5428 | $L_{A475}$ | $L_{B32}$ |
| III-2284 | $L_{A391}$ | $L_{B14}$ | III-5429 | $L_{A476}$ | $L_{B32}$ |
| III-2285 | $L_{A392}$ | $L_{B14}$ | III-5430 | $L_{A477}$ | $L_{B32}$ |
| III-2286 | $L_{A393}$ | $L_{B14}$ | III-5431 | $L_{A478}$ | $L_{B32}$ |
| III-2287 | $L_{A394}$ | $L_{B14}$ | III-5432 | $L_{A479}$ | $L_{B32}$ |
| III-2288 | $L_{A395}$ | $L_{B14}$ | III-5433 | $L_{A480}$ | $L_{B32}$ |
| III-2289 | $L_{A396}$ | $L_{B14}$ | III-5434 | $L_{A481}$ | $L_{B32}$ |
| III-2290 | $L_{A397}$ | $L_{B14}$ | III-5435 | $L_{A482}$ | $L_{B32}$ |
| III-2291 | $L_{A398}$ | $L_{B14}$ | III-5436 | $L_{A483}$ | $L_{B32}$ |
| III-2292 | $L_{A399}$ | $L_{B14}$ | III-5437 | $L_{A484}$ | $L_{B32}$ |
| III-2293 | $L_{A400}$ | $L_{B14}$ | III-5438 | $L_{A485}$ | $L_{B32}$ |
| III-2294 | $L_{A401}$ | $L_{B14}$ | III-5439 | $L_{A486}$ | $L_{B32}$ |
| III-2295 | $L_{A402}$ | $L_{B14}$ | III-5440 | $L_{A487}$ | $L_{B32}$ |
| III-2296 | $L_{A403}$ | $L_{B14}$ | III-5441 | $L_{A318}$ | $L_{B33}$ |
| III-2297 | $L_{A404}$ | $L_{B14}$ | III-5442 | $L_{A319}$ | $L_{B33}$ |
| III-2298 | $L_{A405}$ | $L_{B14}$ | III-5443 | $L_{A320}$ | $L_{B33}$ |
| III-2299 | $L_{A406}$ | $L_{B14}$ | III-5444 | $L_{A321}$ | $L_{B33}$ |
| III-2300 | $L_{A407}$ | $L_{B14}$ | III-5445 | $L_{A322}$ | $L_{B33}$ |
| III-2301 | $L_{A408}$ | $L_{B14}$ | III-5446 | $L_{A323}$ | $L_{B33}$ |
| III-2302 | $L_{A409}$ | $L_{B14}$ | III-5447 | $L_{A324}$ | $L_{B33}$ |
| III-2303 | $L_{A410}$ | $L_{B14}$ | III-5448 | $L_{A325}$ | $L_{B33}$ |
| III-2304 | $L_{A411}$ | $L_{B14}$ | III-5449 | $L_{A326}$ | $L_{B33}$ |
| III-2305 | $L_{A412}$ | $L_{B14}$ | III-5450 | $L_{A327}$ | $L_{B33}$ |
| III-2306 | $L_{A413}$ | $L_{B14}$ | III-5451 | $L_{A328}$ | $L_{B33}$ |
| III-2307 | $L_{A414}$ | $L_{B14}$ | III-5452 | $L_{A329}$ | $L_{B33}$ |
| III-2308 | $L_{A415}$ | $L_{B14}$ | III-5453 | $L_{A330}$ | $L_{B33}$ |
| III-2309 | $L_{A416}$ | $L_{B14}$ | III-5454 | $L_{A331}$ | $L_{B33}$ |
| III-2310 | $L_{A417}$ | $L_{B14}$ | III-5455 | $L_{A332}$ | $L_{B33}$ |
| III-2311 | $L_{A418}$ | $L_{B14}$ | III-5456 | $L_{A333}$ | $L_{B33}$ |
| III-2312 | $L_{A419}$ | $L_{B14}$ | III-5457 | $L_{A334}$ | $L_{B33}$ |
| III-2313 | $L_{A420}$ | $L_{B14}$ | III-5458 | $L_{A335}$ | $L_{B33}$ |
| III-2314 | $L_{A421}$ | $L_{B14}$ | III-5459 | $L_{A336}$ | $L_{B33}$ |
| III-2315 | $L_{A422}$ | $L_{B14}$ | III-5460 | $L_{A337}$ | $L_{B33}$ |
| III-2316 | $L_{A423}$ | $L_{B14}$ | III-5461 | $L_{A338}$ | $L_{B33}$ |
| III-2317 | $L_{A424}$ | $L_{B14}$ | III-5462 | $L_{A339}$ | $L_{B33}$ |
| III-2318 | $L_{A425}$ | $L_{B14}$ | III-5463 | $L_{A340}$ | $L_{B33}$ |
| III-2319 | $L_{A426}$ | $L_{B14}$ | III-5464 | $L_{A341}$ | $L_{B33}$ |
| III-2320 | $L_{A427}$ | $L_{B14}$ | III-5465 | $L_{A342}$ | $L_{B33}$ |
| III-2321 | $L_{A428}$ | $L_{B14}$ | III-5466 | $L_{A343}$ | $L_{B33}$ |
| III-2322 | $L_{A429}$ | $L_{B14}$ | III-5467 | $L_{A344}$ | $L_{B33}$ |
| III-2323 | $L_{A430}$ | $L_{B14}$ | III-5468 | $L_{A345}$ | $L_{B33}$ |
| III-2324 | $L_{A431}$ | $L_{B14}$ | III-5469 | $L_{A346}$ | $L_{B33}$ |
| III-2325 | $L_{A432}$ | $L_{B14}$ | III-5470 | $L_{A347}$ | $L_{B33}$ |
| III-2326 | $L_{A433}$ | $L_{B14}$ | III-5471 | $L_{A348}$ | $L_{B33}$ |
| III-2327 | $L_{A434}$ | $L_{B14}$ | III-5472 | $L_{A349}$ | $L_{B33}$ |

-continued

| Compound Number | $L_A$ | $L_B$ | Compound Number | $L_A$ | $L_B$ | Compound Number | $L_A$ | $L_B$ | Compound Number | $L_A$ | $L_B$ |
|---|---|---|---|---|---|---|---|---|---|---|---|
| III-2328 | $L_{A435}$ | $L_{B14}$ | III-5473 | $L_{A350}$ | $L_{B33}$ | III-2404 | $L_{A341}$ | $L_{B15}$ | III-5549 | $L_{A426}$ | $L_{B33}$ |
| III-2329 | $L_{A436}$ | $L_{B14}$ | III-5474 | $L_{A351}$ | $L_{B33}$ | III-2405 | $L_{A342}$ | $L_{B15}$ | III-5550 | $L_{A427}$ | $L_{B33}$ |
| III-2330 | $L_{A437}$ | $L_{B14}$ | III-5475 | $L_{A352}$ | $L_{B33}$ | III-2406 | $L_{A343}$ | $L_{B15}$ | III-5551 | $L_{A428}$ | $L_{B33}$ |
| III-2331 | $L_{A438}$ | $L_{B14}$ | III-5476 | $L_{A353}$ | $L_{B33}$ | III-2407 | $L_{A344}$ | $L_{B15}$ | III-5552 | $L_{A429}$ | $L_{B33}$ |
| III-2332 | $L_{A439}$ | $L_{B14}$ | III-5477 | $L_{A354}$ | $L_{B33}$ | III-2408 | $L_{A345}$ | $L_{B15}$ | III-5553 | $L_{A430}$ | $L_{B33}$ |
| III-2333 | $L_{A440}$ | $L_{B14}$ | III-5478 | $L_{A355}$ | $L_{B33}$ | III-2409 | $L_{A346}$ | $L_{B15}$ | III-5554 | $L_{A431}$ | $L_{B33}$ |
| III-2334 | $L_{A441}$ | $L_{B14}$ | III-5479 | $L_{A356}$ | $L_{B33}$ | III-2410 | $L_{A347}$ | $L_{B15}$ | III-5555 | $L_{A432}$ | $L_{B33}$ |
| III-2335 | $L_{A442}$ | $L_{B14}$ | III-5480 | $L_{A357}$ | $L_{B33}$ | III-2411 | $L_{A348}$ | $L_{B15}$ | III-5556 | $L_{A433}$ | $L_{B33}$ |
| III-2336 | $L_{A443}$ | $L_{B14}$ | III-5481 | $L_{A358}$ | $L_{B33}$ | III-2412 | $L_{A349}$ | $L_{B15}$ | III-5557 | $L_{A434}$ | $L_{B33}$ |
| III-2337 | $L_{A444}$ | $L_{B14}$ | III-5482 | $L_{A359}$ | $L_{B33}$ | III-2413 | $L_{A350}$ | $L_{B15}$ | III-5558 | $L_{A435}$ | $L_{B33}$ |
| III-2338 | $L_{A445}$ | $L_{B14}$ | III-5483 | $L_{A360}$ | $L_{B33}$ | III-2414 | $L_{A351}$ | $L_{B15}$ | III-5559 | $L_{A436}$ | $L_{B33}$ |
| III-2339 | $L_{A446}$ | $L_{B14}$ | III-5484 | $L_{A361}$ | $L_{B33}$ | III-2415 | $L_{A352}$ | $L_{B15}$ | III-5560 | $L_{A437}$ | $L_{B33}$ |
| III-2340 | $L_{A447}$ | $L_{B14}$ | III-5485 | $L_{A362}$ | $L_{B33}$ | III-2416 | $L_{A353}$ | $L_{B15}$ | III-5561 | $L_{A438}$ | $L_{B33}$ |
| III-2341 | $L_{A448}$ | $L_{B14}$ | III-5486 | $L_{A363}$ | $L_{B33}$ | III-2417 | $L_{A354}$ | $L_{B15}$ | III-5562 | $L_{A439}$ | $L_{B33}$ |
| III-2342 | $L_{A449}$ | $L_{B14}$ | III-5487 | $L_{A364}$ | $L_{B33}$ | III-2418 | $L_{A355}$ | $L_{B15}$ | III-5563 | $L_{A440}$ | $L_{B33}$ |
| III-2343 | $L_{A450}$ | $L_{B14}$ | III-5488 | $L_{A365}$ | $L_{B33}$ | III-2419 | $L_{A356}$ | $L_{B15}$ | III-5564 | $L_{A441}$ | $L_{B33}$ |
| III-2344 | $L_{A451}$ | $L_{B14}$ | III-5489 | $L_{A366}$ | $L_{B33}$ | III-2420 | $L_{A357}$ | $L_{B15}$ | III-5565 | $L_{A442}$ | $L_{B33}$ |
| III-2345 | $L_{A452}$ | $L_{B14}$ | III-5490 | $L_{A367}$ | $L_{B33}$ | III-2421 | $L_{A358}$ | $L_{B15}$ | III-5566 | $L_{A443}$ | $L_{B33}$ |
| III-2346 | $L_{A453}$ | $L_{B14}$ | III-5491 | $L_{A368}$ | $L_{B33}$ | III-2422 | $L_{A359}$ | $L_{B15}$ | III-5567 | $L_{A444}$ | $L_{B33}$ |
| III-2347 | $L_{A454}$ | $L_{B14}$ | III-5492 | $L_{A369}$ | $L_{B33}$ | III-2423 | $L_{A360}$ | $L_{B15}$ | III-5568 | $L_{A445}$ | $L_{B33}$ |
| III-2348 | $L_{A455}$ | $L_{B14}$ | III-5493 | $L_{A370}$ | $L_{B33}$ | III-2424 | $L_{A361}$ | $L_{B15}$ | III-5569 | $L_{A446}$ | $L_{B33}$ |
| III-2349 | $L_{A456}$ | $L_{B14}$ | III-5494 | $L_{A371}$ | $L_{B33}$ | III-2425 | $L_{A362}$ | $L_{B15}$ | III-5570 | $L_{A447}$ | $L_{B33}$ |
| III-2350 | $L_{A457}$ | $L_{B14}$ | III-5495 | $L_{A372}$ | $L_{B33}$ | III-2426 | $L_{A363}$ | $L_{B15}$ | III-5571 | $L_{A448}$ | $L_{B33}$ |
| III-2351 | $L_{A458}$ | $L_{B14}$ | III-5496 | $L_{A373}$ | $L_{B33}$ | III-2427 | $L_{A364}$ | $L_{B15}$ | III-5572 | $L_{A449}$ | $L_{B33}$ |
| III-2352 | $L_{A459}$ | $L_{B14}$ | III-5497 | $L_{A374}$ | $L_{B33}$ | III-2428 | $L_{A365}$ | $L_{B15}$ | III-5573 | $L_{A450}$ | $L_{B33}$ |
| III-2353 | $L_{A460}$ | $L_{B14}$ | III-5498 | $L_{A375}$ | $L_{B33}$ | III-2429 | $L_{A366}$ | $L_{B15}$ | III-5574 | $L_{A451}$ | $L_{B33}$ |
| III-2354 | $L_{A461}$ | $L_{B14}$ | III-5499 | $L_{A376}$ | $L_{B33}$ | III-2430 | $L_{A367}$ | $L_{B15}$ | III-5575 | $L_{A452}$ | $L_{B33}$ |
| III-2355 | $L_{A462}$ | $L_{B14}$ | III-5500 | $L_{A377}$ | $L_{B33}$ | III-2431 | $L_{A368}$ | $L_{B15}$ | III-5576 | $L_{A453}$ | $L_{B33}$ |
| III-2356 | $L_{A463}$ | $L_{B14}$ | III-5501 | $L_{A378}$ | $L_{B33}$ | III-2432 | $L_{A369}$ | $L_{B15}$ | III-5577 | $L_{A454}$ | $L_{B33}$ |
| III-2357 | $L_{A464}$ | $L_{B14}$ | III-5502 | $L_{A379}$ | $L_{B33}$ | III-2433 | $L_{A370}$ | $L_{B15}$ | III-5578 | $L_{A455}$ | $L_{B33}$ |
| III-2358 | $L_{A465}$ | $L_{B14}$ | III-5503 | $L_{A380}$ | $L_{B33}$ | III-2434 | $L_{A371}$ | $L_{B15}$ | III-5579 | $L_{A456}$ | $L_{B33}$ |
| III-2359 | $L_{A466}$ | $L_{B14}$ | III-5504 | $L_{A381}$ | $L_{B33}$ | III-2435 | $L_{A372}$ | $L_{B15}$ | III-5580 | $L_{A457}$ | $L_{B33}$ |
| III-2360 | $L_{A467}$ | $L_{B14}$ | III-5505 | $L_{A382}$ | $L_{B33}$ | III-2436 | $L_{A373}$ | $L_{B15}$ | III-5581 | $L_{A458}$ | $L_{B33}$ |
| III-2361 | $L_{A468}$ | $L_{B14}$ | III-5506 | $L_{A383}$ | $L_{B33}$ | III-2437 | $L_{A374}$ | $L_{B15}$ | III-5582 | $L_{A459}$ | $L_{B33}$ |
| III-2362 | $L_{A469}$ | $L_{B14}$ | III-5507 | $L_{A384}$ | $L_{B33}$ | III-2438 | $L_{A375}$ | $L_{B15}$ | III-5583 | $L_{A460}$ | $L_{B33}$ |
| III-2363 | $L_{A470}$ | $L_{B14}$ | III-5508 | $L_{A385}$ | $L_{B33}$ | III-2439 | $L_{A376}$ | $L_{B15}$ | III-5584 | $L_{A461}$ | $L_{B33}$ |
| III-2364 | $L_{A471}$ | $L_{B14}$ | III-5509 | $L_{A386}$ | $L_{B33}$ | III-2440 | $L_{A377}$ | $L_{B15}$ | III-5585 | $L_{A462}$ | $L_{B33}$ |
| III-2365 | $L_{A472}$ | $L_{B14}$ | III-5510 | $L_{A387}$ | $L_{B33}$ | III-2441 | $L_{A378}$ | $L_{B15}$ | III-5586 | $L_{A463}$ | $L_{B33}$ |
| III-2366 | $L_{A473}$ | $L_{B14}$ | III-5511 | $L_{A388}$ | $L_{B33}$ | III-2442 | $L_{A379}$ | $L_{B15}$ | III-5587 | $L_{A464}$ | $L_{B33}$ |
| III-2367 | $L_{A474}$ | $L_{B14}$ | III-5512 | $L_{A389}$ | $L_{B33}$ | III-2443 | $L_{A380}$ | $L_{B15}$ | III-5588 | $L_{A465}$ | $L_{B33}$ |
| III-2368 | $L_{A475}$ | $L_{B14}$ | III-5513 | $L_{A390}$ | $L_{B33}$ | III-2444 | $L_{A381}$ | $L_{B15}$ | III-5589 | $L_{A466}$ | $L_{B33}$ |
| III-2369 | $L_{A476}$ | $L_{B14}$ | III-5514 | $L_{A391}$ | $L_{B33}$ | III-2445 | $L_{A382}$ | $L_{B15}$ | III-5590 | $L_{A467}$ | $L_{B33}$ |
| III-2370 | $L_{A477}$ | $L_{B14}$ | III-5515 | $L_{A392}$ | $L_{B33}$ | III-2446 | $L_{A383}$ | $L_{B15}$ | III-5591 | $L_{A468}$ | $L_{B33}$ |
| III-2371 | $L_{A478}$ | $L_{B14}$ | III-5516 | $L_{A393}$ | $L_{B33}$ | III-2447 | $L_{A384}$ | $L_{B15}$ | III-5592 | $L_{A469}$ | $L_{B33}$ |
| III-2372 | $L_{A479}$ | $L_{B14}$ | III-5517 | $L_{A394}$ | $L_{B33}$ | III-2448 | $L_{A385}$ | $L_{B15}$ | III-5593 | $L_{A470}$ | $L_{B33}$ |
| III-2373 | $L_{A480}$ | $L_{B14}$ | III-5518 | $L_{A395}$ | $L_{B33}$ | III-2449 | $L_{A386}$ | $L_{B15}$ | III-5594 | $L_{A471}$ | $L_{B33}$ |
| III-2374 | $L_{A481}$ | $L_{B14}$ | III-5519 | $L_{A396}$ | $L_{B33}$ | III-2450 | $L_{A387}$ | $L_{B15}$ | III-5595 | $L_{A472}$ | $L_{B33}$ |
| III-2375 | $L_{A482}$ | $L_{B14}$ | III-5520 | $L_{A397}$ | $L_{B33}$ | III-2451 | $L_{A388}$ | $L_{B15}$ | III-5596 | $L_{A473}$ | $L_{B33}$ |
| III-2376 | $L_{A483}$ | $L_{B14}$ | III-5521 | $L_{A398}$ | $L_{B33}$ | III-2452 | $L_{A389}$ | $L_{B15}$ | III-5597 | $L_{A474}$ | $L_{B33}$ |
| III-2377 | $L_{A484}$ | $L_{B14}$ | III-5522 | $L_{A399}$ | $L_{B33}$ | III-2453 | $L_{A390}$ | $L_{B15}$ | III-5598 | $L_{A475}$ | $L_{B33}$ |
| III-2378 | $L_{A485}$ | $L_{B14}$ | III-5523 | $L_{A400}$ | $L_{B33}$ | III-2454 | $L_{A391}$ | $L_{B15}$ | III-5599 | $L_{A476}$ | $L_{B33}$ |
| III-2379 | $L_{A486}$ | $L_{B14}$ | III-5524 | $L_{A401}$ | $L_{B33}$ | III-2455 | $L_{A392}$ | $L_{B15}$ | III-5600 | $L_{A477}$ | $L_{B33}$ |
| III-2380 | $L_{A487}$ | $L_{B14}$ | III-5525 | $L_{A402}$ | $L_{B33}$ | III-2456 | $L_{A393}$ | $L_{B15}$ | III-5601 | $L_{A478}$ | $L_{B33}$ |
| III-2381 | $L_{A318}$ | $L_{B15}$ | III-5526 | $L_{A403}$ | $L_{B33}$ | III-2457 | $L_{A394}$ | $L_{B15}$ | III-5602 | $L_{A479}$ | $L_{B33}$ |
| III-2382 | $L_{A319}$ | $L_{B15}$ | III-5527 | $L_{A404}$ | $L_{B33}$ | III-2458 | $L_{A395}$ | $L_{B15}$ | III-5603 | $L_{A480}$ | $L_{B33}$ |
| III-2383 | $L_{A320}$ | $L_{B15}$ | III-5528 | $L_{A405}$ | $L_{B33}$ | III-2459 | $L_{A396}$ | $L_{B15}$ | III-5604 | $L_{A481}$ | $L_{B33}$ |
| III-2384 | $L_{A321}$ | $L_{B15}$ | III-5529 | $L_{A406}$ | $L_{B33}$ | III-2460 | $L_{A397}$ | $L_{B15}$ | III-5605 | $L_{A482}$ | $L_{B33}$ |
| III-2385 | $L_{A322}$ | $L_{B15}$ | III-5530 | $L_{A407}$ | $L_{B33}$ | III-2461 | $L_{A398}$ | $L_{B15}$ | III-5606 | $L_{A483}$ | $L_{B33}$ |
| III-2386 | $L_{A323}$ | $L_{B15}$ | III-5531 | $L_{A408}$ | $L_{B33}$ | III-2462 | $L_{A399}$ | $L_{B15}$ | III-5607 | $L_{A484}$ | $L_{B33}$ |
| III-2387 | $L_{A324}$ | $L_{B15}$ | III-5532 | $L_{A409}$ | $L_{B33}$ | III-2463 | $L_{A400}$ | $L_{B15}$ | III-5608 | $L_{A485}$ | $L_{B33}$ |
| III-2388 | $L_{A325}$ | $L_{B15}$ | III-5533 | $L_{A410}$ | $L_{B33}$ | III-2464 | $L_{A401}$ | $L_{B15}$ | III-5609 | $L_{A486}$ | $L_{B33}$ |
| III-2389 | $L_{A326}$ | $L_{B15}$ | III-5534 | $L_{A411}$ | $L_{B33}$ | III-2465 | $L_{A402}$ | $L_{B15}$ | III-5610 | $L_{A487}$ | $L_{B33}$ |
| III-2390 | $L_{A327}$ | $L_{B15}$ | III-5535 | $L_{A412}$ | $L_{B33}$ | III-2466 | $L_{A403}$ | $L_{B15}$ | III-5611 | $L_{A318}$ | $L_{B34}$ |
| III-2391 | $L_{A328}$ | $L_{B15}$ | III-5536 | $L_{A413}$ | $L_{B33}$ | III-2467 | $L_{A404}$ | $L_{B15}$ | III-5612 | $L_{A319}$ | $L_{B34}$ |
| III-2392 | $L_{A329}$ | $L_{B15}$ | III-5537 | $L_{A414}$ | $L_{B33}$ | III-2468 | $L_{A405}$ | $L_{B15}$ | III-5613 | $L_{A320}$ | $L_{B34}$ |
| III-2393 | $L_{A330}$ | $L_{B15}$ | III-5538 | $L_{A415}$ | $L_{B33}$ | III-2469 | $L_{A406}$ | $L_{B15}$ | III-5614 | $L_{A321}$ | $L_{B34}$ |
| III-2394 | $L_{A331}$ | $L_{B15}$ | III-5539 | $L_{A416}$ | $L_{B33}$ | III-2470 | $L_{A407}$ | $L_{B15}$ | III-5615 | $L_{A322}$ | $L_{B34}$ |
| III-2395 | $L_{A332}$ | $L_{B15}$ | III-5540 | $L_{A417}$ | $L_{B33}$ | III-2471 | $L_{A408}$ | $L_{B15}$ | III-5616 | $L_{A323}$ | $L_{B34}$ |
| III-2396 | $L_{A333}$ | $L_{B15}$ | III-5541 | $L_{A418}$ | $L_{B33}$ | III-2472 | $L_{A409}$ | $L_{B15}$ | III-5617 | $L_{A324}$ | $L_{B34}$ |
| III-2397 | $L_{A334}$ | $L_{B15}$ | III-5542 | $L_{A419}$ | $L_{B33}$ | III-2473 | $L_{A410}$ | $L_{B15}$ | III-5618 | $L_{A325}$ | $L_{B34}$ |
| III-2398 | $L_{A335}$ | $L_{B15}$ | III-5543 | $L_{A420}$ | $L_{B33}$ | III-2474 | $L_{A411}$ | $L_{B15}$ | III-5619 | $L_{A326}$ | $L_{B34}$ |
| III-2399 | $L_{A336}$ | $L_{B15}$ | III-5544 | $L_{A421}$ | $L_{B33}$ | III-2475 | $L_{A412}$ | $L_{B15}$ | III-5620 | $L_{A327}$ | $L_{B34}$ |
| III-2400 | $L_{A337}$ | $L_{B15}$ | III-5545 | $L_{A422}$ | $L_{B33}$ | III-2476 | $L_{A413}$ | $L_{B15}$ | III-5621 | $L_{A328}$ | $L_{B34}$ |
| III-2401 | $L_{A338}$ | $L_{B15}$ | III-5546 | $L_{A423}$ | $L_{B33}$ | III-2477 | $L_{A414}$ | $L_{B15}$ | III-5622 | $L_{A329}$ | $L_{B34}$ |
| III-2402 | $L_{A339}$ | $L_{B15}$ | III-5547 | $L_{A424}$ | $L_{B33}$ | III-2478 | $L_{A415}$ | $L_{B15}$ | III-5623 | $L_{A330}$ | $L_{B34}$ |
| III-2403 | $L_{A340}$ | $L_{B15}$ | III-5548 | $L_{A425}$ | $L_{B33}$ | III-2479 | $L_{A416}$ | $L_{B15}$ | III-5624 | $L_{A331}$ | $L_{B34}$ |

-continued

| Compound Number | $L_A$ | $L_B$ | Compound Number | $L_A$ | $L_B$ |
|---|---|---|---|---|---|
| III-2480 | $L_{A417}$ | $L_{B15}$ | III-5625 | $L_{A332}$ | $L_{B34}$ |
| III-2481 | $L_{A418}$ | $L_{B15}$ | III-5626 | $L_{A333}$ | $L_{B34}$ |
| III-2482 | $L_{A419}$ | $L_{B15}$ | III-5627 | $L_{A334}$ | $L_{B34}$ |
| III-2483 | $L_{A420}$ | $L_{B15}$ | III-5628 | $L_{A335}$ | $L_{B34}$ |
| III-2484 | $L_{A421}$ | $L_{B15}$ | III-5629 | $L_{A336}$ | $L_{B34}$ |
| III-2485 | $L_{A422}$ | $L_{B15}$ | III-5630 | $L_{A337}$ | $L_{B34}$ |
| III-2486 | $L_{A423}$ | $L_{B15}$ | III-5631 | $L_{A338}$ | $L_{B34}$ |
| III-2487 | $L_{A424}$ | $L_{B15}$ | III-5632 | $L_{A339}$ | $L_{B34}$ |
| III-2488 | $L_{A425}$ | $L_{B15}$ | III-5633 | $L_{A340}$ | $L_{B34}$ |
| III-2489 | $L_{A426}$ | $L_{B15}$ | III-5634 | $L_{A341}$ | $L_{B34}$ |
| III-2490 | $L_{A427}$ | $L_{B15}$ | III-5635 | $L_{A342}$ | $L_{B34}$ |
| III-2491 | $L_{A428}$ | $L_{B15}$ | III-5636 | $L_{A343}$ | $L_{B34}$ |
| III-2492 | $L_{A429}$ | $L_{B15}$ | III-5637 | $L_{A344}$ | $L_{B34}$ |
| III-2493 | $L_{A430}$ | $L_{B15}$ | III-5638 | $L_{A345}$ | $L_{B34}$ |
| III-2494 | $L_{A431}$ | $L_{B15}$ | III-5639 | $L_{A346}$ | $L_{B34}$ |
| III-2495 | $L_{A432}$ | $L_{B15}$ | III-5640 | $L_{A347}$ | $L_{B34}$ |
| III-2496 | $L_{A433}$ | $L_{B15}$ | III-5641 | $L_{A348}$ | $L_{B34}$ |
| III-2497 | $L_{A434}$ | $L_{B15}$ | III-5642 | $L_{A349}$ | $L_{B34}$ |
| III-2498 | $L_{A435}$ | $L_{B15}$ | III-5643 | $L_{A350}$ | $L_{B34}$ |
| III-2499 | $L_{A436}$ | $L_{B15}$ | III-5644 | $L_{A351}$ | $L_{B34}$ |
| III-2500 | $L_{A437}$ | $L_{B15}$ | III-5645 | $L_{A352}$ | $L_{B34}$ |
| III-2501 | $L_{A438}$ | $L_{B15}$ | III-5646 | $L_{A353}$ | $L_{B34}$ |
| III-2502 | $L_{A439}$ | $L_{B15}$ | III-5647 | $L_{A354}$ | $L_{B34}$ |
| III-2503 | $L_{A440}$ | $L_{B15}$ | III-5648 | $L_{A355}$ | $L_{B34}$ |
| III-2504 | $L_{A441}$ | $L_{B15}$ | III-5649 | $L_{A356}$ | $L_{B34}$ |
| III-2505 | $L_{A442}$ | $L_{B15}$ | III-5650 | $L_{A357}$ | $L_{B34}$ |
| III-2506 | $L_{A443}$ | $L_{B15}$ | III-5651 | $L_{A358}$ | $L_{B34}$ |
| III-2507 | $L_{A444}$ | $L_{B15}$ | III-5652 | $L_{A359}$ | $L_{B34}$ |
| III-2508 | $L_{A445}$ | $L_{B15}$ | III-5653 | $L_{A360}$ | $L_{B34}$ |
| III-2509 | $L_{A446}$ | $L_{B15}$ | III-5654 | $L_{A361}$ | $L_{B34}$ |
| III-2510 | $L_{A447}$ | $L_{B15}$ | III-5655 | $L_{A362}$ | $L_{B34}$ |
| III-2511 | $L_{A448}$ | $L_{B15}$ | III-5656 | $L_{A363}$ | $L_{B34}$ |
| III-2512 | $L_{A449}$ | $L_{B15}$ | III-5657 | $L_{A364}$ | $L_{B34}$ |
| III-2513 | $L_{A450}$ | $L_{B15}$ | III-5658 | $L_{A365}$ | $L_{B34}$ |
| III-2514 | $L_{A451}$ | $L_{B15}$ | III-5659 | $L_{A366}$ | $L_{B34}$ |
| III-2515 | $L_{A452}$ | $L_{B15}$ | III-5660 | $L_{A367}$ | $L_{B34}$ |
| III-2516 | $L_{A453}$ | $L_{B15}$ | III-5661 | $L_{A368}$ | $L_{B34}$ |
| III-2517 | $L_{A454}$ | $L_{B15}$ | III-5662 | $L_{A369}$ | $L_{B34}$ |
| III-2518 | $L_{A455}$ | $L_{B15}$ | III-5663 | $L_{A370}$ | $L_{B34}$ |
| III-2519 | $L_{A456}$ | $L_{B15}$ | III-5664 | $L_{A371}$ | $L_{B34}$ |
| III-2520 | $L_{A457}$ | $L_{B15}$ | III-5665 | $L_{A372}$ | $L_{B34}$ |
| III-2521 | $L_{A458}$ | $L_{B15}$ | III-5666 | $L_{A373}$ | $L_{B34}$ |
| III-2522 | $L_{A459}$ | $L_{B15}$ | III-5667 | $L_{A374}$ | $L_{B34}$ |
| III-2523 | $L_{A460}$ | $L_{B15}$ | III-5668 | $L_{A375}$ | $L_{B34}$ |
| III-2524 | $L_{A461}$ | $L_{B15}$ | III-5669 | $L_{A376}$ | $L_{B34}$ |
| III-2525 | $L_{A462}$ | $L_{B15}$ | III-5670 | $L_{A377}$ | $L_{B34}$ |
| III-2526 | $L_{A463}$ | $L_{B15}$ | III-5671 | $L_{A378}$ | $L_{B34}$ |
| III-2527 | $L_{A464}$ | $L_{B15}$ | III-5672 | $L_{A379}$ | $L_{B34}$ |
| III-2528 | $L_{A465}$ | $L_{B15}$ | III-5673 | $L_{A380}$ | $L_{B34}$ |
| III-2529 | $L_{A466}$ | $L_{B15}$ | III-5674 | $L_{A381}$ | $L_{B34}$ |
| III-2530 | $L_{A467}$ | $L_{B15}$ | III-5675 | $L_{A382}$ | $L_{B34}$ |
| III-2531 | $L_{A468}$ | $L_{B15}$ | III-5676 | $L_{A383}$ | $L_{B34}$ |
| III-2532 | $L_{A469}$ | $L_{B15}$ | III-5677 | $L_{A384}$ | $L_{B34}$ |
| III-2533 | $L_{A470}$ | $L_{B15}$ | III-5678 | $L_{A385}$ | $L_{B34}$ |
| III-2534 | $L_{A471}$ | $L_{B15}$ | III-5679 | $L_{A386}$ | $L_{B34}$ |
| III-2535 | $L_{A472}$ | $L_{B15}$ | III-5680 | $L_{A387}$ | $L_{B34}$ |
| III-2536 | $L_{A473}$ | $L_{B15}$ | III-5681 | $L_{A388}$ | $L_{B34}$ |
| III-2537 | $L_{A474}$ | $L_{B15}$ | III-5682 | $L_{A389}$ | $L_{B34}$ |
| III-2538 | $L_{A475}$ | $L_{B15}$ | III-5683 | $L_{A390}$ | $L_{B34}$ |
| III-2539 | $L_{A476}$ | $L_{B15}$ | III-5684 | $L_{A391}$ | $L_{B34}$ |
| III-2540 | $L_{A477}$ | $L_{B15}$ | III-5685 | $L_{A392}$ | $L_{B34}$ |
| III-2541 | $L_{A478}$ | $L_{B15}$ | III-5686 | $L_{A393}$ | $L_{B34}$ |
| III-2542 | $L_{A479}$ | $L_{B15}$ | III-5687 | $L_{A394}$ | $L_{B34}$ |
| III-2543 | $L_{A480}$ | $L_{B15}$ | III-5688 | $L_{A395}$ | $L_{B34}$ |
| III-2544 | $L_{A481}$ | $L_{B15}$ | III-5689 | $L_{A396}$ | $L_{B34}$ |
| III-2545 | $L_{A482}$ | $L_{B15}$ | III-5690 | $L_{A397}$ | $L_{B34}$ |
| III-2546 | $L_{A483}$ | $L_{B15}$ | III-5691 | $L_{A398}$ | $L_{B34}$ |
| III-2547 | $L_{A484}$ | $L_{B15}$ | III-5692 | $L_{A399}$ | $L_{B34}$ |
| III-2548 | $L_{A485}$ | $L_{B15}$ | III-5693 | $L_{A400}$ | $L_{B34}$ |
| III-2549 | $L_{A486}$ | $L_{B15}$ | III-5694 | $L_{A401}$ | $L_{B34}$ |
| III-2550 | $L_{A487}$ | $L_{B15}$ | III-5695 | $L_{A402}$ | $L_{B34}$ |
| III-2551 | $L_{A318}$ | $L_{B16}$ | III-5696 | $L_{A403}$ | $L_{B34}$ |
| III-2552 | $L_{A319}$ | $L_{B16}$ | III-5697 | $L_{A404}$ | $L_{B34}$ |
| III-2553 | $L_{A320}$ | $L_{B16}$ | III-5698 | $L_{A405}$ | $L_{B34}$ |
| III-2554 | $L_{A321}$ | $L_{B16}$ | III-5699 | $L_{A406}$ | $L_{B34}$ |
| III-2555 | $L_{A322}$ | $L_{B16}$ | III-5700 | $L_{A407}$ | $L_{B34}$ |

-continued

| Compound Number | $L_A$ | $L_B$ | Compound Number | $L_A$ | $L_B$ |
|---|---|---|---|---|---|
| III-2556 | $L_{A323}$ | $L_{B16}$ | III-5701 | $L_{A408}$ | $L_{B34}$ |
| III-2557 | $L_{A324}$ | $L_{B16}$ | III-5702 | $L_{A409}$ | $L_{B34}$ |
| III-2558 | $L_{A325}$ | $L_{B16}$ | III-5703 | $L_{A410}$ | $L_{B34}$ |
| III-2559 | $L_{A326}$ | $L_{B16}$ | III-5704 | $L_{A411}$ | $L_{B34}$ |
| III-2560 | $L_{A327}$ | $L_{B16}$ | III-5705 | $L_{A412}$ | $L_{B34}$ |
| III-2561 | $L_{A328}$ | $L_{B16}$ | III-5706 | $L_{A413}$ | $L_{B34}$ |
| III-2562 | $L_{A329}$ | $L_{B16}$ | III-5707 | $L_{A414}$ | $L_{B34}$ |
| III-2563 | $L_{A330}$ | $L_{B16}$ | III-5708 | $L_{A415}$ | $L_{B34}$ |
| III-2564 | $L_{A331}$ | $L_{B16}$ | III-5709 | $L_{A416}$ | $L_{B34}$ |
| III-2565 | $L_{A332}$ | $L_{B16}$ | III-5710 | $L_{A417}$ | $L_{B34}$ |
| III-2566 | $L_{A333}$ | $L_{B16}$ | III-5711 | $L_{A418}$ | $L_{B34}$ |
| III-2567 | $L_{A334}$ | $L_{B16}$ | III-5712 | $L_{A419}$ | $L_{B34}$ |
| III-2568 | $L_{A335}$ | $L_{B16}$ | III-5713 | $L_{A420}$ | $L_{B34}$ |
| III-2569 | $L_{A336}$ | $L_{B16}$ | III-5714 | $L_{A421}$ | $L_{B34}$ |
| III-2570 | $L_{A337}$ | $L_{B16}$ | III-5715 | $L_{A422}$ | $L_{B34}$ |
| III-2571 | $L_{A338}$ | $L_{B16}$ | III-5716 | $L_{A423}$ | $L_{B34}$ |
| III-2572 | $L_{A339}$ | $L_{B16}$ | III-5717 | $L_{A424}$ | $L_{B34}$ |
| III-2573 | $L_{A340}$ | $L_{B16}$ | III-5718 | $L_{A425}$ | $L_{B34}$ |
| III-2574 | $L_{A341}$ | $L_{B16}$ | III-5719 | $L_{A426}$ | $L_{B34}$ |
| III-2575 | $L_{A342}$ | $L_{B16}$ | III-5720 | $L_{A427}$ | $L_{B34}$ |
| III-2576 | $L_{A343}$ | $L_{B16}$ | III-5721 | $L_{A428}$ | $L_{B34}$ |
| III-2577 | $L_{A344}$ | $L_{B16}$ | III-5722 | $L_{A429}$ | $L_{B34}$ |
| III-2578 | $L_{A345}$ | $L_{B16}$ | III-5723 | $L_{A430}$ | $L_{B34}$ |
| III-2579 | $L_{A346}$ | $L_{B16}$ | III-5724 | $L_{A431}$ | $L_{B34}$ |
| III-2580 | $L_{A347}$ | $L_{B16}$ | III-5725 | $L_{A432}$ | $L_{B34}$ |
| III-2581 | $L_{A348}$ | $L_{B16}$ | III-5726 | $L_{A433}$ | $L_{B34}$ |
| III-2582 | $L_{A349}$ | $L_{B16}$ | III-5727 | $L_{A434}$ | $L_{B34}$ |
| III-2583 | $L_{A350}$ | $L_{B16}$ | III-5728 | $L_{A435}$ | $L_{B34}$ |
| III-2584 | $L_{A351}$ | $L_{B16}$ | III-5729 | $L_{A436}$ | $L_{B34}$ |
| III-2585 | $L_{A352}$ | $L_{B16}$ | III-5730 | $L_{A437}$ | $L_{B34}$ |
| III-2586 | $L_{A353}$ | $L_{B16}$ | III-5731 | $L_{A438}$ | $L_{B34}$ |
| III-2587 | $L_{A354}$ | $L_{B16}$ | III-5732 | $L_{A439}$ | $L_{B34}$ |
| III-2588 | $L_{A355}$ | $L_{B16}$ | III-5733 | $L_{A440}$ | $L_{B34}$ |
| III-2589 | $L_{A356}$ | $L_{B16}$ | III-5734 | $L_{A441}$ | $L_{B34}$ |
| III-2590 | $L_{A357}$ | $L_{B16}$ | III-5735 | $L_{A442}$ | $L_{B34}$ |
| III-2591 | $L_{A358}$ | $L_{B16}$ | III-5736 | $L_{A443}$ | $L_{B34}$ |
| III-2592 | $L_{A359}$ | $L_{B16}$ | III-5737 | $L_{A444}$ | $L_{B34}$ |
| III-2593 | $L_{A360}$ | $L_{B16}$ | III-5738 | $L_{A445}$ | $L_{B34}$ |
| III-2594 | $L_{A361}$ | $L_{B16}$ | III-5739 | $L_{A446}$ | $L_{B34}$ |
| III-2595 | $L_{A362}$ | $L_{B16}$ | III-5740 | $L_{A447}$ | $L_{B34}$ |
| III-2596 | $L_{A363}$ | $L_{B16}$ | III-5741 | $L_{A448}$ | $L_{B34}$ |
| III-2597 | $L_{A364}$ | $L_{B16}$ | III-5742 | $L_{A449}$ | $L_{B34}$ |
| III-2598 | $L_{A365}$ | $L_{B16}$ | III-5743 | $L_{A450}$ | $L_{B34}$ |
| III-2599 | $L_{A366}$ | $L_{B16}$ | III-5744 | $L_{A451}$ | $L_{B34}$ |
| III-2600 | $L_{A367}$ | $L_{B16}$ | III-5745 | $L_{A452}$ | $L_{B34}$ |
| III-2601 | $L_{A368}$ | $L_{B16}$ | III-5746 | $L_{A453}$ | $L_{B34}$ |
| III-2602 | $L_{A369}$ | $L_{B16}$ | III-5747 | $L_{A454}$ | $L_{B34}$ |
| III-2603 | $L_{A370}$ | $L_{B16}$ | III-5748 | $L_{A455}$ | $L_{B34}$ |
| III-2604 | $L_{A371}$ | $L_{B16}$ | III-5749 | $L_{A456}$ | $L_{B34}$ |
| III-2605 | $L_{A372}$ | $L_{B16}$ | III-5750 | $L_{A457}$ | $L_{B34}$ |
| III-2606 | $L_{A373}$ | $L_{B16}$ | III-5751 | $L_{A458}$ | $L_{B34}$ |
| III-2607 | $L_{A374}$ | $L_{B16}$ | III-5752 | $L_{A459}$ | $L_{B34}$ |
| III-2608 | $L_{A375}$ | $L_{B16}$ | III-5753 | $L_{A460}$ | $L_{B34}$ |
| III-2609 | $L_{A376}$ | $L_{B16}$ | III-5754 | $L_{A461}$ | $L_{B34}$ |
| III-2610 | $L_{A377}$ | $L_{B16}$ | III-5755 | $L_{A462}$ | $L_{B34}$ |
| III-2611 | $L_{A378}$ | $L_{B16}$ | III-5756 | $L_{A463}$ | $L_{B34}$ |
| III-2612 | $L_{A379}$ | $L_{B16}$ | III-5757 | $L_{A464}$ | $L_{B34}$ |
| III-2613 | $L_{A380}$ | $L_{B16}$ | III-5758 | $L_{A465}$ | $L_{B34}$ |
| III-2614 | $L_{A381}$ | $L_{B16}$ | III-5759 | $L_{A466}$ | $L_{B34}$ |
| III-2615 | $L_{A382}$ | $L_{B16}$ | III-5760 | $L_{A467}$ | $L_{B34}$ |
| III-2616 | $L_{A383}$ | $L_{B16}$ | III-5761 | $L_{A468}$ | $L_{B34}$ |
| III-2617 | $L_{A384}$ | $L_{B16}$ | III-5762 | $L_{A469}$ | $L_{B34}$ |
| III-2618 | $L_{A385}$ | $L_{B16}$ | III-5763 | $L_{A470}$ | $L_{B34}$ |
| III-2619 | $L_{A386}$ | $L_{B16}$ | III-5764 | $L_{A471}$ | $L_{B34}$ |
| III-2620 | $L_{A387}$ | $L_{B16}$ | III-5765 | $L_{A472}$ | $L_{B34}$ |
| III-2621 | $L_{A388}$ | $L_{B16}$ | III-5766 | $L_{A473}$ | $L_{B34}$ |
| III-2622 | $L_{A389}$ | $L_{B16}$ | III-5767 | $L_{A474}$ | $L_{B34}$ |
| III-2623 | $L_{A390}$ | $L_{B16}$ | III-5768 | $L_{A475}$ | $L_{B34}$ |
| III-2624 | $L_{A391}$ | $L_{B16}$ | III-5769 | $L_{A476}$ | $L_{B34}$ |
| III-2625 | $L_{A392}$ | $L_{B16}$ | III-5770 | $L_{A477}$ | $L_{B34}$ |
| III-2626 | $L_{A393}$ | $L_{B16}$ | III-5771 | $L_{A478}$ | $L_{B34}$ |
| III-2627 | $L_{A394}$ | $L_{B16}$ | III-5772 | $L_{A479}$ | $L_{B34}$ |
| III-2628 | $L_{A395}$ | $L_{B16}$ | III-5773 | $L_{A480}$ | $L_{B34}$ |
| III-2629 | $L_{A396}$ | $L_{B16}$ | III-5774 | $L_{A481}$ | $L_{B34}$ |
| III-2630 | $L_{A397}$ | $L_{B16}$ | III-5775 | $L_{A482}$ | $L_{B34}$ |
| III-2631 | $L_{A398}$ | $L_{B16}$ | III-5776 | $L_{A483}$ | $L_{B34}$ |

-continued

| Compound Number | $L_A$ | $L_B$ | Compound Number | $L_A$ | $L_B$ |
|---|---|---|---|---|---|
| III-2632 | $L_{A399}$ | $L_{B16}$ | III-5777 | $L_{A484}$ | $L_{B34}$ |
| III-2633 | $L_{A400}$ | $L_{B16}$ | III-5778 | $L_{A485}$ | $L_{B34}$ |
| III-2634 | $L_{A401}$ | $L_{B16}$ | III-5779 | $L_{A486}$ | $L_{B34}$ |
| III-2635 | $L_{A402}$ | $L_{B16}$ | III-5780 | $L_{A487}$ | $L_{B34}$ |
| III-2636 | $L_{A403}$ | $L_{B16}$ | III-5781 | $L_{A318}$ | $L_{B35}$ |
| III-2637 | $L_{A404}$ | $L_{B16}$ | III-5782 | $L_{A319}$ | $L_{B35}$ |
| III-2638 | $L_{A405}$ | $L_{B16}$ | III-5783 | $L_{A320}$ | $L_{B35}$ |
| III-2639 | $L_{A406}$ | $L_{B16}$ | III-5784 | $L_{A321}$ | $L_{B35}$ |
| III-2640 | $L_{A407}$ | $L_{B16}$ | III-5785 | $L_{A322}$ | $L_{B35}$ |
| III-2641 | $L_{A408}$ | $L_{B16}$ | III-5786 | $L_{A323}$ | $L_{B35}$ |
| III-2642 | $L_{A409}$ | $L_{B16}$ | III-5787 | $L_{A324}$ | $L_{B35}$ |
| III-2643 | $L_{A410}$ | $L_{B16}$ | III-5788 | $L_{A325}$ | $L_{B35}$ |
| III-2644 | $L_{A411}$ | $L_{B16}$ | III-5789 | $L_{A326}$ | $L_{B35}$ |
| III-2645 | $L_{A412}$ | $L_{B16}$ | III-5790 | $L_{A327}$ | $L_{B35}$ |
| III-2646 | $L_{A413}$ | $L_{B16}$ | III-5791 | $L_{A328}$ | $L_{B35}$ |
| III-2647 | $L_{A414}$ | $L_{B16}$ | III-5792 | $L_{A329}$ | $L_{B35}$ |
| III-2648 | $L_{A415}$ | $L_{B16}$ | III-5793 | $L_{A330}$ | $L_{B35}$ |
| III-2649 | $L_{A416}$ | $L_{B16}$ | III-5794 | $L_{A331}$ | $L_{B35}$ |
| III-2650 | $L_{A417}$ | $L_{B16}$ | III-5795 | $L_{A332}$ | $L_{B35}$ |
| III-2651 | $L_{A418}$ | $L_{B16}$ | III-5796 | $L_{A333}$ | $L_{B35}$ |
| III-2652 | $L_{A419}$ | $L_{B16}$ | III-5797 | $L_{A334}$ | $L_{B35}$ |
| III-2653 | $L_{A420}$ | $L_{B16}$ | III-5798 | $L_{A335}$ | $L_{B35}$ |
| III-2654 | $L_{A421}$ | $L_{B16}$ | III-5799 | $L_{A336}$ | $L_{B35}$ |
| III-2655 | $L_{A422}$ | $L_{B16}$ | III-5800 | $L_{A337}$ | $L_{B35}$ |
| III-2656 | $L_{A423}$ | $L_{B16}$ | III-5801 | $L_{A338}$ | $L_{B35}$ |
| III-2657 | $L_{A424}$ | $L_{B16}$ | III-5802 | $L_{A339}$ | $L_{B35}$ |
| III-2658 | $L_{A425}$ | $L_{B16}$ | III-5803 | $L_{A340}$ | $L_{B35}$ |
| III-2659 | $L_{A426}$ | $L_{B16}$ | III-5804 | $L_{A341}$ | $L_{B35}$ |
| III-2660 | $L_{A427}$ | $L_{B16}$ | III-5805 | $L_{A342}$ | $L_{B35}$ |
| III-2661 | $L_{A428}$ | $L_{B16}$ | III-5806 | $L_{A343}$ | $L_{B35}$ |
| III-2662 | $L_{A429}$ | $L_{B16}$ | III-5807 | $L_{A344}$ | $L_{B35}$ |
| III-2663 | $L_{A430}$ | $L_{B16}$ | III-5808 | $L_{A345}$ | $L_{B35}$ |
| III-2664 | $L_{A431}$ | $L_{B16}$ | III-5809 | $L_{A346}$ | $L_{B35}$ |
| III-2665 | $L_{A432}$ | $L_{B16}$ | III-5810 | $L_{A347}$ | $L_{B35}$ |
| III-2666 | $L_{A433}$ | $L_{B16}$ | III-5811 | $L_{A348}$ | $L_{B35}$ |
| III-2667 | $L_{A434}$ | $L_{B16}$ | III-5812 | $L_{A349}$ | $L_{B35}$ |
| III-2668 | $L_{A435}$ | $L_{B16}$ | III-5813 | $L_{A350}$ | $L_{B35}$ |
| III-2669 | $L_{A436}$ | $L_{B16}$ | III-5814 | $L_{A351}$ | $L_{B35}$ |
| III-2670 | $L_{A437}$ | $L_{B16}$ | III-5815 | $L_{A352}$ | $L_{B35}$ |
| III-2671 | $L_{A438}$ | $L_{B16}$ | III-5816 | $L_{A353}$ | $L_{B35}$ |
| III-2672 | $L_{A439}$ | $L_{B16}$ | III-5817 | $L_{A354}$ | $L_{B35}$ |
| III-2673 | $L_{A440}$ | $L_{B16}$ | III-5818 | $L_{A355}$ | $L_{B35}$ |
| III-2674 | $L_{A441}$ | $L_{B16}$ | III-5819 | $L_{A356}$ | $L_{B35}$ |
| III-2675 | $L_{A442}$ | $L_{B16}$ | III-5820 | $L_{A357}$ | $L_{B35}$ |
| III-2676 | $L_{A443}$ | $L_{B16}$ | III-5821 | $L_{A358}$ | $L_{B35}$ |
| III-2677 | $L_{A444}$ | $L_{B16}$ | III-5822 | $L_{A359}$ | $L_{B35}$ |
| III-2678 | $L_{A445}$ | $L_{B16}$ | III-5823 | $L_{A360}$ | $L_{B35}$ |
| III-2679 | $L_{A446}$ | $L_{B16}$ | III-5824 | $L_{A361}$ | $L_{B35}$ |
| III-2680 | $L_{A447}$ | $L_{B16}$ | III-5825 | $L_{A362}$ | $L_{B35}$ |
| III-2681 | $L_{A448}$ | $L_{B16}$ | III-5826 | $L_{A363}$ | $L_{B35}$ |
| III-2682 | $L_{A449}$ | $L_{B16}$ | III-5827 | $L_{A364}$ | $L_{B35}$ |
| III-2683 | $L_{A450}$ | $L_{B16}$ | III-5828 | $L_{A365}$ | $L_{B35}$ |
| III-2684 | $L_{A451}$ | $L_{B16}$ | III-5829 | $L_{A366}$ | $L_{B35}$ |
| III-2685 | $L_{A452}$ | $L_{B16}$ | III-5830 | $L_{A367}$ | $L_{B35}$ |
| III-2686 | $L_{A453}$ | $L_{B16}$ | III-5831 | $L_{A368}$ | $L_{B35}$ |
| III-2687 | $L_{A454}$ | $L_{B16}$ | III-5832 | $L_{A369}$ | $L_{B35}$ |
| III-2688 | $L_{A455}$ | $L_{B16}$ | III-5833 | $L_{A370}$ | $L_{B35}$ |
| III-2689 | $L_{A456}$ | $L_{B16}$ | III-5834 | $L_{A371}$ | $L_{B35}$ |
| III-2690 | $L_{A457}$ | $L_{B16}$ | III-5835 | $L_{A372}$ | $L_{B35}$ |
| III-2691 | $L_{A458}$ | $L_{B16}$ | III-5836 | $L_{A373}$ | $L_{B35}$ |
| III-2692 | $L_{A459}$ | $L_{B16}$ | III-5837 | $L_{A374}$ | $L_{B35}$ |
| III-2693 | $L_{A460}$ | $L_{B16}$ | III-5838 | $L_{A375}$ | $L_{B35}$ |
| III-2694 | $L_{A461}$ | $L_{B16}$ | III-5839 | $L_{A376}$ | $L_{B35}$ |
| III-2695 | $L_{A462}$ | $L_{B16}$ | III-5840 | $L_{A377}$ | $L_{B35}$ |
| III-2696 | $L_{A463}$ | $L_{B16}$ | III-5841 | $L_{A378}$ | $L_{B35}$ |
| III-2697 | $L_{A464}$ | $L_{B16}$ | III-5842 | $L_{A379}$ | $L_{B35}$ |
| III-2698 | $L_{A465}$ | $L_{B16}$ | III-5843 | $L_{A380}$ | $L_{B35}$ |
| III-2699 | $L_{A466}$ | $L_{B16}$ | III-5844 | $L_{A381}$ | $L_{B35}$ |
| III-2700 | $L_{A467}$ | $L_{B16}$ | III-5845 | $L_{A382}$ | $L_{B35}$ |
| III-2701 | $L_{A468}$ | $L_{B16}$ | III-5846 | $L_{A383}$ | $L_{B35}$ |
| III-2702 | $L_{A469}$ | $L_{B16}$ | III-5847 | $L_{A384}$ | $L_{B35}$ |
| III-2703 | $L_{A470}$ | $L_{B16}$ | III-5848 | $L_{A385}$ | $L_{B35}$ |
| III-2704 | $L_{A471}$ | $L_{B16}$ | III-5849 | $L_{A386}$ | $L_{B35}$ |
| III-2705 | $L_{A472}$ | $L_{B16}$ | III-5850 | $L_{A387}$ | $L_{B35}$ |
| III-2706 | $L_{A473}$ | $L_{B16}$ | III-5851 | $L_{A388}$ | $L_{B35}$ |
| III-2707 | $L_{A474}$ | $L_{B16}$ | III-5852 | $L_{A389}$ | $L_{B35}$ |

-continued

| Compound Number | $L_A$ | $L_B$ | Compound Number | $L_A$ | $L_B$ |
|---|---|---|---|---|---|
| III-2708 | $L_{A475}$ | $L_{B16}$ | III-5853 | $L_{A390}$ | $L_{B35}$ |
| III-2709 | $L_{A476}$ | $L_{B16}$ | III-5854 | $L_{A391}$ | $L_{B35}$ |
| III-2710 | $L_{A477}$ | $L_{B16}$ | III-5855 | $L_{A392}$ | $L_{B35}$ |
| III-2711 | $L_{A478}$ | $L_{B16}$ | III-5856 | $L_{A393}$ | $L_{B35}$ |
| III-2712 | $L_{A479}$ | $L_{B16}$ | III-5857 | $L_{A394}$ | $L_{B35}$ |
| III-2713 | $L_{A480}$ | $L_{B16}$ | III-5858 | $L_{A395}$ | $L_{B35}$ |
| III-2714 | $L_{A481}$ | $L_{B16}$ | III-5859 | $L_{A396}$ | $L_{B35}$ |
| III-2715 | $L_{A482}$ | $L_{B16}$ | III-5860 | $L_{A397}$ | $L_{B35}$ |
| III-2716 | $L_{A483}$ | $L_{B16}$ | III-5861 | $L_{A398}$ | $L_{B35}$ |
| III-2717 | $L_{A484}$ | $L_{B16}$ | III-5862 | $L_{A399}$ | $L_{B35}$ |
| III-2718 | $L_{A485}$ | $L_{B16}$ | III-5863 | $L_{A400}$ | $L_{B35}$ |
| III-2719 | $L_{A486}$ | $L_{B16}$ | III-5864 | $L_{A401}$ | $L_{B35}$ |
| III-2720 | $L_{A487}$ | $L_{B16}$ | III-5865 | $L_{A402}$ | $L_{B35}$ |
| III-2721 | $L_{A318}$ | $L_{B17}$ | III-5866 | $L_{A403}$ | $L_{B35}$ |
| III-2722 | $L_{A319}$ | $L_{B17}$ | III-5867 | $L_{A404}$ | $L_{B35}$ |
| III-2723 | $L_{A320}$ | $L_{B17}$ | III-5868 | $L_{A405}$ | $L_{B35}$ |
| III-2724 | $L_{A321}$ | $L_{B17}$ | III-5869 | $L_{A406}$ | $L_{B35}$ |
| III-2725 | $L_{A322}$ | $L_{B17}$ | III-5870 | $L_{A407}$ | $L_{B35}$ |
| III-2726 | $L_{A323}$ | $L_{B17}$ | III-5871 | $L_{A408}$ | $L_{B35}$ |
| III-2727 | $L_{A324}$ | $L_{B17}$ | III-5872 | $L_{A409}$ | $L_{B35}$ |
| III-2728 | $L_{A325}$ | $L_{B17}$ | III-5873 | $L_{A410}$ | $L_{B35}$ |
| III-2729 | $L_{A326}$ | $L_{B17}$ | III-5874 | $L_{A411}$ | $L_{B35}$ |
| III-2730 | $L_{A327}$ | $L_{B17}$ | III-5875 | $L_{A412}$ | $L_{B35}$ |
| III-2731 | $L_{A328}$ | $L_{B17}$ | III-5876 | $L_{A413}$ | $L_{B35}$ |
| III-2732 | $L_{A329}$ | $L_{B17}$ | III-5877 | $L_{A414}$ | $L_{B35}$ |
| III-2733 | $L_{A330}$ | $L_{B17}$ | III-5878 | $L_{A415}$ | $L_{B35}$ |
| III-2734 | $L_{A331}$ | $L_{B17}$ | III-5879 | $L_{A416}$ | $L_{B35}$ |
| III-2735 | $L_{A332}$ | $L_{B17}$ | III-5880 | $L_{A417}$ | $L_{B35}$ |
| III-2736 | $L_{A333}$ | $L_{B17}$ | III-5881 | $L_{A418}$ | $L_{B35}$ |
| III-2737 | $L_{A334}$ | $L_{B17}$ | III-5882 | $L_{A419}$ | $L_{B35}$ |
| III-2738 | $L_{A335}$ | $L_{B17}$ | III-5883 | $L_{A420}$ | $L_{B35}$ |
| III-2739 | $L_{A336}$ | $L_{B17}$ | III-5884 | $L_{A421}$ | $L_{B35}$ |
| III-2740 | $L_{A337}$ | $L_{B17}$ | III-5885 | $L_{A422}$ | $L_{B35}$ |
| III-2741 | $L_{A338}$ | $L_{B17}$ | III-5886 | $L_{A423}$ | $L_{B35}$ |
| III-2742 | $L_{A339}$ | $L_{B17}$ | III-5887 | $L_{A424}$ | $L_{B35}$ |
| III-2743 | $L_{A340}$ | $L_{B17}$ | III-5888 | $L_{A425}$ | $L_{B35}$ |
| III-2744 | $L_{A341}$ | $L_{B17}$ | III-5889 | $L_{A426}$ | $L_{B35}$ |
| III-2745 | $L_{A342}$ | $L_{B17}$ | III-5890 | $L_{A427}$ | $L_{B35}$ |
| III-2746 | $L_{A343}$ | $L_{B17}$ | III-5891 | $L_{A428}$ | $L_{B35}$ |
| III-2747 | $L_{A344}$ | $L_{B17}$ | III-5892 | $L_{A429}$ | $L_{B35}$ |
| III-2748 | $L_{A345}$ | $L_{B17}$ | III-5893 | $L_{A430}$ | $L_{B35}$ |
| III-2749 | $L_{A346}$ | $L_{B17}$ | III-5894 | $L_{A431}$ | $L_{B35}$ |
| III-2750 | $L_{A347}$ | $L_{B17}$ | III-5895 | $L_{A432}$ | $L_{B35}$ |
| III-2751 | $L_{A348}$ | $L_{B17}$ | III-5896 | $L_{A433}$ | $L_{B35}$ |
| III-2752 | $L_{A349}$ | $L_{B17}$ | III-5897 | $L_{A434}$ | $L_{B35}$ |
| III-2753 | $L_{A350}$ | $L_{B17}$ | III-5898 | $L_{A435}$ | $L_{B35}$ |
| III-2754 | $L_{A351}$ | $L_{B17}$ | III-5899 | $L_{A436}$ | $L_{B35}$ |
| III-2755 | $L_{A352}$ | $L_{B17}$ | III-5900 | $L_{A437}$ | $L_{B35}$ |
| III-2756 | $L_{A353}$ | $L_{B17}$ | III-5901 | $L_{A438}$ | $L_{B35}$ |
| III-2757 | $L_{A354}$ | $L_{B17}$ | III-5902 | $L_{A439}$ | $L_{B35}$ |
| III-2758 | $L_{A355}$ | $L_{B17}$ | III-5903 | $L_{A440}$ | $L_{B35}$ |
| III-2759 | $L_{A356}$ | $L_{B17}$ | III-5904 | $L_{A441}$ | $L_{B35}$ |
| III-2760 | $L_{A357}$ | $L_{B17}$ | III-5905 | $L_{A442}$ | $L_{B35}$ |
| III-2761 | $L_{A358}$ | $L_{B17}$ | III-5906 | $L_{A443}$ | $L_{B35}$ |
| III-2762 | $L_{A359}$ | $L_{B17}$ | III-5907 | $L_{A444}$ | $L_{B35}$ |
| III-2763 | $L_{A360}$ | $L_{B17}$ | III-5908 | $L_{A445}$ | $L_{B35}$ |
| III-2764 | $L_{A361}$ | $L_{B17}$ | III-5909 | $L_{A446}$ | $L_{B35}$ |
| III-2765 | $L_{A362}$ | $L_{B17}$ | III-5910 | $L_{A447}$ | $L_{B35}$ |
| III-2766 | $L_{A363}$ | $L_{B17}$ | III-5911 | $L_{A448}$ | $L_{B35}$ |
| III-2767 | $L_{A364}$ | $L_{B17}$ | III-5912 | $L_{A449}$ | $L_{B35}$ |
| III-2768 | $L_{A365}$ | $L_{B17}$ | III-5913 | $L_{A450}$ | $L_{B35}$ |
| III-2769 | $L_{A366}$ | $L_{B17}$ | III-5914 | $L_{A451}$ | $L_{B35}$ |
| III-2770 | $L_{A367}$ | $L_{B17}$ | III-5915 | $L_{A452}$ | $L_{B35}$ |
| III-2771 | $L_{A368}$ | $L_{B17}$ | III-5916 | $L_{A453}$ | $L_{B35}$ |
| III-2772 | $L_{A369}$ | $L_{B17}$ | III-5917 | $L_{A454}$ | $L_{B35}$ |
| III-2773 | $L_{A370}$ | $L_{B17}$ | III-5918 | $L_{A455}$ | $L_{B35}$ |
| III-2774 | $L_{A371}$ | $L_{B17}$ | III-5919 | $L_{A456}$ | $L_{B35}$ |
| III-2775 | $L_{A372}$ | $L_{B17}$ | III-5920 | $L_{A457}$ | $L_{B35}$ |
| III-2776 | $L_{A373}$ | $L_{B17}$ | III-5921 | $L_{A458}$ | $L_{B35}$ |
| III-2777 | $L_{A374}$ | $L_{B17}$ | III-5922 | $L_{A459}$ | $L_{B35}$ |
| III-2778 | $L_{A375}$ | $L_{B17}$ | III-5923 | $L_{A460}$ | $L_{B35}$ |
| III-2779 | $L_{A376}$ | $L_{B17}$ | III-5924 | $L_{A461}$ | $L_{B35}$ |
| III-2780 | $L_{A377}$ | $L_{B17}$ | III-5925 | $L_{A462}$ | $L_{B35}$ |
| III-2781 | $L_{A378}$ | $L_{B17}$ | III-5926 | $L_{A463}$ | $L_{B35}$ |
| III-2782 | $L_{A379}$ | $L_{B17}$ | III-5927 | $L_{A464}$ | $L_{B35}$ |
| III-2783 | $L_{A380}$ | $L_{B17}$ | III-5928 | $L_{A465}$ | $L_{B35}$ |

-continued

| Compound Number | $L_A$ | $L_B$ | Compound Number | $L_A$ | $L_B$ |
|---|---|---|---|---|---|
| III-2784 | $L_{A381}$ | $L_{B17}$ | III-5929 | $L_{A466}$ | $L_{B35}$ |
| III-2785 | $L_{A382}$ | $L_{B17}$ | III-5930 | $L_{A467}$ | $L_{B35}$ |
| III-2786 | $L_{A383}$ | $L_{B17}$ | III-5931 | $L_{A468}$ | $L_{B35}$ |
| III-2787 | $L_{A384}$ | $L_{B17}$ | III-5932 | $L_{A469}$ | $L_{B35}$ |
| III-2788 | $L_{A385}$ | $L_{B17}$ | III-5933 | $L_{A470}$ | $L_{B35}$ |
| III-2789 | $L_{A386}$ | $L_{B17}$ | III-5934 | $L_{A471}$ | $L_{B35}$ |
| III-2790 | $L_{A387}$ | $L_{B17}$ | III-5935 | $L_{A472}$ | $L_{B35}$ |
| III-2791 | $L_{A388}$ | $L_{B17}$ | III-5936 | $L_{A473}$ | $L_{B35}$ |
| III-2792 | $L_{A389}$ | $L_{B17}$ | III-5937 | $L_{A474}$ | $L_{B35}$ |
| III-2793 | $L_{A390}$ | $L_{B17}$ | III-5938 | $L_{A475}$ | $L_{B35}$ |
| III-2794 | $L_{A391}$ | $L_{B17}$ | III-5939 | $L_{A476}$ | $L_{B35}$ |
| III-2795 | $L_{A392}$ | $L_{B17}$ | III-5940 | $L_{A477}$ | $L_{B35}$ |
| III-2796 | $L_{A393}$ | $L_{B17}$ | III-5941 | $L_{A478}$ | $L_{B35}$ |
| III-2797 | $L_{A394}$ | $L_{B17}$ | III-5942 | $L_{A479}$ | $L_{B35}$ |
| III-2798 | $L_{A395}$ | $L_{B17}$ | III-5943 | $L_{A480}$ | $L_{B35}$ |
| III-2799 | $L_{A396}$ | $L_{B17}$ | III-5944 | $L_{A481}$ | $L_{B35}$ |
| III-2800 | $L_{A397}$ | $L_{B17}$ | III-5945 | $L_{A482}$ | $L_{B35}$ |
| III-2801 | $L_{A398}$ | $L_{B17}$ | III-5946 | $L_{A483}$ | $L_{B35}$ |
| III-2802 | $L_{A399}$ | $L_{B17}$ | III-5947 | $L_{A484}$ | $L_{B35}$ |
| III-2803 | $L_{A400}$ | $L_{B17}$ | III-5948 | $L_{A485}$ | $L_{B35}$ |
| III-2804 | $L_{A401}$ | $L_{B17}$ | III-5949 | $L_{A486}$ | $L_{B35}$ |
| III-2805 | $L_{A402}$ | $L_{B17}$ | III-5950 | $L_{A487}$ | $L_{B35}$ |
| III-2806 | $L_{A403}$ | $L_{B17}$ | III-5951 | $L_{A318}$ | $L_{B36}$ |
| III-2807 | $L_{A404}$ | $L_{B17}$ | III-5952 | $L_{A319}$ | $L_{B36}$ |
| III-2808 | $L_{A405}$ | $L_{B17}$ | III-5953 | $L_{A320}$ | $L_{B36}$ |
| III-2809 | $L_{A406}$ | $L_{B17}$ | III-5954 | $L_{A321}$ | $L_{B36}$ |
| III-2810 | $L_{A407}$ | $L_{B17}$ | III-5955 | $L_{A322}$ | $L_{B36}$ |
| III-2811 | $L_{A408}$ | $L_{B17}$ | III-5956 | $L_{A323}$ | $L_{B36}$ |
| III-2812 | $L_{A409}$ | $L_{B17}$ | III-5957 | $L_{A324}$ | $L_{B36}$ |
| III-2813 | $L_{A410}$ | $L_{B17}$ | III-5958 | $L_{A325}$ | $L_{B36}$ |
| III-2814 | $L_{A411}$ | $L_{B17}$ | III-5959 | $L_{A326}$ | $L_{B36}$ |
| III-2815 | $L_{A412}$ | $L_{B17}$ | III-5960 | $L_{A327}$ | $L_{B36}$ |
| III-2816 | $L_{A413}$ | $L_{B17}$ | III-5961 | $L_{A328}$ | $L_{B36}$ |
| III-2817 | $L_{A414}$ | $L_{B17}$ | III-5962 | $L_{A329}$ | $L_{B36}$ |
| III-2818 | $L_{A415}$ | $L_{B17}$ | III-5963 | $L_{A330}$ | $L_{B36}$ |
| III-2819 | $L_{A416}$ | $L_{B17}$ | III-5964 | $L_{A331}$ | $L_{B36}$ |
| III-2820 | $L_{A417}$ | $L_{B17}$ | III-5965 | $L_{A332}$ | $L_{B36}$ |
| III-2821 | $L_{A418}$ | $L_{B17}$ | III-5966 | $L_{A333}$ | $L_{B36}$ |
| III-2822 | $L_{A419}$ | $L_{B17}$ | III-5967 | $L_{A334}$ | $L_{B36}$ |
| III-2823 | $L_{A420}$ | $L_{B17}$ | III-5968 | $L_{A335}$ | $L_{B36}$ |
| III-2824 | $L_{A421}$ | $L_{B17}$ | III-5969 | $L_{A336}$ | $L_{B36}$ |
| III-2825 | $L_{A422}$ | $L_{B17}$ | III-5970 | $L_{A337}$ | $L_{B36}$ |
| III-2826 | $L_{A423}$ | $L_{B17}$ | III-5971 | $L_{A338}$ | $L_{B36}$ |
| III-2827 | $L_{A424}$ | $L_{B17}$ | III-5972 | $L_{A339}$ | $L_{B36}$ |
| III-2828 | $L_{A425}$ | $L_{B17}$ | III-5973 | $L_{A340}$ | $L_{B36}$ |
| III-2829 | $L_{A426}$ | $L_{B17}$ | III-5974 | $L_{A341}$ | $L_{B36}$ |
| III-2830 | $L_{A427}$ | $L_{B17}$ | III-5975 | $L_{A342}$ | $L_{B36}$ |
| III-2831 | $L_{A428}$ | $L_{B17}$ | III-5976 | $L_{A343}$ | $L_{B36}$ |
| III-2832 | $L_{A429}$ | $L_{B17}$ | III-5977 | $L_{A344}$ | $L_{B36}$ |
| III-2833 | $L_{A430}$ | $L_{B17}$ | III-5978 | $L_{A345}$ | $L_{B36}$ |
| III-2834 | $L_{A431}$ | $L_{B17}$ | III-5979 | $L_{A346}$ | $L_{B36}$ |
| III-2835 | $L_{A432}$ | $L_{B17}$ | III-5980 | $L_{A347}$ | $L_{B36}$ |
| III-2836 | $L_{A433}$ | $L_{B17}$ | III-5981 | $L_{A348}$ | $L_{B36}$ |
| III-2837 | $L_{A434}$ | $L_{B17}$ | III-5982 | $L_{A349}$ | $L_{B36}$ |
| III-2838 | $L_{A435}$ | $L_{B17}$ | III-5983 | $L_{A350}$ | $L_{B36}$ |
| III-2839 | $L_{A436}$ | $L_{B17}$ | III-5984 | $L_{A351}$ | $L_{B36}$ |
| III-2840 | $L_{A437}$ | $L_{B17}$ | III-5985 | $L_{A352}$ | $L_{B36}$ |
| III-2841 | $L_{A438}$ | $L_{B17}$ | III-5986 | $L_{A353}$ | $L_{B36}$ |
| III-2842 | $L_{A439}$ | $L_{B17}$ | III-5987 | $L_{A354}$ | $L_{B36}$ |
| III-2843 | $L_{A440}$ | $L_{B17}$ | III-5988 | $L_{A355}$ | $L_{B36}$ |
| III-2844 | $L_{A441}$ | $L_{B17}$ | III-5989 | $L_{A356}$ | $L_{B36}$ |
| III-2845 | $L_{A442}$ | $L_{B17}$ | III-5990 | $L_{A357}$ | $L_{B36}$ |
| III-2846 | $L_{A443}$ | $L_{B17}$ | III-5991 | $L_{A358}$ | $L_{B36}$ |
| III-2847 | $L_{A444}$ | $L_{B17}$ | III-5992 | $L_{A359}$ | $L_{B36}$ |
| III-2848 | $L_{A445}$ | $L_{B17}$ | III-5993 | $L_{A360}$ | $L_{B36}$ |
| III-2849 | $L_{A446}$ | $L_{B17}$ | III-5994 | $L_{A361}$ | $L_{B36}$ |
| III-2850 | $L_{A447}$ | $L_{B17}$ | III-5995 | $L_{A362}$ | $L_{B36}$ |
| III-2851 | $L_{A448}$ | $L_{B17}$ | III-5996 | $L_{A363}$ | $L_{B36}$ |
| III-2852 | $L_{A449}$ | $L_{B17}$ | III-5997 | $L_{A364}$ | $L_{B36}$ |
| III-2853 | $L_{A450}$ | $L_{B17}$ | III-5998 | $L_{A365}$ | $L_{B36}$ |
| III-2854 | $L_{A451}$ | $L_{B17}$ | III-5999 | $L_{A366}$ | $L_{B36}$ |
| III-2855 | $L_{A452}$ | $L_{B17}$ | III-6000 | $L_{A367}$ | $L_{B36}$ |
| III-2856 | $L_{A453}$ | $L_{B17}$ | III-6001 | $L_{A368}$ | $L_{B36}$ |
| III-2857 | $L_{A454}$ | $L_{B17}$ | III-6002 | $L_{A369}$ | $L_{B36}$ |
| III-2858 | $L_{A455}$ | $L_{B17}$ | III-6003 | $L_{A370}$ | $L_{B36}$ |
| III-2859 | $L_{A456}$ | $L_{B17}$ | III-6004 | $L_{A371}$ | $L_{B36}$ |
| III-2860 | $L_{A457}$ | $L_{B17}$ | III-6005 | $L_{A372}$ | $L_{B36}$ |
| III-2861 | $L_{A458}$ | $L_{B17}$ | III-6006 | $L_{A373}$ | $L_{B36}$ |
| III-2862 | $L_{A459}$ | $L_{B17}$ | III-6007 | $L_{A374}$ | $L_{B36}$ |
| III-2863 | $L_{A460}$ | $L_{B17}$ | III-6008 | $L_{A375}$ | $L_{B36}$ |
| III-2864 | $L_{A461}$ | $L_{B17}$ | III-6009 | $L_{A376}$ | $L_{B36}$ |
| III-2865 | $L_{A462}$ | $L_{B17}$ | III-6010 | $L_{A377}$ | $L_{B36}$ |
| III-2866 | $L_{A463}$ | $L_{B17}$ | III-6011 | $L_{A378}$ | $L_{B36}$ |
| III-2867 | $L_{A464}$ | $L_{B17}$ | III-6012 | $L_{A379}$ | $L_{B36}$ |
| III-2868 | $L_{A465}$ | $L_{B17}$ | III-6013 | $L_{A380}$ | $L_{B36}$ |
| III-2869 | $L_{A466}$ | $L_{B17}$ | III-6014 | $L_{A381}$ | $L_{B36}$ |
| III-2870 | $L_{A467}$ | $L_{B17}$ | III-6015 | $L_{A382}$ | $L_{B36}$ |
| III-2871 | $L_{A468}$ | $L_{B17}$ | III-6016 | $L_{A383}$ | $L_{B36}$ |
| III-2872 | $L_{A469}$ | $L_{B17}$ | III-6017 | $L_{A384}$ | $L_{B36}$ |
| III-2873 | $L_{A470}$ | $L_{B17}$ | III-6018 | $L_{A385}$ | $L_{B36}$ |
| III-2874 | $L_{A471}$ | $L_{B17}$ | III-6019 | $L_{A386}$ | $L_{B36}$ |
| III-2875 | $L_{A472}$ | $L_{B17}$ | III-6020 | $L_{A387}$ | $L_{B36}$ |
| III-2876 | $L_{A473}$ | $L_{B17}$ | III-6021 | $L_{A388}$ | $L_{B36}$ |
| III-2877 | $L_{A474}$ | $L_{B17}$ | III-6022 | $L_{A389}$ | $L_{B36}$ |
| III-2878 | $L_{A475}$ | $L_{B17}$ | III-6023 | $L_{A390}$ | $L_{B36}$ |
| III-2879 | $L_{A476}$ | $L_{B17}$ | III-6024 | $L_{A391}$ | $L_{B36}$ |
| III-2880 | $L_{A477}$ | $L_{B17}$ | III-6025 | $L_{A392}$ | $L_{B36}$ |
| III-2881 | $L_{A478}$ | $L_{B17}$ | III-6026 | $L_{A393}$ | $L_{B36}$ |
| III-2882 | $L_{A479}$ | $L_{B17}$ | III-6027 | $L_{A394}$ | $L_{B36}$ |
| III-2883 | $L_{A480}$ | $L_{B17}$ | III-6028 | $L_{A395}$ | $L_{B36}$ |
| III-2884 | $L_{A481}$ | $L_{B17}$ | III-6029 | $L_{A396}$ | $L_{B36}$ |
| III-2885 | $L_{A482}$ | $L_{B17}$ | III-6030 | $L_{A397}$ | $L_{B36}$ |
| III-2886 | $L_{A483}$ | $L_{B17}$ | III-6031 | $L_{A398}$ | $L_{B36}$ |
| III-2887 | $L_{A484}$ | $L_{B17}$ | III-6032 | $L_{A399}$ | $L_{B36}$ |
| III-2888 | $L_{A485}$ | $L_{B17}$ | III-6033 | $L_{A400}$ | $L_{B36}$ |
| III-2889 | $L_{A486}$ | $L_{B17}$ | III-6034 | $L_{A401}$ | $L_{B36}$ |
| III-2890 | $L_{A487}$ | $L_{B17}$ | III-6035 | $L_{A402}$ | $L_{B36}$ |
| III-2891 | $L_{A318}$ | $L_{B18}$ | III-6036 | $L_{A403}$ | $L_{B36}$ |
| III-2892 | $L_{A319}$ | $L_{B18}$ | III-6037 | $L_{A404}$ | $L_{B36}$ |
| III-2893 | $L_{A320}$ | $L_{B18}$ | III-6038 | $L_{A405}$ | $L_{B36}$ |
| III-2894 | $L_{A321}$ | $L_{B18}$ | III-6039 | $L_{A406}$ | $L_{B36}$ |
| III-2895 | $L_{A322}$ | $L_{B18}$ | III-6040 | $L_{A407}$ | $L_{B36}$ |
| III-2896 | $L_{A323}$ | $L_{B18}$ | III-6041 | $L_{A408}$ | $L_{B36}$ |
| III-2897 | $L_{A324}$ | $L_{B18}$ | III-6042 | $L_{A409}$ | $L_{B36}$ |
| III-2898 | $L_{A325}$ | $L_{B18}$ | III-6043 | $L_{A410}$ | $L_{B36}$ |
| III-2899 | $L_{A326}$ | $L_{B18}$ | III-6044 | $L_{A411}$ | $L_{B36}$ |
| III-2900 | $L_{A327}$ | $L_{B18}$ | III-6045 | $L_{A412}$ | $L_{B36}$ |
| III-2901 | $L_{A328}$ | $L_{B18}$ | III-6046 | $L_{A413}$ | $L_{B36}$ |
| III-2902 | $L_{A329}$ | $L_{B18}$ | III-6047 | $L_{A414}$ | $L_{B36}$ |
| III-2903 | $L_{A330}$ | $L_{B18}$ | III-6048 | $L_{A415}$ | $L_{B36}$ |
| III-2904 | $L_{A331}$ | $L_{B18}$ | III-6049 | $L_{A416}$ | $L_{B36}$ |
| III-2905 | $L_{A332}$ | $L_{B18}$ | III-6050 | $L_{A417}$ | $L_{B36}$ |
| III-2906 | $L_{A333}$ | $L_{B18}$ | III-6051 | $L_{A418}$ | $L_{B36}$ |
| III-2907 | $L_{A334}$ | $L_{B18}$ | III-6052 | $L_{A419}$ | $L_{B36}$ |
| III-2908 | $L_{A335}$ | $L_{B18}$ | III-6053 | $L_{A420}$ | $L_{B36}$ |
| III-2909 | $L_{A336}$ | $L_{B18}$ | III-6054 | $L_{A421}$ | $L_{B36}$ |
| III-2910 | $L_{A337}$ | $L_{B18}$ | III-6055 | $L_{A422}$ | $L_{B36}$ |
| III-2911 | $L_{A338}$ | $L_{B18}$ | III-6056 | $L_{A423}$ | $L_{B36}$ |
| III-2912 | $L_{A339}$ | $L_{B18}$ | III-6057 | $L_{A424}$ | $L_{B36}$ |
| III-2913 | $L_{A340}$ | $L_{B18}$ | III-6058 | $L_{A425}$ | $L_{B36}$ |
| III-2914 | $L_{A341}$ | $L_{B18}$ | III-6059 | $L_{A426}$ | $L_{B36}$ |
| III-2915 | $L_{A342}$ | $L_{B18}$ | III-6060 | $L_{A427}$ | $L_{B36}$ |
| III-2916 | $L_{A343}$ | $L_{B18}$ | III-6061 | $L_{A428}$ | $L_{B36}$ |
| III-2917 | $L_{A344}$ | $L_{B18}$ | III-6062 | $L_{A429}$ | $L_{B36}$ |
| III-2918 | $L_{A345}$ | $L_{B18}$ | III-6063 | $L_{A430}$ | $L_{B36}$ |
| III-2919 | $L_{A346}$ | $L_{B18}$ | III-6064 | $L_{A431}$ | $L_{B36}$ |
| III-2920 | $L_{A347}$ | $L_{B18}$ | III-6065 | $L_{A432}$ | $L_{B36}$ |
| III-2921 | $L_{A348}$ | $L_{B18}$ | III-6066 | $L_{A433}$ | $L_{B36}$ |
| III-2922 | $L_{A349}$ | $L_{B18}$ | III-6067 | $L_{A434}$ | $L_{B36}$ |
| III-2923 | $L_{A350}$ | $L_{B18}$ | III-6068 | $L_{A435}$ | $L_{B36}$ |
| III-2924 | $L_{A351}$ | $L_{B18}$ | III-6069 | $L_{A436}$ | $L_{B36}$ |
| III-2925 | $L_{A352}$ | $L_{B18}$ | III-6070 | $L_{A437}$ | $L_{B36}$ |
| III-2926 | $L_{A353}$ | $L_{B18}$ | III-6071 | $L_{A438}$ | $L_{B36}$ |
| III-2927 | $L_{A354}$ | $L_{B18}$ | III-6072 | $L_{A439}$ | $L_{B36}$ |
| III-2928 | $L_{A355}$ | $L_{B18}$ | III-6073 | $L_{A440}$ | $L_{B36}$ |
| III-2929 | $L_{A356}$ | $L_{B18}$ | III-6074 | $L_{A441}$ | $L_{B36}$ |
| III-2930 | $L_{A357}$ | $L_{B18}$ | III-6075 | $L_{A442}$ | $L_{B36}$ |
| III-2931 | $L_{A358}$ | $L_{B18}$ | III-6076 | $L_{A443}$ | $L_{B36}$ |
| III-2932 | $L_{A359}$ | $L_{B18}$ | III-6077 | $L_{A444}$ | $L_{B36}$ |
| III-2933 | $L_{A360}$ | $L_{B18}$ | III-6078 | $L_{A445}$ | $L_{B36}$ |
| III-2934 | $L_{A361}$ | $L_{B18}$ | III-6079 | $L_{A446}$ | $L_{B36}$ |
| III-2935 | $L_{A362}$ | $L_{B18}$ | III-6080 | $L_{A447}$ | $L_{B36}$ |

| Compound Number | $L_A$ | $L_B$ | Compound Number | $L_A$ | $L_B$ | Compound Number | $L_A$ | $L_B$ | Compound Number | $L_A$ | $L_B$ |
|---|---|---|---|---|---|---|---|---|---|---|---|
| III-2936 | $L_{A363}$ | $L_{B18}$ | III-6081 | $L_{A448}$ | $L_{B36}$ | III-3012 | $L_{A439}$ | $L_{B18}$ | III-6157 | $L_{A354}$ | $L_{B37}$ |
| III-2937 | $L_{A364}$ | $L_{B18}$ | III-6082 | $L_{A449}$ | $L_{B36}$ | III-3013 | $L_{A440}$ | $L_{B18}$ | III-6158 | $L_{A355}$ | $L_{B37}$ |
| III-2938 | $L_{A365}$ | $L_{B18}$ | III-6083 | $L_{A450}$ | $L_{B36}$ | III-3014 | $L_{A441}$ | $L_{B18}$ | III-6159 | $L_{A356}$ | $L_{B37}$ |
| III-2939 | $L_{A366}$ | $L_{B18}$ | III-6084 | $L_{A451}$ | $L_{B36}$ | III-3015 | $L_{A442}$ | $L_{B18}$ | III-6160 | $L_{A357}$ | $L_{B37}$ |
| III-2940 | $L_{A367}$ | $L_{B18}$ | III-6085 | $L_{A452}$ | $L_{B36}$ | III-3016 | $L_{A443}$ | $L_{B18}$ | III-6161 | $L_{A358}$ | $L_{B37}$ |
| III-2941 | $L_{A368}$ | $L_{B18}$ | III-6086 | $L_{A453}$ | $L_{B36}$ | III-3017 | $L_{A444}$ | $L_{B18}$ | III-6162 | $L_{A359}$ | $L_{B37}$ |
| III-2942 | $L_{A369}$ | $L_{B18}$ | III-6087 | $L_{A454}$ | $L_{B36}$ | III-3018 | $L_{A445}$ | $L_{B18}$ | III-6163 | $L_{A360}$ | $L_{B37}$ |
| III-2943 | $L_{A370}$ | $L_{B18}$ | III-6088 | $L_{A455}$ | $L_{B36}$ | III-3019 | $L_{A446}$ | $L_{B18}$ | III-6164 | $L_{A361}$ | $L_{B37}$ |
| III-2944 | $L_{A371}$ | $L_{B18}$ | III-6089 | $L_{A456}$ | $L_{B36}$ | III-3020 | $L_{A447}$ | $L_{B18}$ | III-6165 | $L_{A362}$ | $L_{B37}$ |
| III-2945 | $L_{A372}$ | $L_{B18}$ | III-6090 | $L_{A457}$ | $L_{B36}$ | III-3021 | $L_{A448}$ | $L_{B18}$ | III-6166 | $L_{A363}$ | $L_{B37}$ |
| III-2946 | $L_{A373}$ | $L_{B18}$ | III-6091 | $L_{A458}$ | $L_{B36}$ | III-3022 | $L_{A449}$ | $L_{B18}$ | III-6167 | $L_{A364}$ | $L_{B37}$ |
| III-2947 | $L_{A374}$ | $L_{B18}$ | III-6092 | $L_{A459}$ | $L_{B36}$ | III-3023 | $L_{A450}$ | $L_{B18}$ | III-6168 | $L_{A365}$ | $L_{B37}$ |
| III-2948 | $L_{A375}$ | $L_{B18}$ | III-6093 | $L_{A460}$ | $L_{B36}$ | III-3024 | $L_{A451}$ | $L_{B18}$ | III-6169 | $L_{A366}$ | $L_{B37}$ |
| III-2949 | $L_{A376}$ | $L_{B18}$ | III-6094 | $L_{A461}$ | $L_{B36}$ | III-3025 | $L_{A452}$ | $L_{B18}$ | III-6170 | $L_{A367}$ | $L_{B37}$ |
| III-2950 | $L_{A377}$ | $L_{B18}$ | III-6095 | $L_{A462}$ | $L_{B36}$ | III-3026 | $L_{A453}$ | $L_{B18}$ | III-6171 | $L_{A368}$ | $L_{B37}$ |
| III-2951 | $L_{A378}$ | $L_{B18}$ | III-6096 | $L_{A463}$ | $L_{B36}$ | III-3027 | $L_{A454}$ | $L_{B18}$ | III-6172 | $L_{A369}$ | $L_{B37}$ |
| III-2952 | $L_{A379}$ | $L_{B18}$ | III-6097 | $L_{A464}$ | $L_{B36}$ | III-3028 | $L_{A455}$ | $L_{B18}$ | III-6173 | $L_{A370}$ | $L_{B37}$ |
| III-2953 | $L_{A380}$ | $L_{B18}$ | III-6098 | $L_{A465}$ | $L_{B36}$ | III-3029 | $L_{A456}$ | $L_{B18}$ | III-6174 | $L_{A371}$ | $L_{B37}$ |
| III-2954 | $L_{A381}$ | $L_{B18}$ | III-6099 | $L_{A466}$ | $L_{B36}$ | III-3030 | $L_{A457}$ | $L_{B18}$ | III-6175 | $L_{A372}$ | $L_{B37}$ |
| III-2955 | $L_{A382}$ | $L_{B18}$ | III-6100 | $L_{A467}$ | $L_{B36}$ | III-3031 | $L_{A458}$ | $L_{B18}$ | III-6176 | $L_{A373}$ | $L_{B37}$ |
| III-2956 | $L_{A383}$ | $L_{B18}$ | III-6101 | $L_{A468}$ | $L_{B36}$ | III-3032 | $L_{A459}$ | $L_{B18}$ | III-6177 | $L_{A374}$ | $L_{B37}$ |
| III-2957 | $L_{A384}$ | $L_{B18}$ | III-6102 | $L_{A469}$ | $L_{B36}$ | III-3033 | $L_{A460}$ | $L_{B18}$ | III-6178 | $L_{A375}$ | $L_{B37}$ |
| III-2958 | $L_{A385}$ | $L_{B18}$ | III-6103 | $L_{A470}$ | $L_{B36}$ | III-3034 | $L_{A461}$ | $L_{B18}$ | III-6179 | $L_{A376}$ | $L_{B37}$ |
| III-2959 | $L_{A386}$ | $L_{B18}$ | III-6104 | $L_{A471}$ | $L_{B36}$ | III-3035 | $L_{A462}$ | $L_{B18}$ | III-6180 | $L_{A377}$ | $L_{B37}$ |
| III-2960 | $L_{A387}$ | $L_{B18}$ | III-6105 | $L_{A472}$ | $L_{B36}$ | III-3036 | $L_{A463}$ | $L_{B18}$ | III-6181 | $L_{A378}$ | $L_{B37}$ |
| III-2961 | $L_{A388}$ | $L_{B18}$ | III-6106 | $L_{A473}$ | $L_{B36}$ | III-3037 | $L_{A464}$ | $L_{B18}$ | III-6182 | $L_{A379}$ | $L_{B37}$ |
| III-2962 | $L_{A389}$ | $L_{B18}$ | III-6107 | $L_{A474}$ | $L_{B36}$ | III-3038 | $L_{A465}$ | $L_{B18}$ | III-6183 | $L_{A380}$ | $L_{B37}$ |
| III-2963 | $L_{A390}$ | $L_{B18}$ | III-6108 | $L_{A475}$ | $L_{B36}$ | III-3039 | $L_{A466}$ | $L_{B18}$ | III-6184 | $L_{A381}$ | $L_{B37}$ |
| III-2964 | $L_{A391}$ | $L_{B18}$ | III-6109 | $L_{A476}$ | $L_{B36}$ | III-3040 | $L_{A467}$ | $L_{B18}$ | III-6185 | $L_{A382}$ | $L_{B37}$ |
| III-2965 | $L_{A392}$ | $L_{B18}$ | III-6110 | $L_{A477}$ | $L_{B36}$ | III-3041 | $L_{A468}$ | $L_{B18}$ | III-6186 | $L_{A383}$ | $L_{B37}$ |
| III-2966 | $L_{A393}$ | $L_{B18}$ | III-6111 | $L_{A478}$ | $L_{B36}$ | III-3042 | $L_{A469}$ | $L_{B18}$ | III-6187 | $L_{A384}$ | $L_{B37}$ |
| III-2967 | $L_{A394}$ | $L_{B18}$ | III-6112 | $L_{A479}$ | $L_{B36}$ | III-3043 | $L_{A470}$ | $L_{B18}$ | III-6188 | $L_{A385}$ | $L_{B37}$ |
| III-2968 | $L_{A395}$ | $L_{B18}$ | III-6113 | $L_{A480}$ | $L_{B36}$ | III-3044 | $L_{A471}$ | $L_{B18}$ | III-6189 | $L_{A386}$ | $L_{B37}$ |
| III-2969 | $L_{A396}$ | $L_{B18}$ | III-6114 | $L_{A481}$ | $L_{B36}$ | III-3045 | $L_{A472}$ | $L_{B18}$ | III-6190 | $L_{A387}$ | $L_{B37}$ |
| III-2970 | $L_{A397}$ | $L_{B18}$ | III-6115 | $L_{A482}$ | $L_{B36}$ | III-3046 | $L_{A473}$ | $L_{B18}$ | III-6191 | $L_{A388}$ | $L_{B37}$ |
| III-2971 | $L_{A398}$ | $L_{B18}$ | III-6116 | $L_{A483}$ | $L_{B36}$ | III-3047 | $L_{A474}$ | $L_{B18}$ | III-6192 | $L_{A389}$ | $L_{B37}$ |
| III-2972 | $L_{A399}$ | $L_{B18}$ | III-6117 | $L_{A484}$ | $L_{B36}$ | III-3048 | $L_{A475}$ | $L_{B18}$ | III-6193 | $L_{A390}$ | $L_{B37}$ |
| III-2973 | $L_{A400}$ | $L_{B18}$ | III-6118 | $L_{A485}$ | $L_{B36}$ | III-3049 | $L_{A476}$ | $L_{B18}$ | III-6194 | $L_{A391}$ | $L_{B37}$ |
| III-2974 | $L_{A401}$ | $L_{B18}$ | III-6119 | $L_{A486}$ | $L_{B36}$ | III-3050 | $L_{A477}$ | $L_{B18}$ | III-6195 | $L_{A392}$ | $L_{B37}$ |
| III-2975 | $L_{A402}$ | $L_{B18}$ | III-6120 | $L_{A487}$ | $L_{B36}$ | III-3051 | $L_{A478}$ | $L_{B18}$ | III-6196 | $L_{A393}$ | $L_{B37}$ |
| III-2976 | $L_{A403}$ | $L_{B18}$ | III-6121 | $L_{A318}$ | $L_{B37}$ | III-3052 | $L_{A479}$ | $L_{B18}$ | III-6197 | $L_{A394}$ | $L_{B37}$ |
| III-2977 | $L_{A404}$ | $L_{B18}$ | III-6122 | $L_{A319}$ | $L_{B37}$ | III-3053 | $L_{A480}$ | $L_{B18}$ | III-6198 | $L_{A395}$ | $L_{B37}$ |
| III-2978 | $L_{A405}$ | $L_{B18}$ | III-6123 | $L_{A320}$ | $L_{B37}$ | III-3054 | $L_{A481}$ | $L_{B18}$ | III-6199 | $L_{A396}$ | $L_{B37}$ |
| III-2979 | $L_{A406}$ | $L_{B18}$ | III-6124 | $L_{A321}$ | $L_{B37}$ | III-3055 | $L_{A482}$ | $L_{B18}$ | III-6200 | $L_{A397}$ | $L_{B37}$ |
| III-2980 | $L_{A407}$ | $L_{B18}$ | III-6125 | $L_{A322}$ | $L_{B37}$ | III-3056 | $L_{A483}$ | $L_{B18}$ | III-6201 | $L_{A398}$ | $L_{B37}$ |
| III-2981 | $L_{A408}$ | $L_{B18}$ | III-6126 | $L_{A323}$ | $L_{B37}$ | III-3057 | $L_{A484}$ | $L_{B18}$ | III-6202 | $L_{A399}$ | $L_{B37}$ |
| III-2982 | $L_{A409}$ | $L_{B18}$ | III-6127 | $L_{A324}$ | $L_{B37}$ | III-3058 | $L_{A485}$ | $L_{B18}$ | III-6203 | $L_{A400}$ | $L_{B37}$ |
| III-2983 | $L_{A410}$ | $L_{B18}$ | III-6128 | $L_{A325}$ | $L_{B37}$ | III-3059 | $L_{A486}$ | $L_{B18}$ | III-6204 | $L_{A401}$ | $L_{B37}$ |
| III-2984 | $L_{A411}$ | $L_{B18}$ | III-6129 | $L_{A326}$ | $L_{B37}$ | III-3060 | $L_{A487}$ | $L_{B18}$ | III-6205 | $L_{A402}$ | $L_{B37}$ |
| III-2985 | $L_{A412}$ | $L_{B18}$ | III-6130 | $L_{A327}$ | $L_{B37}$ | III-3061 | $L_{A318}$ | $L_{B19}$ | III-6206 | $L_{A403}$ | $L_{B37}$ |
| III-2986 | $L_{A413}$ | $L_{B18}$ | III-6131 | $L_{A328}$ | $L_{B37}$ | III-3062 | $L_{A319}$ | $L_{B19}$ | III-6207 | $L_{A404}$ | $L_{B37}$ |
| III-2987 | $L_{A414}$ | $L_{B18}$ | III-6132 | $L_{A329}$ | $L_{B37}$ | III-3063 | $L_{A320}$ | $L_{B19}$ | III-6208 | $L_{A405}$ | $L_{B37}$ |
| III-2988 | $L_{A415}$ | $L_{B18}$ | III-6133 | $L_{A330}$ | $L_{B37}$ | III-3064 | $L_{A321}$ | $L_{B19}$ | III-6209 | $L_{A406}$ | $L_{B37}$ |
| III-2989 | $L_{A416}$ | $L_{B18}$ | III-6134 | $L_{A331}$ | $L_{B37}$ | III-3065 | $L_{A322}$ | $L_{B19}$ | III-6210 | $L_{A407}$ | $L_{B37}$ |
| III-2990 | $L_{A417}$ | $L_{B18}$ | III-6135 | $L_{A332}$ | $L_{B37}$ | III-3066 | $L_{A323}$ | $L_{B19}$ | III-6211 | $L_{A408}$ | $L_{B37}$ |
| III-2991 | $L_{A418}$ | $L_{B18}$ | III-6136 | $L_{A333}$ | $L_{B37}$ | III-3067 | $L_{A324}$ | $L_{B19}$ | III-6212 | $L_{A409}$ | $L_{B37}$ |
| III-2992 | $L_{A419}$ | $L_{B18}$ | III-6137 | $L_{A334}$ | $L_{B37}$ | III-3068 | $L_{A325}$ | $L_{B19}$ | III-6213 | $L_{A410}$ | $L_{B37}$ |
| III-2993 | $L_{A420}$ | $L_{B18}$ | III-6138 | $L_{A335}$ | $L_{B37}$ | III-3069 | $L_{A326}$ | $L_{B19}$ | III-6214 | $L_{A411}$ | $L_{B37}$ |
| III-2994 | $L_{A421}$ | $L_{B18}$ | III-6139 | $L_{A336}$ | $L_{B37}$ | III-3070 | $L_{A327}$ | $L_{B19}$ | III-6215 | $L_{A412}$ | $L_{B37}$ |
| III-2995 | $L_{A422}$ | $L_{B18}$ | III-6140 | $L_{A337}$ | $L_{B37}$ | III-3071 | $L_{A328}$ | $L_{B19}$ | III-6216 | $L_{A413}$ | $L_{B37}$ |
| III-2996 | $L_{A423}$ | $L_{B18}$ | III-6141 | $L_{A338}$ | $L_{B37}$ | III-3072 | $L_{A329}$ | $L_{B19}$ | III-6217 | $L_{A414}$ | $L_{B37}$ |
| III-2997 | $L_{A424}$ | $L_{B18}$ | III-6142 | $L_{A339}$ | $L_{B37}$ | III-3073 | $L_{A330}$ | $L_{B19}$ | III-6218 | $L_{A415}$ | $L_{B37}$ |
| III-2998 | $L_{A425}$ | $L_{B18}$ | III-6143 | $L_{A340}$ | $L_{B37}$ | III-3074 | $L_{A331}$ | $L_{B19}$ | III-6219 | $L_{A416}$ | $L_{B37}$ |
| III-2999 | $L_{A426}$ | $L_{B18}$ | III-6144 | $L_{A341}$ | $L_{B37}$ | III-3075 | $L_{A332}$ | $L_{B19}$ | III-6220 | $L_{A417}$ | $L_{B37}$ |
| III-3000 | $L_{A427}$ | $L_{B18}$ | III-6145 | $L_{A342}$ | $L_{B37}$ | III-3076 | $L_{A333}$ | $L_{B19}$ | III-6221 | $L_{A418}$ | $L_{B37}$ |
| III-3001 | $L_{A428}$ | $L_{B18}$ | III-6146 | $L_{A343}$ | $L_{B37}$ | III-3077 | $L_{A334}$ | $L_{B19}$ | III-6222 | $L_{A419}$ | $L_{B37}$ |
| III-3002 | $L_{A429}$ | $L_{B18}$ | III-6147 | $L_{A344}$ | $L_{B37}$ | III-3078 | $L_{A335}$ | $L_{B19}$ | III-6223 | $L_{A420}$ | $L_{B37}$ |
| III-3003 | $L_{A430}$ | $L_{B18}$ | III-6148 | $L_{A345}$ | $L_{B37}$ | III-3079 | $L_{A336}$ | $L_{B19}$ | III-6224 | $L_{A421}$ | $L_{B37}$ |
| III-3004 | $L_{A431}$ | $L_{B18}$ | III-6149 | $L_{A346}$ | $L_{B37}$ | III-3080 | $L_{A337}$ | $L_{B19}$ | III-6225 | $L_{A422}$ | $L_{B37}$ |
| III-3005 | $L_{A432}$ | $L_{B18}$ | III-6150 | $L_{A347}$ | $L_{B37}$ | III-3081 | $L_{A338}$ | $L_{B19}$ | III-6226 | $L_{A423}$ | $L_{B37}$ |
| III-3006 | $L_{A433}$ | $L_{B18}$ | III-6151 | $L_{A348}$ | $L_{B37}$ | III-3082 | $L_{A339}$ | $L_{B19}$ | III-6227 | $L_{A424}$ | $L_{B37}$ |
| III-3007 | $L_{A434}$ | $L_{B18}$ | III-6152 | $L_{A349}$ | $L_{B37}$ | III-3083 | $L_{A340}$ | $L_{B19}$ | III-6228 | $L_{A425}$ | $L_{B37}$ |
| III-3008 | $L_{A435}$ | $L_{B18}$ | III-6153 | $L_{A350}$ | $L_{B37}$ | III-3084 | $L_{A341}$ | $L_{B19}$ | III-6229 | $L_{A426}$ | $L_{B37}$ |
| III-3009 | $L_{A436}$ | $L_{B18}$ | III-6154 | $L_{A351}$ | $L_{B37}$ | III-3085 | $L_{A342}$ | $L_{B19}$ | III-6230 | $L_{A427}$ | $L_{B37}$ |
| III-3010 | $L_{A437}$ | $L_{B18}$ | III-6155 | $L_{A352}$ | $L_{B37}$ | III-3086 | $L_{A343}$ | $L_{B19}$ | III-6231 | $L_{A428}$ | $L_{B37}$ |
| III-3011 | $L_{A438}$ | $L_{B18}$ | III-6156 | $L_{A353}$ | $L_{B37}$ | III-3087 | $L_{A344}$ | $L_{B19}$ | III-6232 | $L_{A429}$ | $L_{B37}$ |

-continued

| Compound Number | $L_A$ | $L_B$ | Compound Number | $L_A$ | $L_B$ |
|---|---|---|---|---|---|
| III-3088 | $L_{A345}$ | $L_{B19}$ | III-6233 | $L_{A430}$ | $L_{B37}$ |
| III-3089 | $L_{A346}$ | $L_{B19}$ | III-6234 | $L_{A431}$ | $L_{B37}$ |
| III-3090 | $L_{A347}$ | $L_{B19}$ | III-6235 | $L_{A432}$ | $L_{B37}$ |
| III-3091 | $L_{A348}$ | $L_{B19}$ | III-6236 | $L_{A433}$ | $L_{B37}$ |
| III-3092 | $L_{A349}$ | $L_{B19}$ | III-6237 | $L_{A434}$ | $L_{B37}$ |
| III-3093 | $L_{A350}$ | $L_{B19}$ | III-6238 | $L_{A435}$ | $L_{B37}$ |
| III-3094 | $L_{A351}$ | $L_{B19}$ | III-6239 | $L_{A436}$ | $L_{B37}$ |
| III-3095 | $L_{A352}$ | $L_{B19}$ | III-6240 | $L_{A437}$ | $L_{B37}$ |
| III-3096 | $L_{A353}$ | $L_{B19}$ | III-6241 | $L_{A438}$ | $L_{B37}$ |
| III-3097 | $L_{A354}$ | $L_{B19}$ | III-6242 | $L_{A439}$ | $L_{B37}$ |
| III-3098 | $L_{A355}$ | $L_{B19}$ | III-6243 | $L_{A440}$ | $L_{B37}$ |
| III-3099 | $L_{A356}$ | $L_{B19}$ | III-6244 | $L_{A441}$ | $L_{B37}$ |
| III-3100 | $L_{A357}$ | $L_{B19}$ | III-6245 | $L_{A442}$ | $L_{B37}$ |
| III-3101 | $L_{A358}$ | $L_{B19}$ | III-6246 | $L_{A443}$ | $L_{B37}$ |
| III-3102 | $L_{A359}$ | $L_{B19}$ | III-6247 | $L_{A444}$ | $L_{B37}$ |
| III-3103 | $L_{A360}$ | $L_{B19}$ | III-6248 | $L_{A445}$ | $L_{B37}$ |
| III-3104 | $L_{A361}$ | $L_{B19}$ | III-6249 | $L_{A446}$ | $L_{B37}$ |
| III-3105 | $L_{A362}$ | $L_{B19}$ | III-6250 | $L_{A447}$ | $L_{B37}$ |
| III-3106 | $L_{A363}$ | $L_{B19}$ | III-6251 | $L_{A448}$ | $L_{B37}$ |
| III-3107 | $L_{A364}$ | $L_{B19}$ | III-6252 | $L_{A449}$ | $L_{B37}$ |
| III-3108 | $L_{A365}$ | $L_{B19}$ | III-6253 | $L_{A450}$ | $L_{B37}$ |
| III-3109 | $L_{A366}$ | $L_{B19}$ | III-6254 | $L_{A451}$ | $L_{B37}$ |
| III-3110 | $L_{A367}$ | $L_{B19}$ | III-6255 | $L_{A452}$ | $L_{B37}$ |
| III-3111 | $L_{A368}$ | $L_{B19}$ | III-6256 | $L_{A453}$ | $L_{B37}$ |
| III-3112 | $L_{A369}$ | $L_{B19}$ | III-6257 | $L_{A454}$ | $L_{B37}$ |
| III-3113 | $L_{A370}$ | $L_{B19}$ | III-6258 | $L_{A455}$ | $L_{B37}$ |
| III-3114 | $L_{A371}$ | $L_{B19}$ | III-6259 | $L_{A456}$ | $L_{B37}$ |
| III-3115 | $L_{A372}$ | $L_{B19}$ | III-6260 | $L_{A457}$ | $L_{B37}$ |
| III-3116 | $L_{A373}$ | $L_{B19}$ | III-6261 | $L_{A458}$ | $L_{B37}$ |
| III-3117 | $L_{A374}$ | $L_{B19}$ | III-6262 | $L_{A459}$ | $L_{B37}$ |
| III-3118 | $L_{A375}$ | $L_{B19}$ | III-6263 | $L_{A460}$ | $L_{B37}$ |
| III-3119 | $L_{A376}$ | $L_{B19}$ | III-6264 | $L_{A461}$ | $L_{B37}$ |
| III-3120 | $L_{A377}$ | $L_{B19}$ | III-6265 | $L_{A462}$ | $L_{B37}$ |
| III-3121 | $L_{A378}$ | $L_{B19}$ | III-6266 | $L_{A463}$ | $L_{B37}$ |
| III-3122 | $L_{A379}$ | $L_{B19}$ | III-6267 | $L_{A464}$ | $L_{B37}$ |
| III-3123 | $L_{A380}$ | $L_{B19}$ | III-6268 | $L_{A465}$ | $L_{B37}$ |
| III-3124 | $L_{A381}$ | $L_{B19}$ | III-6269 | $L_{A466}$ | $L_{B37}$ |
| III-3125 | $L_{A382}$ | $L_{B19}$ | III-6270 | $L_{A467}$ | $L_{B37}$ |
| III-3126 | $L_{A383}$ | $L_{B19}$ | III-6271 | $L_{A468}$ | $L_{B37}$ |
| III-3127 | $L_{A384}$ | $L_{B19}$ | III-6272 | $L_{A469}$ | $L_{B37}$ |
| III-3128 | $L_{A385}$ | $L_{B19}$ | III-6273 | $L_{A470}$ | $L_{B37}$ |
| III-3129 | $L_{A386}$ | $L_{B19}$ | III-6274 | $L_{A471}$ | $L_{B37}$ |
| III-3130 | $L_{A387}$ | $L_{B19}$ | III-6275 | $L_{A472}$ | $L_{B37}$ |
| III-3131 | $L_{A388}$ | $L_{B19}$ | III-6276 | $L_{A473}$ | $L_{B37}$ |
| III-3132 | $L_{A389}$ | $L_{B19}$ | III-6277 | $L_{A474}$ | $L_{B37}$ |
| III-3133 | $L_{A390}$ | $L_{B19}$ | III-6278 | $L_{A475}$ | $L_{B37}$ |
| III-3134 | $L_{A391}$ | $L_{B19}$ | III-6279 | $L_{A476}$ | $L_{B37}$ |
| III-3135 | $L_{A392}$ | $L_{B19}$ | III-6280 | $L_{A477}$ | $L_{B37}$ |
| III-3136 | $L_{A393}$ | $L_{B19}$ | III-6281 | $L_{A478}$ | $L_{B37}$ |
| III-3137 | $L_{A394}$ | $L_{B19}$ | III-6282 | $L_{A479}$ | $L_{B37}$ |
| III-3138 | $L_{A395}$ | $L_{B19}$ | III-6283 | $L_{A480}$ | $L_{B37}$ |
| III-3139 | $L_{A396}$ | $L_{B19}$ | III-6284 | $L_{A481}$ | $L_{B37}$ |
| III-3140 | $L_{A397}$ | $L_{B19}$ | III-6285 | $L_{A482}$ | $L_{B37}$ |
| III-3141 | $L_{A398}$ | $L_{B19}$ | III-6286 | $L_{A483}$ | $L_{B37}$ |
| III-3142 | $L_{A399}$ | $L_{B19}$ | III-6287 | $L_{A484}$ | $L_{B37}$ |
| III-3143 | $L_{A400}$ | $L_{B19}$ | III-6288 | $L_{A485}$ | $L_{B37}$ |
| III-3144 | $L_{A401}$ | $L_{B19}$ | III-6289 | $L_{A486}$ | $L_{B37}$ |
| III-3145 | $L_{A402}$ | $L_{B19}$ | III-6290 | $L_{A487}$ | $L_{B37}$. |

17. The compound of claim 16, wherein the compound is selected from the group consisting of: Compound III-1, Compound III-2, Compound III-3, Compound III-5, Compound III-8, Compound III-11, Compound III-14, Compound III-25, Compound III-26, Compound III-27, Compound III-29, Compound III-32, Compound III-34, Compound III-35, Compound III-37, Compound III-38, Compound III-44, Compound III-46, Compound III-47, Compound III-49, Compound III-50, Compound III-53, Compound III-56, Compound III-59, Compound III-62, Compound III-65, Compound III-68, Compound III-71, Compound III-73, Compound III-74, Compound III-82, Compound III-98, Compound III-97, Compound III-110, Compound III-122, Compound III-133, Compound III-134, Compound III-137, Compound III-143, Compound III-145, Compound III-146, Compound III-151, Compound III-152, Compound III-163, Compound III-164, Compound III-196, Compound III-220, Compound III-1559, Compound III-1604, Compound III-1738, Compound III-1750, Compound III-4285, Compound III-4300, Compound III-4470, Compound III-4622, Compound III-4640, Compound III-4690, Compound III-4736, Compound III-4907, Compound III-5076, Compound III-5979, Compound III-6139, Compound III-4810, Compound III-4980, Compound III-5150, Compound III-5320, Compound III-5475, Compound III-5490, and Compound III-5660.

18. The compound of claim 1, wherein $A^1$-$A^4$ and $A^6$-$A^8$ are C;

$A^5$ is N; and said compound having a structure according to Formula III

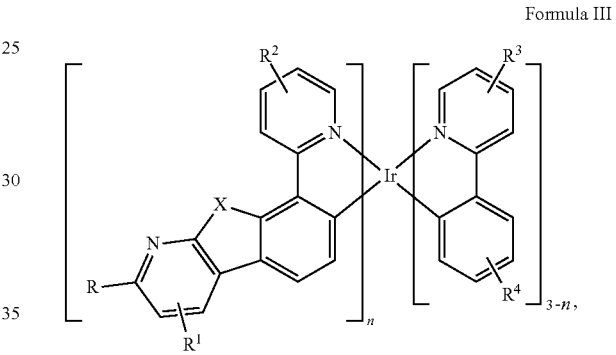

Formula III wherein R is selected from the group consisting of alkyl, cycloalkyl, and combinations thereof.

19. The compound of claim 18, wherein $R^2$ is phenyl or substituted phenyl.

20. The compound of claim 18, wherein $R^2$ is pyridine or substituted pyridine.

21. The compound of claim 18, wherein $R^2$ represents mono-substitution.

22. The compound of claim 18, wherein n is 1.

23. The compound of claim 18, wherein X is O.

24. The compound of claim 18, wherein R is alkyl.

25. The compound of claim 18, wherein R is cycloalkyl.

26. The compound of claim 18, wherein R is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, partially or fully deuterated variants thereof, and combinations thereof.

27. The compound of claim 18, wherein $R^1$, $R^3$, and $R^4$ are independently selected from the group consisting of hydrogen, deuterium, alkyl, and combinations thereof.

28. The compound of claim 18, wherein $R^3$ is alkyl, or partially or fully deuterated alkyl.

29. The compound of claim 18, wherein $L_A$ is selected from the group consisting of:
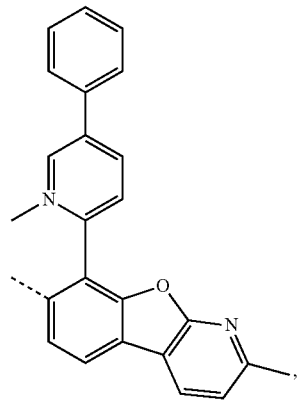
$L_{A342}$
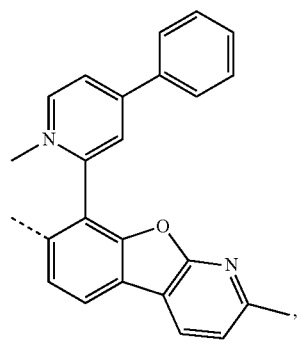
$L_{A343}$
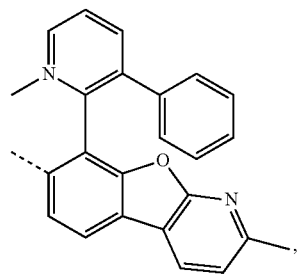
$L_{A344}$
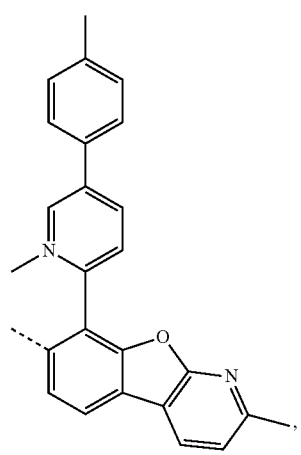
$L_{A345}$
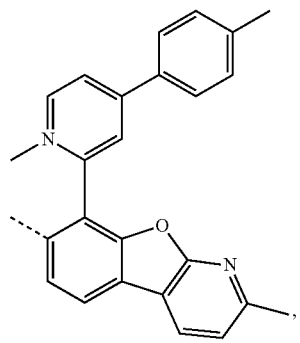
$L_{A346}$
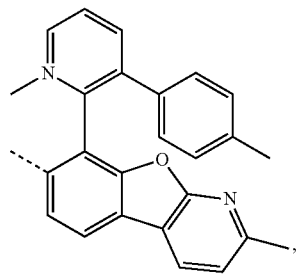
$L_{A347}$
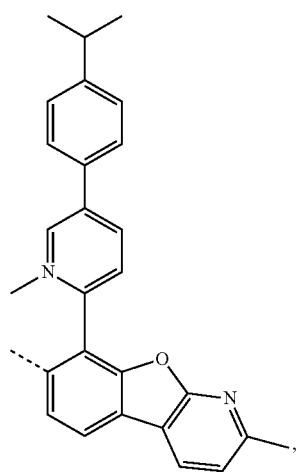
$L_{A348}$
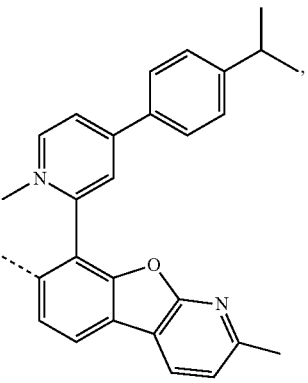
$L_{A349}$ 357
-continued
L_{A350}
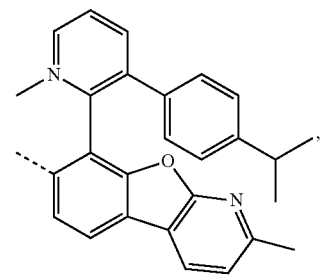
L_{A351}
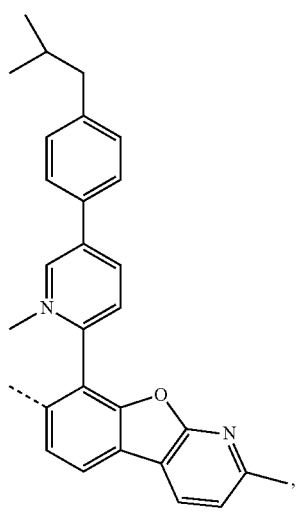
L_{A352}
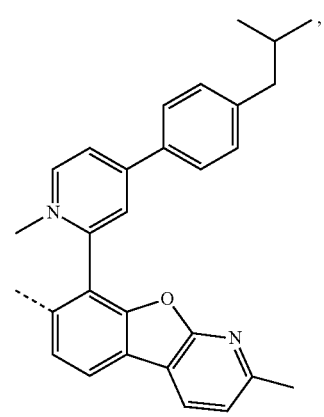
L_{A353}
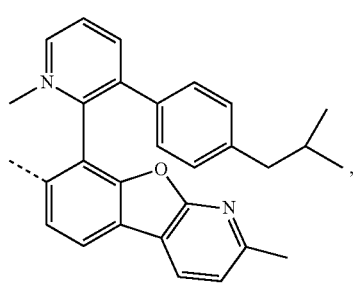
358
-continued
L_{A354}
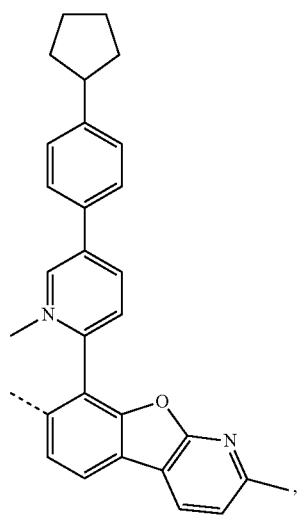
L_{A355}
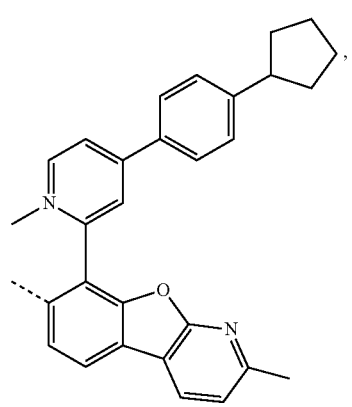
L_{A356}
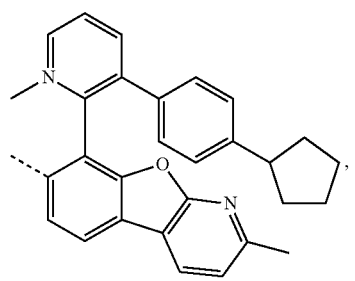
L_{A357}
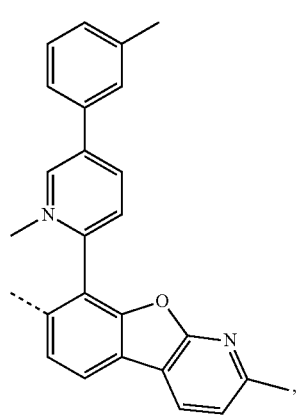

359
-continued
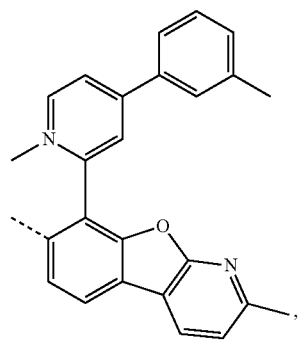
L<sub>A358</sub>
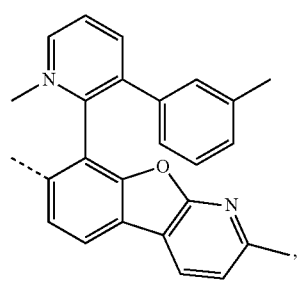
L<sub>A359</sub>
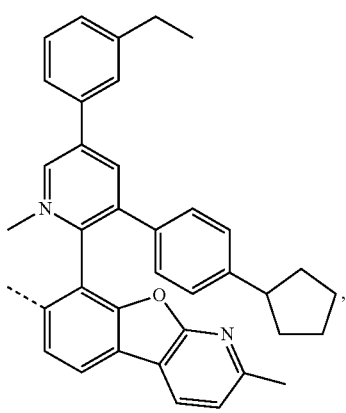
L<sub>A360</sub>
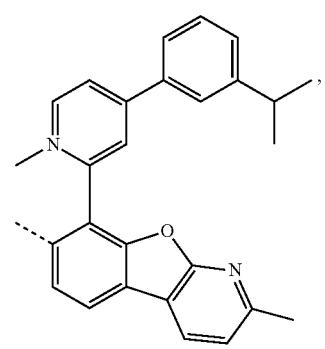
L<sub>A361</sub>
360
-continued
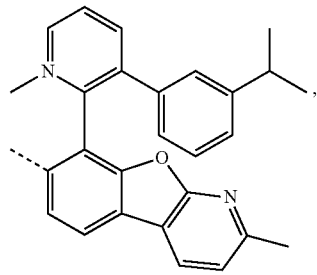
L<sub>A362</sub>
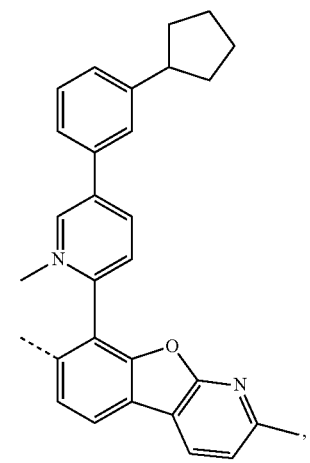
L<sub>A363</sub>
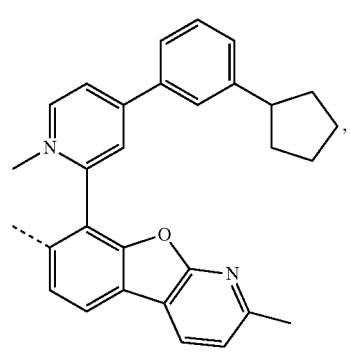
L<sub>A364</sub>
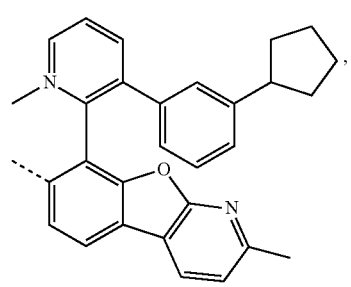
L<sub>A365</sub>

L<sub>A366</sub> 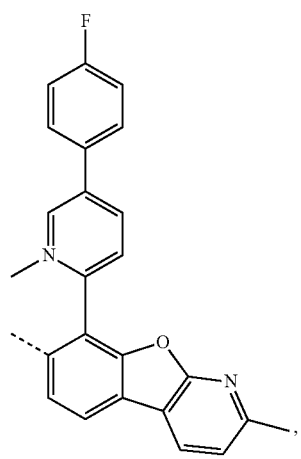
L<sub>A367</sub> 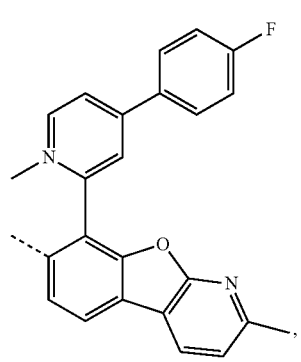
L<sub>A368</sub> 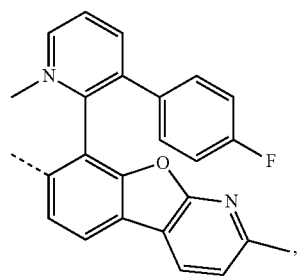
L<sub>A369</sub> 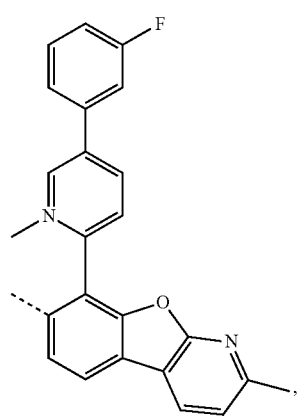
L<sub>A370</sub> 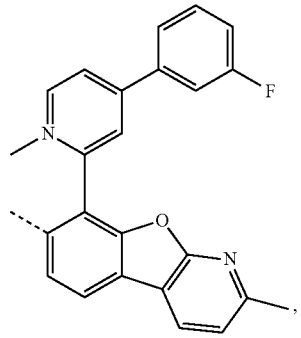
L<sub>A371</sub> 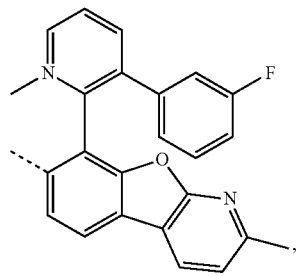
L<sub>A372</sub> 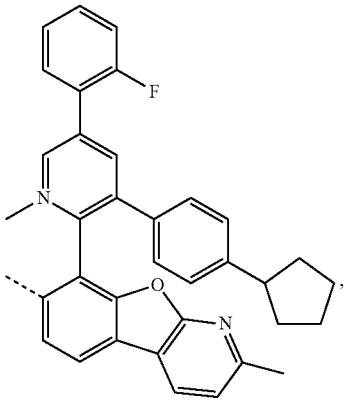
L<sub>A373</sub> 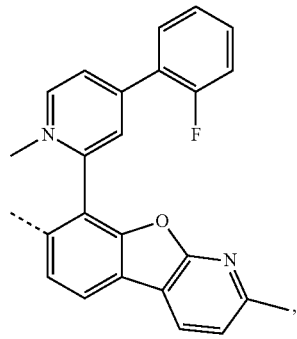

L_{A374}
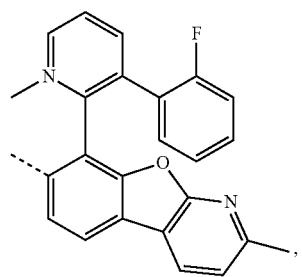
L_{A375}
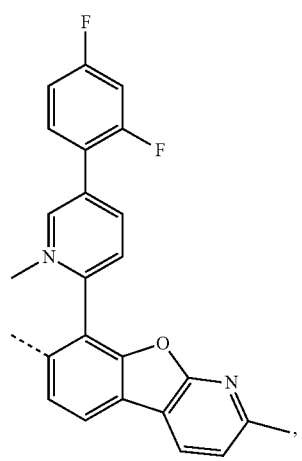
L_{A376}
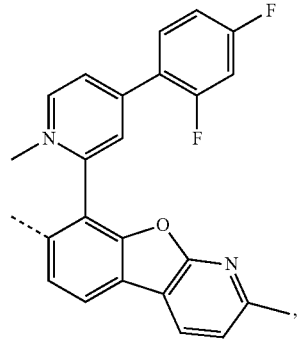
L_{A377}
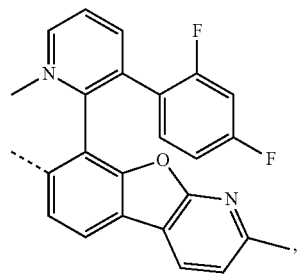
L_{A378}
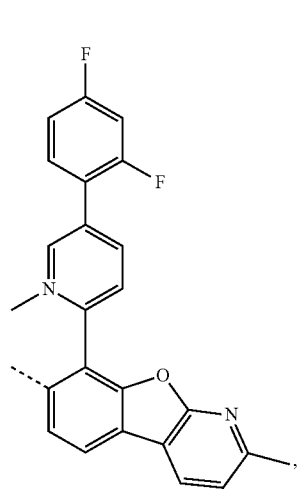
L_{A379}
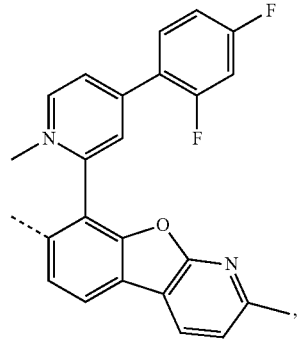
L_{A380}
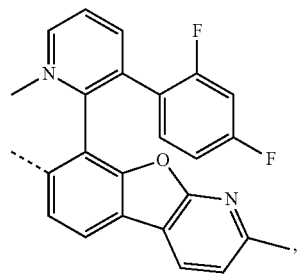
L_{A381}

-continued
L<sub>A382</sub>
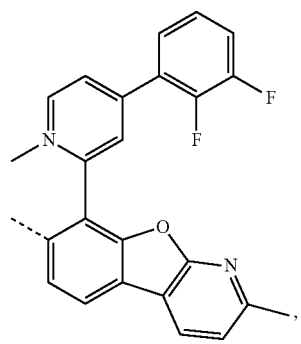
L<sub>A383</sub>
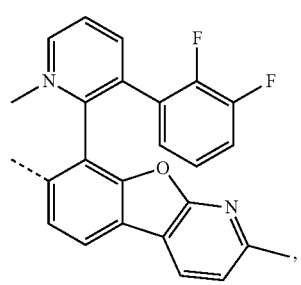
L<sub>A384</sub>
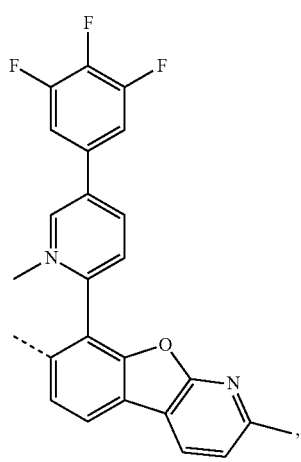
L<sub>A385</sub>
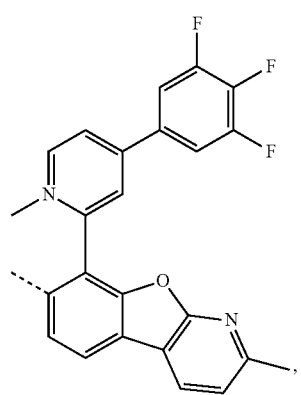
L<sub>A386</sub>
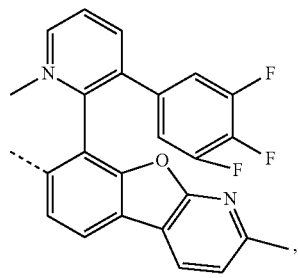
L<sub>A387</sub>
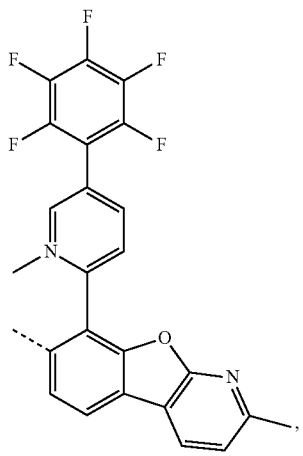
L<sub>A388</sub>
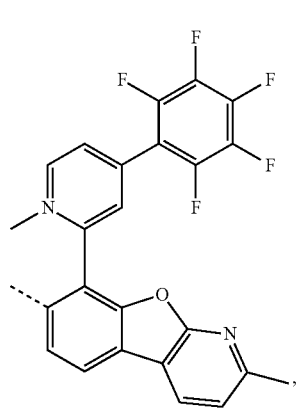
L<sub>A389</sub>
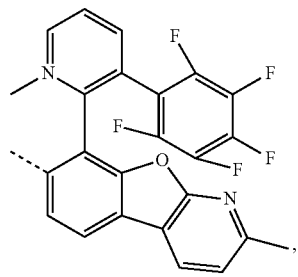

367
-continued
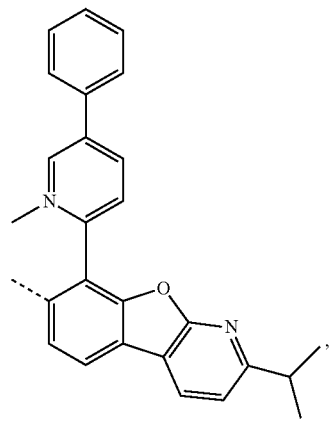
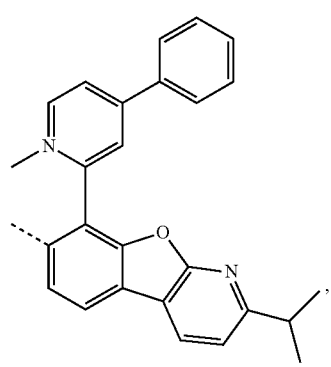
$L_{A392}$
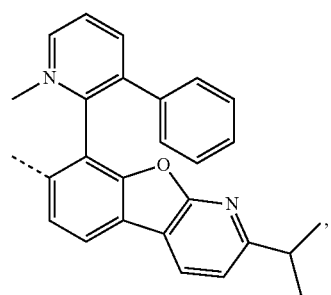
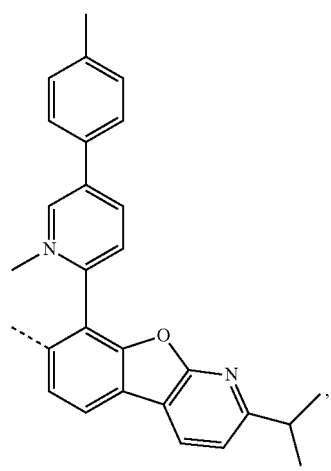
368
-continued
$L_{A390}$
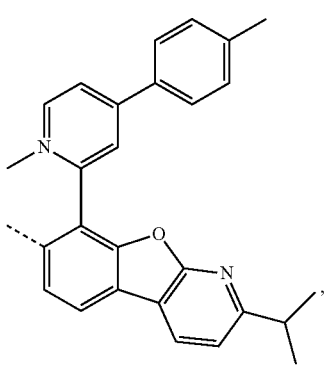
$L_{A390}$
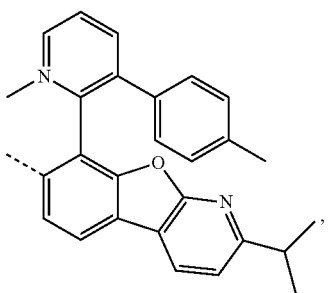
$L_{A393}$
$L_{A394}$
$L_{A395}$
$L_{A396}$
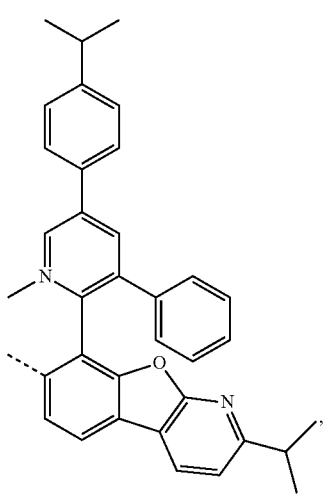
$L_{A397}$
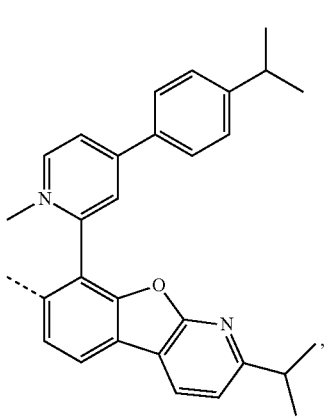

| 369 -continued | 370 -continued |
|---|---|
| 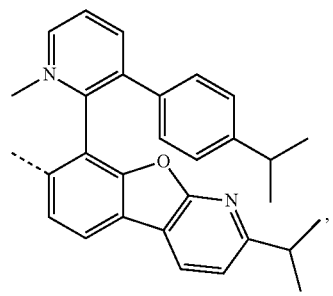 L<sub>A398</sub> | 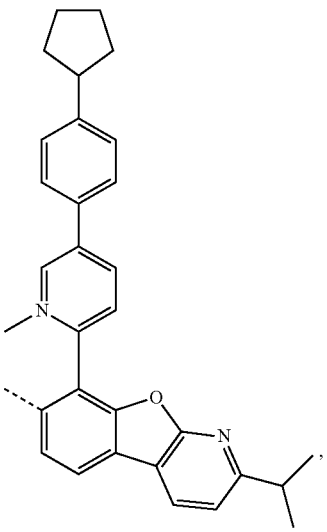 L<sub>A402</sub> |
| 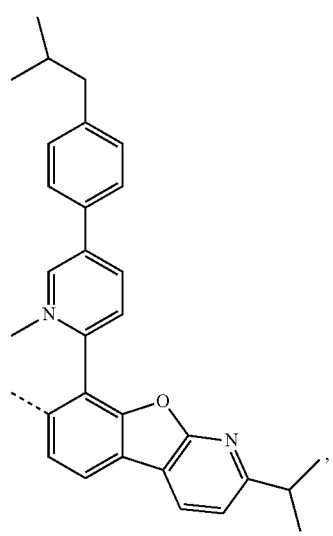 L<sub>A399</sub> | |
| 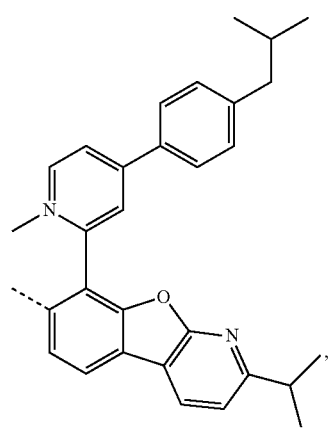 L<sub>A400</sub> | 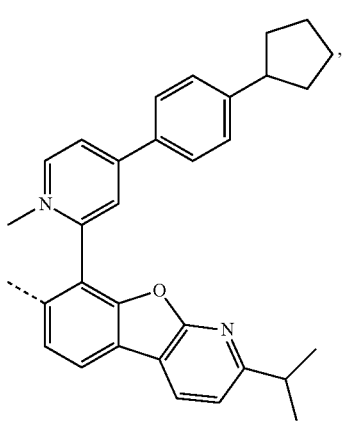 L<sub>A403</sub> |
| 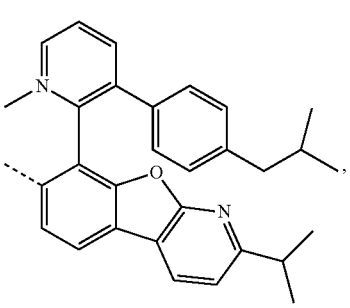 L<sub>A401</sub> | 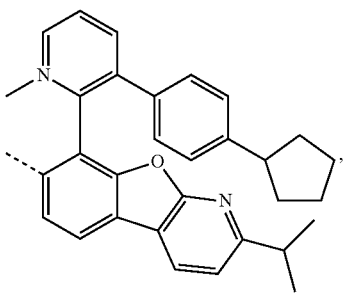 L<sub>A404</sub> |

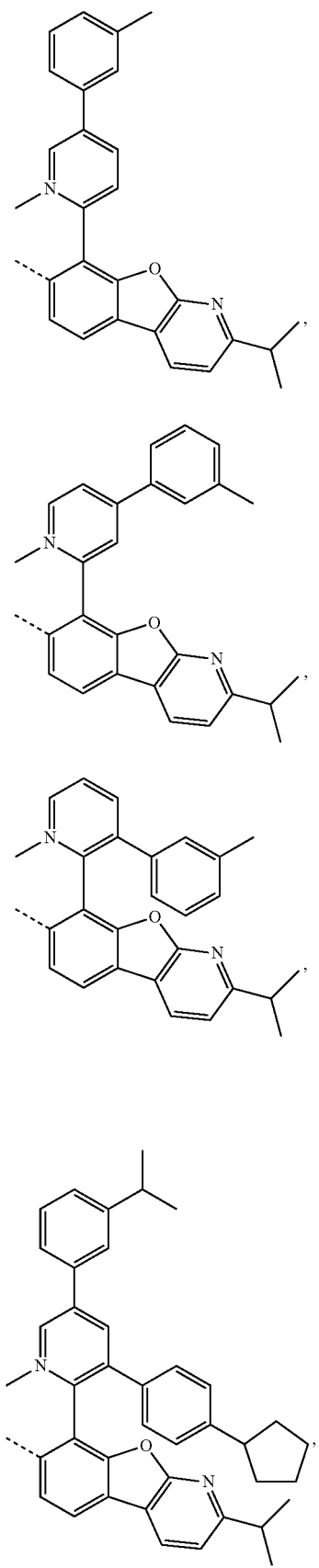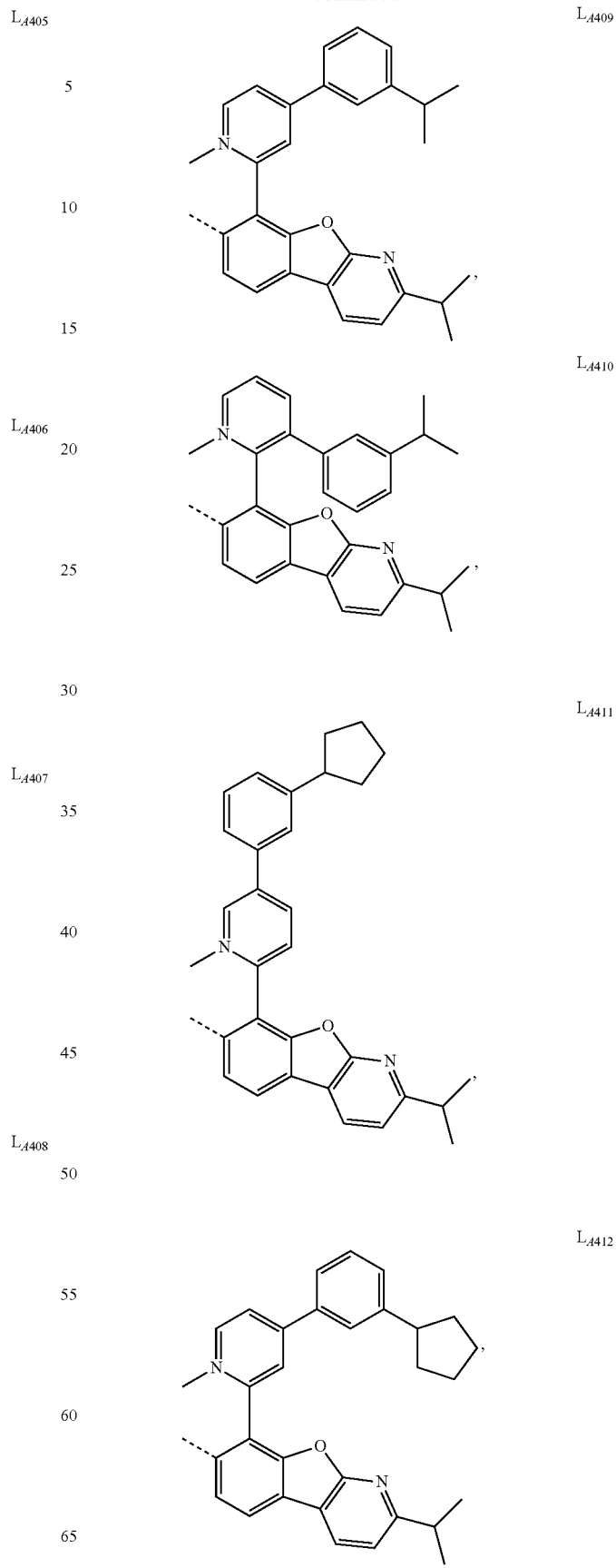

| | |
|---|---|
| 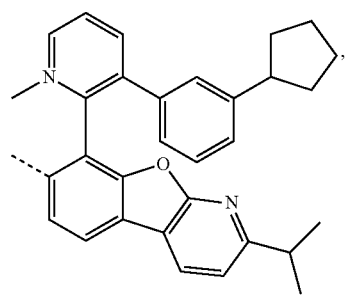 | 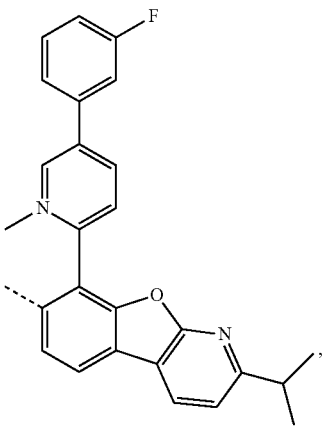 $L_{A413}$ |
| 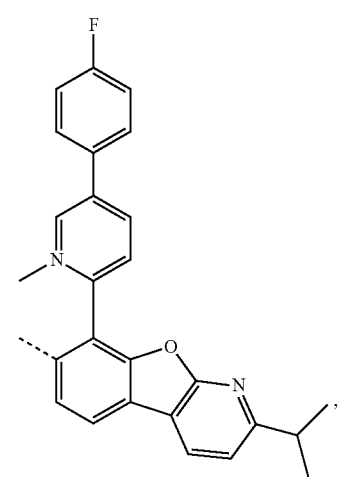 | 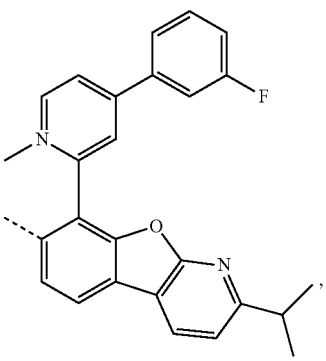 $L_{A414}$ |
| 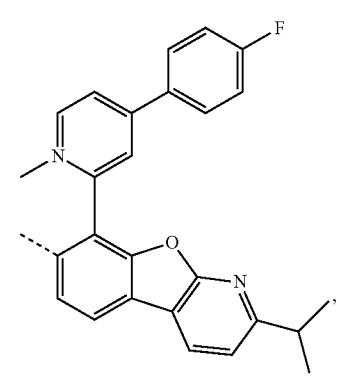 | 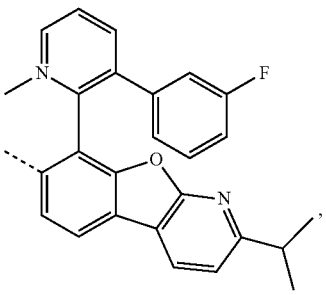 $L_{A415}$ |
| 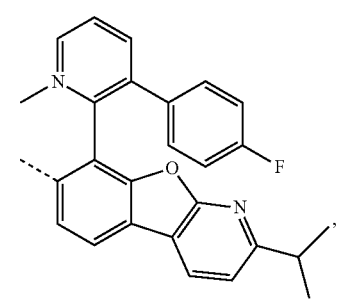 | 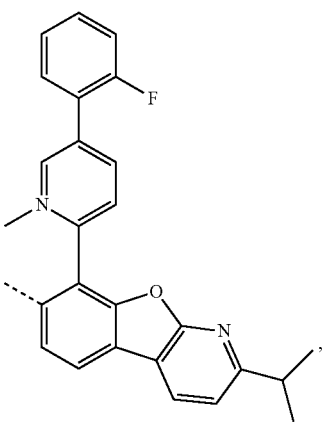 $L_{A416}$ |
$L_{A417}$
$L_{A418}$
$L_{A419}$
$L_{A420}$ -continued
L<sub>A421</sub>
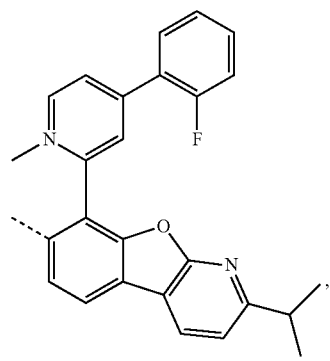
L<sub>A422</sub>
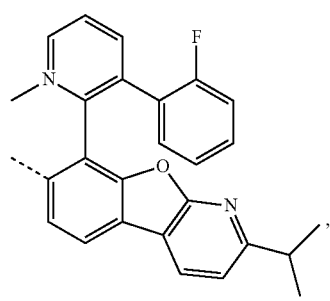
L<sub>A423</sub>
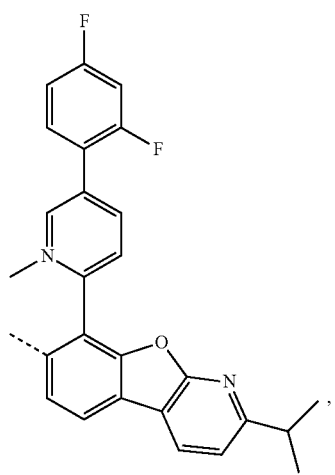
L<sub>A424</sub>
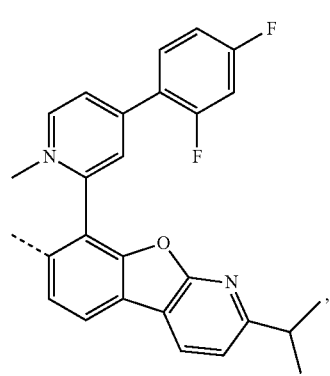
-continued
L<sub>A425</sub>
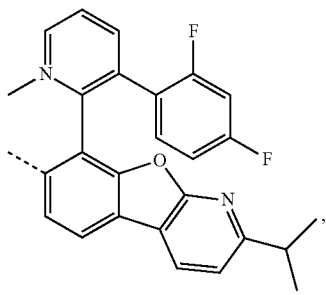
L<sub>A426</sub>
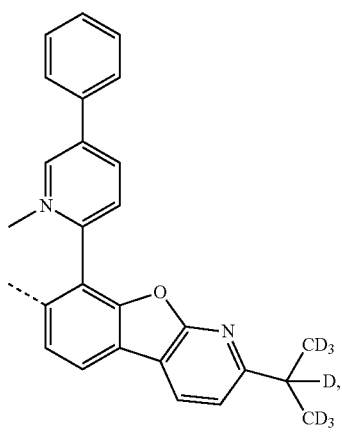
L<sub>A427</sub>
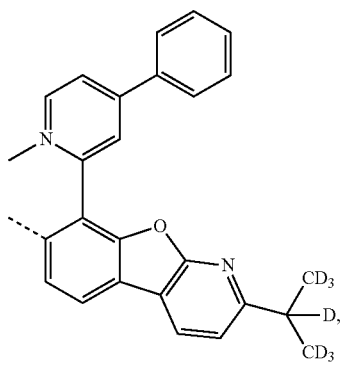
L<sub>A428</sub>
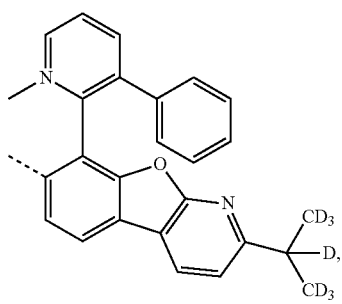

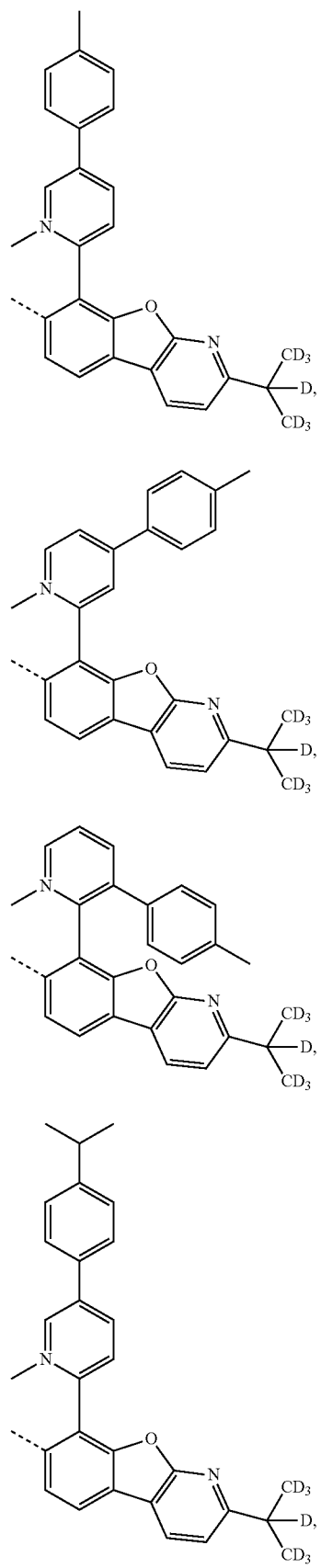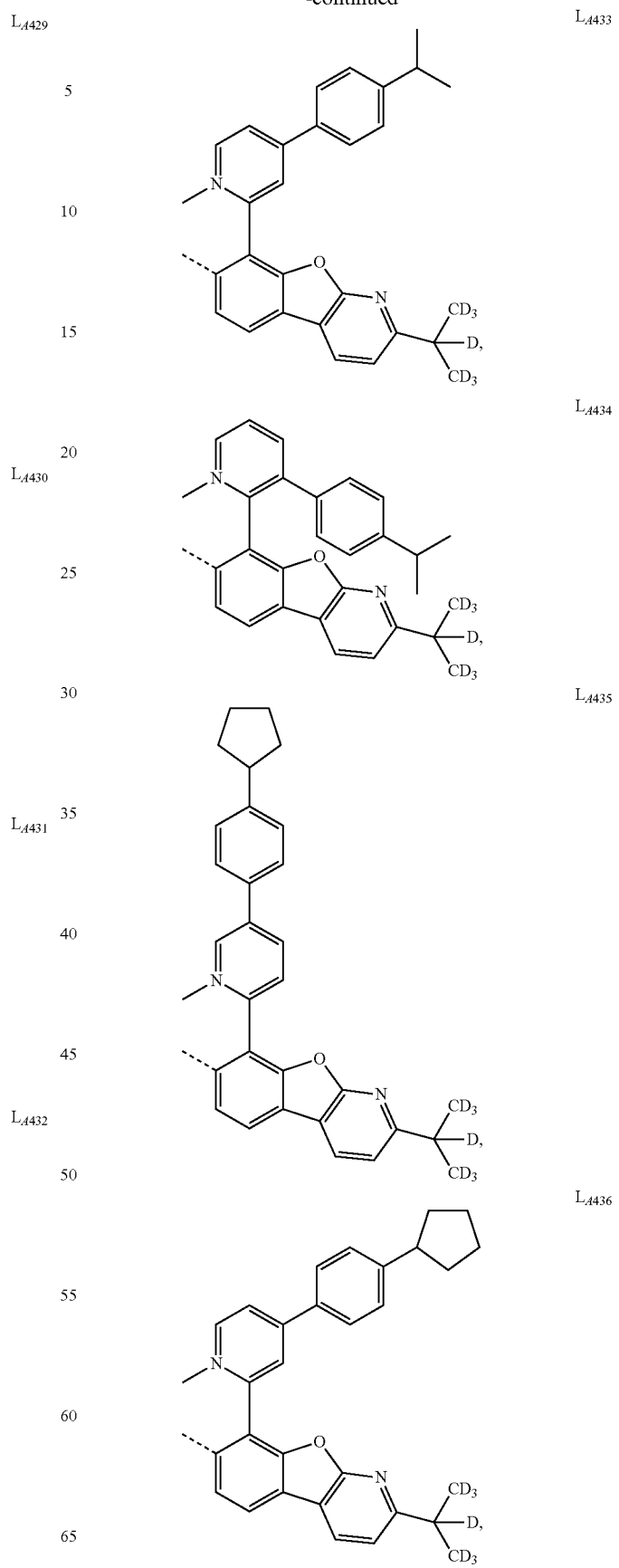

L_{A437}
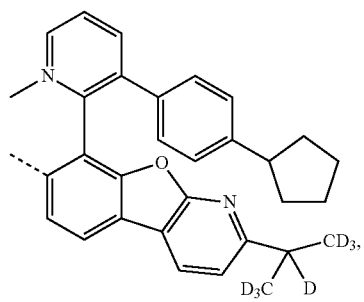
L_{A438}
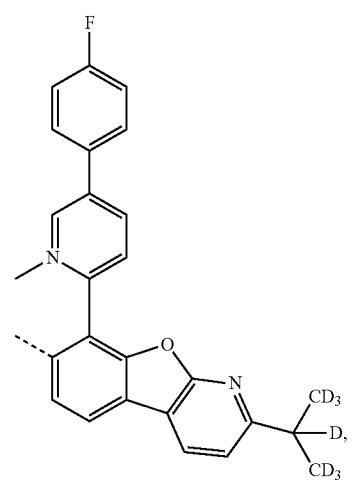
L_{A439}
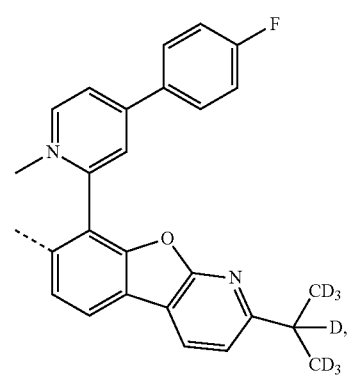
L_{A440}
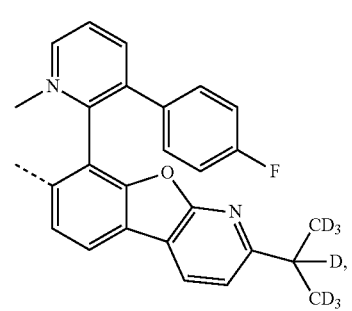
L_{A441}
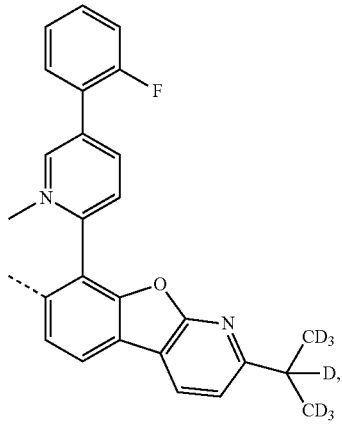
L_{A442}
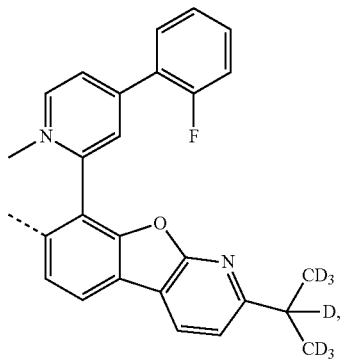
LA443
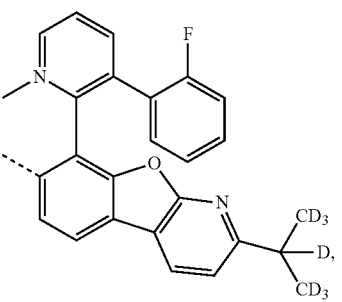
L_{A444}
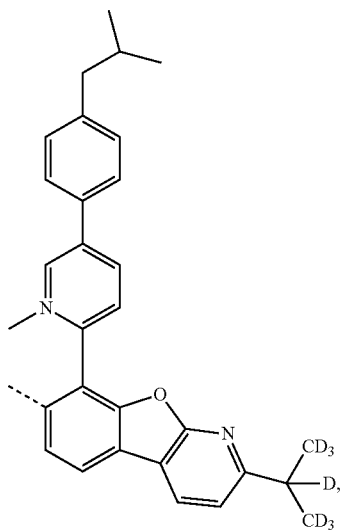

| | |
|---|---|
| 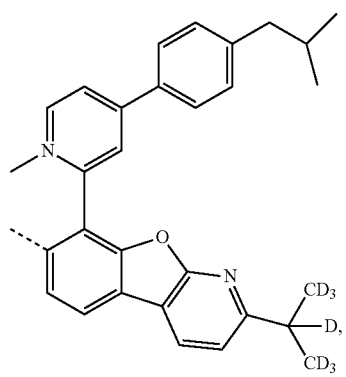 | $L_{A445}$ |
| 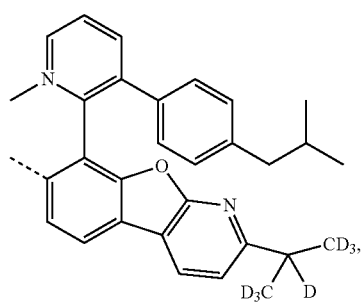 | $L_{A446}$ |
| 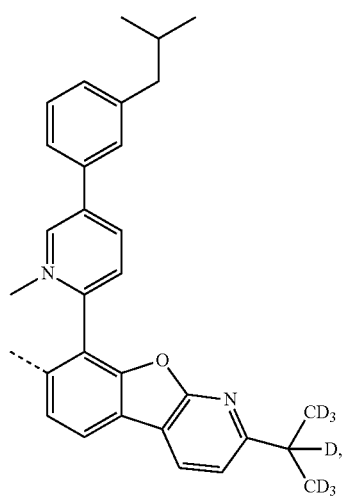 | $L_{A447}$ |
| 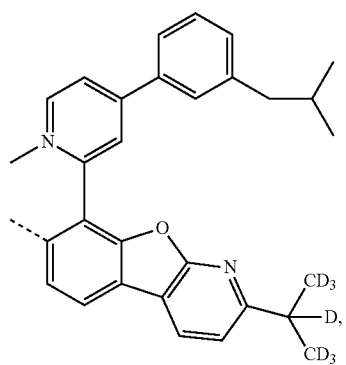 | $L_{A448}$ |
| 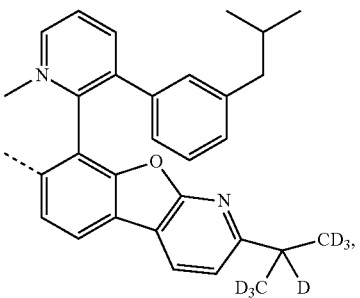 | $L_{A449}$ |
| 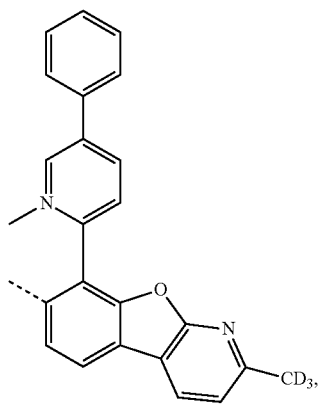 | $L_{A450}$ |
| 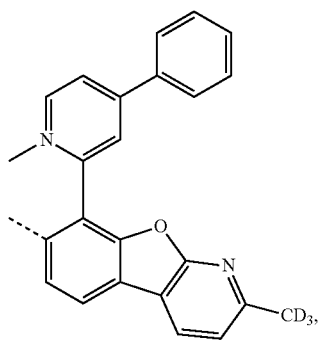 | $L_{A451}$ |
| 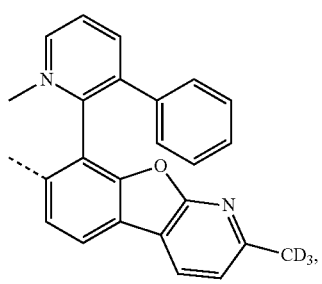 | $L_{A452}$ |

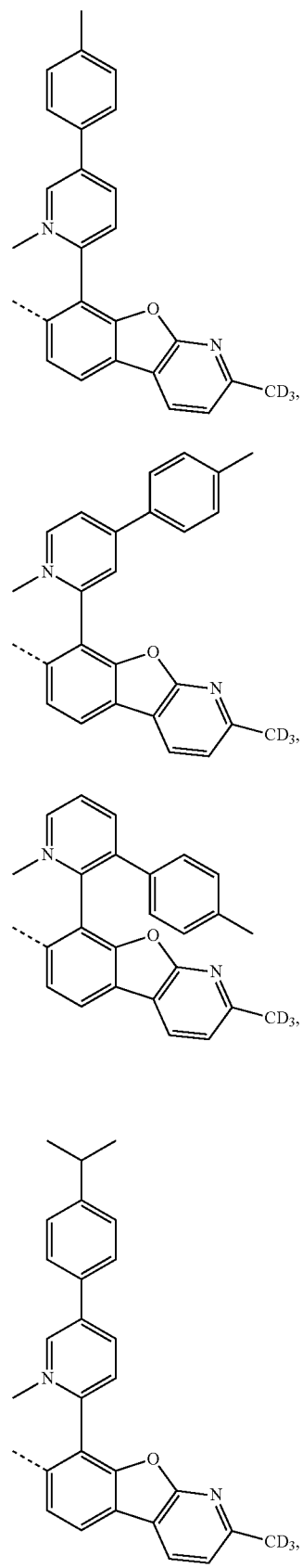
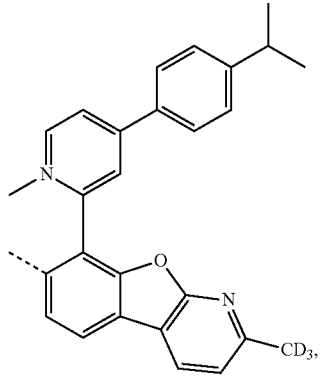
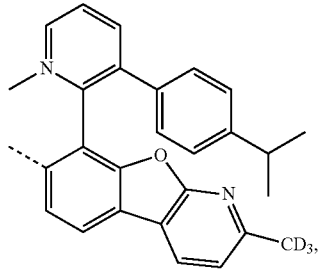
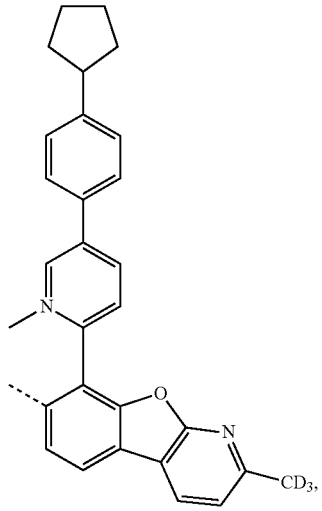
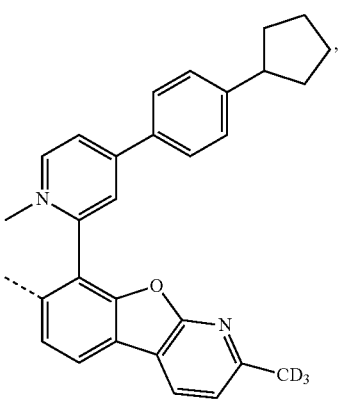

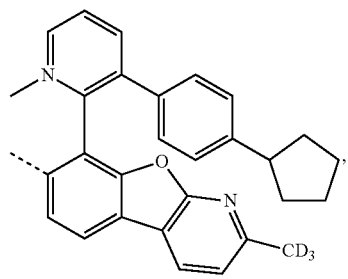
L<sub>A461</sub>
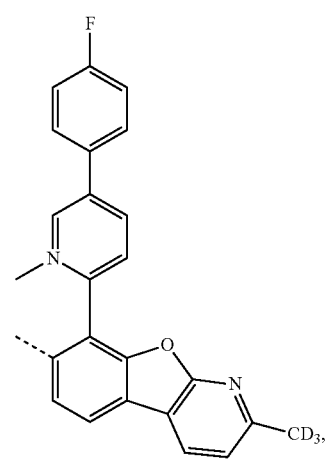
L<sub>A462</sub>
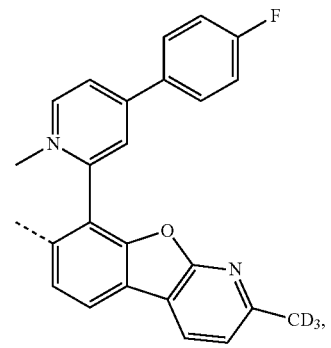
L<sub>A463</sub>
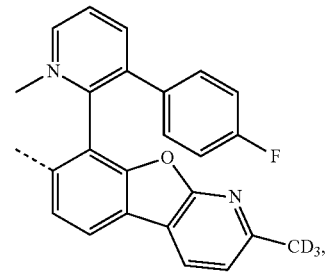
L<sub>A464</sub>
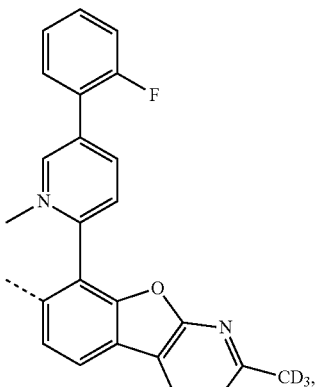
L<sub>A465</sub>
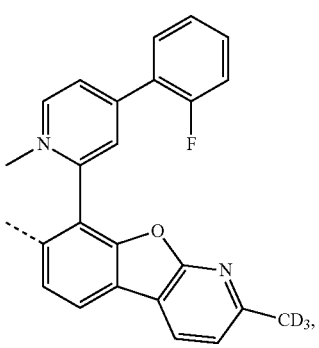
L<sub>A466</sub>
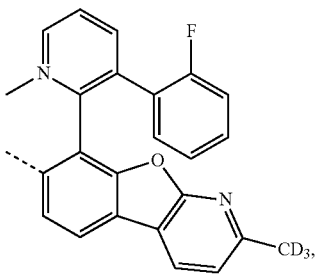
L<sub>A467</sub>
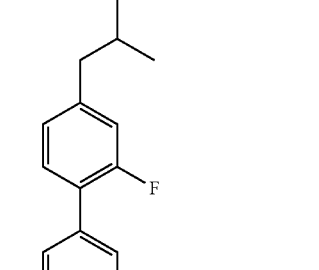
L<sub>A468</sub>

L_{A469}
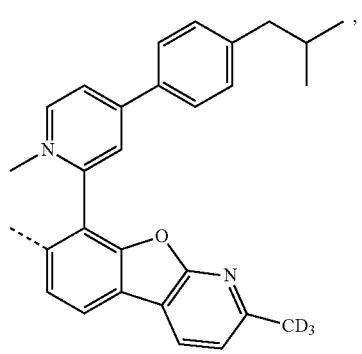
L_{A470}
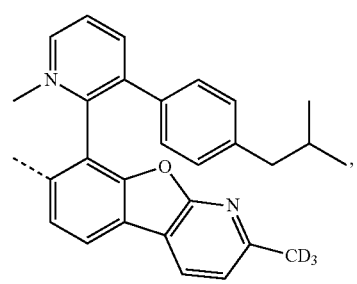
L_{A471}
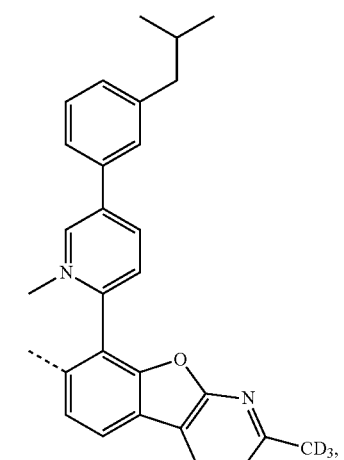
L_{A472}
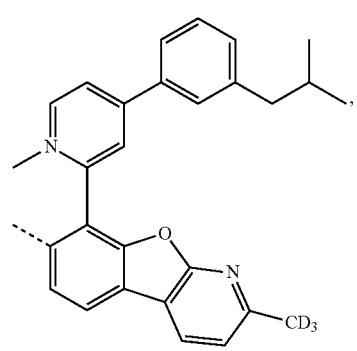
L_{A473}
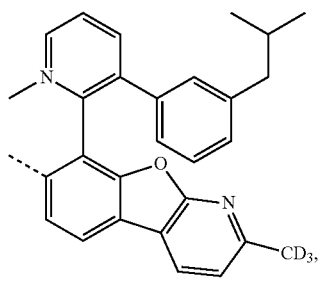
L_{A474}
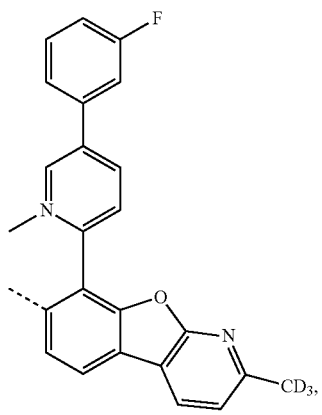
L_{A475}
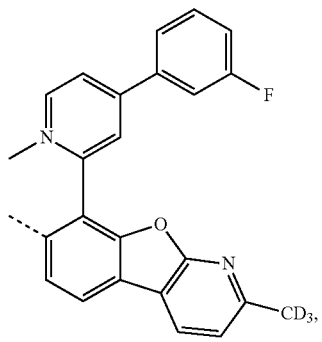
L_{A476}
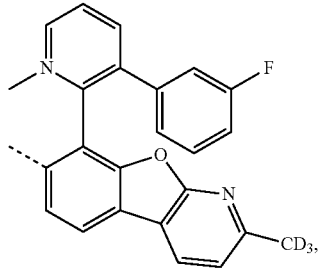

30. The compound of claim 18, wherein $L_B$ is selected from the group consisting of:

391                                                         392
-continued                                                  -continued
L_{B2}
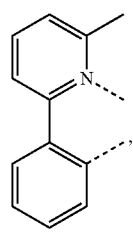
L_{B8}
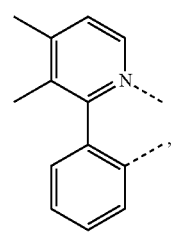
L_{B3}
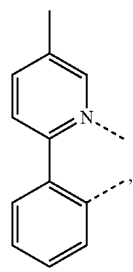
L_{B9}
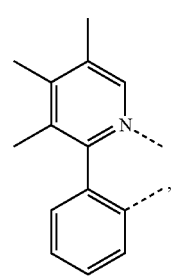
L_{B4}
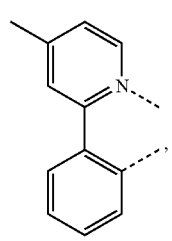
L_{B10}
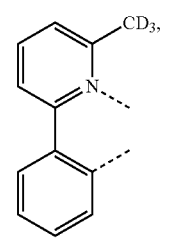
L_{B5}
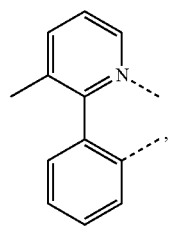
L_{B11}
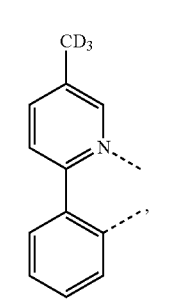
L_{B6}
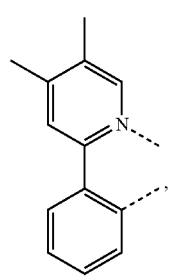
L_{B12}
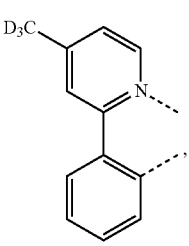
L_{B7}
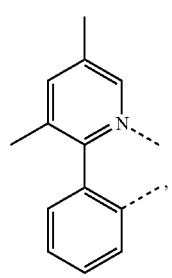
L_{B13}
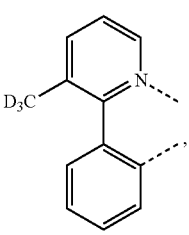

L_B14 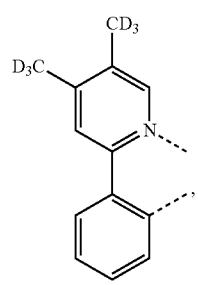
L_B15 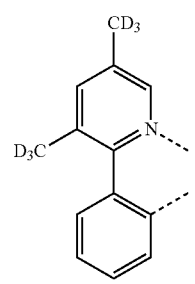
L_B16 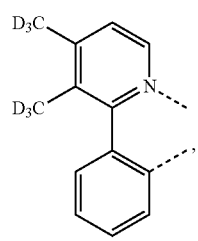
L_B17 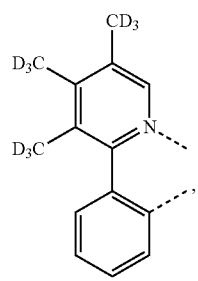
L_B18 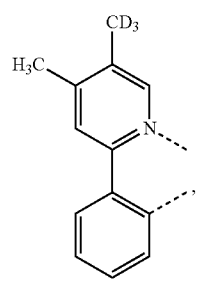
L_B19 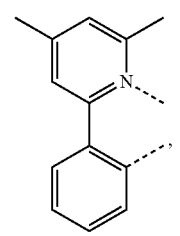
L_B20 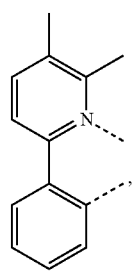
L_B21 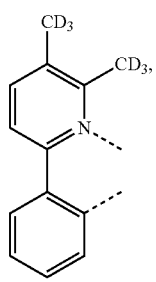
L_B22 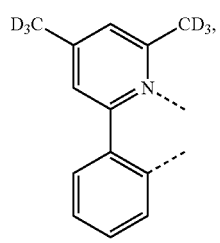
L_B23 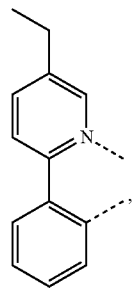
L_B24 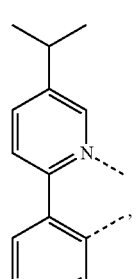
L_B25 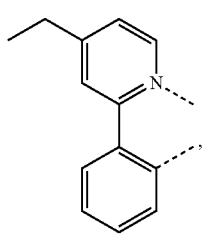

| | |
|---|---|
| 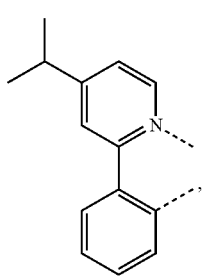 | $L_{B26}$ |
| 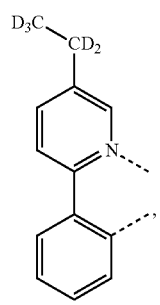 | $L_{B27}$ |
| 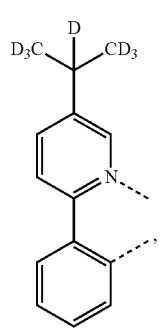 | $L_{B28}$ |
| 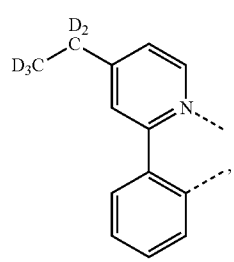 | $L_{B29}$ |
| 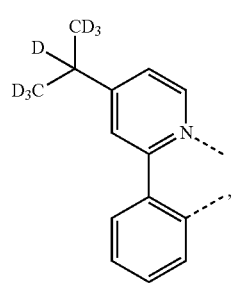 | $L_{B30}$ |
| | |
|---|---|
| 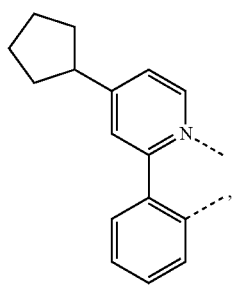 | $L_{B31}$ |
| 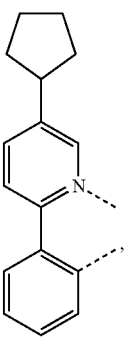 | $L_{B32}$ |
| 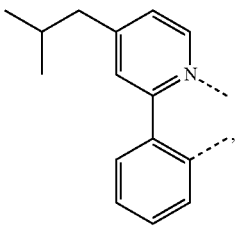 | $L_{B33}$ |
| 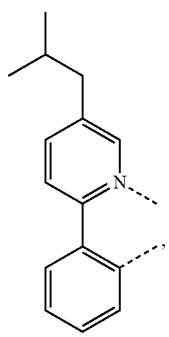 | $L_{B34}$ |
| 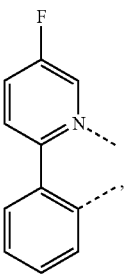 | $L_{B35}$ |

-continued

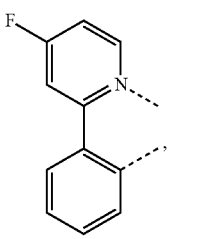
$L_{B36}$
and

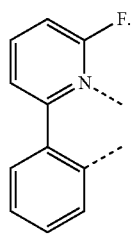
$L_{B37}$

31. A first device comprising a first organic light emitting device, further comprising:
an anode;
a cathode; and
an organic layer, disposed between the anode and the cathode, comprising a compound having the formula $Ir(L_A)_n(L_B)_{3-n}$, having the structure:

Formula I

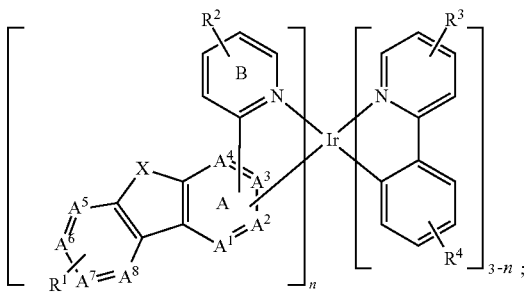

wherein $A^1, A^2, A^3, A^4, A^5, A^6, A^7,$ and $A^8$ comprise carbon or nitrogen;
wherein at least one of $A^1, A^2, A^3, A^4, A^5, A^6, A^7,$ and $A^8$ is nitrogen;
wherein ring B is bonded to ring A through a C—C bond;
wherein the iridium is bonded to ring A through a Ir—C bond;
wherein X is O, S, or Se;
wherein $R^1, R^2, R^3,$ and $R^4$ independently represent mono-, di-, tri-, tetra-substitution, or no substitution;
wherein any adjacent substitutions in $R^1, R^2, R^3,$ and $R^4$ are optionally linked together to form a ring;
wherein $R^1, R^3,$ and $R^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R^2$ is selected from the group consisting of aryl, substituted aryl, heteroaryl, and substituted heteroaryl; and
wherein n is an integer from 1 to 3.

32. The first device of claim 31, wherein $R^2$ is phenyl or substituted phenyl.
33. The first device of claim 31, wherein $R^2$ is pyridine or substituted pyridine.
34. The first device of claim 31, wherein $R^2$ represents mono-substitution.
35. The first device of claim 31, wherein the organic layer is an emissive layer and the compound is an emissive dopant.
36. The first device of claim 31, wherein the organic layer is an emissive layer and the compound is a non-emissive dopant.
37. The first device of claim 31, wherein the organic layer further comprises a host.
38. The first device of claim 37, wherein the host comprises a triphenylene containing benzo-fused thiophene or benzo-fused furan;
wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC_nH_{2n+1}$, $Ar_1$, $Ar_1-Ar_2$, $C_nH_{2n}-Ar_1$, or no substitution;
wherein n is from 1 to 10; and
wherein $Ar_1$ and $Ar_2$ are independently selected from the group consisting of benzene, biphenyl, naphthalene, triphenylene, carbazole, and heteroaromatic analogs thereof.
39. The first device of claim 37, wherein the host comprises at least one chemical group selected from the group consisting of carbazole, dibenzothiphene, dibenzofuran, dibenzoselenophene, azacarbazole, aza-dibenzothiophene, aza-dibenzofuran, and aza-dibenzoselenophene.
40. The first device of claim 37, wherein the host is selected from the group consisting of:

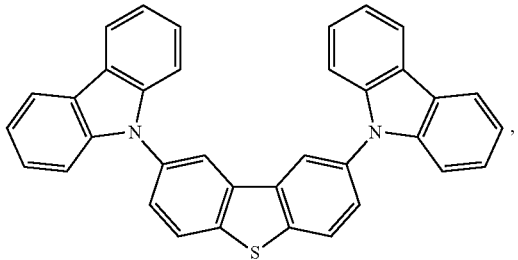 [SMILES: c1ccc2c(c1)c1ccccc1n2-c1ccc2sc3ccc(-n4c5ccccc5c5ccccc54)cc3c2c1]

,

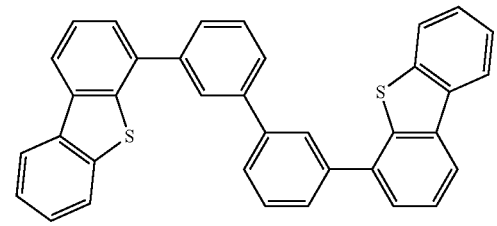

,

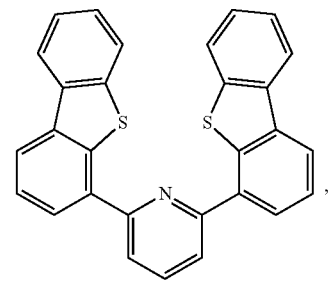 [SMILES: c1cc(-c2cccc3c2sc2ccccc23)nc(-c2cccc3c2sc2ccccc23)c1]

,

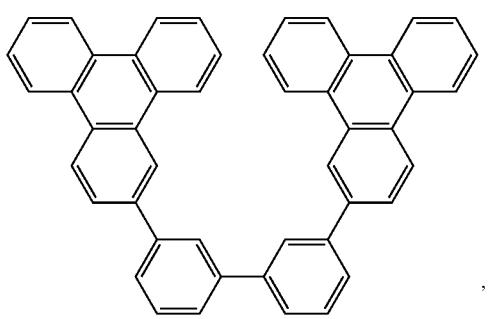 [SMILES: c1cc(-c2cccc(-c3ccc4c5ccccc5c5ccccc5c4c3)c2)cc(-c2ccc3c4ccccc4c4ccccc4c3c2)c1]
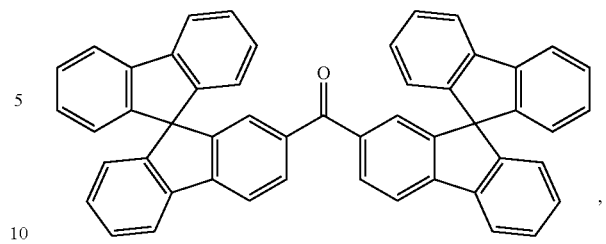
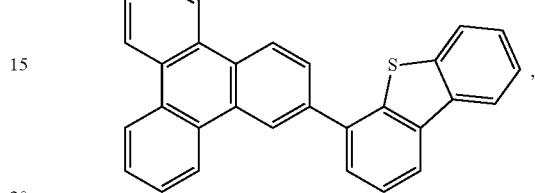
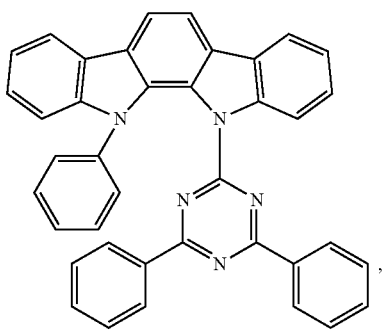 [SMILES: c1ccc(-c2nc(-c3ccccc3)nc(-n3c4ccccc4c4ccc5c6ccccc6n(-c6ccccc6)c5c43)n2)cc1]
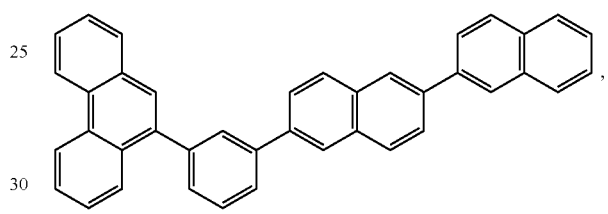
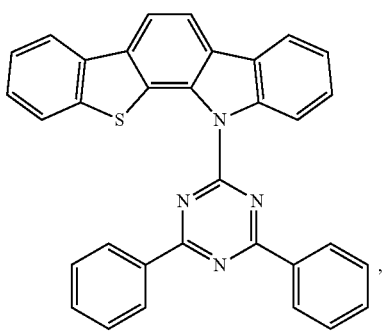 [SMILES: c1ccc(-c2nc(-c3ccccc3)nc(-n3c4ccccc4c4ccc5c6ccccc6sc5c43)n2)cc1]
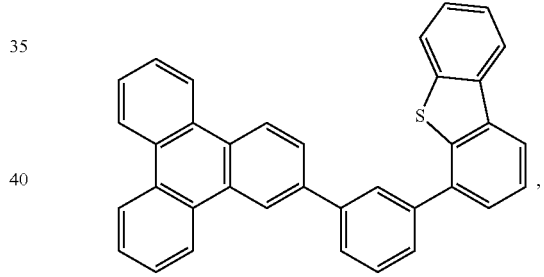
and combinations thereof.
41. The first device of claim 37, wherein the host comprises a metal complex.
42. The first device of claim 31, wherein the compound having the formula Ir(L$_A$)$_n$(L$_B$)$_{3-n}$ has the structure according to Formula II
Formula II
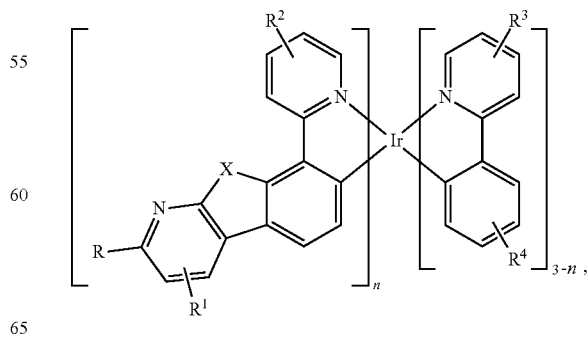
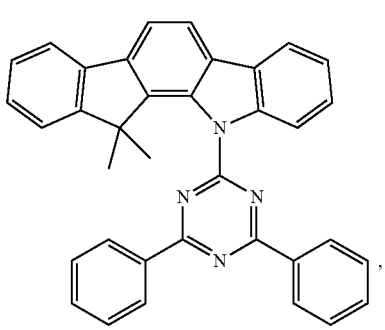
wherein R is selected from the group consisting of alkyl, cycloalkyl, and combinations thereof.

43. A formulation comprising a compound a compound having the formula $Ir(L_A)_n(L_B)_{3-n}$, having the structure:

Formula I

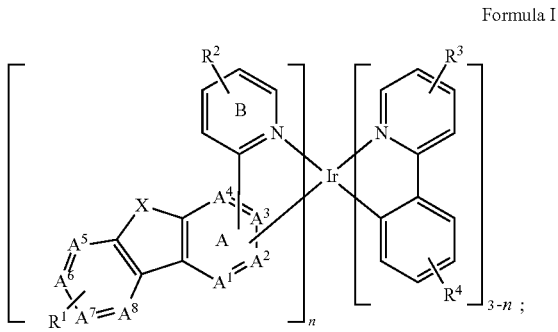

wherein $A^1, A^2, A^3, A^4, A^5, A^6, A^7$, and $A^8$ comprise carbon or nitrogen;

wherein at least one of $A^1, A^2, A^3, A^4, A^5, A^6, A^7$, and $A^8$ is nitrogen;

wherein ring B is bonded to ring A through a C—C bond;

wherein the iridium is bonded to ring A through a Ir—C bond;

wherein X is O, S, or Se;

wherein $R^1, R^2, R^3$, and $R^4$ independently represent mono-, di-, tri-, tetra-substitution, or no substitution;

wherein any adjacent substitutions in $R^1, R^2, R^3$, and $R^4$ are optionally linked together to form a ring;

wherein $R^1, R^3$, and $R^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein $R^2$ is selected from the group consisting of aryl, substituted aryl, heteroaryl, and substituted heteroaryl; and wherein n is an integer from 1 to 3.

* * * * *